(12) United States Patent
Gao et al.

(10) Patent No.: US 12,325,855 B2
(45) Date of Patent: Jun. 10, 2025

(54) GENE EDITING USING HOMOLOGY-INDEPENDENT UNIVERSAL GENOME ENGINEERING TECHNOLOGY

(71) Applicant: c/o Duke University, Durham, NC (US)

(72) Inventors: Yudong Gao, Durham, NC (US); Scott Soderling, Durham, NC (US)

(73) Assignee: Duke University, Durham, NC (US)

( * ) Notice: Subject to any disclaimer, the term of this patent is extended or adjusted under 35 U.S.C. 154(b) by 986 days.

(21) Appl. No.: 16/968,904

(22) PCT Filed: Feb. 15, 2019

(86) PCT No.: PCT/US2019/018353
§ 371 (c)(1),
(2) Date: Aug. 11, 2020

(87) PCT Pub. No.: WO2019/161304
PCT Pub. Date: Aug. 22, 2019

(65) Prior Publication Data
US 2021/0047643 A1 Feb. 18, 2021

Related U.S. Application Data

(60) Provisional application No. 62/631,360, filed on Feb. 15, 2018.

(51) Int. Cl.
*C12N 15/113* (2010.01)
*C12N 15/10* (2006.01)
*C12N 15/63* (2006.01)

(52) U.S. Cl.
CPC .......... *C12N 15/113* (2013.01); *C12N 15/102* (2013.01); *C12N 15/63* (2013.01); *C12N 2310/20* (2017.05)

(58) Field of Classification Search
CPC .... C12N 15/113; C12N 15/102; C12N 15/63; C12N 2310/20
See application file for complete search history.

(56) References Cited

U.S. PATENT DOCUMENTS

| | | | |
|---|---|---|---|
| 5,593,972 | A | 1/1997 | Weiner et al. |
| 5,962,428 | A | 10/1999 | Carrano et al. |
| 2015/0232827 | A1 | 8/2015 | Raab et al. |
| 2017/0268022 | A1 | 9/2017 | Liu et al. |
| 2018/0037877 | A1 | 2/2018 | Gao et al. |
| 2018/0155789 | A1* | 6/2018 | Maeder ................ C12N 15/102 |

FOREIGN PATENT DOCUMENTS

| | | | |
|---|---|---|---|
| WO | WO 1994/016737 A1 | 8/1994 | |
| WO | WO 2009/086132 A2 | 7/2009 | |

OTHER PUBLICATIONS

European Patent Office Extended Search Report for Application No. 19753997.6 dated Sep. 8, 2021 (8 pages).
Gao et al., "Plug-and-Play Protein Modification Using Homology-Independent Universal Genome Engineering," Neuron, 2019, 103(4): 583-597.
Bae et al., "Cas-OFFinder: a fast and versatile algorithm that searches for potential off-target sites of Cas9 RNA-guided endonucleases," Bioinformatics, 2014, 30(10): 1473-1475.
Bae et al., "Microhomology-based choice of Cas9 nuclease target sites," Nat Methods, 2014, 11: 705-706.
Baker, et al., "Nonsense-mediated mRNA decay: terminating erroneous gene expression," Curr Opin Cell Biol, 2004, 16: 293-299.
Bear et al., "Negative regulation of fibroblast motility by Ena/VASP proteins," Cell, 2000, 101: 717-728.
Berglund et al., "A genecentric Human Protein Atlas for expression profiles based on antibodies," Mol Cell Proteomics, 2008, 7(10): 2019-2027.
Bhargava et al., "C-NHEJ without indels is robust and requires synergistic function of distinct XLF domains," Nat Commun, 2018, 9(1): 2484.
Bradbury et al., "Reproducibility: Standardize antibodies used in research," Nature, 2015, 518(7537): 27-29.
Chen et al., "Deficiency of methyl-CpG binding protein-2 in CNS neurons results in a Rett-like phenotype in mice," Nat Genet, 2001, 27: 327-331.
Chen et al., "Enhanced proofreading governs CRISPR-Cas9 targeting accuracy," Nature, 2017, 550(7676): 407-410.
Chen et al., "Linear DNAs concatemerize in vivo and result in sustained transgene expression in mouse liver," Mol Ther, 2001, 3(3): 403-410.
Chen et al., "Minicircle DNA vectors devoid of bacterial DNA result in persistent and high-level transgene expression in vivo," Mol Ther, 2003, 8(3): 495-500.
Cheriyan et al., "Faster protein splicing with the Nostoc punctiforme DnaE intein using non- native extein residues," J Biol Chem, 2013, 288(9): 6202-6211.
Doudna et al., "Genome editing. The new frontier of genome engineering with CRISPR-Cas9," Science, 2014, 346: 1258096.
Egelhofer et al., "An assessment of histone-modification antibody quality," Nat Struct Mol Biol, 2011, 18: 91-93.
Ezkurdia et al., "Multiple evidence strands suggest that there may be as few as 19,000 human protein-coding genes," Hum Mol Genet, 2014, 23(22): 5866-5878.
Francis et al., "Doublecortin Is a Developmentally Regulated, Microtubule-Associated Protein Expressed in Migrating and Differentiating Neurons," Neuron, 1999, 23: 247-256.

(Continued)

*Primary Examiner* — J. E. Angell
(74) *Attorney, Agent, or Firm* — Michael Best & Friedrich LLP

(57) ABSTRACT

Disclosed herein are the genetic constructs for a Homology-Independent Universal Genome Editing (HiUGE) system and methods of using said HiUGE system for genome editing. The invention relates to compositions comprising gRNA polynucleotides, insert polynucleotides, and a CRISPR-based nuclease or polynucleotide encoding a CRISPR-based nuclease.

15 Claims, 62 Drawing Sheets

Specification includes a Sequence Listing.

(56) References Cited

OTHER PUBLICATIONS

Gdalyahu et al., "DCX, a new mediator of the JNK pathway," EMBO J, 2004, 23: 823-832.
Global Market Insights, "Gene Editing Market Size By Application (Cell Line Engineering, Animal Genetic Engineering, Plant Genetic Engineering), By Technology (CRISPR/Cas9, Zinc Finger Nucleases (ZFNs), TALENs), By End-user (Biotech and Pharma Companies, Contract Research Organizations (CROs), Research Institutes), Industry Analysis Report, Regional Outlook, Growth Potential, Price Trends, Competitive Market Share & Forecast, 2020-2026," <https://www.gminsights.com/industry-analysis/gene-editing-market> (2020).
Haeussler et al., "Evaluation of off-target and on-target scoring algorithms and integration into the guide RNA selection tool CRISPOR," Genome Biol, 2016, 17(1): 148.
Heyer et al., "Regulation of homologous recombination in eukaryotes," Annu Rev Genet, 2010, 44: 113-139.
Hirano et al., "Structural Basis for the Altered PAM Specificities of Engineered CRISPR-Cas9," Mol Cell, 2016, 61(6): 886-894.
Hogins et al., "Excitotoxicity triggered by Neurobasal culture medium," PLoS One, 2011, 6(9): e25633.
Hsu et al., "Development and applications of CRISPR-Cas9 for genome engineering," Cell, 2014, 157: 1262-1278.
Hsu et al., "DNA targeting specificity of RNA-guided Cas9 nucleases," Nat Biotechnol, 2013, 31: 827-832.
Hu et al., "Evolved Cas9 variants with broad PAM compatibility and high DNA specificity," Nature, 2018, 556(7699): 57-63.
Hug et al., "Mechanism and regulation of the nonsense-mediated decay pathway," Nucleic Acids Res, 2016, 44(4): 1483-1495.
Ipsaro et al., "Molecular epitopes of the ankyrin-spectrin interaction," Biochemistry, 2018, 47: 7452-7464.
Jinek et al., "A programmable dual-RNA-guided DNA endonuclease in adaptive bacterial immunity," Science, 2012, 337: 816-821.
Jones et al., "Axon Initial Segment Cytoskeleton: Architecture, Development, and Role in Neuron Polarity," Neural Plast, 2016, 6808293.
Kalderon et al., "A short amino acid sequence able to specify nuclear location," Cell, 1984, 39: 499-509.
Karvelis et al., "Harnessing the natural diversity and in vitro evolution of Cas9 to expand the genome editing toolbox," Curr Opin Microbiol, 2017, 37: 88-94.
Katoh et al., "Practical method for targeted disruption of cilia-related genes by using CRISPR/Cas9-mediated, homology-independent knock-in system, " Molecular Biology of the Cell, 2017, 28(7): 843-996.
Kennedy et al., "Ankyrin binds to the 15th repetitive unit of erythroid and nonerythroid beta-spectrin," J Cell Biol, 1991, 115: 267-277.
Kim et al., "Disruption of Arp2/3 results in asymmetric structural plasticity of dendritic spines and progressive synaptic and behavioral abnormalities," J Neurosci, 2013, 33: 6081-6092.
Kleinstiver et al., "High-fidelity CRISPR-Cas9 nucleases with No. detectable genome-wide off- target effects," Nature, 2016, 529: 490-495.
Kosugi et al., "Six classes of nuclear localization signals specific to different binding grooves of importin alpha," J Biol Chem, 2009, 284: 478-485.
Kyte et al., "A Simple Method for Displaying the Hydropathic Character of a Protein," J Mol Biol, 1982, 157: 105-132.
Lange et al., "Classical nuclear localization signals: definition, function, and interaction with importin alpha," J Biol Chem, 2007, 282: 5101-5105.
Le Cong et al., "Multiplex genome engineering using CRISPR/Cas systems," Science, 2013, 339: 819-823.
Lein et al., "Genome-wide atlas of gene expression in the adult mouse brain," Nature, 2007, 445: 168-176.
Levskaya et al., "Engineering Escherichia coli to see light," Nature, 2005, 438: 441-442.
Li et al., "Fast and accurate short read alignment with Burrows-Wheeler transform," Bioinformatics, 2009, 25: 1754-1760.
Li et al., "The Sequence Alignment/Map format and SAMtools," Bioinformatics, 2009, 25: 2078-2079.
Liu et al., "Sequence features associated with the cleavage efficiency of CRISPR/Cas9 system," Sci Rep, 2016, 6: 19675.
Livet et al., "Transgenic strategies for combinatorial expression of fluorescent proteins in the nervous system," Nature, 2007, 450: 56-62.
Mali et al., "RNA-guided human genome engineering via Cas9," Science, 2013, 339: 823-826.
Mao et al., "DNA repair by nonhomologous end joining and homologous recombination during cell cycle in human cells," Cell Cycle, 2008, 7: 2902-2906.
Markets and Markets, Genome Editing/Genome Engineering Market worth $11.2 billion by 2025, Market Research Report <http://www.marketsandmarkets.com/PressReleases/genome-editing-engineering.asp> (2020).
Martin, "Cutadapt removes adapter sequences from high-throughput sequencing reads," EMBnetjournal, 2011, 17: 10-12.
McKenna et al., "The Genome Analysis Toolkit: a MapReduce framework for analyzing next-generation DNA sequencing data," Genome Res, 2010, 20: 1297-1303.
Metzakopian et al., "Enhancing the genome editing toolbox: genome wide CRISPR arrayed libraries," Sci Rep, 2017, 7(1): 2244.
Michel et al., "How reliable are G-protein-coupled receptor antibodies?," Naunyn Schmiedebergs Arch Pharmacol, 2009, 379: 385-388.
Mikuni et al., "High-Throughput, High-Resolution Mapping of Protein Localization in Mammalian Brain by In Vivo Genome Editing," Cell, 2016, 165: 1803-1817.
Niopek et al., "Engineering light-inducible nuclear localization signals for precise spatiotemporal control of protein dynamics in living cells," Nat Commun, 2014, 5: 4404.
Nishimasu et al., "Engineered CRISPR-Cas9 nuclease with expanded targeting space," Science, 2018, 361: 1259-1262.
Nishiyama et al., "Virus-Mediated Genome Editing via Homology-Directed Repair in Mitotic and Postmitotic Cells in Mammalian Brain," Neuron, 2017, 96: 755-768 e755.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23: 635-646.
Platt et al., "CRISPR-Cas9 knockin mice for genome editing and cancer modeling," Cell, 2014, 159(2): 440-455.
Saleh-Gohari et al., "Conservative homologous recombination preferentially repairs DNA double-strand breaks in the S phase of the cell cycle in human cells," Nucleic Acids Res, 2004, 32: 3683-3688.
Schindelin et al., "Fiji: an open-source platform for biological-image analysis," Nat Methods, 2012, 9: 676-682.
Schmid-Burgk et al., "CRISPaint allows modular base-specific gene tagging using a ligase-4-dependent mechanism," Nat Commun, 2016, 7: 12338.
Schneider et al., "NIH Image to ImageJ: 25 years of image analysis," Nat Methods, 2012, 9: 671-675.
Shaner et al., "Improved monomeric red, orange and yellow fluorescent proteins derived from *Discosoma* sp. red fluorescent protein," Nat Biotechnol, 2004, 22: 1567-1572.
Slaymaker et al., "Rationally engineered Cas9 nucleases with improved specificity," Science, 2016, 351: 84-88.
Spence et al., "Actin Out: Regulation of the Synaptic Cytoskeleton," J Biol Chem, 2015, 290: 28613-28622.
Suzuki et al., "In vivo genome editing via CRISPR/Cas9 mediated homology-independent targeted integration," Nature, 2016, 540(7631): 144-149.
Tervo et al., "A Designer AAV Variant Permits Efficient Retrograde Access to Projection Neurons," Neuron, 2016, 92: 372-382.
Transparency Market Research, "Genome Engineering Market—Global Industry Analysis, Size, Share, Growth, Trends, and Forecast 2019-2027," Market Research Report, <http://www.transparencymarketresearch.com/genome-editing-engineering-market.html> (2020).
Truong et al., "Development of an intein-mediated split-Cas9 system for gene therapy," Nucleic Acids Res, 2015, 43(13): 6450-6458.
Uezu et al., "Identification of an elaborate complex mediating postsynaptic inhibition," Science, 2016, 353(6304): 1123-1129.

(56) References Cited

OTHER PUBLICATIONS

Viswanathan et al., "High-performance probes for light and electron microscopy," Nat Methods, 2015, 12: 568-576.
Yang et al., "βIV spectrin is recruited to axon initial segments and nodes of Ranvier by ankyrinG," J Cell Biol, 2007, 176: 509-519.
Zacharias et al., "Partitioning of lipid-modified monomeric GFPs into membrane microdomains of live cells," Science, 2002, 296: 913-916.
International Search Report and Written Opinion for Application No. PCT/US2019/018353 dated May 15, 2019 (14 pages).
Japanese Patent Office Action for Application No. 2020-543480 dated Feb. 22, 2023 (8 pages).
Lackner et al., "A generic strategy for CRISPR-Cas9-mediated gene tagging," Nature Communications, 2015, 6: 10237.
Chen et al., "Silencing of episomal transgene expression by plasmid bacterial DNA elements in vivo," Gene Ther., 2004, 11: 856-864.
European Patent Office Action for Application No. 19753997.6 dated Jan. 29, 2024 (5 pages).

\* cited by examiner

↑ Stop + Kozac + ATG

▰ Inserted tag (payload)

✂ Cas9

☒ Stop codon cassette

```
       ORF1 ORF2 ORF3
       ↓    ↓    ↓
5' ... tagctagctagctag ... 3'    SEQ ID NO: 29
3' ... atcgatcgatcgatc ... 5'    SEQ ID NO: 30
       ↑    ↑    ↑
       ORF3 ORF2 ORF1
```

⌐ ¬
⌊_⌋  DRS arm that is bound by the rules

⌐ ¬
⌊_⌋  DRS arm that is exempted from the rules

* For C-term bi-directional payloads (e.g., Toolkits 1 and 4), DRS arms on both sides of the insert must met the corresponding rules according to the specific DRS usage scenario.

FIG. 3B

| Examples | Mismatches[†] against MM10 | Specificity Score[†] against MM10 | Scenario 1 | | | Scenario 2 | | | Scenario 3 | | | Scenario 4 | | |
|---|---|---|---|---|---|---|---|---|---|---|---|---|---|---|
| Donor Recognition Sequence (DRS) | | | ORF+0 | ORF+1 | ORF+2 | ORF+0 | ORF+1 | ORF+2 | ORF+0 | ORF+1 | ORF+2 | ORF+0 | ORF+1 | ORF+2 |
| GTCATAGTATCGCGGAGTTCAGG | 0-0-0-0-27 | 95 | ✓ | · | ✓ | ✓ | ✓ | ✓ | ✓ | · | ✓ | ✓ | · | ✓ |
| CACGCTTCCGASTACGGTACAGG | 0-0-0-0-7 | 98 | ✓ | ✓ | ✓ | ✓ | ✓ | ✓ | ✓ | ✓ | · | ✓ | ✓ | · |
| GGTTCTACGAGGATACGTCTTGG | 0-0-0-1-15 | 98 | ✓ | ✓ | ✓ | ✓ | ✓ | ✓ | ✓ | ✓ | ✓ | ✓ | ✓ | ✓ |
| GCGTATGCGAAGCATAGCCGGGG | 0-0-0-2-22 | 96 | · | ✓ | · | ✓ | ✓ | ✓ | ✓ | ✓ | ✓ | ✓ | ✓ | ✓ |
| GCGATTGACCGTGCTGTCGCGG | 0-0-0-0-8 | 98 | · | ✓ | · | ✓ | ✓ | ✓ | ✓ | ✓ | ✓ | ✓ | ✓ | ✓ |

†: off-target mismatches and specificity scores predicted by Crispor, searching against MM10 genomic assembly (http://crispor.tefor.net)

FIG. 3C

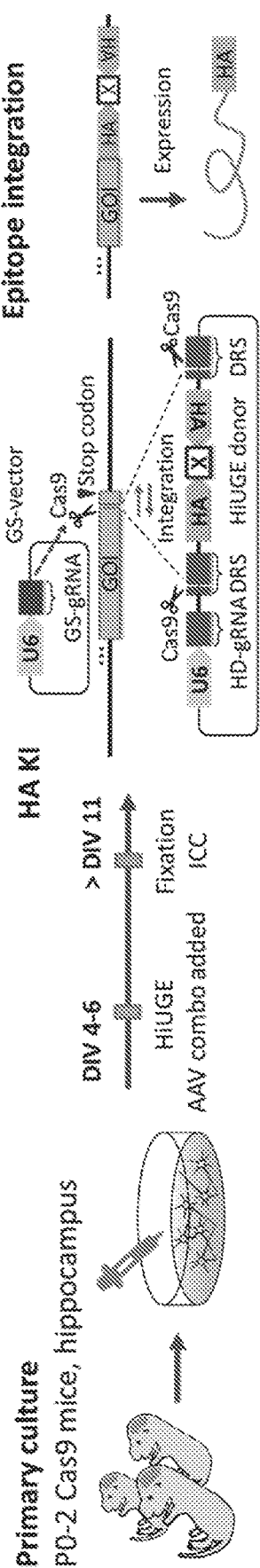
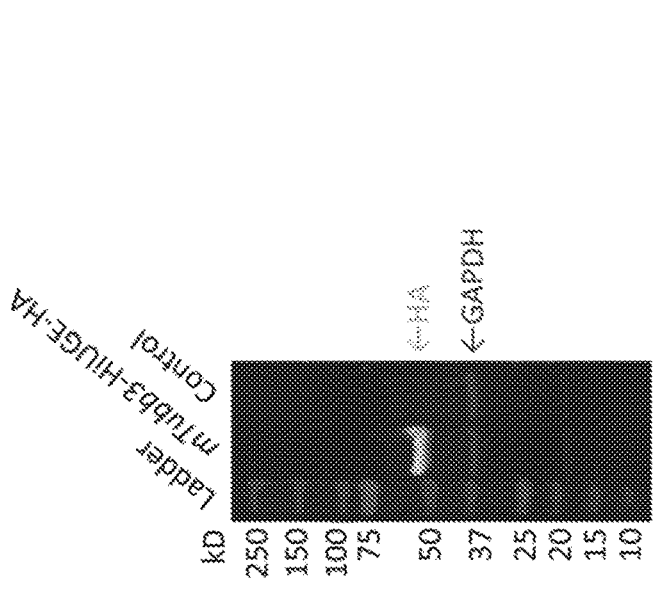
FIG. 4A
FIG. 4C
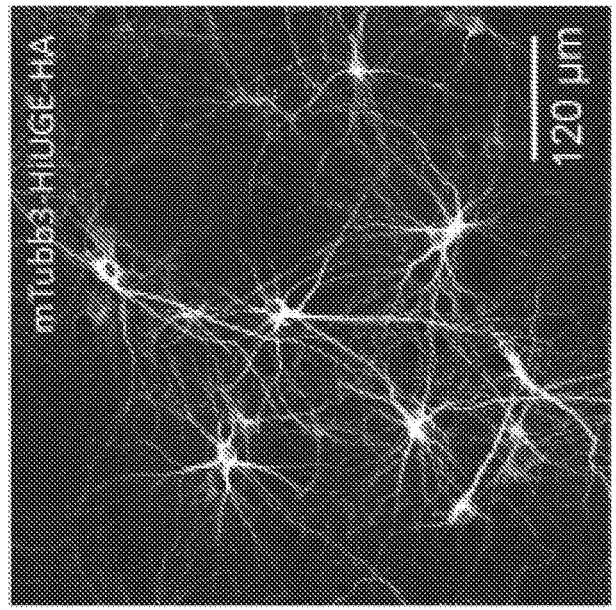
FIG. 4B

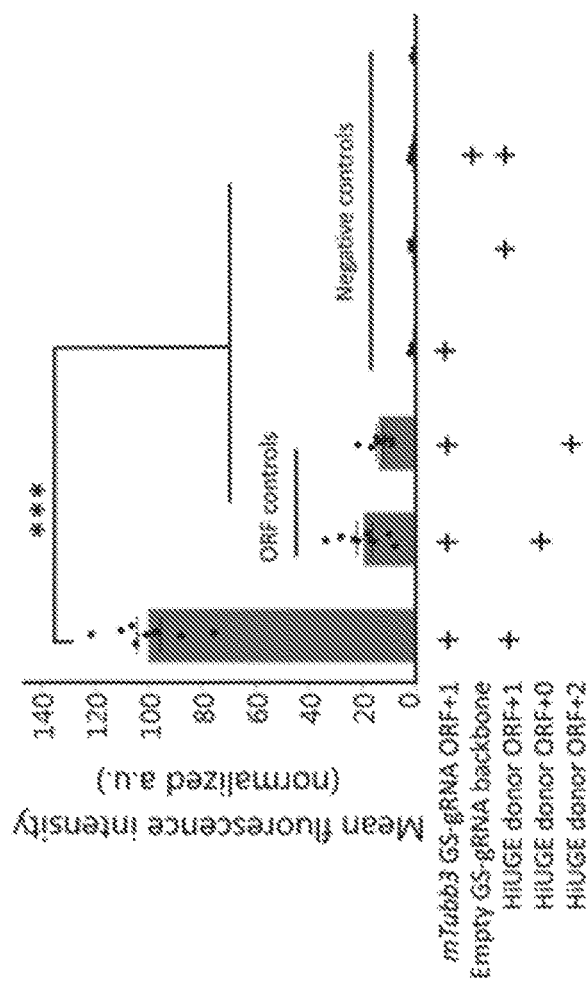

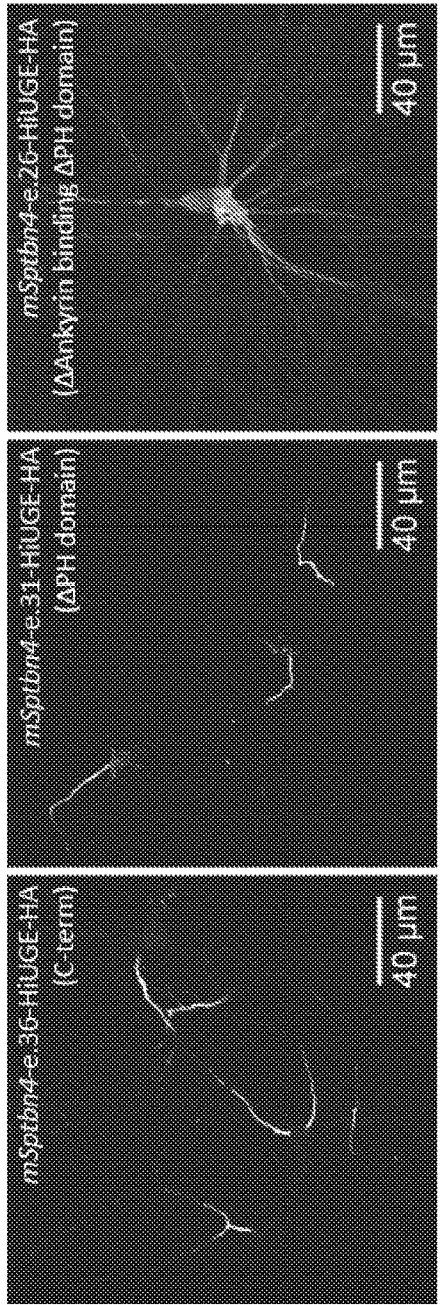
FIG. 9C
FIG. 9D
FIG. 9E
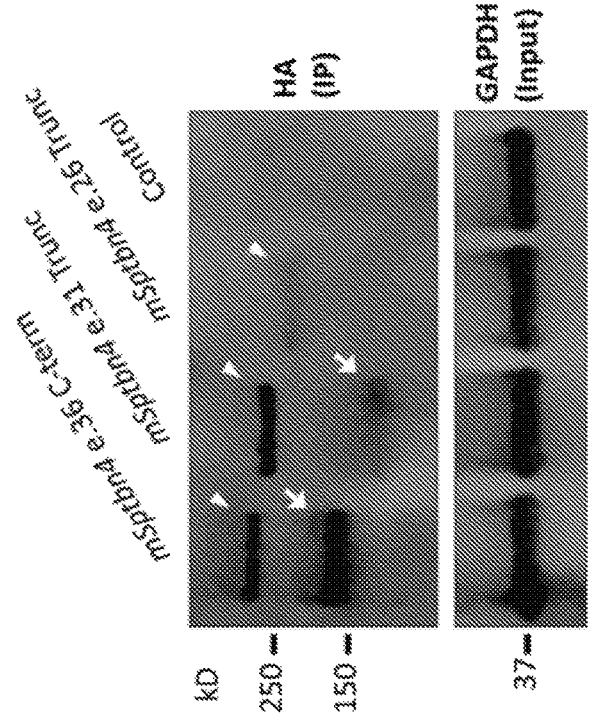
FIG. 9F

Top ranked predicted off-target (PreOff) sites

| ID | gRNA | Off-target locus | Off-target pattern | Type |
|---|---|---|---|---|
| PreOFF_1 | HD-gRNA | chr7:100530941-100530963 | GACACTTCAGAATACGCTAC | intergenic |
| PreOFF_2 | HD-gRNA | chr5:28532374-28532396 | CATTCTTCCCAGTACGGTAC | intergenic |
| PreOFF_3 | HD-gRNA | chr17:69170700-69170722 | GAAGCTTCTGAGGACGTTAC | intron |
| PreOFF_4 | mScn2a | chr3:87516175-87516197 | TGAAAAAGGGAGAGATATCA | intergenic |
| PreOFF_5 | mScn2a | chr16:69713426-69713448 | GGAAAAAGGGAAAAATATCA | intergenic |
| PreOFF_6 | mScn2a | chr17:72335621-72335643 | AGACAAGGGAAAAGAAATCG | intron |
| PreOFF_7 | mScn2a | chr12:30436113-30436135 | TGATAAGGGAAAAAATATCA | intergenic |
| PreOFF_8 | mScn2a | chr1:160895203-160895225 | GGAAAAAGGGAAAAAAATCA | intergenic |

FIG. 19A

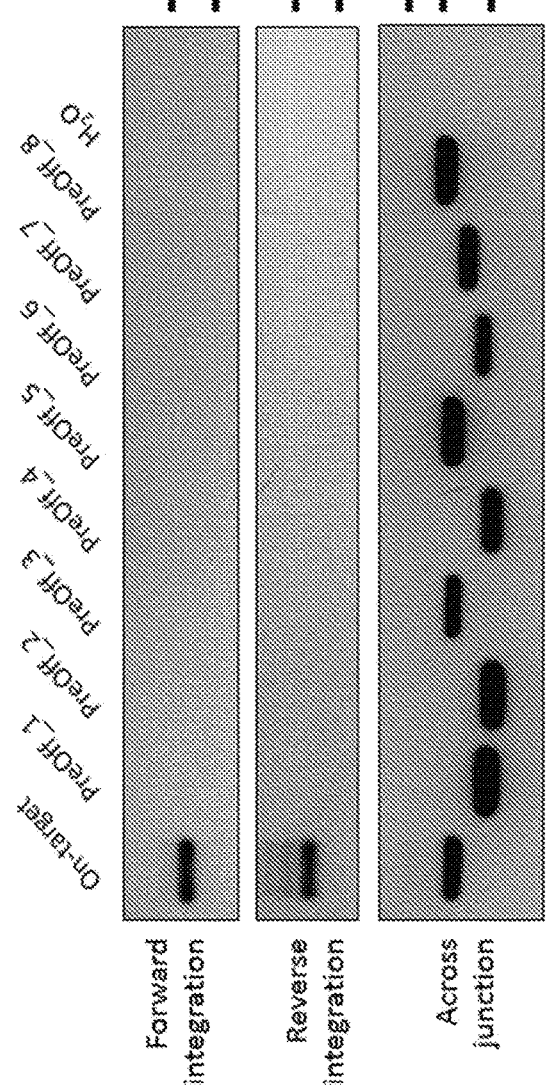

FIG. 19B

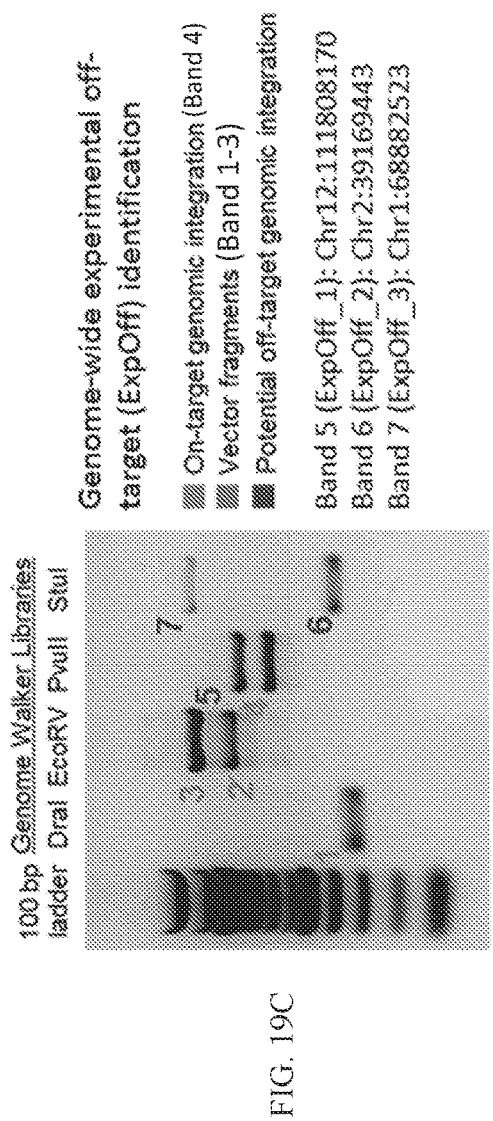
FIG. 19C
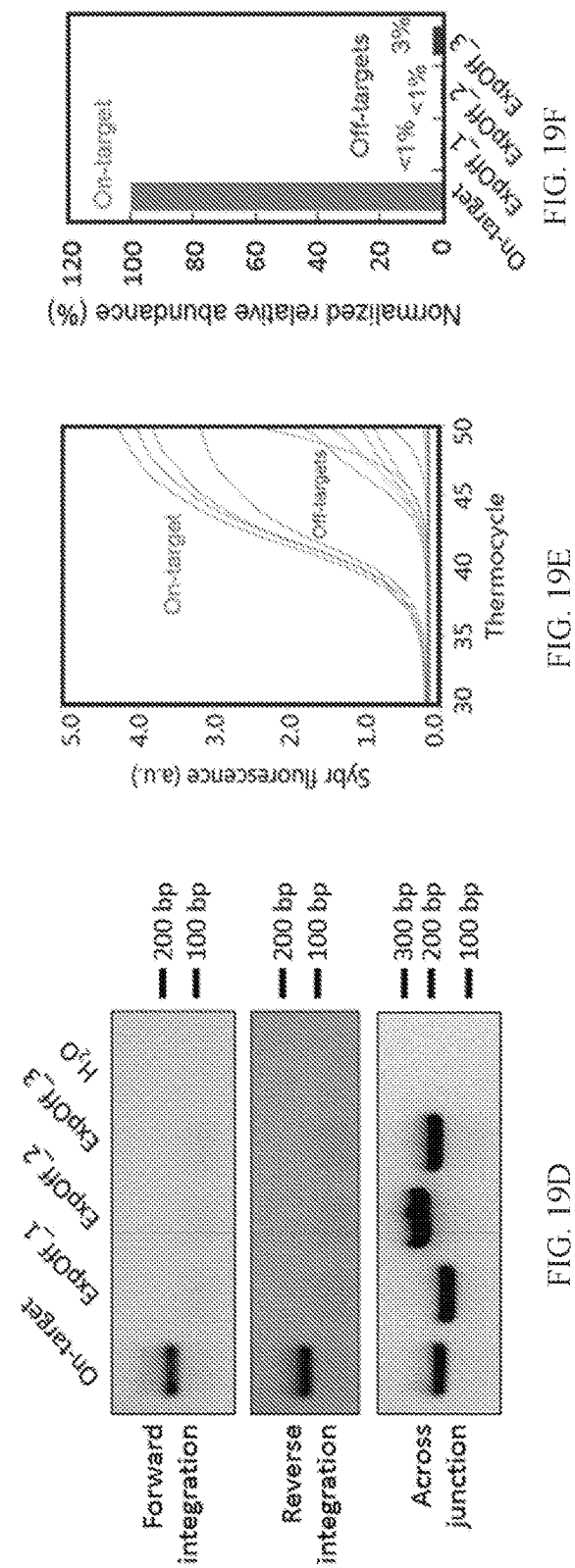
FIG. 19D
FIG. 19E
FIG. 19F

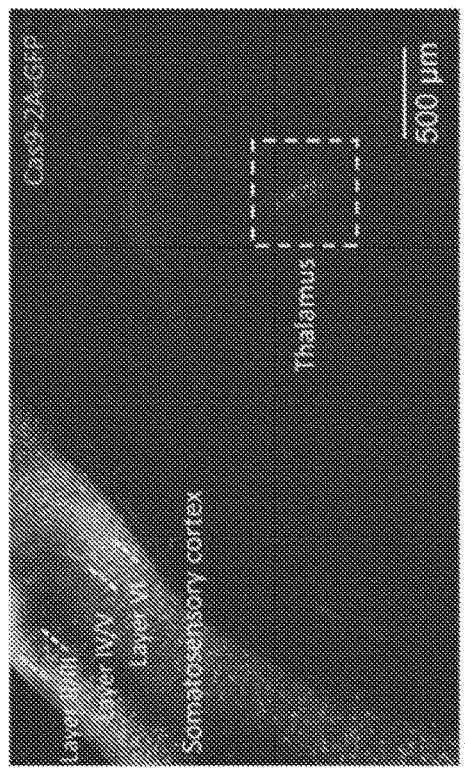
FIG. 20H
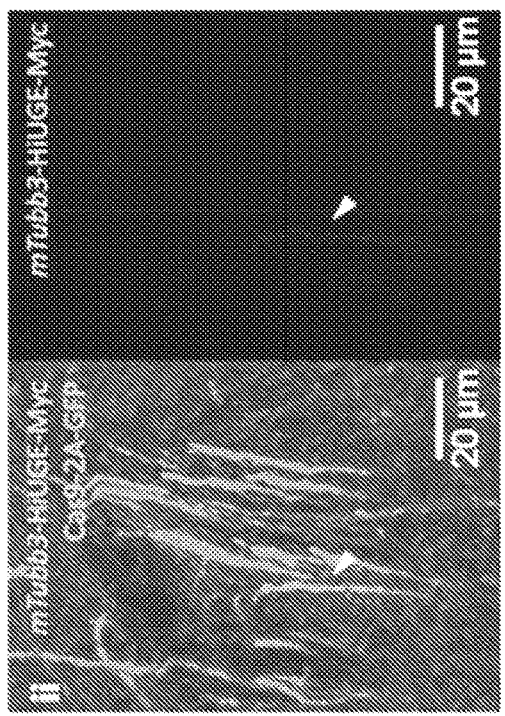
FIG. 20I
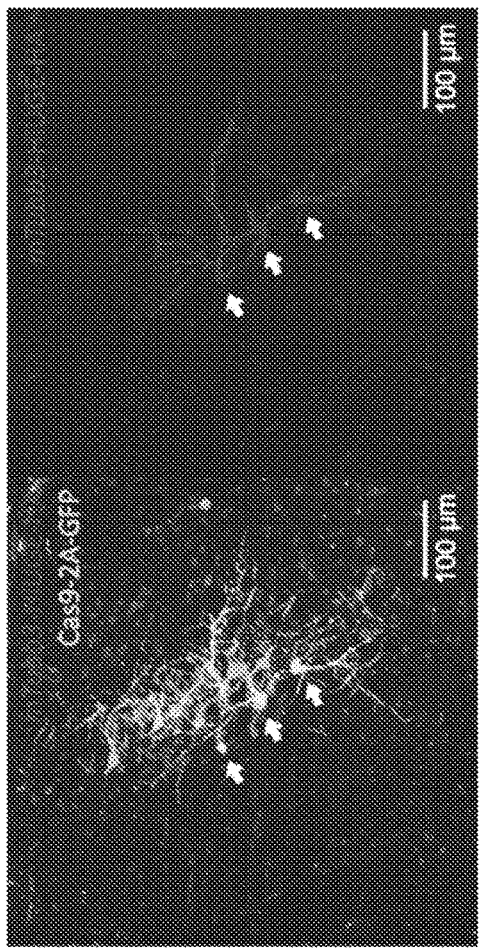
FIG. 20J
FIG. 20K
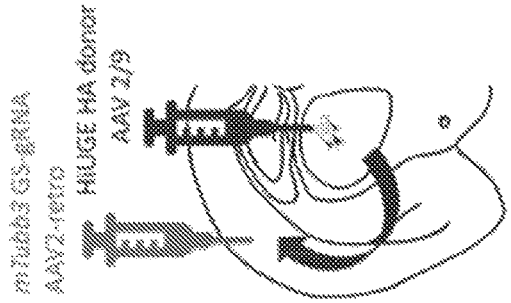

GENE EDITING USING HOMOLOGY-INDEPENDENT UNIVERSAL GENOME ENGINEERING TECHNOLOGY

CROSS-REFERENCE TO RELATED APPLICATIONS

This application is the U.S. national stage entry, under 35 U.S.C. § 371, of International Application Number PCT/US2019/018353, filed Feb. 15, 2019, which claims the benefit of U.S. Provisional Application No. 62/631,360, filed Feb. 15, 2018, the entire contents of each of which are hereby incorporated by reference.

STATEMENT OF GOVERNMENT INTEREST

This invention was made with government support under federal grant numbers R01MH103374 and R01NS102456 awarded by NIH. The U.S. Government has certain rights to this invention.

SEQUENCE LISTING

The sequence listing is filed with the application in electronic format only and is incorporated by reference herein. The sequence listing text file "028193-9276-WO01_As_Filed_Sequence_Listing.txt" was created on Feb. 15, 2019, and is 509,751 bytes in size.

TECHNICAL FIELD

The present disclosure relates to the field of gene editing using Homology-Independent Universal Genome Engineering (HiUGE) Technology and viral delivery systems. The present disclosure also relates to the field of high throughput screening though protein labeling, expression marking, and disruption of protein expression in both in vitro cell culture systems and in model laboratory organisms in vivo.

BACKGROUND

Manipulating and selective labeling of endogenous proteins is essential to delineating the molecular mechanisms of cell and organismal biology. Techniques to enable these strategies are a fundamental cornerstone of biomedical research, however they are often inefficient, labor intensive, or imprecise. For example, protein depletion strategies using RNAi are susceptible to off-target effects in a concentration-dependent manner and gene knockout approaches require considerable investments in time and resources. Common antibody methods to label endogenous proteins are also problematic. It is estimated that a large fraction of available antibodies have limited utility due to unsuspected cross-reactivity to other proteins, lot-to-lot variability of quality, and improper validation of antibodies across the array of applications they are used for. Questionable antibodies are likely the key reagent driving disparate and irreproducible findings across laboratories, leading to a call for a solution to the large number of suspect antibodies currently flooding the market. Additionally, overexpression of recombinant protein to visualize protein localization and dynamics or to create dominant negative phenotypes is highly sensitive to the concentration of the expressed protein, available cellular docking sites, and unforeseen artifactual cellular effects.

Clustered regularly interspaced short palindromic repeats (CRISPR)-associated endonuclease Cas9-based strategies have great promise to enable highly precise genome editing to address many of the above limitations. CRISPR-Cas9 introduces double strand breaks (DSBs) at guide RNA (gRNA) specified genomic sites. The requirement for gRNA directed targeting of Cas9-mediated double stranded breaks is based on a "protospacer adjacent motif" (PAM) sequence at the end of a 20-21 bp nucleotide gene specific sequence. The PAM sequence for Cas9 derived from *Streptococcus pyogenes* (the most common variant in use) is 5'-NGG-3', where N represents any nucleotide. It is estimated this sequence is found on average about every 10 nucleotides (+ and − strand combined), opening up the potential to target essentially every gene. Double strand genomic breaks are repaired via two pathways in cells. Non-homology end joining (NHEJ) is the preferred pathway, which can introduce insertions or deletions (Indels) that introduce non-sense mutations during the repair process. Alternatively, DSBs can be repaired by the less frequent pathway of homology-directed repair (HDR).

Both pathways (NHEJ and HDR) are currently utilized to manipulate endogenous proteins in cells or tissue via donor vectors to insert foreign sequences (payloads) into genes of interest (GOIs). Single cell labeling of endogenous proteins (SLENDR and viral (v)SLENDR) is based on HDR, using oligo or Adeno-Associated Virus (AAV) donors containing homologous gene-specific sequences of hundreds of base-pairs flanking the DSB cut site to deliver sequences into a GOI (Mikuni et al., Cell 165:1803-1817 (2016); Nishiyama et al., Neuron 96:755-768 e755 (2017)). Alternatively, CRISPaint pairs NHEJ with a generalized donor vector that is linearized and integrated into the gene of interest (Schmid-Burgk et al., Nat Commun 7:12338 (2016)). However, it requires specially prepared mini-circular vectors that are not compatible with viral delivery methods important for many in vivo applications, or the bacterial vector backbones are necessarily co-inserted into genomes, which can interfere long-term transgene expression (Chen et al., Mol Ther 8:495-500 (2003); Chen et al., Mol Ther 3:403-410 (2001)). These issues limit its potential applicability, especially for in vivo applications.

Homology-Independent Transgene Insertion (HITI) also leverages NHEJ to insert foreign sequences into a GOI without carrying over vector elements (Suzuki et al., Nature 540: 144-149 (2016)). HITI utilizes a donor vector containing the 23 bp gene-specific guide RNA recognition sequences flanking the payload to simultaneously direct DSB cuts to the gene and vector, facilitating payload insertion during NHEJ. Although SLENDR and HITI are flexible in their ability to modify proteins at both termini, an important limitation is the necessity for boutique vectors specific to the GOI and payload. This shared requirement limits the scalability and throughput, by requiring the generation of custom donor vectors for each DSB cut site in each GOI. For example, to target each protein within the human genome with an antibody epitope tag would require approximately 19,000-20,000 gene specific SLENDR or HITI donor vectors. Testing different linker amino acid sequences, different antibody epitopes, or fluorescent protein fusions, which are common steps for optimal labeling and detection of proteins, additively scales to the obstacles for the wider adoption of these strategies. Likewise, because each donor vector is GOI sequence-specific, they are necessarily species specific, further limiting the generality of current approaches. In addition, the current ability to target proteins for cellular localization, expression analysis, and purification of interacting partners relies on protein specific antibody technologies. These technologies can often be fairly non-specific depending on the relative selectivity of the available antibodies. Thus, there still remains a need for a precise and efficient gene editing tool for high-throughput genome wide editing, screening, and protein labeling.

SUMMARY

The present disclosure is directed to a Homology-Independent Universal Genome Engineering (HiUGE) system for gene editing a subject genome, the HiUGE system comprising: (a) (i) a CRISPR-based nuclease or (ii) a nucleic acid sequence that encodes a CRISPR-based nuclease; (b) a Homology-Independent Universal Genome Engineering (HiUGE) vector comprising: (i) a first polynucleotide sequence encoding at least one insert; (ii) at least one donor recognition sequence (DRS) flanking each side of the first polynucleotide sequence, the DRS comprising a cleavage site for the CRISPR-based nuclease; and (iii) a second polynucleotide sequence encoding a HiUGE vector specific gRNA, wherein the HiUGE vector specific gRNA targets the CRISPR-based nuclease to the DRS and does not target a specific sequence within the subject genome; and (c) (i) a target gene specific gRNA that targets the CRISPR-based nuclease to a target gene specific sequence within the subject genome or (ii) a target gene vector comprising a third polynucleotide sequence that encodes a target gene specific gRNA which targets the CRISPR-based nuclease to a target gene specific sequence within the subject genome.

The present disclosure is directed to a Homology-Independent Universal Genome Engineering (HiUGE) system for gene editing a subject genome, the HiUGE system comprising: (a) a Homology-Independent Universal Genome Engineering (HiUGE) vector comprising: (i) a first polynucleotide sequence encoding at least one insert; (ii) at least one donor recognition sequence (DRS) flanking each side of the first polynucleotide sequence, the DRS comprising a cleavage site for the CRISPR-based nuclease; (iii) a second polynucleotide sequence encoding a HiUGE vector specific gRNA, wherein the HiUGE vector specific gRNA targets the CRISPR-based nuclease to the DRS and does not target a specific sequence within the subject genome; (iv) a third polynucleotide sequence encoding a first portion of a CRISPR-based nuclease having a first split-intein; and (b) a gene specific vector comprising: (i) a fourth polynucleotide sequence encoding a second portion of a CRISPR-based nuclease having a second split-intein complementary to the first split-intein, wherein the first portion of the CRISPR-based nuclease and the second portion of the CRISPR-based nuclease can join together to form a CRISPR-based nuclease; and (ii) a fifth polynucleotide sequence that encodes a target gene specific gRNA which targets the CRISPR-based nuclease to a target gene specific sequence within the subject genome.

The present disclosure is directed to a method of Homology-Independent Universal Genome Engineering (HiUGE) of a target gene in a subject genome, the method comprising contacting a cell with the HiUGE system described above.

The present disclosure is directed to a kit comprising the HiUGE system described above.

BRIEF DESCRIPTION OF THE DRAWINGS

FIG. 3B shows the legend for FIG. 3A. FIG. 3C shows a list of 5 exemplary DRS sequences (SEQ ID NOS: 22-26, starting from the top to the bottom). FIGS. 3D and 3E show HA antibody immunostaining, while FIGS. 3F and 3G show DAPI (3',6-diamidino-2-phenylindole) staining to visualize nuclei in each corresponding image in FIGS. 3D and 3E, respectively, demonstrating similar cell densities in each panel. Scale bar is indicated in each panel.

FIG. 4A shows a schematic illustration of HiUGE application for bidirectional HA epitope knock-in (KI) in vitro. FIG. 4B shows a representative image of immunostaining showing HA epitope KI into the mouse Tubb3 (mTubb3) gene, which encodes β-tubulin, showing microtubule labeling. FIG. 4C shows a Western blot for HA-epitope of HiUGE edited sample in a comparison against a negative control (transduced with empty GS-gRNA backbone and HiUGE donor AAVs), showing a single band of HA-epitope labeled protein at the expected molecular mass (~51 kD) for βIII-tubulin.

FIGS. 4G-4I show additional qualitative and quantitative data experiments. FIG. 4G shows the normalized mean fluorescence intensity (arbitrary units, a.u.) across experimental groups. Error bars represent standard error of the mean (SEM). Correct ORF pairing of mTubb3 GS-gRNA and HiUGE donor showed significantly higher HA-epitope fluorescence intensity over ORF-mismatched controls and negative controls (p<0.001, one-way ANOVA followed by Tukey-Kramer HSD post hoc test). FIG. 4H demonstrates the flexibility of GS-gRNA selection and the capability of HiUGE donor vectors of all three open reading frames (ORFs) to facilitate protein modification. Three different GS-gRNAs, one for each ORF (ORF+0, ORF+1, ORF+2), were designed to target mouse Map2 (mMap2) gene. Shaded DNA triplets denote the protospacer adjacent motif (PAM)

of the target sequence for each GS-gRNA. Underlined DNA triplets denote the last codon before the Cas9 cleavage site for each GS-gRNA. FIG. 4I shows representative images showing comparable detection of HA-epitope KI when GS-gRNAs of each ORF were paired with HiUGE donors of the corresponding ORF. Scale bars are indicated in each panel.

FIGS. 5B-5M show HA epitope KI of mouse Tubb3 gene (FIG. 5B), mouse Map2 gene (FIG. 5C), mouse Mecp2 gene (FIG. 5D; inset is higher magnification view of boxed region), mouse Nrcam gene (FIG. 5E), mouse Actr2 gene (FIG. 5F; inset is higher magnification view of boxed region), mouse Clta gene (FIG. 5G; inset is higher magnification view of boxed region), mouse Ank3 gene (FIG. 5H), mouse Sptbn4gene (FIG. 5I), and mouse Scn2a gene (FIG. 5J), mouse GFAP gene (FIG. 5K), mouse Pdha1 gene (FIG. 5L; inset is higher magnification view of boxed region), and mouse Dcx gene (FIG. 5M; inset is higher magnification view of boxed region). Scale bar is indicated in each panel. Scale bar within the insets represents 2 μm. Arrowheads represent the subcellular features associated with the gene of interest, such as the dendritic spines, mitochondria, or the distal end of neurites.

FIGS. 9C-9D show representative images of immunostaining demonstrating truncation of PH domain from βIV-spectrin using a GS-gRNA targeting exon 31 (e.31) of mouse Sptbn4 gene (FIG. 9D) compared to carboxy-terminus KI using a GS-gRNA targeting exon 36 (e.36) (FIG. 9C). FIG. 9E shows disruption of spectrin repeat 14 and truncation of downstream sequences by targeting exon 26 (e.26), which completely disrupts the AIS localization. FIG. 9F shows a Western blot showing step-wise truncation of the βIV-spectrin protein.

FIGS. 13F, 13H, and 13J show representative images of HA-epitope KI to the human TUBB or mouse Tubb5 gene, showing the distinctive microtubule localization of the tagged proteins in (FIG. 13F) HeLa cell, (FIG. 13H) HEK293T cell and (FIG. 13J) NIH3T3 cell. FIGS. 13G, 13I, and 13K show representative images of GFP KI to the human TUBB or mouse Tubb5 gene, showing the distinctive microtubule localization of the tagged proteins in (FIG. 13G) HeLa cell, (FIG. 13) HEK293T cell and (FIG. 13K) NIH3T3 cell.

FIG. 15A shows a schematic illustration of HiUGE KI application for C- or N-term protein labeling in vitro. FIGS. 15B-15D show C-term smFP-HA KI to mouse (FIG. 15B) Insyn1, (FIG. 15C) Insyn2, and (FIG. 15D) Arhgap32 genes, which encode the inhibitory postsynaptic density (iPSD) proteins Inhibitory Synaptic protein 1, 2, and Rho GTPase activating protein 32. Colocalization of the HA-immunoreactivity with the juxtaposed inhibitory presynaptic marker vesicular GABA transporter (VGAT) immunosignal is shown in the insets. FIGS. 15E-15G show N-term Myc-epitope KI to (FIG. 15E) Actb (β-Actin), (FIG. 15F) Lmnb1 (Lamin B1), and (FIG. 15G) Nefm (Neurofilament Medium), showing their characteristic expression patterns at dendritic spines, nuclear envelopes, and neurofilaments. Scale bar is indicated in each panel, or within insets (2 µm). GFP fluorescence of the Cas9-2A-GFP and nuclei labeling with DAPI are also shown. Arrowheads represent the subcellular features associated with the targeted genes, such as the dendritic spines, AIS, mitochondria, distal end of neurites, inhibitory synapses, and neurofilaments.

FIG. 16A shows a schematic design of genomic PCR to detect dual-orientation HA-epitope payload integration into various genomic loci. FIG. 16B shows an insert-specific PCRs for both forward and reverse payload integration showed positive bands (~150-200 bp) in edited samples, compared to no band in negative controls (no edit). FIGS. 16C-16D show an analysis of indel frequencies by deep sequencing the PCR products of either forward or reverse payload integrations.

FIG. 17A shows a schematic illustration of HiUGE C-term smFP-HA KI to mouse Insyn1, directed by three different GS-gRNAs. Shaded DNA triplets denote the protospacer adjacent motif (PAM) of the target sequence for each GS-gRNA. Arrowheads denote the Cas9 cleavage sites. FIGS. 17B-17D show successful and comparable punctate labeling at inhibitory synapses was observed across all three GS-gRNAs. Colocalization of the HA-immunoreactivity with the juxtaposed inhibitory presynaptic marker vesicular GABA transporter (VGAT) immunosignal is shown in the insets (arrowheads). Scale bar is indicated in each panel, or within insets (2 µm).

FIG. 18A shows representative images of HiUGE labeling of AIS proteins βIV-Spectrin and NaV1.2 by C-term HA-epitope KI to mouse Sptbn4 and Scn2a, under high AAV concentrations ($2.5 \times 10^{11}$ GC/mL per virus) in primary neurons. FIG. 18B shows quantification results showing the estimated efficiencies of cellular labeling across several AAV concentrations under 1:1 virus ratio (GS-gRNA:donor). FIG. 18C shows quantification results showing the estimated efficiencies of cellular labeling across several ratios of AAVs (GS-gRNA:donor) under $1 \times 10^{11}$ GC/mL combined viral concentration.

FIGS. 19A-19F show an assessment of off-target effects of HiUGE. FIG. 19A shows top ranked CRISPOR-predicted off-target loci for both HD-gRNA and mScn2a GS-gRNA (SEQ ID NOS: 155-162, starting from the top to the bottom, shows the off-target pattern). FIG. 19B shows genomic PCR reactions using gene-specific primers paired with payload-specific primers successfully detected on-target integrations, while the off-target genomic integrations of the payload were undetected for the predicted sites (PreOff_1-8). FIG. 19C shows genome Walker experiment detected on-target integration (band 4), and 3 potential off-target integrations into the non-coding genomic regions (band 5-7). FIG. 19D shows genomic PCR reactions using gene-specific primers paired with payload-specific primers successfully detected on-target integrations, while the genomic integrations of the payload were undetected for the experimentally identified potential off-target sites (ExpOff_1-3). FIG. 19E shows real-time PCR amplification curve of the reactions for on-target integrations (green) versus off-target integrations (red). FIG. 19F shows semi-quantitative estimations of the relative abundances showed that the off-target integrations were rare compared to on-target integrations.

FIGS. 20A-20K show neural circuit-based HiUGE labeling. FIG. 20A shows an illustration of cortico-striatal circuit-selective C-term HiUGE labeling of βIII-tubulin by injection of AAV2-retro mTubb3 GS-gRNA into the striatum and 2 lateral injections of AAV2/9 HA and Myc-epitope donors in the motor cortex. FIG. 20B shows a representative image showing GFP labeling in the motor cortex, indicating retrogradely accessed Cre-dependent Cas9-2A-GFP expression in cortical projection neurons. FIG. 20C shows an immunolabeling of HA (arrows) and Myc-epitope (arrowheads) tagged βIII-tubulin, imaged from the boxed area in (FIG. 20B). FIG. 20D shows an enlarged images from the boxed areas in (FIG. 20C), showing cells positive for (i) HA or (ii) Myc-epitope. FIG. 20E shows a GFP signal from the AAV2-retro injected striatum. FIG. 20F shows a zoomed image of the boxed area in (FIG. 20E), showing GFP-positive axon bundles that contain fibers positive for HA or Myc-epitope. FIGS. 20G-20H show enlarged images showing fibers positive for (i) HA or (ii) Myc-epitope within GFP-positive axon bundles from boxed areas in (FIG. 20F). FIG. 20I shows an illustration of thalamo-cortical circuit-selective C-term HiUGE labeling of βIII-tubulin by injection of AAV2-retro mTubb3 GS-gRNA in the somatosensory cortex and injection of AAV2/9 HA-epitope donor in the thalamus. FIG. 20J shows a representative image showing retrogradely activated Cas9-2A-GFP expression within the thalamus (boxed area) and local cortical networks (mostly cells within layer II/III and layer VI). FIG. 20K shows a zoomed image of the boxed area in (FIG. 20J), showing retrogradely accessed and HiUGE edited thalamic neurons positive for HA-epitope (arrows) and Cas9-2A-GFP. Scale bar is indicated in each panel.

FIG. 21A shows a schematic of the "Kaleidoscope" payload that contain interspersed epitope tags spaced by rigid linkers (RL) and a flexible linker (FL). FIG. 21B graphs the quantification of immunofluorescence signals from cells using Kaleidoscope compared to single HA epitope tag or spaghetti monster-HA (smFP-HA) for HiUGE labeling of mTubb3. FIG. 21C shows a representative image of Kaleidoscope used to label and detect low abundant proteins, such as inhibitory synaptic protein 1 (InSyn1).

DETAILED DESCRIPTION

Figure 1:
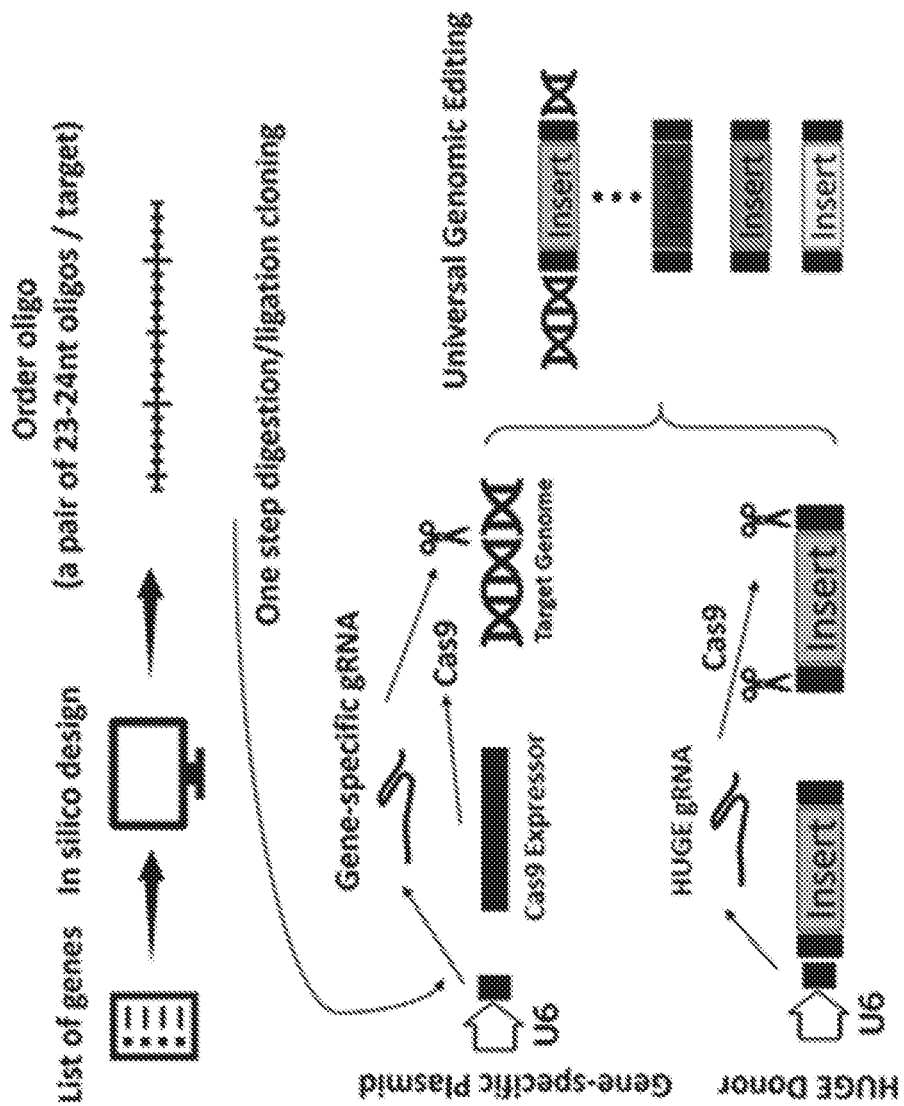
FIG. 1 shows a schematic of the HiUGE system where gene specific gRNAs are expressed from a gene-specific vector or plasmid and are paired with a HiUGE vector expressing HiUGE vector specific gRNAs.

Described herein are Homology-Independent Universal Gene Editing (HiUGE) systems and methods of using said HiUGE systems that are useful for high-throughput genome wide editing, screening, protein labeling, expression marking, or disruption of protein expression. The HiUGE system is a CRISPR-based system that includes universal payload containing donor vectors (HiUGE vectors). The disclosed HiUGE vectors can be used to edit any gene within a genome without the need to create individual gene-specific payload donor vectors that require extensive molecular biology expertise. The HiUGE vector functions within a CRISPR-based gene editing system and includes a CRISPR-based nuclease and a target gene specific gRNA. In the disclosed gene editing system, CRISPR-based nucleases will complex with the gene specific gRNA to cleave the genomic DNA and with the HiUGE vector specific gRNA to cleave the HiUGE vector on either side of the insert (payload) polynucleotide sequence. The insert payload can then be selectively integrated into the target gene by NHEJ as shown in FIG. 1.

The disclosed HiUGE systems and methods obviate many of the constraints to the current state-of-art. One unique capability of a CRISPR-based gene editing system is the straightforward ability to simultaneously cut multiple distinct targets by utilizing single CRISPR-based nuclease with two or more gRNAs. Using HiUGE, a single donor vector can deliver a payload without simultaneously inserting the donor vector across diverse GOIs and species, greatly simplifying strategies to manipulate and label endogenous proteins. As demonstrated herein, HiUGE libraries of different universal payloads can also be generated and used in cells and tissues for a variety of applications in evolutionarily diverse species. These applications include antibody epitope and fluorescent protein labeling, in situ proximity-dependent biotinylation, protein truncation for depletion and structure-function studies, and subcellular trapping of endogenous protein. Because this method is highly modular and scalable, it opens new avenues to pair high-throughput proteomic and genome applications with experimental validation and phenotypic screening to address molecular mechanisms of cell and organismal biology.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%1, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"Adeno-associated virus" or "AAV" as used interchangeably herein refers to a small virus belonging to the genus Dependovirus of the Parvoviridae family that infects a wide range of vertebrate species, including humans and other primate species, sheep, pigs, and chicken. AAV is not currently known to cause disease and consequently the virus causes a very mild immune response.

"Binding region" as used herein refers to the region within a nuclease target region that is recognized and bound by the nuclease.

"Cleave" or "cleavage" as used herein means the act of breaking the covalent sugar-phosphate bond between two adjacent nucleotides within a polynucleotide. In the case of a double-stranded polynucleotide, a covalent sugar-phosphate bond on both strands will be broken, unless otherwise specified.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimized.

"Complement" or "complementary" as used herein means a nucleic acid can Watson-Crick (e.g., A-T/U and C-G) or Hoogsteen base pair between nucleotides or nucleotide analogs of nucleic acid molecules. "Complementarity" refers to a property shared between two nucleic acid sequences, such that when they are aligned antiparallel to each other, the nucleotide bases at each position will be complementary.

"Donor vector", "donor template" and "donor DNA" as used interchangeably herein refers to a double-stranded DNA fragment or molecule that includes the insert being introduced into the genomic DNA. The donor vector may encode a fully-functional protein, a partially-functional protein or a short polypeptide. The donor vector may also encode an RNA molecule.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein or an RNA molecule. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the CRISPR/Cas9-based gene editing system, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to introduce a label onto a protein.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mismatch" as used herein means a nucleotide can not form a Watson-Crick (e.g., A-T/U and C-G) or Hoogsteen base pair with another nucleotide on the opposite strand of a double-stranded polynucleotide or with another nucleotide from a different polynucleotide.

"Non-homologous end joining (NHEJ) pathway" as used herein refers to a pathway that repairs double-strand breaks in DNA by directly ligating the break ends without the need for a homologous template. The template-independent religation of DNA ends by NHEJ is a stochastic, error-prone repair process that can introduce random micro-insertions and micro-deletions (indels) at the DNA breakpoint. This method may be used to intentionally disrupt, delete, or alter the reading frame of targeted gene sequences. NHEJ typically uses short homologous DNA sequences called microhomologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Promoter" as used herein means a synthetic or naturally-derived nucleic acid sequence which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

"Reading frame", "Open Reading Frame" or "Coding Frame" as used herein interchangeably means a grouping of three successive bases in a sequence of DNA that potentially constitutes the codons for specific amino acids during translation into a polypeptide.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human.

"Target gene" as used herein refers to any nucleotide sequence encoding a known or putative gene product.

"Target gene specific sequence" as used herein refers to the region of the target gene to which the HiUGE system is designed to bind and cleave.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of 2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within 2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode an insert and/or at least one gRNA molecule.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. HIUGE SYSTEM

The present invention is directed to a Homology-Independent Universal Genome Engineering (HiUGE) system for gene editing a subject genome. The HiUGE system includes (a)(i) a CRISPR-based nuclease or (ii) a nucleic acid sequence that encodes a CRISPR-based nuclease, (b) a Homology-Independent Universal Genome Engineering (HiUGE) vector, and a (c)(i) a target gene specific gRNA that targets the CRISPR-based nuclease to a target gene specific sequence within the subject genome or (ii) a target gene vector comprising a third polynucleotide sequence that encodes a target gene specific gRNA which targets the CRISPR-based nuclease to a target gene specific sequence within the subject genome. The HiUGE vector includes a first polynucleotide sequence encoding at least one insert, at least one donor recognition sequence (DRS) flanking each side of the first polynucleotide sequence (payload), and a second polynucleotide sequence encoding a HiUGE vector specific gRNA. The DRS includes a cleavage site for the CRISPR-based nuclease. The HiUGE vector specific gRNA (HD-gRNA) targets the CRISPR-based nuclease to the DRS and does not target a specific sequence within the subject genome.

Figure 2A:
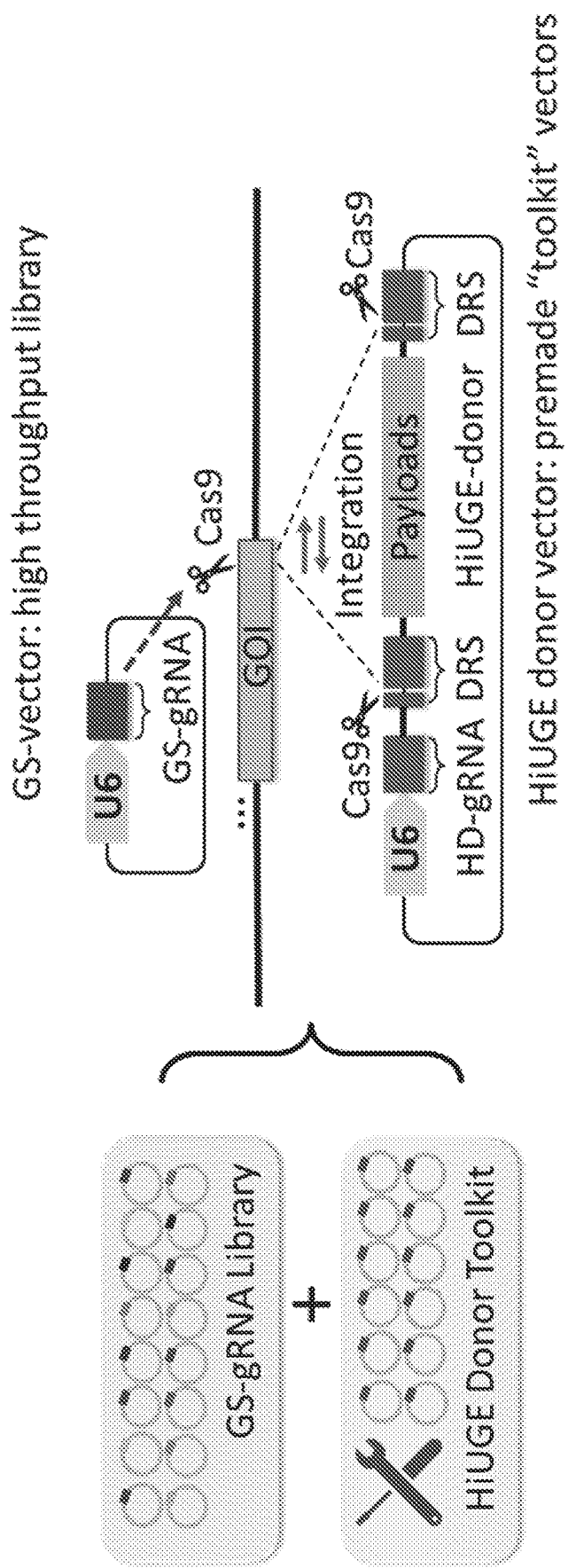
FIG. 2A shows a schematic illustration of homology-independent universal genomic engineering (HiUGE) system.
Figure 2B:
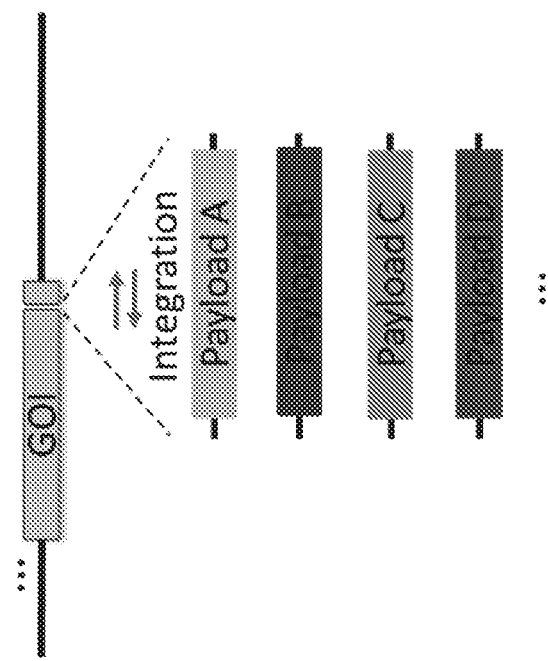
FIG. 2B shows a schematic illustration of the interchangeability of the payload to be inserted into a given genomic loci.

FIG. 2A shows a schematic illustration of homology-independent universal genomic engineering (HiUGE) system. In FIG. 2A, the top left and right panels show that a gene specific gRNA (GS-gRNA) library mediates cleavage of the targeted genomic loci of the gene of interest (GOI); the bottom left and right panels show that the HiUGE vector is a self-cleaving vector that expresses a HiUGE vector specific gRNA (HD-gRNA) that specifically recognizes the donor recognition sequence (DRS) and directs the cleavage and release of the donor payload to be inserted at the GS-gRNA targeted genomic loci. In some embodiments, each GS-gRNA vector can be paired with any of the pre-made HiUGE vectors (toolkits) for targeted homology-independent knock-in (KI). For example, FIG. 2B shows a schematic illustration of the interchangeability of the payload to be inserted into a given genomic loci and FIGS. 2C-2G show an illustration of HiUGE vector toolkits, with examples of (toolkit 1) antibody epitope tags, (toolkit 2) enzymes, (toolkit 3) fluorescent proteins, (toolkit 4) cellular trafficking tags (NLS=nuclear localization signal, NES=nuclear export sequence, mito=mitochondrial targeting sequence), and (toolkit 5) other payloads for specialized applications. In some embodiments, HiUGE vectors harboring short tag sequences, such as epitope tags and cellular trafficking tags, employ a dual-orientation design for efficient expression of the tag following either forward or reverse integration of the insert into the targeted genomic loci. In some embodiments, HiUGE vectors harboring longer insert sequences typically use a single orientation design that allows expression of the KI payload following forward integration. In some embodiments, where there is a reverse integration of the payload into the genomic target, translation can be terminated by a stop codon cassette (FIG. 2H) in all three possible open reading frames (ORFs). In some embodiments, the HiUGE system comprises at least one polynucleotide sequence of SEQ ID NO: 108-127, or combination thereof.

3. HIUGE SYSTEM USING INTEIN-MEDIATED PROTEIN SPLICING SYSTEM

The present invention is also directed to a Homology-Independent Universal Genome Engineering (HiUGE) system for gene editing a subject genome using an intein-mediated protein splicing system to provide greater control of the CRISPR-based nuclease. The HiUGE system using an intein-mediated protein splicing system can be used in the same manner as the HiUGE system as described above. "Intein" as used herein refers to a segment of a protein that is able to excise itself and joining the remaining portions (the exteins) with a peptide bond via protein splicing. Inteins are also known as "protein introns." Intein-mediated protein splicing occurs after the intein-containing mRNA has been translated into a protein. The precursor protein contains three segments: an N-extein followed by the intein followed by a C-extein. After splicing has taken place, the resulting protein contains the N-extein linked to the C-extein and the splicing product is also termed an extein. A "split intein" refers to an intein of the precursor protein that comes from two genes. Examples of inteins, including split inteins, are disclosed in U.S. Pat. Appl. Publ. No. 20150232827, which is incorporated by reference herein.

The HiUGE system using an Intein-Mediated Protein Splicing System includes a Homology-Independent Universal Genome Engineering (HiUGE) vector and a gene specific vector. The HiUGE vector includes a first polynucleotide sequence encoding at least one insert, at least one donor recognition sequence (DRS) flanking each side of the first polynucleotide sequence, a second polynucleotide sequence encoding a HiUGE vector specific gRNA, and a third polynucleotide sequence encoding a first portion of a CRISPR-based nuclease having a first split-intein. The DRS includes a cleavage site for the CRISPR-based nuclease. The HiUGE vector specific gRNA (HD-gRNA) targets the CRISPR-based nuclease to the DRS and does not target a specific sequence within the subject genome. The gene specific vector includes a fourth polynucleotide sequence encoding a second portion of a CRISPR-based nuclease having a second split-intein and a fifth polynucleotide sequence that encodes a target gene specific gRNA which targets the CRISPR-based nuclease to a target gene specific sequence within the subject genome. The first portion of the CRISPR-based nuclease having a first split-intein and the second portion of the CRISPR-based nuclease having a second split-intein can join together to form a CRISPR-based nuclease. The expression of the third polynucleotide sequence and fourth polynucleotide sequence results in the generation of a first portion of the CRISPR-based nuclease polypeptide having a first split-intein and a second portion of the CRISPR-based nuclease polypeptide having a second split-intein. The first split-intein and second split-intein come together and splice the first portion of the CRISPR-based nuclease polypeptide and the second portion of the CRISPR-based nuclease polypeptide together to form an intact CRISPR-based nuclease. Thus, a fully functional CRISPR-based nuclease can be reconstituted after intein-mediated protein splicing.

In some embodiments, the first split-intein is a N-intein and the second split-intein is a C-intein. In some embodiments, the N-intein comprises a polynucleotide sequence of SEQ ID NO: 60 and the second split-intein comprises a sequence of SEQ ID NO: 61. In some embodiments, the first portion of the CRISPR-based nuclease comprises the polypeptide sequence of SEQ ID NO: 55 and the second portion of the CRISPR-based nuclease comprises the polypeptide sequence of SEQ ID NO: 56. In some embodiments, the HiUGE system using an Intein-Mediated Protein Splicing System can include at least one polynucleotide sequence of SEQ ID NO: 108-127, or combination thereof.

4. HIUGE VECTOR

The disclosed HiUGE systems include a HiUGE vector, also referred herein as a donor vector or HiUGE donor vector, which contains at least one polynucleotide sequence insert (payload) for insertion into the target genome, at least one donor recognition sequence (DRS) on either side of the insert sequence, and a second polynucleotide sequence encoding a HiUGE vector specific gRNA (HD-gRNA). The DRS contains a cleavage site for a CRISPR-based nuclease. The HD-gRNA targets the CRISPR-based nuclease to the DRS found on either side of the insert. If the HiUGE system uses an intein-mediated protein splicing system, the HiUGE vector can further include a third polynucleotide sequence encoding a first portion of a CRISPR-based nuclease having a first split-intein, as described above.

a. Donor Recognition Sequence DRS

The DRS includes a donor target sequence and a protospacer-adjacent motif (PAM) sequence. The donor target sequence is recognized through homologous base-pairing with a HD-gRNA molecule, as described below, complexed with a CRISPR-based nuclease, as described below. The PAM sequence is recognized by the CRISPR-based nuclease. Only sites containing the correct donor target sequence and the corresponding PAM will be cleaved. The donor target sequence ensures specificity for the CRISPR-based nuclease cleavage to the HiUGE vector (donor vector) by being sufficiently different from any similar length sequence in the subject genome. In some embodiments, the donor target sequence comprises at least one base pair mismatch to any sequence of equal length in the subject genome. In certain embodiments, the donor target sequence comprises at least two base pair mismatches to any sequence of equal length in the subject genome.

The HiUGE vector can include at least one donor recognition sequence (DRS) on each of the flanking sides of at least one insert. In some embodiments, the HiUGE vector can include at least one DRS or two DRS on each side of an insert. In some embodiments, if there are more than one insert, each insert has at least one DRS on each side.

The DRS can be designed using the following rules or steps.

(1) Step 1

The first 20 nucleotides (nt) of the sequence is chosen to ensure that the corresponding HD-gRNA does not facilitate Cas9-mediated cleavage of genomic sequences of the target genome (the gRNA should be inert with respect to the target genome). In other word, the HD-gRNA should be foreign to the target genome and incapable of directing Cas9 cleavage activity within the target genome. Several bioinformatics tools are available to predicted such "off-target" activity, such as Cas-Offinder and Crispor. In general, a basic requirement is for the gRNA sequence to have at least 1 base pair (bp) mismatch in the seed region (12 bp PAM-proximal sequence) when compared against the target genome if wild-type SpCas9 is used, or to have at least 1 bp mismatch within an extended range (18 bp PAM-proximal sequences) when using high fidelity Cas9 variants such as the hypaCas9 enzyme.

(2) Step 2:

As the HiUGE donor recognition sequence (DRS) (sequence targeted by the HD-gRNA) can be used in either the forward or reverse orientation, this step is separately analyzed by generating its reverse complement, with X representing the reverse complement of N. "|" represents the site of Cas9 dependent double strand break and nucleotides surrounding the break site numbered $_{-2, -1, 1, 2}$.

```
DRS Seq1: 5'- NNNNNNNNNNNNNNNNNN_-2N_-1 | N_1N_2NNGG -3'
```
when the DRS is used in forward orientation.

```
DRS Seq2: 5'- CCXXX_-2X_-1 | X_1X_2XXXXXXXXXXXXXXXX- 3'
```
when the DRS is used in reverse orientation.

Definition of genomic open reading frame (ORF) phase regarding to the gene-specific gRNA (GS-gRNA) guided Cas9 cutting site (the last coding triplet before the cleavage loci is highlighted in grey), with Z representing any target genomic nucleotide A,G,C,T and "|" representing the genomic double strand break site and the surrounding nucleotides numbered as defined above.

ORF+0: ... ZZZ |$Z_1Z_2Z$ ...
ORF+1: ... ZZZ $Z_{-1}|Z_1Z_2$ ...
ORF+2: ... ZZZ $Z_{-2}Z_{-1}|Z_1$ ...

Overall, 4 possible different usage scenarios for the HiUGE donor recognition sequence needs to be tested for each ORF possibility. These take into account insertion of foreign DNA to create fusion proteins between the target genome encoded protein and the inserted foreign encoded protein sequence. The foreign encoded protein sequence can be either N-terminal (N-term) or C-terminal (C-term) to the target genome encoded protein sequence.

Scenario 1:
  N-term tagging in forward orientation, upstream of the targeted gene, downstream of the insert, ORF+0
  N-term tagging in forward orientation, upstream of the targeted gene, downstream of the insert, ORF+1
  N-term tagging in forward orientation, upstream of the targeted gene, downstream of the insert, ORF+2
Scenario 2:
  C-term tagging in forward orientation, downstream of the targeted gene, upstream of the insert, ORF+0
  C-term tagging in forward orientation, downstream of the targeted gene, upstream of the insert, ORF+1
  C-term tagging in forward orientation, downstream of the targeted gene, upstream of the insert, ORF+2
Scenario 3:
  N-term tagging in reverse orientation, upstream of the targeted gene, downstream of the insert, ORF+0
  N-term tagging in reverse orientation, upstream of the targeted gene, downstream of the insert, ORF+1
  N-term tagging in reverse orientation, upstream of the targeted gene, downstream of the insert, ORF+2
Scenario 4:
  C-term tagging in reverse orientation, downstream of the targeted gene, upstream of the insert, ORF+0
  C-term tagging in reverse orientation, downstream of the targeted gene, upstream of the insert, ORF+1
  C-term tagging in reverse orientation, downstream of the targeted gene, upstream of the insert, ORF+2

(3) Step 3a:

To satisfy the scenarios when the DRS is used in forward orientation (DRS Seq1).

Scenario 1: DRS Rules for N-term tagging, (see dark dashed region in FIG. 3A).

Criteria 1: For the DRS to be used universally in any loci, the border sequence ($N_{-2}N_{-1}$) must be incapable of yielding any stop codon when spliced with the targeted genomic loci, as defined by the genomic gene of interest (GOI) ORF.

ORF+0: No constraint.
ORF+1: $N_{-1}$ can only be A, C, or G; can not be T. ($N_{-1}Z_1Z_2$ can not be a stop codon)
ORF+2: $N_{-2}N_{-1}$ can only be TT, TC, AA, AT, AC, AG, CA, CT, CC, CG, GA, GT, GC, or GG; cannot be TA or TG. ($N_{-2}N_{-1}Z_1$ cannot be a stop codon)

Criteria 2: NNNNNNNNNNNNNNNN$_{-2}N_{-1}$ does not introduce a stop codon in reference to the GOI ORF:

ORF+0: NN NNN NNN NNN NNN NN$_{-2}N_{-1}$: grey triplets cannot contain any stop codon.
ORF+1: N NNN NNN NNN NNN NNN $N_{-1}$: grey triplets cannot contain any stop codon.
ORF+2: NNN NNN NNN NNN NNN $N_{-2}N_{-1}$: grey triplets cannot contain any stop codon.

Scenario 2: DRS Rules for C-term tagging, (see dark dashed region in FIG. 3B).

Criteria 1: For the DRS to be used universally in any loci, the border sequence ($N_1N_2$) must be incapable of yielding any stop codon when spliced with the targeted genomic loci, as defined by the genomic gene of interest (GOI) ORF.

ORF+0: No constraint.
ORF+1: $N_1N_2$ can only be AC, AT, TA, TT, TC, TG, CA, CT, CC, CG, GT, GC, or GG; cannot be AA, AG, or GA. ($Z_{-1}N_1N_2$ cannot be a stop codon)
ORF+2: $N_1$ can only be T or C; can not be A or G. ($Z_{-2}Z_{-1}N_1$ cannot be a stop codon)

Criteria 2: $N_1N_2$NNGG does not introduce a stop codon in reference to the GOI ORF.

ORF+0: NNN NGG : grey triplets cannot contain any stop codon.
ORF+1: $N_1N_2$ NNG G: grey triplets cannot contain any stop codon.
ORF+2: $N_1$ NNN GG: grey triplets cannot contain any stop codon.

(4) Step 3b:

To satisfy the scenarios when the DRS is used in reverse orientation (DRS Seq2)

Scenario 3: DRS Rules for N-term tagging, (see dark dashed region in FIG. 3C).

Criteria 1: For the DRS to be used universally in any loci, the border sequence ($X_{-2}X_{-1}$) must be incapable of yielding any stop codon when spliced with the targeted genomic loci, as defined by the genomic gene of interest (GOI) ORF.

ORF+0: No constraint.
ORF+1: $X_{-1}$ can only be A, C, or G; can not be T. ($X_{-1}Z_1Z_2$ cannot be a stop codon)
ORF+2: $X_{-2}X_{-1}$ can only be TT, TC, AA, AT, AC, AG, CA, CT, CC, CG, GA, GT, GC, or GG; can not be TA or TG. ($X_{-2}X_{-1}Z_1$ cannot be a stop codon)

Criteria 2: CCXXX$_{-2}X_{-1}$ does not introduce a stop codon in reference to the GOI ORF.

ORF+0: CCX XX X : grey triplets cannot contain any stop codon.

ORF+1: CC XXX $X_{-1}$: grey triplets cannot contain any stop codon.

ORF+2: C XXX $X_{-2}X_{-1}$: grey triplets cannot contain any stop codon.

Scenario 4: DRS Rules for C-term tagging, (see dark dashed region in FIG. 3D).

Criteria 1: For the DRS to be used universally in any loci, the border sequence ($X_1X_2$) must be incapable of yielding any stop codon when spliced with the targeted genomic loci, as defined by the genomic gene of interest (GOI) ORF.

ORF+0: No constraint.

ORF+1: $X_1X_2$ can only be AC, AT, TA, TT, TC, TG, CA, CT, CC, CG, GT, GC, or GG. cannot be AA, AG, or GA. ($Z_{-1}X_1X_2$ cannot be a stop codon)

ORF+2: $X_1$ can only be T or C, can not be A or G. ($Z_{-2}Z_{-1}X_1$ cannot be a stop codon)

Criteria 2: $X_1X_2$XXXXXXXXXXXXXXX does not introduce a stop codon in reference to the GOI ORF.

ORF+0: XXX XXX XXX XXX XXX XX: grey triplets cannot contain any stop codon

ORF+1: $X_1X_2$ XXX XXX XXX XXX XXX : grey triplets cannot contain any stop codon.

ORF+2: $X_1$ XXX XXX XXX XXX XXX X: grey triplets cannot contain any stop codon.

(5) Step 4:

In this final step, the GS-gRNA are tested to determine the compatibility with the final edited genomic loci after integration. A general rule is that after integration, no recognition sequence for either the GS-gRNA or the HD-gRNA should be reconstituted to ensure that Cas9 cannot subsequently cleave the edited genomic sequence. In some embodiments, for the scenario when GS-gRNA is chosen to target the sense genomic strand, DRS would be best to be used in the reverse orientation for either N- and C-term tagging. In some embodiments, for the scenario when GS-gRNA is chosen to target the anti-sense genomic strand, DRS would be best to be used in the forward orientation for either N- and C-term tagging. In all experiments, it should be checked that after genomic integrating, the reconstituted sequence exhibits sufficient dissimilarity to both the HD-gRNA and the GS-gRNA.

For example, in case of C-term tagging, when the GS-gRNA is targeting the sense-strand and when the DRS is used in the forward orientation, the following checks should be performed: Genomic sequence:

zzzzzzzzzzzzzzzzz | zzz PAM:

GS-gRNA recognition site is underlined.

After donor integration:

zzzzzzzzzzzzzzzzz | NNN PAM:

the underlined sequence be sufficiently dissimilar to the GS-gRNA sequence in reference to the fidelity of the particular Cas9 enzyme used. Once the HiUGE donor recognition sequence is chosen, it needs to be experimentally tested for gRNA cleavage efficiency, as well as in negative control experiments to assess off-target insertion into gene coding sequences. This is achieved by targeting cells with the HiUGE vector and HD-gRNA and no GS-gRNA, followed by the analysis of donor protein expression by immunocytochemistry or other related techniques.

In some embodiments, the DRS length can vary according to the variant of Cas9 utilized in the HiUGE system. In some embodiments, the DRS can include a donor target sequence of about 19 to 24 nucleotides in length and a PAM sequence. In some embodiments, the donor target sequence can be about 15 to about 30 nucleotides in length, about 15 to about 28 nucleotides in length, about 15 to about 25 nucleotides in length, about 15 to about 20 nucleotides in length, about 19 to about 30 nucleotides in length, about 19 to about 28 nucleotides in length, about 19 to about 25 nucleotides in length, or about 19 to about 24 nucleotides in length. In some embodiments, the donor target sequence is at least about 15 nucleotides, at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, or at least about 30 nucleotides in length.

In some embodiments, the donor target sequence can include a sequence of 5'-NNNNNNNNNNNNNNNN$_{-2}$N$_{-1}$N$_1$N$_2$N-3' (SEQ ID NO: 15) in the forward orientation and the Cas9 dependent double stranded break in the cleavage site occurs between positions N$_{-1}$ and N$_1$, or the donor target sequence can include a sequence of 5'-XX$_{-2}$X$_{-1}$X$_1$X$_2$XXXXXXXXXXXXXXX-3' (SEQ ID NO: 16) in the reverse orientation and the Cas9 dependent double stranded break in the cleavage site occurs between positions X$_{-1}$ and X$_1$, wherein N is any of the four deoxyribonucleic acids adenine (A), thymine (T), guanine (G), or cytosine (C), wherein X is the reverse complement of N, wherein N$_{-2}$N$_{-1}$N$_1$N$_2$(SEQ ID NO: 17) is a border sequence in 5'-NNNNNNNNNNNNNNNN$_{-2}$N$_{-1}$N$_1$N$_2$N-3' (SEQ ID NO: 15) and X$_{-2}$X$_{-1}$X$_1$X$_2$(SEQ ID NO: 18) is a border sequence in 5'-XX$_{-2}$X$_{-1}$X$_1$X$_2$XXXXXXXXXXXXXXX-3' (SEQ ID NO: 16), and wherein the donor target sequence does not introduce an in-frame stop codon after the insert is integrated into the target gene.

In some embodiments, the donor target sequence can include at least 1 base pair mismatch compared to any sequence of equal length in the subject genome. In some embodiments, the donor target sequence can include at least 2 base pair mismatches compared to any sequence of equal length in the subject genome. In some embodiments, the donor target sequence can include at least 1 base pair mismatch within about 8 to 12 nucleotides of the donor target sequence that is adjacent to the PAM sequence compared to any sequence of equal length in the subject genome. In some embodiments, the donor target sequence can include at least 1 base pair mismatch, at least 2 base pair mismatch, at least 3 base pair mismatch, at least 4 base pair mismatch, or at least 5 base pair mismatch within about 8 to 12 nucleotides of the donor target sequence that is adjacent to the PAM sequence compared to any sequence of equal length in the subject genome.

HiUGE vectors can be paired with any gene-specific gRNA to drive the integration of an insert sequence into a specific target gene. However, for the insert to be correctly transcribed and translated, the reading frame at the gene specific cut site needs to match the reading frame of the donor insert. In some embodiments, the target gene specific sequence can include a sequence of ZZZZ$_{-2}$Z$_{-1}$Z$_1$Z$_2$Z (SEQ ID NO: 19), wherein the Cas9 dependent double stranded break in the cleavage site occurs between positions Z$_{-1}$ and Z$_1$, wherein Z is any of the four deoxyribonucleic acids adenine (A), thymine (T), guanine (G), or cytosine (C), wherein the border sequence does not yield an in-frame stop codon after the insert is integrated into the target gene, and wherein the genomic open reading frame (ORF) phase of the target gene is selected from the group consisting of:

ORF+0: positions $ZZ_{-2}Z_{-1}$ corresponding to $ZZZZ_{-2}Z_{-1}Z_1Z_2Z$ (SEQ ID NO: 19), ORF+1: positions $ZZZ_{-2}$ corresponding to $ZZZZ_{-2}Z_{-1}Z_1Z_2Z$ (SEQ ID NO: 19), and ORF+2: positions $ZZZ$ corresponding to $ZZZZ_{-2}Z_{-1}Z_1Z_2Z$ (SEQ ID NO: 19).

In some embodiments, if the genomic ORF phase is ORF+1, the DRS is 5'-NNNNNNNNNNNNNNNN$_{-2}$N$_{-1}$N$_1$N$_2$N-3' (SEQ ID NO: 15) in the forward orientation, and the at least one insert is used to generate an N-terminal tagged fusion protein, then $N_{-1}$ is A, C, or G.

In some embodiments, if the genomic ORF phase is ORF+2, the DRS is 5'-NNNNNNNNNNNNNNNN$_{-2}$N$_{-1}$N$_1$N$_2$N-3' (SEQ ID NO: 15) in the forward orientation, and the at least one insert is used to generate a N-terminal tagged fusion protein, then $N_{-2}N_{-1}$ is selected from the group consisting of TT, TC, AA, AT, AC, AG, CA, CT, CC, CG, GA, GT, GC, and GG.

In some embodiments, if the genomic ORF phase is ORF+1, the DRS is 5'-NNNNNNNNNNNNNNNN$_{-2}$N$_{-1}$N$_1$N$_2$N-3' (SEQ ID NO: 15) in the forward orientation, and the at least one insert is used to generate a C-terminal tagged fusion protein, then $N_1N_2$ is selected from the group consisting of AC, AT, TA, TT, TC, TG, CA, CT, CC, CG, GT, GC, and GG.

In some embodiments, if the genomic ORF phase is ORF+2, the DRS is 5'-NNNNNNNNNNNNNNNN$_{-2}$N$_{-1}$N$_1$N$_2$N-3' (SEQ ID NO: 15) in the forward orientation, and the at least one insert is used to generate a C-terminal tagged fusion protein, then $N_1$ is T or C.

In some embodiments, if the genomic ORF phase is ORF+1, the DRS is 5'-XX$_{-2}$X$_{-1}$X$_1$X$_2$XXXXXXXXXXXXXXXX-3' (SEQ ID NO: 16) in the reverse orientation, and the at least one insert is used to generate an N-terminal tagged fusion protein, then X is A, C, or G.

In some embodiments, if the genomic ORF phase is ORF+2, the DRS is 5'-XX$_{-2}$X$_{-1}$X$_1$X$_2$XXXXXXXXXXXXXXXX-3' (SEQ ID NO: 16) in the reverse orientation, and the at least one insert is used to generate a N-terminal tagged fusion protein, then $X_{-2}X_{-1}$ is selected from the group consisting of TT, TC, AA, AT, AC, AG, CA, CT, CC, CG, GA, GT, GC, and GG.

In some embodiments, if the genomic ORF phase is ORF+1, the DRS is 5'-XX$_{-2}$X$_{-1}$X$_1$X$_2$XXXXXXXXXXXXXXXX-3' (SEQ ID NO: 16) in the reverse orientation, and the at least one insert is used to generate a C-terminal tagged fusion protein, then $X_1X_2$ is selected from the group consisting of AC, AT, TA, TT, TC, TG, CA, CT, CC, CG, GT, GC, and GG.

In some embodiments, if the genomic ORF phase is ORF+2, the DRS is 5'-XX$_{-2}$X$_{-1}$X$_1$X$_2$XXXXXXXXXXXXXXXX-3' (SEQ ID NO: 16) in the reverse orientation, and the at least one insert is used to generate a C-terminal tagged fusion protein, then $X_1$ is T or C.

In some embodiments, the DRS is recognized by a SpCas9, or variant thereof, and can include a sequence of 5'-NNNNNNNNNNNNNNNN$_{-2}$N$_{-1}$N$_1$N$_2$NNGG-3' (SEQ ID NO: 20) in the forward orientation or a sequence of 5'-CCXXX$_{-2}$X$_{-1}$X$_1$X$_2$XXXXXXXXXXXXXXXX-3' (SEQ ID NO: 21) in the reverse orientation.

In some embodiments, the DRS can include a polynucleotide sequence of

```
                                        (SEQ ID NO: 22)
GTCATAGTATCGCGGAGTTCAGG, (SEQ ID NO: 23)
GACGCTTCCGAGTACGGTACAGG, (SEQ ID NO: 24)
GGTTCTACGAGGATACGTCTTGG, (SEQ ID NO: 25)
GCGTATGGCAAGCATAGCCGGGG, (SEQ ID NO: 26)
GCGATTGACCCGTGCTGTCGCGG,
or (SEQ ID NO: 27)
CCTGTACCGTACTCGGAAGCGTC.
``` b. Insert Polynucleotide(s)

The HiUGE vector includes one or more insert polynucleotide(s) (payloads), that are cleaved from the HiUGE vector and inserted in the target genomic DNA. The present disclosure embodies a single HiUGE vector that can contain at least one insert. In some embodiments, the single HiUGE vector can contain a single insert. In some embodiments, the single HiUGE vector can contain two inserts. In some embodiments, the single HiUGE vector can contain three inserts.

In certain embodiments, at least one insert can be inserted at the N-terminal end of a promoter region, an enhancer region, a repressor region, an insulator region, a silencer region, a region involved in DNA looping with the promoter region, a gene splicing region, or a transcribed region thereby generating a N-terminal tagged fusion protein. In certain other embodiments, the at least one insert is inserted at the C-terminal end of a promoter region, an enhancer region, a repressor region, an insulator region, a silencer region, a region involved in DNA looping with the promoter region, a gene splicing region, or a transcribed region thereby generating a C-terminal tagged fusion protein. In certain embodiments, the C-terminal tag can contain a Stop codon.

In some embodiments, at least one insert is inserted into the sense strand of the genome. In certain other embodiments, at least one insert is inserted into the anti-sense strand of the genome. In some embodiments, at least one insert is inserted into the sense strand of the genome and at least one insert is inserted into the anti-sense strand of the genome. In some embodiments, at least one insert is inserted in a forward orientation. In some embodiments, at least one insert is inserted in a reverse orientation. In some embodiments, at least one insert is inserted in a forward orientation and at least one insert is inserted in a reverse orientation.

In some embodiments, the at least one insert encodes a marker or tag. In certain embodiments, the at least one insert encodes an antibody epitope tag, a fluorescent protein tag, an affinity purification tag, a proteomic labeling enzyme, a split Cre-recombinase, an internal ribosomal entry sequence (IRES), a 2A peptide, a localization sequence, an enzyme, an epitope, or a combination thereof. In some embodiments, the at least one insert encodes at least one antibody epitope tag. For example, the at least one insert can encode at least one antibody epitope tag, at least two antibody epitope tags, at least three antibody epitope tags, at least four antibody epitope tags, at least five antibody epitope tags, at least six antibody epitope tags, at least seven antibody epitope tags, at least eight antibody epitope tags, at least nine antibody epitope tags, or at least ten antibody epitope tags. In some embodiments, the at least one insert can encode, one antibody epitope tag, two antibody epitope tags, three antibody epitope tags, four antibody epitope tags, five antibody epitope tags, six antibody epitope tags, seven antibody epitope tags, eight antibody epitope tags, nine antibody epitope tags, or ten antibody epitope tags. In some embodiments, the at least two or more antibody epitope tags are different. In some embodiments, the at least two or more antibody epitope tags are the same. In some embodiments, the at least one insert comprises one or more copies of the antibody epitope tag. In some embodiments, the antibody epitope tags are separated by a linker. In some embodiments, the linkers can be a rigid linkers (RL) and/or a flexible linker (FL). Exemplary linkers are described in International Patent Publication No. WO2009/086132A2.

Figure 2C:
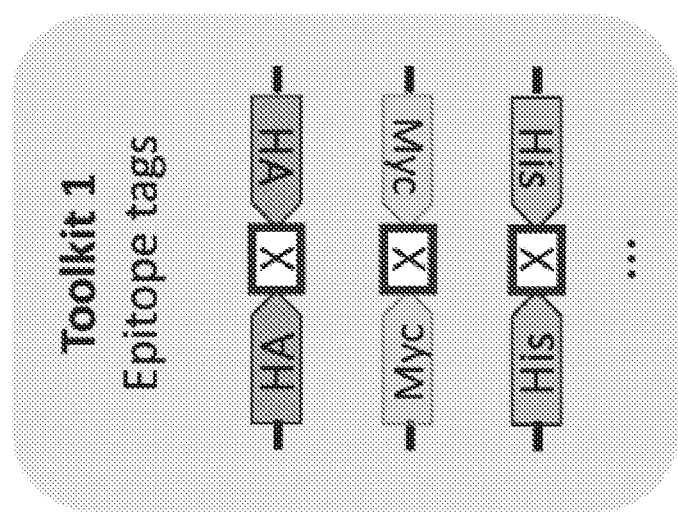
FIGS. 2C-2G show illustrations of HiUGE vector toolkits, with examples of (toolkit 1) antibody epitope tags, (toolkit 2) enzymes, (toolkit 3) fluorescent proteins, (toolkit 4) cellular trafficking tags (NLS=nuclear localization signal, NES=nuclear export sequence, mito=mitochondrial targeting sequence), and (toolkit 5) other payloads for specialized applications.
Figure 2D:
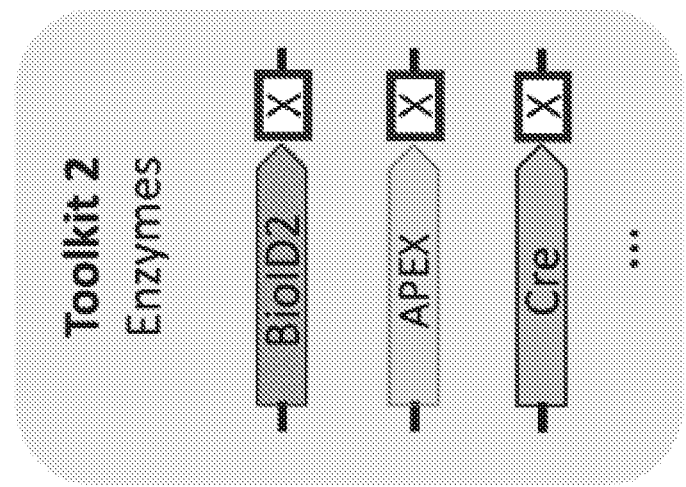
Figure 2G:
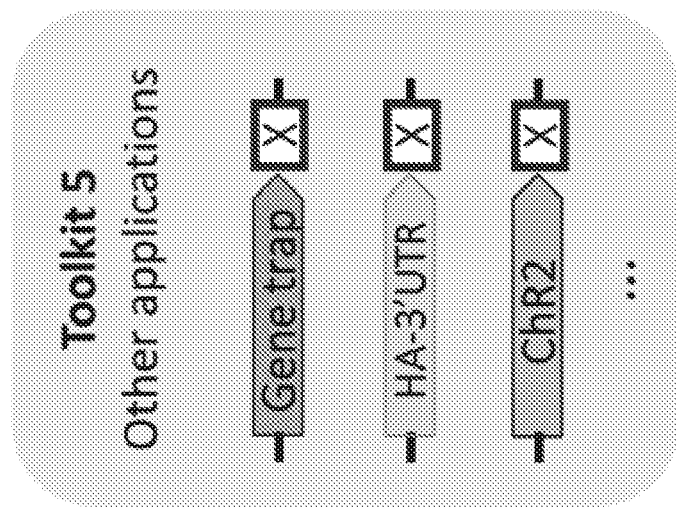
Figure 2F:
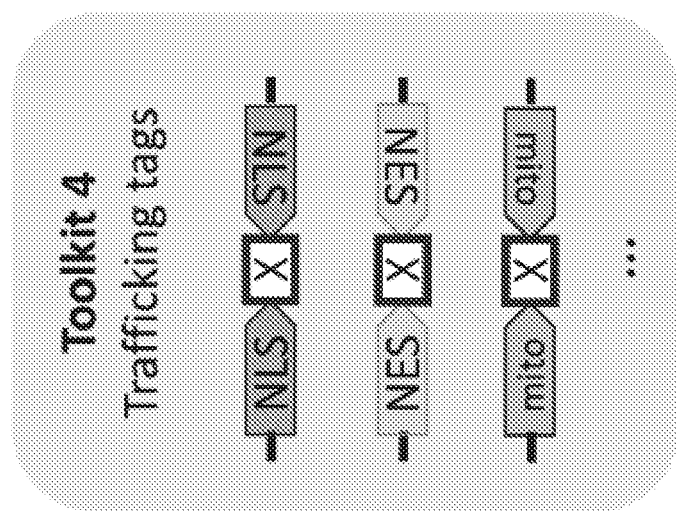
Figure 2E:
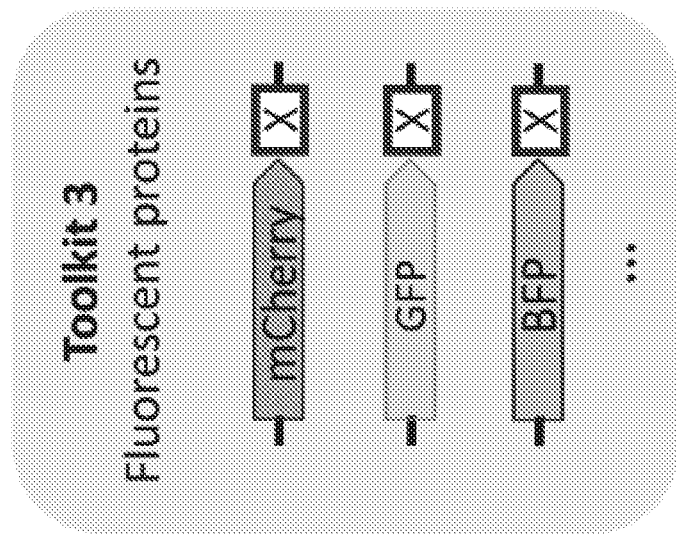
Figure 2H:
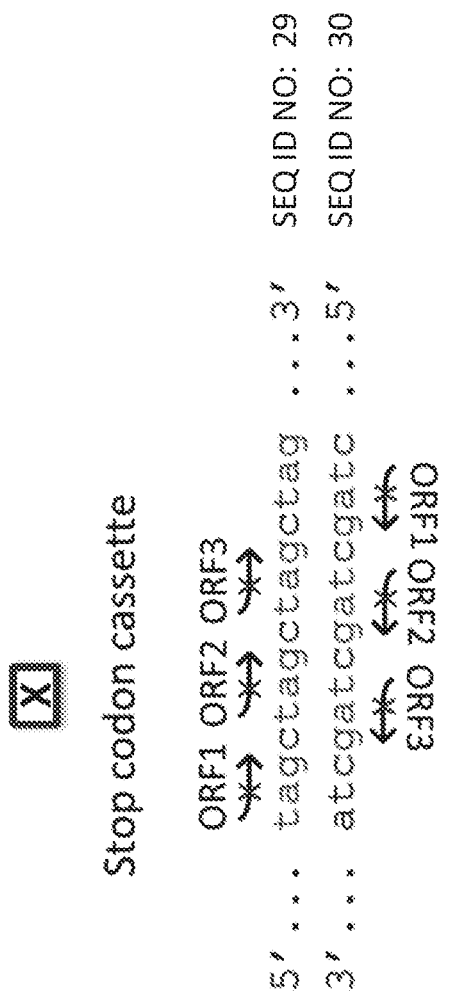
FIG. 2H shows a stop codon cassette in all three possible open reading frames on both strands: tagctagctagctag (SEQ ID NO: 29) and ctagctagctagcta (SEQ ID NO: 30).

In some embodiments, the HiUGE vector can include a dual orientation cassette or "turbo" cassettes in which the insert or donor sequences is in a dual orientation to facilitate high-efficiency labeling regardless of the which orientation the insert or "payload" is inserted into the genome (see e.g., FIGS. 2C and 2F). In some embodiments, the HiUGE vector can include a forward copy of the first polynucleotide sequence or polynucleotide sequence encoding the insert and a reverse copy of the first polynucleotide sequence or polynucleotide sequence encoding the insert encoded on the same strand. In some embodiments, a polynucleotide sequence encoding a stop cassesstte can be linked between the forward copy of the first polynucleotide sequence and a reverse copy of the first polynucleotide sequence.

In certain embodiments, the insert can encode a human influenze hemagglutinin (HA) antibody tag, a Myc antibody epitope tag, a fluorescent protein eGFP, a fluorescent protein mNeonGreen, a fluorescent protein TdTomato, a Biotin affinity purification tag, and/or a 6× His affinity purification tag. In certain embodiments, the insert can encode two HA tags flanking a Stop codon cassette where one of the HA tags is in the reverse orientation. In certain embodiments, the insert can encode a Myc antibody epitope tag with a Stop codon. In certain embodiments, the insert can encode the fluorescent protein eGFP with a C-terminal stop codon. In certain embodiments, the insert can encode the fluorescent protein mNeonGreen with a C-terminal stop codon. In certain embodiments, the insert can encode the fluorescent protein TdTomato with a C-terminal stop codon. In certain embodiments, the insert can encode a Biotin affinity purification tag with a HA antibody epitope tag with a Stop codon. In certain embodiments, the insert can encode a 6× His affinity purification tag with a Stop codon. In certain embodiments, the insert can encode a HA antibody epitope tag N-terminal to a 2A peptide from porcine teschovirus-1, N-terminal to a Cre recombinase with a Stop codon. In certain embodiments, the insert can encode a HA antibody epitope tag N-terminal to a 2A peptide from porcine teschovirus-1, N-terminal to an enhanced blue variant of GFP with a Stop codon. In certain embodiments, the insert can encode a HA antibody epitope tag with a Stop codon N-terminal to a woodchuck hepatits virus posttransciprtional regulatory element, N-terminal to a bovine growth hormone polyadenylation signal. In some embodiments, the least one insert can include a polynucleotide sequence encoding at least one amino acid sequence of SEQ ID NO: 34, 39, 41-50, or combination thereof.

In certain embodiments, the insert can encode a HA antibody tag, a Myc antibody epitope tag, a V5 antibody epitope tag, and/or a combination thereof. In some embodiments, the insert can encode at least one copy of Myc, V5 tag, and HA. In some embodiments, the insert can encode two copies of Myc, V5 tag, and HA. In some embodiments, the least one insert comprises a polynucleotide sequence corresponding to positions 542-949 of SEQ ID NO: 152, SEQ ID NO: 153, or SEQ ID NO: 154.

c. HiUGE Vector Specific gRNA (HD-gRNA)

The HiUGE vector includes a second polynucleotide sequence encoding a HiUGE vector specific gRNA (HD-gRNA). The HD-gRNA complexes with the CRISPR-nuclease and targets the complex to the DRS on either side of the insert(s) in the HiUGE vector. Once targeted to the DRSs, the CRISPR-nuclease can cleave the vector to create the linear insert polynucleotide(s) or cleaved insert. The HD-gRNA is specific to the HiUGE vector DRS and does not target a specific sequence within the subject genome. In some embodiments, the HD-gRNA can include a nucleotide sequence corresponding to a sequence of SEQ ID NO: 28.

5. TARGET GENE SPECIFIC GRNA

The HiUGE systems, described above, include a target gene specific gRNA (GS-gRNA) or a nucleic acid encoding a GS-gRNA. The GS-gRNA forms a complex with the CRISPR-based nuclease and assists in the recognition of the intended cleavage site in the target gene or target gene specific sequence within the subject genome by homologous basepairing with the target gene specific sequence. In some embodiments, the GS-gRNA is provided on a target gene vector or gene specific vector encoding a polynucleotide sequence for the GS-gRNA.

The HiUGE system can be designed to target any target gene or target gene specific sequence. In some embodiments, the target gene can bean endogenous gene or a transgene. In some embodiments, the target gene or target gene specific sequence is located adjacent to or flanked by a PAM (protospacer adjacent motif). In some embodiments, the target gene specific sequence is a consecutive polynucleotide sequence of about 15 to 25 nucleotides within a target gene of the subject genome. In some embodiments, the target gene specific sequence is about 15 to 25 nucleotides within a target gene of the subject genome. In some embodiments, the target gene specific sequence is about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, or about 25 nucleotides within a target gene of the subject genome.

In some embodiments, the GS-gRNA targets at least one region of the target gene. In some embodiments, the target gene specific gRNA (GS-gRNA) targets at least one region of the target gene selected from the group consisting of a promoter region, an enhancer region, a repressor region, an insulator region, a silencer region, a region involved in DNA looping with the promoter region, a gene splicing region, or a transcribed region. In certain embodiments, the gene specific gRNA targets a promoter region. In certain embodiments, the gene specific gRNA targets an enhancer region. In certain embodiments, the gene specific gRNA targets a repressor region. In certain embodiments, the gene specific gRNA targets an insulator region. In certain embodiments, the gene specific gRNA targets a silencer region. In certain embodiments, the gene specific gRNA targets a region involved in DNA looping with the promoter region. In certain embodiments, the gene specific gRNA targets a gene splicing region. In certain embodiments, the gene specific gRNA targets a transcribed region.

The gene specific gRNA targets the CRISPR-based nuclease to the target gene or target gene specific sequence. In some embodiments, the HiUGE system can include more than 1 GS-gRNA that targets more than one target gene or target gene specific sequence. In some embodiments, the HiUGE system can include more than 1 different GS-gRNAs that targets more than one different target gene or target gene specific sequence. In some embodiments, the different GS-gRNAs bind to different target genes or target gene specific sequence. For example, the different GS-gRNAs can bind to target gene specific sequences of different target genes and the two or more target genes are edited.

In some embodiments, a target gene or target gene specific sequence can be in the genome of a eukaryotic cell (e.g., in a chromosome of the eukaryotic cell) or can be on an extrachromosomal element residing in the cell. In representative embodiments, the target gene or target gene specific sequence can be unique to a eukaryotic cell type (e.g., a mutation in a cancer cell), or unique to a species, genus, family or kingdom (e.g., a virus infecting a eukaryotic cell).

In some embodiments, the GS-gRNA targets a target nucleotide sequence comprising a polynucleotide sequence of any one of SEQ ID NOs: 128-139, or combinations thereof. In some embodiments, the target gene can be TUBB3 gene, MAP2 gene, MECP2 gene, NRCAM gene, ACTR2 gene, CLTA gene, ANK3 gene, SPTBN4 gene, SCN2A gene, GFAP gene, PDHA1 gene, or DCX gene. In some embodiments, the target gene can be TUBBS gene, INSYN1 gene, INS1N72 gene, ARHGAP32 gene, TUBB gene, ACTB gene, INNB gene, or NEM gene. In some embodiments, the GS-gRNA comprises a polynucleotide sequence of any one of SEQ ID Nos: 140-151. In some embodiments, the GS-gRNA comprises a polynucleotide sequence of any one of SEQ ID Nos: 169-195.

The mouse TUBB3 gene (also referred to herein as "mTUBB3" or "mTubb3") encodes β-tubulin III, which is a microtubule element of the tubulin family found almost exclusively in neurons and in testis cells. The MAP2 gene (also referred to herein as "Map2") encodes Microtubule-associated protein 2, which belongs to the microtubule-associated protein family. Proteins of this family are thought to be involved in microtubule assembly, which is an essential step in neuritogenesis. MAP2 serves to stabilize microtubules (MT) growth by crosslinking MT with intermediate filaments and other MTs. The MECP2 gene (also referred to herein as "Mecp2") encodes nuclear-localized methyl CpG binding protein 2 (MECP2) protein, which is involved in the normal function of nerve cells. The NRCAM gene (also referred to herein as "Nrcam") encodes neuronal cell adhesion molecule that interacts with ankyrin and is enriched on the axonal initial segment. The ACTR2 gene (also referred to herein as "Actr2") encodes actin-related protein 2, which is known to be a major constituent of the ARP2/3 complex. The ARP2/3 complex is an essential protein complex that induces de novo actin polymerization of branched actin filaments that modulate cell shape and motility. The CLTA gene (also referred to herein as "Clta") encodes clathrin protein, which is a protein that plays a major role in the formation of endocytic and protein trafficking vesicles. The ANK3 gene (also referred to herein as "Ank3") encodes ankyrin-3, which is an immunologically distinct gene product from ankyrins ANK1 and ANK2. Ankyrin-3 is found at the axonal initial segment and nodes of Ranvier of neurons in the central and peripheral nervous. The SPTBN4 gene (also referred to herein as "Sptbn4") encodes Spectrin, beta, non-erythrocytic 4 (PIV-spectrin), which is a member of a family of beta-spectrin genes. The encoded protein localizes to the axonal initial segment in neurons. The SCN2A gene (also referred to herein as "Scn2a") encodes sodium channel, voltage-gated, type II, alpha subunit (NaV 1.2 sodium channel subtype). Sodium channels which contain the Navα1.2 subunit are called Nav1.2 channels. The GFAP gene (also referred to herein as "GFAP") encodes glial acidic fibriallary protein, which is an intermediate filament (IF) protein that is expressed by in cell types of the central nervous system (CNS) including astrocytes and ependymal cells. The PDHA1 gene (also referred to herein as "Pdha1") encodes pyruvate dehydrogenase (lipoamide) alpha 1, which is a mitochondrial matrix enzyme that catalyzes the oxidative decarboxylation of pyruvate, producing acetyl-CoA and $CO_2$. The DCX gene (also referred to herein as "Dcx") encodes the neuronal migration protein doublecortin, also known as doublin or lissencephalin-X, which is a microtubule binding protein.

In some embodiments, the target gene vector further includes the nucleic acid encoding a CRISPR-based nuclease, as described below. In some embodiments, the target gene vector can further include a nucleic acid sequence that encodes a CRISPR-based nuclease, as described below. In some embodiments, the nucleic acid encoding a CRISPR-based nuclease comprises DNA. In some embodiments, the nucleic acid encoding a CRISPR-based nuclease comprises RNA.

6. CRISPR-BASED NUCLEASE

The HiUGE system includes a CRISPR-based nuclease or a nucleic acid sequence encoding a CRISPR-based nuclease. In some embodiments, the nucleic acid sequence encoding a CRISPR-based nuclease is DNA. In some embodiments, the nucleic acid sequence encoding a CRISPR-based nuclease is RNA. In some embodiments, a nucleic acid sequence encoding a CRISPR-based nuclease is encoded on the HiUGE vector. In some embodiments, a nucleic acid sequence encoding a CRISPR-based nuclease is encoded on the gene specific vector. In some embodiments, a nucleic acid sequence encoding a first portion of a CRISPR-based nuclease having a first split-intein is encoded on the HiUGE vector and a nucleic acid sequence encoding a second portion of a CRISPR-based nuclease having a second split-intein complementary to the first split-intein is encoded on the gene specific vector. In some embodiments, the target cell which is to be gene edited expresses and includes a CRISPR-based nuclease.

The CRISPR system is a microbial nuclease system involved in the defense against invading phages and plasmids and provides a form of acquired immunity. The CRISPR loci in microbial hosts contain a combination of CRISPR-associated (Cas) genes as well as non-coding RNA elements responsible for the specificity of the CRISPR-mediated nucleic acid cleavage.

CRISPR systems are organized into two classes, each composed of 3 system types with are further divided into 19 different subtypes. Class 1 systems use a complex of multiple Cas proteins to aid in the cleavage of foreign nucleic acids. Class 2 uses a single large Cas protein for the same purpose. Since class 2 only requires a single Cas protein, class 2 Cas proteins have been exploited and adapted for use in eukaryotic systems. Each type and most subtypes are characterized by a 'signature gene' found almost exclusively in that category. CRISPR/Cas9 is the most well-known class 2 protein used for genome engineering.

The CRISPR-based nuclease forms a complex with the 3' end of a gRNA. The specificity of the CRISPR-based system depends on two factors: the target sequence and the protospacer-adjacent motif (PAM). The target sequence is located on the 5' end of the gRNA and is designed to bond with base pairs on the host DNA at the correct DNA sequence known as the protospacer. By simply exchanging the recognition sequence of the gRNA, the CRISPR-based nuclease can be directed to new genomic targets. The PAM sequence is located on the DNA to be cleaved and is recognized by a CRISPR-based nuclease. PAM recognition sequences of the CRISPR-based nuclease can be species specific. In some embodiments, the CRISPR-based nuclease can be a Cas9 endonuclease or a Cpf1 endonuclease.

In some embodiments, the CRISPR-based nuclease is a Cas9 endonuclease derived from a bacterial genus of *Streptococcus, Staphylococcus, Brevibacillus, Corynebacter, Sutterella, Legionella, Francisella, Treponema, Filifactor, Eubacterium, Lactobacillus, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma,* or *Campylobacter.* In some embodiments, the Cas9 protein is selected from the group, including, but not limited to, *Streptococcus pyogenes, Francisella novicida, Staphylococcus aureus, Neisseria meningitides, Streptococcus thermophiles, Treponema denticola, Brevibacillus laterosporus, Campylobacter jejuni, Corynebacterium diphtheria, Eubacterium ventriosum, Streptococcus pasteurianus, Lactobacillus farciminis, Sphaerochaeta globus, Azospirillum, Gluconacetobacter diazotrophicus, Neisseria cinerea, Roseburia intestinalis, Parvibaculum lavamentivorans, Nitratifractor salsuginis,* and *Campylobacter lari.*

In some embodiments, the Cas9 protein is selected from the group including, but not limited to, *Streptococcus pyogenes* Cas9 (SpCas9) endonuclease, a *Francisella novicida* Cas9 (FnCas9) endonuclease, a *Staphylococcus aureus* Cas9 (SaCas9) endonuclease, *Neisseria meningitides* Cas9 (NmCas9) endonuclease, *Streptococcus thermophiles* Cas9 (StCas9) endonuclease, *Treponema denticola* Cas9 (TdCas9) endonuclease, *Brevibacillus laterosporus* Cas9 (BlatCas9) endonuclease, *Campylobacter jejuni* Cas9 (CjCas9) endonuclease, a variant endonuclease thereof, or a chimera endonuclease thereof. In some embodiments, the Cas9 endonuclease is a SpCas9 variant endonuclease, a SaCas9 variant endonuclease, or a StCas9 endonuclease. In some embodiments, the SpCas9 variant is a SpCas9 Cas9 VRER variant endonuclease, a SpCas9 Cas9 EQR variant endonuclease, a SpCas9 VQR variant endonuclease, a SpCas9-HF1 variant endonuclease, or an eSpCas9(1.1) variant endonuclease. In some embodiments, the SaCas9 variant is a SaCas9 Cas9 KKH variant. In some embodiments, the StCas9 endonuclease is a St1Cas9 endonuclease or StcCas9 endonuclease. In some embodiments, the Cas9 endonuclease is a chimera Sp-St3Cas9 endonuclease comprising SpCas9 with a Protospacer Adjacent Motif (PAM)-interacting (PI) domain of St3Cas9 or a chimera St3-SpCas9 endonuclease comprising St3Cas9 with a PI domain of SpCas9.

a. PAM Sequence Recognition

The CRISPR nuclease complex unwinds a DNA duplex and searches for sequences complementary to the gRNA and the correct PAM. The nuclease only mediates cleavage of the target DNA if both conditions are met. By specifying the type CRISPR-based nuclease and the sequence of one or more gRNA molecules, DNA cleavage sites can be localized to a specific target domain. Given that PAM sequences are variant and species specific, target sequences can be engineered to be recognized by only certain CRISPR-based nucleases.

In some embodiments, the Cas9 endonuclease can recognize a PAM sequence YG (SEQ ID NO: 1), NGG (SEQ ID NO: 2), NGA (SEQ ID NO: 3), NGCG (SEQ ID NO: 4), NGAG (SEQ ID NO: 5), NGGNG (SEQ ID NO: 6), NNGRRT (SEQ ID NO: 7), NNGRRT (SEQ ID NO: 8), NNNRRT (SEQ ID NO: 9). NAAAAC (SEQ ID NO: 10), NNNNGNNT (SEQ ID NO: 11), NNAGAAW (SEQ ID NO: 12), NNNNCNDD (SEQ ID NO: 13), or NNNNRYAC (SEQ ID NO: 14).

In some embodiments, the Cas9 endonuclease is a SpCas9 endonuclease and recognizes the PAM sequence of NGG (SEQ ID NO: 2). In some embodiments, the Cas9 endonuclease is a SpCas9 variant endonuclease and recognizes the PAM sequence of NGG (SEQ ID NO: 2). In some embodiments, the Cas9 endonuclease is a SpCas9 Cas9 VRER variant endonuclease and recognizes the PAM sequence of NGCG (SEQ ID NO: 4). In some embodiments, the Cas9 endonuclease is a SpCas9 Cas9 EQR variant endonuclease and recognizes the PAM sequence of NGAG (SEQ ID NO: 5). In some embodiments, the Cas9 endonuclease is a SpCas9 VQR variant endonuclease and recognizes the PAM sequence of NGA (SEQ ID NO: 3). In some embodiments, the Cas9 endonuclease is a SaCas9 endonuclease and recognizes the PAM sequence of NNGRRT (SEQ ID NO: 7). In some embodiments, the Cas9 endonuclease is a SaCas9 Cas9 KKH variant endonuclease and recognizes the PAM sequence of NNNRRT (SEQ ID NO: 9). In some embodiments, the Cas9 endonuclease is a St1Cas9 endonuclease and recognizes the PAM sequence of NNAGAAW (SEQ ID NO: 12). In some embodiments, the Cas9 endonuclease is a St3Cas9 endonuclease and recognizes the PAM sequence of NGGNG (SEQ ID NO: 6). In some embodiments, the Cas9 endonuclease is a chimera Sp-St3Cas9 endonuclease and recognizes the PAM sequence of NGGNG (SEQ ID NO: 6). In some embodiments, the Cas9 endonuclease is an NmCas9 endonuclease and recognizes the PAM sequence of NNNNGNNT (SEQ ID NO: 11). In some embodiments, the Cas9 endonuclease is a TdCas9 endonuclease and recognizes the PAM sequence of NAAAAC (SEQ ID NO: 10). In some embodiments, the Cas9 endonuclease is a BlatCas9 endonuclease and recognizes the PAM sequence of NNNNCNDD (SEQ ID NO: 13). In some embodiments, the Cas9 endonuclease is a CjCas9 endonuclease and recognizes the PAM sequence of NNNNRYAC (SEQ ID NO: 14). In some embodiments, the Cas9 endonuclease is an FnCas9 RHA variant endonuclease and recognizes the PAM sequence of YG (SEQ ID NO: 1).

7. COMPOSITIONS FOR GENE EDITING

The present invention is directed to compositions for gene editing, such as editing a gene to insert a marker or a tag. The composition can include the HiUGE system, or at least one polynucleotide sequence coding said system, as disclosed above. The composition can also include a viral delivery system. For example, the viral delivery system can include an adeno-associated virus vector or a modified lentiviral vector.

Methods of introducing a nucleic acid into a host cell are known in the art, and any known method can be used to introduce a nucleic acid (e.g., an expression construct) into a cell. Suitable methods include, include e.g., viral or bacteriophage infection, transfection, conjugation, protoplast fusion, polycation or lipid:nucleic acid conjugates, lipofection, electroporation, nucleofection, immunoliposomes, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like.

The vector can be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector can comprise the nucleic acid sequence encoding the HiUGE system, including the nucleic acid sequence encoding the CRISPR-based nuclease, the nucleic acid sequence encoding the HiUGE vector, and the nucleic acid sequence encoding the GS-gRNA or gene specific vector.

a. Constructs and Plasmids

The genetic construct, such as a plasmid, expression cassette or vector, can comprise a nucleic acid that encodes the HiUGE system, or subcomponents thereof, such as the HiUGE vector, gene specific vector, CRISPR-based nuclease, HD-gRNA, GS-gRNA, and/or insert. The genetic construct can be present in the cell as a functioning extrachromosomal molecule. The genetic construct can be a linear minichromosome including centromere, telomeres or plasmids or cosmids. In some embodiments, the genetic construct can include at least one polynucleotide sequence of SEQ ID NO: 67-127, and/or combinations thereof. In some embodiments, the genetic construct can include at least one polynucleotide sequence of SEQ ID NO: 67-127, 152, 153, 154, and/or combinations thereof.

The genetic construct can also be part of a genome of a recombinant viral vector, including recombinant lentivirus, recombinant adenovirus, recombinant adenovirus associated virus, and recombinant herpes simplex virus (HSV). The genetic construct can be part of the genetic material in attenuated live microorganisms or recombinant microbial vectors which live in cells. The compositions, as described above, can comprise genetic constructs that encodes the modified Adeno-associated virus AAV vector and a nucleic acid sequence that encodes the HiUGE system, or subcomponents thereof, as disclosed herein. In some embodiments, the compositions, as described above, can comprise genetic constructs that encodes the modified adenovirus vector and a nucleic acid sequence that encodes the HiUGE system, or subcomponents thereof, as disclosed herein. The compositions, as described above, can comprise genetic constructs that encodes the modified lentiviral vector and a nucleic acid sequence that encodes the HiUGE system, or subcomponents thereof, as disclosed herein.

The nucleic acid sequences can make up a genetic construct that can be a vector. The vector can be capable of expressing the CRISPR-based nuclease, HD-gRNA, GS-gRNA, and/or insert in the cell of a mammal. The vector can be recombinant. The vector can comprise heterologous nucleic acid encoding the HiUGE vector, gene specific vector, CRISPR-based nuclease, HD-gRNA, GS-gRNA, and/or insert. The vector can be a plasmid. The vector can be useful for transfecting cells with nucleic acid encoding the HiUGE vector, gene specific vector, CRISPR-based nuclease, HD-gRNA, GS-gRNA, and/or insert, which the transformed host cell is cultured and maintained under conditions wherein expression of the CRISPR-based nuclease, HD-gRNA, GS-gRNA, and/or insert takes place.

In further embodiments of the disclosure, the genetic constructs and polynucleotides comprising polynucleotides encoding the CRISPR-based nuclease, HD-gRNA, GS-gRNA, and/or insert can be operatively associated with a variety of promoters, terminators and other regulatory elements for expression in various organisms or cells. In some embodiments, the genetic constructs can comprise regulatory elements for gene expression of the coding sequences of the nucleic acid. In some embodiments, the regulatory elements can be a promoter, an enhancer, an initiation codon, a stop codon, or a polyadenylation signal.

In representative embodiments, at least one promoter and/or terminator can be operably linked to a polynucleotide of the disclosure. Any promoter useful with this disclosure can be used and includes, for example, promoters functional with the organism of interest including but not limited to constitutive, inducible, developmentally regulated, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid. Accordingly, in representative embodiments, a nucleic acid construct encoding a polypeptide of a CRISPR-based nuclease and having a 5' end and a 3' end, can further comprise a promoter operably linked to 5' end of the at least one polynucleotide or nucleic acid construct and a polyA signal operably linked to the 3 end of the at least one polynucleotide or nucleic acid construct.

In some aspects, the polynucleotide, or polynucleotides encoding the HiUGE system that is introduced into a eukaryotic cell are operably linked to a promoter and/or to a polyA signal as known in the art. Therefore, in some aspects, the nucleic acid constructs of the disclosure encoding the polypeptides of the HiUGE system having a 5' end and a 3' end can be operably linked at the 5' end to a promoter and at the 3' end to a polyA signal. In some aspects, the nucleic acid constructs of the disclosure can comprise 2A peptide sequences and/or internal ribosomal entry sites as known in the art for assisting the co-translation of multiple independent polypeptides (proteins). In some aspects, the nucleic acid constructs of the disclosure encoding the polypeptides or proteins of the HiUGE system can be introduced into a eukaryotic cell via a plasmid, a viral vector, or a nanoparticle. In some embodiments, the polynucleotide or genetic construct encoding the HiUGE system, or subcomponents thereof, can be introduced in one construct or in different constructs.

An expression cassette also can optionally include a transcriptional and/or translational termination region (i.e., termination region) that is functional in the selected host cell. A variety of transcriptional terminators is available for use in expression cassettes and can be responsible for the termination of transcription beyond the heterologous nucleotide sequence of interest. The termination region can be native to the transcriptional initiation region, can be native to the operably linked nucleotide sequence of interest, can be native to the host cell, or can be derived from another source (i.e., foreign or heterologous to the promoter, to the nucleotide sequence of interest, to the host, or any combination thereof). In some embodiments of this disclosure, terminators can be operably linked to a recombinant polynucleotide(s) encoding the HiUGE system or subcomponents thereof.

An expression cassette also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence can encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Of course, many examples of suitable selectable markers are known in the art and can be used in the expression cassettes described herein.

In addition to expression cassettes, the recombinant polynucleotides described herein (e.g., polynucleotides comprising a polynucleotide encoding CRISPR-based nuclease) can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a eukaryotic host either by integration into the cellular genome or exist as an extrachromosomal element (e.g., minichromosome). In some embodiments, the recombinant polynucleotides described herein can be delivered as a ribonucleoprotein complex.

Additionally included are shuttle vectors by which is meant a DNA vehicle capable, naturally or by design, of replication in two different host organisms, such as broad-host plasmids or shuttle vectors with multiple origins-of-replication. In some representative embodiments, the nucleic acid in the vector is under the control of, and operably linked to, an appropriate promoter or other regulatory elements for transcription in a host cell. The vector can be a bi-functional expression vector which functions in multiple hosts. In the case of genomic DNA, this can contain its own promoter or other regulatory elements and in the case of cDNA this can be under the control of an appropriate promoter or other regulatory elements for expression in the host cell. Accordingly, a polynucleotide of this disclosure and/or expression cassettes comprising polynucleotides of this disclosure can be comprised in vectors as described herein and as known in the art. In some embodiments, the recombinant polynucleotides described herein can be delivered as a ribonucleoprotein complex.

Coding sequences can be optimized for stability and high levels of expression. In some instances, codons are selected to reduce secondary structure formation of the RNA such as that formed due to intramolecular bonding.

The vector can comprise heterologous nucleic acid encoding the HiUGE system, or subcomponents thereof, and can further comprise an initiation codon, which can be upstream of the HiUGE system, or subcomponents thereof, and a stop codon, which can be downstream of the HiUGE system, or subcomponents thereof. The initiation and termination codon can be in frame with the HiUGE system, or subcomponents thereof. The vector can also comprise a promoter that is operably linked to the HiUGE system, or subcomponents thereof.

The vector can also comprise a polyadenylation signal, which can be downstream of the HiUGE system, or subcomponents thereof. The polyadenylation signal can be a SV40 polyadenylation signal, LTR polyadenylation signal, bovine growth hormone (bGH) polyadenylation signal, human growth hormone (hGH) polyadenylation signal, or human O-globin polyadenylation signal. The SV40 polyadenylation signal can be a polyadenylation signal from a pCEP4 vector (Invitrogen, San Diego, CA).

The vector can also comprise an enhancer upstream of the HiUGE system, or subcomponents thereof. The enhancer can be necessary for DNA expression. The enhancer can be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector can also comprise a mammalian origin of replication in order to maintain the vector extrachromosomally and produce multiple copies of the vector in a cell. The vector can also comprise a regulatory sequence, which can be well suited for gene expression in a mammalian or human cell into which the vector is administered. The vector can also comprise a reporter gene, such as green fluorescent protein ("GFP") and/or a selectable marker, such as hygromycin ("Hygro").

In some embodiments, the genetic constructs can be located in a single vector or included on 3 different vectors. These constructs allow insertions to be made within a subject genome in dividing and non-dividing cells by HiUGE Technology.

(1) Promoters

Some embodiments of the present disclosure include genetic constructs for the polynucleotide sequences encoding the HD-gRNA molecule, the target gene gRNA molecule, and the insert. In some embodiments each may be operably linked to a promoter where the insert is operably linked to a first promoter, the HD-gRNA molecule is operably linked to a second promoter, and the target gene gRNA molecule is linked to a third promoter. In some embodiments, the first promoter, the second promoter, and/or the third promoter may be a constitutive promoter, an inducible promoter, a repressible promoter, or a regulatable promoter. In some embodiments all the polynucleotide sequences for the insert and the gRNA molecules may be operably linked to the same promoter wherein the promoter may be a constitutive promoter, an inducible promoter, a repressible promoter, or a regulatable promoter. In some embodiments, the promoter is a eukaryotic promoter.

Exemplary promoters useful with this disclosure include promoters functional in a eukaryote. Non-limiting examples of a eukaryote include a mammal, an insect, an amphibian, a reptile, a bird, a fish, a fungus, a plant, and/or a nematode.

In some embodiments, expression of a construct of the disclosure can be made constitutive, inducible, temporally regulated, developmentally regulated, or chemically regulated using the recombinant nucleic acid constructs of the disclosure operatively linked to the appropriate promoter functional in an organism of interest. In representative embodiments, repression can be made reversible using the recombinant nucleic acid constructs of the disclosure operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments of the disclosure, inducible promoters can be used. Thus, for example, chemical-regulated promoters can be used to modulate the expression of a gene in an organism through the application of an exogenous chemical regulator. Regulation of the expression of nucleotide sequences of the disclosure via promoters that are chemically regulated enables the RNAs and/or the polypeptides of the disclosure to be synthesized only when, for example, an organism is treated with the inducing chemicals. Depending upon the objective, the promoter can be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya et al. 2005. *Nature* 438:441-442).

In some embodiments, the promoter can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, a U6 promoter, such as the human U6 promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. In some embodiments, the promoter is a type III RNA polymerase III promoter. In some embodiments, the promoter is a U6 promoter, a H1 promoter, or a 7SK promoter. In some embodiments, the promoter can include at least one polynucleotide sequence of SEQ ID NO: 62-66, or combination thereof.

In some embodiments, the second polynucleotide sequence or polynucleotide sequence that encodes a HD-gRNA is operably linked to a first promoter and the third polynucleotide sequence or polynucleotide sequence that encodes a GS-gRNA is operably linked to a second promoter. In some embodiments, if the HIUGE System uses an Intein-Mediated Protein Splicing System Promoter, the second polynucleotide sequence or polynucleotide sequence that encodes a HD-gRNA is operably linked to a first promoter, the third polynucleotide sequence or polynucleotide sequence encoding a first portion of a CRISPR-based nuclease having a first split-intein is operably linked to a second promoter, the fourth polynucleotide sequence or polynucleotide sequence encoding a second portion of a CRISPR-based nuclease having a second split-intein complementary to the first split-intein is operably linked to a third promoter, and the fifth polynucleotide sequence or polynucleotide sequence that encodes a GS-gRNA is operably linked to a fourth promoter. In some embodiments, the fourth polynucleotide sequence and the fifth polynucleotide can be operably linked to the same promoter.

(2) Nuclear Localization Signal (NLS) and/or Nuclear Export Signal (NES)

In further aspects, the nucleic acid constructs of the disclosure can include one or more nuclear localization signals linked to the polynucleotides to move the polynucleotides from the cytoplasm into the nucleus. In further aspects, the nucleic acid constructs of the disclosure can include one or more nuclear export signals linked to the polynucleotides to move the polynucleotides from the nucleus into the cytoplasm. In some aspects, the HiUGE system encoded by the nucleic acid constructs of the disclosure can include separate nuclear localization signals and/or nuclear export signals. In some embodiments, the nuclear localization signal can include a polynucleotide sequence of SEQ ID NO: 52 or 53. In some embodiments, the nuclear export signal can include a polynucleotide sequence of SEQ ID NO: 51.

b. Viral Packaging

In some embodiments, one of, two of, or all three of genetic constructs for the HiUGE vector, the nucleic acid sequence encoding a CRISPR-based nuclease and/or the target gene vector may be packaged in a viral vector. In some embodiments, the HiUGE vector and the nucleic acid sequence encoding a CRISPR-based nuclease are packaged in the same viral vector. In some embodiments, the HiUGE vector and the target gene vector are packaged in the same viral vector. In some embodiments, the nucleic acid sequence encoding a CRISPR-based nuclease and the target gene vector are packaged in the same viral vector. In some embodiments all three of the genetic constructs are packaged in the same viral vector. In some embodiments all three of the genetic constructs are packaged in different viral vectors.

In some embodiments, the vector may be an adeno-associated virus (AAV) or a lentiviral vector. In some embodiments, each of the genetic constructs for the HiUGE vector, the nucleic acid sequence encoding a CRISPR-based nuclease, and the target gene vector are packaged into three separate AAV vectors.

(1) Modified Lentiviral Vector

Lentiviral vector is a vector belonging to the lentivirus family of retroviruses that are able to infect human and other mammalian species. The compositions for gene editing can include a modified lentiviral vector. The modified lentiviral vector can include one or more polynucleotide sequences encoding The CRISPR-based nuclease, the HiUGE vector, and/or a separate polynucleotide sequence encoding at least one GS-gRNA or gene specific vector. The modified lentiviral vector can include a first polynucleotide sequence encoding a HiUGE system, or subcomponents thereof. The one or more polynucleotide sequences can be operably linked to a eukaryotic promoter. The promoter can be a constitutive promoter, an inducible promoter, a repressible promoter, or a regulatable promoter. In some embodiments, the modified lentiviral vector can include a polynucleotide sequence of SEQ ID NO: 67-127, or combinations thereof.

In some embodiments, a second polynucleotide sequence can encode at least 1 GS-gRNA. For example, the second polynucleotide sequence can encode at least 1 GS-gRNA, at least 2 GS-gRNAs, at least 3 GS-gRNAs, at least 4 GS-gRNAs, at least 5 GS-gRNAs, at least 6 GS-gRNAs, at least 7 GS-gRNAs, at least 8 GS-gRNAs, at least 9 GS-gRNAs, at least 10 GS-gRNAs, at least 11 GS-gRNA, at least 12 GS-gRNAs, at least 13 GS-gRNAs, at least 14 GS-gRNAs, at least 15 GS-gRNAs, at least 16 GS-gRNAs, at least 17 GS-gRNAs, at least 18 GS-gRNAs, at least 19 GS-gRNAs, at least 20 GS-gRNAs, at least 25 GS-gRNA, at least 30 GS-gRNAs, at least 35 GS-gRNAs, at least 40 GS-gRNAs, at least 45 GS-gRNAs, or at least 50 GS-gRNAs. In some embodiments, the second polynucleotide sequence can encode between 1 GS-gRNA and 50 GS-gRNAs, between 1 GS-gRNA and 45 GS-gRNAs, between 1 GS-gRNA and 40 GS-gRNAs, between 1 GS-gRNA and 35 GS-gRNAs, between 1 GS-gRNA and 30 GS-gRNAs, between 1 GS-gRNA and 25 different GS-gRNAs, between 1 GS-gRNA and 20 GS-gRNAs, between 1 GS-gRNA and 16 GS-gRNAs, between 1 GS-gRNA and 8 different GS-gRNAs, between 4 different GS-gRNAs and 50 different GS-gRNAs, between 4 different GS-gRNAs and 45 different GS-gRNAs, between 4 different GS-gRNAs and 40 different GS-gRNAs, between 4 different GS-gRNAs and 35 different GS-gRNAs, between 4 different GS-gRNAs and 30 different GS-gRNAs, between 4 different GS-gRNAs and 25 different GS-gRNAs, between 4 different GS-gRNAs and 20 different GS-gRNAs, between 4 different GS-gRNAs and 16 different GS-gRNAs, between 4 different GS-gRNAs and 8 different GS-gRNAs, between 8 different GS-gRNAs and 50 different GS-gRNAs, between 8 different GS-gRNAs and 45 different GS-gRNAs, between 8 different GS-gRNAs and 40 different GS-gRNAs, between 8 different GS-gRNAs and 35 different GS-gRNAs, between 8 different GS-gRNAs and 30 different GS-gRNAs, between 8 different GS-gRNAs and 25 different GS-gRNAs, between 8 different GS-gRNAs and 20 different GS-gRNAs, between 8 different GS-gRNAs and 16 different GS-gRNAs, between 16 different GS-gRNAs and 50 different GS-gRNAs, between 16 different GS-gRNAs and 45 different GS-gRNAs, between 16 different GS-gRNAs and 40 different GS-gRNAs, between 16 different GS-gRNAs and 35 different GS-gRNAs, between 16 different GS-gRNAs and 30 different GS-gRNAs, between 16 different GS-gRNAs and 25 different GS-gRNAs, or between 16 different GS-gRNAs and 20 different GS-gRNAs. In some embodiments, each of the polynucleotide sequences encoding the different GS-gRNAs can be operably linked to a promoter. In some embodiments, the promoters that are operably linked to the different GS-gRNAs can be the same promoter. In some embodiments, the promoters that are operably linked to the different GS-gRNAs can be different promoters. The promoter can be a constitutive promoter, an inducible promoter, a repressible promoter, or a regulatable promoter. At least one GS-gRNA can bind to a target gene or loci. If more than one GS-gRNA is included, each of the GS-gRNAs binds to a different target region within one target loci or each of the GS-gRNA binds to a different target region within different gene loci.

(2) Adeno-Associated Virus Vectors

The AAV vector is a small virus belonging to the genus Dependovirus of the Parvoviridae family that infects humans and some other primate species. AAV can be used to deliver the compositions to the cell using various construct configurations. For example, AAV can deliver genetic constructs encoding CRISPR-based nucleases, inserts, and/or gRNA expression cassettes on separate vectors. The composition, as described above, includes a modified adeno-associated virus (AAV) vector. The modified AAV vector can be capable of delivering and expressing the CRISPR-based nuclease in the cell of a mammal. For example, the modified AAV vector can be an AAV-SASTG vector (Piacentino et al. (2012) Human Gene Therapy 23:635-646). The modified AAV vector can be based on one or more of several capsid types, including AAV1, AAV2, AAV5, AAV6, AAV8, AAV9, and AAV-PHP.eB. In some embodiments the AAV can transduce neurons retrogradely for neural circuit manipulations in brain tissue. In some embodiments, the AAV vector can include a polynucleotide sequence of SEQ ID NO: 152, 153, 154, or combinations thereof.

8. METHODS OF USING HOMOLOGY-INDEPENDENT UNIVERSAL GENOME ENGINEERING TECHNOLOGY

The present disclosure is also directed to methods of gene editing using the HiUGE systems, described above. The disclosed methods can be used for genome-wide protein labelling, expression marking, disruption of protein expression, protein re-localization, alteration of protein expression, or high throughput screening. In accordance with these embodiments, the method would allow for both speed and precision in applications including but not limited to antibody staining of fixed cells or tissues, live imaging of protein in cells or tissues, protein capture or affinity purification for protein complex identification, cell-type lineage tracing or labeling, and production of transgenic organisms with multiple different fusions to an individual gene. For example, the methods can be used with any of the HiUGE vector toolkits illustrated in FIGS. 2C-2G. For example, the methods can be used with (toolkit 1) antibody epitope tags, (toolkit 2) enzymes, (toolkit 3) fluorescent proteins, (toolkit 4) cellular trafficking tags (NLS=nuclear localization signal, NES=nuclear export sequence, mito=mitochondrial targeting sequence), and (toolkit 5) other payloads for specialized applications. In some embodiments, the methods can include using HiUGE vectors harboring short tag sequences, such as epitope tags and cellular trafficking tags, employ a dual-orientation design for efficient expression of the tag following either forward or reverse integration of the insert into the targeted genomic loci. In some embodiments, the methods can include using HiUGE vectors harboring longer insert sequences typically use a single orientation design that allows expression of the KI payload following forward integration. In some embodiments, in methods where there is a reverse integration of the payload into the genomic target, translation can be terminated by a stop codon cassette (FIG. 2H) in all three possible open reading frames (ORFs).

The disclosed methods involve contacting a cell with the HiUGE system described herein. In some embodiments, the CRISPR-based nuclease cleaves the at least one DRS flanking each side of the first polynucleotide and the target gene specific sequence, thereby generating a cleaved first polynucleotide sequence and a cleaved site of the target gene, wherein the cleaved first polynucleotide sequence is integrated into the cleaved site of the target gene by non-homologous end joining. In some embodiments, the CRISPR-based nuclease cleaves the at least one DRS and the target gene specific sequence consecutively or concurrently, thereby generating a cleaved insert. In some embodiments, the at least one insert or cleaved insert(s) is inserted at the N-terminal end of a promoter region, an enhancer region, a repressor region, an insulator region, a silencer region, a region involved in DNA looping with the promoter region, a gene splicing region, or a transcribed region to generate a N-terminal tagged fusion protein. In some embodiments, the at least one insert or cleaved insert(s) is inserted at the C-terminal end of a promoter region, an enhancer region, a repressor region, an insulator region, a silencer region, a region involved in DNA looping with the promoter region, a gene splicing region, or a transcribed region to generate a C-terminal tagged fusion protein.

In some embodiments, the at least one insert or cleaved insert(s) is inserted into the sense strand of the genome. In some embodiments, the at least one insert or cleaved insert(s) is inserted into the anti-sense strand of the genome. In some embodiments, the at least one insert or cleaved insert(s) is inserted in a forward orientation. In some embodiments, the at least one insert or cleaved insert(s) is inserted in a reverse orientation.

In some embodiments, the cell is a differentiating cell or a non-dividing cell. In some embodiments, the cell is a eukaryotic cell. In some embodiments, the cell is a human cell. In some embodiments, the cell is derived from endoderm, ectoderm, or mesoderm. In some embodiments, the subject genome is from a eukaryotic subject. In some embodiments, the subject genome is a mammalian subject. In some embodiments, the mammalian subject is a rodent or a primate.

9. METHODS OF DELIVERY

The genetic constructs disclosed in the present invention may be delivered using any method of DNA delivery to cells, including non-viral and viral methods. Common non-viral delivery methods include transformation and transfection. Non-viral gene delivery can be mediated by physical methods such as electroporation, microinjection, particle-medicated gene transfer ('gene gun'), impalefection, hydrostatic pressure, continuous infusion, sonication, chemical transfection, lipofection, or DNA injection (DNA vaccination) with and without in vivo electroporation. Viral mediated gene delivery, or viral transduction, utilizes the ability of a virus to inject its DNA inside a host cell. The genetic constructs intended for delivery are packaged into a replication-deficient viral particle. Common viruses used include retrovirus, lentivirus, adenovirus, adeno-associated virus, and herpes simplex virus. In some embodiments of the present invention, the adeno-associated virus is used for delivery of the genetic constructs.

10. CELL TYPES

Any of these delivery methods can be utilized with a myriad of cell types, including, but not limited to, prokaryotic cells or eukaryotic cells, such plant cells, insect cells, animal cells, such as mouse, rat, hamster, non-human primate, pig, or human cells. In some embodiments, the cell is a differentiating cell. In some embodiments, the cell is a non-dividing cell. In some embodiments, the cell is a eukaryotic cell. In some embodiments, the cell is a human cell. In some embodiments, the cell is a rodent cell.

In certain embodiments, the cell is transformed cell. In certain embodiments, the cell is selected from the group including, but not limited to, a myoblast, a fibroblast, a glioblastoma, a carcinoma, an epithelial cell, a stem cell. In certain embodiments, the cell is selected from the group including, but not limited to, a HEK cell, a HeLa cell, a vero cell, a BHK cell, a MDCK cell, a NIH 3T3 cell, a Neuro-2a cell, and a CHO cell.

In certain embodiments, the cell is derived from tissue (primary cell). In certain embodiments, the primary cell is a neuron. In certain embodiments, the primary cell is a a cardiomyocyte. In some embodiments, the cell is derived from endoderm, ectoderm, or mesoderm.

11. KITS

Provided herein is a kit, which may be used for gene editing, such as editing a gene to insert a marker or tag. The kit comprises a HiUGE system, as disclosed above. In some embodiments, the kit includes a HiUGE vector and a CRISPR-based nuclease. The kit comprises genetic constructs or a composition comprising thereof for genome editing, as described above, and instructions for using said composition. The genetic constructs (e.g., vectors) or a composition comprising thereof for making an insertion into a gene may include a modified AAV vector that includes an insert, gRNA molecule(s), and a CRISPR-based nuclease, as described above. The HiUGE system, as described above, may be included in the kit to specifically insert a certain type of tag or marker into the genome.

Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

12. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Homology-Independent Universal Genomic Engineering (HiUGE) Methods

Construction of HiUGE vectors. Both the gene-specific plasmid and the universal donor plasmid (HiUGE vector) were derived from the AAV:ITR-U6-gRNA(backbone)-hSyn-Cre-2A-EGFP-KASH-WPRE-shortPA-ITR plasmid (Addgene plasmid #60231).

$1^{st}$ generation ($1^{st}$ gen) HiUGE system: Two versions of the $1^{st}$ gen gene-specific gRNA (GS-gRNA) vector backbone were prepared by removing the HA-T2A-EGFP-KASH fragment and then for second non-neuronal version, the neuronal specific hSyn promoter was replaced with the Ef1α promotor. These vectors express Cre-recombinase and can be used in conjunction with Gt(ROSA) 26Sor$^{tm1(CAG-cas9*,-EGFP)Fezh}$ mice (Cas9 mice) for the induction of conditional Cas9 expression. For each gene of interest (GOI), GS-gRNA sequences targeting either the amino-terminus or the carboxyl-terminus were designed using an online gRNA evaluation tool "Crispor" (Haeussler et al., Genome Biol. (2016) 17(1):148), and cloned into the SapI site using restriction digestion/ligation cloning method for the U6 promotor-driven expression of GS-gRNA. 10 ng (~2 fmol) of the GS-gRNA backbone plasmid was digested with SapI enzyme (NEB R0569, 1 µL) and simultaneously ligated with 50 fmol of annealed 23-24 mer (including SapI sticky ends) GS-gRNA oligos with T4 DNA ligase (NEB M0202, 1 µL) in a 10 µL reaction, by 10 repeats of thermocycling between 37° C. (5 min) and 21° C. (5 min). Colony PCR was performed to detect GS-gRNA integration into the backbone plasmid using a forward primer in the upstream U6 promoter region, paired with the reverse GS-gRNA oligo as the reverse primer to amplify an ~100 bp amplicon. GS-gRNA target sequences used are listed in Table 1.

TABLE 1

| Oligonucleotides (gRNAs targets, payloads, primers) | Sequence (5'-3') | SEQ ID NO |
|---|---|---|
| mTubb3 GS-gRNA C-term ORF + 1 target | GATGTATGAAGATGATGACG | 169 |
| mMap2 GS-gRNA C-term ORF + 1 target (#1) | AGTGACATCCTCAGCCAAAG | 170 |
| mMap2 GS-gRNA C-term ORF + 0 target (#2) | TCAGCCAAAGTGGCAAGCTG | 171 |
| mMap2 GS-gRNA C-term ORF + 2 target (#3) | ACTGCGGCGCTTGCTAAGCA | 172 |
| mMecp2 GS-gRNA C-term ORF + 1 target | GTAAAGTCAGCTAACTCTCT | 173 |
| mActr2 GS-gRNA C-term ORF + 1 target | AGAAAGGGTGTCCGTGTGC | 174 |
| mClta GS-gRNA C-term ORF + 1 target | GGCTCTTCAGTGCACCAGGG | 175 |
| mNrcam GS-gRNA C-term ORF + 1 target | GAAAGAGAAAGAGCCAGCAG | 176 |
| mAnk3 GS-gRNA C-term ORF + 1 target | GAAGAAGGAAATCCGGAACG | 177 |
| mSptbn4-Exon36 GS-gRNA C-term ORF + 1 target | TACCACATCATCCACAGATG | 178 |
| mSptbn4-Exon31 GS-gRNA Trunc ORF + 1 target | CCAGGAGTTAGCGGATCGTG | 179 |
| mSptbn4-Exon26 GS-gRNA Trunc ORF + 1 target | GCTGGCGGCGGTCAACCAGA | 180 |
| mScn2a GS-gRNA C-term ORF + 1 target | GGACAAGGGGAAAGATATCA | 181 |
| mGfap GS-gRNA C-term ORF + 1 target | TATCTAAGGGAGAGCTGGCA | 182 |
| mPdha1 GS-gRNA C-term ORF + 1 target | GTTTAAGTCAGTCAGTTAAT | 183 |
| mDcx GS-gRNA C-term ORF + 1 target | CCTGTACCTGCCGCTGTCAT | 184 |
| mTubb5 GS-gRNA C-term ORF + 1 target | GGAAGAGGATTTCGGAGAGG | 185 |
| mInsyn1 (C15orf59) GS-gRNA C-term ORF + 1 target (#1) | GGCCACCAAACAGAAAGCTA | 186 |
| mInsyn1 (C15orf59) GS-gRNA C-term ORF + 1 target (#2) | TTTCTGTTTGGTGGCCGTAT | 187 |
| mInsyn1 (C15orf59) GS-gRNA C-term ORF + 0 target (#3) | AAGCTAAGGGCAAGAACTAG | 188 |

TABLE 1-continued

| Oligonucleotides (gRNAs targets, payloads, primers) | Sequence (5'-3') | SEQ ID NO |
|---|---|---|
| mInsyn2 (Fam196a) GS-gRNA C-term ORF + 0 target | AGTCCAAAAAGCATGGCAGG | 189 |
| mArhgap32 GS-gRNA C-term ORF + 0 target | TCTGCATGGATCTGCGTGTC | 190 |
| hTUBB GS-gRNA C-term ORF + 1 target | CGGTGAGGAGGCCGAAGAGG | 191 |
| mMap2 GS-gRNA N-term ORF + 1 target | TCCTTCATCTTTCCGCTCGT | 192 |
| mActb GS-gRN N-term ORF + 1 target | GGATGACGATATCGCTGCGC | 193 |
| mLmnb1 GS-gRNA N-term ORF + 1 target | CTGCTGCTGCACGGGGGTCG | 194 |
| mNefm GS-gRNA N-term ORF + 1 target | GGTCTCGGTGACCCGCCGGT | 195 |
| Primer mTubb3 (genomic) - Fwd | TGACCTGGTGTCCGAGTACCAGC | 196 |
| Primer mTubb3 (genomic) - Rev | GGACAGATGCTGCTTGTCTTGGC | 197 |
| Primer mMap2 (genomic) - Fwd | CGACGACTCAGCAAcurcT | 198 |
| Primer mMap2 (genomic) - Rev | GCCAAGAGCTCATGCCTAAATG | 199 |
| Primer mActr2 (genomic) - Fwd | GTTCTTGGGTGGCGCAGTC | 200 |
| Primer mActr2 (genomic) - Rev | CATTAGAGGCGTGATGGGGAC | 201 |
| Primer mClta (genomic) - Fwd | GCCAAAGATGTCTCTCGCAT | 202 |
| Primer mClta (genomic) - Rev | TTGGTCCAAAAGAACTCAACATAAT | 203 |
| Primer mSptbn4 (genomic) - Fwd | AACTCCGTGGCAGAACACG | 204 |
| Primer mSptbn4 (genomic) - Rev | CAGACTCCAAGGTGGGGAA | 205 |
| Primer mScn2a (genomic) - Fwd | GATAGCGTGACCAAACCGGA | 206 |
| Primer mScn2a (genomic) - Rev | ACATCACCAACACAGGCTGTAA | 207 |
| Primer HA payload (forward integration) - Rev | GCTCGAGCTTATCCCTATGACGTTCCT | 208 |
| Primer HA payload (reverse integration) - Rev | CGGATCCTACCCTTACGATGTACC | 209 |
| Primer U6 promotor (colony PCR) - Fwd | GGACTATCATATGCTTACCGTAACTTGAAAGTATTTCG | 210 |
| Primer ITR (AAV titering) - Fwd | GGAACCCCTAGTGATGGAGTT | 211 |

TABLE 1-continued

| Oligonucleotides (gRNAs targets, payloads, primers) | Sequence (5'-3') | SEQ ID NO |
|---|---|---|
| Primer ITR (AAV titering) - Rev | CGGCCTCAGTGAGCGA | 212 |
| Genome Walker GSP1 | CTCGAGCTTATCCCTATGACGTTCCTG | 213 |
| Genome Walker GSP2 | CTATGCTCTAGCTAGCTAGCTATGCGT | 214 |
| Primer PreOff_1 (genomic) - Fwd | GGAAGTTTGCCTGCTTAGCG | 215 |
| Primer PreOff_1 (genomic) - Rev | TAAAGAGGATCCATCGCCGC | 216 |
| Primer PreOff_2 (genomic) - Fwd | TCCTGTCTTATGCAGGTGGTC | 217 |
| Primer PreOff_2 (genomic) - Rev | AACCTTTTAGCATCTGGCCCAT | 218 |
| Primer PreOff_3 (genomic) - Fwd | TGAAAGATAGTGGCCTCGTGAA | 219 |
| Primer PreOff_3 (genomic) - Rev | CCCAGGTCCTGATTAACTGACA | 220 |
| Primer PreOff_4 (genomic) - Fwd | CCTGCTCTGAAGACGTCCAG | 221 |
| Primer PreOff_4 (genomic) - Rev | GGTGAGTCATGGTCACCACTAT | 222 |
| Primer PreOff_5 (genomic) - Fwd | CATTTGACATCCATTCTGATAAAGC | 223 |
| Primer PreOff_5 (genomic) - Rev | CCGAAGAGGAGATAAAGGCTGT | 224 |
| Primer PreOff_6 (genomic) - Fwd | GGGAGCTTTGGCTCCATTACATA | 225 |
| Primer PreOff_6 (genomic) - Rev | CGGTAAGAAGAGACCACAAGGAA | 226 |
| Primer PreOff_7 (genomic) - Fwd | GGCCATGAGTGGAAGATGGTATT | 227 |
| Primer PreOff_7 (genomic) - Rev | TCTCACAGATTAAAGTTAGGGTGTC | 228 |
| Primer PreOff_8 (genomic) - Fwd | GTGAAATGAATCCAGATGGAACCT | 229 |
| Primer PreOff_8 (genomic) - Rev | TCCAGTCAATTCCCCTTCCGC | 230 |
| Primer ExpOff_1 (genomic) - Fwd | TGGCACCAGCATCATCAAGT | 231 |
| Primer ExpOff_1 (genomic) - Rev | CTATCTCATGCCGGCTCTCC | 232 |
| Primer ExpOff_2 (genomic) - Fwd | GGGCATTGGCAAGAGCTGATAA | 233 |
| Primer ExpOff_2 (genomic) - Rev | ATTAGGGCTGGCTGTAGTGG | 234 |
| Primer ExpOff_3 (genomic) - Fwd | TGTCTTTTTCCATGACTACAACTC | 235 |
| Primer ExpOff_3 (genomic) - Rev | TTTGCTACGCTTTCTTCCCA | 236 |

For 1st gen HiUGE vectors, HiUGE vector specific gRNA (HD-gRNA) was cloned into the SapI site behind the U6 promotor. The fragment between the XbaI and PmlI restriction sites was replaced with a donor sequence containing the payload sequences (epitope tags, enzymes, fluorescent proteins, cellular trafficking tags, etc.) to be inserted to the targeted genomic loci. The payload sequence was flanked on both sides by donor recognition sequences (DRS) that were specifically recognized by the HD-gRNA. The HD-gRNA directed Cas9-mediated cleavage and release of the donor payload sequence to be inserted into the targeted genomic loci. Table 2 lists the 1st Generation HiUGE vectors used in the following Examples wherein the HD-gRNA of V2 has a sequence corresponding to gacgcttccgagtacggtac (SEQ ID NO:28) and the DRS Version was V1 (cctgtaccgtactcggaagcgtc (SEQ ID NO: 27)) or V2 (gacgcttccgagtacggtacagg (SEQ ID NO: 23)).

For HiUGE donor vectors, a donor-specific gRNA (HD-gRNA) was cloned into the SapI site behind the U6 promoter. The fragment between the XbaI and PmlI restriction sites was replaced with payload sequences to be inserted to the targeted genomic loci, such as epitope tags (HA, Myc, and V5), fluorescent proteins (see e.g., Shaner et al., 2004; Zacharias et al., 2002), "spaghetti monster" fluorescent protein-HA (Viswanathan et al., 2015), and cellular trafficking tag (SV40 nuclear localization signal, NLS). The payload sequences were flanked on both ends by a donor recognition sequence (DRS), that is an artificial sequence not present in the human or mouse genome and is specifically recognized by the HD-gRNA with low genomic off-target liability (specificity score of 98 or higher against human or mouse genome, no genomic targets within 3-base-pair mismatches), as predicted by CRISPOR and Cas-OFFinder (Bae et al., 2014b; Haeussler et al., 2016; Hsu et al., 2013). The HD-gRNA directs Cas9-mediated DRS cleavage and release of the payload sequence to be inserted into the targeted genomic locus. Exemplary DRS and payload sequences used in this study can be found in Table 1.

TABLE 2

| | Vector | SEQ ID NO | Insert | Insert | Insert | signal sequence | linker | HD-gRNA | DRS Version |
|---|---|---|---|---|---|---|---|---|---|
| 1st Gen HiUGE donor | 7 nm linker BioID2 3UTR ORF + 0.gb | 67 | BioID2 | | | | linker | V2 | V2 |
| | 7 nm linker BioID2 3UTR ORF + 1.gb | 68 | BioID2 | | | | linker | V2 | V2 |
| | 7 nm linker BioID2 3UTR ORF + 2.gb | 69 | BioID2 | | | | linker | V2 | V2 |
| | 7 nm linker BioID2 ORF + 0.gb | 70 | BioID2 | | | | linker | V2 | V2 |
| | 7 nm linker BioID2 ORF + 1.gb | 71 | Bio1D2 | | | | linker | V2 | V2 |
| | 7 nm linker BioID2 ORF + 2.gb | 72 | BioID2 | | | | linker | V2 | V2 |
| | 7 nm linker mCherry ORF + 0.gb | 73 | mCherry | | | | linker | V2 | V2 |
| | 7 nm linker mCherry ORF + 1.gb | 74 | mCherry | | | | linker | V2 | V2 |
| | 7 nm linker mCherry ORF + 2.gb | 75 | mCherry | | | | linker | V2 | V2 |
| | 7 nm linker mEGFP ORF + 0.gb | 76 | mEGFP | | | | linker | V2 | V2 |
| | 7 nm linker mEGFP ORF + 1.gb | 77 | mEGFP | | | | linker | V2 | V2 |
| | 7 nm linker mEGFP ORF + 2.gb | 78 | mEGFP | | | | linker | V2 | V2 |
| | HANES-X-revHANES ORF + 0.gb | 79 | HA | | | NES | | V2 | V1 |
| | HANES-X-revHANES ORF + 1.gb | 80 | HA | | | NES | | V2 | V1 |
| | HANES-X-revHANES ORF + 2.gb | 81 | HA | | | NES | | V2 | V1 |
| | HANLS-X-revHANLS ORF + 0.gb | 82 | HA | | | c-myc NLS | | V2 | VI |
| | HANLS-X-revHANLS ORF + 1.gb | 83 | HA | | | c-myc NLS | | V2 | V1 |
| | HANLS-X-revHANLS ORF + 2.gb | 84 | HA | | | c-myc NLS | | V2 | V1 |
| | HA-P2A-mCh-Fill ORF + 0.gb | 85 | HA | mCherry | P2A | | | V2 | V2 |
| | HA-P2A-mCh-Fill ORF + 1.gb | 86 | HA | mCherry | P2A | | | V2 | V2 |
| | HA-P2A-mCh-Fill ORF + 2.gb | 87 | HA | mCherry | P2A | | | V2 | V2 |
| | HA-P2A-mCh-Stop-3UTR Gene trap ORF + 0.gb | 88 | HA | mCherry | P2A | | | V2 | V2 |
| | HA-P2A-mCh-Stop-3UTR Gene trap ORF + 1.gb | 89 | HA | mCherry | P2A | | | V2 | V2 |
| | HA-P2A-mCh-Stop-3UTR Gene trap ORF + 2.gb | 90 | HA | mCherry | P2A | | | V2 | V2 |
| | HA-X-3UTR Truncation ORF + 0.gb | 91 | HA | | | | | V2 | V2 |
| | HA-X-3UTR Truncation ORF + 1.gb | 92 | HA | | | | | V2 | V2 |
| | HA-X-3UTR Truncation ORF + 2.gb | 93 | HA | | | | | V2 | V2 |
| | HA-X-revHA Turbo ORF + 0.gb | 94 | HA | | | | | V2 | V1 |
| | HA-X-revHA Turbo ORF + 1.gb | 95 | HA | | | | | V2 | V1 |
| | HA-X-revHA Turbo ORF + 2.gb | 96 | HA | | | | | V2 | V1 |
| | Myc-X-revMyc Turbo ORF + 0.gb | 97 | Myc | | | | | V2 | V1 |
| | Myc-X-revMyc Turbo ORF + 1.gb | 98 | Myc | | | | | V2 | V1 |
| | Myc-X-revMyc Turbo ORF + 2.gb | 99 | Myc | | | | | V2 | V1 |
| | N-term Myc ORF − 0.gb | 100 | Myc | | | | | V2 | V2 |
| | N-term Myc ORF − 1.gb | 101 | Myc | | | | | V2 | V2 |
| | N-term Myc ORF − 2.gb | 102 | Myc | | | | | V2 | V2 |
| | V5-X-revV5 Turbo ORF − 0.gb | 103 | V5 | | | | | V2 | V1 |
| | V5-X-revV5 Turbo ORE − 1.gb | 104 | V5 | | | | | V2 | V1 |
| | V5-X-revV5 Turbo ORF − 2.gb | 105 | V5 | | | | | V2 | V1 |
| 1st Gen HiUGE GS-Vector SapI | SapI-Ef1a-Cre.gb | 106 | | | | SV40 NLS | | None | None |
| | SapI-hSyn-Cre.gb | 107 | | | | SV40 NLS | | None | None |

2$^{nd}$ gen HiUGE system: For the 2$^{nd}$ gen HiUGE system, an intein-split-cas9 system (Truong et al., Nucleic Acids Res. (2015) 43(13):6450-8) was used to distribute Cas9 coding sequences to both the GS-gRNA vector and the HiUGE vector. In brief, the GS-gRNA vector was constructed by replacing hSyn-Cre of the 1$^{st}$ generation GS-gRNA vector with the EF1α/HTLV (nEF) promotor driving C-intein-C-Cas9 coding sequences. The 2$^{nd}$ gen HiUGE donor plasmid was similar to the 1$^{st}$ gen, with the addition of N-Cas9-N-intein coding sequences, also driven by EF1α/HTLV (nEF) promotor, behind the donor payload sequences. These plasmids were constructed with blocks of synthetic DNA fragments. Table 3 lists the 2nd Generation HiUGE vectors used in Example 7. These 2$^{nd}$ Generation HiUGE vectors included a signal sequence of SV40 NLS, a HD-gRNA of V2 (having a sequence corresponding to gacgcttccgagtacggtac (SEQ ID NO:28)) and a DRS of V2 (gacgcttccgagtacggtacagg (SEQ ID NO: 23)).

Glutamax and 10% FBS for 3 days. The AAV-containing supernatant medium was collected and filtered through a 0.45 µm cellulose acetate Spin-X centrifuge tube filter (Costar), and temporarily stored at 4° C. until ready to use.

Testing HiUGE application in vitro and in vivo. For testing 1$^1$ generation HiUGE system, a Cre-dependent conditional Cas9 expressing mouse line (Gt(ROSA) 26Sor$^{tm1(CAG-cas9*,-EGFP)Fezh}$ mice (Cas9 mice)) was used. Primary neuron cultures were prepared on poly-L-lysine coated coverslips using these Cas9 mice, and transduced with small scale AAV supernatant combinations. The filtered supernatant was added directly to primary culture together with media change on day in vitro (DIV) 4-6 for transduction (100-200 µL per well). NMDA receptor antagonist D-APV (33-66 µM final concentration) was added to protect neurons against toxicity associated with media change (Hogins et al., PLoS One. (2011) 6(9):e25633). Alternatively, combinations of small-scale AAV supernatants were added

TABLE 3

| Vector Base | Vector | SEQ ID NO | Insert | Insert | Insert linker | HD-gRNA | DRS | Cas |
|---|---|---|---|---|---|---|---|---|
| 2nd Gen HiUGE Donor | HA-P2A-Cre ORF + 0.gb | 108 | HA | Cre | P2A | V2 | V2 | N-Cas |
| | HA-P2A-Cre ORF + 1.gb | 109 | HA | Cre | P2A | V2 | V2 | N-Cas |
| | HA-P2A-Cre ORF + 2.gb | 110 | HA | Cre | P2A | V2 | V2 | N-Cas |
| | HA-P2A-Cre SV40-pA ORF + 0.gb | 111 | HA | Cre | P2A | V2 | V2 | N-Cas |
| | HA-P2A-Cre SV40-pA ORF + 1.gb | 112 | HA | Cre | P2A | V2 | V2 | N-Cas |
| | HA-P2A-Cre SV40-pA ORF + 2.gb | 113 | HA | Cre | P2A | V2 | V2 | N-Cas |
| | HA-X-3UTR ORF + 0.gb | 114 | HA | | | V2 | V2 | N-Cas |
| | HA-X-3UTR ORF + 1.gb | 115 | HA | | | V2 | V2 | N-Cas |
| | HA-X-3UTR ORF + 2.gb | 116 | HA | | | V2 | V2 | N-Cas |
| | HA-X-revHA Turbo ORF + 0.gb | 117 | HA | | | V2 | V2 | N-Cas |
| | HA-X-revHA Turbo ORF + 1.gb | 118 | HA | | | V2 | V2 | N-Cas |
| | HA-X-revHA Turbo ORF + 2.gb | 119 | HA | | | V2 | V2 | N-Cas |
| | mCherry ORF + 0.gb | 120 | mCherry | | linker | V2 | V2 | N-Cas |
| | mCherry ORF + 1.gb | 121 | mCherry | | linker | V2 | V2 | N-Cas |
| | mCherry ORF + 2.gb | 122 | mCherry | | linker | V2 | V2 | N-Cas |
| | mGFP ORF + 0.gb | 123 | mEGFP | | linker | V2 | V2 | N-Cas |
| | mGFP ORF + 1.gb | 124 | mEGFP | | linker | V2 | V2 | N-Cas |
| | mGFP ORF + 2.gb | 125 | mEGFP | | linker | V2 | V2 | N-Cas |
| 2nd Gen HiUGE GS-Vector SapI | SapI-nEF-Split HypaCas9.gb | 126 | | | | None | None | C-Cas9 (Hyper-accurate Cas9) |
| | SapI-nEF-Split SpCas9.gb | 127 | | | | None | None | C-Cas9 (S. pyogenes) |

AAV production. Purified AAV was produced based on a previously-described protocol (Uezu et al., Science. (2016) 353(6304):1123-9). Briefly, HEK293T cells were plated on six 15 cm dishes and transfected with 15 µg AAV vector, 30 µg helper plasmid pAd-DeltaF6, and 15 µg AAV serotype 2/9 plasmid with PEI when reaching 60-80% confluency. Cells were then incubated in antibiotic-free DMEM containing 10% fetal bovine serum (FBS), glutamine, and pyruvate. Cells were harvested 3 days after transfection and lysed with repeated (3 times) freeze-thaw cycles. Cell lysate was then applied to an Optiprep density gradient (Sigma, 15%, 25%, 40% and 60%) for ultracentrifugation purification. AAV-containing fraction was collected, then further concentrated by repeated washes with PBS in an Amicon Ultra filtration unit (NMWL: 100 kDa) to a final volume of ~100 µL and aliquoted for storage at −80° C. For small-scale AAV crude supernatant, HEK293T cells were plated on a 12 well plate, then transfected with 0.4 µg AAV plasmid, 0.8 µg helper plasmid, and 0.4 µg serotype 2/1 plasmid with PEI when cell density reached 60-80% confluency. Cells were incubated in glutamine-free DMEM supplemented with 1% to primary cultures at DIV 1 (in this case D-APV is not necessary); and incubated together with the neurons until the day of fixation to extend the accumulation period of the nascently modified proteins. For quantitative experiments, purified AAVs were added to primary cultures with the final concentration of 5×10$^{10}$ genome copies/mL per virus in the culture medium. On the day of fixation (DIV 11-14), cells were treated with 4% PFA+4% sucrose in PBS for 15 minutes at 4° C. and used for immunocytochemistry to detect HiUGE-mediated KI. For qualitative in vivo applications, purified high-titer AAVs were combined (GS-gRNA and donor payload, 1:1 v/v) and intracranially injected (—2 µL per hemisphere) to neonatal pups of Cas9 mice (P0-P2). For neural circuit-selective applications, adult Cas9 mice received a stereotaxic injection of purified AAV2-retro GS-gRNA virus into the brain area containing axon terminals of a specific neural circuit, whereas separate injections of purified AAV2/9 HiUGE donor virus were delivered into the brain area containing projection neuron cell bodies. 2-3 weeks after injection, mice were euthanized, and brains were isolated either fresh frozen with dry ice, or after transcardial perfusion, for immunohistochemistry to detect HiUGE-mediated KI.

For BioID applications, cells were treated with 20 μM biotin overnight the day before fixation. On the day of fixation (DIV11-14), cells were treated with 4% PFA+4% sucrose in PBS for 15 minutes at 4° C. and used for immunocytochemistry to detect HiUGE-mediated knock-in. For in vivo testing, purified AAV combinations were intracerebroventricularly injected to neonatal mouse pups. After 2 weeks, mice were sacrificed, and the brain were isolated either fresh frozen or after intracardial perfusion, for immunocytochemistry to detect HiUGE-mediated knock-in. For testing $2^{nd}$ generation HiUGE system, cells from wild-type mice or other common cell lines were used in place of the Cas9 mice for similar applications.

For HiUGE vectors that have built-in intein-split-Cas9 expression, primary culture derived from WT C57BL/6J mice (P0-P2) or other common cell lines (HeLa, HEK293T, NIH3T3) were used. Small-scale AAVs were used to transduce primary neurons as described above in similar applications. Further, to demonstrate that these HiUGE components were also suitable to be delivered via plasmid transfection rather than AAV transduction in common cell lines of human or mouse origin, HiUGE GS-gRNA and donor plasmids were co-transfected into HeLa, HEK293T, or NIH3T3 cells with PEI MAX (Polysciences 24765) or Lipofectamine 3000 (ThermoFisher L3000008) following manufacturer's protocol. Cells were fixed 2-4 days after transfection for immunocytochemistry to detect HiUGE-mediated KI. For in vivo testing, purified high-titer AAVs (GS-gRNA and donor payload) were combined, then stereotaxically injected to specific brain areas of adult WT mice. 2-3 weeks after injection, mice were euthanized, and transcardially perfused. Brains were isolated for immunohistochemistry to detect HiUGE-mediated KI.

Immunohistochemistry and immunocytochemistry. For immunohistochemistry (IHC), both fresh frozen specimen and perfused specimen were used. For fresh frozen specimen (mostly when working with axonal initial segment proteins), the animal was euthanized, and the brain was quickly isolated, frozen on crushed dry ice, coronally sectioned at 20 μm thickness and mounted on glass slides (VWR). The specimen was fixed with 4% PFA+4% sucrose in PBS for 15 minutes at 4° C. IHC was then performed. The specimen was blocked and permeabilized with blocking buffer containing 0.3% Triton-X, 5% normal goat serum (NGS, Sigma G9023) in PBS for 30-60 min at room temperature, and primary antibodies were applied for 2 hr at room temperature or at 4° C. overnight. Fluorescent secondary antibodies were applied for 30-60 min at room temperature, and counterstained with DAPI. For perfused specimen (when working with most other proteins), animal was euthanized and intracardially perfused with ice cold heparinized PBS, followed by 4% PFA in PBS, then post-fixed in 4% PFA overnight at 4° C. and cryoprotected in 30% sucrose+10% glycerol in PBS at 4° C. Brains were coronally sectioned at 40 μm thickness (free float). Similar IHC procedure was carried out as described above. The specimens were then mounted to glass slides with FluorSave medium (Calbiochem).

For immunocytochemistry (ICC), cells were fixed with 4% PFA+4% sucrose in PBS for 15 minutes at 4° C., then blocked and permeabilized with blocking buffer containing 0.3% Triton-X, 5% NGS in PBS for 30-60 min at room temperature. Primary antibodies were applied for 2 hr at room temperature or at 4° C. overnight. Fluorescent secondary antibodies were applied for 30-60 min at room temperature, and counterstained with DAPI. The coverslips were then mounted to glass slides with FluorSave medium (Calbiochem).

Primary antibodies used in this study were listed as following with dilutions indicated in parentheses: rat anti-HA (Roche/Sigma 11867423001, 1:1000), rabbit anti-Myc (Santa Cruz sc-789, 1:250), mouse anti-V5 (Thermo R960-25, 1:500), chicken anti-GFP (Abcam ab13970, 1:2000), rabbit anti-mCherry (Abcam ab167453, 1:1000), rabbit anti-Map2 (Synaptic Systems 188002, 1:5000). Additional primary antibodies used in this study were mouse anti-Ankyrin G (Santa Cruz sc-12719, 1:250) and guinea pig anti-VGAT (Synaptic Systems 131004, 1:2000). Fluorophore-conjugated secondary antibodies or reagents used in this study were listed as following: goat anti-rat Alexa 568 (Thermo A11077 1:1000), donkey anti-rabbit Alexa 647 (Thermo A31573, 1:1000), donkey anti-mouse Alexa 647 (Jackson ImmunoResearch 715-605-150, 1:1000), goat anti-chicken Alexa 488 (Thermo A11039 1:1000), goat anti-mouse Alexa 405 (Thermo A31553 1:1000), goat anti-rabbit Alexa 555 (Thermo A21428, 1:1000), goat anti-rat Alexa 647 (Thermo A21247, 1:1000), streptavidin Alexa 647 (Thermo S32357, 1:1000). Additional fluorophore-conjugated secondary antibodies or reagents used in this study were listed as following: donkey anti-rat Alexa 488 (ThermoFisher A21208, 1:1000), goat anti-rabbit Alexa 568 (ThermoFisher A11036, 1:1000), donkey anti-guinea pig Alexa 647 (Jackson ImmunoResearch 706-605-148, 1:1000), goat anti-rat Alexa 594 (Jackson ImmunoResearch 112-585-167, 1:1000), and goat anti-mouse Alexa 647 (Jackson ImmunoResearch 115-605-166, 1:1000).

Microscopic images were acquired with Zeiss 710 or Zeiss 880 inverted confocal microscopes, or with Zeiss Imager M2 upright microscope equipped with the Apotome 2.0 module. Exposures were manually adjusted for optimal dynamic range of each image. When experimental comparisons with control conditions were necessary, same exposure parameter was used across all specimen cohort. Tiling and z-stack were performed when necessary. Brightness, contrast, and gamma correction were adjusted for each channel using FIJI or Zeiss Zen. When comparisons against control conditions were necessary, identical exposure and adjustment parameters were used across the cohort. Live imaging was performed on Zeiss 710 microscope at 37° C., with 5% C02 incubation. Time series of z-stacked images were acquired every 100 s, then processed and exported at 6 fps in FIJI as videoclip followed by annotation in Adobe After Effects. All images were pseudo-colored for presentation with color assignments indicated in each panel.

Target Sequences: Table 4 shows a non-exhaustive list of target sequences used in the following examples.

TABLE 4

| Target Gene | Target Sequenee + PAM | SEQ ID NO: | gRNA | SEQ ID NO: |
|---|---|---|---|---|
| mTubb3 | gatgtatgaagatgatgacgagg | 128 | gatgtatgaagatgatgacg | 140 |
| mMap2 | agtgacatcctcagccaaagtgg | 129 | gagtgacatcctcagccaaag | 141 |

TABLE 4-continued

| Target Gene | Target Sequenee + PAM | SEQ ID NO: | gRNA | SEQ ID NO: |
|---|---|---|---|---|
| mMecp2 | gtaaagtcagctaactctctcgg | 130 | gtaaagtcagcctaactctct | 142 |
| mNrCam | gaaagagaaagagccagcagagg | 131 | gaaagagaaagagccagcag | 143 |
| mActr2 | agaaaagggtgtccgtgtgctgg | 132 | gagaaaagggtgtccgtgtgc | 144 |
| mClta | ggctcttcagtgcaccaggggggg | 133 | ggctcttcagtgcaccaggg | 145 |
| mAnk3 | gaagaaggaaatccggaacgtgg | 134 | gaagaaggaaatccggaacg | 146 |
| mSptbn4 | taccacatcatccacagatgagg | 135 | gtaccacatcatccacagatg | 147 |
| mScn2a | ggacaaggggaaagatatcaggg | 136 | ggacaaggggaaagatatca | 148 |
| mGfap | tatctaagggagagctggcaggg | 137 | gtatctaagggagagctggca | 149 |
| mPdha1 | gtttaagtcagtcagttaatggg | 118 | gtttaagtcagtcagttaat | 150 |
| mDcx | cctgtacctgccgctgtcattgg | 139 | gcctgtacctgccgctgtcat | 151 |

Primary mouse hippocampal and cortical neuron/glia culture. Primary neuron/glia cultures were derived from Gt(ROSA)26Sor$^{tm1(CAG\text{-}cas9^*,\text{-}EGFP)Fezh}$ or C57BL/6J (Jackson Laboratory) neonatal pups (P0-P2). Primary culture was performed following a previously described method (Uezu et al., 2016). Briefly, after euthanasia, brains were rapidly collected, and hippocampi or cortices were isolated. Cells were gently dissociated with fire polished glass pipettes following papain digestion (Worthington), and plated at a density of ~100,000 cells per cm2 (for imaging, hippocampal cells), or ~300,000 cells per cm$^2$ (for DNA/protein preparation, cortical cells) on poly-L-lysine (Sigma P2636) coated surfaces. Cells were then maintained in Neurobasal A medium (ThermoFisher 10888022) supplemented with 2% B27 (ThermoFisher 17504044) and 1% GlutaMAX (ThermoFisher 35050061) at 37° C., 5% $CO_2$. Glia growth was inhibited by adding cytosine arabinoside (Sigma C1768, 5 uM final concentration) together with media change between DIV 4-6, when necessary.

Cell culture of HEK293T, HeLa, and NIH3T3 cell lines. Cell lines used in this study include HEK293T (ATCC CRL-11268), HeLa (ATCC CCL-2), and NIH3T3 (ATCC CRL-1658). All cell lines were maintained in DMEM (Gibco 11965-092) supplemented with 10% fetal bovine serum (Sigma F4135) and 1% Penicillin-Streptomycin (ThermoFisher 15140122) at 37° C., 5% $CO_2$, and passaged by trypsin/EDTA digestion (ThermoFisher 25200056) upon reaching ~95% confluency.

Stereotaxic Injections. For stereotaxic injections, adult mice were anesthetized through inhalation of 1.5% isofluorane gas and placed in a stereotaxic frame (Kopf Instruments). Mice were administered meloxicam (~10 μL/25 g) subcutaneously before the beginning of surgery to reduce inflammation. After confirming that Lambda and Bregma were on the same dorsal-ventral plane, craniotomies were made with a high speed drill (Foredom MH-170) over either motor cortex (0.5 A/P, 0.6-1.0 L, 1.2 V), striatum (0.5 A/P, 2.0 L, 3.2 V), thalamus (~1.7 AP, 1.2 L, 3.4 V), posterior somatosensory cortex (~1.7 A/P, 3.5 L, 1.2 V), or dorsal hippocampus (~1.6 A/P, 2.2 L, 1.3 V), in reference to the Allen Mouse Brain Atlas (Lein et al., 2007). Using a precision pressure injection system (Drummond Nanoject), a glass pipette filled with virus was lowered to the desired depth, slightly retracted (~0.2 mm), and small amounts of virus were injected over a period of ~10 minutes (30 injections of 18-32 nL every 20 seconds). After waiting for an additional 5-10 minutes to prevent efflux of virus during pipette retraction, the glass pipette was retracted from the brain and the skin over the craniotomy was sutured shut. After applying several drops of topical anesthetic to the incision (bupivacaine) and administering an analgesic subcutaneously (buprenorphine, —25 μL/25 g), mice were allowed to recover under a heat lamp for 20-30 minutes and then placed in their home cage.

Western Blot. Cells were collected in ice cold RIPA buffer supplemented with proteinase inhibitor cocktail and sonicated. Protein concentrations were determined by BCA method and equal amounts of protein were heated in sample buffer at 95° C. for 5 min, loaded for SDS/PAGE electrophoresis, then transferred to a nitrocellulose membrane. Following blocking in blocking buffer (Rockland), the membrane was sequentially probed for HA-epitope (primary: rat anti-HA, Roche/Sigma 11867423001, 1:2000; secondary: IRDye 800CW goat anti-rat, 1:10,000) and house-keeping gene GAPDH (primary: rabbit anti-GAPDH, Abcam ab9485, 1:5000; secondary: IRDye 680RD goat anti-rabbit, 1:10,000). Both primary and secondary antibodies were incubated for 1 hr at room temperature. Immunofluorescence signal was detected on Odyssey FC imager (LI-COR). For immunoprecipitation (IP)-enriched Western blot, equal amount of inputs (300 μg) were mixed with 30 μL mouse anti-HA beads (ThermoFisher 26181) and incubated at 4° C. overnight on a nutator. After washes with RIPA buffer, proteins were eluted by boiling in 80 μL sample buffer at 95° C. for 5 min. Equal volume of the eluted IP-samples and equal amount of the input samples were loaded for SDS/PAGE and then transferred to nitrocellulose membranes. The IP-membrane was sequentially probed for HA-epitope (primary: Sigma H6908, 1:2000; secondary: IRDye 800CW goat anti-rabbit, 1:10,000) and the input membrane was probed for house-keeping gene GAPDH (primary: Abcam ab9485, 1:5000; secondary: IRDye 680RD goat anti-rabbit, 1:10,000). Both primary and secondary antibodies were incubated for 1 hr at room temperature in CanGetSignal solutions (TOYOBO NKB-101T). Immunofluorescence signal was detected on Odyssey FC imager (LI-COR).

Genomic PCR, TOPO Cloning and DNA Sequencing. Genomic DNA was extracted by MyTaq Extraction-PCR kit (Bioline BIO-21127) or PureLink Genomic DNA Mini Kit (ThermoFisher K182001) from primary neurons after HiUGE editing. Genomic polymerase chain reaction (PCR) using MyTaq HS polymerase (Bioline BIO-25045 or BIO-25047) was performed to detect the insertion of the dual-orientation HA-epitope payload using primers indicated in Table 1. A primer specific for the endogenous genomic sequence upstream of the edited locus was paired with an orientation-selective HA-epitope payload primer to amplify the edited genomic locus and differentiate forward versus reverse payload integration. PCR products were isolated by gel purification (NucleoSpin Gel and PCR Clean-up kit, Macherey Nagel 740609) and TOPO-cloned (ThermoFisher K457501) for sequencing using a common M13F(−21) primer (Eton Bioscience). For indel estimation, genomic DNA were extracted from triplicate neuronal samples following HiUGE-mediated HA-epitope KI. Genomic PCRs were performed as described above. The PCR products were cleaned up (NucleoSpin Gel and PCR Clean-up kit, Macherey Nagel 740609), combined into three independent pools, and deep sequenced on a MiSeq system (Illumina) by the Duke Sequencing and Genomic Technologies Shared Resource.

QUANTIFICATION AND STATISTICAL ANALYSIS. For immunofluorescence quantification of C-term HA-epitope KI to mTubb3, microscopic images were taken by an experimenter blinded to the experimental groups, using identical exposure parameter across the cohort. Three coverslips were used per experimental group, with three microscopic images taken per coverslip at random locations. The HA immunofluorescence intensity of an image was quantified by FIJI after automatic background subtraction. The total cell count of an image was estimated by particle analysis of DAPI fluorescence in FIJI. A ratio of mean HA immunoreactivity over cell count was computed, then normalized on a scale of 0-100 arbitrary unit (a.u.), against the negative group (no virus added) and the positive group (mTubb3 GS-gRNA plus HiUGE donor ORF+1). The normalized ratio was defined as the "mean fluorescence intensity". The quantification results were averaged for each coverslip, and reported as a data point (n=3 coverslips). For immunofluorescence quantification of C-term HA-epitope KI to AIS protein targets, microscopic images were taken by an experimenter blinded to the experimental groups, using identical exposure parameter across the cohort. Three coverslips were used per experimental group, with three microscopic images taken per coverslip at random locations. The number of AIS structures positive for HA-epitope immunofluorescence and the total number of Ank-G-positive AIS were manually counted, then converted into percentages for analysis. The quantification results were averaged for each coverslip, and reported as a data point (n=3 coverslips). Error bars represent standard error of the mean (SEM). To detect pairwise differences, one-way ANOVA followed by post-hoc Tukey-Kramer HSD was performed in JMP Pro (v13, SAS), with significance level set at 0.05.

Quantitative estimation of indel rate at the edited junctions was performed by the Duke Genomic Analysis and Bioinformatics Shared Resource. Raw single-end read sequences were trimmed of adapter and poor-quality sequences using the Trim Galore Toolkit (v 0.5.0, available at URL: www.bioinformatics.babraham.ac.uk/projects/trim_galore), which employs Cutadapt (Martin, 2011) (v 1.18). The quality of the raw reads was verified by examining the FastQC (v 0.11.5, available at URL: www.bioinformatics.babraham.ac.uk/projects/fastqc) output from Trim Galore. A reference FASTA file containing the amplicon sequence for each of the genes by integration (forward and reverse) combinations was prepared, which included ten sequences in total. Quality-trimmed reads were aligned to the reference FASTA file with bwa-mem (Li and Durbin, 2009) (v0.7.17) with default parameters and post-processed with SAMtools (Li et al., 2009) (v.9). A custom Python script was used to filter the SAM file for aligned reads with the supplementary alignment (0×800) flag, and to filter for reads with overlap of the integration site. Specifically, the start alignment position of the read was used to verify that the read started at least 30 bp downstream of the integration site and the cigar string was parsed to verify that the read extended past 30 bp upstream of the integration site; the integration site position varied with each gene. For cumulative read counts, the SAM file was then parsed with a custom Python script and each read that contained an indel was tallied. For positional read counts, Picard (available at URL: broadinstitute.github.io/picard) was used to add read group information and index the bam file. Indels were then called with GATK HaplotypeCaller (McKenna et al., 2010) (v3.8-1-0-gf15c1c3 ef). In order to call indels on all reads, some parameters were modified from default (min_mapping_quality_score=0; min_base_quality_score=0, max_alternate_alleles=50, output_mode=EMIT_ALL_SITES, emitRefConfidence=BP_RESOLUTION). The resulting VCF file was then filtered to exclude any sites with single nucleotide polymorphisms and to count the number of reads at each site containing an insertion or deletion. For all analyses, each of the three pools were treated independently until calculation of mean and standard error of the mean for both positional and cumulative data.

Example 2

HiUGE vector Recognition Sequence Rules

Figure 3A:
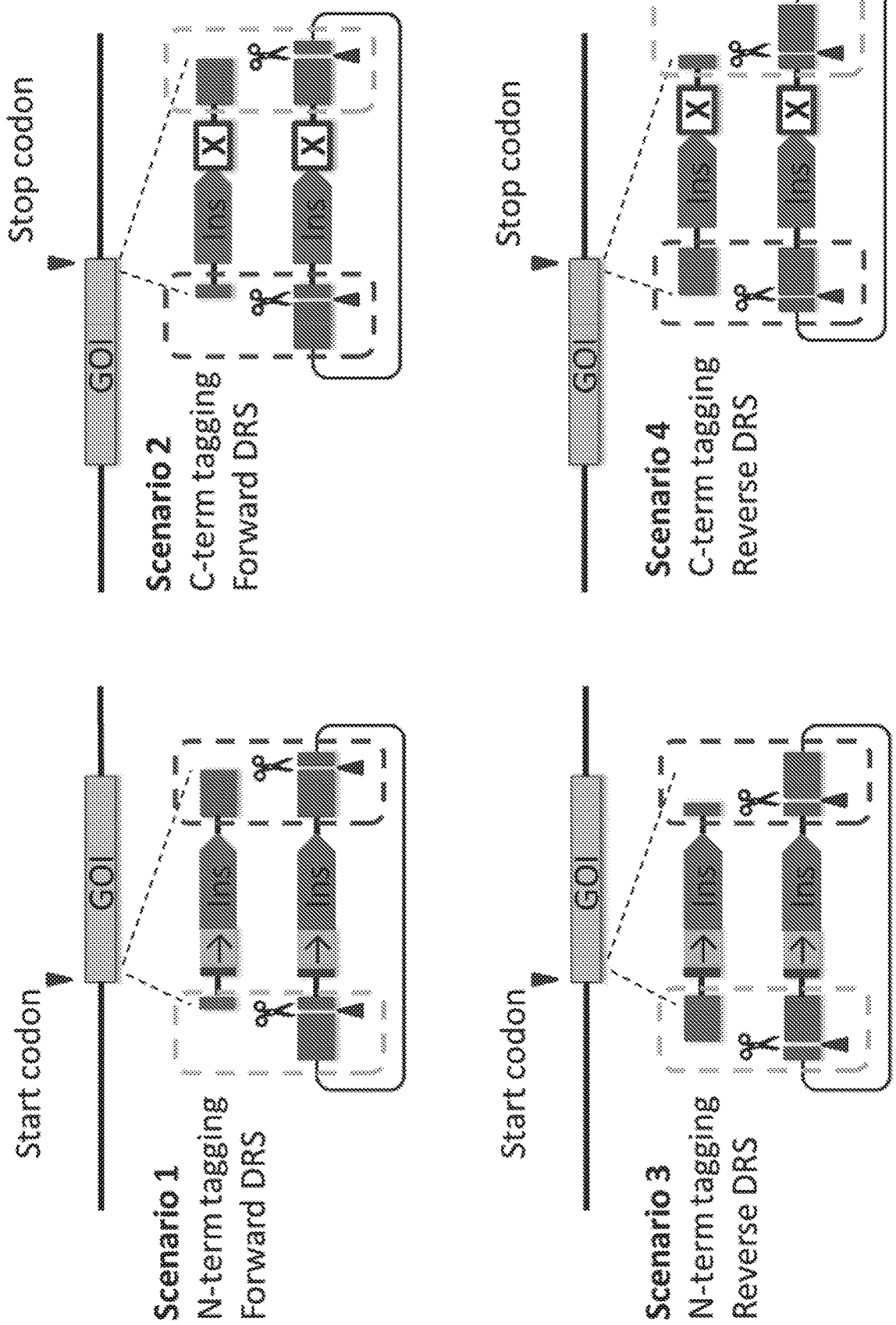
FIG. 3A shows an illustration of example donor recognition sequence (DRS) usage scenarios and the corresponding applicability of the rules governing the DRS sequences.
Figure 3D:
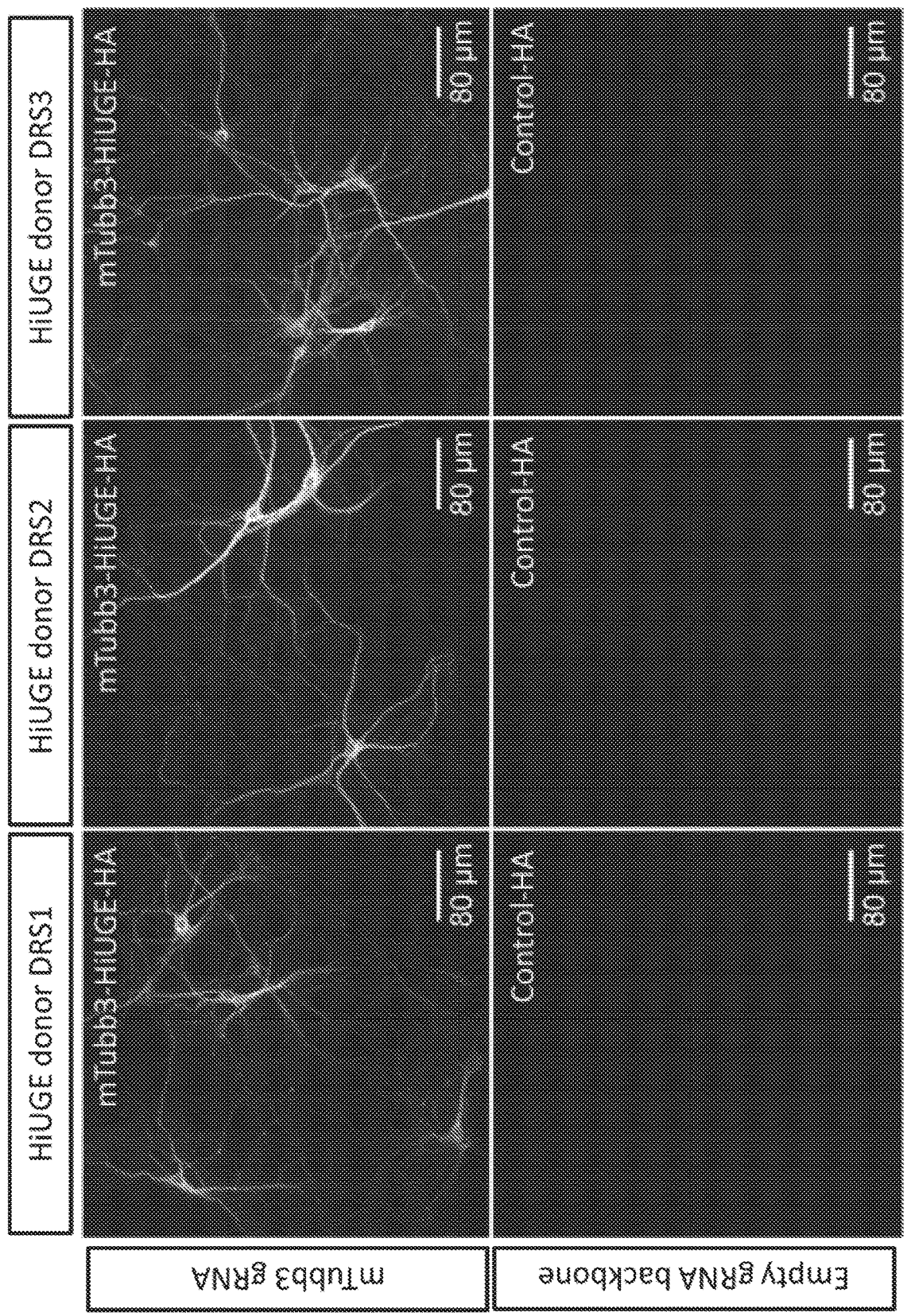
FIGS. 3D-3G show representative images showing in vitro testing of the 5 exemplary DRS for HiUGE mediated hemagglutinin (HA) antibody epitope knock-in to the mouse Tubb3 gene in cultured hippocampal neurons derived from Cas9 expressing mice by HA antibody immunostaining.
Figure 3E:
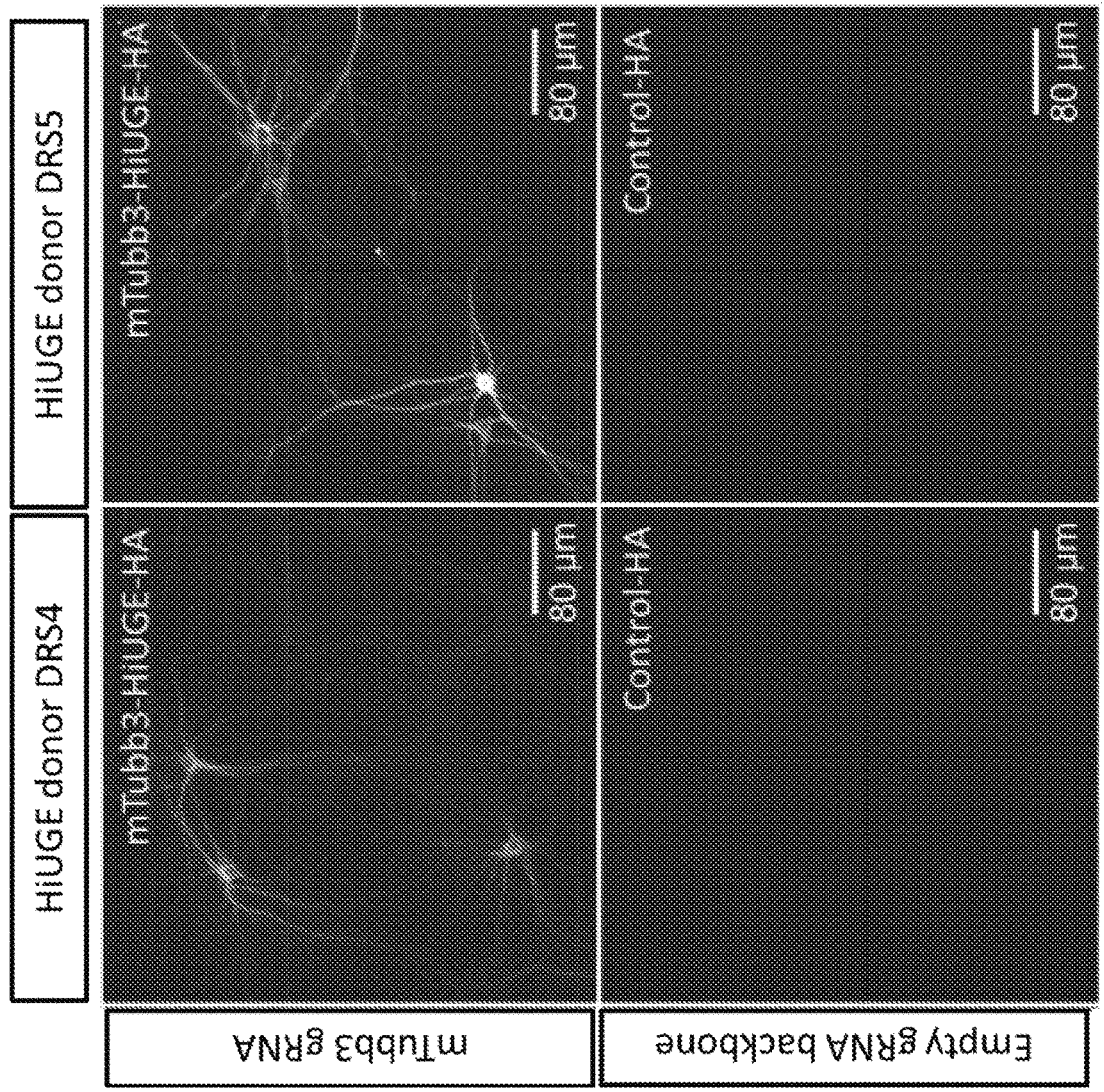

FIG. 3A shows an illustration of example donor recognition sequence (DRS) usage scenarios and the corresponding applicability of the rules governing the DRS sequences with FIG. 3B showing the legend for FIG. 3A. In FIG. 3A, HiUGE vectors are represented as circular plasmids at the bottom of each panel. The orientation of the Donor Recognition Sequence (DRS) is represented by the orientation of the Cas9 cleavage site relative to the insert (forward orientation in top panels, reverse orientation in bottom panels). Following donor vector cleavage, the foreign sequence (payload) to be inserted into the target genome gene of interest (GOI) is represented in each panel as a linear cassette. Sequences referred to in the text for determining the rules of the DRS in each scenario are encircled by dark dashed lines.

FIG. 3C shows a list of 5 exemplary DRS sequences. The specificities of the corresponding HiUGE vector specific gRNA (HD-gRNA) for each exemplary DRS sequence against the target genome (mouse MM10 genomic assembly) was predicted by the online gRNA evaluation tool "Crispor." High specificity scores of these HD-gRNAs indicate their low likelihood of inducing genomic cleavages. Check marks indicate the suitability of the DRS for specific usage scenarios and ORFs. Dots indicate the DRS does not meet criteria for a specific usage scenario and ORF.

Figure 3F:
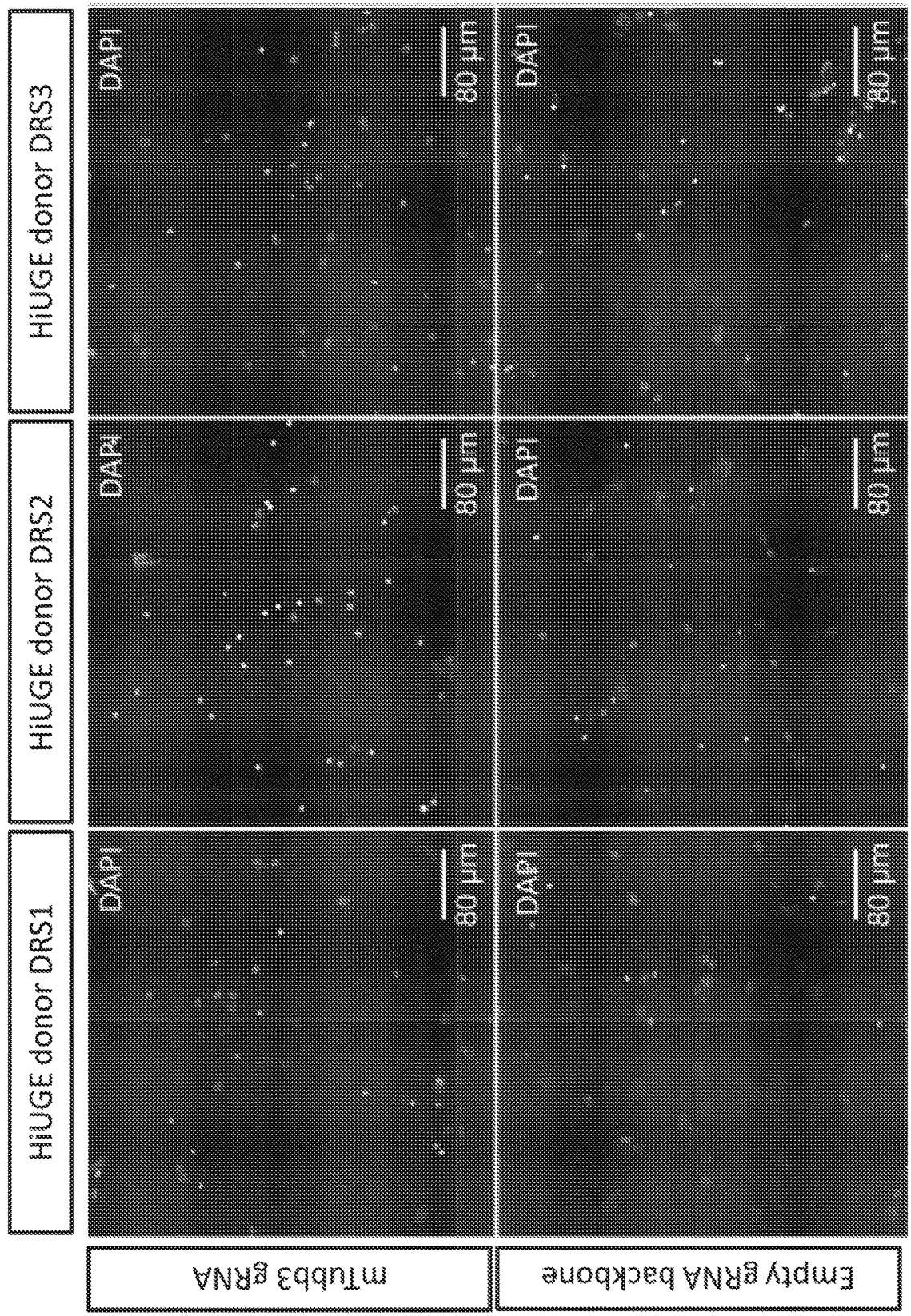
Figure 3G:
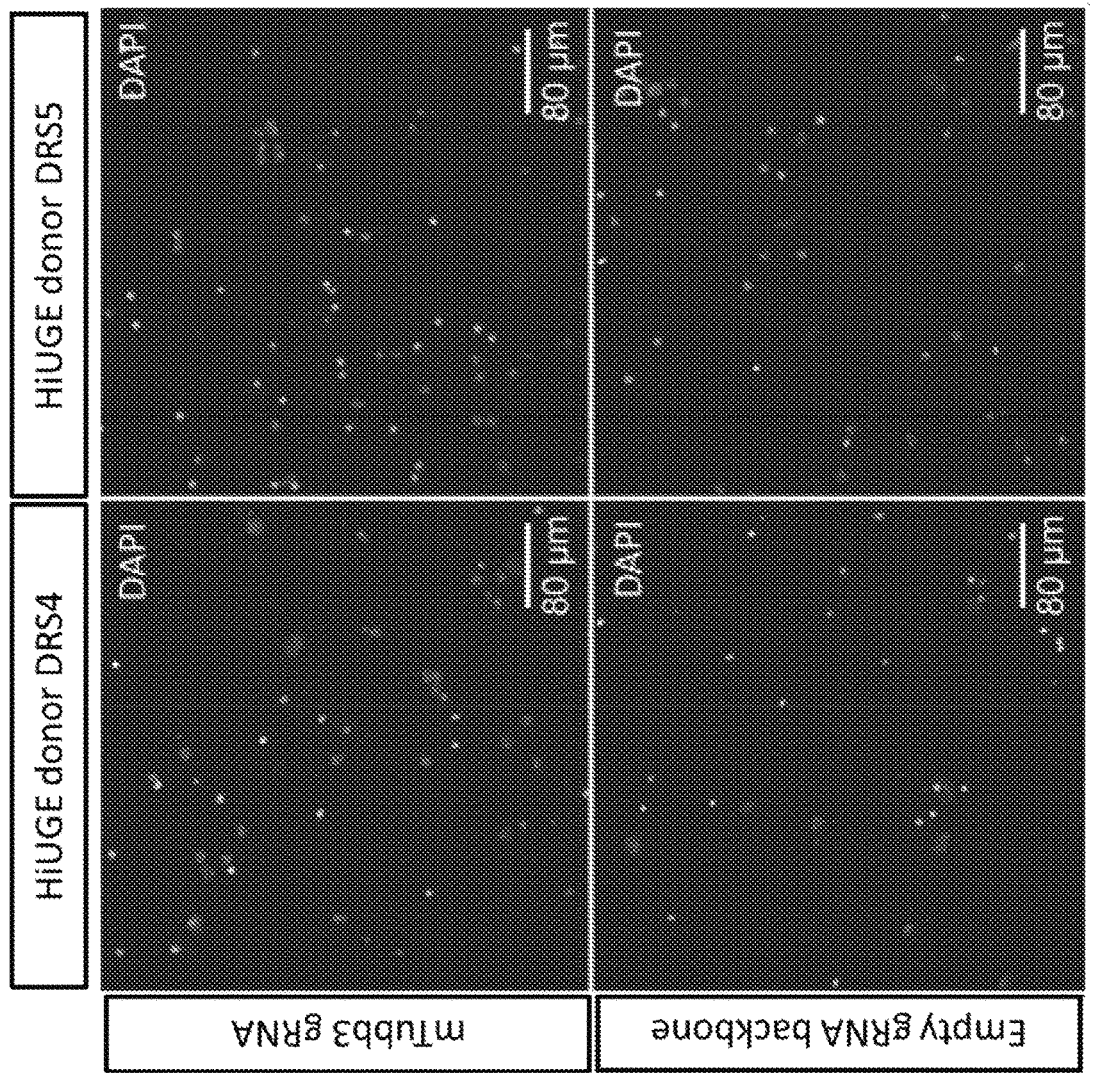

FIGS. 3D-3G show representative images of in vitro testing of the 5 exemplary DRS for HiUGE mediated HA antibody epitope knock-in to the mouse Tubb3 gene in cultured hippocampal neurons derived from Cas9 expressing mice by HA antibody immunostaining. All 5 HiUGE vectors constructed with the 5 exemplary DRS sequences successfully induced HA-epitope KI when paired with Tubb3 GS-gRNA vector (upper row panels in FIGS. 3D and 3E). Control experiments where the donor vectors were paired with an empty GS-gRNA backbone vector (lower row) were negative for HA immunoreactivity. FIGS. 3F and 3G show DAPI (3',6-diamidino-2-phenylindole) staining to visualize nuclei in each corresponding image in FIGS. 3D and 3E, respectively, demonstrating similar cell densities in each panel. Scale bar is indicated in each panel.

Example 3

HiUGE Concept and Specificity

Figure 4D:
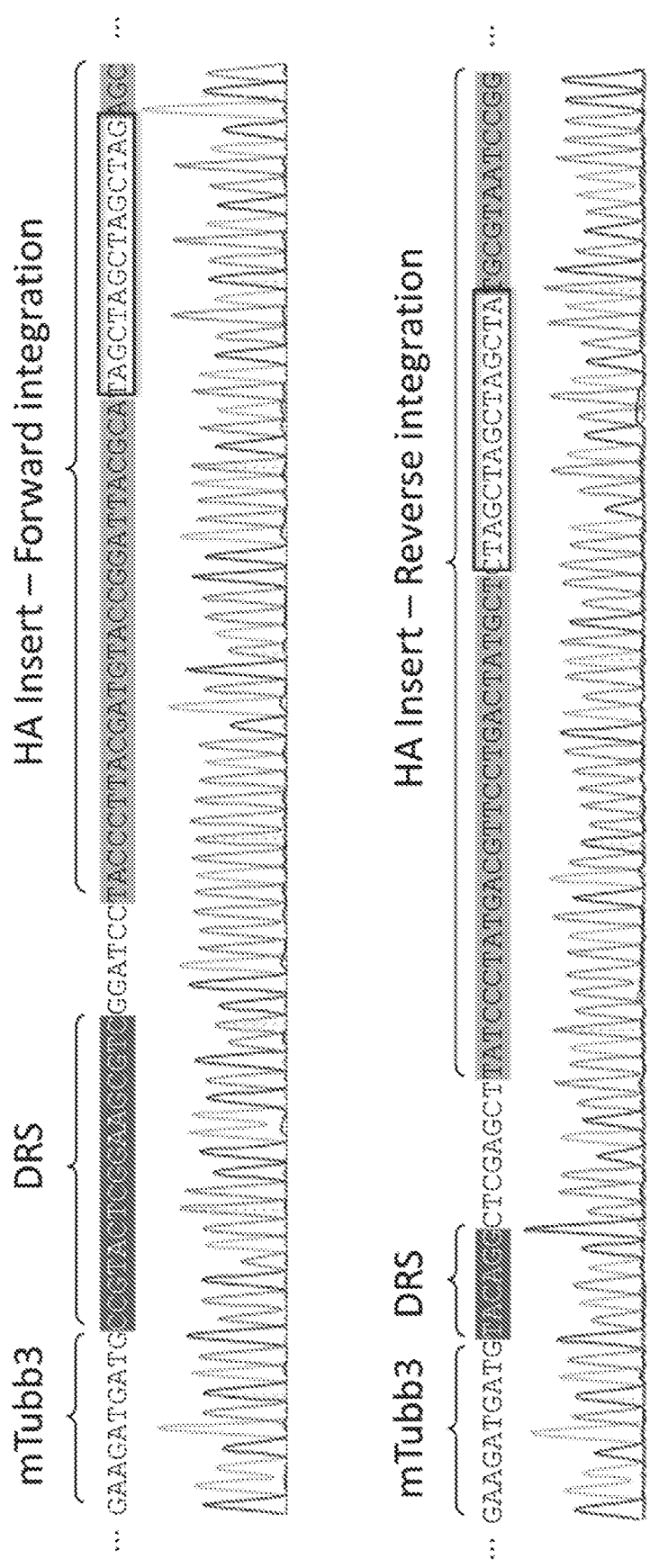
FIG. 4D shows representative sequencing results (SEQ ID NOS: 32 (top) and 33 (bottom)) demonstrating correct HA epitope integration in both forward or reverse orientation. Boxed sequences correspond to the stop codon cassettes (SEQ ID NOS: 29 and 30).

FIG. 4A shows a schematic illustration of an example of HiUGE application for bidirectional HA epitope knock-in (KI) in vitro. Primary hippocampal cells from Cas9 mice were transduced with a combination of GS-gRNA AAV vector and HiUGE donor AAV vector between day in vitro (DIV) 4-6. Cells were fixed after DIV 11 for immunocytochemistry to detect HA epitope KI. FIG. 4B shows a representative image of immunostaining showing HA epitope KI into the mouse Tubb3 (mTubb3) gene showing microtubule labeling. FIG. 4B shows the characteristic microtubule expression pattern of the HA-epitope labeled III-tubulin following HiUGE editing. GFP fluorescence of the Cas9-2A-GFP and nuclei labeling with DAPI (4',6-diamidino-2-phenylindole) are also shown. Approximately 1 week following infection, immunofluorescent detection of HA showed successful HA-epitope labeling of endogenous DIII-tubulin, with localization characteristics specific to microtubules (FIG. 4B). FIG. 4D shows the genomic integration locus was isolated by polymerase chain reaction (PCR). The PCR product was isolated and cloned into pCR4-TOPO vector for sequencing. Representative sequencing results demonstrating correct HA epitope integration in both forward or reverse orientation are shown. Regions of sequence containing genomic mTubb3, DRS, or HA cassette are indicated above. Boxed sequence represents the stop codon cassette of FIG. 4D.

As a proof-of-principle experiment, small-scale AAVs of a GS-gRNA targeting the mouse Tubb3 (mTubb3) gene and a dual-orientation HA-epitope HiUGE donor were used to co-transduce primary neurons prepared from neonatal pups of conditional Cas9 mice. The GS-gRNA AAV simultaneously expresses Cre-recombinase to induce conditional Cas9-2A-GFP expression. Approximately 1 week following infection, immunofluorescent detection of HA showed successful HA-epitope labeling of endogenous βIII-tubulin, with localization characteristics specific to microtubules (FIG. 4B). FIG. 4B shows the characteristic microtubule expression pattern of the HA-epitope labeled βIII-tubulin following HiUGE editing. Western blot detection of the HA-epitope showed a single band (~51 kD) consistent with the predicted molecular mass of βIII-tubulin (FIG. 4C).

Figure 4E:
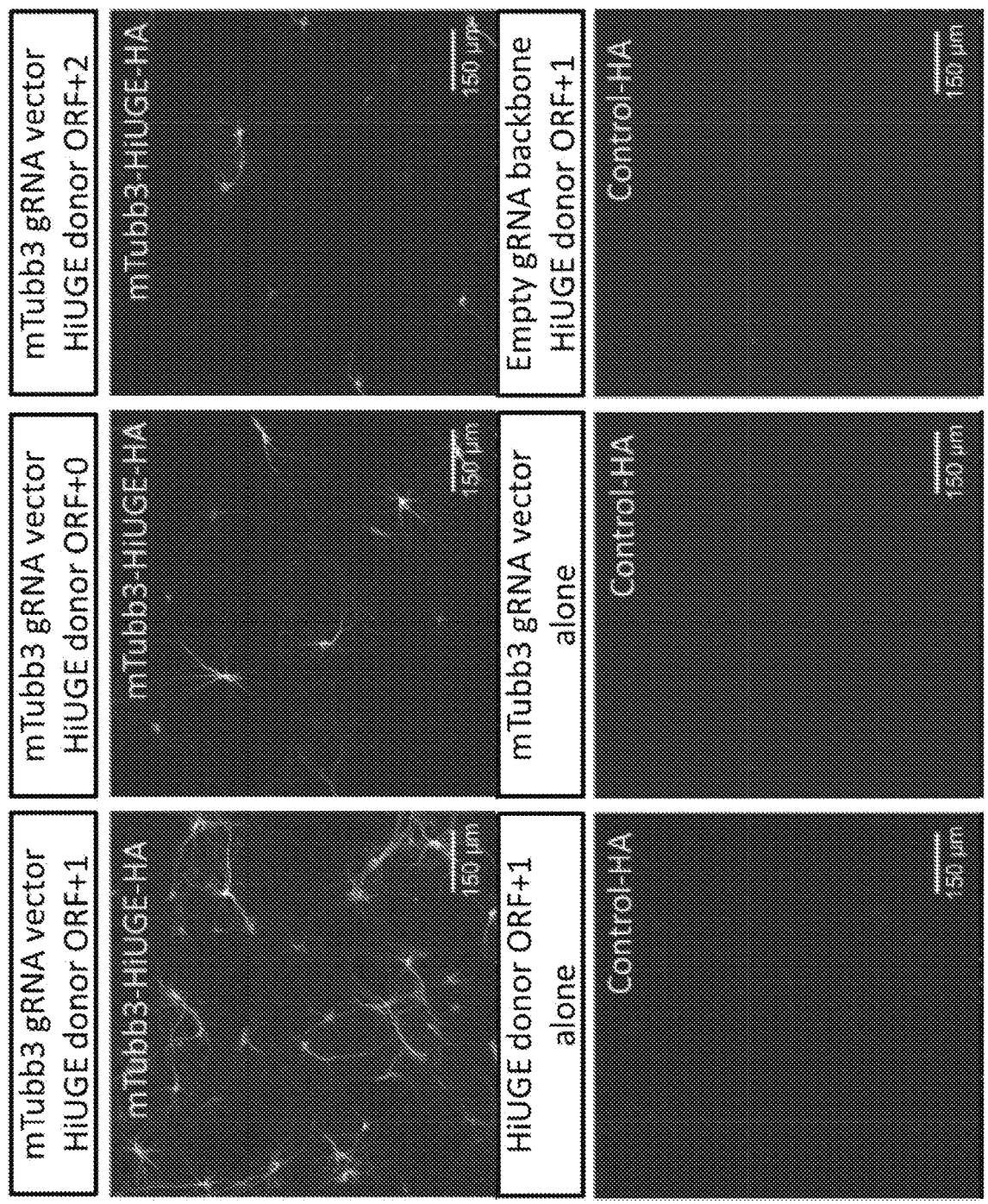
FIG. 4E shows representative images of HA immunostaining of primary neurons transduced with different combinations of vectors to demonstrate the high efficiency labeling when the gRNA vector is paired with the correct ORF donor vector (ORF+1) versus out of frame donors (ORF+0 or ORF+2).
Figure 4F:
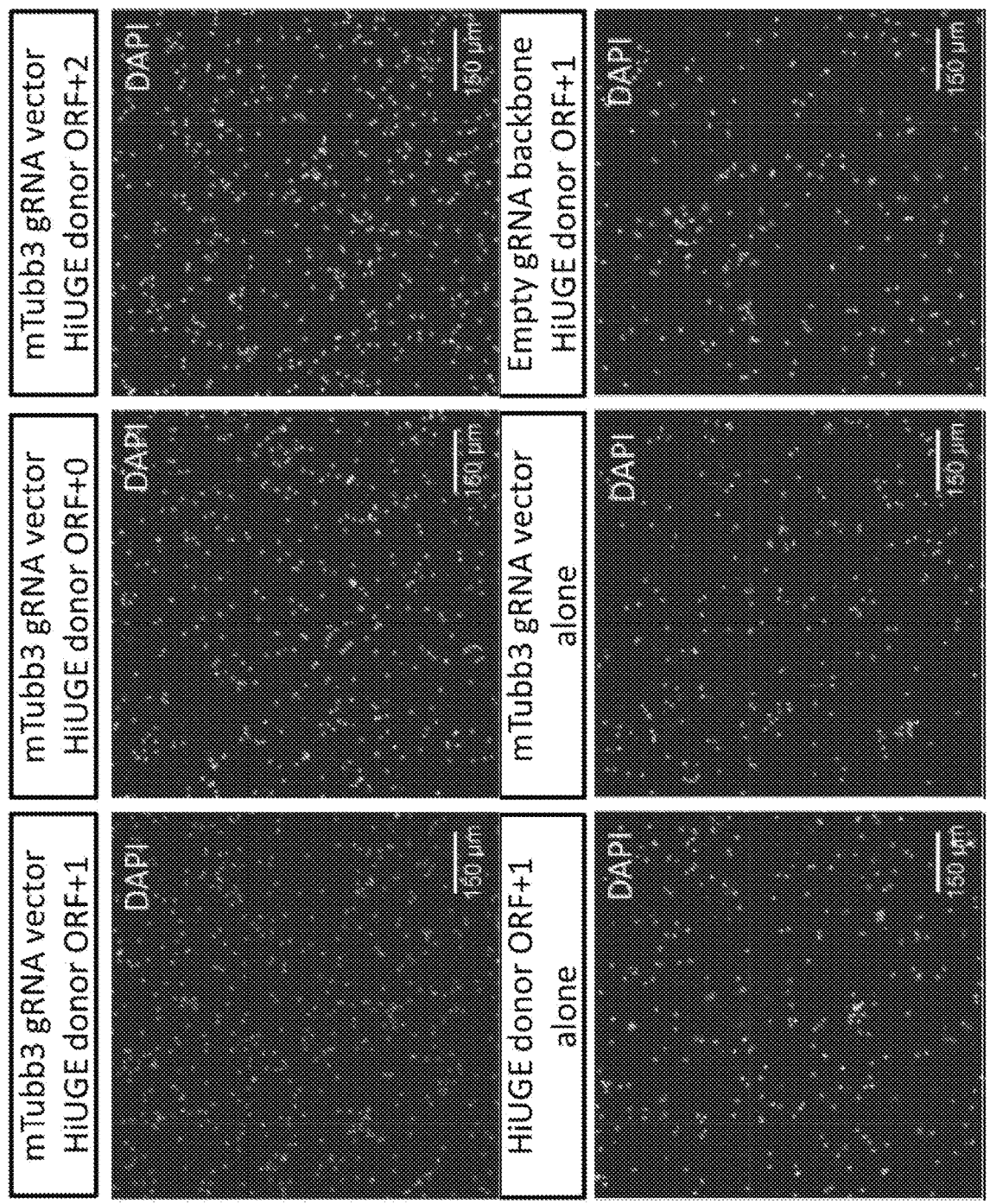
FIG. 4F shows DAPI (4',6-diamidino-2-phenylindole) staining to visualize nuclei in each corresponding image in FIG. 4E, demonstrating similar cell densities in each panel. Scale bar is indicated in each panel.

FIG. 4E shows representative images of HA immunostaining of primary neurons transduced with different combinations of vectors to demonstrate the high efficiency labeling when paired with the correct ORF donor vector (ORF+1) versus out of frame donors (ORF+0 or ORF+2). Additional negative controls (Donor vector ORF+1 alone, mTubb3 gRNA vector alone, empty gRNA vector with Donor ORF+1 vector) demonstrated the requirement for GS-gRNA and Donor vector pairing for HA epitope labeling. Note: limited HA-positive cells were identified when the mouse Tubb3 GS-gRNA vector (ORF+1) was paired with donor vectors in wrong ORFs (ORF+0 or ORF+2), likely due to frame-shifting indel events. FIG. 4F shows DAPI (4',6-diamidino-2-phenylindole) staining to visualize nuclei in each corresponding image in FIG. 4E, demonstrating similar cell densities in each panel. Scale bar is indicated in each panel.

Figure 4I:
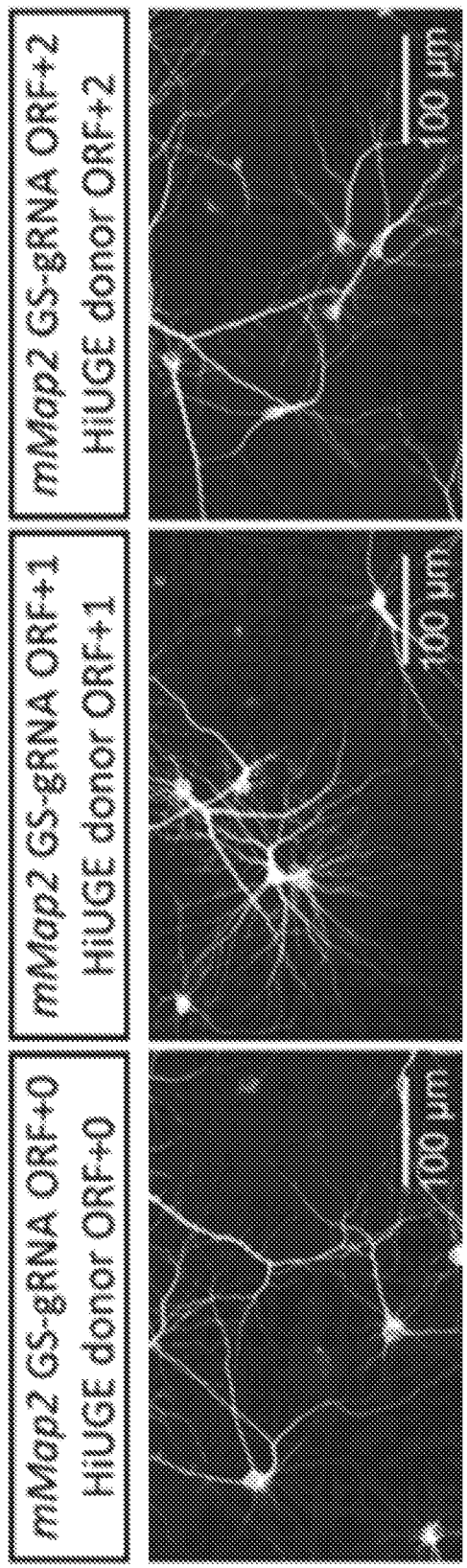

Relative immunofluorescence intensities were quantified across these conditions, showing that the correct ORF pairing was significantly more efficient when compared to all other conditions (FIG. 4G). Further, to demonstrate that donor vectors for all 3 ORFs are equally capable of facilitating HiUGE, three GS-gRNAs, one for each ORF, were designed to target mouse Map2 gene. Pairing these GS-gRNA AAVs with HA-epitope donor AAVs in their corresponding ORFs resulted in comparable and efficient labeling (FIG. 4H-4I). These data confirmed that payload sequences can be excised and inserted into the targeted genome for labeling endogenous proteins, using an autonomous HiUGE donor vector unrelated to the GOI.

Example 4

HiUGE Application Across Diverse Genomic and Protein Targets

Figure 5A:
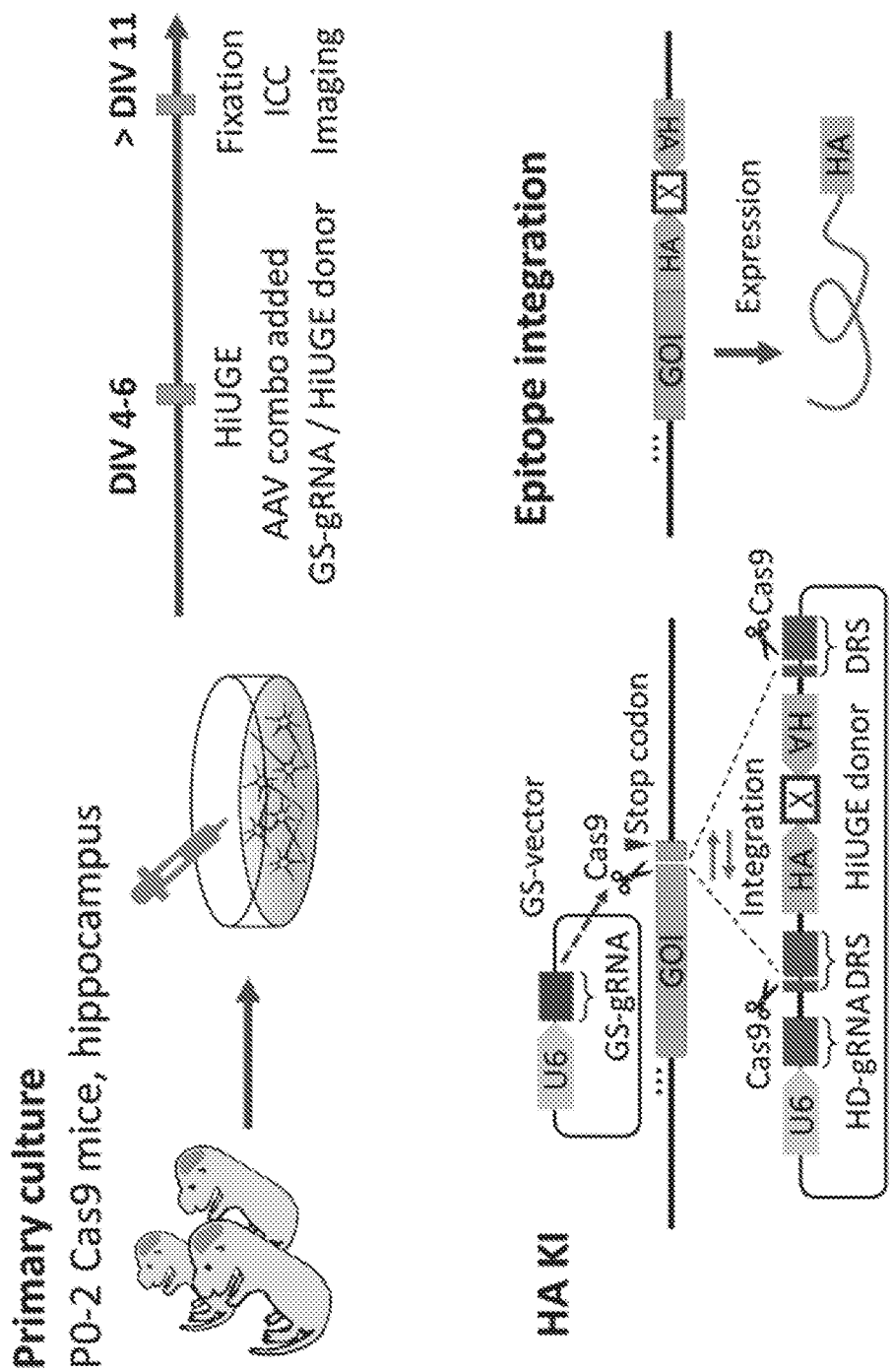
FIG. 5A shows a schematic illustration of scaled-up application of HiUGE for carboxy-terminal bidirectional HA epitope knock-in (KI) into 12 different proteins shown in FIGS. 5B-5M.
Figure 5B:
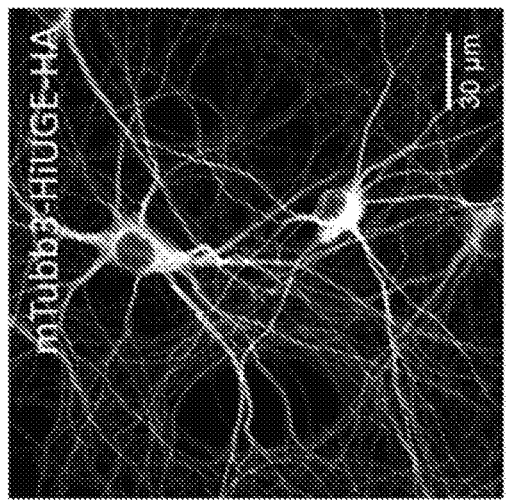
FIGS. 5B-5M show representative images of primary hippocampal cells from Cas9 expressing mice transduced with a combination of gene specific (GS)-gRNA AAV vector and HiUGE donor AAV vector on day in vitro (DIV) 4-6.
Figure 5C:
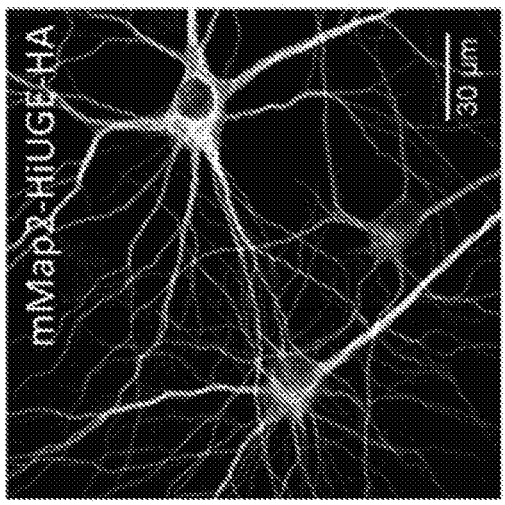
Figure 5D:
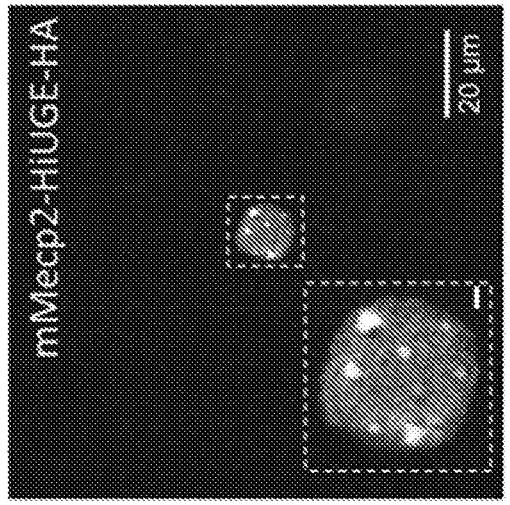
Figure 5E:
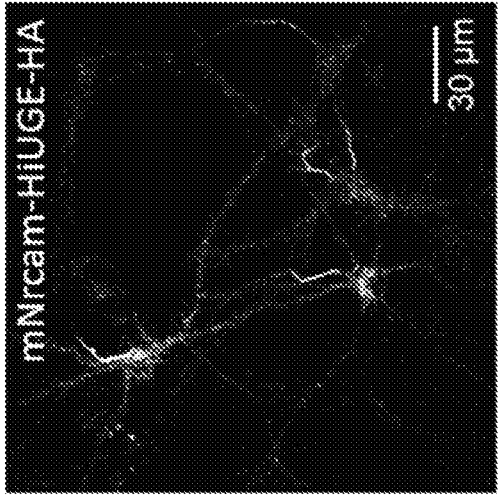
Figure 5F:
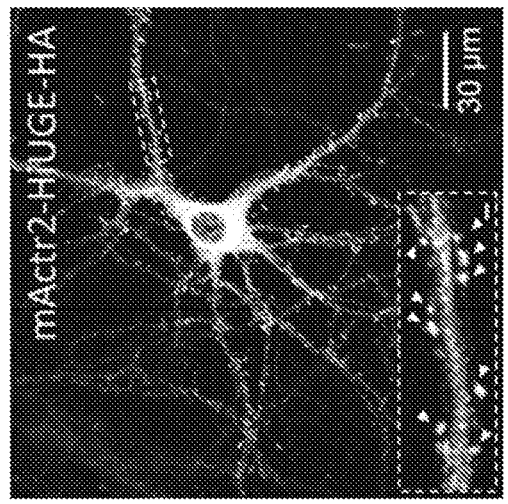
Figure 5G:
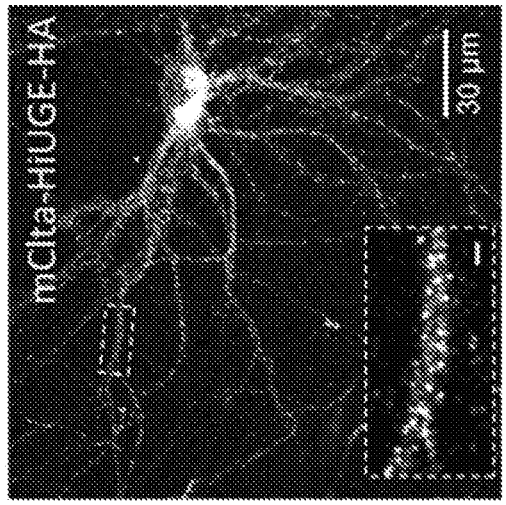
Figure 5H:
Figure 5I:
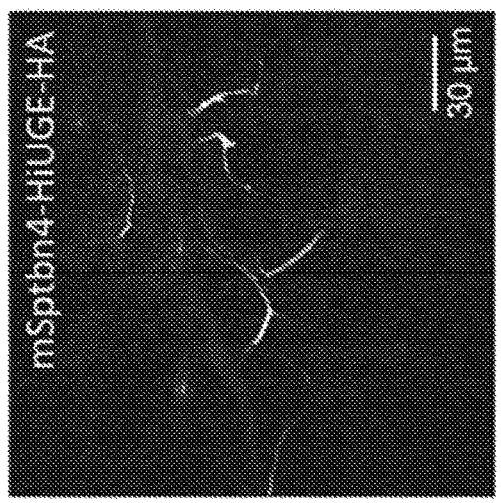
Figure 5J:
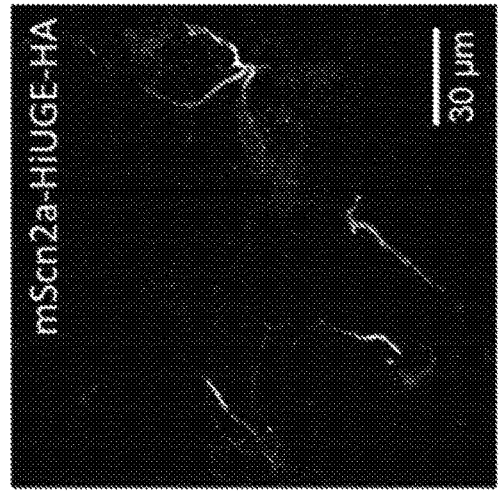
Figure 5K:
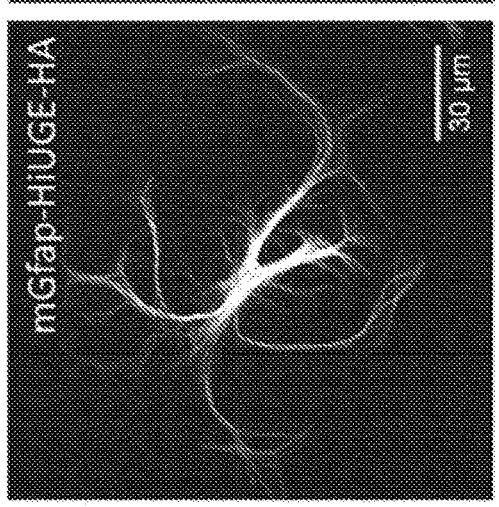
Figure 5L:
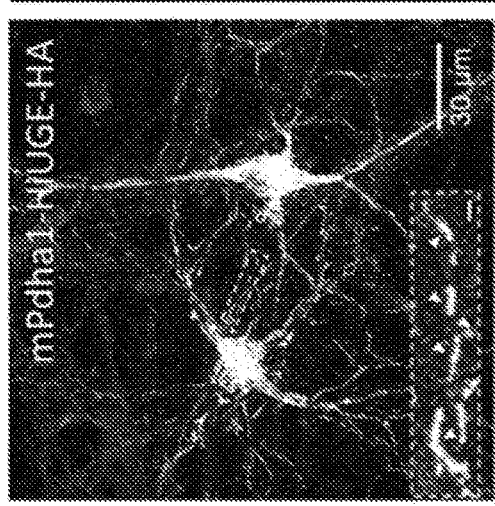
Figure 5M:
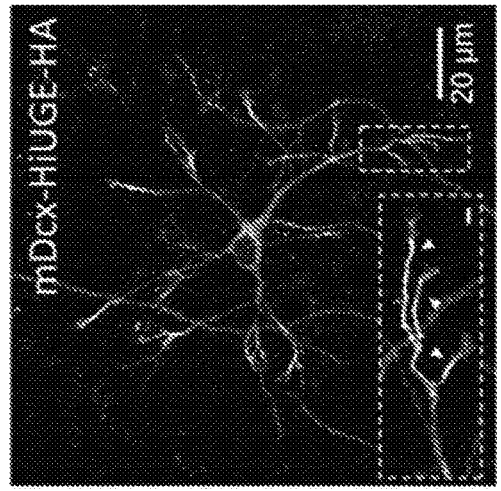

FIG. 5A shows a schematic illustration of example scaled-up applications of HiUGE for carboxy-terminal bidirectional HA epitope knock-in (KI) into 12 different proteins. Primary hippocampal cells from Cas9 expressing mice were transduced with a combination of GS-gRNA AAV vector and HiUGE donor AAV vector on DIV 4-5. Cells were fixed after DIV 11 for immunocytochemistry to detect HA epitope KI, with representative images displayed in FIGS. 5B-5M. FIGS. 5B-5C show HA epitope KI of mouse Tubb3 gene (FIG. 5B) and mouse Map2 gene (FIG. 5C), which encode proteins that were localized to the microtubules. FIG. 5D shows HA epitope KI of mouse MeCP2 gene, which encodes the nuclear-localized MCP2 protein (inset is higher magnification view of boxed region). FIG. 5E show HA epitope KI of mouse Nrcam gene, which encodes neuronal cell adhesion molecule that is enriched on the axonal initial segment (AIS). FIG. 5F shows HA epitope KI of mouse Actr2 gene which encodes actin-related protein 2 that is enriched within neuronal dendritic spines. FIG. 5G shows HA epitope KI of mouse C/ta gene, which encodes a clathrin protein enriched at sites of vesicular clathrin-dependent protein trafficking. FIGS. 5H-5J show HA epitope KI of mouse Ank3 gene (FIG. 5H), mouse Sptbn4 gene (FIG. 5I), and mouse Scn2a gene (FIG. 5J), which encode ankyrin, βIV-spectrin, and NaV1.2 sodium channel subtype proteins that were enriched within the AIS of neurons. FIG. 5K shows HA epitope KI of mouse GFAP gene, which encodes the glial acidic fibrillary protein that was selectively expressed in glia. FIG. 5L shows HA epitope KI of mouse Pdha1 gene, which encodes a mitochondria-localized pyruvate dehydrogenase protein. FIG. 5M shows HA epitope KI of mouse Dcx gene, which encodes the microtubule binding protein doublecortin. Scale bar is indicated in each panel. Scale bar within the insets represents 2 μm. Arrowheads represent the subcellular features associated with the gene of interest, such as the dendritic spines (FIG. 5F), mitochondria (FIG. 5L), or the distal end of neurites (FIG. 5M).

To confirm payload integration and estimate the indel rates, genomic PCRs were performed for five targets to amplify the region around the edited junctions. Dual-orientation HA-epitope integrations were confirmed by positive PCR results (FIGS. 16A-16B), with deep sequencing of the amplicons revealing the positional indel occurrences and the estimated proportions of seamless editing following either forward or reverse payload insertions (FIG. 16C-16D). Also, the efficiencies of C-term epitope labeling were estimated for several AIS-specific targets, as each neuron typically has only one AIS, and their distinct expression pattern is suitable for easy visual identification and quantification. The ratios of HiUGE-labeled AIS structures compared to all AIS (stained with an antibody against the AIS-marker Ankyrin-G) were quantified (FIGS. 18A-18C), demonstrating the estimated efficiencies of cellular labeling at different viral doses. Further, HiUGE-mediated endogenous protein labeling at the C-term was tested to visualize several members of the recently uncovered inhibitory postsynaptic density (iPSD) proteome (Uezu et al., 2016), using larger inserts such as spaghetti-monster HA (smFP-HA) FIG. 15A), which exhibits enhanced antigenicity suitable for low-expression proteins (Viswanathan et al., 2015). These novel iPSD proteins included Inhibitory Synaptic protein 1 (Insyn1), Inhibitory Synaptic protein 2 (Insyn2), and Rho GTPase Activating Protein 32 (Arhgap32). Immunodetection of these labeled proteins demonstrated that they were localized juxtaposed to the Vesicular GABA Transporter (VGAT) (FIGS. 15B-15D), confirming their presence at inhibitory synapses. Finally, three different GS-gRNAs (Table 1) were tested in parallel for Insyn1, and all of them yield successful and comparable inhibitory synaptic labeling (FIGS. 17B-17D), demonstrating the flexibility of GS-gRNA selection and the robustness of the labeling method. These data verify that single HiUGE donor vectors of various insert sizes can effectively modify multiple endogenous proteins for easy and higher-throughput localization of well characterized or newly discovered proteins.

Figure 11A:
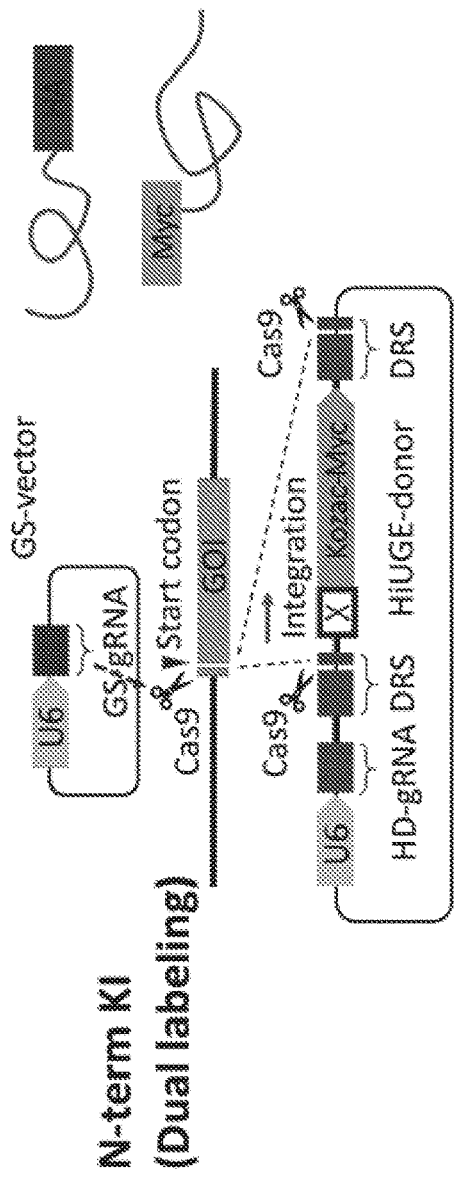
FIG. 11A shows a schematic illustration of HiUGE amino-terminal (N-term) KI construct.
Figure 11B:
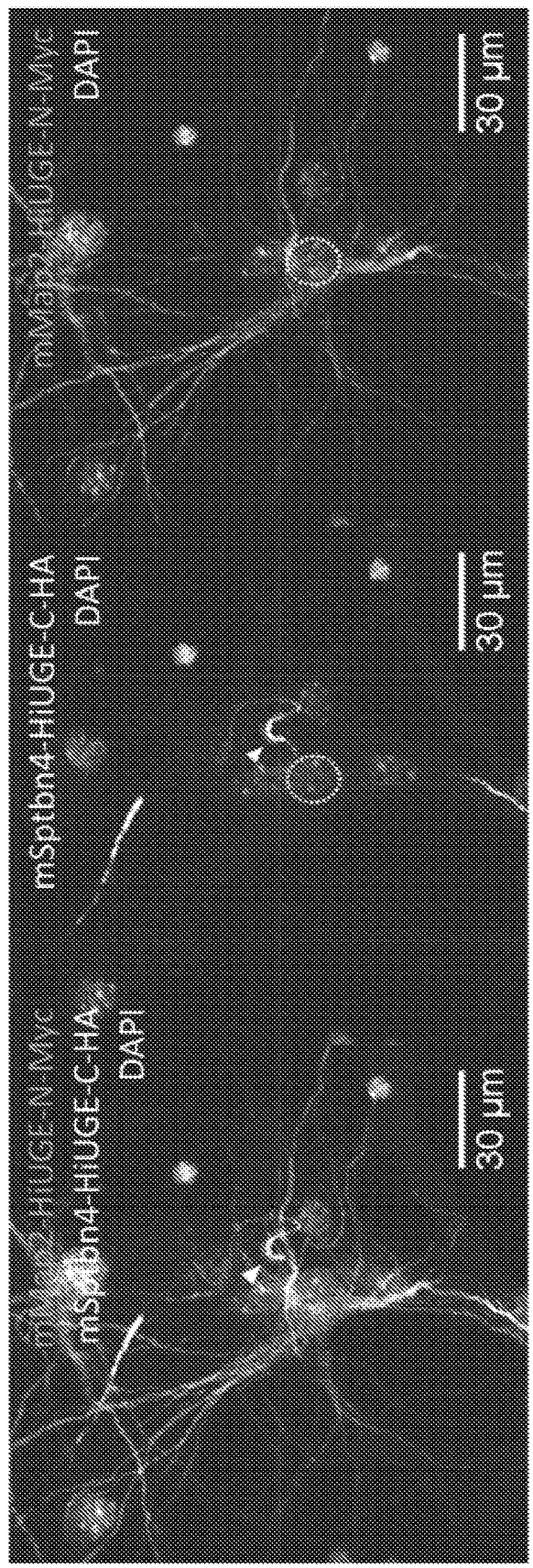
FIG. 11B shows a representative immunostaining image of dual labeling of Map2 and Sptbn4 encoded proteins by N-term KI of the Myc-epitope to Map2 (MAP2, arrows), and C-term KI of HA-epitope to Sptbn4 (arrowhead), encoding protein βIV-spectrin. Dashed circle represents the neuronal soma of the dual-labeled neuron.
Figure 15A:
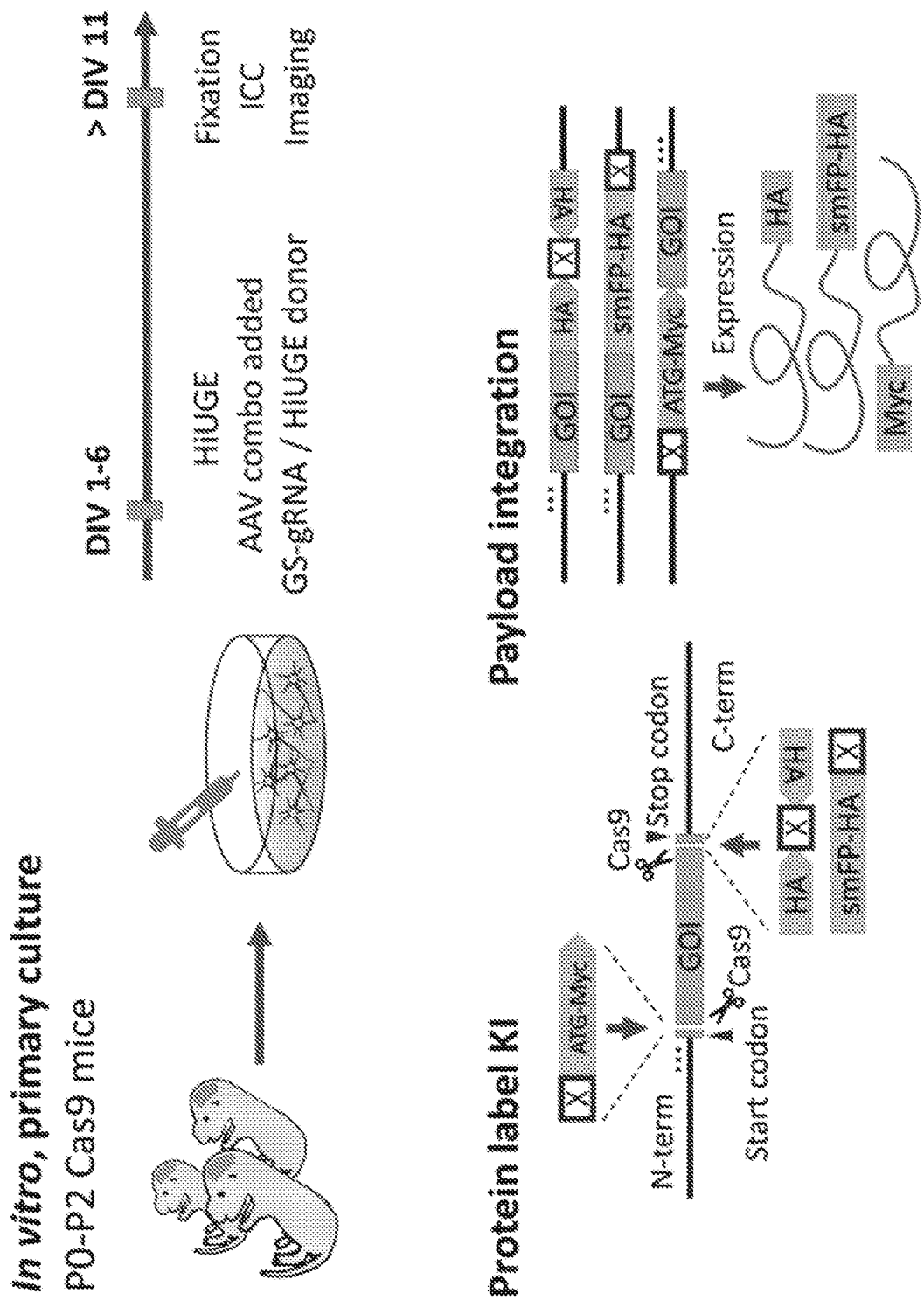
FIGS. 15A-15G show rapid protein modification across diverse genomic and protein targets with HiUGE in vitro.
Figure 15C:
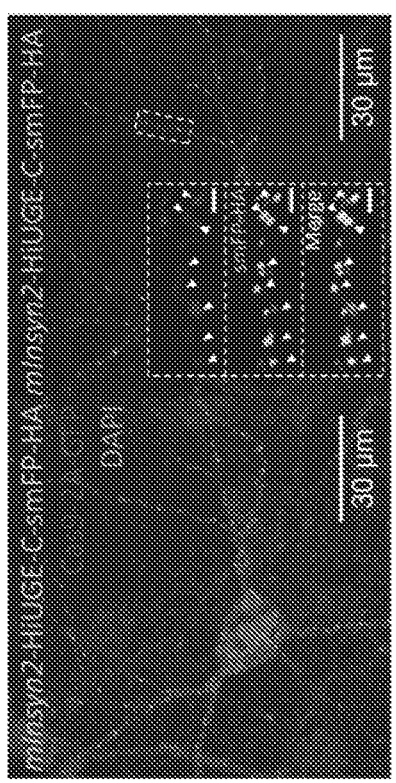
Figure 15E:
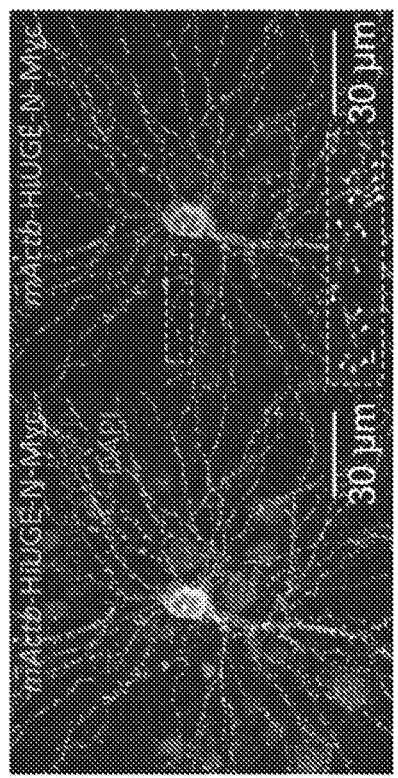
Figure 15B:
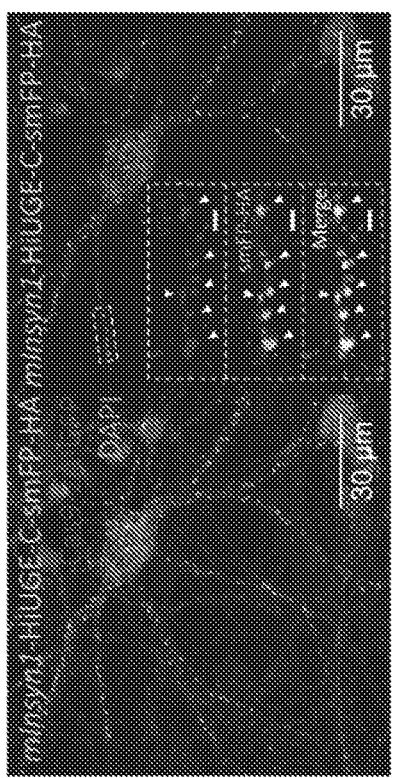
Figure 15D:
Figure 15F:
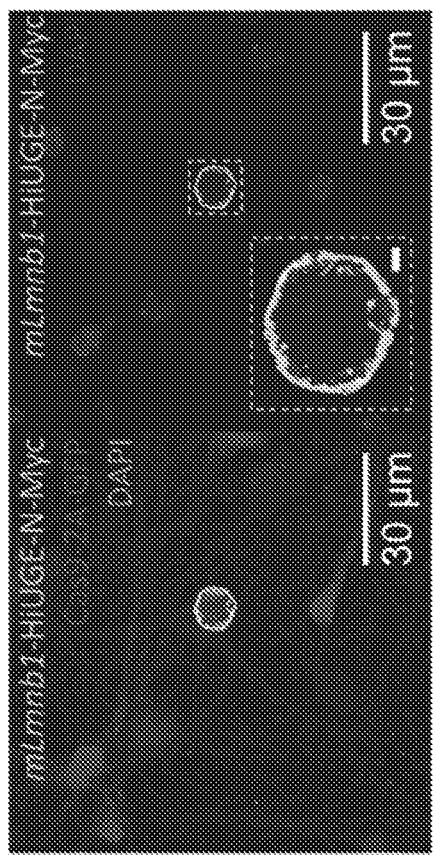
Figure 15G:
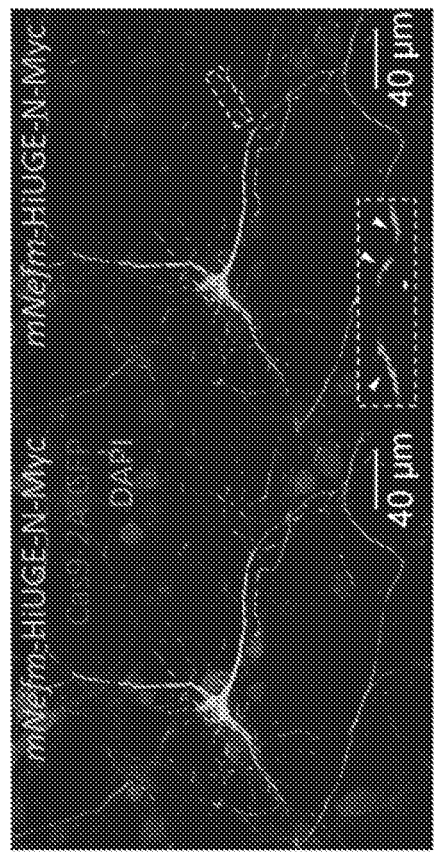

Next, amino-terminal (N-term) modifications were tested using a single Myc-epitope payload with an upstream stop codon cassette to constrain its expression to the N-term across multiple different proteins (FIG. 15A). GS-gRNAs targeting the N-term of three proteins were tested, including proteins of the actin cytoskeleton (β-Actin, Actb), nuclear envelope (Lamin B1, Lmnb1), and neurofilaments (Neurofilament medium, Nefm). Myc-epitope immunolabeling was observed for each of the targets that was consistent with the protein localization (FIGS. 15E-15G). The possibility of dual-labeling was explored by combining this N-term selective Myc-epitope payload with the HA-epitope HiUGE payload described above, which contains a stop codon cassette following the epitope tag that enforces its expression at the C-term (FIG. 11A). This construct can be used to achieve dual-labeling of two different targets by differentially targeting the N-term or the C-term of two different proteins. The stop codon cassette within the N-term HiUGE donor vector ensures that in the event of integration into the C-term, the translation will terminate upstream of the Myc-epitope, thus this payload is selective for N-term expression. These donors were co-infected with GS-gRNA AAVs targeting the N-term of dendritic MAP2 (Map2) and the C-term of AIS-enriched βIV-spectrin (Sptbn4). Co-staining for HA and Myc-epitopes revealed selective labeling for each protein, with instances of co-staining in single neurons (FIG. 11B). Thus, HiUGE N- and C-term selective payloads can be used to co-label proteins simultaneously to reveal the spatial relationships of two endogenous proteins.

Together, using rapidly constructed GS-gRNA libraries via simple oligonucleotide ligations, HiUGE integrates universal payloads into diverse protein coding regions in a highly specific and higher-throughput manner for mapping endogenous protein localizations. HiUGE is thus suitable for rapid and robust labeling of neuronal proteins, including post hoc localization analysis following large-scale proteomic or gene expression studies.

Figure 16A:
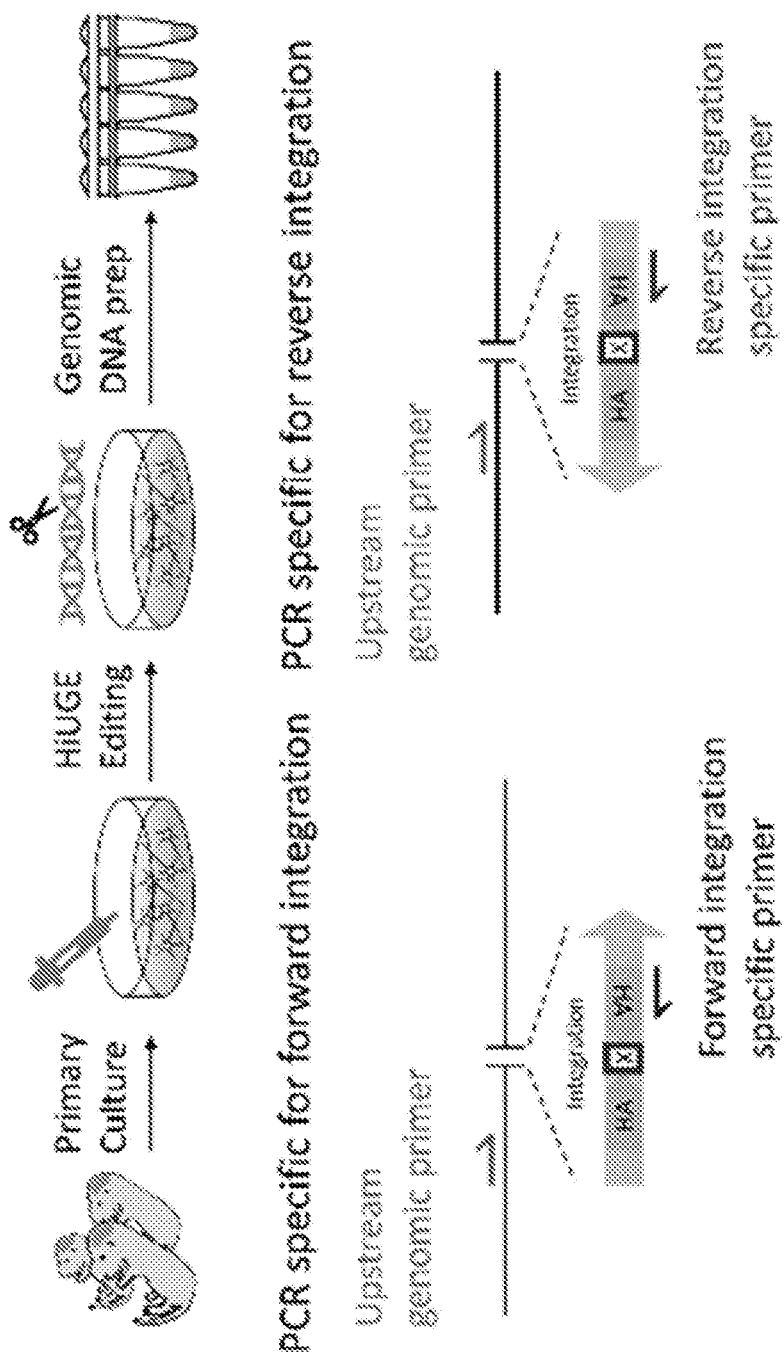
FIGS. 16A-16D show that genomic PCR and deep sequencing to confirm payload integration and estimated indel rate.
Figure 16B:
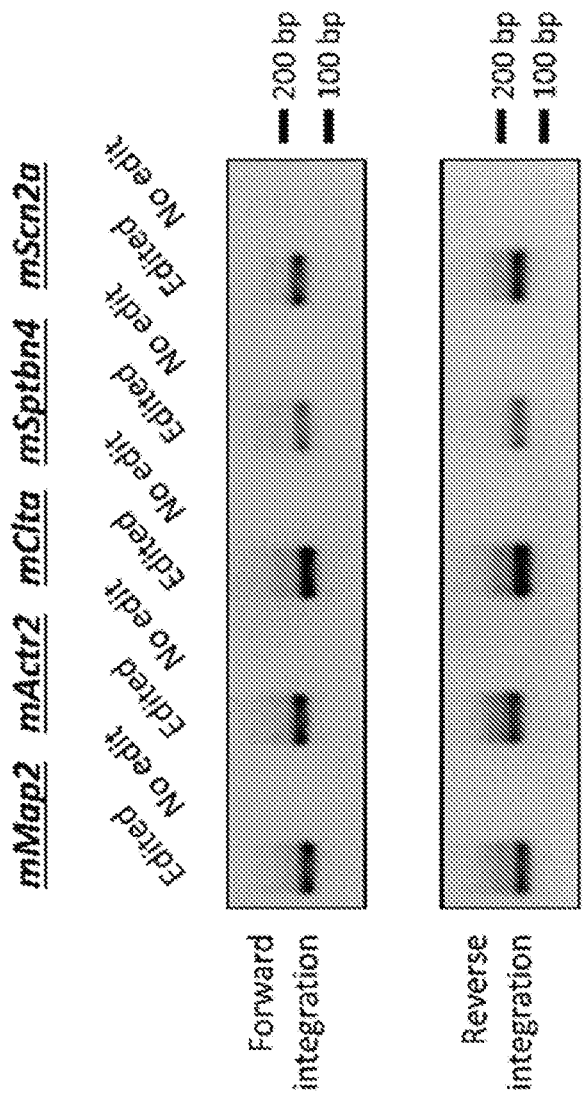
Figure 16C:
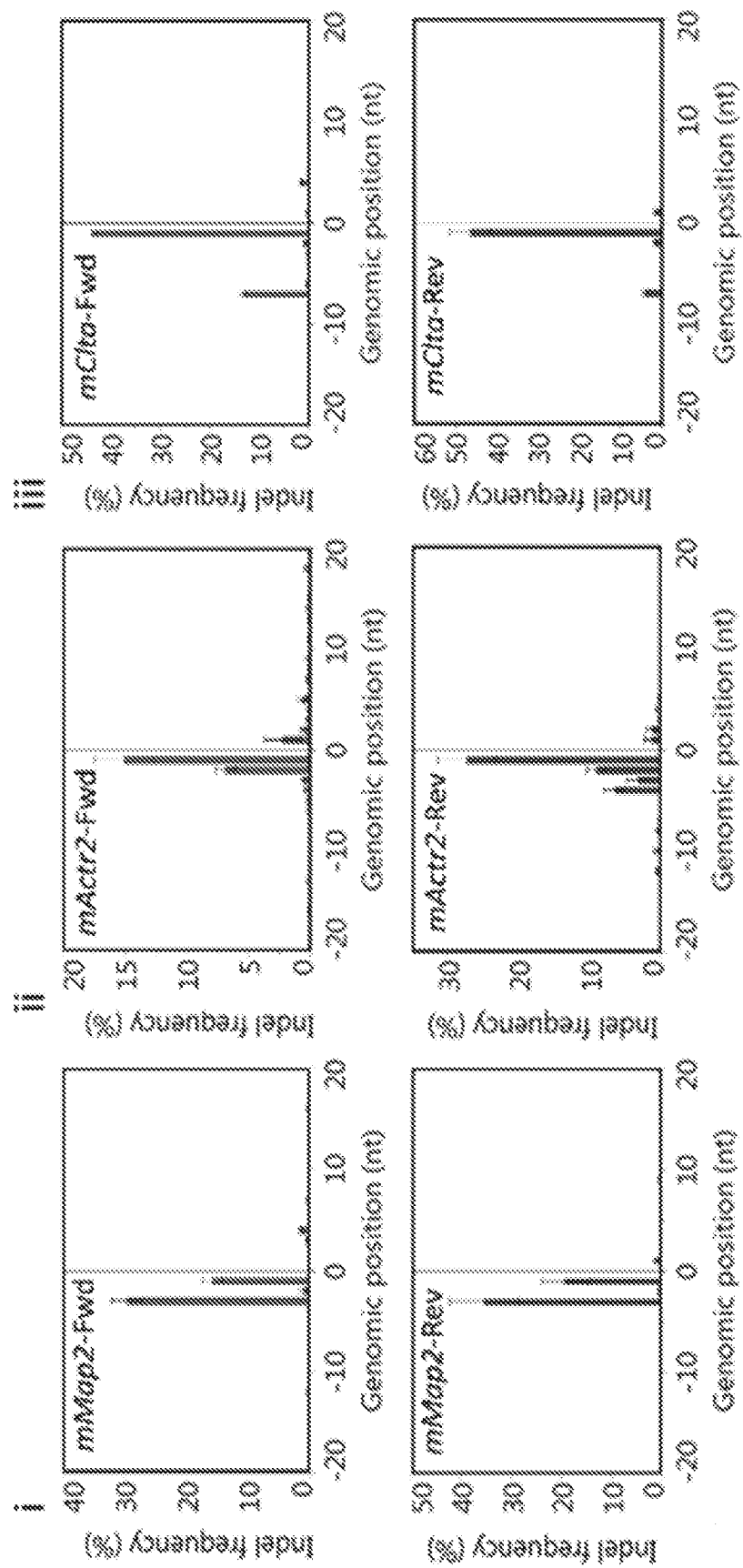
Figure 16D:
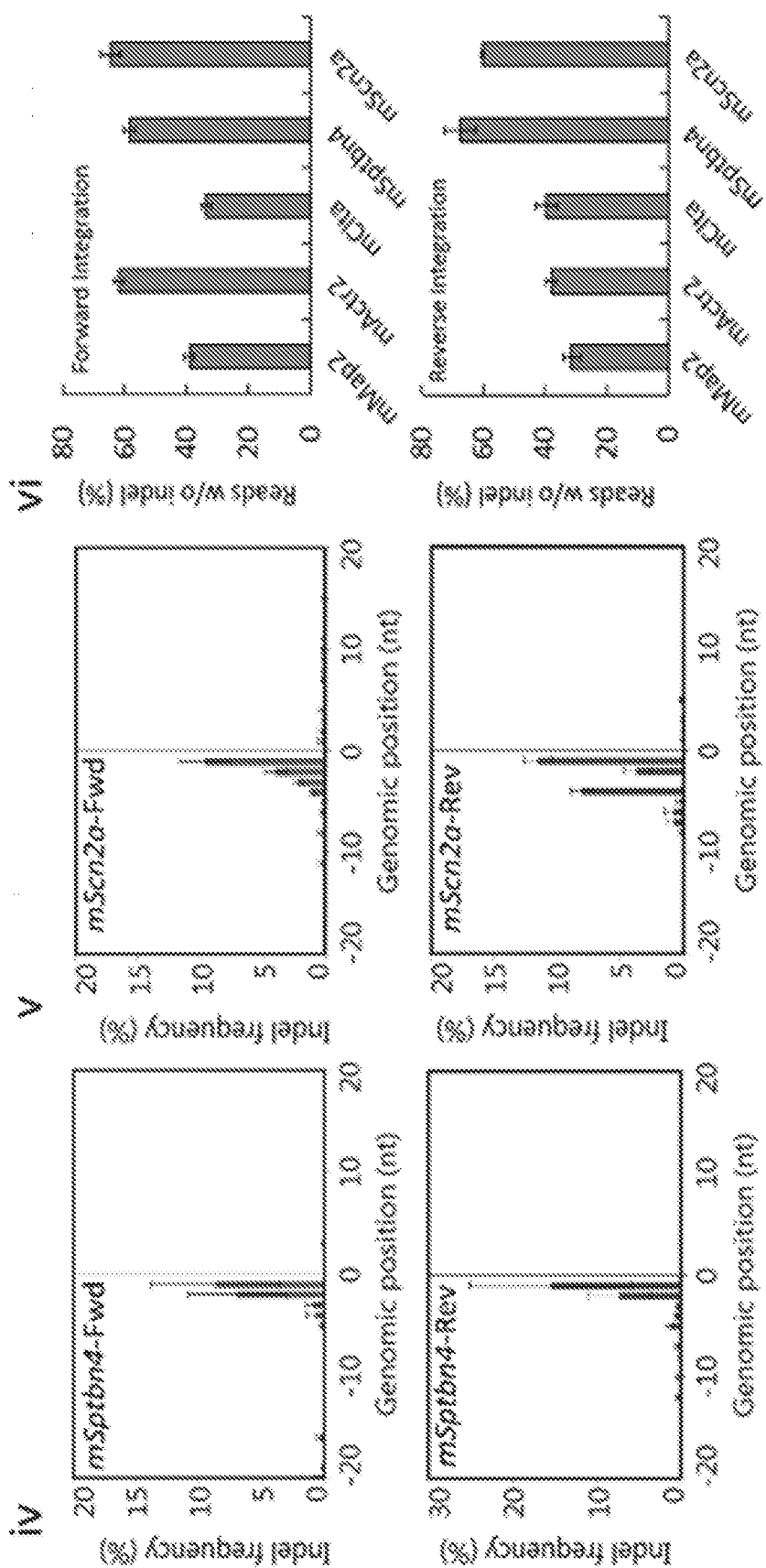
Figure 17A:
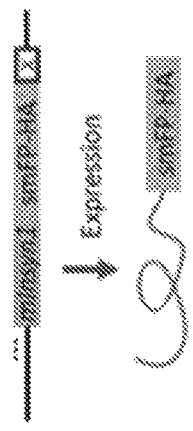
FIGS. 17A-17D shows additional data of localization mapping application using HiUGE.
Figure 17B:
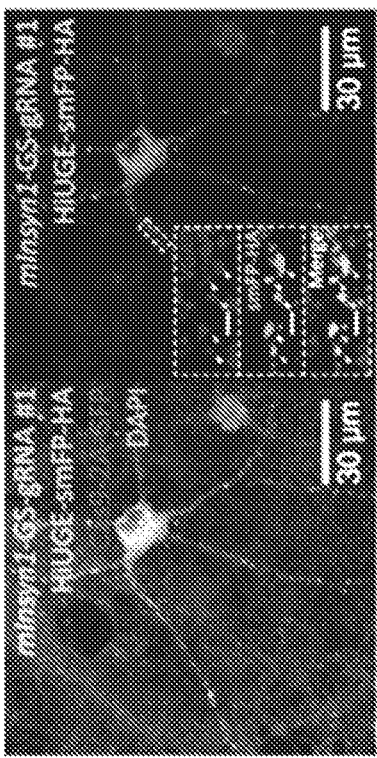
Figure 17C:
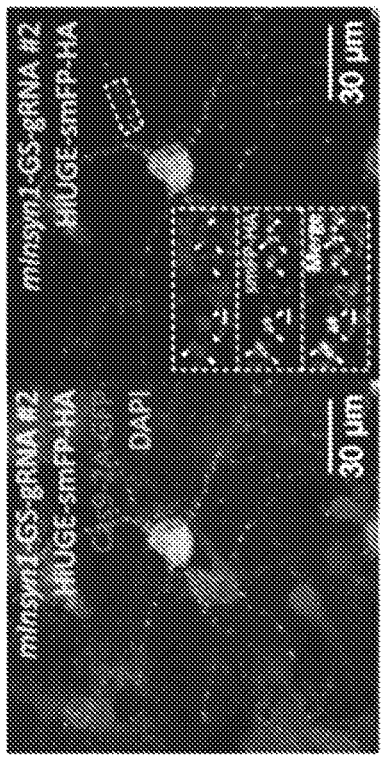
Figure 17D:
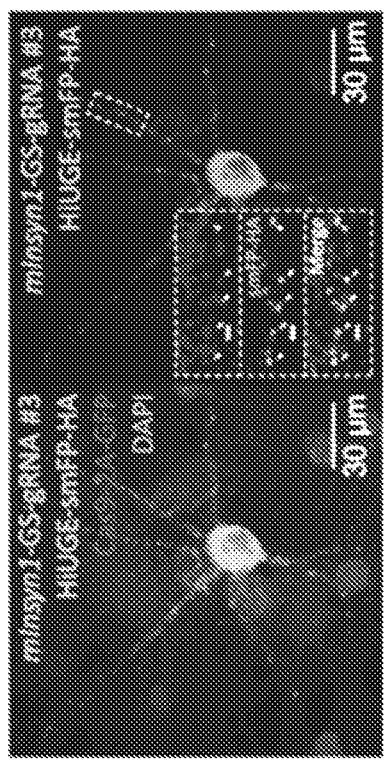

Genomic PCR and Deep Sequencing to Confirm Payload Integration and Estimated Indel Rate. Next generation sequencing was performed to show the frequencies of correct insertions into the genomic sites without insertion or deletion at the junctions. FIG. 16A shows a schematic design of genomic PCR to detect dual-orientation HA-epitope payload integration into various genomic loci. Genomic DNAs were extracted from primary neuronal cultures either with or without HiUGE editing. PCR reactions were performed using upstream genomic forward primers of 5 genes (mouse Map2, Actr2, Clta, Sptbn4, and Scn2a), paired with either a reverse primer specific for the forward payload integration event, or a reverse primer specific for the reverse payload integration event. FIG. 16B shows an insert-specific PCRs for both forward and reverse payload integration showed positive bands (~150-200 bp) in edited samples, compared to no band in negative controls (no edit). FIGS. 16C-16D show an analysis of indel frequencies by deep sequencing the PCR products of either forward or reverse payload integrations. The values on x-axis denote the onset positions of indels called by GATK HaplotypeCaller, with the inserted or deleted sequences immediately succeeding that position. Detections of indel positions (i-v) showed that most indel events initiated immediately adjacent to the edited junction (denoted by 0 on the x-axis, red line). Proportions of reads without an indel are also plotted (vi), showing the estimated frequencies of seamless payload integrations across five genes in both orientations.

Figure 18A:
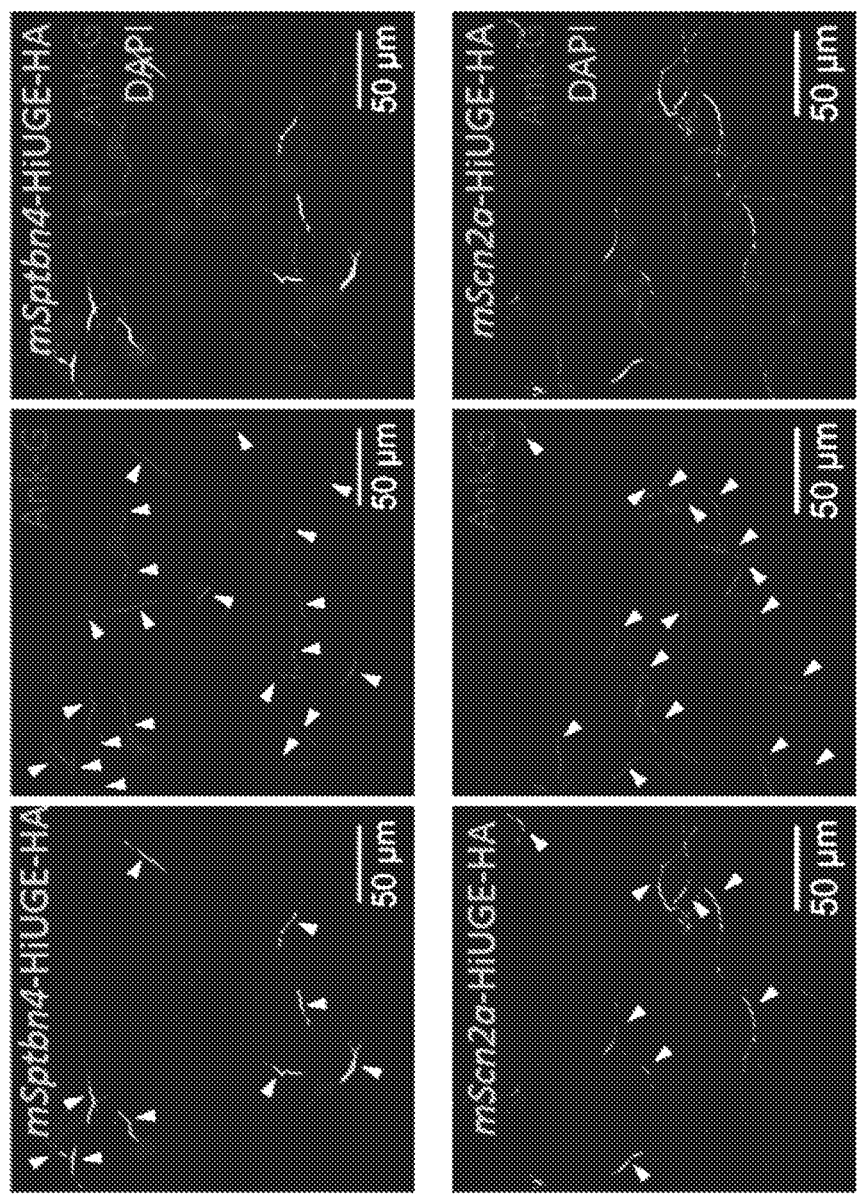
FIGS. 18A-18C show quantification of cellular labeling efficiency using HiUGE.
Figure 18C:
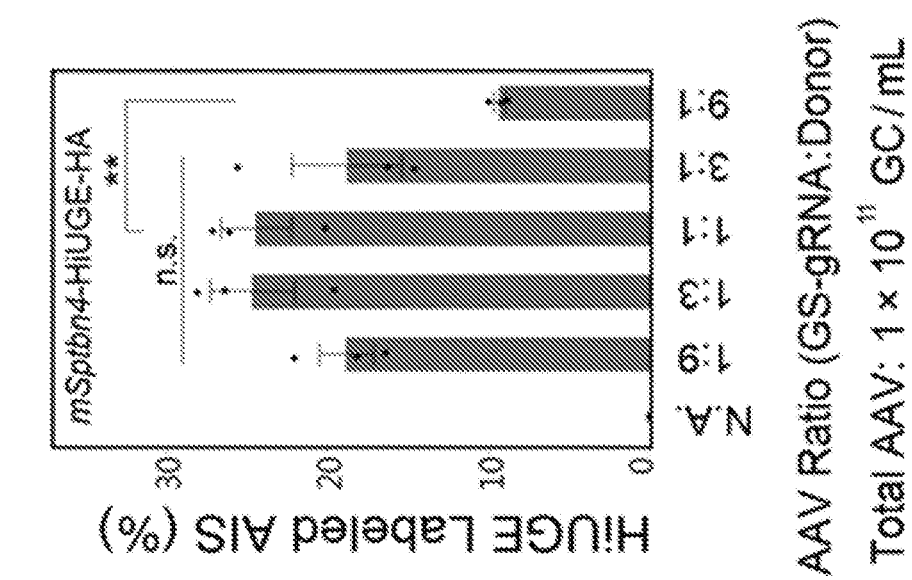
Figure 18B:
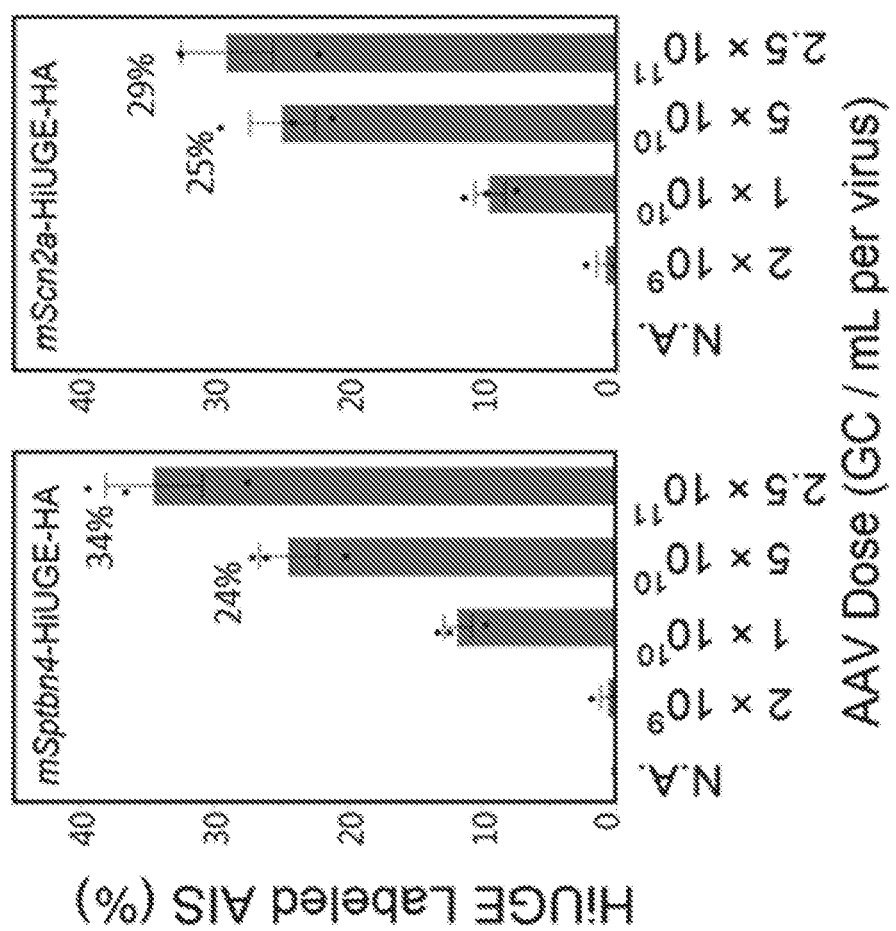

FIGS. 18A-18C show quantification of cellular labeling efficiency using HiUGE. FIG. 18A shows representative images of HiUGE labeling of AIS proteins βIV-Spectrin and NaV1.2 by C-term HA-epitope KI to mouse Sptbn4 and Scn2a, under high AAV concentrations ($2.5 \times 10^{11}$ GC/mL per virus) in primary neurons. Immunofluorescent staining with an antibody against AIS-marker Ankyrin-G (Ank-G) is also shown. Immunofluorescent staining with an antibody against AIS-marker Ankyrin-G (Ank-G) is also shown. Negative control (empty GS-gRNA backbone+Myc-epitope donor) showed no HiUGE labeled AIS. FIG. 18B shows quantification results showing the estimated efficiencies of cellular labeling across several AAV concentrations under 1:1 virus ratio (GS-gRNA:donor). Efficient labeling (>20%) was achieved at a dose of $5 \times 10^{10}$ GC/mL per virus or higher. FIG. 18C shows quantification results showing the estimated efficiencies of cellular labeling across several ratios of AAVs (GS-gRNA:donor) under $1 \times 10^{11}$ GC/mL combined viral concentration. Ratios of 1:9, 1:3, 1:1 and 3:1 showed no significant differences in labeling efficiency, suggesting a broad range of acceptable viral ratios for HiUGE labeling. However, ratio 9:1 showed significantly lower labeling efficiency compared to the 1:1 ratio ($p<0.01$, one-way ANOVA followed by Tukey-Kramer HSDpost hoc test, n=3), suggesting that sufficient donor AAV is required for efficient HiUGE editing.

FIGS. 19A-19F show an assessment of off-target effects of HiUGE; specifically, the off-target insertion and rates relative to on-target insertion into the genome. FIG. 19A shows top ranked CRISPOR-predicted off-target loci for both HD-gRNA and mScn2a GS-gRNA. FIG. 19B shows genomic PCR reactions using gene-specific primers paired with payload-specific primers successfully detected on-target integrations, while the off-target genomic integrations of the payload were undetected for the predicted sites (Pre-Off_1-8). Across junction PCR reactions showed robust and specific amplifications using these genomic primers. FIG. 19C shows genome Walker experiment detected on-target integration (band 4), and 3 potential off-target integrations into the non-coding genomic regions (band 5-7). Vector fragments were also detected as expected (band 1-3). FIG. 19D shows genomic PCR reactions using gene-specific primers paired with payload-specific primers successfully detected on-target integrations, while the genomic integrations of the payload were undetected for the experimentally identified potential off-target sites (ExpOff_1-3). Across junction PCR reactions showed robust and specific amplifications using these genomic primers. FIG. 19E shows Real-time PCR amplification curve of the reactions for on-target integrations (green) versus off-target integrations (red). FIG. 19F shows semi-quantitative estimations of the relative abundances showed that the off-target integrations were rare compared to on-target integrations.

Example 5

In Vivo Application of HiUGE Method

Figure 6A:
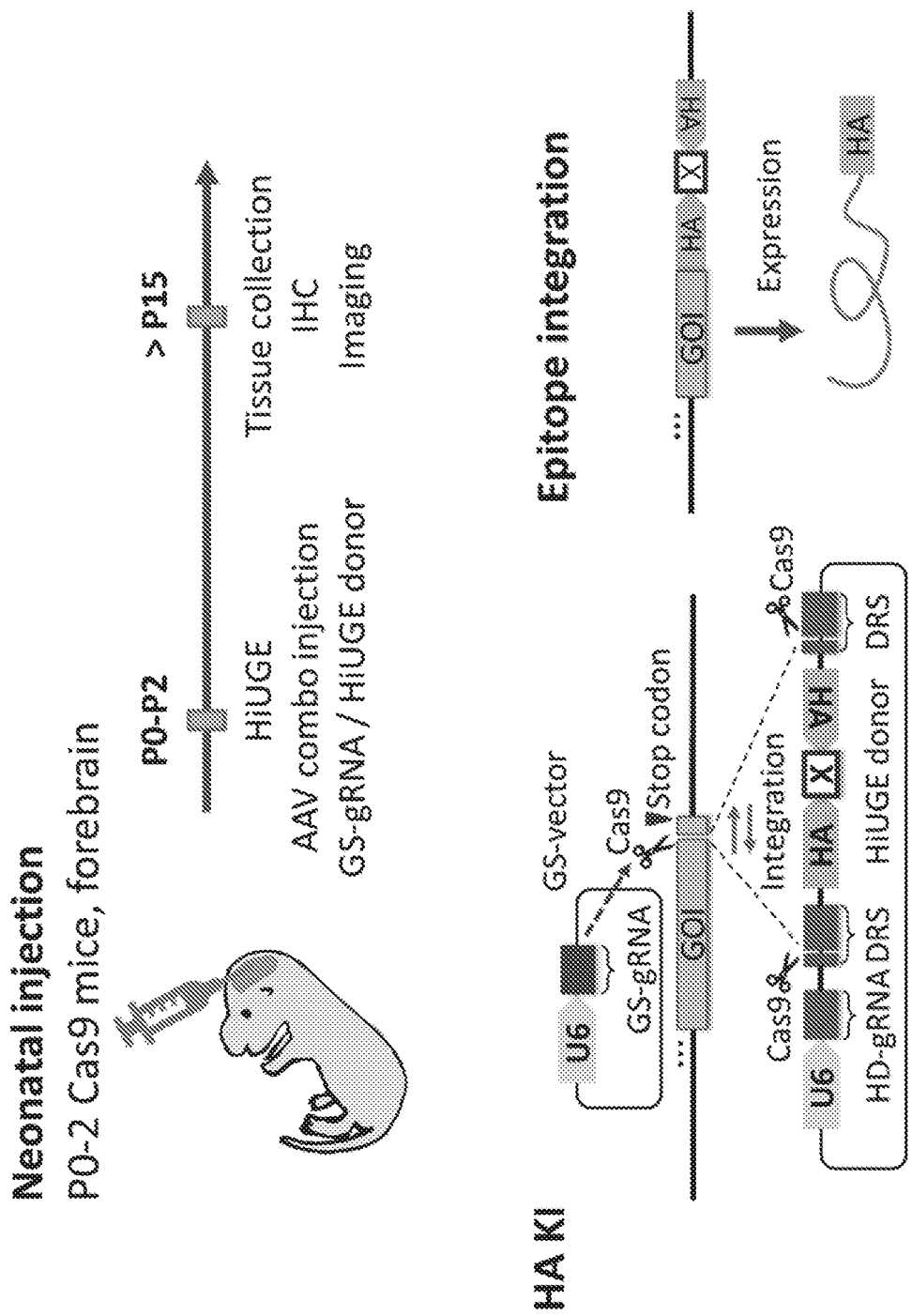
FIG. 6A shows a schematic illustration of HiUGE application for carboxy-terminal bidirectional HA epitope knock-in (KI) in vivo.
Figure 6B:
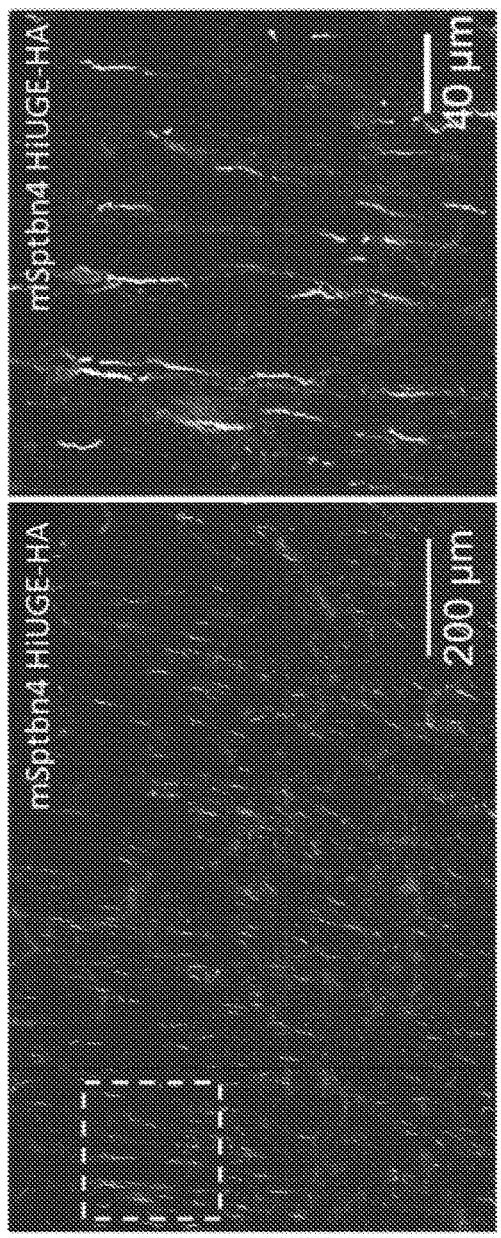
FIGS. 6B, 6D, 6F, and 6H show representative images of HA epitope immunostaining of mouse Sptbn4 gene (FIG. 6B), mouse Scn2a gene (FIG. 6D), mouse Tubb3 gene (FIG. 6F), and mouse Mecp2 gene (FIG. 6H).
Figure 6C:
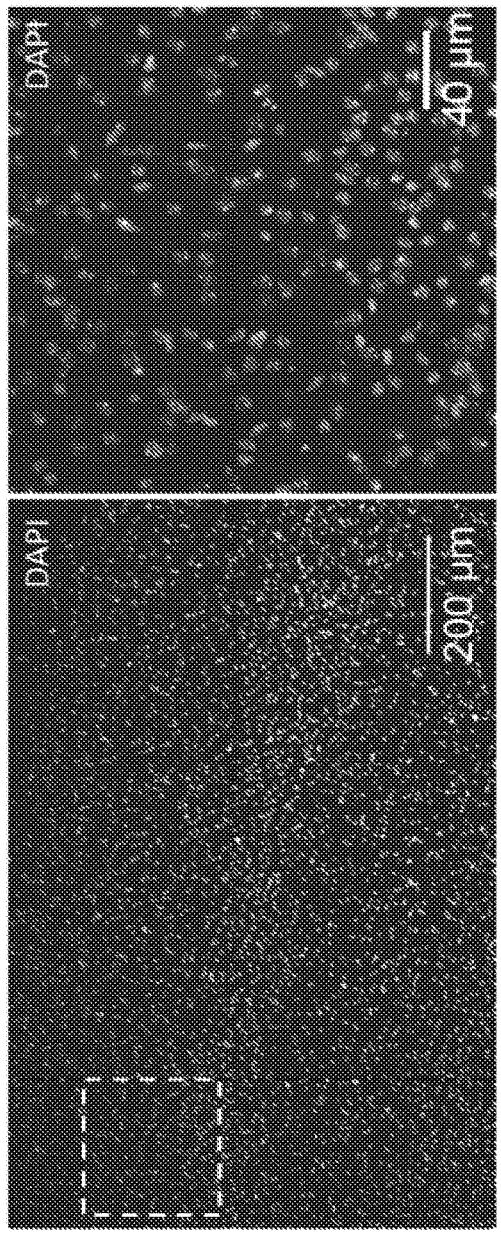
FIGS. 6C, 6E, 6G, and 6I show DAPI (4′,6-diamidino-2-phenylindole) staining to visualize nuclei in each corresponding image in FIGS. 6B, 6D, 6F, and 6H. Scale bar is indicated in each panel. Higher magnification images in right panels correspond to boxed regions in left panels.
Figure 6D:
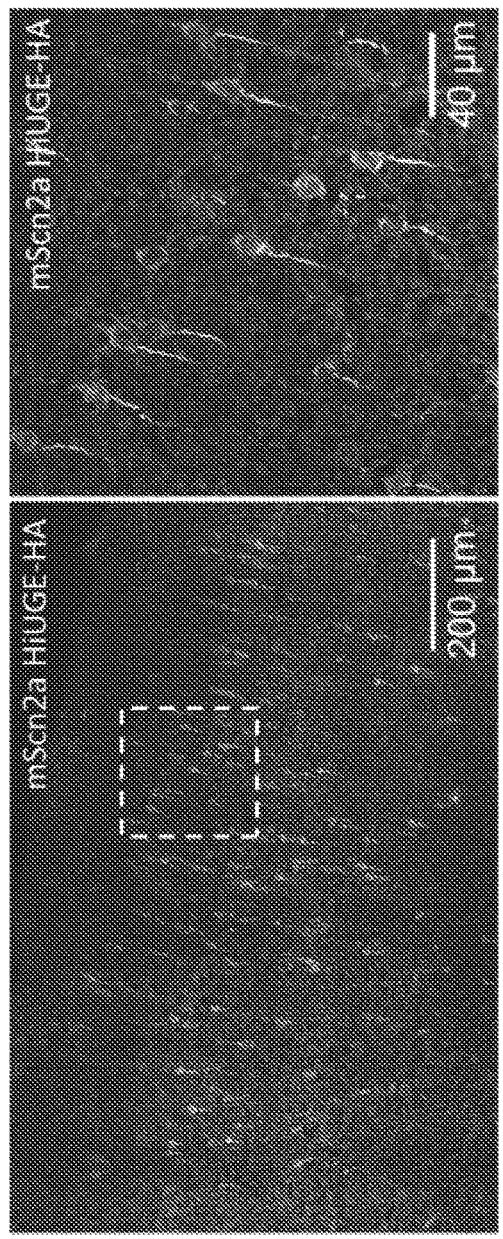
Figure 6E:
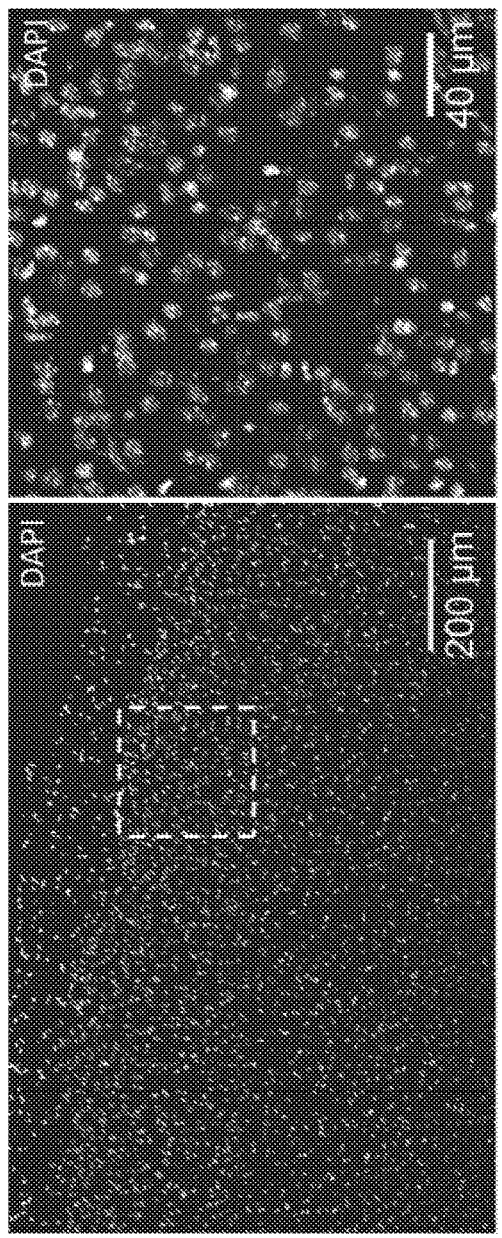
Figure 6F:
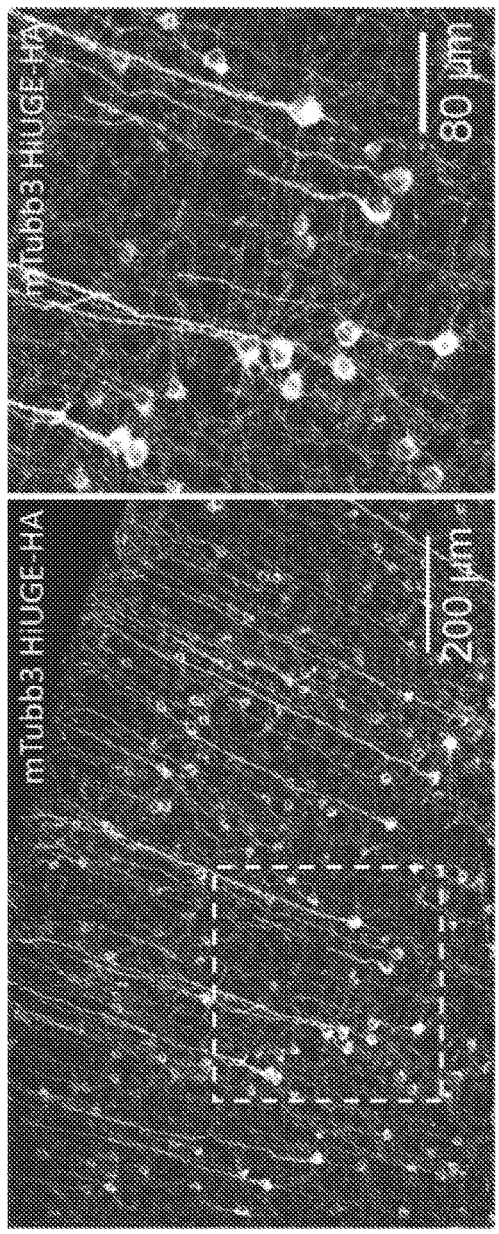
Figure 6G:
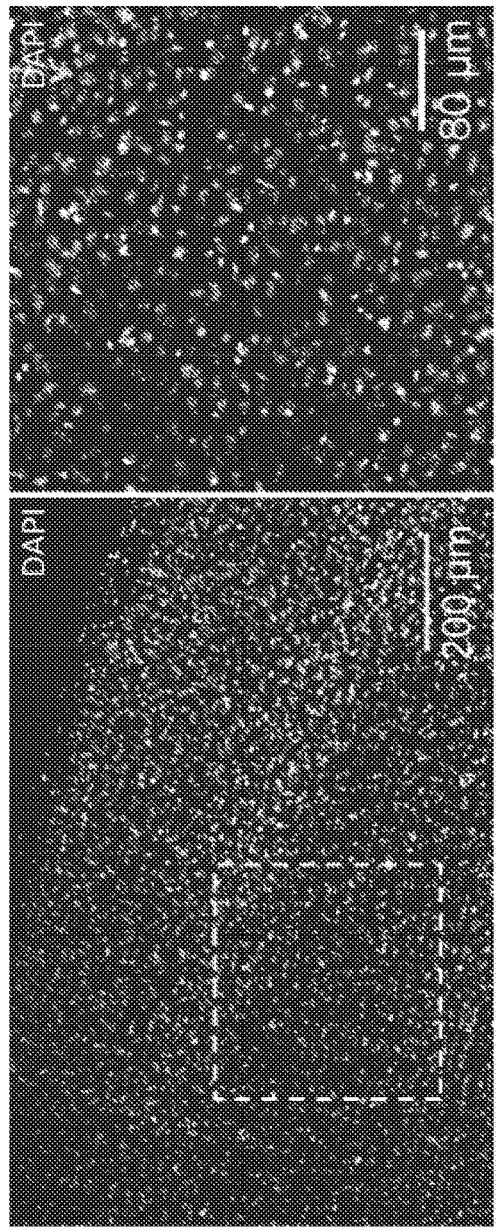
Figure 6H:
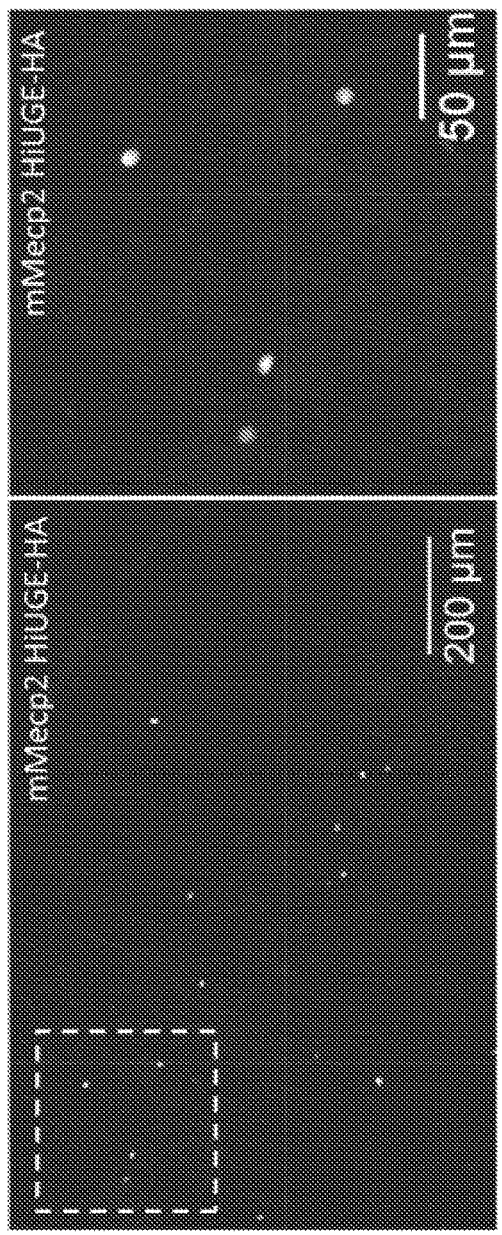
Figure 6I:
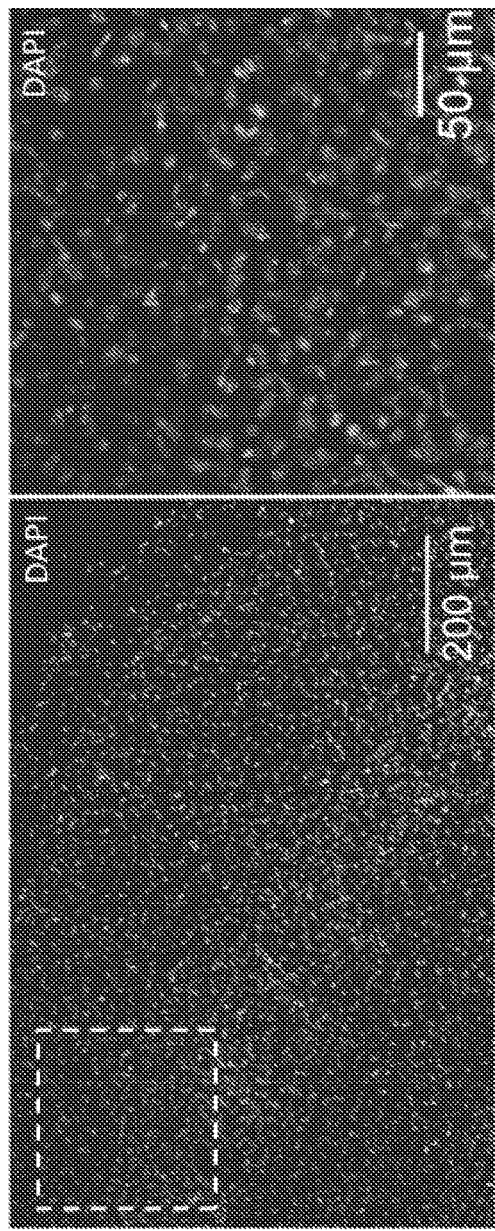

FIG. 6A shows a schematic illustration of an example HiUGE application for carboxy-terminal bidirectional HA epitope knock-in (KI) in vivo. Neonatal Cas9 expressing mouse pups were intracerebroventricularly injected with a combination of purified GS-gRNA AAV and HiUGE donor AAV at postnatal days 0-2 (P0-2), and euthanized after P15 for immunohistochemistry to detect HA epitope KI. FIGS. 6B and 6D show representative images of HA epitope immunostaining of mouse Sptbn4 gene (FIG. 6B) and mouse Scn2a gene (FIG. 6D), which encode βIV-spectrin and NaV1.2 sodium channel subtype proteins that were enriched on the axonal initial segment. FIG. 6F shows a representative image of HA epitope immunostaining of mouse Tubb3 gene (FIG. 6F), which encode β-tubulin localized to microtubules. FIG. 6H shows HA epitope immunostaining of mouse Mecp2 gene, which encodes nuclear-localized MCP2 protein. FIGS. 6C, 6E, 6G, and 6I show DAPI (4',6-diamidino-2-phenylindole) staining to visualize nuclei in each corresponding image in FIGS. 6B, 6D, 6F, and 6H, demonstrating similar cell densities in each panel. Scale bar is indicated in each panel.

Example 6

Exemplary Applications of the HiUGE Method

Figure 7A:
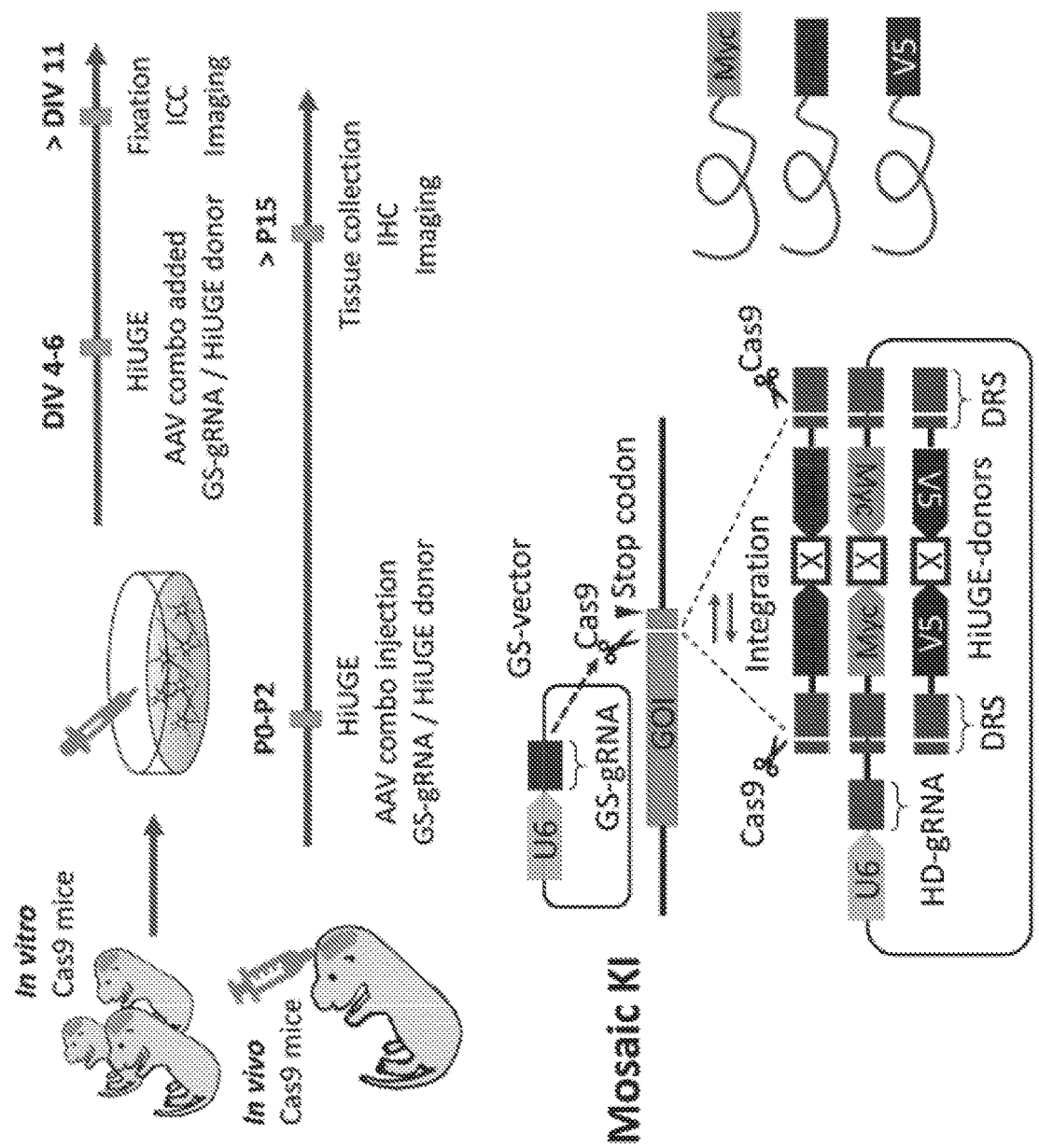
FIG. 7A shows a schematic illustration of HiUGE mosaic epitope knock-in (KI) application.
Figure 7B:
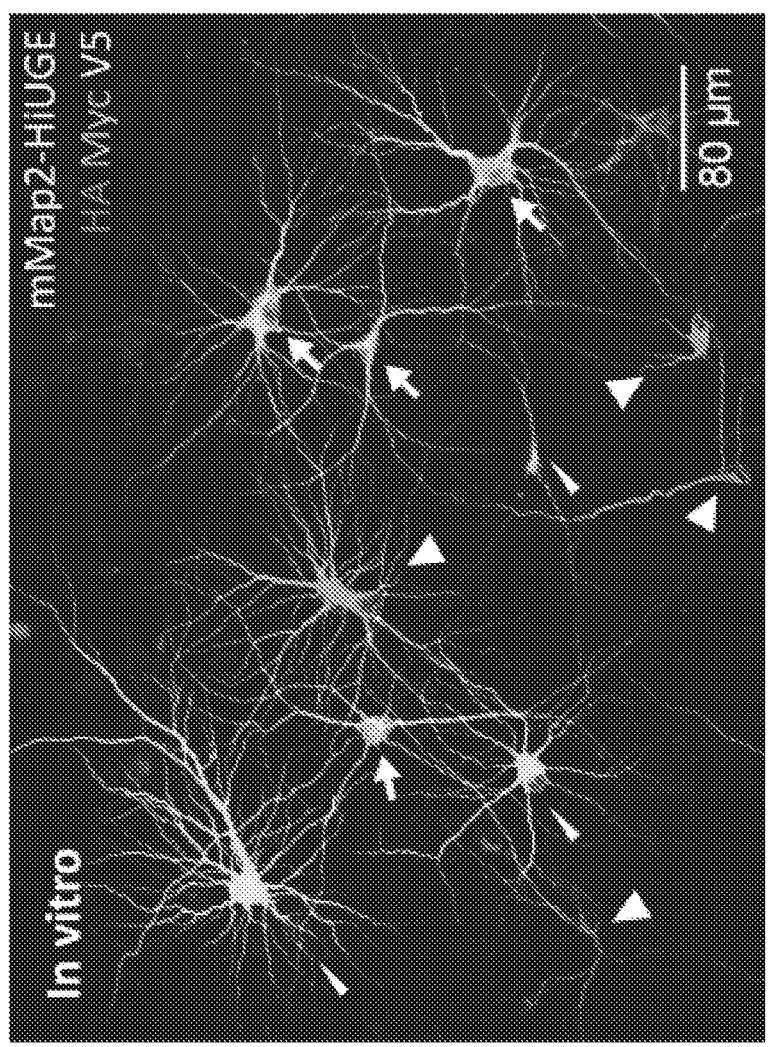
FIG. 7B shows a representative image of immunostaining of mosaic epitope KI into the mouse Map2 gene in primary hippocampal neurons (wide arrowhead, myc epitope staining; arrow, HA epitope staining; narrow arrowhead, V5 epitope staining).
Figure 7C:
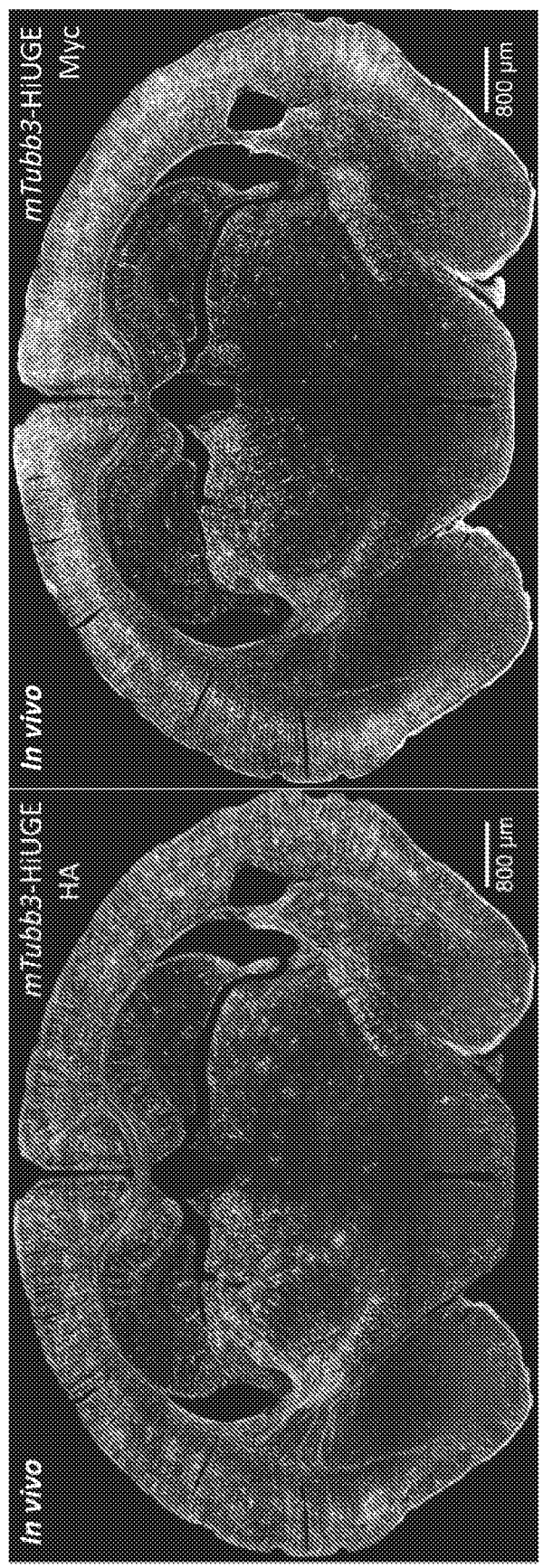
FIG. 7C shows a representative image of immunostaining of coronal brain section from mosaic epitope KI of mouse Tubb3 gene in vivo stained for both HA epitope and myc epitope.
Figure 7D:
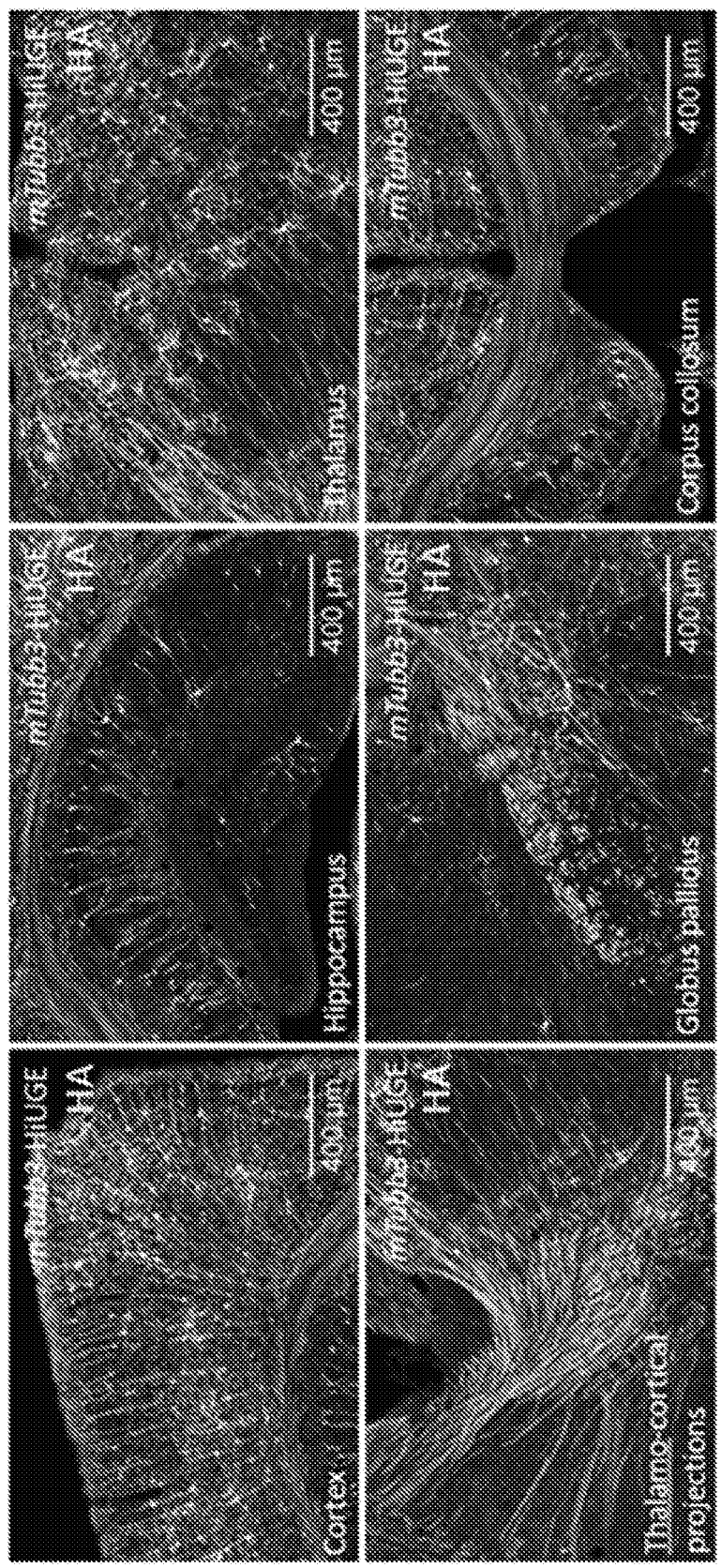
FIGS. 7D-7E shows zomed images showing the cortex, hippocampus, thalamus, thalamo-cortical projections, globus pallidus, and corpus collosum of FIG. 7C. Scale bar is indicated in each panel.
Figure 7E:
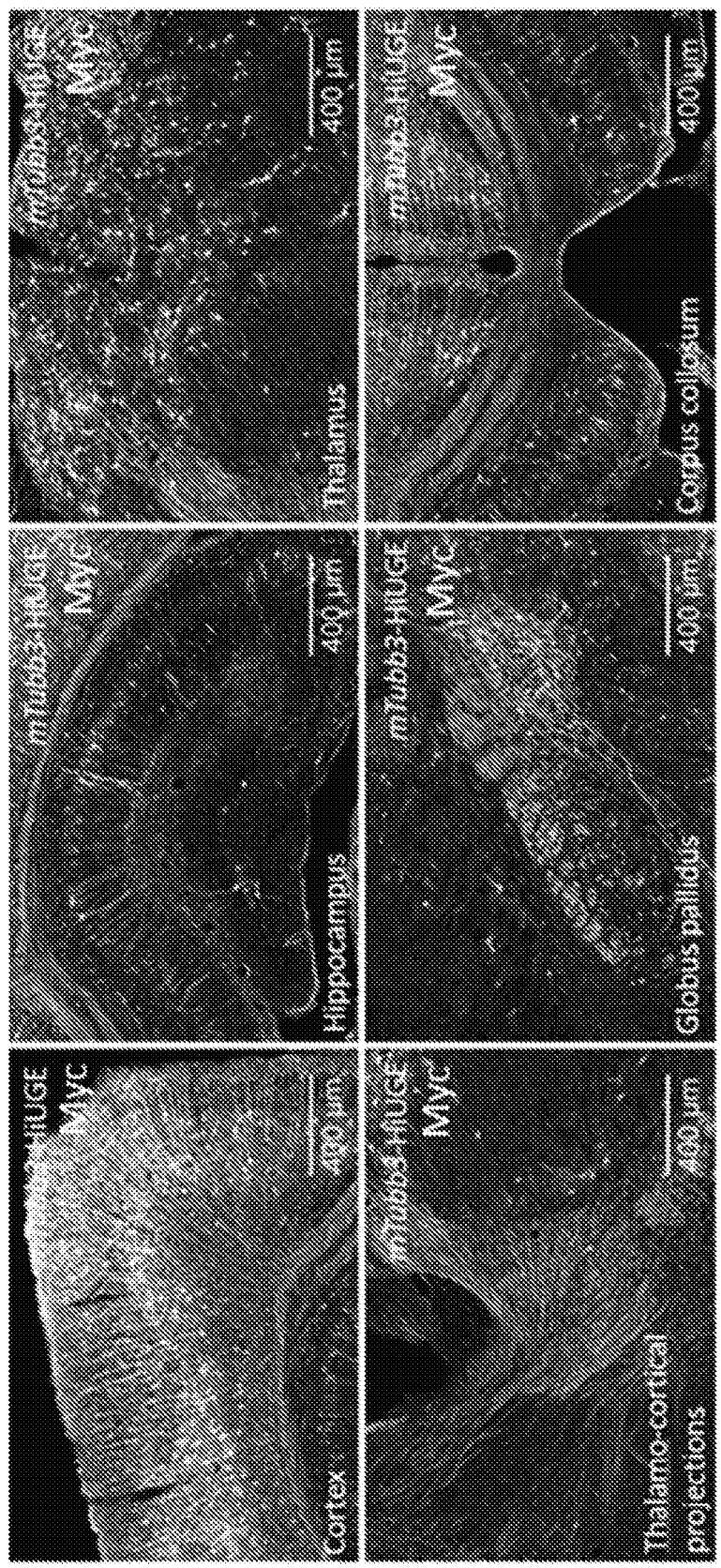

FIG. 7A shows a schematic illustration of an example HiUGE mosaic epitope knock-in (KI) application, which demonstrate that different donor vectors were able to incorporate different payloads into the same gene. A combination of GS-gRNA AAV vector and different epitope HiUGE donor AAV vectors was applied to cultured Cas9 expressing neurons (FIG. 7B), or delivered via intracerebroventricular injection to neonatal Cas9 expressing pups (FIG. 7C). Immunostaining was performed to visualize expression of different epitopes. FIG. 7B shows a representative image of immunostaining of mosaic epitope KI into the mouse Map2 gene in primary hippocampal neurons (wide arrowhead, myc epitope staining; arrow, HA epitope staining; narrow arrowhead, V5 epitope staining). FIG. 7C shows a representative image of immunostaining of coronal brain section from mosaic epitope KI of mouse Tubb3 gene in vivo stained for both HA epitope and myc epitope.

Figure 8A:
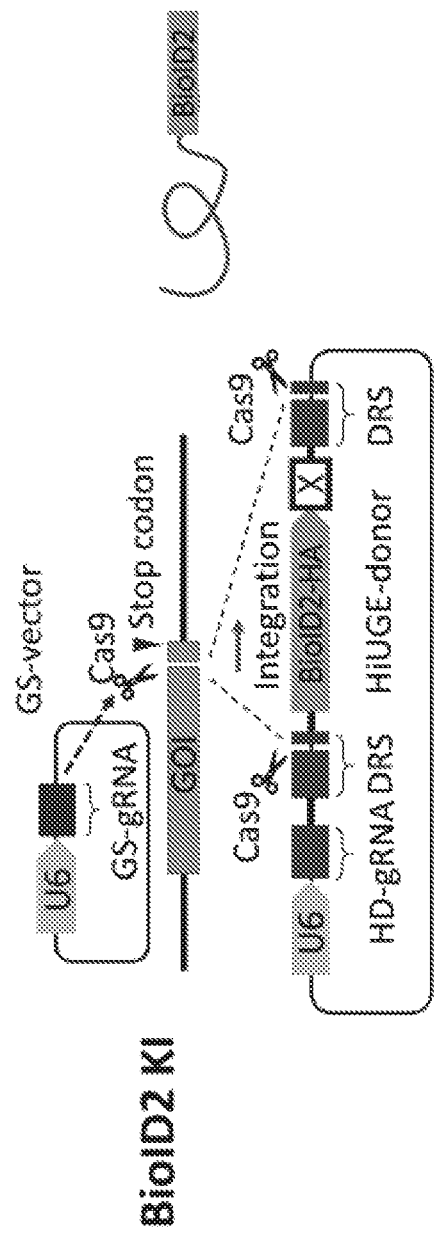
FIG. 8A shows a schematic illustration of HiUGE BioID2 enzyme KI application for proximity biotinylation experiments.
Figure 8B:
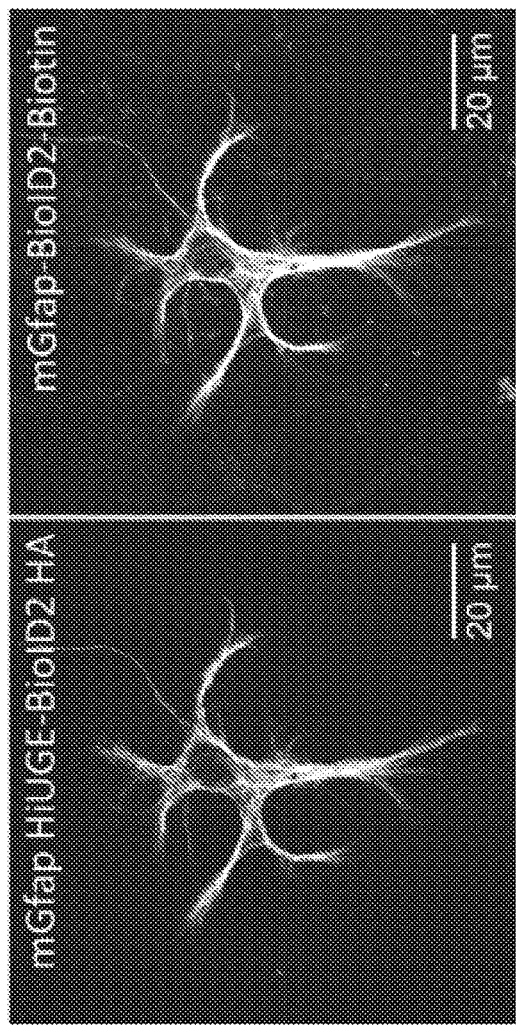
FIG. 8B shows a representative image of immunostaining demonstrating BioID2-HA KI into the carboxy-terminus of the glial acidic fibrillary protein encoded by the mouse GFAP gene, and corresponding detection of biotinylated proteins using fluorescent streptavidin (rightpanel).
Figure 8C:
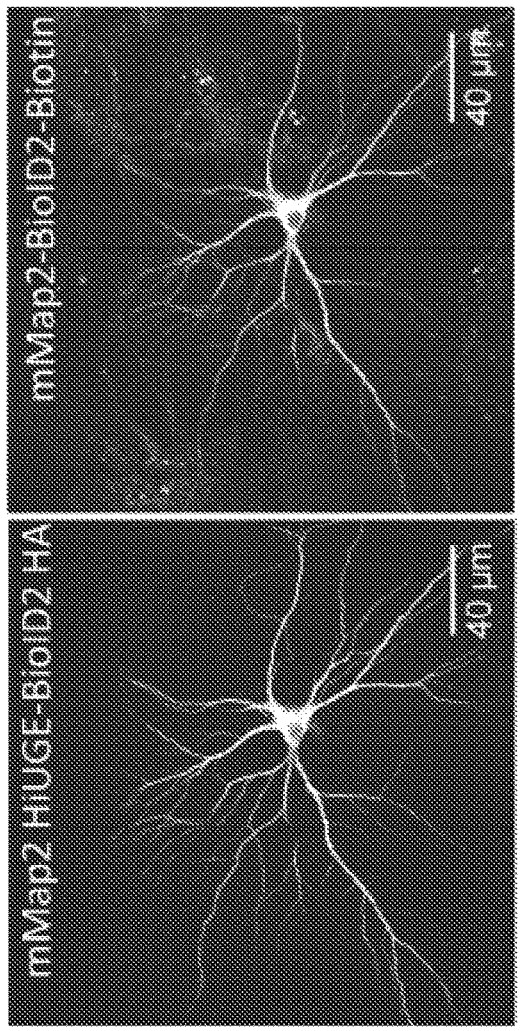
FIG. 8C shows a representative image of immunostaining demonstrating BioID2-HA KI into the carboxy-terminus of the Map2 protein encoded by the mouse Map2 gene, and corresponding positive detection of biotinylated proteins using fluorescent streptavidin (right panel).

FIG. 8A shows a schematic illustration of an example HiUGE BioID2 enzyme KI application for proximity biotinylation experiments. Cells were treated with 20 μM biotin overnight before fixation. Immunocytochemistry was performed to visualize BioID2-HA KI and biotinylation activity. FIG. 8B shows a representative image of immunostaining demonstrating BioID2-HA KI into the carboxy-terminus of the glial acidic fibrillary protein encoded by the mouse GFAP gene, and corresponding detection of biotinylated proteins using fluorescent streptavidin (right panel). FIG. 8C shows a representative image of immunostaining demonstrating BioID2-HA KI into the carboxy-terminus of the Map2 protein encoded by the mouse Map2 gene, and corresponding positive detection of biotinylated proteins using fluorescent streptavidin (right panel).

Figure 9A:
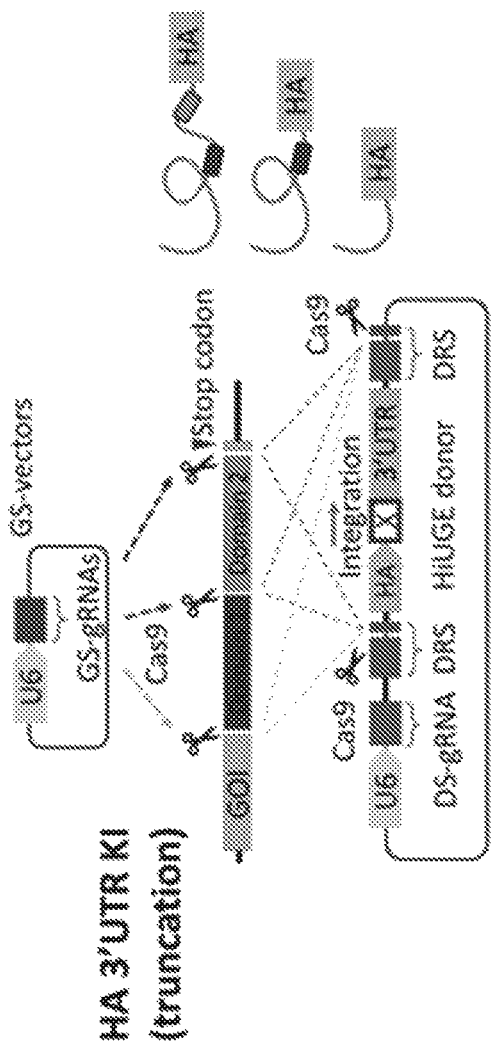
FIG. 9A shows a schematic illustration of HiUGE HA-3′ untranslated region (3′-UTR) KI to truncate endogenous proteins for conducting structure-function relationship studies.
Figure 9B:
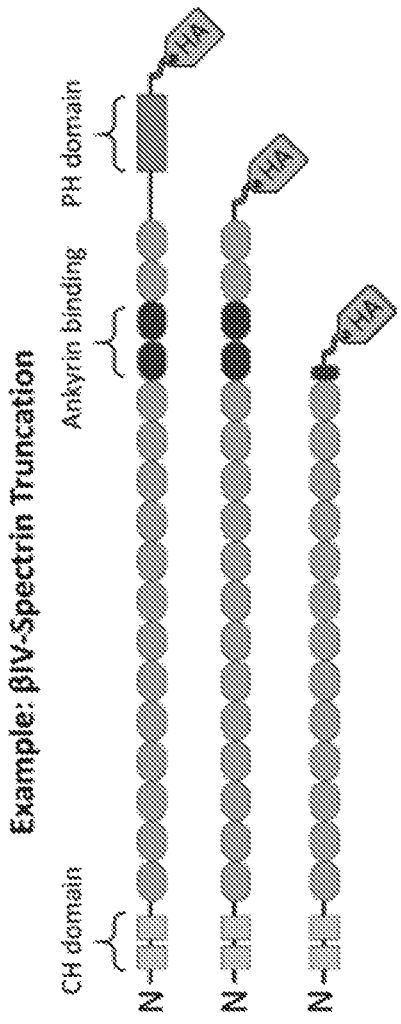
FIG. 9B shows an example using HA-3′UTR KI strategy to truncate the pleckstrin homology (PH) domain or the more upstream spectrin repeats from βIV-spectrin.

Protein truncation experiments identify functional domains, unveil protein interactions, and delineate structure-function relationships. Once again, conventional methods typically rely on over-expression of exogenous constructs. To enable truncation studies of endogenously expressed proteins, an HA-Stop-3'UTR HiUGE payload was designed (FIG. 9A). This construct enables the labeling of truncated endogenous proteins with an epitope, while facilitating escape from non-sense mediated decay by the addition of the 3'UTR containing a poly-adenylation sequence. This application is exemplified by truncation of βIV-spectrin, as it is enriched at the AIS and is composed of a modular domain architecture consisting of a calponin homology (CH) domain, multiple spectrin repeats (which contain an Ankyrin binding site within the 14th-15th repeat), and a C-term pleckstrin-homology (PH) domain (FIG. 9B).

FIGS. 9C-9D show that truncation of PH domain from βIV-spectrin by using a GS-gRNA targeting exon 31 (e.31) of mouse Sptbn4 gene does not alter its localization to the AIS when compared to carboxy-terminus KI using a GS-gRNA targeting exon 36 (e.36). Pairing the GS-gRNA targeting the last coding exon near the stop codon (exon 36 of the canonical Σ1 isoform) with the HA-Stop-3'UTR donor resulted in strong HA-epitope immunoreactivity restricted to the AIS (FIG. 9C). Targeting exon 31 to delete the PH domain from βIV-spectrin did not disrupt its AIS localization (FIG. 9D), consistent with previous work suggesting the PH domain is not required for its localization to the AIS. Remarkably, targeting the more upstream exon 26 to truncate βIV-spectrin within the 14th spectrin repeat completely abrogated its AIS-enriched immunoreactivity and resulted in a diffuse cytosolic staining (FIG. 9E). These results demonstrated that the region between the 14th spectrin repeat and the PH domain of βIV-spectrin is required for its enrichment within the AIS. This is consistent with previous studies that indicate βIV-spectrin interacts with the AIS-scaffold protein Ankyrin within the 14th-15th spectrin repeats, suggesting this interaction is important for its proper AIS localization.

HiUGE-mediated truncations of βIV-spectrin were further confirmed by Western blot analysis, revealing a stepwise reduction of the protein molecular mass that was consistent with the predicted serial truncation (FIG. 9F). Three GS-gRNA AAVs targeting different regions of mouse Sptbn4 gene (described above) were individually co-transduced with the HA-3'UTR HiUGE payload AAV to primary Cas9 neurons. Negative control group received no virus. HA-epitope tagged proteins were first enriched by immunoprecipitation with mouse anti-HA agarose beads, then subjected to SDS-PAGE and immunoblotted using a separate rabbit anti-HA antibody. Stepwise reduction of molecular mass in agreement with the serial truncation conditions is evident (arrowheads). Arrowheads indicate the 1 isoform of βIV-spectrin, while arrows indicate the 76 isoform. The 76 isoform of the truncation at exon 26 (e.26) appeared undetectable. Scale bar is indicated in each panel. Thus, HiUGE enables rapid serial truncation of endogenous proteins to interrogate the structure-function relationship associated with the underlying cellular mechanisms in situ.

Together, libraries of HiUGE payloads with different functional moieties can be interchanged to facilitate multiple independent approaches to investigate endogenous proteins, illustrated here by the visualization of protein localization and dynamics, targeted manipulation of protein subcellular residency, as well as analysis of structure-function relationships. Due to the interchangeable nature of HiUGE, other DNA sequences can also be incorporated as payloads to be delivered to diverse GS-gRNA specified genomic loci, opening a myriad of new possibilities for gene/protein modification and manipulation.

Figure 10A:
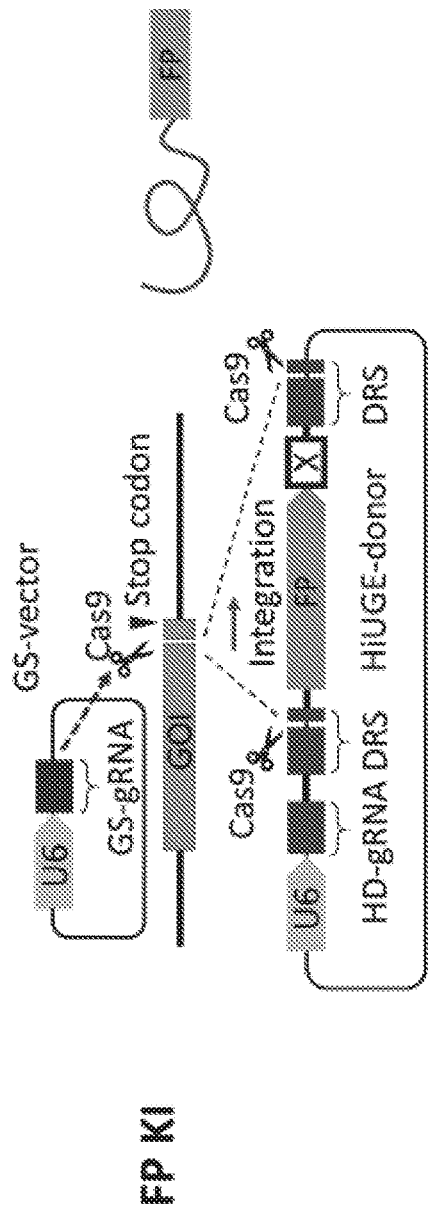
FIG. 10A shows a schematic illustration of HiUGE fluorescent protein (FP) KI.
Figure 10D:
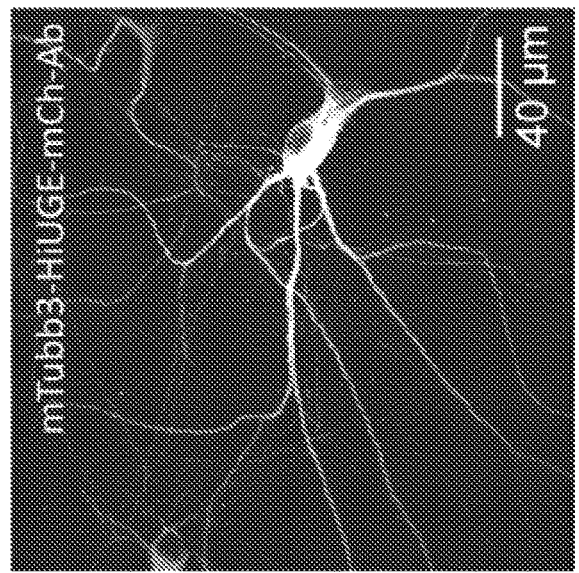
FIG. 10B, FIG. 10C, and FIG. OD show mCherry fluorescent protein (mCh) KI into different genomic targets (GFAP (FIG. 10B), Pdha1 (FIG. 10C), and Tubb3 (FIG. 10D)).
Figure 10C:
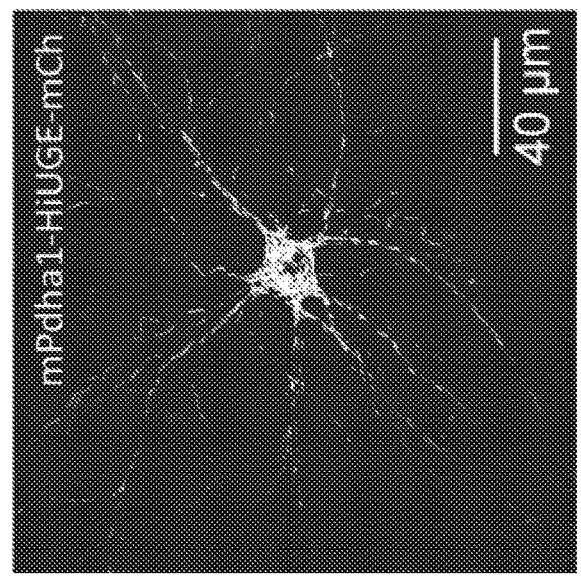
Figure 10B:
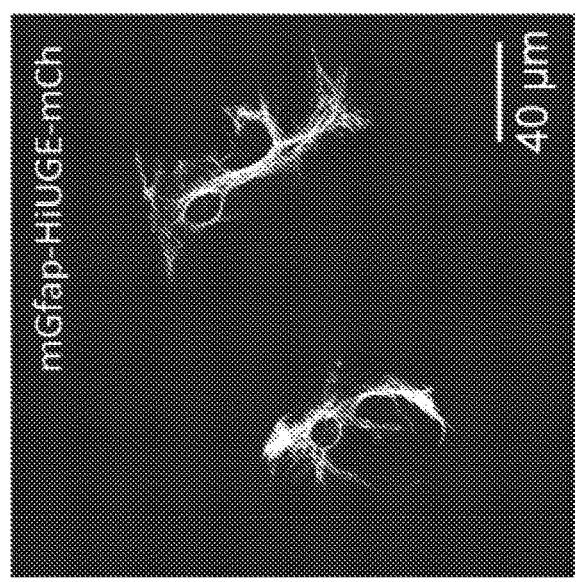

FIG. 10A shows a schematic illustration of an example HiUGE fluorescent protein (FP) KI. FIG. 10B shows mCherry fluorescent protein (mCh) KI into GFAP, FIG. 10C shows mCherry fluorescent protein (mCh) KI into Pdha1. FIG. 10D shows mCherry fluorescent protein (mCh) KI into Tubb3. FIGS. 10B-10D show that the mCh fluorescence can be either directly imaged (FIG. 10B, FIG. 10C), or imaged following immunocytochemistry using an antibody against mCherry (FIG. 10D).

FIG. 11A shows a schematic illustration of an example HiUGE amino-terminal (N-term) KI construct. The purpose of this design was to achieve dual labeling of two different targets by differentially targeting the N-term or the carboxy-terminal (C-term) of two different proteins. The stop codon cassette within the N-term HiUGE vector ensured that in the event of integration into the C-term, the translation would terminate upstream of the Myc-tag epitope. FIG. 11B shows a representative immunostaining image of dual labeling of Map2 and Sptbn4 encoded proteins by N-term KI of the Myc epitope to Map2, and C-term KI of HA-epitope to Sptbn4 (arrowhead), encoding protein βIV-spectrin. Dashed circle represents the neuronal soma of the dual-labeled neuron.

Figure 12A:
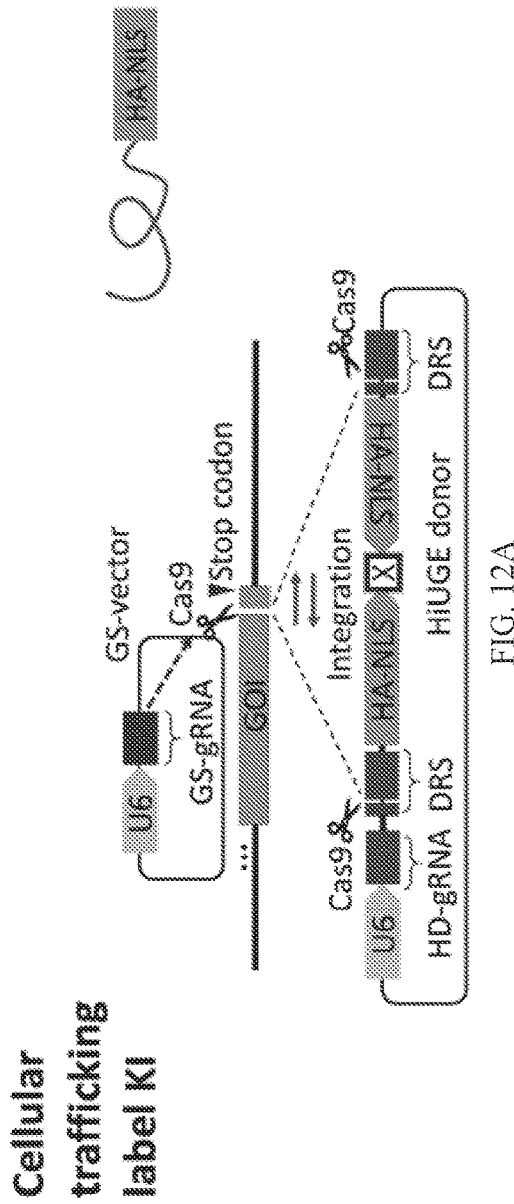
FIG. 12A shows a schematic illustration of HiUGE subcellular re-localization construct.
Figure 12B:
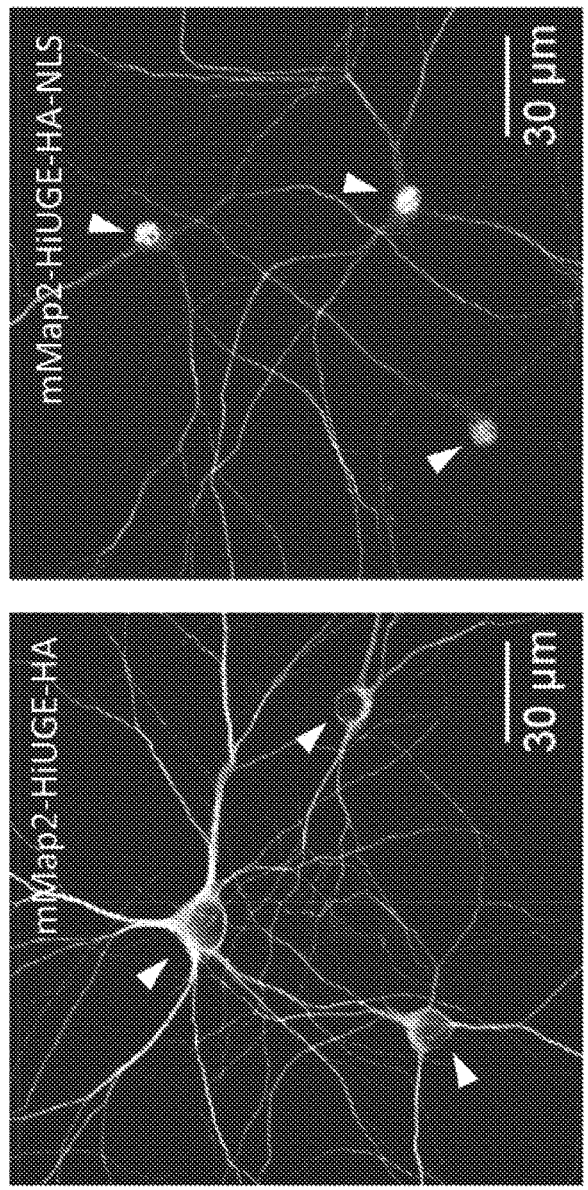
FIG. 12B shows a representative image of immunostaining (Left pane) of Map2 tagged at the c-terminus with HA and Map2 tagged with a nuclear localization signal (HA-NLS) (Rightpane). Arrowheads in both panels indicate site of nucleus. Scale bar is indicated in each panel.
Figure 12D:
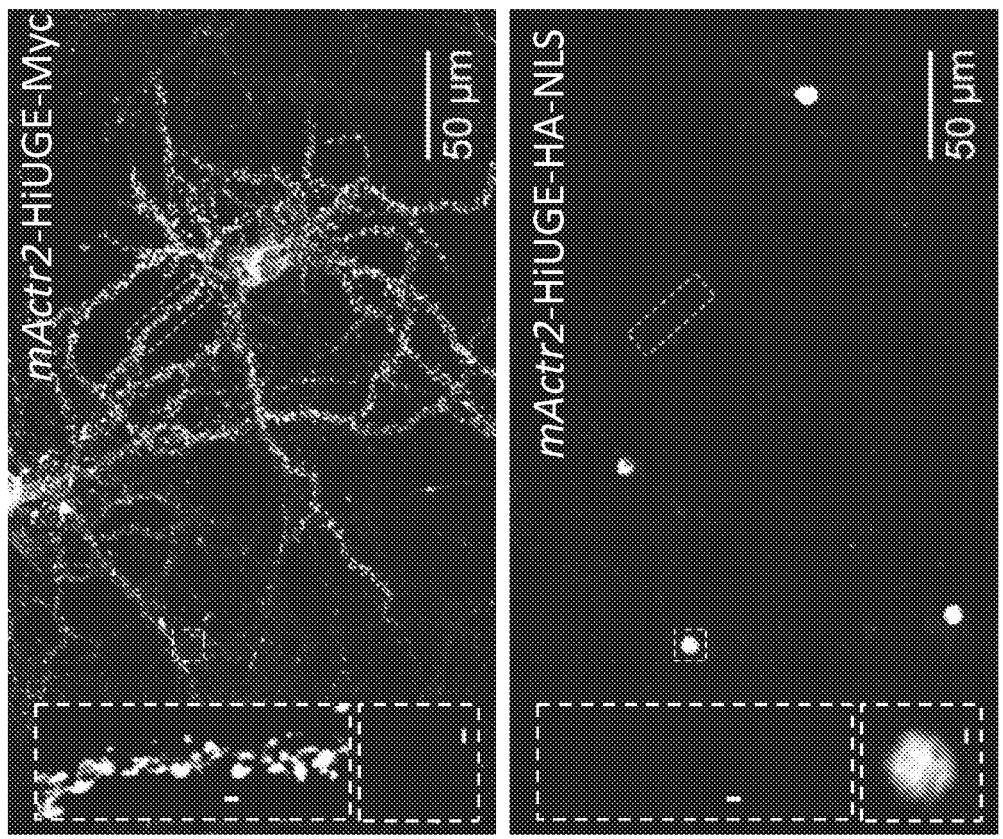
FIG. 12D shows a representative image of immunostaining following C-term HA-NLS KI to mouse Actr2 gene, showing the HA-NLS-tagged Arp2 (red) redirected to the nucleus. Simultaneously, the Myc-epitope (no NLS) tagged Arp2 (green) was enriched at the dendritic spines, consistent with the normal localization of Arp2.
Figure 12C:
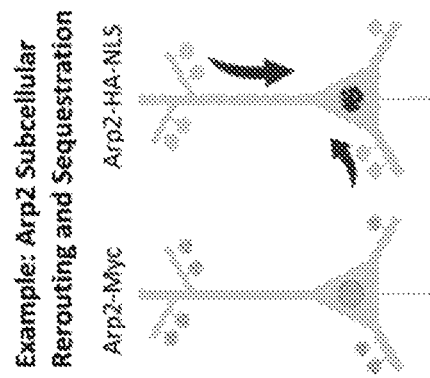
FIG. 12C shows an example using a HiUGE payload with HA-epitope and nuclear localization signal (HA-NLS) to reroute and sequester an actin cytoskeletal protein Arp2 to the nucleus.

A dual-orientation HA-NLS HiUGE payload (FIG. 12A was targeted to the C-term of mouse Arp2 to determine if this abundant cytoskeletal protein could be manipulated to relocate to the nucleus (FIG. 12C). FIG. 12A shows a schematic illustration of an example HiUGE subcellular re-localization construct. The purpose of this design was to re-localize endogenous proteins away from their normal site of function, which can be an effective way to create loss of function or gain of function experimental designs. FIG. 12B shows a representative image of immunostaining (Left panel) of Map2 tagged at the c-terminus with HA to demonstrate its normal distribution in neurons within the cell body and neuronal process, but not within the nucleus. Alternatively, tagging Map2 with a nuclear localization signal (NLS) (Right pane) re-localized the majority of the Map2 to the nucleus. Arrowheads in both panels indicate site of nucleus. Scale bar is indicated in each panel. Neurons were transduced with mouse Actr2 GS-gRNA AAV and a mixture of HA-NLS and Myc-epitope (no NLS) HiUGE payloads. HA-NLS-tagged Arp2 (red) was completely redirected to the nuclei, whereas the Myc-tagged Arp2 (green) was mostly found in the dendritic spines, representing the normal localization of Arp2 (FIG. 12D). Thus, HiUGE payloads of subcellular trafficking tags, such as an NLS, can be harnessed to manipulate the subcellular residency of endogenous proteins, for purposes such as creating potential loss-of-function or gain-of-function experiments.

Example 7

Figure 13A:
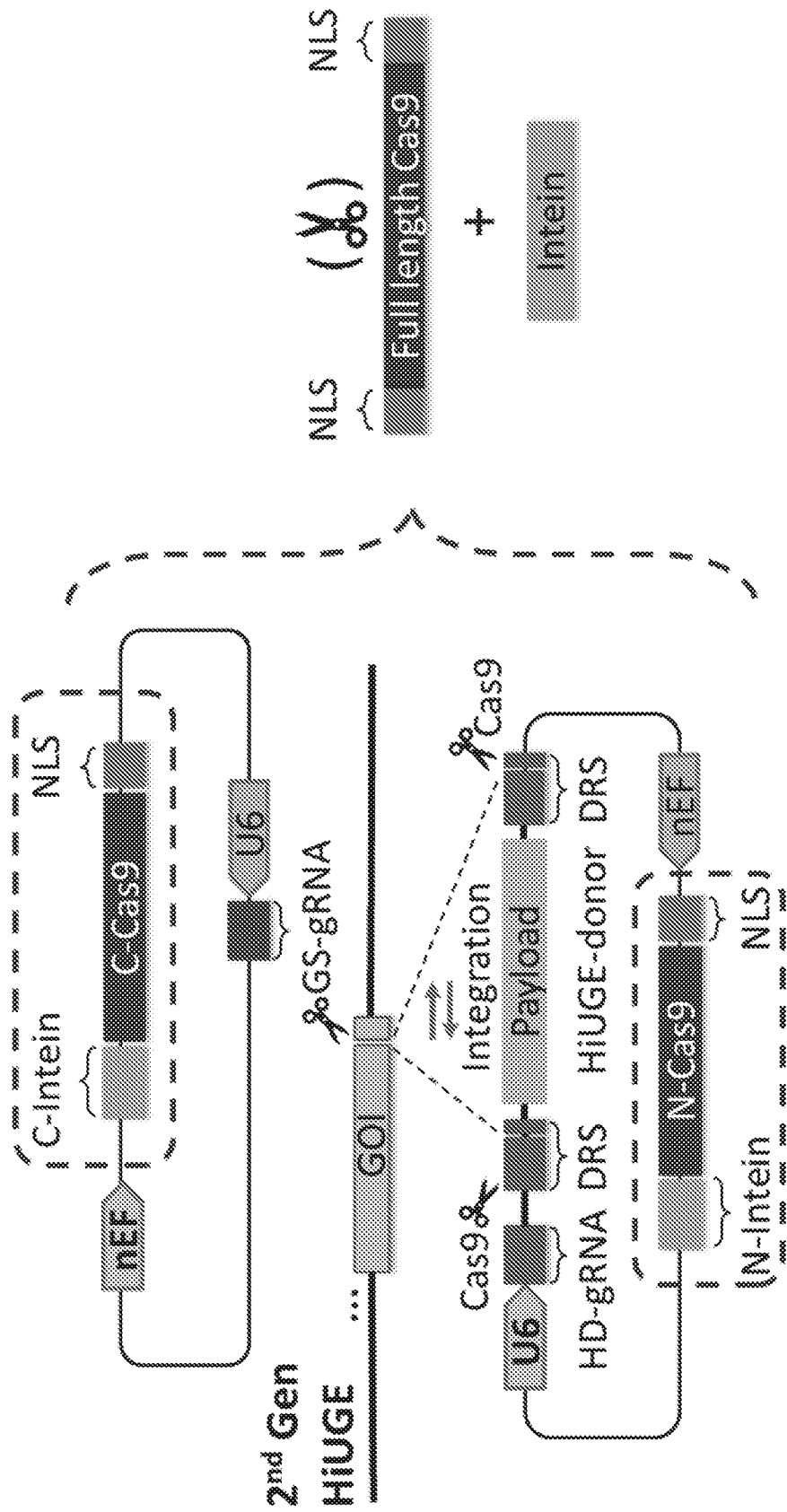
FIG. 13A shows a schematic illustration of the $2^{nd}$ generation HiUGE system that harbors built-in Cas9 coding sequences.
Figure 13C:
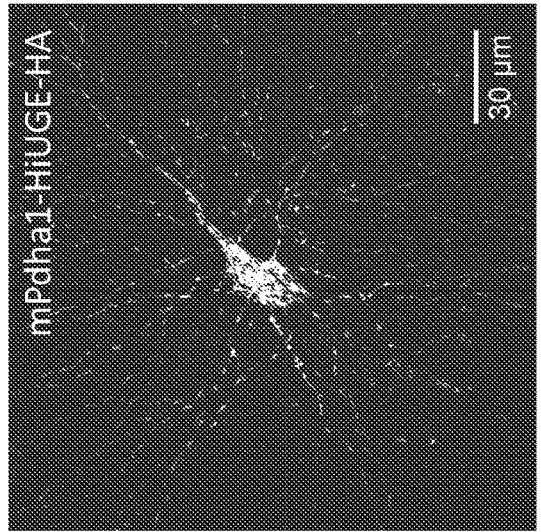
FIGS. 13B-13C show representative images of HA epitope KI into the mouse Tubb3 gene (FIG. 13B) and mouse Pdha1 gene (FIG. 13C).
Figure 13E:
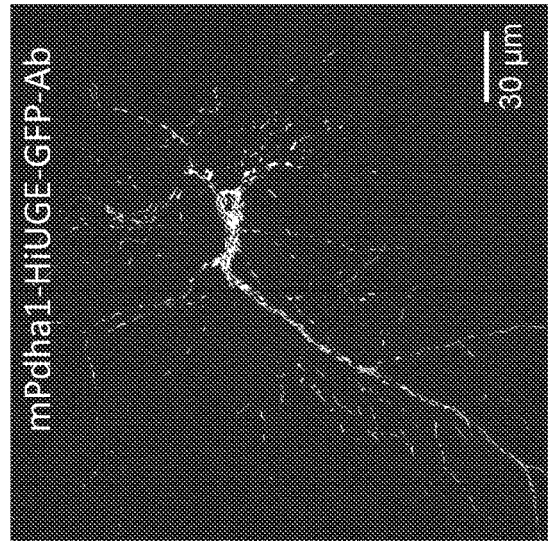
FIGS. 13D-13E show representative images of GFP KI of mouse Tubb3 gene (FIG. 13D) and mouse Pdha1 gene (FIG. 13E). Scale bar is indicated in each panel. Wild-type (WT) primary mouse neurons were AAV transduced.
Figure 13B:
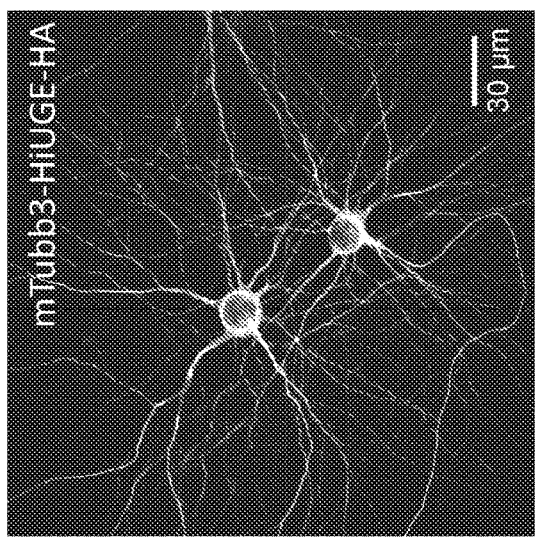
Figure 13D:
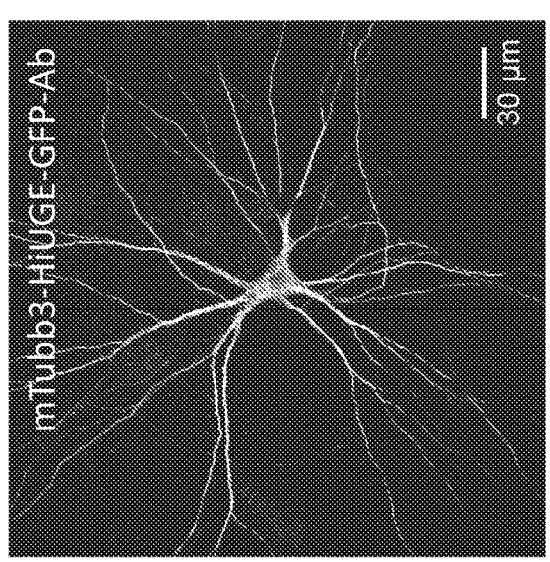
Figure 13G:
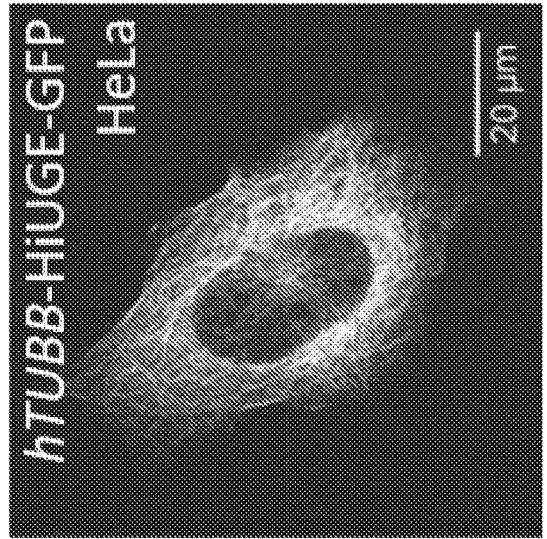
FIGS. 13F-13K show common human or mouse cell lines that were plasmid transfected with a combination of GS-gRNAs and HiUGE donors, followed by immunostaining for HA-epitope or GFP to detect payload KI.
Figure 13F:
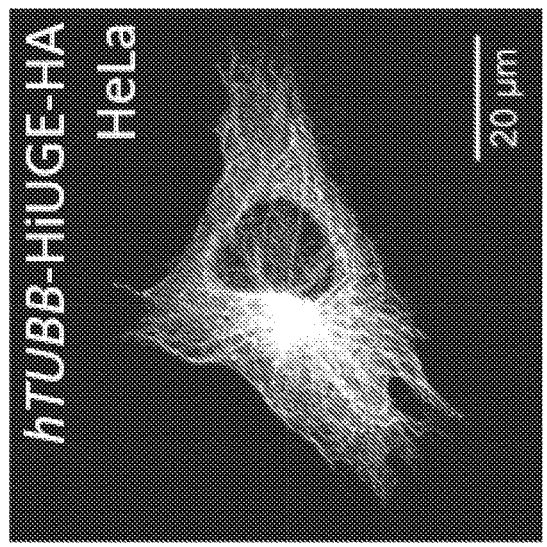
Figure 13I:
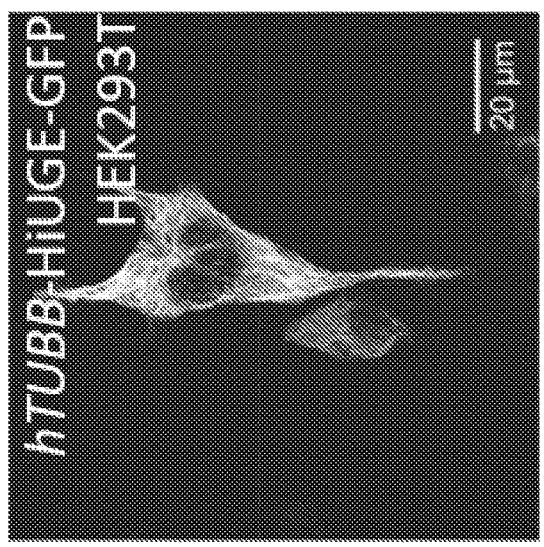
Figure 13H:
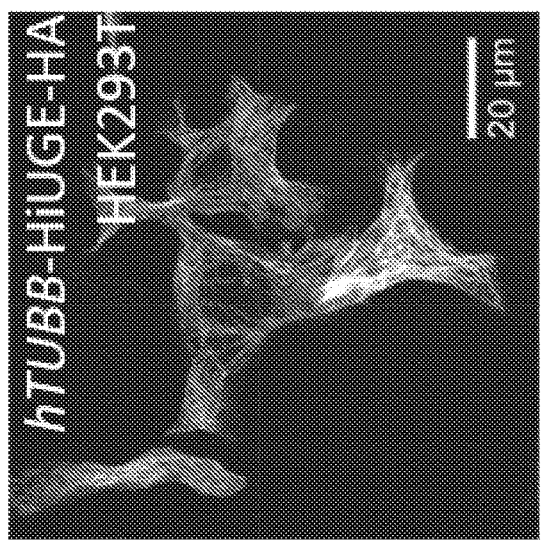

Conceptual Schematic and Experimental Evidence for the Second Generation HiUGE Method FIG. 13A shows a schematic illustration of an example of a $2^{nd}$ generation HiUGE system that harbors built-in Cas9 coding sequences. An intein-mediated split Cas9 design was used to distribute Cas9 coding sequence to both the GS-gRNA vector and the HiUGE vector, so that both vectors meet AAV size limit and have enough space for the payload. Fully functional Cas9 was reconstituted after intein-mediated protein splicing. All applications of the $1^{st}$ generation HiUGE method can also apply to the $2^{nd}$ generation method.

FIGS. 13B-13E show example applications of $2^{nd}$ generation HiUGE technique in wild-type (WT) primary cultured mouse neurons. Cells were transduced with a combination of $2^{nd}$ generation GS-gRNA AAV vector and $2^{nd}$ gen HiUGE donor AAV vector on DIV 4-6, and fixed after DIV 11 for immunocytochemistry to detect HA epitope or green fluorescent protein (GFP) KI by immunostaining. Representative images of HA epitope KI into the mouse Tubb3 gene (FIG. 13B) and Pdha1 gene (FIG. 13C) showed the distinctive (FIG. 13B) microtubule or (FIG. 13C) mitochondrial localization of HA immunoreactivity. Representative images of GFP KI of mouse Tubb3 gene (FIG. 13D) and Pdha1 gene (FIG. 13E) showed the immunostaining of (FIG. 13D) microtubules or (FIG. 13E) mitochondria. Scale bar is indicated in each panel.

The HiUGE system relies upon exogenous Cas9 expression such as Cre-dependent activation of Cas9 in lox-stop-lox Cas9-2A-GFP mice. To simplify the application of HiUGE system in diverse wild-type (WT) cells and animals, sequences for Cas9 expression were incorporated into the HiUGE vectors. One limitation to AAV-based delivery of spCas9 (coding sequence ~4.1 kb), is that AAV viral vectors can only accommodate inserts sizes of ~4.5 kb. To overcome this constraint, spCas9 was split in half between each HiUGE vector, with each half incorporating Npu split-intein sequences. Intein mediated protein trans-splicing of spCas9 would thus enable spCas9 expression in cells transduced with both HiUGE vectors (FIG. 13A). Diverse HiUGE payloads can be readily accommodated in this system for application in WT cells and animals. The feasibility of this approach was tested in WT primary mouse neurons, as well as in common human or mouse cell lines using dual-orientation HA-epitope or GFP HiUGE payloads, paired with GS-gRNA AAVs targeting either mouse Tubb3, Map2, Pdha1, Tubb5, or human TUBB gene. Immunostaining of transduced neurons indicated successful HA-epitope and GFP KI showing tubulin cytoskeletal or mitochondrial networks ((FIGS. 13B-13E). Likewise, HiUGE components delivered by plasmid co-transfection into common cell lines such as HeLa, HEK293T, and NIH3T3 also demonstrated successful HA-epitope and GFP KI showing tubulin networks ((FIGS. 13F-13K).

Figure 13L:
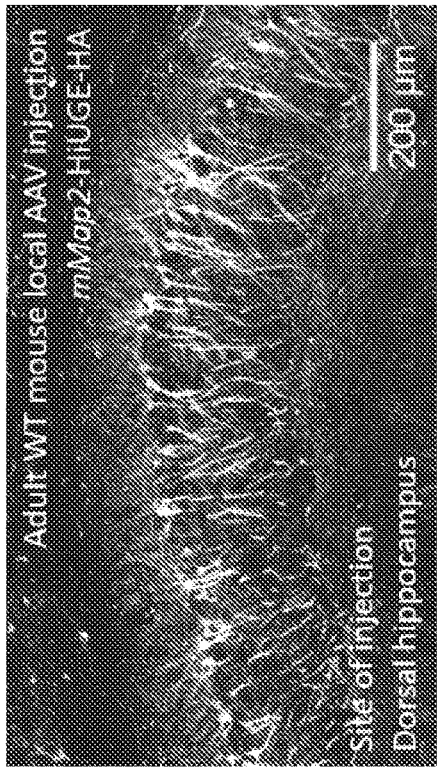
FIG. 13M shows a representative image of HA-epitope KI to mouse Map2 gene following local AAV injection in the dorsal hippocampus of adult WT mice, showing efficient labeling of the neurons at the injection site compared to negative labeling on the contralateral side. Zoomed view of the boxed area is shown in FIG. 13L. Scale bar is indicated in each panel.
Figure 13K:
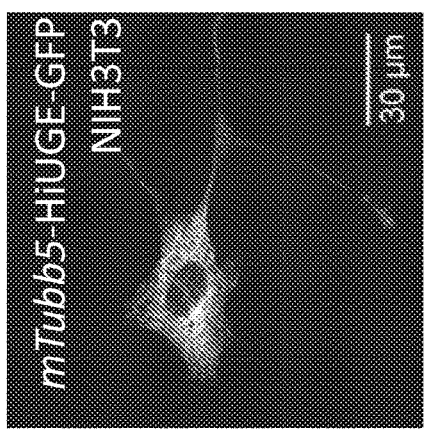
Figure 13J:
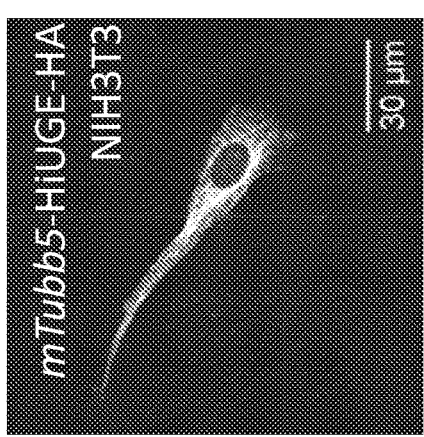
Figure 13M:
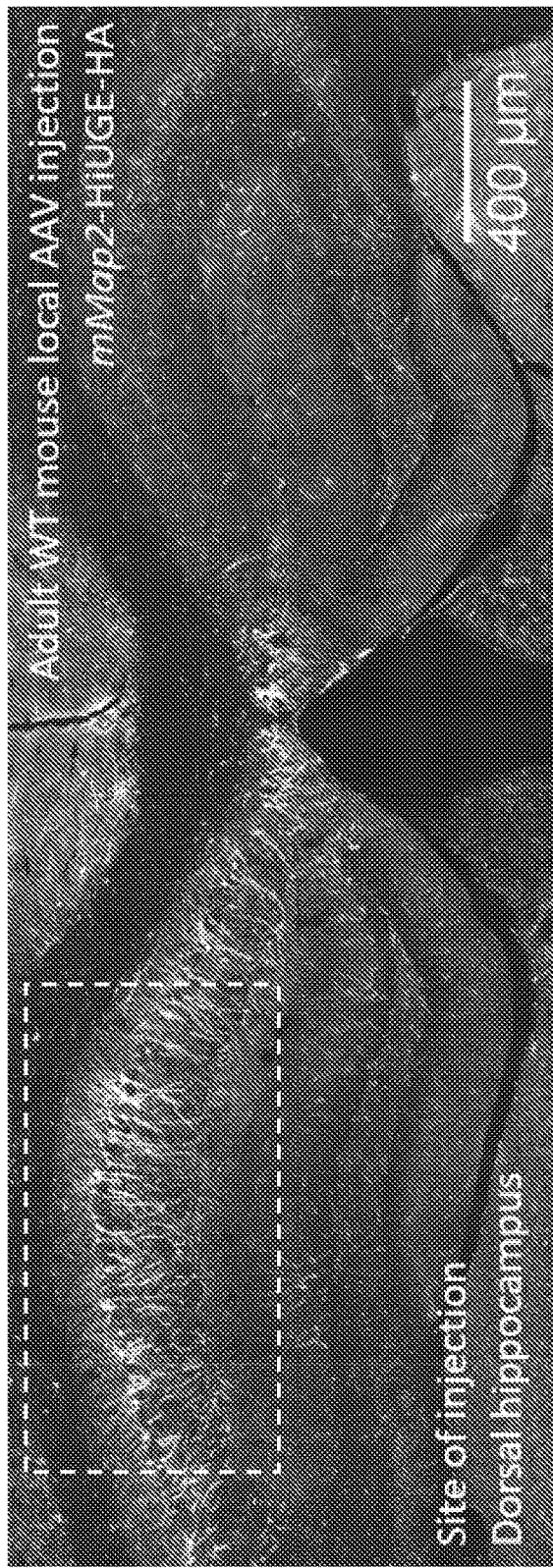
Figure 14A:
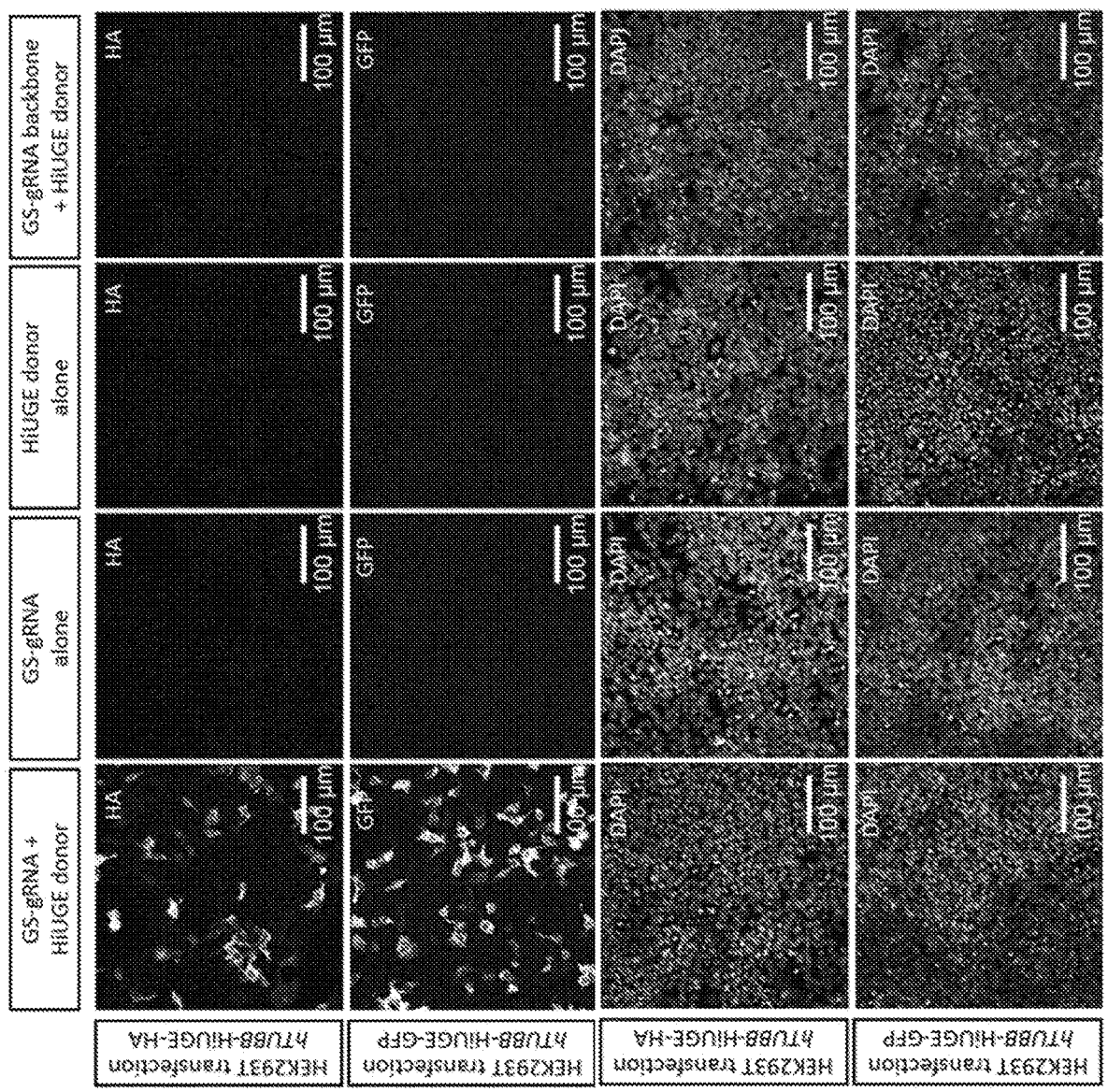
FIGS. 14A-14B show control experiments for HiUGE vectors with intein-split-Cas9. Scale bar is indicated in each panel.
Figure 14B:
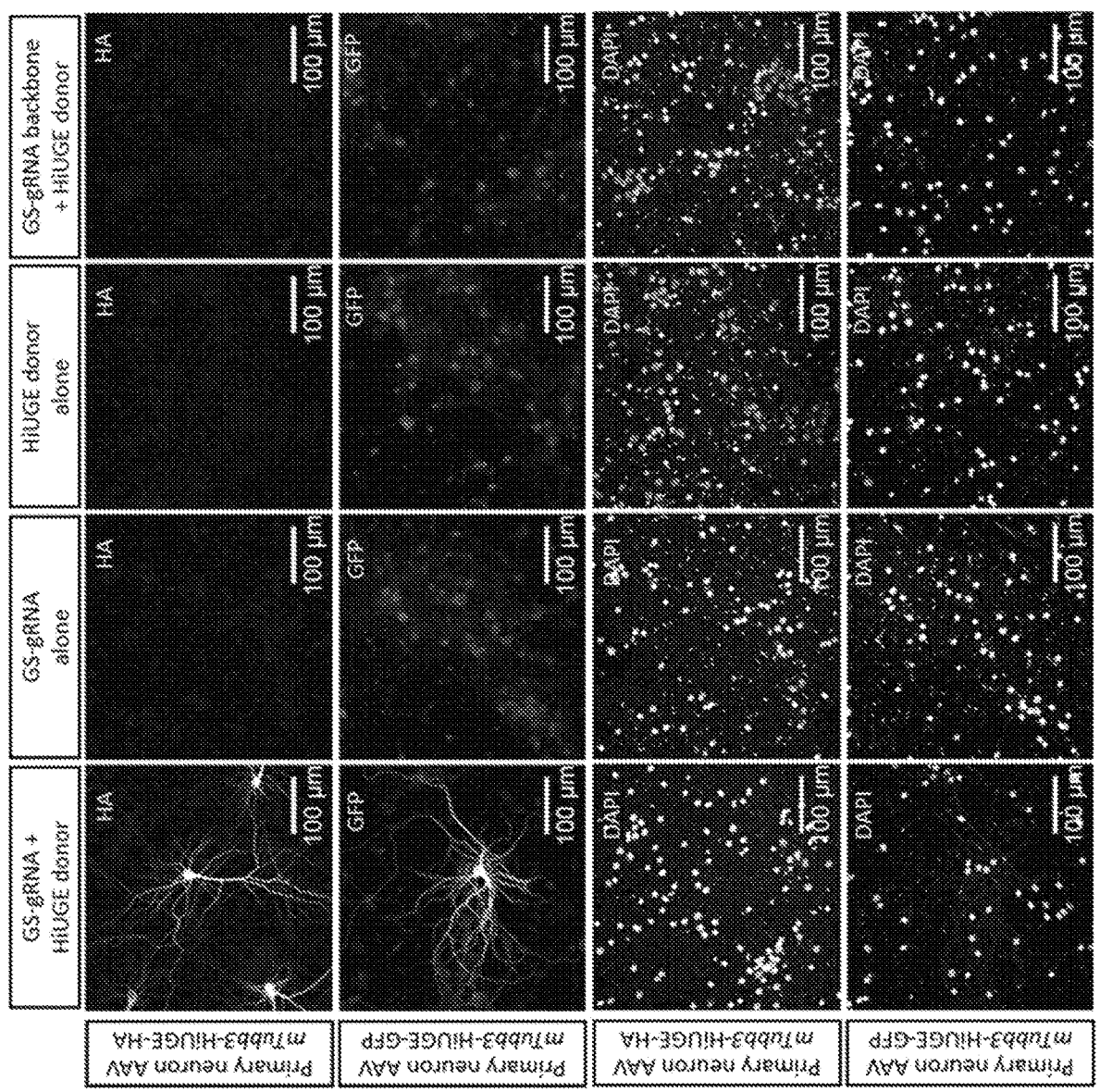

Control experiments for intein-split-Cas9 mediated HiUGE vectors in HEK293T cells and WT primary neurons were conducted. HEK293T Cells were plasmid transfected and primary neurons were AAV transduced with HiUGE GS-gRNAs and donors to knock-in HA-epitope or GFP payloads to human TUBB (hTUBB) or mouse Tubb3 (mTubb3) genomic loci. Experimental conditions are indicated in the figure. Positive HA-epitope or GFP immunoreactivity showing tubulin-like expression pattern was only found when GS-gRNAs were paired with the corresponding HiUGE donors (leftmost column). No HA-epitope or GFP KI was detected when GS-gRNA or HiUGE donor was applied alone, or when an empty GS-gRNA backbone was paired with the donor. These specificity control experiments showed that the incorporation of the HA-epitope or GFP payloads requires both the GS-gRNA vector and the payload vector (FIGS. 14A-14B). Further, the applicability of intein-split-Cas9 mediated HiUGE was tested in vivo. Purified high-titer AAVs (dual-orientation HA-epitope payload and GS-gRNA targeting mouse Map2) were unilaterally co-injected into the dorsal hippocampal formation of adult WT mice. Approximately 2 weeks after infection, HA-epitope immunolabeling revealed robust MAP2 labeling in dendrites and cell bodies within the injected hippocampus, but not on the contralateral uninfected side (FIGS. 13L and 13M). Further, viral titers of the purified AAVs ($\sim 10^{10}$-$10^{11}$ genome copies/μL) were not substantially different from the analogous HiUGE AAVs without the intein-split-Cas9, demonstrating the incorporated sequences did not impede viral production. Thus, intein-split-Cas9 mediated HiUGE facilitates the expression of Cas9 and effective genome modification, simplifying the application across WT mammalian species and experimental models.

Example 8

Neural Circuit-Based HiUGE Payload Delivery

Figures 20A, 20B, 20C:
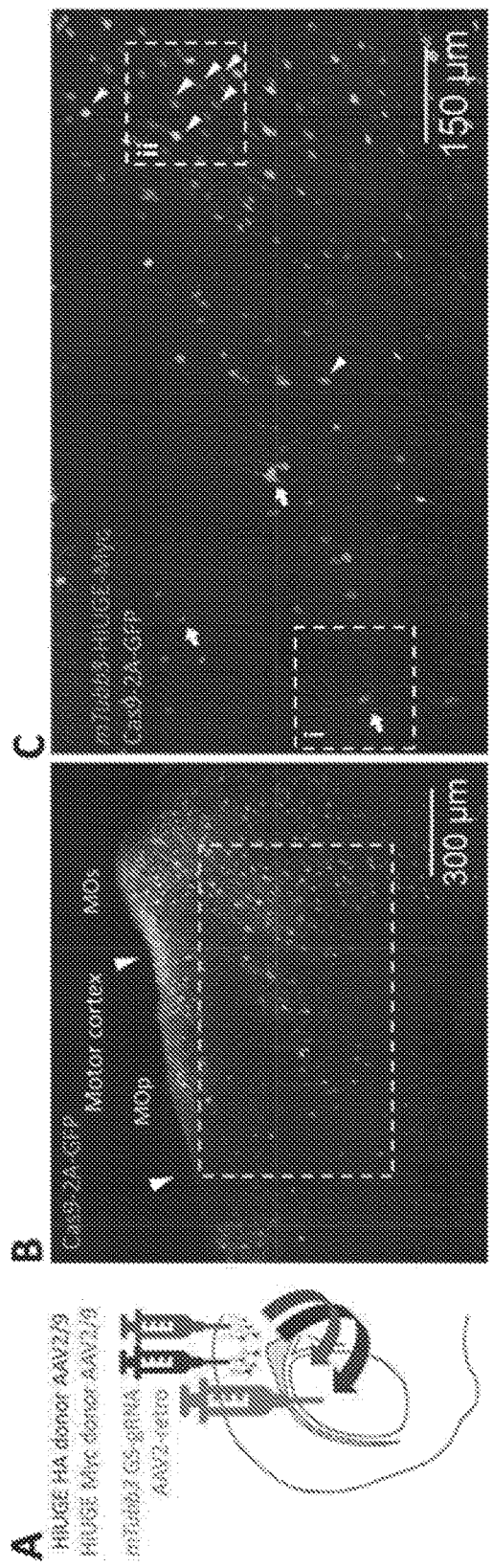
Figures 20D, 20E, 20F, 20G:
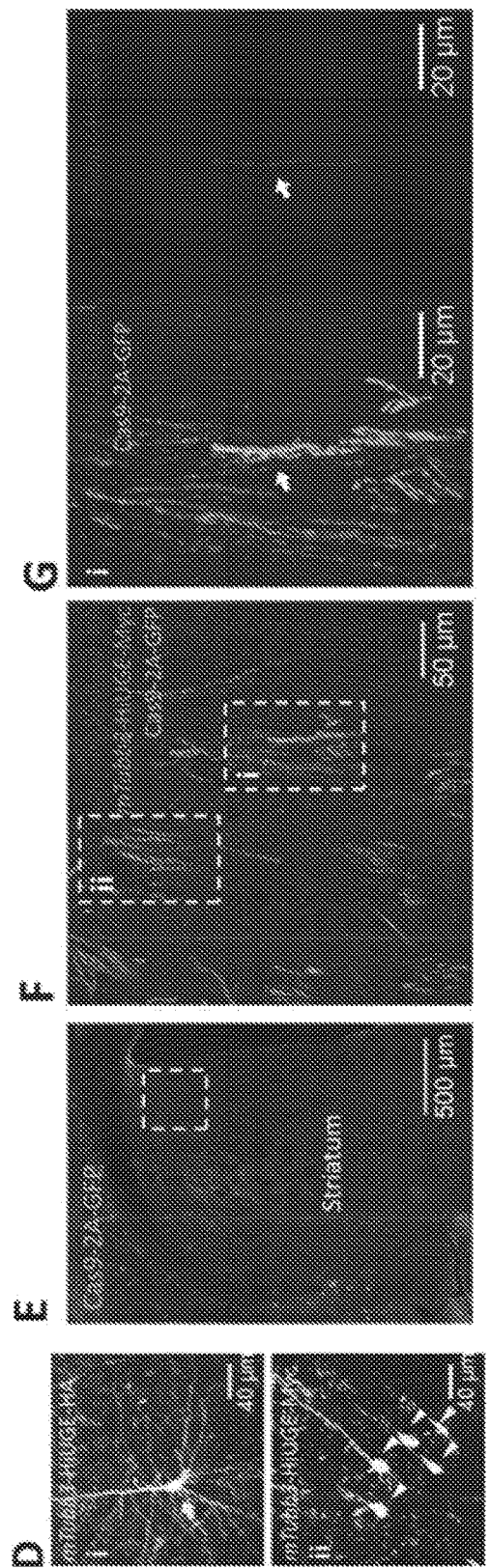

The genome editing activity was limited to specific neural circuits by utilizing a recently reported retrograde-transported AAV2-retro serotype (Tervo et al., 2016), thus enabling circuit-specific studies using HiUGE tools. AAV2-retro GS-gRNA injected into a brain area containing projection axon terminals of a circuit was paired with injection of regular AAV HiUGE donor into a specific projection region to enable circuit-selectivity. This combination allowed retrograde access of projection areas from a target brain region, and HiUGE-mediated genome editing of projection neurons for neural circuit-selective proteome manipulations. The cortico-striatal circuit and the thalamo-cortical circuit was used. For the cortico-striatal circuit, mTubb3 GS-gRNA AAV2-retro was injected to the striatum, whereas individual AAV2/9 HiUGE donor AAVs were injected laterally into either the primary motor cortex (MOp, HA-epitope) or secondary motor cortex (MOs, Myc-epitope) of adult conditional Cas9 mice (FIG. 20A). Retrograde access to the projection neurons in the motor cortex was confirmed by positive GFP labeling, indicating Cre-dependent activation of Cas9-2A-GFP (FIG. 20B). Cell bodies and neurites of HiUGE-edited projection neurons within the motor cortex were clearly delineated by HA and Myc-epitope labeled βIII-tubulin, corresponding to the injection sites (FIGS. 20C-20D). Bundles of GFP-positive fibers were also observed in the striatum representing cortico-striatal projections (FIGS. 20E-20F). Individual axons immuno-positive for either the HA or Myc-epitope, which presumably originated from neurons of different motor cortical sub-regions, were present within neighboring cortico-striatal axon bundles (FIGS. 20G-20H). Similar circuit-selective HA-epitope tagging of βIII-tubulin within thalamic projection neurons was also observed in the thalamo-cortical circuit (FIGS. 20I-20K). Thus, by pairing the HiUGE system with AAV2-retro, retrograde infection of projection neurons enabled HiUGE-mediated protein modification specific to circuit connectivity. This provides a new venue for using diverse HiUGE payloads in vivo to study the molecular mechanisms underlying neural circuit functions.

Example 9

Kaleidoscope Payloads

Figure 21A:
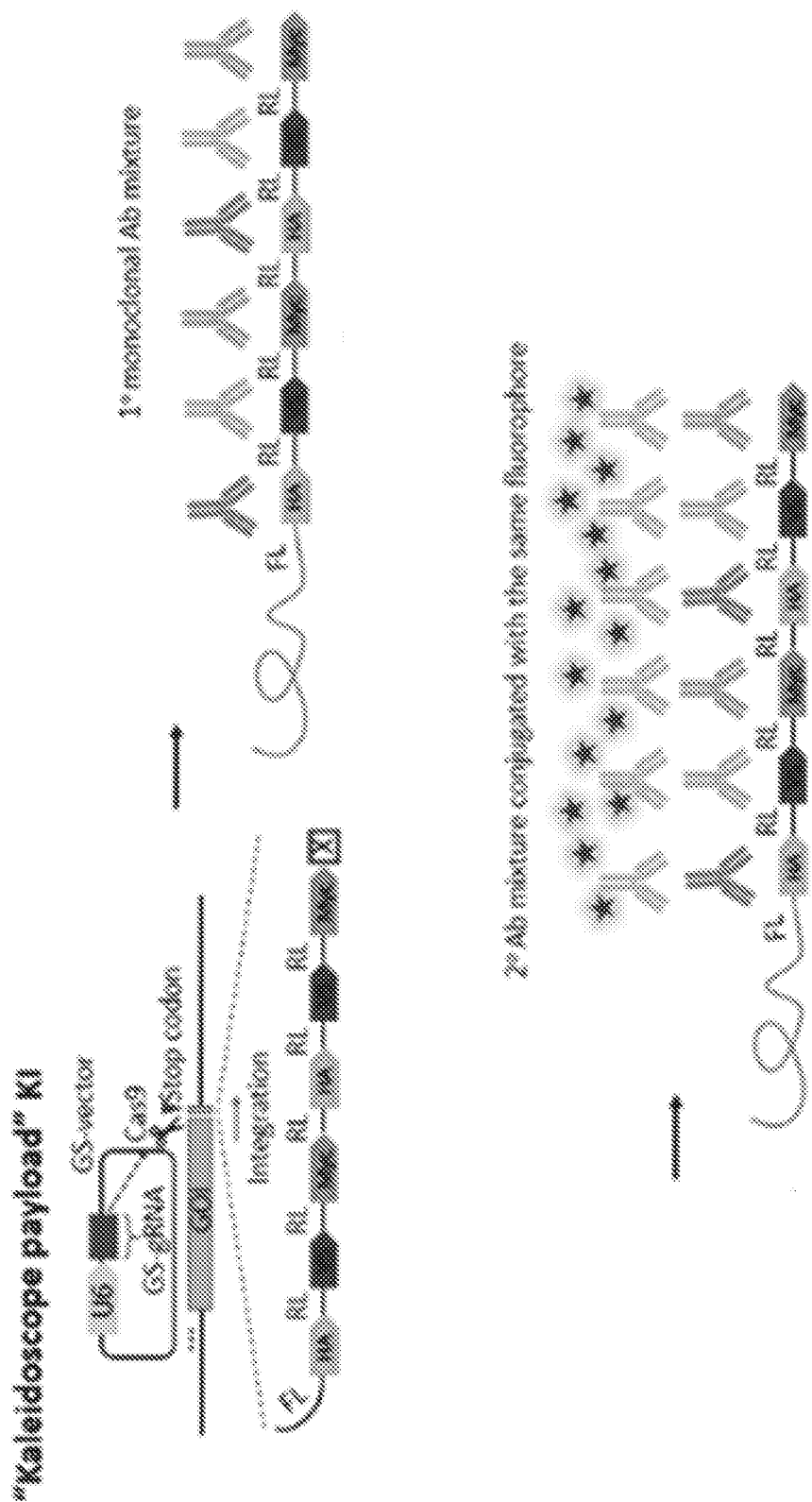
FIGS. 21A-21C show that "Kaleidoscope" payloads facilitate improved immunodetection of HiUGE labeled proteins.

Knock-in of Antibody Labeling Epitopes for Improved Detection in Microscopy ("Kaleidoscope") payloads that contain mixed antibody epitopes were generated. A mixture of multiple monoclonal primary antibodies can bind simultaneously to the labeled protein. This approach mimics the robust antigen recognition mechanism of polyclonal antibodies that detect multiple epitopes, yet at the same time retains the affinity and specificity of monoclonal antibodies. Further, the payload is smaller in size (~410 bp) compared to spaghetti monsters (~1 kb). FIG. 21A shows a schematic of the "Kaleidoscope" payload that contain interspersed epitope tags spaced by rigid linkers (RL) and a flexible linker (FL). Examples of Kaleidoscope containing vectors include the 1 Gen HiUGE donor Kleidoscope ORF+0 vector (3741 bp) (SEQ ID NO: 152), 1 Gen HiUGE donor Kleidoscope ORF+1 vector (3740 bp) (SEQ ID NO: 153), and 1 Gen HiUGE donor Kleidoscope ORF+2 vector (3742 bp) (SEQ ID NO: 154).

Figure 21C:
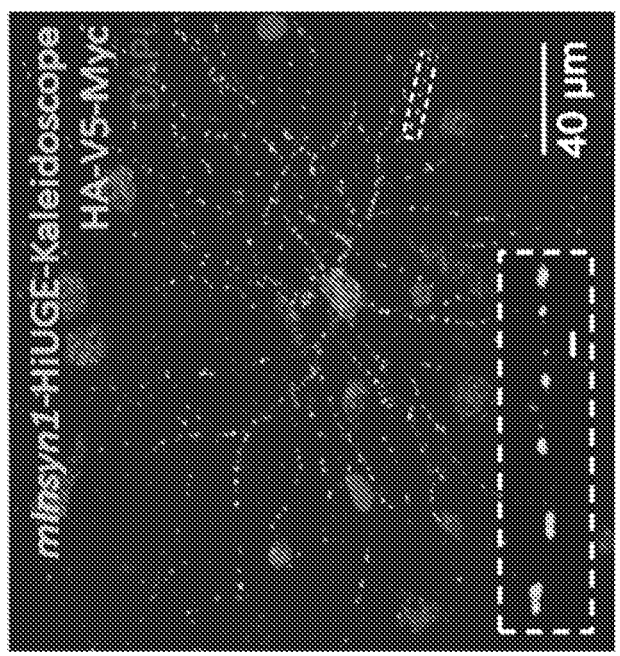
Figure 21B:
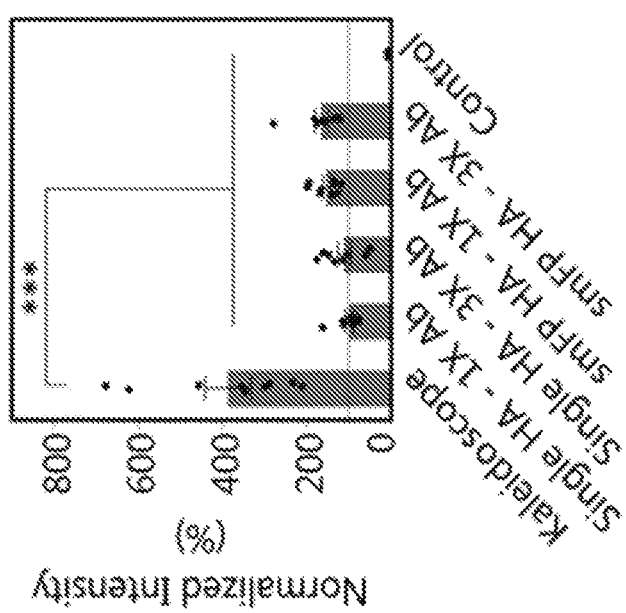

FIG. 21B shows that the immunofluorescence signal using a mixture of anti-HA, Myc and V5 antibodies to detect Kaleidoscope labeled mouse βIII-tubulin in neuron is higher than using anti-HA antibody (Ab) to detect single HA-epitope or smFP-HA labeling, even when the anti-HA primary antibody was applied 3 times more concentrated (lx Ab versus 3×Ab). FIG. 21C shows that Kaleidoscope can be used to label and detect low abundant proteins, such as inhibitory synaptic protein 1 (InSyn1) that has recently identified in a proteomics study of the inhibitory postsynaptic density. Kaleidoscope facilitated improved immunofluorescent detection compared to single HA epitope tag or spaghetti monster-HA (smFP-HA) for HiUGE.

For reasons of completeness, various aspects of the invention are set out in the following numbered clauses:

Clause 1. A Homology-Independent Universal Genome Engineering (HiUGE) system for gene editing a subject genome, the HiUGE system comprising: (a) (i) a CRISPR-based nuclease or (ii) a nucleic acid sequence that encodes a CRISPR-based nuclease; (b) a Homology-Independent Universal Genome Engineering (HiUGE) vector comprising: (i) a first polynucleotide sequence encoding at least one insert; (ii) at least one donor recognition sequence (DRS) flanking each side of the first polynucleotide sequence, the DRS comprising a cleavage site for the CRISPR-based nuclease; and (iii) a second polynucleotide sequence encoding a HiUGE vector specific gRNA, wherein the HiUGE vector specific gRNA targets the CRISPR-based nuclease to the DRS and does not target a specific sequence within the subject genome; and (c) (i) a target gene specific gRNA that targets the CRISPR-based nuclease to a target gene specific sequence within the subject genome or (ii) a target gene vector comprising a third polynucleotide sequence that encodes a target gene specific gRNA which targets the CRISPR-based nuclease to a target gene specific sequence within the subject genome.

Clause 2. A Homology-Independent Universal Genome Engineering (HiUGE) system for gene editing a subject genome, the HiUGE system comprising: (a) a Homology-Independent Universal Genome Engineering (HiUGE) vector comprising: (i) a first polynucleotide sequence encoding at least one insert; (ii) at least one donor recognition sequence (DRS) flanking each side of the first polynucleotide sequence, the DRS comprising a cleavage site for the CRISPR-based nuclease; (iii) a second polynucleotide sequence encoding a HiUGE vector specific gRNA, wherein the HiUGE vector specific gRNA targets the CRISPR-based nuclease to the DRS and does not target a specific sequence within the subject genome; (iv) a third polynucleotide sequence encoding a first portion of a CRISPR-based nuclease having a first split-intein; and (b) a gene specific vector comprising: (i) a fourth polynucleotide sequence encoding a second portion of a CRISPR-based nuclease having a second split-intein complementary to the first split-intein, wherein the first portion of the CRISPR-based nuclease and the second portion of the CRISPR-based nuclease can join together to form a CRISPR-based nuclease; and (ii) a fifth polynucleotide sequence that encodes a target gene specific gRNA which targets the CRISPR-based nuclease to a target gene specific sequence within the subject genome.

Clause 3. The HiUGE system of clause 2, wherein the first split-intein is a N-intein and the second split-intein is a C-intein.

Clause 4. The HiUGE system of clause 2 or 3, wherein the N-intein comprises a polynucleotide sequence of SEQ ID NO: 60 and the second split-intein comprises a sequence of SEQ ID NO: 61.

Clause 5. The HiUGE system of any one of clauses 2-4, wherein the first portion of the CRISPR-based nuclease comprises the polypeptide sequence of SEQ ID NO: 55 and the second portion of the CRISPR-based nuclease comprises the polypeptide sequence of SEQ ID NO: 56.

Clause 6. The HiUGE system of any one of clauses 1-5, wherein the target gene specific sequence is a consecutive polynucleotide sequence of about 15 to 25 nucleotides within a target gene of the subject genome.

Clause 7. The HiUGE system of clause 6, wherein the target gene specific gRNA targets at least one region of the target gene selected from the group consisting of a promoter region, an enhancer region, a repressor region, an insulator region, a silencer region, a region involved in DNA looping with the promoter region, a gene splicing region, or a transcribed region.

Clause 8. The HiUGE system of any one of clauses 1-7, wherein the CRISPR-based nuclease cleaves the at least one DRS flanking each side of the first polynucleotide and the target gene specific sequence, thereby generating a cleaved first polynucleotide sequence and a cleaved site of the target gene, wherein the cleaved first polynucleotide sequence is integrated into the cleaved site of the target gene by non-homologous end joining.

Clause 9. The HiUGE system of clause 8, wherein the CRISPR-based nuclease cleaves the at least one DRS and the target gene specific sequence consecutively or concurrently.

Clause 10. The HiUGE system of any one of clauses 1-9, wherein the at least one insert is inserted at the N-terminal end of a gene splicing region, or a transcribed region to generate a N-terminal tagged fusion protein.

Clause 11. The HiUGE system of any one of clauses 1-9, wherein the at least one insert is inserted at the C-terminal end of a promoter region, an enhancer region, a repressor region, an insulator region, a silencer region, a region involved in DNA looping with the promoter region, a gene splicing region, or a transcribed region to generate a C-terminal tagged fusion protein.

Clause 12. The HiUGE system of clause 10 or 11, wherein the at least one insert is inserted into the sense strand of the genome.

Clause 13. The HiUGE system of clause 10 or 11, wherein the at least one insert is inserted into the anti-sense strand of the genome.

Clause 14. The HiUGE system of any one of clauses 10-13, wherein the at least one insert is inserted in a forward orientation.

Clause 15. The HiUGE system of any one of clauses 10-13, wherein the at least one insert is inserted in a reverse orientation.

Clause 16. The HiUGE system of any one of clauses 1-15, wherein the CRISPR-based nuclease is a Cas9 endonuclease derived from a bacterial genus of *Streptococcus, Staphylococcus, Brevibacillus, Corynebacter, Sutterella, Legionella, Francisella, Treponema, Filifactor, Eubacterium, Lactobacillus, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma,* or *Campylobacter.*

Clause 17. The HiUGE system of clause 16, wherein the Cas9 endonuclease is derived from a bacterial species selected from the group consisting of *Streptococcus pyogenes, Francisella novicida, Staphylococcus aureus, Neisseria meningitides, Streptococcus thermophiles, Treponema denticola, Brevibacillus laterosporus, Campylobacter jejuni, Corynebacterium diphtheria, Eubacterium ventriosum, Streptococcus pasteurianus, Lactobacillus farciminis, Sphaerochaeta globus, Azospirillum, Gluconacetobacter diazotrophicus, Neisseria cinerea, Roseburia intestinalis, Parvibaculum lavamentivorans, Nitratifractor salsuginis,* and *Campylobacter lari.*

Clause 18. The HiUGE system of clause 16 or 17, wherein the Cas9 endonuclease is a *Streptococcus pyogenes* Cas9 (SpCas9) endonuclease, a *Francisella novicida* Cas9 (FnCas9) endonuclease, a *Staphylococcus aureus* Cas9 (SaCas9) endonuclease, *Neisseria meningitides* Cas9 (NmCas9) endonuclease, *Streptococcus thermophiles* Cas9 (SCas9) endonuclease, *Treponema denticola* Cas9 (TdCas9) endonuclease, *Brevibacillus laterosporus* Cas9 (BatCas9) endonuclease, *Campylobacter jejuni* Cas9 (CjCas9) endonuclease, a variant endonuclease thereof, or a chimera endonuclease thereof.

Clause 19. The HiUGE system of any one of clauses 16-18, wherein the Cas9 endonuclease is a SpCas9 variant endonuclease, a SaCas9 variant endonuclease, or a StCas9 endonuclease.

Clause 20. The HiUGE system of clause 19, wherein: the SpCas9 variant is a SpCas9 Cas9 VRER variant endonuclease, a SpCas9 Cas9 EQR variant endonuclease, a SpCas9 VQR variant endonuclease, a SpCas9-HF1 variant endonuclease, or an eSpCas9(1.1) variant endonuclease; the SaCas9 variant is a SaCas9 Cas9 KKH variant; or the StCas9 endonuclease is a St1Cas9 endonuclease or StcCas9 endonuclease.

Clause 21. The HiUGE system of any one of clauses 16-20, wherein the Cas9 endonuclease is a chimera Sp-St3Cas9 endonuclease comprising SpCas9 with a Protospacer Adjacent Motif (PAM)-interacting (PI) domain of St3Cas9 or a chimera St3-SpCas9 endonuclease comprising St3Cas9 with a PI domain of SpCas9.

Clause 22. The HiUGE system of any one of clauses 16-21, wherein the Cas9 endonuclease recognizes a Protospacer Adjacent Motif (PAM) of YG (SEQ ID NO: 1), NGG (SEQ ID NO: 2), NGA (SEQ ID NO: 3), NGCG (SEQ ID NO: 4), NGAG (SEQ ID NO: 5), NGGNG (SEQ ID NO: 6), NNGRRT (SEQ ID NO: 7), NNGRRT (SEQ ID NO: 8), NNNRRT (SEQ ID NO: 9). NAAAAC (SEQ ID NO: 10), NNNNGNNT (SEQ ID NO: 11), NNAGAAW (SEQ ID NO: 12), NNNNCNDD (SEQ ID NO: 13), or NNNNRYAC (SEQ ID NO: 14).

Clause 23. The HiUGE system of any one of clauses 16-22, wherein the Cas9 endonuclease is: a SpCas9 endonuclease and recognizes the PAM sequence of NGG (SEQ ID NO: 2); a SpCas9 variant endonuclease and recognizes the PAM sequence of NGG (SEQ ID NO: 2); a SpCas9 Cas9 VRER variant endonuclease and recognizes the PAM sequence of NGCG (SEQ ID NO: 4); a SpCas9 Cas9 EQR variant endonuclease and recognizes the PAM sequence of NGAG (SEQ ID NO: 5); a SpCas9 VQR variant endonuclease and recognizes the PAM sequence of NGA (SEQ ID NO: 3); a SaCas9 endonuclease and recognizes the PAM sequence of NNGRRT (SEQ ID NO: 7); a SaCas9 Cas9 KKH variant endonuclease and recognizes the PAM sequence of NNNRRT (SEQ ID NO: 9); a St1Cas9 endonuclease and recognizes the PAM sequence of NNAGAAW (SEQ ID NO: 12); a St3Cas9 endonuclease and recognizes the PAM sequence of NGGNG (SEQ ID NO: 6); a Sp-St3Cas9 chimera endonuclease and recognizes the PAM sequence of NGGNG (SEQ ID NO: 6); an NmCas9 endonuclease and recognizes the PAM sequence of NNNNG-NNT (SEQ ID NO: 11). a TdCas9 endonuclease and recognizes the PAM sequence of NAAAAC (SEQ ID NO: 10); a BlatCas9 endonuclease and recognizes the PAM sequence of NNNNCNDD (SEQ ID NO: 13); a CjCas9 endonuclease and recognizes the PAM sequence of NNNNRYAC (SEQ ID NO: 14); or an FnCas9 RHA variant endonuclease and recognizes the PAM sequence of YG (SEQ ID NO: 1).

Clause 24. The HiUGE system of any one of clauses 1-23, wherein the DRS comprises a donor target sequence of about 19 to 24 nucleotides in length and a PAM sequence.

Clause 25. The HiUGE system of clause 24, wherein: the donor target sequence comprises a sequence of 5'-NNNNNNNNNNNNNNNN-2N-1N1N2N-3' (SEQ ID NO: 15) in the forward orientation and the Cas9 dependent double stranded break in the cleavage site occurs between positions N-1 and N1; or the donor target sequence comprises a sequence of 5'-XX-2X-1X1X2XXXXXXXXXXXXXXXX-3' (SEQ ID NO: 16) in the reverse orientation and the Cas9 dependent double stranded break in the cleavage site occurs between positions X-1 and X1, wherein N is any of the four deoxyribonucleic acids adenine (A), thymine (T), guanine (G), or cytosine (C), wherein X is the reverse complement of N, wherein N-2N-1N1N2 (SEQ ID NO: 17) is a border sequence in 5'-NNNNNNNNNNNNNNNN-2N-1N1N2N-3' (SEQ ID NO: 15) and X-2X-1X1X2 (SEQ ID NO: 18) is a border sequence in 5'-XX-2X-1X1X2XXXXXXXXXXXXXXXX-3' (SEQ ID NO: 16), and wherein the donor target sequence does not introduce an in-frame stop codon after the insert is integrated into the target gene.

Clause 26. The HiUGE system of clause 25, wherein the donor target sequence comprises at least 1 base pair mismatch compared to any sequence of equal length in the subject genome.

Clause 27. The HiUGE system of clause 25 or 26, wherein the donor target sequence comprises at least 2 base pair mismatches compared to any sequence of equal length in the subject genome.

Clause 28. The HiUGE system of any one of clauses 25-27, wherein the donor target sequence comprises at least 1 base pair mismatch within about 8 to 12 nucleotides of the donor target sequence that is adjacent to the PAM sequence compared to any sequence of equal length in the subject genome.

Clause 29. The HiUGE system of any one of clauses 25-28, wherein the target gene specific sequence comprises a sequence of ZZZZ-2Z-1Z1Z2Z (SEQ ID NO: 19), wherein the Cas9 dependent double stranded break in the cleavage site occurs between positions Z-1 and Z1, wherein Z is any of the four deoxyribonucleic acids adenine (A), thymine (T), guanine (G), or cytosine (C), wherein the border sequence does not yield an in-frame stop codon after the insert is integrated into the target gene, and wherein the genomic open reading frame (ORF) phase of the target gene is selected from the group consisting of: ORF+0: positions ZZ-2Z-1 corresponding to ZZZZ-2Z-1Z1Z2Z (SEQ ID NO: 19), ORF+1: positions ZZZ-2 corresponding to ZZZZ-2Z-1Z1Z2Z (SEQ ID NO: 19), and ORF+2: positions ZZZ corresponding to ZZZZ-2Z-1Z1Z2Z (SEQ ID NO: 19).

Clause 30. The HiUGE system of clause 29, wherein if the genomic ORF phase is ORF+1, the DRS is 5'-NNNNNNNNNNNNNNNN-2N-1N1N2N-3' (SEQ ID NO: 15) in the forward orientation, and the at least one insert is used to generate an N-terminal tagged fusion protein, then N-1 is A, C, or G.

Clause 31. The HiUGE system of clause 29, wherein if the genomic ORF phase is ORF+2, the DRS is 5'-NNNNNNNNN-2N-1N1N2N-3' (SEQ ID NO: 15) in the forward orientation, and the at least one insert is used to generate a N-terminal tagged fusion protein, then N-2N-1 is selected from the group consisting of TT, TC, AA, AT, AC, AG, CA, CT, CC, CG, GA, GT, GC, and GG.

Clause 32. The HiUGE system of clause 29, wherein if the genomic ORF phase is ORF+1, the DRS is 5'-NNNNNNNNNNNNNNNN-2N-1N1N2N-3' (SEQ ID NO: 15) in the forward orientation, and the at least one insert is used to generate a C-terminal tagged fusion protein, then N1N2 is selected from the group consisting of AC, AT, TA, TT, TC, TG, CA, CT, CC, CG, GT, GC, and GG.

Clause 33. The HiUGE system of clause 29, wherein if the genomic ORF phase is ORF+2, the DRS is 5'-NNNNNNNNNNNNNNNN-2N-1N1N2N-3' (SEQ ID NO: 15) in the forward orientation, and the at least one insert is used to generate a C-terminal tagged fusion protein, then N1 is T or C.

Clause 34. The HiUGE system of clause 29, wherein if the genomic ORF phase is ORF+1, the DRS is 5'-XX-2X-1X1X2XXXXXXXXXXXXXXXX-3' (SEQ ID NO: 16) in the reverse orientation, and the at least one insert is used to generate an N-terminal tagged fusion protein, then X-1 is A, C, or G.

Clause 35. The HiUGE system of clause 29, wherein if the genomic ORF phase is ORF+2, the DRS is 5'-XX-2X-1X1X2XXXXXXXXXXXXXXXX-3' (SEQ ID NO: 16) in the reverse orientation, and the at least one insert is used to generate a N-terminal tagged fusion protein, then X-2X-1 is selected from the group consisting of TT, TC, AA, AT, AC, AG, CA, CT, CC, CG, GA, GT, GC, and GG.

Clause 36. The HiUGE system of clause 29, wherein if the genomic ORF phase is ORF+1, the DRS is 5'-XX-2X-1X1X2XXXXXXXXXXXXXXXX-3' (SEQ ID NO: 16) in the reverse orientation, and the at least one insert is used to generate a C-terminal tagged fusion protein, then X1X2 is selected from the group consisting of AC, AT, TA, TT, TC, TG, CA, CT, CC, CG, GT, GC, and GG.

Clause 37. The HiUGE system of clause 29, wherein if the genomic ORF phase is ORF+2, the DRS is 5'-XX-2X-1X1X2XXXXXXXXXXXXXXXX-3' (SEQ ID NO: 16) in the reverse orientation, and the at least one insert is used to generate a C-terminal tagged fusion protein, then X1 is T or C.

Clause 38. The HiUGE system of any one of clauses 25-37, wherein the DRS is recognized by a SpCas9, or variant thereof, and comprises a sequence of 5'-NNNNNNNNNNNNNNNN-2N-1N1N2NNGG-3' (SEQ ID NO: 20) in the forward orientation or a sequence of 5'-CCXXX-2X-1X1X2XXXXXXXXXXXXXXXX-3' (SEQ ID NO: 21) in the reverse orientation.

Clause 39. The HiUGE system of any one of clauses 1-38, wherein the at least one insert is a marker or a tag.

Clause 40. The HiUGE system of any one of clauses 1-39, wherein the at least one insert is an antibody epitope tag, a fluorescent protein tag, an affinity purification tag, a proteomic labeling enzyme, a split Cre-recombinase, an internal ribosomal entry sequence (IRES), a 2A peptide, a localization sequence, an enzyme, an epitope, or a combination thereof.

Clause 40b. The HiUGE system of any one of clauses 1-40, wherein the at least one insert comprises at least one antibody epitope tag.

Clause 40c. The HiUGE system of any one of clauses 1-40, wherein the at least one insert comprises at least two or more antibody epitope tags.

Clause 40d. The HiUGE system of clause 40c, wherein the at least two or more antibody epitope tags are different.

Clause 40e. The HiUGE system of clause 40c, wherein the at least two or more antibody epitope tags are the same.

Clause 40f. The HiUGE system of any one of clauses 40b-40e, wherein the at least one insert comprises one or more copies of the antibody epitope tag.

Clause 40g. The HiUGE system of any one of clauses 41c-41f, wherein the antibody epitope tags are separated by a linker.

Clause 41. The HiUGE system of any one of clauses 1-40, wherein the least one insert comprises a polynucleotide sequence encoding at least one amino acid sequence of SEQ ID NO: 34, 39, 41-50, or combination thereof.

Clause 41b. The HiUGE system of any one of clauses 1-40, wherein the least one insert comprises a polynucleotide sequence corresponding to positions 542-949 of SEQ ID NO: 152, SEQ ID NO: 153, or SEQ ID NO: 154.

Clause 42. The HiUGE system of any one of clauses 1-40, wherein the HiUGE vector comprises a forward copy of the first polynucleotide sequence and a reverse copy of the first polynucleotide sequence encoded on the same strand.

Clause 43. The HiUGE system of clause 42, wherein polynucleotide sequence encoding a stop cassesstte is linked between the forward copy of the first polynucleotide sequence and a reverse copy of the first polynucleotide sequence.

Clause 44. The HiUGE system of any one of clauses 1-43, wherein the DRS comprises a polynucleotide sequence of GTCATAGTATCGCGGAGTTCAGG (SEQ ID NO: 22), GACGCTTCCGAGTACGGTACAGG (SEQ ID NO: 23), GGTTCTACGAGGATACGTCTTGG (SEQ ID NO: 24), GCGTATGGCAAGCATAGCCGGGG (SEQ ID NO: 25), GCGATTGACCCGTGCTGTCGCGG (SEQ ID NO: 26), or CCTGTACCGTACTCGGAAGCGTC (SEQ ID NO: 27).

Clause 45. The HiUGE system of any one of clauses 1 or 6-44, wherein the second polynucleotide sequence is operably linked to a first promoter and the third polynucleotide sequence is operably linked to a second promoter.

Clause 46. The HiUGE system of any one of clauses 2-44, wherein the second polynucleotide sequence is operably linked to a first promoter, the third polynucleotide sequence is operably linked to a second promoter, the fourth polynucleotide sequence is operably linked to a third promoter, and the fifth polynucleotide sequence is operably linked to a fourth promoter.

Clause 47. The HiUGE system of any one of clauses 2-44, wherein the fourth polynucleotide sequence and the fifth polynucleotide are operably linked to the same promoter.

Clause 48. The HiUGE system of any one of clauses 43-47, wherein the promoter is a constitutive promoter, an inducible promoter, a repressible promoter, or a regulatable promoter.

Clause 49. The HiUGE system of any one of clauses 43-48, wherein the promoter is a eukaryotic promoter.

Clause 50. The HiUGE system of clause 49, wherein the promoter is a type III RNA polymerase III promoter.

Clause 51. The HiUGE system of clause 50, wherein the promoter is a U6 promoter, a H1 promoter, or a 7SK promoter.

Clause 52. The HiUGE system of any one of clauses 49-51, wherein the promoter comprises at least one polynucleotide sequence of SEQ ID NO: 62-66, or combination thereof.

Clause 53. The HiUGE system of any one of clauses 1-52, wherein at least one of the polynucleotides further comprises a nuclear localization signal and/or a nuclear export signal.

Clause 54. The HiUGE system of any one of clauses 1-53, wherein the nuclear localization signal comprises a polynucleotide sequence of SEQ ID NO: 52 or 53 and a nuclear export signal comprises a polynucleotide sequence of SEQ ID NO: 51.

Clause 55. The HiUGE system of any one of clauses 1, 6-45, or 48-54, wherein the target gene vector of 1(c)(ii) further comprises the nucleic acid sequence that encodes a CRISPR-based nuclease of 1(a)(ii).

Clause 56. The HiUGE system of any one of clauses any one of clauses 1, 6-45, or 48-54, wherein the nucleic acid of 1(a)(ii) comprises DNA.

Clause 57. The HiUGE system of any one of clauses any one of clauses 1, 6-45, or 48-54, wherein the nucleic acid of 1(a)(ii) comprises RNA.

Clause 58. The HiUGE system of any one of clauses 1, 6-45, or 48-57, wherein one of, two of, or all three of 1(a)(ii), 1(b), and 1(c)(ii) are packaged in a viral vector.

Clause 59. The HiUGE system of any one of clauses 1, 6-45, or 48-58, wherein 1(a)(ii) and 1(b) are packaged in the same viral vector, 1(a)(ii) and 1(c)(ii) are packaged in the same viral vector, 1(b) and 1(c)(ii) are packaged in the same viral vector, or 1(a), 1(b), and 1(c)(ii) are packaged in the same viral vector.

Clause 60. The HiUGE system of any one of clauses 1, 6-45, or 48-58, wherein 1(a)(ii) is packaged in a first viral vector, 1(b) is packaged in a second viral vector, and 1(c)(ii) is packaged in a third viral vector.

Clause 61. The HiUGE system of anyone of clauses 2-44 or 46-54, wherein at least one of the polynucleotide sequences is packaged in a viral vector Clause 62. The HiUGE system of any one of clauses 58-61, wherein the viral vector comprises an adeno-associated virus (AAV) vector or a lentiviral vector.

Clause 63. The HiUGE system of any one of clauses 1, 6-45, or 48-60 and 62, wherein the HiUGE system comprises at least one polynucleotide sequence of SEQ ID NO: 67-107, or combination thereof.

Clause 64. The HiUGE system of any one of clauses 2-44 or 46-54, 61, and 62, wherein the HiUGE system comprises at least one polynucleotide sequence of SEQ ID NO: 108-127, or combination thereof.

Clause 65. The HiUGE system of any one of clauses 1-624, wherein the subject genome is from a eukaryotic subject.

Clause 66. The HiUGE system of clause 65, wherein the subject genome is a mammalian subject.

Clause 67. The HiUGE system of clause 66, wherein the mammalian subject is a rodent or a primate.

Clause 68. The HiUGE system of any one of clauses 1-67, wherein the HiUGE system targets a target gene specific sequence of a TUBB3 gene, MAP2 gene, MECP2 gene, NRCAM gene, ACTR2 gene, CLTA gene, ANK3 gene, SPTBN4 gene, SCN2A gene, GFAP gene, PDHA1 gene, or DCX gene.

Clause 69. A method of Homology-Independent Universal Genome Engineering (HiUGE) of a target gene in a subject genome, the method comprising contacting a cell with the HiUGE system of any one of clauses 1-68.

Clause 70. The method of clause 69, wherein the method is used in genome-wide protein labelling, expression marking, disruption of protein expression, protein re-localization, alteration of protein expression, or high throughput screening.

Clause 71. The method of 68 or 69, wherein the CRISPR-based nuclease cleaves the at least one DRS flanking each side of the first polynucleotide and the target gene specific sequence, thereby generating a cleaved first polynucleotide sequence and a cleaved site of the target gene, wherein the cleaved first polynucleotide sequence is integrated into the cleaved site of the target gene by non-homologous end joining.

Clause 72. The method of clause 71, wherein the CRISPR-based nuclease cleaves the at least one DRS and the target gene specific sequence consecutively or concurrently.

Clause 73. The method of any one of clauses 69-72, wherein the cell is a differentiating cell or a non-dividing cell.

Clause 74. The method of clause 73, wherein the cell is a eukaryotic cell.

Clause 75. The method of clause 73 or 74, wherein the cell is a human cell.

Clause 76. The method of any one of clauses 69-75, wherein the cell is derived from endoderm, ectoderm, or mesoderm.

Clause 77. A kit comprising the HiUGE system of any one of clauses 1-68.

Clause 78. A HiUGE system comprising a polynucleotide sequence of SEQ ID NO: 152, SEQ ID NO: 153, or SEQ ID NO: 154.

APPENDIX

```
SEQ ID NO: 152
CCTGCAGGCAGCTGCGCGCTCGCTCGCTCACTGAGGCCGCCCGGGCAAAGCCCGGGCGTCGGGCGACCTTTGGTCGC
CCGGCCTCAGTGAGCGAGCGAGCGCGCAGAGAGGGAGTGGCCAACTCCATCACTAGGGGTTCCTGCGGCCGCACGCG
TGAGGGCCTATTTCCCATGATTCCTTCATATTTGCATATACGATACAAGGCTGTTAGAGAGATAATTGGAATTAATT
TGACTGTAAACACAPAGATATTAGTACAAAATACGTGACGTAGAAAGTAATAATTTCTTGGGTAGTTTGCAGTTTTA
AAATTATGTTTTAAAATGGACTATCATATGCTTACCGTAACTTGAAAGTATTTCGATTTCTTGGCTTTATATATCTT
GTGGAAAGGACGAAACACCGACGCTTCCGAGTACGGTACGTTTTAGAGCTAGAAATAGCAAGTTAAAATAAGGCTAG
TCCGTTATCAACTTGAAAAAGTGGCACCGAGTCGGTGCTTTTTTTCTAGACCTGTACCGTACTCGGAAGCGTCGGAT
CCCTAGCTAGCTAGCTAAAGGTCCTCCTCGCTGATCAGTTTCTGCTCAGCCTTAGCTGCGGCTTCTTTAGCTGCTGC
TTCTGCGGTAGAATCAAGGCCCAGAAGTGGGTTGGGGATGGGTTTCCCGGCTTTTGCAGCTGCTTCTTTTGCGGCGG
CTTCGGCTGCATAGTCGGGGACATCATAGGGATATGCGTTGGCAGCTGCTTCCTTGGCAGCGGCTTCGGCCAGATCC
TCTTCGCTAATCAACTTTTGCTCTGCTTTAGCTGCAGCCTCCTTGGCGGCAGCTTCTGCAGTAGAATCCAATCCCAA
CAGTGGGTTTGGAATTGGTTTCCCAGCTTTGGCGGCGGCCTCCTTAGCAGCTGCCTCGGCGGCGTAATCTGGCACAT
CATATGGGTAGCTCCCTCCACCACCCTCTCGAGACCTGTACCGTACTCGGAAGCGTCCACGTGCGGACCGAGCGGCC
GCAGGAACCCCTAGTGATGGAGTTGGCCACTCCCTCTCTGCGCGCTCGCTCGCTCACTGAGGCCGGGCGACCAAAGG
TCGCCCGACGCCCGGGCTTTGCCCGGGCGGCCTCAGTGAGCGAGCGAGCGCGCAGCTGCCTGCAGGGGCGCCTGATG
CGGTATTTTCTCCTTACGCATCTGTGCGGTATTTCACACCGCATACGTCAAAGCAACCATAGTACGCGCCCTGTAGC
GGCGCATTAAGCGCGGCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTTGGGTGATGGTTCACGTAGTGGGCCATCG
CCCTGATAGACGGTTTTTCGCCCTTTGACGTTGGAGTCCACGTTCTTTAATAGTGGACTCTTGTTCCAAACTGGAAC
AACACTCAACCCTATCTCGGGCTATTCTTTTGATTTATAAGGGATTTTGCCGATTTCGGCCTATTGGTTAAAAAATG
AGCTGATTTAACAAAAATTTAACGCGAATTTTAACAAAATATTAACGTTTACAATTTTATGGTGCACTCTCAGTACA
ATCTGCTCTGATGCCGCATAGTTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTCAGAGGTTTTCACCGTCATCAC
CGAAACGCGCGAGACGAAAGGGCCTCGTGATACGCCTATTTTTATAGGTTAATGTCATGATAATAATGGTTTCTTAG
ACGTCAGGTGGCACTTTTCGGGGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCCTTGAGAGTTT
TCGCCCCGAAGAACGTTTTCCAATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGCCTGTAGCAATGGCAACA
ACGTTGCGCAAACTATTAACTGGCGAACTACTTACTCTAGCTTCCCGGCAACAATTAATAGACTGGATGGAGGCGGA
TAAAGTTGCAGGACCACTTCTGCGCTCGGCCCTTCCGGCTGGCTGGTTTATTGCTGATAAATCTGGAGCCGGTGAGC
GTGGGTCTCGCGGTATCATTGCAGCACTGGGGCCAGATGGTAAGCCCTCCCGTATCGTAGTTATCTACACGACGGGG
AGTCAGGCAACTATGGATGAACGAAATAGACAGATCGCTGAGATAGGTGCCTCACTGATTAAGCATTGGTAACTGTC
AGACCAAGTTTACTCATATATACTTTAGATTGATTTAAAACTTCATTTTTAATTTAAAAGGATCTAGGTGAAGATCC
TTTTTGATAATCTCATGACCAAAATCCCTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCAAACAAAAAAACCACCGCTACCAGCGGT
GGTTTGTTTGCCGGATCAAGAGCTACCAACTCTTTTTCCGAAGGTAACTGGCTTCAGCAGAGCGCAGATACCAAATA
CTGTCCTTCTAGTGTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTATAGTCCTGTCGGGTTTCG
CCACCTCTGACTTGAGCGTCGATTTTTGTGATGCTCGTCAGGGGGCGGAGCCTATGGAAAAACGCCAGCAACGCGG
CCTTTTTACGGTTCCTGGCCTTTTGCTGGCCTTTTGCTCACATGT
```

| | | | | |
|---|---|---|---|---|
| source | 1 ... 3741 | 3741 | == | source |
| AAV2 ITR | 1 ... 141 | 141 | == | repeat_region |
| U6 promoter | 156 ... 396 | 241 | == | promoter |
| HD-gRNA | 405 ... 424 | 20 | == | misc_feature |
| chimeric gRNA scaffold | 425 ... 500 | 76 | == | misc_feature |

APPENDIX-continued

| | | | | | |
|---|---|---|---|---|---|
| gRNA scaffold | 425 | . . . 500 | 76 | => | misc_RNA |
| T6 | 501 | . . . 506 | 6 | == | misc_feature |
| DRS | 513 | . . . 535 | 23 | == | misc_feature |
| Kaleidoscope | 542 | . . . 949 | 408 | <= | CDS |
| XcXcXcX | 542 | . . . 556 | 15 | == | misc_feature |
| Myc | 557 | . . . 586 | 30 | <= | CDS |
| V5 tag | 623 | . . . 664 | 42 | <= | CDS |
| HA | 701 | . . . 727 | 27 | <= | CDS |
| Myc | 764 | . . . 793 | 30 | <= | CDS |
| V5 tag | 830 | . . . 871 | 42 | <= | CDS |
| HA | 908 | . . . 934 | 27 | <= | CDS |
| DRS | 959 | . . . 981 | 23 | == | misc_feature |
| AAV2 ITR | 1004 | . . . 1144 | 141 | == | repeat_region |
| f1 ori | 1219 | . . . 1674 | 456 | => | rep_origin |
| bla AmpR promoter | 1956 | . . . 2060 | 105 | == | promoter |
| bla | 2061 | . . . 2921 | 861 | => | CDS |
| ori | 3092 | . . . 3680 | 589 | => | rep_origin |
| ITR | 3741 | . . . 3741 | 1 | == | misc_feature |

SEQ ID NO: 153
CCTGCAGGCAGCTGCGCGCTCGCTCGCTCACTGAGGCCGCCCGGGCAAAGCCCGGGCGTCGGGCGACCTTTGGTCGC
CCGGCCTCAGTGAGCGAGCGAGCGCGCAGAGAGGGAGTGGCCAACTCCATCACTAGGGGTTCCTGCGGCCGCACGCG
TGAGGGCCTATTTCCCATGATTCCTTCATATTTGaATATACGATACAAGGCTGTTAGAGAGATAATTGGAATTAATT
TGACTGTAAACACAAAGATATTAGTACAAAATACGTGACGTAGAAAGTAATAATTTCTTGGGTAGTTTGCAGTTTTA
AAATTATGTTTTAAAATGGACTATCATATGCTTACCGTAACTTGAAAGTATTTCGATTTCTTGGCTTTATATATCTT
GTGGAAAGGACGAAACACCGACGCTTCCGAGTACGGTACGTTTTAGAGCTAGAAATAGCAAGTTAAAATAAGGCTAG
TCCGTTATCAACTTGAAAAAGTGGCACCGAGTCGGTGCTTTTTTTCTAGACCTGTACCGTACTCGGAAGCGTCGGAT
CCCTAGCTAGCTAGCTAAAGGTCCTCCTCGCTGATCAGTTTCTGCTCAGCCTTAGCTGCGGCTTCTTTAGCTGCTGC
TTCTGCGGTAGAATCAAGGCCCAGAAGTGGGTTGGGGATGGGTTTCCAGCTGCGTCTGCTTCTTTTGCGGCCGG
CTTCGGCTGCATAGTCGGGGACATCATAGGGATATGCCTTGGCAGCTGCTTCCTTGGCAGCGGCT7CGGCCAGATCC
TCTTCGCTAATCAACTTTTGCTCTGCTTTAGCTGCAGCCTCCTTGGCGGCAGCTTCTGCAGTAGAATCCAATCCCAA
CAGTGGGTTTGGAATTGGTTTCCCAGCTTTGGCGGCGGCCTCCTTAGCAGCTGCCTCGGCGGCGTAATCTGGCACAT
CATATGGGTAGCTCCCTCCACCACCCTCTCGAGCCTGTACCGTACTCGGAAGCGTCCACGTGCGGACCGAGCGGCCG
CAGGAACCCCTAGTGATGGAGTTGGCCACTCCCTCTCTGCGCGCTCGCTCGCTCACTGAGGCCGGGCGACCAAAGGT
CGCCCGACGCCCGGGCTTTGCCCGGGCGGCCTCAGTGAGCGAGCGAGCGCGCAGCTGCCTGCAGGGGCGCCTGATGC
GGTATTTTCTCCTTACGCATCTGTGCGGTATTTCACACCGCATACGTCAAAGCAACCATAGTACGCGCCCTGTAGCG
GCGCATTAAGCGCGGCGGGTGTGGTGGTTACGCGCAGCGTGACCGCTACACTTGCCAGCGCCCTAGCGCCCGCTCCT
TTCGCTTTCTTCCCTTCTCGCCACGTTCGCCGGCTTTCCCCGTCAAGCTCTAAATCGGGGGGCTCCCTTTAGG
GTTCCGATTTAGTGCTTTACGGCACCTCGACCCCAAAAAACTTGATTTGGGTGATGGTTCACGTAGTGGGCCATCGC
CCTGATAGACGGTTTTTCGCCCTTTGACGTTGGAGTCCACGTTCTTTAATAGTGGACTCTTGTTCCAAACTGGAACA
ACACTCAACCCTATCTCGGGCTATTCTTTTGATTTATAAGGGATTTTGCCGATTTCGGCCTATTGGTTAAAAAATGA
GCTGATTTAACAAAAATTTAACGCGAATTTTAACAAAATATTAACGTTTACAATTTTATGGTGCACTCTCAGTACAA
TCTGCTCTGATGCCGCATAGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGGTTTTCACCGTCATCACC
GAAACGCGCGAGACGAAAGGGCCTCGTGATACGCCTATTTTTATAGGTTAATGTCATGATAATAATGGTTTCTTAGA
CGTCAGGTGGCACTTTTCGGGGAAATGTGCGCGGAACCCCTATTTGTTTATTTTTCTAAATACATTCAAATATGTAT
CCGCTCATGAGACAATAACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAACGCTGGTGAAAGTAAAAG
ATGCTGAAGATCAGTTGGGTGCACGAGTGGGTTACATCGAACTGGATCTCAACAGCGGTAAGATCCTTGAGAGTTTT
CGCCCCGAAGAACGTTTTCCAATGATGAGCACTTTTAAAGTTCTGCTATGTGGCGCGGTATTATCCCGTATTGACGC
CGGGCAAGAGCAACTCGGTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATAACACTGCGGCCAACTTA
CTTCTGACAACGATCGGAGGACCGAAGGAGCTAACCGCTTTTTTGCACAACATGGGGGATCATGTAACTCGCCTTGA
TCGTTGGGAACCGGAGCTGAATGAAGCCATACCAAACGACGAGCGTGACACCACGATGCCTGTAGCAATGGCAACAA
CGTTGCGCAAACTATTAACTGGCGAACTACTTACTCTAGCTTCCCGGCAACAATTAATAGACTGGATGGAGGCGGAT
AAAGTTGCAGGACCACTTCTGCGCTCGGCCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACCCCGTAGAAAAGATCA
AAGGATCTTCTTGAGATCCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGTTGGACTCAAGACGATAGTTACCGGAT
AAGGCGCAGCGGTCGGGCTGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCGGACAGGTATCCGGTAAGCGGCA
GGGTCGGAACAGGAGAGCGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCTATGGAAAAACGCCAGCAACGCGGC
CTTTTTACGGTTCCTGGCCTTTTGCTGGCCTTTTGCTCACATGT

| | | | | | |
|---|---|---|---|---|---|
| source | 1 | . . . 3740 | 3740 | == | source |
| AAV2 ITR | 1 | . . . 141 | 141 | == | repeat_region |
| U6 promoter | 156 | . . . 396 | 241 | == | promoter |
| HD-gRNA | 405 | . . . 424 | 20 | == | misc_feature |
| gRNA scaffold | 425 | . . . 500 | 76 | => | misc_RNA |
| chimeric gRNA scaffold | 425 | . . . 500 | 76 | == | misc_feature |
| T6 | 501 | . . . 506 | 6 | == | misc_feature |
| DRS | 513 | . . . 535 | 23 | == | misc_feature |
| Kaleidoscope | 542 | . . . 949 | 408 | <= | CDS |
| XcXcXcX | 542 | . . . 556 | 15 | == | misc_feature |

APPENDIX-continued

| | | | | | |
|---|---|---|---|---|---|
| Myc | 557 | ... 586 | 30 | <= | CDS |
| V5 taG | 623 | ... 664 | 42 | <= | CDS |
| HA | 701 | ... 727 | 27 | <= | CDS |
| Myc | 764 | ... 793 | 30 | <= | CDS |
| V5 tag | 830 | ... 871 | 42 | <= | CDS |
| HA | 908 | ... 934 | 27 | <= | CDS |
| DRS | 958 | ... 980 | 23 | == | misc_feature |
| AAV2 ITR | 1003 | ... 1143 | 141 | == | repeat_region |
| f1 ori | 1218 | ... 1673 | 456 | => | rep_origin |
| bla AmpR promoter | 1955 | ... 2059 | 105 | == | promoter |
| bla | 2060 | ... 2920 | 861 | => | CDS |
| ori | 3091 | ... 3679 | 589 | => | rep_origin |
| ITR | 3740 | ... 3740 | 1 | == | misc_feature |

SEQ ID NO: 154
CCTGCAGGCAGCTGCGCGCTCGCTCGCTCACTGAGGCCGCCCGGGCAAAGCCCGGGCGTCGGGCGACCTTTGGTCGC
CCGGCCTCAGTGAGCGAGCGAGCGCGCAGAGAGGGAGTGGCCAACTCEATCACTAGGGGTTCCTGCGGCCGCACGCG
TGAGGGCCTATTTCCCATGATTCCTTCATATTTGCATATACGATACAAGGCTGTTAGAGAGATAATTGGAATTAATT
TGACTGTAAACACAAAGATATTAGTACAAAATACGTGACGTAGAAAGTAATAATTTCTTGGGTAGTTTGCAGTTTTA
AAATTATGTTTTAAAATGGACTATCATATGCTTACCGTAACTTGAAAGTATTTCGATTTCTTGGCTTTATATATCTT
GTGGAAAGGACGAPACACCGACGCTTCCGAGTACGGTACGTTTCGGTGGCTAGAAATGACAAGTTAAAATAAGGCTAG
TCCGTTATCAACTTGAAAAAGTGGCACCGAGTCGGTGCTTTTTTCTAGACCTGTACCGTACTCGGAAGCGTCGGAT
CCCTAGCTAGCTAGCTAAAGGTCCTCCTCGCTGATCAGTTTCTGCTCAGCCTTAGCTGCGGCTTCTTTAGCTGCTGC
TTCTGCGGTAGAATCAAGGCCCAGAAGTGGGTTGGGGATGGGTTTCCCGGCTTTTGCAGCTGCTTCTTTTGCGGCGG
CTTCGGCTGCATAGTCGGGGACATCATAGGGATATGCCTTGGCAGCTGCTTCCTTGGCAGCGGCTTCGGCCAGATCC
TCTTCGCTAATCAACTTTTGCTCTGCTTTAGCTGCAGCCTCCTTGGCGGCAGCTTCTGCAGTAGAATCCAATCCCAA
CAGTGGGTTTGGAATTGGTTTCCCAGCTTTGGCGGCGGCCTCCTTAGCAGCTGCCTCGGCGGCGTAATCTGGCACAT
CATATGGGTAGCTCCCTCCACCACCCTCTCGAGATCCTGTACCGTACTCGGAAGCGTCCACGTGCGGACCGAGCGGC
CGCAGGAACCCCTAGTGATGGAGTTGGCCACTCCCTCTCTGCGCGCTCGCTCGCTCACTGAGGCCGGGCGGGCGACCAAAG
GTCGCCCGACGCCCGGGCTTTGCCCGGGCGGCTCAGTGAGCGAGGAGCGCAGCTGCCTGCAGGGGCGCCTGAT
GCGGTATTTTCTCCTTACGCATCTGTGCGGTATTTCACACCGCATACGTCAAAGCAACCATAGTACGCGCCCTGTAG
CGGCGCATTAAGCGCGGCGGGTGTGGTGGTTACGCGCAGCGTGACCGCTACACTTGCCAGCGCCCTAGCGCCCGCTC
CTTTCGCTTTCTTCCCTTCCTTTCTCGCCACGTTCGCCGGCTTTCCCCGTCAAGCTCTAAATCGGGGGCTCCCTTTA
GGGTTCCGATTTAGTGCTTTACGGCACCTCGACCCCAAAAAACTTGATTTGGGTGATGGTTCACGTAGTGGGCCATC
GCCCTGATAGACGGTTTTTCGCCCTTTGACGTTGGAGTCCACGTTCTTTAATAGTGGACTCTTGTTCCAAACTGGAA
CAACACTCAACCCTATCTCGGGCTATTCTTTTGATTTATAAGGGATTTTGCCGATTTCGGCCTATTGGTTAAAAAAT
GAGCTGATTTAACAAAAATTTAACGCGAATTTTAACAAAATATTAACGTTTACAATTTTATGGTGCACTCTCAGTAC
AATCTGCTCTGATGCCGCATAGTTAAGCCAGCCCCGACACCCGCCAACACCCGCTGACGCGCCCTGACGGGCTTGTC
TGCTCCCGGCATCCGCTTACAGACAAGCTGTGACCGTCTCCGGGAGCTGCATGTGTCAGAGGTTTTCACCGTCATCA
CCGAAACGCGCGAGACGAAAGGGCCTCGTGATACGCCTATTTTTATAGGTTAATGTCATGATAATAATGGTTTCTTA
GACGTCAGGTGGCACTTTTCGGGGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGAAGATATGAGTATTCAACATTTC
CGTGTCGCCCTTATTCCCTTTTTTGCGGCATTTTGCCTTCCTGTTTTTGCTCACCCAGAAACGCTGGTGAAAGTAAA
AGATGCTGAAGATCAGTTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAGTACTCACCAGTCACAGAAAA
GCATCTTACGGATGGCATGACAGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGGGGGATCATGTAACTCGCCTT
GATCGTTGGGAACCGGAGCTGAATGAAGCCATACCAAACGACGAGCGTGACACCACGATGCCTGTAGCAATGGCAAC
AACGTTGCGCAAACTATTAACTGGCGAACTACTTACTCTAGCTTCCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATCGTAGTTATCTACACGACGGG
GAGTCAGGCAACTATGGATGAACGAAATAGACAGATCGCTGAGATAGGTGCCTCACTGATTAAGCATTGGTAACTGT
CAGACCAAGTTTACTCATATATACTTTAGATTGATTTAAAACTTCATTTTTAATTTAAAAGGATCTAGGTGAAGATC
CTTTTTGATAATCTCATGACCAAAATCCCTTAACGTGAGTTTTCGTTCCACTGAGCGTCAGACCCCGTAGAAAAGAT
CAAAGGATCTTCTTGAGATCCTTTTTTTCTGCGCGTAATCTGCTGCTTGCAAACAAAAAAACCACCGCTACCAGCGG
TGGTTTGTTGCCGGATCAAGAGCTACCAACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTGTAGCACCGCCTACATACCTCGCTCTGCT
AATCCTGTTACCAGTGGCTGCTGCCAGTGGCGATAAGTCGTGTCTTACCGGGTTGGACTCAAGACGATAGTTACCGG
ATAAGGCGCAGCGGTCGGGCTGAACGGGGGGTTCGTGCACACAGCCCAGCTTGGAGCGAACGACCTACACCGAACTG
AGATACCTACAGCGTGAGCTATGAGAAAGCGCCACGCTTCCCGAAGGGAGAAAGGCGGACAGGTATCCGGTAAGCGG
CAGGGTCGGAACAGGAGAGCGCACGAGGGAGCTTCCAGGGGGAAACGCCTGCTATCTTTATAGTCCTGTCGGGTTTC
GCCACCTCTGACTTGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGT

| | | | | | |
|---|---|---|---|---|---|
| source | 1 | ... 3742 | 3742 | == | source |
| AAV2 ITR | 1 | ... 141 | 141 | == | region_repeat |
| U6 promoter | 156 | ... 396 | 241 | == | promoter |
| HD-gRNA | 405 | ... 424 | 20 | == | misc_feature |
| chimeric gRNA scaffold | 425 | ... 500 | 76 | == | misc_feature |
| gRNA scaffold | 425 | ... 500 | 76 | => | misc_RNA |
| T6 | 501 | ... 506 | 6 | == | misc_feature |
| DRS | 513 | ... 535 | 23 | == | misc_feature |
| Kaleidoscope | 542 | ... 949 | 408 | <= | CDS |
| XcXcXcX | 542 | ... 556 | 15 | == | misc_feature |
| Myc | 557 | ... 586 | 30 | <= | CDS |
| V5 tag | 623 | ... 664 | 42 | <= | CDS |
| HA | 701 | ... 727 | 27 | <= | CDS |
| Myc | 764 | ... 793 | 30 | <= | CDS |
| V5 tag | 830 | ... 871 | 42 | <= | CDS |

APPENDIX-continued

| | | | | |
|---|---|---|---|---|
| HA | 908 . . . 934 | 27 | <= | CDS |
| DRS | 960 . . . 982 | 23 | == | misc_feature |
| AAV2 ITR | 1005 . . . 1145 | 141 | == | repeat_region |
| f1 ori | 1220 . . . 1675 | 456 | => | rep_origin |
| bla AmpR promoter | 1957 . . . 2061 | 105 | == | promoter |
| bla | 2062 . . . 2922 | 861 | => | CDS |
| ori | 3093 . . . 3681 | 589 | => | rep_origin |
| ITR | 3742 . . . 3742 | 1 | == | misc_feature |

What is claimed is:

1. A Homology-Independent Universal Genome Engineering (HiUGE) system for gene editing a subject genome, the HiUGE system comprising:
   (a) a Homology-Independent Universal Genome Engineering (HiUGE) vector comprising:
      (i) a first polynucleotide sequence encoding at least one insert;
      (ii) at least one donor recognition sequence (DRS) flanking each side of the first polynucleotide sequence, the DRS comprising a cleavage site for a CRISPR-based nuclease;
      (iii) a second polynucleotide sequence encoding a HiUGE vector specific gRNA, wherein the HiUGE vector specific gRNA targets the CRISPR-based nuclease to the DRS and does not target a specific sequence within the subject genome;
      (iv) a third polynucleotide sequence encoding a first portion of a CRISPR-based nuclease having a first split-intein; and
   (b) a gene specific vector comprising:
      (i) a fourth polynucleotide sequence encoding a second portion of a CRISPR-based nuclease having a second split-intein complementary to the first split-intein, wherein the first portion of a CRISPR-based nuclease and the second portion of a CRISPR-based nuclease can join together to form the CRISPR-based nuclease; and
      (ii) a fifth polynucleotide sequence that encodes a target gene specific gRNA which targets the CRISPR-based nuclease to a target gene specific sequence within the subject genome.

2. The HiUGE system of claim 1, wherein the N-intein comprises a polynucleotide sequence of SEQ ID NO: 60 and the second split-intein comprises a sequence of SEQ ID NO: 61.

3. The HiUGE system of claim 1, wherein the first portion of a CRISPR-based nuclease comprises the polypeptide sequence of SEQ ID NO: 55 and the second portion of a CRISPR-based nuclease comprises the polypeptide sequence of SEQ ID NO: 56.

4. The HiUGE system of claim 1, wherein the CRISPR-based nuclease cleaves the at least one DRS flanking each side of the first polynucleotide and the target gene specific sequence, thereby generating a cleaved first polynucleotide sequence and a cleaved site of the target gene, wherein the cleaved first polynucleotide sequence is integrated into the cleaved site of the target gene by non-homologous end joining.

5. The HiUGE system of claim 1, wherein the at least one insert is inserted at the N-terminal end of a gene splicing region, or a transcribed region to generate a N-terminal tagged fusion protein.

6. The HiUGE system of claim 1, wherein the at least one insert is inserted at the C-terminal end of a promoter region, an enhancer region, a repressor region, an insulator region, a silencer region, a region involved in DNA looping with the promoter region, a gene splicing region, or a transcribed region to generate a C-terminal tagged fusion protein.

7. The HiUGE system of claim 1, wherein the CRISPR-based nuclease is a Cas9 endonuclease or a variant thereof and is derived from a bacterial species selected from the group consisting of *Streptococcus pyogenes, Francisella novicida, Staphylococcus aureus, Neisseria meningitides, Streptococcus thermophiles, Treponema denticola, Brevibacillus laterosporus, Campylobacter jejuni, Corynebacterium diphtheria, Eubacterium ventriosum, Streptococcus pasteurianus, Lactobacillus farciminis, Sphaerochaeta globus, Azospirillum, Gluconacetobacter diazotrophicus, Neisseria*

*cinerea, Roseburia intestinalis, Parvibaculum lavamentivorans, Nitratifractor salsuginis,* and *Campylobacter lari.*

8. The HiUGE system of claim 1, wherein the DRS comprises a donor target sequence of about 19 to 24 nucleotides in length and a PAM sequence, and wherein:
  the donor target sequence comprises a sequence of 5'-NNNNNNNNNNNNNNNN$_{-2}$N$_{-1}$N$_1$N$_2$N-3' (SEQ ID NO: 15) in the forward orientation and the Cas9 dependent double stranded break in the cleavage site occurs between positions N$_{-1}$ and N$_1$; or
  the donor target sequence comprises a sequence of 5'-XX$_{-2}$ X$_{-1}$X$_1$X$_2$XXX XXXX-3' (SEQ ID NO: 16) in the reverse orientation and the Cas9 dependent double stranded break in the cleavage site occurs between positions X$_{-1}$ and X$_1$,
  wherein N is any of the four deoxyribonucleic acids adenine (A), thymine (T), guanine (G), or cytosine (C),
  wherein X is the reverse complement of N,
  wherein N$_{-2}$N$_{-1}$N$_1$N$_2$ (SEQ ID NO: 17) is a border sequence in 5'-NNNNNNNNNNNNNNNN$_{-2}$N$_{-1}$N$_1$N$_2$N-3' (SEQ ID NO: 15) and X$_{-2}$X$_{-1}$X$_1$X$_2$ (SEQ ID NO: 18) is a border sequence in 5'-XX$_2$X$_{-1}$X$_1$X$_2$XXXXX (XXXXX-3' (SEQ ID NO: 16), and
  wherein the donor target sequence does not introduce an in-frame stop codon after the insert is integrated into the target gene.

9. The HiUGE system of claim 8, wherein the target gene specific sequence comprises a sequence of ZZZZ$_{-2}$Z$_{-1}$Z$_1$Z$_2$Z (SEQ ID NO: 19), wherein the Cas9 dependent double stranded break in the cleavage site occurs between positions Z$_{-1}$ and Z$_1$, wherein Z is any of the four deoxyribonucleic acids adenine (A), thymine (T), guanine (G), or cytosine (C), wherein the border sequence does not yield an in-frame stop codon after the insert is integrated into the target gene, and wherein the genomic open reading frame (ORF) phase of the target gene is selected from the group consisting of:
  ORF+0: positions ZZ$_{-2}$Z$_{-1}$ corresponding to ZZZZ$_{-2}$Z$_{-1}$Z$_1$Z$_2$Z (SEQ ID NO: 19),
  ORF+1: positions ZZZ$_{-2}$ corresponding to ZZZZ$_{-2}$Z$_{-1}$Z$_1$Z$_2$Z (SEQ ID NO: 19), and
  ORF+2: positions ZZZ corresponding to ZZZZ$_{-2}$Z$_{-1}$Z$_1$Z$_2$Z (SEQ ID NO: 19).

10. The HiUGE system of claim 1, wherein the least one insert comprises a polynucleotide sequence encoding at least one amino acid sequence of SEQ ID NO: 34, 39, 41-50, or combination thereof.

11. The HiUGE system of claim 1, wherein the DRS comprises a polynucleotide sequence of GTCATAGTATCGCGGAGTTCAGG (SEQ ID NO: 22), GACGCTTCCGAGTACGGTACAGG (SEQ ID NO: 23), GGTTCTACGAGGATACGTCTTGG (SEQ ID NO: 24), GCGTATGGCAAGCATAGCCGGGG (SEQ ID NO: 25), GCGATTGACCCGTGCTGTCGCGG (SEQ ID NO: 26), or CCTGTACCGTACTCGGAAGCGTC (SEQ ID NO: 27).

12. A Homology-Independent Universal Genome Engineering (HiUGE) system for gene editing a subject genome, the HiUGE system comprising:
  (a) (i) a CRISPR-based nuclease or (ii) a nucleic acid sequence that encodes a CRISPR-based nuclease;
  (b) a Homology-Independent Universal Genome Engineering (HiUGE) vector comprising:
    (i) a first polynucleotide sequence encoding at least one insert;
    (ii) at least one donor recognition sequence (DRS) flanking each side of the first polynucleotide sequence, the DRS comprising a cleavage site for the CRISPR-based nuclease; and
    (iii) a second polynucleotide sequence encoding a HiUGE vector specific gRNA, wherein the HiUGE vector specific gRNA targets the CRISPR-based nuclease to the DRS and does not target a specific sequence within the subject genome; and
  (c) (i) a target gene specific gRNA that targets the CRISPR-based nuclease to a target gene specific sequence within the subject genome or (ii) a target gene vector comprising a third polynucleotide sequence that encodes a target gene specific gRNA which targets the CRISPR-based nuclease to a target gene specific sequence within the subject genome,
  wherein the HiUGE system comprises at least one polynucleotide sequence of SEQ ID NO: 67-107, or combination thereof.

13. The HUGE system of claim 1, wherein the HiUGE system comprises at least one polynucleotide sequence of SEQ ID NOs: 108-127, or a combination thereof.

14. The HiUGE system of claim 1, wherein the HiUGE system targets a target gene specific sequence of a TUBB3 gene, MAP2 gene, MECP2 gene, NRCAM gene, ACTR2 gene, CLTA gene, ANK3 gene, SPTBN4 gene, SCN2A gene, GFAP gene, PDHA1 gene, or DCX gene.

15. A kit comprising the HiUGE system of claim 1.

* * * * *

SEQUENCE LISTING

<160> NUMBER OF SEQ ID NOS: 236

<210> SEQ ID NO 1
<211> LENGTH: 2
<212> TYPE: DNA
<213> ORGANISM: Artificial Sequence
<220> FEATURE:
<223> OTHER INFORMATION: Synthetic

<400> SEQUENCE: 1 yg                                                                      2

<210> SEQ ID NO 2
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 2 ngg                                                                     3

<210> SEQ ID NO 3
<211> LENGTH: 3
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 3 nga                                                                     3

<210> SEQ ID NO 4
<211> LENGTH: 4
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 4 ngcg                                                                    4

<210> SEQ ID NO 5
<211> LENGTH: 4

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 5 ngag                                                                    4

<210> SEQ ID NO 6
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 6 nggng                                                                   5

<210> SEQ ID NO 7
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 7 nngrrt                                                                  6

<210> SEQ ID NO 8
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 8 nngrrt                                                                  6

<210> SEQ ID NO 9
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is a, c, g, or t

<400> SEQUENCE: 9
```

```
nnnrrt                                                              6

<210> SEQ ID NO 10
<211> LENGTH: 6
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 10 naaaac                                                              6

<210> SEQ ID NO 11
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 11 nnnngnnt                                                            8

<210> SEQ ID NO 12
<211> LENGTH: 7
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: n is a, c, g, or t

<400> SEQUENCE: 12 nnagaaw                                                             7

<210> SEQ ID NO 13
<211> LENGTH: 8
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 13 nnnncndd                                                            8

<210> SEQ ID NO 14
<211> LENGTH: 8
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 14 nnnnryac                                                                      8

<210> SEQ ID NO 15
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, t, c, or g

<400> SEQUENCE: 15
nnnnnnnnnn nnnnnnnnnn                                                         20

<210> SEQ ID NO 16
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: n is a, t, c, or g

<400> SEQUENCE: 16
nnnnnnnnnn nnnnnnnnnn                                                         20

<210> SEQ ID NO 17
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, t, c, or g

<400> SEQUENCE: 17 nnnnn                                                                         5

<210> SEQ ID NO 18
<211> LENGTH: 5
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: n is a, t, c, or g

<400> SEQUENCE: 18 nnnnn                                                                         5

<210> SEQ ID NO 19
<211> LENGTH: 8
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: n is a, t, c, or g

<400> SEQUENCE: 19 nnnnnnnn                                                                 8

<210> SEQ ID NO 20
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n is a, t, c, or g

<400> SEQUENCE: 20
nnnnnnnnnn nnnnnnnnnn ngg                                               23

<210> SEQ ID NO 21
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(29)
<223> OTHER INFORMATION: n is a, t, c, or g

<400> SEQUENCE: 21
ccnnnnnnnn nnnnnnnnnn nnnnnnnnn                                         29

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
gtcatagtat cgcggagttc agg                                               23

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
gacgcttccg agtacggtac agg                                               23

<210> SEQ ID NO 24
<211> LENGTH: 23
<212> TYPE: DNA
<213> ORGANISM: Artificial Sequence
<220> FEATURE:
<223> OTHER INFORMATION: Synthetic

<400> SEQUENCE: 24
ggttctacga ggatacgtct tgg                                               23
```

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
gcgtatggca agcatagccg ggg                                              23

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
gcgattgacc cgtgctgtcg cgg                                              23

<210> SEQ ID NO 27
<211> LENGTH: 23
<212> TYPE: DNA
<213> ORGANISM: Artificial Sequence
<220> FEATURE:
<223> OTHER INFORMATION: Synthetic

<400> SEQUENCE: 27
cctgtaccgt actcggaagc gtc                                              23

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gacgcttccg agtacggtac                                                  20

<210> SEQ ID NO 29
<211> LENGTH: 76
<212> TYPE: DNA
<213> ORGANISM: Artificial Sequence
<220> FEATURE:
<223> OTHER INFORMATION: Synthetic

<400> SEQUENCE: 29
gttttagagc tagaaatagc aagttaaaat aaggctagtc cgttatcaac ttgaaaagt       60 ggcaccgagt cggtgc                                                      76

<210> SEQ ID NO 30
<211> LENGTH: 15
<212> TYPE: DNA
<213> ORGANISM: Artificial Sequence
<220> FEATURE:
<223> OTHER INFORMATION: Synthetic

<400> SEQUENCE: 30
tagctagcta gctag                                                       15

<210> SEQ ID NO 31
<211> LENGTH: 15
<212> TYPE: DNA

```
<213> ORGANISM: Artificial Sequence
<220> FEATURE:
<223> OTHER INFORMATION: Synthetic

<400> SEQUENCE: 31
ctagctagct agcta                                                          15

<210> SEQ ID NO 32
<211> LENGTH: 78
<212> TYPE: DNA
<213> ORGANISM: Artificial Sequence
<220> FEATURE:
<223> OTHER INFORMATION: Synthetic

<400> SEQUENCE: 32
gaagatgatg ccgtactcgg aagcgtcgga tcctacccct acgatgtacc ggattacgca        60
tagctagcta gctagagc                                                       78

<210> SEQ ID NO 33
<211> LENGTH: 78
<212> TYPE: DNA
<213> ORGANISM: Artificial Sequence
<220> FEATURE:
<223> OTHER INFORMATION: Synthetic

<400> SEQUENCE: 33
gaagatgatg tacaggctcg agcttatccc tatgacgttc ctgactatgc tctagctagc        60
tagctatgcg taatccgg                                                       78

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Tyr Pro Tyr Asp Val Pro Asp Tyr Ala
1               5

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35 taccctttacg atgtaccgga ttacgca                                            27

<210> SEQ ID NO 36
<211> LENGTH: 27
<212> TYPE: DNA
<213> ORGANISM: Artificial Sequence
<220> FEATURE:
<223> OTHER INFORMATION: Synthetic

<400> SEQUENCE: 36
tatccctatg acgttcctga ctatgct                                             27

<210> SEQ ID NO 37
<211> LENGTH: 69
<212> TYPE: DNA
<213> ORGANISM: Artificial Sequence
<220> FEATURE:
```

<223> OTHER INFORMATION: Synthetic

<400> SEQUENCE: 37

```
taccccttacg atgtaccgga ttacgcatag ctagctagct agagcatagt caggaacgtc    60
atagggata                                                             69
```

<210> SEQ ID NO 38
<211> LENGTH: 69
<212> TYPE: DNA
<213> ORGANISM: Artificial Sequence
<220> FEATURE:
<223> OTHER INFORMATION: Synthetic

<400> SEQUENCE: 38

```
tatccctatg acgttcctga ctatgctcta gctagctagc tatgcgtaat ccggtacatc    60
gtaagggta                                                             69
```

<210> SEQ ID NO 39
<211> LENGTH: 233
<212> TYPE: PRT
<213> ORGANISM: Artificial Sequence
<220> FEATURE:
<223> OTHER INFORMATION: Synthetic

<400> SEQUENCE: 39

```
Met Phe Lys Asn Leu Ile Trp Leu Lys Glu Val Asp Ser Thr Gln Glu
1               5                   10                  15

Arg Leu Lys Glu Trp Asn Val Ser Tyr Gly Thr Ala Leu Val Ala Asp
            20                  25                  30

Arg Gln Thr Lys Gly Arg Gly Gly Leu Gly Arg Lys Trp Leu Ser Gln
        35                  40                  45

Glu Gly Gly Leu Tyr Phe Ser Phe Leu Leu Asn Pro Lys Glu Phe Glu
    50                  55                  60

Asn Leu Leu Gln Leu Pro Leu Val Leu Gly Leu Ser Val Ser Glu Ala
65                  70                  75                  80

Leu Glu Glu Ile Thr Glu Ile Pro Phe Ser Leu Lys Trp Pro Asn Asp
                85                  90                  95

Val Tyr Phe Gln Glu Lys Lys Val Ser Gly Val Leu Cys Glu Leu Ser
            100                 105                 110

Lys Asp Lys Leu Ile Val Gly Ile Gly Ile Asn Val Asn Gln Arg Glu
        115                 120                 125

Ile Pro Glu Glu Ile Lys Asp Arg Ala Thr Thr Leu Tyr Glu Ile Thr
    130                 135                 140

Gly Lys Asp Trp Asp Arg Lys Glu Val Leu Leu Lys Val Leu Lys Arg
145                 150                 155                 160

Ile Ser Glu Asn Leu Lys Lys Phe Lys Glu Lys Ser Phe Lys Glu Phe
                165                 170                 175

Lys Gly Lys Ile Glu Ser Lys Met Leu Tyr Leu Gly Glu Glu Val Lys
            180                 185                 190

Leu Leu Gly Glu Gly Lys Ile Thr Gly Lys Leu Val Gly Leu Ser Glu
        195                 200                 205

Lys Gly Gly Ala Leu Ile Leu Thr Glu Glu Gly Ile Lys Glu Ile Leu
    210                 215                 220

Ser Gly Glu Phe Ser Leu Arg Arg Ser
225                 230
```

<210> SEQ ID NO 40

```
<211> LENGTH: 286
<212> TYPE: PRT
<213> ORGANISM: Artificial Sequence
<220> FEATURE:
<223> OTHER INFORMATION: Synthetic

<400> SEQUENCE: 40

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 41
<211> LENGTH: 236
<212> TYPE: PRT
<213> ORGANISM: Artificial Sequence
<220> FEATURE:
<223> OTHER INFORMATION: Synthetic

<400> SEQUENCE: 41

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
```

```
            35                  40                  45
Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys
225                 230                 235

<210> SEQ ID NO 42
<211> LENGTH: 239
<212> TYPE: PRT
<213> ORGANISM: Artificial Sequence
<220> FEATURE:
<223> OTHER INFORMATION: Synthetic

<400> SEQUENCE: 42

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
```

```
                165                 170                 175
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 43
<211> LENGTH: 236
<212> TYPE: PRT
<213> ORGANISM: Artificial Sequence
<220> FEATURE:
<223> OTHER INFORMATION: Synthetic

<400> SEQUENCE: 43

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Thr Gly Asn Pro Asn Asp Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Gly Tyr Gly Phe His Gln Tyr Leu Pro Tyr Pro Asp Gly
65                  70                  75                  80

Met Ser Pro Phe Gln Ala Ala Met Val Asp Gly Ser Gly Tyr Gln Val
                85                  90                  95

His Arg Thr Met Gln Phe Glu Asp Gly Ala Ser Leu Thr Val Asn Tyr
            100                 105                 110

Arg Tyr Thr Tyr Glu Gly Ser His Ile Lys Gly Glu Ala Gln Val Lys
        115                 120                 125

Gly Thr Gly Phe Pro Ala Asp Gly Pro Val Met Thr Asn Ser Leu Thr
    130                 135                 140

Ala Ala Asp Trp Cys Arg Ser Lys Lys Thr Tyr Pro Asn Asp Lys Thr
145                 150                 155                 160

Ile Ile Ser Thr Phe Lys Trp Ser Tyr Thr Thr Gly Asn Gly Lys Arg
                165                 170                 175

Tyr Arg Ser Thr Ala Arg Thr Thr Tyr Thr Phe Ala Lys Pro Met Ala
            180                 185                 190

Ala Asn Tyr Leu Lys Asn Gln Pro Met Tyr Val Phe Arg Lys Thr Glu
        195                 200                 205

Leu Lys His Ser Lys Thr Glu Leu Asn Phe Lys Glu Trp Gln Lys Ala
    210                 215                 220

Phe Thr Asp Val Met Gly Met Asp Glu Leu Tyr Lys
225                 230                 235

<210> SEQ ID NO 44
<211> LENGTH: 476
<212> TYPE: PRT
<213> ORGANISM: Artificial Sequence
<220> FEATURE:
<223> OTHER INFORMATION: Synthetic

<400> SEQUENCE: 44
```

```
Met Val Ser Lys Gly Glu Glu Val Ile Lys Glu Phe Met Arg Phe Lys
1               5                   10                  15

Val Arg Met Glu Gly Ser Met Asn Gly His Glu Phe Glu Ile Glu Gly
                20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ala Trp Asp Ile Leu Ser Pro
50                      55                  60

Gln Phe Met Tyr Gly Ser Lys Ala Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Leu Val Thr Val Thr Gln Asp Ser
                100                 105                 110

Ser Leu Gln Asp Gly Thr Leu Ile Tyr Lys Val Lys Met Arg Gly Thr
            115                 120                 125

Asn Phe Pro Pro Asp Gly Pro Val Met Gln Lys Thr Met Gly Trp
130                     135                 140

Glu Ala Ser Thr Glu Arg Leu Tyr Pro Arg Asp Gly Val Leu Lys Gly
145                 150                 155                 160

Glu Ile His Gln Ala Leu Lys Leu Lys Asp Gly Gly His Tyr Leu Val
                165                 170                 175

Glu Phe Lys Thr Ile Tyr Met Ala Lys Lys Pro Val Gln Leu Pro Gly
            180                 185                 190

Tyr Tyr Tyr Val Asp Thr Lys Leu Asp Ile Thr Ser His Asn Glu Asp
        195                 200                 205

Tyr Thr Ile Val Glu Gln Tyr Glu Arg Ser Glu Gly Arg His His Leu
210                 215                 220

Phe Leu Gly His Gly Thr Gly Ser Thr Gly Ser Gly Ser Ser Gly Thr
225                 230                 235                 240

Ala Ser Ser Glu Asp Asn Asn Met Ala Val Ile Lys Glu Phe Met Arg
                245                 250                 255

Phe Lys Val Arg Met Glu Gly Ser Met Asn Gly His Glu Phe Glu Ile
            260                 265                 270

Glu Gly Glu Gly Glu Gly Arg Pro Tyr Glu Gly Thr Gln Thr Ala Lys
        275                 280                 285

Leu Lys Val Thr Lys Gly Gly Pro Leu Pro Phe Ala Trp Asp Ile Leu
    290                 295                 300

Ser Pro Gln Phe Met Tyr Gly Ser Lys Ala Tyr Val Lys His Pro Ala
305                 310                 315                 320

Asp Ile Pro Asp Tyr Lys Lys Leu Ser Phe Pro Glu Gly Phe Lys Trp
                325                 330                 335

Glu Arg Val Met Asn Phe Glu Asp Gly Gly Leu Val Thr Val Thr Gln
            340                 345                 350

Asp Ser Ser Leu Gln Asp Gly Thr Leu Ile Tyr Lys Val Lys Met Arg
        355                 360                 365

Gly Thr Asn Phe Pro Pro Asp Gly Pro Val Met Gln Lys Thr Met
370                 375                 380

Gly Trp Glu Ala Ser Thr Glu Arg Leu Tyr Pro Arg Asp Gly Val Leu
385                 390                 395                 400

Lys Gly Glu Ile His Gln Ala Leu Lys Leu Lys Asp Gly Gly His Tyr
                405                 410                 415

Leu Val Glu Phe Lys Thr Ile Tyr Met Ala Lys Lys Pro Val Gln Leu
```

```
                420            425            430
Pro Gly Tyr Tyr Tyr Val Asp Thr Lys Leu Asp Ile Thr Ser His Asn
        435            440            445

Glu Asp Tyr Thr Ile Val Glu Gln Tyr Glu Arg Ser Glu Gly Arg His
        450            455            460

His Leu Phe Leu Tyr Gly Met Asp Glu Leu Tyr Lys
465            470            475

<210> SEQ ID NO 45
<211> LENGTH: 239
<212> TYPE: PRT
<213> ORGANISM: Artificial Sequence
<220> FEATURE:
<223> OTHER INFORMATION: Synthetic

<400> SEQUENCE: 45

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 46
<211> LENGTH: 343
<212> TYPE: PRT
<213> ORGANISM: Artificial Sequence
<220> FEATURE:
<223> OTHER INFORMATION: Synthetic

<400> SEQUENCE: 46

Met Ala Asn Leu Leu Thr Val His Gln Asn Leu Pro Ala Leu Pro Val
1               5                   10                  15
```

```
Asp Ala Thr Ser Asp Glu Val Arg Lys Asn Leu Met Asp Met Phe Arg
             20                  25                  30

Asp Arg Gln Ala Phe Ser Glu His Thr Trp Lys Met Leu Leu Ser Val
         35                  40                  45

Cys Arg Ser Trp Ala Ala Trp Cys Lys Leu Asn Asn Arg Lys Trp Phe
 50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
             85                  90                  95

Met Leu His Arg Arg Ser Gly Leu Pro Arg Pro Ser Asp Ser Asn Ala
        100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
        130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
        210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
        290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Gly Lys Pro Ile Pro Asn Pro Leu Leu Gly Leu Asp Ser Thr
1                5                  10

<210> SEQ ID NO 48
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 48

Glu Gln Lys Leu Ile Ser Glu Glu Asp Leu
1               5                   10

<210> SEQ ID NO 49
<211> LENGTH: 19
<212> TYPE: PRT
<213> ORGANISM: Artificial Sequence
<220> FEATURE:
<223> OTHER INFORMATION: Synthetic

<400> SEQUENCE: 49

Ala Thr Asn Phe Ser Leu Leu Lys Gln Ala Gly Asp Val Glu Glu Asn
1               5                   10                  15

Pro Gly Pro

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Ile Glu Gly Arg
1

<210> SEQ ID NO 51
<211> LENGTH: 10
<212> TYPE: PRT
<213> ORGANISM: Artificial Sequence
<220> FEATURE:
<223> OTHER INFORMATION: Synthetic

<400> SEQUENCE: 51

Leu Ala Leu Lys Leu Ala Gly Leu Asp Leu
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Pro Ala Ala Lys Arg Val Lys Leu Asp
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic

<400> SEQUENCE: 53

Pro Lys Lys Lys Arg Lys Val
1               5

<210> SEQ ID NO 54
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 54

His His His His His His
1               5

<210> SEQ ID NO 55
<211> LENGTH: 572
<212> TYPE: PRT
<213> ORGANISM: Artificial Sequence
<220> FEATURE:
<223> OTHER INFORMATION: Synthetic

<400> SEQUENCE: 55

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
```

```
                305                 310                 315                 320
        Ile Lys Arg Tyr Asp Glu His His Gln Asp Leu Thr Leu Leu Lys Ala
                        325                 330                 335

Leu Val Arg Gln Gln Leu Pro Glu Lys Tyr Lys Glu Ile Phe Phe Asp
                        340                 345                 350

Gln Ser Lys Asn Gly Tyr Ala Gly Tyr Ile Asp Gly Gly Ala Ser Gln
                        355                 360                 365

Glu Glu Phe Tyr Lys Phe Ile Lys Pro Ile Leu Glu Lys Met Asp Gly
                        370                 375                 380

Thr Glu Leu Leu Val Lys Leu Asn Arg Glu Asp Leu Leu Arg Lys
        385                 390                 395                 400

Gln Arg Thr Phe Asp Asn Gly Ser Ile Pro His Gln Ile His Leu Gly
                        405                 410                 415

Glu Leu His Ala Ile Leu Arg Arg Gln Glu Asp Phe Tyr Pro Phe Leu
                        420                 425                 430

Lys Asp Asn Arg Glu Lys Ile Glu Lys Ile Leu Thr Phe Arg Ile Pro
                        435                 440                 445

Tyr Tyr Val Gly Pro Leu Ala Arg Gly Asn Ser Arg Phe Ala Trp Met
                        450                 455                 460

Thr Arg Lys Ser Glu Glu Thr Ile Thr Pro Trp Asn Phe Glu Glu Val
        465                 470                 475                 480

Val Asp Lys Gly Ala Ser Ala Gln Ser Phe Ile Glu Arg Met Thr Asn
                        485                 490                 495

Phe Asp Lys Asn Leu Pro Asn Glu Lys Val Leu Pro Lys His Ser Leu
                        500                 505                 510

Leu Tyr Glu Tyr Phe Thr Val Tyr Asn Glu Leu Thr Lys Val Lys Tyr
                        515                 520                 525

Val Thr Glu Gly Met Arg Lys Pro Ala Phe Leu Ser Gly Glu Gln Lys
                        530                 535                 540

Lys Ala Ile Val Asp Leu Leu Phe Lys Thr Asn Arg Lys Val Thr Val
        545                 550                 555                 560

Lys Gln Leu Lys Glu Asp Tyr Phe Lys Lys Ile Glu
                        565                 570

<210> SEQ ID NO 56
<211> LENGTH: 795
<212> TYPE: PRT
<213> ORGANISM: Artificial Sequence
<220> FEATURE:
<223> OTHER INFORMATION: Synthetic

<400> SEQUENCE: 56

Cys Phe Asp Ser Val Glu Ile Ser Gly Val Glu Asp Arg Phe Asn Ala
        1               5                   10                  15

Ser Leu Gly Thr Tyr His Asp Leu Leu Lys Ile Ile Lys Asp Lys Asp
                        20                  25                  30

Phe Leu Asp Asn Glu Glu Asn Glu Asp Ile Leu Glu Asp Ile Val Leu
                        35                  40                  45

Thr Leu Thr Leu Phe Glu Asp Arg Glu Met Ile Glu Glu Arg Leu Lys
        50                  55                  60

Thr Tyr Ala His Leu Phe Asp Asp Lys Val Met Lys Gln Leu Lys Arg
        65                  70                  75                  80

Arg Arg Tyr Thr Gly Trp Gly Arg Leu Ser Arg Lys Leu Ile Asn Gly
                        85                  90                  95

Ile Arg Asp Lys Gln Ser Gly Lys Thr Ile Leu Asp Phe Leu Lys Ser
```

```
                100                 105                 110
Asp Gly Phe Ala Asn Arg Ala Phe Ala Ala Leu Ile Ala Asp Asp Ser
            115                 120                 125

Leu Thr Phe Lys Glu Asp Ile Gln Lys Ala Gln Val Ser Gly Gln Gly
    130                 135                 140

Asp Ser Leu His Glu His Ile Ala Asn Leu Ala Gly Ser Pro Ala Ile
145                 150                 155                 160

Lys Lys Gly Ile Leu Gln Thr Val Lys Val Asp Glu Leu Val Lys
                165                 170                 175

Val Met Gly Arg His Lys Pro Glu Asn Ile Val Ile Glu Met Ala Arg
            180                 185                 190

Glu Asn Gln Thr Thr Gln Lys Gly Gln Lys Asn Ser Arg Glu Arg Met
    195                 200                 205

Lys Arg Ile Glu Glu Gly Ile Lys Glu Leu Gly Ser Gln Ile Leu Lys
    210                 215                 220

Glu His Pro Val Glu Asn Thr Gln Leu Gln Asn Glu Lys Leu Tyr Leu
225                 230                 235                 240

Tyr Tyr Leu Gln Asn Gly Arg Asp Met Tyr Val Asp Gln Glu Leu Asp
            245                 250                 255

Ile Asn Arg Leu Ser Asp Tyr Asp Val Asp His Ile Val Pro Gln Ser
            260                 265                 270

Phe Leu Lys Asp Asp Ser Ile Asp Asn Lys Val Leu Thr Arg Ser Asp
            275                 280                 285

Lys Asn Arg Gly Lys Ser Asp Asn Val Pro Ser Glu Glu Val Val Lys
            290                 295                 300

Lys Met Lys Asn Tyr Trp Arg Gln Leu Leu Asn Ala Lys Leu Ile Thr
305                 310                 315                 320

Gln Arg Lys Phe Asp Asn Leu Thr Lys Ala Glu Arg Gly Gly Leu Ser
            325                 330                 335

Glu Leu Asp Lys Ala Gly Phe Ile Lys Arg Gln Leu Val Glu Thr Arg
            340                 345                 350

Gln Ile Thr Lys His Val Ala Gln Ile Leu Asp Ser Arg Met Asn Thr
            355                 360                 365

Lys Tyr Asp Glu Asn Asp Lys Leu Ile Arg Glu Val Lys Val Ile Thr
            370                 375                 380

Leu Lys Ser Lys Leu Val Ser Asp Phe Arg Lys Asp Phe Gln Phe Tyr
385                 390                 395                 400

Lys Val Arg Glu Ile Asn Asn Tyr His His Ala His Asp Ala Tyr Leu
            405                 410                 415

Asn Ala Val Val Gly Thr Ala Leu Ile Lys Lys Tyr Pro Lys Leu Glu
            420                 425                 430

Ser Glu Phe Val Tyr Gly Asp Tyr Lys Val Tyr Asp Val Arg Lys Met
            435                 440                 445

Ile Ala Lys Ser Glu Gln Glu Ile Gly Lys Ala Thr Ala Lys Tyr Phe
450                 455                 460

Phe Tyr Ser Asn Ile Met Asn Phe Phe Lys Thr Glu Ile Thr Leu Ala
465                 470                 475                 480

Asn Gly Glu Ile Arg Lys Arg Pro Leu Ile Glu Thr Asn Gly Glu Thr
            485                 490                 495

Gly Glu Ile Val Trp Asp Lys Gly Arg Asp Phe Ala Thr Val Arg Lys
            500                 505                 510

Val Leu Ser Met Pro Gln Val Asn Ile Val Lys Lys Thr Glu Val Gln
            515                 520                 525
```

```
Thr Gly Gly Phe Ser Lys Glu Ser Ile Leu Pro Lys Arg Asn Ser Asp
        530                 535                 540
Lys Leu Ile Ala Arg Lys Asp Trp Asp Pro Lys Lys Tyr Gly Gly
545                 550                 555                 560
Phe Asp Ser Pro Thr Val Ala Tyr Ser Val Leu Val Ala Lys Val
                565                 570                 575
Glu Lys Gly Lys Ser Lys Lys Leu Lys Ser Val Lys Glu Leu Leu Gly
                580                 585                 590
Ile Thr Ile Met Glu Arg Ser Ser Phe Glu Lys Asn Pro Ile Asp Phe
        595                 600                 605
Leu Glu Ala Lys Gly Tyr Lys Glu Val Lys Lys Asp Leu Ile Ile Lys
        610                 615                 620
Leu Pro Lys Tyr Ser Leu Phe Glu Leu Glu Asn Gly Arg Lys Arg Met
625                 630                 635                 640
Leu Ala Ser Ala Gly Glu Leu Gln Lys Gly Asn Glu Leu Ala Leu Pro
                645                 650                 655
Ser Lys Tyr Val Asn Phe Leu Tyr Leu Ala Ser His Tyr Glu Lys Leu
                660                 665                 670
Lys Gly Ser Pro Glu Asp Asn Glu Gln Lys Gln Leu Phe Val Glu Gln
                675                 680                 685
His Lys His Tyr Leu Asp Glu Ile Ile Glu Gln Ile Ser Glu Phe Ser
        690                 695                 700
Lys Arg Val Ile Leu Ala Asp Ala Asn Leu Asp Lys Val Leu Ser Ala
705                 710                 715                 720
Tyr Asn Lys His Arg Asp Lys Pro Ile Arg Glu Gln Ala Glu Asn Ile
                725                 730                 735
Ile His Leu Phe Thr Leu Thr Asn Leu Gly Ala Pro Ala Ala Phe Lys
                740                 745                 750
Tyr Phe Asp Thr Thr Ile Asp Arg Lys Arg Tyr Thr Ser Thr Lys Glu
                755                 760                 765
Val Leu Asp Ala Thr Leu Ile His Gln Ser Ile Thr Gly Leu Tyr Glu
        770                 775                 780
Thr Arg Ile Asp Leu Ser Gln Leu Gly Gly Asp
785                 790                 795
```

<210> SEQ ID NO 57
<211> LENGTH: 2385
<212> TYPE: DNA
<213> ORGANISM: Artificial Sequence
<220> FEATURE:
<223> OTHER INFORMATION: Synthetic

<400> SEQUENCE: 57

| | | | | | |
|---|---|---|---|---|---|
| tgtttcgatt | ccgtcgaaat | ctccggcgta | gaggatcgat | ttaacgctag | tttgggaacc | 60 |
| tatcacgacc | tcctcaagat | cataaaggac | aaggacttct | tggacaacga | ggaaaacgaa | 120 |
| gatattttgg | aggacattgt | ccttacccct | actctgttcg | aagatcggga | aatgatagag | 180 |
| gagcgcctta | aaacatacgc | tcacctgttt | gatgataagg | ttatgaagca | gcttaagcga | 240 |
| agaaggtaca | cagggtgggg | tcgcctttca | aggaaactta | tcaacggaat | tcgagataaa | 300 |
| caaagcggta | agaccatatt | ggattttttg | aaatcagatg | gcttcgcaaa | ccggaacttt | 360 |
| atgcaactca | tccatgatga | ttccctgact | tttaagagg | atatacaaaa | agcccaggtt | 420 |
| tccggacaag | gcgactcctt | gcatgagcat | atcgccaatc | tggccggcag | tcccgctatt | 480 |
| aaaaagggaa | tacttcagac | agtgaaggtg | gtcgatgagc | tcgtgaaggt | aatgggccgg | 540 |

```
cacaagcctg aaaatattgt tatcgaaatg gccagagaaa atcaaactac tcagaagggg    600
caaaagaatt caagagagcg aatgaaacga attgaagagg gtatcaaaga gttgggctcc    660
caaattttga aggagcaccc tgtcgaaaac acccaacttc aaaatgaaaa gctgtatctc    720
tattacctcc aaaacggacg ggatatgtat gttgaccagg agcttgacat aaatcgcctt    780
tcagactatg atgttgatca tatagtgcct caaagcttct tgaaagacga cagcatagat    840
aataaggtac ttcacgaag tgataaaaac agaggtaaga gtgacaacgt tcccagcgaa    900
gaagttgtta aaagatgaa gaactactgg aggcaattgc tgaacgctaa acttatcaca    960
cagagaaagt ttgataattt gacaaaggct gaacggggtg gactgagcga actggataag   1020
gcaggattca tcaagcggca gctcgttgaa acacgacaaa ttacaaagca tgtagctcag   1080
atacttgact cacgaatgaa taccaaatac gatgagaacg ataaacttat aagagaagtc   1140
aaagtgataa ccctgaaatc aaagcttgtt tctgacttta ggaaggattt ccagttctac   1200
aaagtacggg aaatcaacaa ttatcatcat gctcacgacg cctatttgaa cgcagtagtc   1260
ggtacagccc tgattaaaaa atatccaaag cttgaaagcg agtttgttta tggcgattac   1320
aaggtctatg acgtgagaaa aatgattgct aagtccgaac aagaaattgg gaaggccact   1380
gccaaatatt tcttttattc aacatcatg aacttcttta aaaccgagat tactctggct   1440
aatggcgaga tccgcaaaag acctctcatt gaaacaaatg cgaaaccgg agaaattgtc   1500 tgggataagg ggcgggactt cgcaacagtc cgaaaagtgt tgtcaatgcc ccaagttaac   1560
atagtgaaaa aaaccgaagt gcaaactggc ggcttttcca aagaatccat cttgccaaag   1620
aggaacagtg acaagctgat cgccaggaaa aaagattggg accccaaaaa atacggtggt   1680
ttcgattcac ccaccgtagc ttatagcgtt cttgttgtag ccaaagtcga aaggaaaa    1740 tccaaaaagc ttaagtccgt gaaagagctt ctcgggatca ctattatgga aaggtcatct   1800
tttgaaaaga atcctatcga ttttttggag gctaagggtt ataaagaggt gaaaaaggat   1860
cttataatta agctccctaa gtatagtctg tttgagttgg aaaacgggcg gaaacgaatg   1920
ttggcctccg ccggggagct tcaaaagggc aatgaactgg ccttgccatc caagtacgta   1980
aatttctctt atctggcctc tcattacgaa aaactgaaag gctcccccga ggacaacgag   2040
cagaaacaat tgttcgtcga gcaacacaag cactacttgg acgaaataat tgaacaaatc   2100
tcagagttct ctaagcgcgt aatacttgcc gacgcaaatc tggataaagt cctctccgca   2160
tacaataaac accgcgacaa gccaattcgg gagcaagctg agaacatcat acacctcttt   2220
acactgacta accttggagc tcccgctgca tttaagtatt tcgacaccac aatcgatcga   2280
aagagataca caagcactaa agaagtactc gatgccactt tgattcacca agtatcaca    2340 ggtctttacg aaactagaat cgacctgagc caacttggcg agac                    2385
```

<210> SEQ ID NO 58
<211> LENGTH: 2385
<212> TYPE: DNA
<213> ORGANISM: Artificial Sequence
<220> FEATURE:
<223> OTHER INFORMATION: Synthetic

<400> SEQUENCE: 58

```
tgtttcgatt ccgtcgaaat ctccggcgta gaggatcgat ttaacgctag tttgggaacc      60
tatcacgacc tcctcaagat cataaaggac aaggacttct tggacaacga ggaaaacgaa    120
gatattttgg aggacattgt ccttacccct actctgttcg aagatcggga aatgatagag    180
```

```
gagcgcctta aaacatacgc tcacctgttt gatgataagg ttatgaagca gcttaagcga    240
agaaggtaca cagggtgggg tcgcctttca aggaaactta tcaacggaat tcgagataaa    300
caaagcggta agaccatatt ggattttttg aaatcagatg gcttcgcaaa ccgggccttt    360
gcagccctga tcgctgatga ttccctgact tttaaagagg atatacaaaa agcccaggtt    420
tccggacaag gcgactcctt gcatgagcat atcgccaatc tggccggcag tcccgctatt    480
aaaaagggaa tacttcagac agtgaaggtg gtcgatgagc tcgtgaaggt aatgggccgg    540
cacaagcctg aaaatattgt tatcgaaatg gccagagaaa atcaaactac tcagaagggg    600
caaaagaatt caagagagcg aatgaaacga attgagaagg gtatcaaaga gttgggctcc    660
caaattttga aggagcaccc tgtcgaaaac acccaacttc aaaatgaaaa gctgtatctc    720
tattacctcc aaaacggacg ggatatgtat gttgaccagg agcttgacat aaatcgcctt    780
tcagactatg atgttgatca tatagtgcct caaagcttct tgaaagacga cagcatagat    840
aataaggtac ttacacgaag tgataaaaac agaggtaaga gtgacaacgt tcccagcgaa    900
gaagttgtta aaaagatgaa gaactactgg aggcaattgc tgaacgctaa acttatcaca    960
cagagaaagt ttgataattt gacaaaggct gaacggggtg gactgagcga actggataag   1020
gcaggattca tcagcggca gctcgttgaa acacgacaaa ttacaaagca tgtagctcag   1080
atacttgact cacgaatgaa taccaaatac gatgagaacg ataaacttat aagagaagtc   1140
aaagtgataa ccctgaaatc aaagcttgtt tctgacttta ggaaggattt ccagttctac   1200
aaagtacggg aaatcaacaa ttatcatcat gctcacgacg cctatttgaa cgcagtagtc   1260
ggtacagccc tgattaaaaa atatccaaag cttgaaagcg agtttgttta tggcgattac   1320
aaggtctatg acgtgagaaa aatgattgct aagtccgaac aagaaattgg gaaggccact   1380
gccaaatatt tcttttattc caacatcatg aacttcttta aaaccgagat tactctggct   1440
aatggcgaga tccgcaaaag acctctcatt gaaacaaatg gcgaaaccgg agaaattgtc   1500
tgggataagg ggcgggactt cgcaacagtc cgaaaagtgt tgtcaatgcc caagttaac    1560 atagtgaaaa aaaccgaagt gcaaactggc ggcttttcca agaatccat cttgccaaag    1620 aggaacagtg acaagctgat cgccaggaaa aaagattggg accccaaaaa atacgggggt   1680
ttcgattcac ccaccgtagc ttatagcgtt cttgttgtag ccaaagtcga gaaggaaaa    1740 tccaaaaagc ttaagtccgt gaaagagctt ctcgggatca ctattatgga aggtcatct    1800 tttgaaaaga atcctatcga ttttttggag gctaagggtt ataaagaggt gaaaaaggat   1860
cttataatta agctccctaa gtatagtctg tttgagttgg aaaacgggcg aaacgaatg    1920 ttggcctccg ccggggagct tcaaaagggc aatgaactgg ccttgccatc caagtacgta   1980
aattttcttt atctggcctc tcattacgaa aaactgaaag gctcccccga ggacaacgag   2040
cagaaacaat tgttcgtcga gcaacacaag cactacttgg acgaaataat tgaacaaatc   2100
tcagagttct ctaagcgcgt aatacttgcc gacgcaaatc tggataaagt cctctccgca   2160
tacaataaac accgcgacaa gccaattcgg gagcaagctg agaacatcat acacctcttt   2220
acactgacta accttggagc tcccgctgca tttaagtatt tcgacaccac aatcgatcga   2280
aagagataca caagcactaa agaagtactc gatgccactt tgattcacca aagtatcaca   2340
ggtctttacg aaactagaat cgacctgagc caacttggcg gagac                   2385
```

<210> SEQ ID NO 59
<211> LENGTH: 795
<212> TYPE: PRT
<213> ORGANISM: Artificial Sequence
<220> FEATURE:
<223> OTHER INFORMATION: Synthetic

<400> SEQUENCE: 59

Cys Phe Asp Ser Val Glu Ile Ser Gly Val Glu Asp Arg Phe Asn Ala
1               5                   10                  15

Ser Leu Gly Thr Tyr His Asp Leu Leu Lys Ile Ile Lys Asp Lys Asp
            20                  25                  30

Phe Leu Asp Asn Glu Glu Asn Glu Asp Ile Leu Glu Asp Ile Val Leu
        35                  40                  45

Thr Leu Thr Leu Phe Glu Asp Arg Glu Met Ile Glu Glu Arg Leu Lys
    50                  55                  60

Thr Tyr Ala His Leu Phe Asp Asp Lys Val Met Lys Gln Leu Lys Arg
65                  70                  75                  80

Arg Arg Tyr Thr Gly Trp Gly Arg Leu Ser Arg Lys Leu Ile Asn Gly
                85                  90                  95

Ile Arg Asp Lys Gln Ser Gly Lys Thr Ile Leu Asp Phe Leu Lys Ser
            100                 105                 110

Asp Gly Phe Ala Asn Arg Ala Phe Ala Ala Leu Ile Ala Asp Asp Ser
        115                 120                 125

Leu Thr Phe Lys Glu Asp Ile Gln Lys Ala Gln Val Ser Gly Gln Gly
    130                 135                 140

Asp Ser Leu His Glu His Ile Ala Asn Leu Ala Gly Ser Pro Ala Ile
145                 150                 155                 160

Lys Lys Gly Ile Leu Gln Thr Val Lys Val Val Asp Glu Leu Val Lys
                165                 170                 175

Val Met Gly Arg His Lys Pro Glu Asn Ile Val Ile Glu Met Ala Arg
            180                 185                 190

Glu Asn Gln Thr Thr Gln Lys Gly Gln Lys Asn Ser Arg Glu Arg Met
        195                 200                 205

Lys Arg Ile Glu Glu Gly Ile Lys Glu Leu Gly Ser Gln Ile Leu Lys
    210                 215                 220

Glu His Pro Val Glu Asn Thr Gln Leu Gln Asn Glu Lys Leu Tyr Leu
225                 230                 235                 240

Tyr Tyr Leu Gln Asn Gly Arg Asp Met Tyr Val Asp Gln Glu Leu Asp
                245                 250                 255

Ile Asn Arg Leu Ser Asp Tyr Asp Val Asp His Ile Val Pro Gln Ser
            260                 265                 270

Phe Leu Lys Asp Asp Ser Ile Asp Asn Lys Val Leu Thr Arg Ser Asp
        275                 280                 285

Lys Asn Arg Gly Lys Ser Asp Asn Val Pro Ser Glu Glu Val Val Lys
    290                 295                 300

Lys Met Lys Asn Tyr Trp Arg Gln Leu Leu Asn Ala Lys Leu Ile Thr
305                 310                 315                 320

Gln Arg Lys Phe Asp Asn Leu Thr Lys Ala Glu Arg Gly Gly Leu Ser
                325                 330                 335

Glu Leu Asp Lys Ala Gly Phe Ile Lys Arg Gln Leu Val Glu Thr Arg
            340                 345                 350

Gln Ile Thr Lys His Val Ala Gln Ile Leu Asp Ser Arg Met Asn Thr
        355                 360                 365

Lys Tyr Asp Glu Asn Asp Lys Leu Ile Arg Glu Val Lys Val Ile Thr
    370                 375                 380

Leu Lys Ser Lys Leu Val Ser Asp Phe Arg Lys Asp Phe Gln Phe Tyr
385                 390                 395                 400

Lys Val Arg Glu Ile Asn Asn Tyr His His Ala His Asp Ala Tyr Leu
            405                 410                 415

Asn Ala Val Val Gly Thr Ala Leu Ile Lys Lys Tyr Pro Lys Leu Glu
            420                 425                 430

Ser Glu Phe Val Tyr Gly Asp Tyr Lys Val Tyr Asp Val Arg Lys Met
            435                 440                 445

Ile Ala Lys Ser Glu Gln Glu Ile Gly Lys Ala Thr Ala Lys Tyr Phe
450                 455                 460

Phe Tyr Ser Asn Ile Met Asn Phe Phe Lys Thr Glu Ile Thr Leu Ala
465                 470                 475                 480

Asn Gly Glu Ile Arg Lys Arg Pro Leu Ile Glu Thr Asn Gly Glu Thr
            485                 490                 495

Gly Glu Ile Val Trp Asp Lys Gly Arg Asp Phe Ala Thr Val Arg Lys
            500                 505                 510

Val Leu Ser Met Pro Gln Val Asn Ile Val Lys Lys Thr Glu Val Gln
            515                 520                 525

Thr Gly Gly Phe Ser Lys Glu Ser Ile Leu Pro Lys Arg Asn Ser Asp
            530                 535                 540

Lys Leu Ile Ala Arg Lys Lys Asp Trp Asp Pro Lys Lys Tyr Gly Gly
545                 550                 555                 560

Phe Asp Ser Pro Thr Val Ala Tyr Ser Val Leu Val Val Ala Lys Val
            565                 570                 575

Glu Lys Gly Lys Ser Lys Lys Leu Lys Ser Val Lys Glu Leu Leu Gly
            580                 585                 590

Ile Thr Ile Met Glu Arg Ser Ser Phe Glu Lys Asn Pro Ile Asp Phe
            595                 600                 605

Leu Glu Ala Lys Gly Tyr Lys Glu Val Lys Lys Asp Leu Ile Ile Lys
610                 615                 620

Leu Pro Lys Tyr Ser Leu Phe Glu Leu Glu Asn Gly Arg Lys Arg Met
625                 630                 635                 640

Leu Ala Ser Ala Gly Glu Leu Gln Lys Gly Asn Glu Leu Ala Leu Pro
            645                 650                 655

Ser Lys Tyr Val Asn Phe Leu Tyr Leu Ala Ser His Tyr Glu Lys Leu
            660                 665                 670

Lys Gly Ser Pro Glu Asp Asn Glu Gln Lys Gln Leu Phe Val Glu Gln
            675                 680                 685

His Lys His Tyr Leu Asp Glu Ile Ile Glu Gln Ile Ser Glu Phe Ser
            690                 695                 700

Lys Arg Val Ile Leu Ala Asp Ala Asn Leu Asp Lys Val Leu Ser Ala
705                 710                 715                 720

Tyr Asn Lys His Arg Asp Lys Pro Ile Arg Glu Gln Ala Glu Asn Ile
            725                 730                 735

Ile His Leu Phe Thr Leu Thr Asn Leu Gly Ala Pro Ala Ala Phe Lys
            740                 745                 750

Tyr Phe Asp Thr Thr Ile Asp Arg Lys Arg Tyr Thr Ser Thr Lys Glu
            755                 760                 765

Val Leu Asp Ala Thr Leu Ile His Gln Ser Ile Thr Gly Leu Tyr Glu
            770                 775                 780

Thr Arg Ile Asp Leu Ser Gln Leu Gly Gly Asp
785                 790                 795

<210> SEQ ID NO 60
<211> LENGTH: 306

```
<212> TYPE: DNA
<213> ORGANISM: Artificial Sequence
<220> FEATURE:
<223> OTHER INFORMATION: Synthetic

<400> SEQUENCE: 60
tgtttgtctt atgagaccga atcctcacc  gtggagtacg ggctcctgcc tatcgggaaa       60
attgtcgaaa agcgcataga gtgcactgtt tactctgtag ataacaatgg aaacatatac     120
acacagcccg tagcacagtg gcacgatcga ggcgagcagg aggtctttga atattgcctg     180
gaagacggca gtcttataag ggcaacaaag gatcacaaat ttatgaccgt agatggacaa     240
atgcttccca tcgacgagat ctttgagcgc gagcttgact tgatgagagt ggataacctg     300
cctaat                                                                306

<210> SEQ ID NO 61
<211> LENGTH: 105
<212> TYPE: DNA
<213> ORGANISM: Artificial Sequence
<220> FEATURE:
<223> OTHER INFORMATION: Synthetic

<400> SEQUENCE: 61
atgatcaaga tagcaacacg caagtatctt ggcaaacaga acgtgtacga tatcggggtc      60
gagcgcgatc ataacttcgc cctcaagaat ggatttatag caagt                    105

<210> SEQ ID NO 62
<211> LENGTH: 241
<212> TYPE: DNA
<213> ORGANISM: Artificial Sequence
<220> FEATURE:
<223> OTHER INFORMATION: Synthetic

<400> SEQUENCE: 62
gagggcctat ttcccatgat tccttcatat ttgcatatac gatacaaggc tgttagagag      60
ataattggaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
c                                                                    241

<210> SEQ ID NO 63
<211> LENGTH: 105
<212> TYPE: DNA
<213> ORGANISM: Artificial Sequence
<220> FEATURE:
<223> OTHER INFORMATION: Synthetic

<400> SEQUENCE: 63
cgcggaaccc ctatttgttt attttttctaa atacattcaa atatgtatcc gctcatgaga     60
caataaccct gataaatgct tcaataatat tgaaaaagga agagt                    105

<210> SEQ ID NO 64
<211> LENGTH: 1178
<212> TYPE: DNA
<213> ORGANISM: Artificial Sequence
<220> FEATURE:
<223> OTHER INFORMATION: Synthetic

<400> SEQUENCE: 64
ggctccggtg cccgtcagtg ggcagagcgc acatcgccca cagtccccga agttgggg        60
```

-continued

```
ggaggggtcg gcaattgaac cggtgcctag agaaggtggc gcggggtaaa ctgggaaagt      120
gatgtcgtgt actggctccg ccttttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccactg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaattttt gatgacctgc tgcgacgctt tttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cgggggtagt ctcaagctgg ccggcctgct ctggtgcctg    720
gcctcgcgcc gccgtgtatc gccccgcccc gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccacgg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgcccctt tttgagtttg gatcttggtt cattctcaag cctcagacag   1140
tggttcaaag ttttttttcttt ccatttcagg tgtcgtga                          1178
```

<210> SEQ ID NO 65
<211> LENGTH: 212
<212> TYPE: DNA
<213> ORGANISM: Artificial Sequence
<220> FEATURE:
<223> OTHER INFORMATION: Synthetic

<400> SEQUENCE: 65

```
gggcagagcg cacatcgccc acagtccccg agaagttggg gggagggtc ggcaattgaa     60
cgggtgccta gagaaggtgg cgcggggtaa actgggaaag tgatgtcgtg tactggctcc   120
gccttttttcc cgagggtggg ggagaaccgt atataagtgc agtagtcgcc gtgaacgttc   180
ttttttcgcaa cgggtttgcc gccagaacac ag                                 212
```

<210> SEQ ID NO 66
<211> LENGTH: 448
<212> TYPE: DNA
<213> ORGANISM: Artificial Sequence
<220> FEATURE:
<223> OTHER INFORMATION: Synthetic

<400> SEQUENCE: 66

```
agtgcaagtg ggttttagga ccaggatgag gcggggtggg ggtgcctacc tgacgaccga     60
ccccgaccca ctggacaagc acccaacccc cattcccaa attgcgcatc ccctatcaga   120
gagggggagg ggaaacagga tgcggcgagg cgcgtgcgca ctgccagctt cagcaccgcg   180
gacagtgcct tcgcccccgc ctggcggcgc gcgccaccgc cgcctcagca ctgaaggcgc   240
gctgacgtca ctcgcggtc ccccgcaaac tccccttccc ggccaccttg gtcgcgtccg   300
cgccgccgcc gggcccagccg gaccgcacca cgcgaggcgc gagatagggg ggcacggggcg   360
cgaccatctg cgctgcgggcg ccggcgactc agcgctgcct cagtctgcgg tgggcagcgg   420
```
aggagtcgtg tcgtgcctga gagcgcag 448

<210> SEQ ID NO 67
<211> LENGTH: 5012
<212> TYPE: DNA
<213> ORGANISM: Artificial Sequence
<220> FEATURE:
<223> OTHER INFORMATION: Synthetic

<400> SEQUENCE: 67

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgacg tagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gagacgcttc cgagtacggt acaggggatc | 540 |
| cggtggagga ggttctggag gcggtggaag tggtggcgga ggtagcggtg gaggaggttc | 600 |
| tatggtgtct aaggaattca tgttcaaaaa tcttatttgg ctgaaggaag ttgatagcac | 660 |
| ccaggagcgg cttaaggaat ggaatgtctc ctatggcact gcactcgtcg ccgatagaca | 720 |
| gaccaaaggt agaggcggtc tcggacggaa gtggttgagt caggagggcg gtctttactt | 780 |
| ctctttcttg ttgaatccaa aagagtttga aaatttgttg caacttccac tggtcttggg | 840 |
| actctccgtg agcgaggcac tcgaagagat tacagagata ccatttagtc tgaagtggcc | 900 |
| caacgacgtt tattttcagg agaaaaaggt ttcaggggtc ctttgtgagc tcagtaagga | 960 |
| caagctgata gtgggaatcg gtataaacgt gaatcaaaga gagatccctg aagagatcaa | 1020 |
| ggatcgggcc acaacacttt atgaaatcac tggaaaggat tggacagaa aggaggtctt | 1080 |
| gctgaaggtt ctcaagcgaa tttccgaaaa tctcaagaaa tttaaggaaa atccttaa | 1140 |
| agagttcaaa ggaaaaattg agtcaaagat gttgtacctt ggagaggagg ttaaactctt | 1200 |
| gggagaaggc aagattaccg ggaaacttgt gggcctgagt gaaaagggcg gtgctttgat | 1260 |
| acttacagag gaaggcataa aggagatact gtccggcgaa tttagcttgc gacggtcagc | 1320 |
| ttacccttac gatgtaccgg attacgcaaa gcttggatag ctagctagct agctcgagaa | 1380 |
| tcaacctctg gattacaaaa tttgtgaaag attgactggt attcttaact atgttgctcc | 1440 |
| ttttacgcta tgtggatacg ctgctttaat gcctttgtat catgctattg cttcccgtat | 1500 |
| ggctttcatt ttctcctcct tgtataaatc ctggttgctg tctctttatg aggagttgtg | 1560 |
| gcccgttgtc aggcaacgtg gcgtggtgtg cactgtgttt gctgacgcaa cccccactgg | 1620 |
| ttggggcatt gccaccacct gtcagctcct ttccgggact ttcgctttcc cctcccctat | 1680 |
| tgccacggcg gaactcatcg ccgcctgcct tgcccgctgc tggacagggg ctcggctgtt | 1740 |
| gggcactgac aattccgtgg tgttgtcggg gaaatcatcg tcctttcctt ggctgctcgc | 1800 |
| ctatgttgcc acctggattc tgcgcgggac gtccttctgc tacgtccctt cggccctcaa | 1860 |
| tccagcggac cttccttccc gcggcctgct gccggctctg cggcctcttc cgcgtcttcg | 1920 |
| ccttcgccct cagacgagtc ggatctccct ttgggccgcc tccccgcatc gataccgctc | 1980 |

```
gatagatctc gactgtgcct tctagttgcc agccatctgt tgtttgcccc tcccccgtgc   2040
cttccttgac cctggaaggt gccactccca ctgtcctttc ctaataaaat gaggaaattg   2100
catcgcattg tctgagtagg tgtcattcta ttctgggggg tggggtgggg caggacagca   2160
aggggggagga ttgggaagac aatagcaggc atgctgggga tgcggtgggc tctatggctc   2220
gaggacgctt ccgagtacgg tacagggtcg accacgtgcg gaccgagcgg ccgcaggaac   2280
ccctagtgat ggagttggcc actccctctc tgcgcgctcg ctcgctcact gaggccgggc   2340
gaccaaaggt cgcccgacgc ccgggctttg cccggcggc ctcagtgagc gagcgagcgc    2400
gcagctgcct gcaggggcgc ctgatgcggt attttctcct tacgcatctg tgcggtattt   2460
cacaccgcat acgtcaaagc aaccatagta cgcgccctgt agcggcgcat taagcgcggc   2520
gggtgtggtg gttacgcgca gcgtgaccgc tacacttgcc agcgccctag cgcccgctcc   2580
tttcgctttc ttcccttcct ttctcgccac gttcgccggc tttccccgtc aagctctaaa   2640
tcggggctc cctttaggg tccgatttag tgctttacgg cacctcgacc ccaaaaaact     2700
tgatttgggt gatggttcac gtagtgggcc atcgccctga tagacggttt ttcgcccttt   2760
gacgttggag tccacgttct ttaatagtgg actcttgttc caaactggaa caacactcaa   2820
ccctatctcg ggctattctt ttgatttata agggattttg ccgatttcgg cctattggtt   2880
aaaaaatgag ctgatttaac aaaaatttaa cgcgaatttt aacaaaatat taacgtttac   2940
aattttatgg tgcactctca gtacaatctg ctctgatgcc gcatagttaa gccagccccg   3000
acacccgcca acacccgctg acgcgccctg acgggcttgt ctgctcccgg catccgctta   3060
cagacaagct gtgaccgtct ccgggagctg catgtgtcag aggttttcac cgtcatcacc   3120
gaaacgcgcg agacgaaagg gcctcgtgat acgcctattt ttataggtta atgtcatgat   3180
aataatggtt tcttagacgt caggtggcac ttttcgggga aatgtgcgcg gaacccctat   3240
ttgtttattt ttctaaatac attcaaatat gtatccgctc atgagacaat aaccctgata   3300
aatgcttcaa taatattgaa aaaggaagag tatgagtatt caacatttcc gtgtcgccct   3360
tattcccttt tttgcggcat tttgccttcc tgttttttgct cacccagaaa cgctggtgaa   3420
agtaaaagat gctgaagatc agttgggtgc acgagtgggt tacatcgaac tggatctcaa   3480
cagcggtaag atccttgaga gttttcgccc cgaagaacgt tttccaatga tgagcacttt   3540
taaagttctg ctatgtggcg cggtattatc ccgtattgac gccgggcaag agcaactcgg   3600
tcgccgcata cactattctc agaatgactt ggttgagtac tcaccagtca cagaaaagca   3660
tcttacggat ggcatgacag taagagaatt atgcagtgct gccataacca tgagtgataa   3720
cactgcggcc aacttacttc tgacaacgat cggaggaccg aaggagctaa ccgcttttttt   3780
gcacaacatg ggggatcatg taactcgcct tgatcgttgg gaaccggagc tgaatgaagc   3840
cataccaaac gacgagcgtg acaccacgat gcctgtagca atggcaacaa cgttgcgcaa   3900
actattaact ggcgaactac ttactctagc ttcccggcaa caattaatag actggatgga   3960
ggcggataaa gttgcaggac cacttctgcg ctcggccctt ccggctggct ggtttattgc   4020
tgataaatct ggagccggtg agcgtgggtc tcgcggtatc attgcagcac tggggccaga   4080
tggtaagccc tcccgtatcg tagttatcta cacgacgggg agtcaggcaa ctatggatga   4140
acgaaataga cagatcgctg agataggtgc ctcactgatt aagcattggt aactgtcaga   4200
ccaagtttac tcatatatac tttagattga tttaaaactt catttttaat ttaaaaggat   4260
ctaggtgaag atccttttttg ataatctcat gaccaaaatc ccttaacgtg agttttcgtt   4320
ccactgagcg tcagaccccg tagaaaagat caaaggatct tcttgagatc ctttttttct   4380
```

```
gcgcgtaatc tgctgcttgc aaacaaaaaa accaccgcta ccagcggtgg tttgtttgcc    4440
ggatcaagag ctaccaactc tttttccgaa ggtaactggc ttcagcagag cgcagatacc    4500
aaatactgtc cttctagtgt agccgtagtt aggccaccac ttcaagaact ctgtagcacc    4560
gcctacatac ctcgctctgc taatcctgtt accagtggct gctgccagtg gcgataagtc    4620
gtgtcttacc gggttggact caagacgata gttaccggat aaggcgcagc ggtcgggctg    4680 aacgggggt tcgtgcacac agcccagctt ggagcgaacg acctacaccg aactgagata    4740
cctacagcgt gagctatgag aaagcgccac gcttcccgaa gggagaaagg cggacaggta    4800
tccggtaagc ggcagggtcg aacaggaga gcgcacgagg gagcttccag ggggaaacgc    4860
ctggtatctt tatagtcctg tcgggtttcg ccacctctga cttgagcgtc gatttttgtg    4920
atgctcgtca gggggcgga gcctatggaa aaacgccagc aacgcggcct ttttacggtt    4980
cctggccttt tgctggcctt ttgctcacat gt                                 5012
```

<210> SEQ ID NO 68
<211> LENGTH: 5014
<212> TYPE: DNA
<213> ORGANISM: Artificial Sequence
<220> FEATURE:
<223> OTHER INFORMATION: Synthetic

<400> SEQUENCE: 68

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta taatttctt gggtagtttg     300 cagttttaaa attatgtttt aaaatggact atcatatgct taccgtaact tgaaagtatt     360
tcgatttctt ggctttatat atcttgtgga aaggacgaaa caccgacgct tccgagtacg     420 gtacgttta gagctagaaa tagcaagtta aaataaggct agtccgttat caacttgaaa     480
aagtggcacc gagtcggtgc ttttttctta gagacgcttc cgagtacggt acaggggatc     540
cagggtggag gaggttctgg aggcggtgga agtggtggcg gaggtagcgg tggaggaggt     600
tctatggtgt ctaaggaatt catgttcaaa aatcttattt ggctgaagga agttgatagc     660
acccaggagc ggcttaagga atggaatgtc tcctatggca ctgcactcgt cgccgataga     720
cagaccaaag gtagaggcgg tctcggacgg aagtggttga gtcaggaggg cggtctttac     780
ttctctttct tgttgaatcc aaaagagttt gaaaatttgt tgcaacttcc actggtcttg     840
ggactctccg tgagcgaggc actcgaagag attacagaga taccatttag tctgaagtgg     900
cccaacgacg tttattttca ggagaaaaag gtttcagggg tcctttgtga gctcagtaag     960
gacaagctga tagtgggaat cggtataaac gtgaatcaaa gagagatccc tgaagagatc    1020
aaggatcggg ccacaacact ttatgaaatc actggaaagg attgggacag aaaggaggtc    1080
ttgctgaagg ttctcaagcg aatttccgaa aatctcaaga aatttaagga aaaatccttt    1140
aaagagttca aaggaaaaat tgagtcaaag atgttgtacc ttggagagga ggttaaactc    1200
ttgggagaag gcaagattac cgggaaactt gtgggcctga gtgaaaaggg cggtgctttg    1260
atacttacag aggaaggcat aaaggagata ctgtccggcg aatttagctt gcgacggtca    1320
gcttaccctt acgatgtacc ggattacgca aagcttggat agctagctag ctagctcgag    1380
```

```
aatcaacctc tggattacaa aatttgtgaa agattgactg gtattcttaa ctatgttgct    1440
ccttttacgc tatgtggata cgctgcttta atgcctttgt atcatgctat tgcttcccgt    1500
atggctttca ttttctcctc cttgtataaa tcctggttgc tgtctcttta tgaggagttg    1560
tggcccgttg tcaggcaacg tggcgtggtg tgcactgtgt ttgctgacgc aaccccact    1620 ggttggggca ttgccaccac ctgtcagctc ctttccggga ctttcgcttt ccccctccct    1680
attgccacgg cggaactcat cgccgcctgc cttgcccgct gctggacagg ggctcggctg    1740
ttgggcactg acaattccgt ggtgttgtcg gggaaatcat cgtcctttcc ttggctgctc    1800
gcctatgttg ccacctggat tctgcgcggg acgtccttct gctacgtccc ttcggccctc    1860
aatccagcgg accttccttc ccgcggcctg ctgccggctc tgcggcctct tccgcgtctt    1920
cgccttcgcc ctcagacgag tcggatctcc ctttgggccg cctccccgca tcgataccgc    1980
tcgatagatc tcgactgtgc cttctagttg ccagccatct gttgtttgcc cctccccgt    2040 gccttccttg accctggaag gtgccactcc cactgtcctt tcctaataaa atgaggaaat    2100
tgcatcgcat tgtctgagta ggtgtcattc tattctgggg ggtggggtgg ggcaggacag    2160 caaggggag gattgggaag acaatagcag gcatgctggg gatgcggtgg gctctatggc    2220
tcgaggacgc ttccgagtac ggtacagggt cgaccacgtg cggaccgagc ggccgcagga    2280
acccctagtg atggagttgg ccactccctc tctgcgcgct cgctcgctca ctgaggccgg    2340
gcgaccaaag gtcgcccgac gcccgggctt gcccgggcg gcctcagtga gcgagcgagc    2400
gcgcagctgc ctgcagggc gcctgatgcg gtattttctc cttacgcatc tgtgcggtat    2460
ttcacaccgc atacgtcaaa gcaaccatag tacgcgccct gtagcggcgc attaagcgcg    2520
gcgggtgtgg tggttacgcg cagcgtgacc gctacacttg ccagcgccct agcgcccgct    2580
cctttcgctt tcttcccttc ctttctcgcc acgttcgccg gctttccccg tcaagctcta    2640 aatcggggc tcccctttagg gttccgattt agtgctttac ggcacctcga ccccaaaaaa    2700
cttgatttgg gtgatggttc acgtagtggg ccatcgccct gatagacggt ttttcgccct    2760
ttgacgttgg agtccacgtt ctttaatagt ggactcttgt tccaaactgg aacaacactc    2820
aaccctatct cgggctattc ttttgattta agggatttt tgccgatttc ggcctattgg    2880
ttaaaaaatg agctgatttta acaaaaattt aacgcgaatt ttaacaaaat attaacgttt    2940
acaattttat ggtgcactct cagtacaatc tgctctgatg ccgcatagtt aagccagccc    3000
cgacacccgc caacacccgc tgacgcgccc tgacgggctt gtctgctccc ggcatccgct    3060
tacagacaag ctgtgaccgt ctccgggagc tgcatgtgtc agaggttttc accgtcatca    3120
ccgaaacgcg cgagacgaaa gggcctcgtg atacgcctat ttttataggt taatgtcatg    3180
ataataatgg tttcttagac gtcaggtggc acttttcggg gaaatgtgcg cggaacccct    3240
atttgtttat ttttctaaat acattcaaat atgtatccgc tcatgagaca ataaccctga    3300
taaatgcttc aataatattg aaaaaggaag agtatgagta ttcaacattt ccgtgtcgcc    3360
cttattccct ttttgcggc attttgcctt cctgttttg ctcacccaga aacgctggtg    3420
aaagtaaaag atgctgaaga tcagttgggt gcacgagtgg gttacatcga actggatctc    3480
aacagcggta agatccttga gagttttcgc cccgaagaac gttttccaat gatgagcact    3540
tttaaagttc tgctatgtgg cgcggtatta tccgtattg acgccgggca agagcaactc    3600
ggtcgccgca tacactattc tcagaatgac ttggttgagt actcaccagt cacagaaaag    3660
catcttacgg atggcatgac agtaagagaa ttatgcagtg ctgccataac catgagtgat    3720
aacactgcgg ccaacttact tctgacaacg atcggaggac cgaaggagct aaccgctttt    3780
```

```
ttgcacaaca tgggggatca tgtaactcgc cttgatcgtt gggaaccgga gctgaatgaa   3840
gccataccaa acgacgagcg tgacaccacg atgcctgtag caatggcaac aacgttgcgc   3900
aaactattaa ctggcgaact acttactcta gcttcccggc aacaattaat agactggatg   3960
gaggcggata aagttgcagg accacttctg cgctcggccc ttccggctgg ctggtttatt   4020
gctgataaat ctggagccgg tgagcgtggg tctcgcggta tcattgcagc actggggcca   4080
gatggtaagc cctcccgtat cgtagttatc tacacgacgg ggagtcaggc aactatggat   4140
gaacgaaata gacagatcgc tgagataggt gcctcactga ttaagcattg gtaactgtca   4200
gaccaagttt actcatatat actttagatt gatttaaaac ttcatttttta atttaaaagg   4260 atctaggtga agatcctttt tgataatctc atgaccaaaa tcccttaacg tgagttttcg   4320
ttccactgag cgtcagaccc cgtagaaaag atcaaaggat cttcttgaga tccttttttt   4380
ctgcgcgtaa tctgctgctt gcaaacaaaa aaaccaccgc taccagcggt ggtttgtttg   4440
ccggatcaag agctaccaac tcttttttccg aaggtaactg gcttcagcag agcgcagata   4500
ccaaatactg tccttctagt gtagccgtag ttaggccacc acttcaagaa ctctgtagca   4560
ccgcctacat acctcgctct gctaatcctg ttaccagtgg ctgctgccag tggcgataag   4620
tcgtgtctta ccgggttgga ctcaagacga tagttaccgg ataaggcgca gcggtcgggc   4680
tgaacggggg gttcgtgcac acagcccagc ttggagcgaa cgacctacac cgaactgaga   4740
tacctacagc gtgagctatg agaaagcgcc acgcttcccg aagggagaaa ggcggacagg   4800
tatccggtaa gcggcagggt cggaacagga gagcgcacga gggagcttcc agggggaaac   4860
gcctggtatc tttatagtcc tgtcgggttt cgccacctct gacttgagcg tcgatttttg   4920
tgatgctcgt caggggggcg gagcctatgg aaaaacgcca gcaacgcggc ctttttacgg   4980
ttcctggcct tttgctggcc ttttgctcac atgt                                5014
```

<210> SEQ ID NO 69
<211> LENGTH: 5013
<212> TYPE: DNA
<213> ORGANISM: Artificial Sequence
<220> FEATURE:
<223> OTHER INFORMATION: Synthetic

<400> SEQUENCE: 69

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggaggat    540
ccggtggagg aggttctgga ggcggtggaa gtggtggcgg aggtagcggt ggaggaggtt    600
ctatggtgtc taaggaattc atgttcaaaa atcttatttg gctgaaggaa gttgatagca    660
cccaggagcg gcttaaggaa tggaatgtct cctatggcac tgcactcgtc gccgatagac    720
agaccaaagg tagaggcggt ctcggacgga agtggttgag tcaggagggc ggtctttact    780
```

```
tctctttctt gttgaatcca aaagagtttg aaaatttgtt gcaacttcca ctggtcttgg      840
gactctccgt gagcgaggca ctcgaagaga ttacagagat accatttagt ctgaagtggc      900
ccaacgacgt ttattttcag gagaaaaagg tttcaggggt cctttgtgag ctcagtaagg      960
acaagctgat agtgggaatc ggtataaacg tgaatcaaag agagatccct gaagagatca     1020
aggatcgggc cacaacactt tatgaaatca ctggaaagga ttgggacaga aaggaggtct     1080
tgctgaaggt tctcaagcga atttccgaaa atctcaagaa atttaaggaa aaatccttta     1140
aagagttcaa aggaaaaatt gagtcaaaga tgttgtacct tggagaggag gttaaactct     1200
tgggagaagg caagattacc gggaaacttg tgggcctgag tgaaaagggc ggtgctttga     1260
tacttacaga ggaaggcata aaggagatac tgtccggcga atttagcttg cgacggtcag     1320
cttaccctta cgatgtaccg gattacgcaa agcttggata gctagctagc tagctcgaga     1380
atcaacctct ggattacaaa atttgtgaaa gattgactgg tattcttaac tatgttgctc     1440
cttttacgct atgtggatac gctgctttaa tgcctttgta tcatgctatt gcttcccgta     1500
tggctttcat tttctcctcc ttgtataaat cctggttgct gtctctttat gaggagttgt     1560
ggcccgttgt caggcaacgt ggcgtggtgt gcactgtgtt tgctgacgca acccccactg     1620 gttgggcat tgccaccacc tgtcagctcc tttccgggac tttcgctttc ccctcccta      1680 ttgccacggc ggaactcatc gccgcctgcc ttgcccgctg ctggacaggg gctcggctgt     1740
tgggcactga caattccgtg tgttgtcgg ggaaatcatc gtccttcct tggctgctcg       1800 cctatgttgc cacctggatt ctgcgcggga cgtccttctg ctacgtccct tcggccctca     1860
atccagcgga ccttccttcc cgcggcctgc tgccggctct gcggcctctt ccgcgtcttc     1920
gccttcgccc tcagacgagt cggatctccc tttgggccgc ctccccgcat cgataccgct     1980
cgatagatct cgactgtgcc ttctagttgc cagccatctg ttgtttgccc ctcccccgtg     2040
ccttccttga ccctggaagg tgccactccc actgtccttt cctaataaaa tgaggaaatt     2100
gcatcgcatt gtctgagtag gtgtcattct attctggggg gtggggtggg caggacagc     2160 aaggggagg attgggaaga caatagcagg catgctgggg atgcggtggg ctctatggct      2220
cgaggacgct tccgagtacg gtacagggtc gaccacgtgc ggaccgagcg gccgcaggaa     2280
cccctagtga tggagttggc cactccctct ctgcgcgctc gctcgctcac tgaggccggg     2340
cgaccaaagg tcgcccgacg cccgggcttt gcccgggcgg cctcagtgag cgagcgagcg     2400
cgcagctgcc tgcaggggcg cctgatgcgg tattttctcc ttacgcatct gtgcggtatt     2460
tcacaccgca tacgtcaaag caaccatagt acgcgcctg tagcggcgca ttaagcgcgg     2520
cgggtgtggt ggttacgcgc agcgtgaccg ctacacttgc cagcgcccta gcgcccgctc     2580
ctttcgcttt cttcccttcc tttctcgcca cgttcgccgg cttccccgt caagctctaa      2640 atcgggggct cctttaggg ttccgattta gtgctttacg gcacctcgac cccaaaaaac      2700
ttgatttggg tgatggttca cgtagtgggc catcgccctg atagacggtt tttcgccctt     2760
tgacgttgga gtccacgttc tttaatagtg gactcttgtt ccaaactgga acaacactca     2820
accctatctc gggctattct tttgatttat aagggatttt gccgatttcg gcctattggt     2880
taaaaaatga gctgatttaa caaaaattta acgcgaattt taacaaaata ttaacgttta     2940 caatttatg gtgcactctc agtacaatct gctctgatgc cgcatagtta agccagcccc      3000
gacacccgcc aacacccgct gacgcgccct gacgggcttg tctgctcccg gcatccgctt     3060
acagacaagc tgtgaccgtc tccgggagct gcatgtgtca gaggttttca ccgtcatcac     3120
cgaaacgcgc gagacgaaag ggcctcgtga tacgcctatt tttataggtt aatgtcatga     3180
```

```
taataatggt ttcttagacg tcaggtggca cttttcgggg aaatgtgcgc ggaaccccta    3240
tttgtttatt tttctaaata cattcaaata tgtatccgct catgagacaa taaccctgat    3300
aaatgcttca ataatattga aaaggaaga gtatgagtat tcaacatttc cgtgtcgccc    3360
ttattccctt ttttgcggca ttttgccttc ctgttttgc tcacccagaa acgctggtga    3420
aagtaaaaga tgctgaagat cagttgggtg cacgagtggg ttacatcgaa ctggatctca    3480
acagcggtaa gatccttgag agttttcgcc ccgaagaacg ttttccaatg atgagcactt    3540
ttaaagttct gctatgtggc gcggtattat cccgtattga cgccgggcaa gagcaactcg    3600
gtcgccgcat acactattct cagaatgact tggttgagta ctcaccagtc acagaaaagc    3660
atcttacgga tggcatgaca gtaagagaat tatgcagtgc tgccataacc atgagtgata    3720
acactgcggc caacttactt ctgacaacga tcggaggacc gaaggagcta accgcttttt    3780
tgcacaacat gggggatcat gtaactcgcc ttgatcgttg ggaaccggag ctgaatgaag    3840
ccataccaaa cgacgagcgt gacaccacga tgcctgtagc aatggcaaca acgttgcgca    3900
aactattaac tggcgaacta cttactctag cttcccggca acaattaata gactggatgg    3960
aggcggataa agttgcagga ccacttctgc gctcggccct tccggctggc tggtttattg    4020
ctgataaatc tggagccggt gagcgtgggt ctcgcggtat cattgcagca ctggggccag    4080
atggtaagcc ctcccgtatc gtagttatct acacgacggg gagtcaggca actatggatg    4140
aacgaaatag acagatcgct gagataggtg cctcactgat taagcattgg taactgtcag    4200
accaagttta ctcatatata ctttagattg atttaaaact tcatttttaa tttaaaagga    4260
tctaggtgaa gatcctttt gataatctca tgaccaaaat cccttaacgt gagttttcgt    4320
tccactgagc gtcagacccc gtagaaaaga tcaaaggatc ttcttgagat cctttttttc    4380
tgcgcgtaat ctgctgcttg caaacaaaaa aaccaccgct accagcggtg gtttgtttgc    4440
cggatcaaga gctaccaact ctttttccga aggtaactgg cttcagcaga gcgcagatac    4500
caaatactgt ccttctagtg tagccgtagt taggccacca cttcaagaac tctgtagcac    4560
cgcctacata cctcgctctg ctaatcctgt taccagtggc tgctgccagt ggcgataagt    4620
cgtgtcttac cgggttggac tcaagacgat agttaccgga taaggcgcag cggtcgggct    4680
gaacgggggg ttcgtgcaca cagcccagct tggagcgaac gacctacacc gaactgagat    4740
acctacagcg tgagctatga gaaagcgcca cgcttcccga agggagaaag gcggacaggt    4800
atccggtaag cggcagggtc ggaacaggag agcgcacgag ggagcttcca gggggaaacg    4860
cctggtatct ttatagtcct gtcgggtttc gccacctctg acttgagcgt cgatttttgt    4920
gatgctcgtc aggggggcgg agcctatgga aaaacgccag caacgcggcc ttttacggt    4980 tcctggcctt ttgctggcct tttgctcaca tgt                                 5013
```

<210> SEQ ID NO 70
<211> LENGTH: 4167
<212> TYPE: DNA
<213> ORGANISM: Artificial Sequence
<220> FEATURE:
<223> OTHER INFORMATION: Synthetic

<400> SEQUENCE: 70

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
```

```
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggggatc    540
cggtggagga ggttctggag gcggtggaag tggtggcgga ggtagcggtg gaggaggttc    600
tatggtgtct aaggaattca tgttcaaaaa tcttatttgg ctgaaggaag ttgatagcac    660
ccaggagcgg cttaaggaat ggaatgtctc ctatggcact gcactcgtcg ccgatagaca    720
gaccaaaggt agaggcggtc tcggacgaa gtggttgagt caggagggcg gtctttactt    780
ctctttcttg ttgaatccaa aagagtttga aaatttgttg caacttccac tggtcttggg    840
actctccgtg agcgaggcac tcgaagagat tacagagata ccatttagtc tgaagtggcc    900
caacgacgtt tattttcagg agaaaaaggt ttcaggggtc ctttgtgagc tcagtaagga    960
caagctgata gtgggaatcg gtataaacgt gaatcaaaga gagatccctg aagagatcaa   1020
ggatcgggcc acaacacttt atgaaatcac tggaaaggat tgggacagaa aggaggtctt   1080
gctgaaggtt ctcaagcgaa tttccgaaaa tctcaagaaa tttaaggaaa aatcctttaa   1140
agagttcaaa ggaaaaattg agtcaaagat gttgtaccct ggagaggagg ttaaactctt   1200
gggagaaggc aagattaccg ggaaacttgt gggcctgagt gaaaagggcg gtgctttgat   1260
acttacagag gaaggcataa aggagatact gtccggcgaa tttagcttgc gacggtcagc   1320
ttacccttac gatgtaccgg attacgcaaa gcttggatag ctagctagct agctcgagga   1380
cgcttccgag tacggtacag ggtcgaccac gtgcggaccg agcggccgca ggaaccccta   1440
gtgatggagt tggccactcc ctctctgcgc gctcgctcgc tcactgaggc cgggcgacca   1500
aaggtcgccc gacgcccggg ctttgccgg gcggcctcag tgagcgagcg agcgcgcagc   1560
tgcctgcagg ggcgcctgat gcggtatttt ctccttacgc atctgtgcgg tatttcacac   1620
cgcatacgtc aaagcaacca tagtacgcgc cctgtagcgg cgcattaagc gcggcgggtg   1680
tggtggttac gcgcagcgtg accgctacac ttgccagcgc cctagcgccc gctcctttcg   1740
ctttcttccc ttcctttctc gccacgttcg ccggctttcc ccgtcaagct ctaaatcggg   1800
ggctcccttt agggttccga tttagtgctt tacggcacct cgaccccaaa aaacttgatt   1860
tgggtgatgg ttcacgtagt gggccatcgc cctgatagac ggttttttcgc cctttgacgt   1920 tggagtccac gttctttaat agtggactct tgttccaaac tggaacaaca ctcaacccta   1980
tctcgggcta ttcttttgat ttataaggga ttttgccgat ttcggcctat tggttaaaaa   2040
atgagctgat ttaacaaaaa tttaacgcga attttaacaa aatattaacg tttacaattt   2100
tatggtgcac tctcagtaca atctgctctg atgccgcata gttaagccag ccccgacacc   2160
cgccaacacc cgctgacgcg ccctgacggg cttgtctgct cccggcatcc gcttacagac   2220
aagctgtgac cgtctccggg agctgcatgt gtcagaggtt ttcaccgtca tcaccgaaac   2280
gcgcgagacg aaagggcctc gtgatacgcc tatttttata ggttaatgtc atgataataa   2340
tggtttctta gacgtcaggt ggcacttttc ggggaaatgt gcgcggaacc cctatttgtt   2400
tatttttcta aatacattca aatatgtatc cgctcatgag acaataaccc tgataaatgc   2460
ttcaataata ttgaaaaagg aagagtatga gtattcaaca tttccgtgtc gcccttattc   2520 cctttttgc ggcattttgc cttcctgttt ttgctcaccc agaaacgctg gtgaaagtaa   2580
```

| | | |
|---|---|---|
| aagatgctga agatcagttg ggtgcacgag tgggttacat cgaactggat ctcaacagcg | 2640 |
| gtaagatcct tgagagtttt cgccccgaag aacgttttcc aatgatgagc acttttaaag | 2700 |
| ttctgctatg tggcgcggta ttatcccgta ttgacgccgg gcaagagcaa ctcggtcgcc | 2760 |
| gcatacacta ttctcagaat gacttggttg agtactcacc agtcacagaa aagcatctta | 2820 |
| cggatggcat gacagtaaga gaattatgca gtgctgccat aaccatgagt gataacactg | 2880 |
| cggccaactt acttctgaca acgatcgag gaccgaagga gctaaccgct tttttgcaca | 2940 |
| acatggggga tcatgtaact cgccttgatc gttgggaacc ggagctgaat gaagccatac | 3000 |
| caaacgacga gcgtgacacc acgatgcctg tagcaatggc aacaacgttg cgcaaactat | 3060 |
| taactggcga actacttact ctagcttccc ggcaacaatt aatagactgg atggaggcgg | 3120 |
| ataaagttgc aggaccactt ctgcgctcgg cccttccggc tggctggttt attgctgata | 3180 |
| aatctggagc cggtgagcgt gggtctcgcg gtatcattgc agcactgggg ccagatggta | 3240 |
| agccctcccg tatcgtagtt atctacacga cggggagtca ggcaactatg gatgaacgaa | 3300 |
| atagacagat cgctgagata ggtgcctcac tgattaagca ttggtaactg tcagaccaag | 3360 |
| tttactcata tatactttag attgatttaa aacttcattt ttaatttaaa aggatctagg | 3420 |
| tgaagatcct ttttgataat ctcatgacca aaatccctta acgtgagttt cgttccact | 3480 |
| gagcgtcaga ccccgtagaa aagatcaaag gatcttcttg atccttttt tttctgcgcg | 3540 |
| taatctgctg cttgcaaaca aaaaaaccac cgctaccagc ggtggtttgt ttgccggatc | 3600 |
| aagagctacc aactcttttt ccgaaggtaa ctggcttcag cagagcgcag ataccaaata | 3660 |
| ctgtccttct agtgtagccg tagttaggcc accacttcaa gaactctgta gcaccgccta | 3720 |
| catacctcgc tctgctaatc ctgttaccag tggctgctgc cagtggcgat aagtcgtgtc | 3780 |
| ttaccgggtt ggactcaaga cgatagttac cggataaggc gcagcggtcg ggctgaacgg | 3840 |
| ggggttcgtg cacacagccc agcttggagc gaacgaccta caccgaactg agatacctac | 3900 |
| agcgtgagct atgagaaagc gccacgcttc ccgaagggag aaaggcggac aggtatccgg | 3960 |
| taagcggcag ggtcggaaca ggagagcgca cgagggagct tccaggggga aacgcctggt | 4020 |
| atctttatag tcctgtcggg tttcgccacc tctgacttga gcgtcgattt ttgtgatgct | 4080 |
| cgtcaggggg gcggagccta tggaaaaacg ccagcaacgc ggcctttta cggttcctgg | 4140 |
| ccttttgctg gccttttgct cacatgt | 4167 |

<210> SEQ ID NO 71
<211> LENGTH: 4169
<212> TYPE: DNA
<213> ORGANISM: Artificial Sequence
<220> FEATURE:
<223> OTHER INFORMATION: Synthetic

<400> SEQUENCE: 71

| | | |
|---|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |

```
gtacgtttta gagctagaaa tagcaagtta aaataaggct agtccgttat caacttgaaa    480
aagtggcacc gagtcggtgc ttttttcta gagacgcttc cgagtacggt acagggatc     540
cagggtggag gaggttctgg aggcggtgga agtggtggcg gaggtagcgg tggaggaggt    600
tctatggtgt ctaaggaatt catgttcaaa atcttattt ggctgaagga agttgatagc    660
acccaggagc ggcttaagga atggaatgtc tcctatggca ctgcactcgt cgccgataga    720
cagaccaaag gtagaggcgg tctcggacgg aagtggttga gtcaggaggg cggtcttttac   780
ttctctttct tgttgaatcc aaaagagttt gaaaatttgt tgcaacttcc actggtcttg    840
ggactctccg tgagcgaggc actcgaagag attacagaga taccatttag tctgaagtgg    900
cccaacgacg tttattttca ggagaaaaag gtttcagggg tcctttgtga gctcagtaag    960
gacaagctga tagtgggaat cggtataaac gtgaatcaaa gagagatccc tgaagagatc   1020
aaggatcggg ccacaacact ttatgaaatc actggaaagg attgggacag aaaggaggtc   1080
ttgctgaagg ttctcaagcg aatttccgaa atctcaaga aatttaagga aaatcctttt   1140
aaagagttca aggaaaaat tgagtcaaag atgttgtacc ttggagagga ggttaaactc   1200
ttgggagaag gcaagattac cgggaaactt gtgggcctga gtgaaaaggg cggtgctttg   1260
atacttacag aggaaggcat aaaggagata ctgtccggcg aatttagctt gcgacggtca   1320
gcttacccett acgatgtacc ggattacgca aagcttggat agctagctag ctagctcgag   1380
gacgcttccg agtacggtac agggtcgacc acgtgcggac cgagcggccg caggaacccc   1440
tagtgatgga gttggccact ccctctctgc gcgctcgctc gctcactgag gccgggcgac   1500
caaaggtcgc ccgacgcccg ggctttgccc gggcggcctc agtgagcgag cgagcgcgca   1560
gctgcctgca ggggcgcctg atgcggtatt ttctccttac gcatctgtgc ggtattcac    1620
accgcatacg tcaaagcaac catagtacgc gccctgtagc ggcgcattaa gcgcggcggg   1680
tgtggtggtt acgcgcagcg tgaccgctac acttgccagc gccctagcgc ccgctccttt   1740
cgctttcttc ccttccttc tcgccacgtt cgccggcttt cccgtcaag ctctaaatcg    1800
ggggctccct ttagggttcc gatttagtgc tttacggcac ctcgacccca aaaaacttga    1860
tttgggtgat ggttcacgta gtgggccatc gccctgatag acggttttc gccctttgac    1920
gttggagtcc acgttcttta atagtggact cttgttccaa actggaacaa cactcaaccc    1980
tatctcgggc tattcttttg atttataagg gattttgccg atttcggcct attggttaaa    2040
aaatgagctg atttaacaaa aatttaacgc gaatttaac aaaatattaa cgtttacaat    2100
tttatggtgc actctcagta caatctgctc tgatgccgca tagttaagcc agccccgaca    2160
cccgccaaca cccgctgacg cgccctgacg ggcttgtctg ctcccggcat ccgcttacag    2220
acaagctgtg accgtctccg ggagctgcat gtgtcagagg ttttcaccgt catcaccgaa    2280
acgcgcgaga cgaaagggcc tcgtgatacg cctatttta taggttaatg tcatgataat    2340
aatggttttct tagacgtcag gtggcacttt tcggggaaat gtgcgcggaa cccctatttg    2400
tttatttttc taaatacatt caaatatgta tccgctcatg agacaataac cctgataaat    2460
gcttcaataa tattgaaaaa ggaagagtat gagtattcaa catttccgtg tcgcccttat    2520
tccctttttt gcggcatttt gccttcctgt tttgctcac ccagaaacgc tggtgaaagt    2580
aaaagatgct gaagatcagt tgggtgcacg agtgggttac atcgaactgg atctcaacag    2640
cggtaagatc cttgagagtt tcgccccga agaacgtttt ccaatgatga gcacttttaa    2700
agttctgcta tgtggcgcgg tattatcccg tattgacgcc gggcaagagc aactcggtcg    2760
ccgcatacac tattctcaga atgacttggt tgagtactca ccagtcacag aaaagcatct    2820
```

```
tacggatggc atgacagtaa gagaattatg cagtgctgcc ataaccatga gtgataacac    2880
tgcggccaac ttacttctga caacgatcgg aggaccgaag gagctaaccg cttttttgca    2940
caacatgggg gatcatgtaa ctcgccttga tcgttgggaa ccggagctga atgaagccat    3000
accaaacgac gagcgtgaca ccacgatgcc tgtagcaatg gcaacaacgt tgcgcaaact    3060
attaactggc gaactactta ctctagcttc ccggcaacaa ttaatagact ggatggaggc    3120
ggataaagtt gcaggaccac ttctgcgctc ggcccttccg gctggctggt ttattgctga    3180
taaatctgga gccggtgagc gtgggtctcg cggtatcatt gcagcactgg ggccagatgg    3240
taagccctcc cgtatcgtag ttatctacac gacggggagt caggcaacta tggatgaacg    3300
aaatagacag atcgctgaga taggtgcctc actgattaag cattggtaac tgtcagacca    3360
agtttactca tatatacttt agattgattt aaaacttcat ttttaattta aaaggatcta    3420
ggtgaagatc ctttttgata atctcatgac caaaatccct aacgtgagt tttcgttcca     3480 ctgagcgtca gacccgtag aaaagatcaa aggatcttct tgagatcctt ttttttctgcg    3540 cgtaatctgc tgcttgcaaa caaaaaaacc accgctacca gcggtggttt gtttgccgga    3600
tcaagagcta ccaactcttt ttccgaaggt aactggcttc agcagagcgc agataccaaa    3660
tactgtcctt ctagtgtagc cgtagttagg ccaccacttc aagaactctg tagcaccgcc    3720
tacatacctc gctctgctaa tcctgttacc agtggctgct gccagtggcg ataagtcgtg    3780
tcttaccggg ttggactcaa gacgatagtt accggataag gcgcagcggt cgggctgaac    3840 gggggggttcg tgcacacagc ccagcttgga gcgaacgacc tacaccgaac tgagatacct    3900
acagcgtgag ctatgagaaa gcgccacgct tcccgaaggg agaaaggcgg acaggtatcc    3960
ggtaagcggc agggtcggaa caggagagcg cacgagggag cttccagggg gaaacgcctg    4020
gtatctttat agtcctgtcg ggtttcgcca cctctgactt gagcgtcgat ttttgtgatg    4080
ctcgtcaggg gggcggagcc tatgaaaaaa cgccagcaac gcggcctttt tacggttcct    4140
ggccttttgc tggccttttg ctcacatgt                                      4169
```

<210> SEQ ID NO 72
<211> LENGTH: 4168
<212> TYPE: DNA
<213> ORGANISM: Artificial Sequence
<220> FEATURE:
<223> OTHER INFORMATION: Synthetic

<400> SEQUENCE: 72

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggaggat    540
ccggtggagg aggttctgga ggcggtggaa gtggtggcgg aggtagcggt ggaggaggtt    600
ctatggtgtc taaggaattc atgttcaaaa atcttatttg gctgaaggaa gttgatagca    660
```

```
cccaggagcg gcttaaggaa tggaatgtct cctatggcac tgcactcgtc gccgatagac    720
agaccaaagg tagaggcggt ctcggacgga agtggttgag tcaggagggc ggtctttact    780 tctcttttctt gttgaatcca aaagagtttg aaaatttgtt gcaacttcca ctggtcttgg    840
gactctccgt gagcgaggca ctcgaagaga ttacagagat accatttagt ctgaagtggc    900
ccaacgacgt ttattttcag gagaaaaagg tttcaggggt cctttgtgag ctcagtaagg    960
acaagctgat agtgggaatc ggtataaacg tgaatcaaag agagatccct gaagagatca   1020
aggatcgggc cacaacactt tatgaaatca ctggaaagga ttgggacaga aaggaggtct   1080
tgctgaaggt tctcaagcga atttccgaaa atctcaagaa atttaaggaa aaatcctttta   1140 aagagttcaa aggaaaaatt gagtcaaaga tgttgtacct tggagaggag gttaaactct   1200
tgggagaagg caagattacc gggaaacttg tgggcctgag tgaaaagggc ggtgctttga   1260
tacttacaga ggaaggcata aaggagatac tgtccggcga atttagcttg cgacggtcag   1320 cttacccta cgatgtaccg gattacgcaa agcttggata gctagctagc tagctcgagg    1380
acgcttccga gtacggtaca gggtcgacca cgtgcggacc gagcggccgc aggaacccct   1440
agtgatggag ttggccactc cctctctgcg cgctcgctcg ctcactgagg ccgggcgacc   1500
aaaggtcgcc cgacgcccgg gctttgcccg ggcggcctca gtgagcgagc gagcgcgcag   1560
ctgcctgcag gggcgcctga tgcggtattt tctccttacg catctgtgcg gtatttcaca   1620
ccgcatacgt caaagcaacc atagtacgcg ccctgtagcg gcgcattaag cgcggcgggt   1680
gtggtggtta cgcgcagcgt gaccgctaca cttgccagcg ccctagcgcc cgctccttc    1740 gctttcttcc cttcctttct cgccacgttc gccggctttc cccgtcaagc tctaaatcgg   1800 gggctcccctt tagggttccg atttagtgct ttacggcacc tcgaccccaa aaaacttgat   1860
ttgggtgatg gttcacgtag tgggccatcg ccctgataga cggttttttcg ccctttgacg   1920 ttggagtcca cgttctttaa tagtggactc ttgttccaaa ctggaacaac actcaaccct   1980
atctcgggct attcttttga tttataaggg attttgccga tttcggccta ttggttaaaa   2040
aatgagctga tttaacaaaa attttaacgcg aattttaaca aaatattaac gtttacaatt   2100
ttatggtgca ctctcagtac aatctgctct gatgccgcat agttaagcca gccccgacac   2160
ccgccaacac ccgctgacgc gccctgacgg gcttgtctgc tcccggcatc cgcttacaga   2220
caagctgtga ccgtctccgg gagctgcatg tgtcagaggt tttcaccgtc atcaccgaaa   2280
cgcgcgagac gaaagggcct cgtgatacgc ctattttttat aggttaatgt catgataata   2340
atggtttctt agacgtcagg tggcacttttt cggggaaatg tgcgcggaac cctatttgt    2400 ttattttttct aaatacattc aaatatgtat ccgctcatga acaataaacc ctgataaatg   2460
cttcaataat attgaaaaag gaagagtatg agtattcaac atttccgtgt cgcccttatt   2520 ccctttttttg cggcattttg ccttcctgtt tttgctcacc cagaaacgct ggtgaaagta   2580
aaagatgctg aagatcagtt gggtgcacga gtgggttaca tcgaactgga tctcaacagc   2640
ggtaagatcc ttgagagttt cgccccgaa gaacgttttc caatgatgag cacttttaaa    2700
gttctgctat gtggcgcggt attatcccgt attgacgccg ggcaagagca actcggtcgc   2760
cgcatacact attctcagaa tgacttggtt gagtactcac cagtcacaga aaagcatctt   2820
acggatggca tgacagtaag agaattatgc agtgctgcca taaccatgag tgataacact   2880
gcggccaact tacttctgac aacgatcgga ggaccgaagg agctaaccgc ttttttgcac   2940
aacatggggg atcatgtaac tcgccttgat cgttgggaac cggagctgaa tgaagccata   3000
ccaaacgacg agcgtgacac cacgatgcct gtagcaatgg caacaacgtt gcgcaaacta   3060
```

| | |
|---|---|
| ttaactggcg aactacttac tctagcttcc cggcaacaat taatagactg gatggaggcg | 3120 |
| gataaagttg caggaccact tctgcgctcg gcccttccgg ctggctggtt tattgctgat | 3180 |
| aaatctggag ccggtgagcg tgggtctcgc ggtatcattg cagcactggg gccagatggt | 3240 |
| aagccctccc gtatcgtagt tatctacacg acggggagtc aggcaactat ggatgaacga | 3300 |
| aatagacaga tcgctgagat aggtgcctca ctgattaagc attggtaact gtcagaccaa | 3360 |
| gtttactcat atatacttta gattgattta aaacttcatt tttaatttaa aaggatctag | 3420 |
| gtgaagatcc ttttttgataa tctcatgacc aaaatccctt aacgtgagtt ttcgttccac | 3480 |
| tgagcgtcag accccgtaga aaagatcaaa ggatcttctt gagatccttt ttttctgcgc | 3540 |
| gtaatctgct gcttgcaaac aaaaaaacca ccgctaccag cggtggtttg tttgccggat | 3600 |
| caagagctac caactctttt tccgaaggta actggcttca gcagagcgca gataccaaat | 3660 |
| actgtccttc tagtgtagcc gtagttaggc caccacttca agaactctgt agcaccgcct | 3720 |
| acatacctcg ctctgctaat cctgttacca gtggctgctg ccagtggcga taagtcgtgt | 3780 |
| cttaccgggt tggactcaag acgatagtta ccggataagg cgcagcggtc gggctgaacg | 3840 |
| gggggttcgt gcacacagcc cagcttggag cgaacgacct acaccgaact gagataccta | 3900 |
| cagcgtgagc tatgagaaag cgccacgctt cccgaaggga gaaaggcgga caggtatccg | 3960 |
| gtaagcggca gggtcggaac aggagagcgc acgagggagc ttccaggggg aaacgcctgg | 4020 |
| tatctttata gtcctgtcgg gtttcgccac ctctgacttg agcgtcgatt tttgtgatgc | 4080 |
| tcgtcagggg ggcggagcct atggaaaaac gccagcaacg cggccttttt acggttcctg | 4140 |
| gccttttgct ggccttttgc tcacatgt | 4168 |

<210> SEQ ID NO 73
<211> LENGTH: 4146
<212> TYPE: DNA
<213> ORGANISM: Artificial Sequence
<220> FEATURE:
<223> OTHER INFORMATION: Synthetic

<400> SEQUENCE: 73

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggggatc | 540 |
| cggtggagga ggttctggag gcggtggaag tggtggcgga ggtagcggtg gaggaggttc | 600 |
| tatggtgtct aaggaattca tggtgagcaa gggcgaggag gataacatgg ccatcatcaa | 660 |
| ggagttcatg cgcttcaagg tgcacatgga gggctccgtg aacggccacg agttcgagat | 720 |
| cgagggcgag ggcgagggcc gcccctacga gggcacccag accgccaagc tgaaggtgac | 780 |
| caagggtggc cccctgccct cgcctggga catcctgtcc cctcagttca tgtacgctc | 840 |
| caaggcctac gtgaagcacc ccgccgacat ccccgactac ttgaagctgt ccttccccga | 900 |

```
gggcttcaag tgggagcgcg tgatgaactt cgaggacggc ggcgtggtga ccgtgaccca    960
ggactcctcc ctgcaggacg gcgagttcat ctacaaggtg aagctgcgcg caccaacttt   1020
cccctccgac ggccccgtaa tgcagaagaa gaccatgggc tgggaggcct cctccgagcg   1080
gatgtacccc gaggacggcg ccctgaaggg cgagatcaag cagaggctga agctgaagga   1140
cggcggccac tacgacgctg aggtcaagac cacctacaag gccaagaagc ccgtgcagct   1200
gcccggcgcc tacaacgtca acatcaagtt ggacatcacc tcccacaacg aggactacac   1260
catcgtggaa cagtacgaac gcgccgaggg ccgccactcc accggcggca tggacgagct   1320
gtacaagaag cttggatagc tagctagcta gctcgaggac gcttccgagt acggtacagg   1380
gtcgaccacg tgcggaccga gcggccgcag gaaccctag tgatggagtt ggccactccc    1440
tctctgcgcg ctcgctcgct cactgaggcc gggcgaccaa aggtcgcccg acgcccgggc   1500
tttgcccggg cggcctcagt gagcgagcga gcgcgcagct gcctgcaggg gcgcctgatg   1560
cggtattttc tccttacgca tctgtgcggt atttcacacc gcatacgtca aagcaaccat   1620
agtacgcgcc ctgtagcggc gcattaagcg cggcgggtgt ggtggttacg cgcagcgtga   1680
ccgctacact tgccagcgcc ctagcgcccg ctcctttcgc tttcttccct tcctttctcg   1740
ccacgttcgc cggctttccc cgtcaagctc taaatcgggg gctcccttta gggttccgat   1800
ttagtgcttt acggcacctc gaccccaaaa aacttgattt gggtgatggt tcacgtagtg   1860
ggccatcgcc ctgatagacg gttttttcgcc cttgacgtt ggagtccacg ttctttaata   1920
gtggactctt gttccaaact ggaacaacac tcaaccctat ctcgggctat tcttttgatt   1980
tataagggat tttgccgatt tcggcctatt ggttaaaaaa tgagctgatt taacaaaaat   2040
ttaacgcgaa ttttaacaaa atattaacgt ttacaatttt atggtgcact ctcagtacaa   2100
tctgctctga tgccgcatag ttaagccagc cccgacaccc gccaacaccc gctgacgcgc   2160
cctgacgggc ttgtctgctc ccggcatccg cttacagaca agctgtgacc gtctccggga   2220
gctgcatgtg tcagaggttt tcaccgtcat caccgaaacg cgcagacga aagggcctcg   2280
tgatacgcct atttttatag gttaatgtca tgataataat ggtttcttag acgtcaggtg   2340
gcacttttcg gggaaatgtg cgcggaaccc ctatttgttt attttctaa atacattcaa   2400
atatgtatcc gctcatgaga caataacct gataaatgct tcaataatat tgaaaagga   2460
agagtatgag tattcaacat ttccgtgtcg cccttattcc cttttttgcg cattttgcc   2520
ttcctgtttt tgctcaccca gaaacgctgg tgaaagtaaa agatgctgaa gatcagttgg   2580
gtgcacgagt gggttacatc gaactggatc tcaacagcgg taagatcctt gagagttttc   2640
gccccgaaga acgttttcca atgatgagca cttttaaagt tctgctatgt ggcgcggtat   2700
tatcccgtat tgacgccggg caagagcaac tcggtcgccg catacactat tctcagaatg   2760
acttggttga gtactcacca gtcacagaaa agcatcttac ggatggcatg acagtaagag   2820
aattatgcag tgctgccata accatgagtg ataacactgc ggccaactta cttctgacaa   2880
cgatcggagg accgaaggag ctaaccgctt ttttgcacaa catgggggat catgtaactc   2940
gccttgatcg ttgggaaccg gagctgaatg aagccatacc aaacgacgag cgtgacacca   3000
cgatgcctgt agcaatggca acaacgttgc gcaaactatt aactggcgaa ctacttactc   3060
tagcttcccg gcaacaatta atagactgga tggaggcgga taaagttgca ggaccacttc   3120
tgcgctcggc ccttccggct ggctggttta ttgctgataa atctggagcc ggtgagcgtg   3180
ggtctcgcgg tatcattgca gcactggggc cagatggtaa gccctcccgt atcgtagtta   3240
tctacacgac ggggagtcag gcaactatgg atgaacgaaa tagacagatc gctgagatag   3300
```

```
gtgcctcact gattaagcat tggtaactgt cagaccaagt ttactcatat atactttaga    3360
ttgatttaaa acttcatttt taatttaaaa ggatctaggt gaagatcctt tttgataatc    3420
tcatgaccaa aatcccttaa cgtgagtttt cgttccactg agcgtcagac cccgtagaaa    3480
agatcaaagg atcttcttga gatccttttt ttctgcgcgt aatctgctgc ttgcaaacaa    3540
aaaaaccacc gctaccagcg gtggtttgtt tgccggatca agagctacca actctttttc    3600
cgaaggtaac tggcttcagc agagcgcaga taccaaatac tgtccttcta gtgtagccgt    3660
agttaggcca ccacttcaag aactctgtag caccgcctac atacctcgct ctgctaatcc    3720
tgttaccagt ggctgctgcc agtggcgata agtcgtgtct taccgggttg gactcaagac    3780
gatagttacc ggataaggcg cagcggtcgg gctgaacggg gggttcgtgc acacagccca    3840
gcttggagcg aacgacctac accgaactga gatacctaca gcgtgagcta tgagaaagcg    3900
ccacgcttcc cgaagggaga aaggcggaca ggtatccggt aagcggcagg gtcggaacag    3960
gagagcgcac gagggagctt ccaggggaaa acgcctggta tctttatagt cctgtcgggt    4020
ttcgccacct ctgacttgag cgtcgatttt tgtgatgctc gtcaggggg cggagcctat    4080 ggaaaaacgc cagcaacgcg gcctttttac ggttcctggc cttttgctgg ccttttgctc    4140
acatgt                                                              4146
```

<210> SEQ ID NO 74
<211> LENGTH: 4148
<212> TYPE: DNA
<213> ORGANISM: Artificial Sequence
<220> FEATURE:
<223> OTHER INFORMATION: Synthetic

<400> SEQUENCE: 74

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggggatc    540
cagggtggag gaggttctgg aggcggtgga agtggtggcg gaggtagcgg tggaggaggt    600
tctatggtgt ctaaggaatt catggtgagc aagggcgagg aggataacat ggccatcatc    660
aaggagttca tgcgcttcaa ggtgcacatg gagggctccg tgaacggcca cgagttcgag    720
atcgagggcg agggcgaggg ccgcccctac gagggcaccc agaccgccaa gctgaaggtg    780
accaagggtg gcccctgcc cttcgcctgg gacatcctgt cccctcagtt catgtacggc    840
tccaaggcct acgtgaagca ccccgccgac atccccgact acttgaagct gtccttcccc    900
gagggcttca gtgggagcg cgtgatgaac ttcgaggacg gcggcgtggt gaccgtgacc    960
caggactcct ccctgcagga cggcgagttc atctacaagg tgaagctgcg cggcaccaac    1020
ttcccctccg acgccccgt aatgcagaag aagaccatgg gctgggaggc ctcctccgag    1080
cggatgtacc ccgaggacgg cgccctgaag ggcgagatca gcagaggct gaagctgaag    1140
```

| | |
|---|---|
| gacggcggcc actacgacgc tgaggtcaag accacctaca aggccaagaa gcccgtgcag | 1200 |
| ctgcccggcg cctacaacgt caacatcaag ttggacatca cctcccacaa cgaggactac | 1260 |
| accatcgtgg aacagtacga acgcgccgag ggccgccact ccaccggcgg catggacgag | 1320 |
| ctgtacaaga agcttggata gctagctagc tagctcgagg acgcttccga gtacggtaca | 1380 |
| gggtcgacca cgtgcggacc gagcggccgc aggaacccct agtgatggag ttggccactc | 1440 |
| cctctctgcg cgctcgctcg ctcactgagg ccgggcgacc aaaggtcgcc cgacgcccgg | 1500 |
| gctttgcccg ggcggcctca gtgagcgagc gagcgcgcag ctgcctgcag ggcgcctga | 1560 |
| tgcggtatttt ctccttacg catctgtgcg gtatttcaca ccgcatacgt caaagcaacc | 1620 |
| atagtacgcg ccctgtagcg gcgcattaag cgcggcgggt gtggtggtta cgcgcagcgt | 1680 |
| gaccgctaca cttgccagcg ccctagcgcc cgctcctttc gctttcttcc cttcctttct | 1740 |
| cgccacgttc gccggctttc cccgtcaagc tctaaatcgg gggctccctt tagggttccg | 1800 |
| atttagtgct ttacggcacc tcgacccccaa aaaacttgat ttgggtgatg gttcacgtag | 1860 |
| tgggccatcg ccctgataga cggttttttcg cccttttgacg ttggagtcca cgttctttaa | 1920 |
| tagtggactc ttgttccaaa ctggaacaac actcaaccct atctcgggct attcttttga | 1980 |
| tttataaggg atttttgccga tttcggccta ttggttaaaa aatgagctga tttaacaaaa | 2040 |
| atttaacgcg aattttaaca aaatattaac gtttacaatt ttatggtgca ctctcagtac | 2100 |
| aatctgctct gatgccgcat agttaagcca gccccgacac ccgccaacac ccgctgacgc | 2160 |
| gccctgacgg gcttgtctgc tcccggcatc cgcttacaga caagctgtga ccgtctccgg | 2220 |
| gagctgcatg tgtcagaggt tttcaccgtc atcaccgaaa cgcgcgagac gaaagggcct | 2280 |
| cgtgatacgc ctatttttat aggttaatgt catgataata atggtttctt agacgtcagg | 2340 |
| tggcactttt cggggaaatg tgcgcggaac ccctatttgt ttatttttct aaatacattc | 2400 |
| aaatatgtat ccgctcatga dacaataacc ctgataaatg cttcaataat attgaaaaag | 2460 |
| gaagagtatg agtattcaac atttccgtgt cgcccttatt ccctttttttg cggcattttg | 2520 |
| ccttcctgtt tttgctcacc cagaaacgct ggtgaaagta aaagatgctg aagatcagtt | 2580 |
| gggtgcacga gtgggttaca tcgaactgga tctcaacagc ggtaagatcc ttgagagttt | 2640 |
| tcgccccgaa gaacgttttc caatgatgag cacttttaaa gttctgctat gtggcgcggt | 2700 |
| attatcccgt attgacgccg ggcaagagca actcggtcgc cgcatacact attctcagaa | 2760 |
| tgacttggtt gagtactcac cagtcacaga aaagcatctt acggatggca tgacagtaag | 2820 |
| agaattatgc agtgctgcca taaccatgag tgataacact gcggccaact tacttctgac | 2880 |
| aacgatcgga ggaccgaagg agctaaccgc ttttttgcac aacatggggg atcatgtaac | 2940 |
| tcgccttgat cgttgggaac cggagctgaa tgaagccata ccaaacgacg agcgtgacac | 3000 |
| cacgatgcct gtagcaatgg caacaacgtt gcgcaaacta ttaactggcg aactacttac | 3060 |
| tctagcttcc cggcaacaat taatagactg gatggaggcg gataaagttg caggaccact | 3120 |
| tctgcgctcg gcccttccgg ctggctggtt tattgctgat aaatctggag ccggtgagcg | 3180 |
| tgggtctcgc ggtatcattg cagcactggg gccagatggt aagccctccc gtatcgtagt | 3240 |
| tatctacacg acggggagtc aggcaactat ggatgaacga atagacaga tcgctgagat | 3300 |
| aggtgcctca ctgattaagc attggtaact gtcagaccaa gtttactcat atatacttta | 3360 |
| gattgattta aaacttcatt tttaatttaa aaggatctag gtgaagatcc ttttttgataa | 3420 |
| tctcatgacc aaaatccctt aacgtgagtt ttcgttccac tgagcgtcag accccgtaga | 3480 |
| aaagatcaaa ggatcttctt gagatccttt ttttctgcgc gtaatctgct gcttgcaaac | 3540 |

| | |
|---|---|
| aaaaaaaacca ccgctaccag cggtggtttg tttgccggat caagagctac caactcttt | 3600 |
| tccgaaggta actggcttca gcagagcgca gataccaaat actgtccttc tagtgtagcc | 3660 |
| gtagttaggc caccacttca agaactctgt agcaccgcct acatacctcg ctctgctaat | 3720 |
| cctgttacca gtggctgctg ccagtggcga taagtcgtgt cttaccgggt tggactcaag | 3780 |
| acgatagtta ccggataagg cgcagcggtc gggctgaacg gggggttcgt gcacacagcc | 3840 |
| cagcttggag cgaacgacct acaccgaact gagataccta cagcgtgagc tatgagaaag | 3900 |
| cgccacgctt cccgaaggga gaaaggcgga caggtatccg gtaagcggca gggtcggaac | 3960 |
| aggagagcgc acgagggagc ttccaggggg aaacgcctgg tatctttata gtcctgtcgg | 4020 |
| gtttcgccac ctctgacttg agcgtcgatt tttgtgatgc tcgtcagggg ggcggagcct | 4080 |
| atggaaaaac gccagcaacg cggccttttt acggttcctg gccttttgct ggccttttgc | 4140 |
| tcacatgt | 4148 |

<210> SEQ ID NO 75
<211> LENGTH: 4147
<212> TYPE: DNA
<213> ORGANISM: Artificial Sequence
<220> FEATURE:
<223> OTHER INFORMATION: Synthetic

<400> SEQUENCE: 75

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta taatttctt gggtagtttg | 300 |
| cagtttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggaggat | 540 |
| ccggtggagg aggttctgga ggcggtggaa gtggtggcgg aggtagcggt ggaggaggtt | 600 |
| ctatggtgtc taaggaattc atggtgagca agggcgagga ggataacatg gccatcatca | 660 |
| aggagttcat gcgcttcaag gtgcacatgg agggctccgt gaacggccac gagttcgaga | 720 |
| tcgagggcga gggcgagggc cgcccctacg agggcaccca gaccgccaag ctgaaggtga | 780 |
| ccaagggtgg ccccctgccc ttcgcctggg acatcctgtc ccctcagttc atgtacggct | 840 |
| ccaaggccta cgtgaagcac cccgccgaca tccccgacta cttgaagctg tccttccccg | 900 |
| agggcttcaa gtgggagcgc gtgatgaact cgaggacgg cggcgtggtg accgtgaccc | 960 |
| aggactcctc cctgcaggac ggcgagttca tctacaaggt gaagctgcgc ggcaccaact | 1020 |
| tcccctccga cggccccgta atgcagaaga gaccatggg ctgggaggcc tcctccgagc | 1080 |
| ggatgtaccc cgaggacggc gccctgaagg gcgagatcaa gcagaggctg aagctgaagg | 1140 |
| acggcggcca ctacgacgct gaggtcaaga ccacctacaa ggccaagaag cccgtgcagc | 1200 |
| tgcccggcgc ctacaacgtc aacatcaagt tggacatcac ctcccacaac gaggactaca | 1260 |
| ccatcgtgga acagtacgaa cgcgccgagg gccgccactc caccggcggc atggacgagc | 1320 |
| tgtacaagaa gcttggatag ctagctagct agctcgagga cgcttccgag tacggtacag | 1380 |

```
ggtcgaccac gtgcggaccg agcggccgca ggaaccccta gtgatggagt tggccactcc    1440
ctctctgcgc gctcgctcgc tcactgaggc cgggcgacca aggtcgccc gacgcccggg    1500 ctttgcccgg gcggcctcag tgagcgagcg agcgcgcagc tgcctgcagg ggcgcctgat    1560
gcggtatttt ctccttacgc atctgtgcgg tatttcacac cgcatacgtc aaagcaacca    1620
tagtacgcgc cctgtagcgg cgcattaagc gcggcgggtg tggtggttac gcgcagcgtg    1680
accgctacac ttgccagcgc cctagcgccc gctcctttcg cttcttccc ttcctttctc    1740 gccacgttcg ccggctttcc ccgtcaagct ctaaatcggg ggctcccttt agggttccga    1800
tttagtgctt tacggcacct cgaccccaaa aaacttgatt tgggtgatgg ttcacgtagt    1860
gggccatcgc cctgatagac ggttttttcgc cctttgacgt tggagtccac gttctttaat    1920
agtggactct tgttccaaac tggaacaaca ctcaaccccta tctcgggcta ttcttttgat    1980
ttataaggga ttttgccgat tcggcctat tggttaaaaa atgagctgat ttaacaaaaa    2040
tttaacgcga attttaacaa aatattaacg tttacaattt tatggtgcac tctcagtaca    2100
atctgctctg atgccgcata gttaagccag ccccgacacc cgccaacacc cgctgacgcg    2160
ccctgacggg cttgtctgct cccggcatcc gcttacagac aagctgtgac cgtctccggg    2220
agctgcatgt gtcagaggtt ttcaccgtca tcaccgaaac gcgcgagacg aaagggcctc    2280
gtgatacgcc tattttttata ggttaatgtc atgataataa tggtttctta gacgtcaggt    2340
ggcacttttc ggggaaatgt gcgcggaacc cctattttgtt tattttttcta aatacattca    2400 aatatgtatc cgctcatgag acaataaccc tgataaatgc ttcaataata ttgaaaaagg    2460
aagagtatga gtattcaaca tttccgtgtc gcccttattc cctttttttgc ggcatttttgc    2520 cttcctgttt ttgctcaccc agaaacgctg gtgaaagtaa aagatgctga agatcagttg    2580
ggtgcacgag tgggttacat cgaactggat ctcaacagcg gtaagatcct tgagagtttt    2640
cgccccgaag aacgttttcc aatgatgagc acttttaaag ttctgctatg tggcgcggta    2700
ttatcccgta ttgacgccgg gcaagagcaa ctcggtcgcc gcatacacta ttctcagaat    2760
gacttggttg agtactcacc agtcacagaa aagcatctta cggatggcat gacagtaaga    2820
gaattatgca gtgctgccat aaccatgagt gataacactg cggccaactt acttctgaca    2880
acgatcggag gaccgaagga gctaaccgct ttttttgcaca acatggggga tcatgtaact    2940
cgccttgatc gttgggaacc ggagctgaat gaagccatac caaacgacga gcgtgacacc    3000
acgatgcctg tagcaatggc aacaacgttg cgcaaactat taactggcga actacttact    3060
ctagcttccc ggcaacaatt aatagactgg atggaggcgg ataaagttgc aggaccactt    3120
ctgcgctcgg cccttccggc tggctggttt attgctgata aatctggagc cggtgagcgt    3180
gggtctcgcg gtatcattgc agcactgggg ccagatggta agccctcccg tatcgtagtt    3240
atctacacga cggggagtca ggcaactatg gatgaacgaa atagacagat cgctgagata    3300
ggtgcctcac tgattaagca ttggtaactg tcagaccaag tttactcata tatactttag    3360
attgatttaa aacttcattt ttaatttaaa aggatctagg tgaagatcct ttttgataat    3420
ctcatgacca aaatccctta acgtgagttt tcgttccact gagcgtcaga ccccgtagaa    3480
aagatcaaag gatcttcttg agatcctttt tttctgcgcg taatctgctg cttgcaaaca    3540
aaaaaaccac cgctaccagc ggtggtttgt ttgccggatc aagagctacc aactctttttt    3600 ccgaaggtaa ctggcttcag cagagcgcag ataccaaata ctgtccttct agtgtagccg    3660
tagttaggcc accacttcaa gaactctgta gcaccgccta catacctcgc tctgctaatc    3720
ctgttaccag tggctgctgc cagtggcgat aagtcgtgtc ttaccgggtt ggactcaaga    3780
```

```
cgatagttac cggataaggc gcagcggtcg ggctgaacgg ggggttcgtg cacacagccc    3840
agcttggagc gaacgaccta caccgaactg agatacctac agcgtgagct atgagaaagc    3900
gccacgcttc ccgaagggag aaaggcggac aggtatccgg taagcggcag ggtcggaaca    3960
ggagagcgca cgagggagct tccagggga aacgcctggt atctttatag tcctgtcggg    4020
tttcgccacc tctgacttga gcgtcgattt ttgtgatgct cgtcaggggg cggagccta    4080 tggaaaaacg ccagcaacgc ggcctttta cggttcctgg cttttgctg gcctttgct    4140 cacatgt                                                              4147

<210> SEQ ID NO 76
<211> LENGTH: 4155
<212> TYPE: DNA
<213> ORGANISM: Artificial Sequence
<220> FEATURE:
<223> OTHER INFORMATION: Synthetic

<400> SEQUENCE: 76
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aggacgaaa caccgacgct tccgagtacg     420
gtacgtttta gagctagaaa tagcaagtta aaataaggct agtccgttat caacttgaaa     480
aagtggcacc gagtcggtgc tttttttcta gagacgcttc cgagtacggt acaggggatc     540
cggtggagga ggttctggag gcggtggaag tggtggcgga ggtagcggtg gaggaggttc     600
tatggtgtct aaggaattca tggtgagcaa gggcgaggag ctgttcaccg gggtggtgcc     660
catcctggtc gagctggacg gcgacgtaaa cggccacaag ttcagcgtgt ccggcgaggg     720
cgagggcgat gccacctacg gcaagctgac cctgaagttc atctgcacca ccggcaagct     780
gcccgtgccc tggcccaccc tcgtgaccac cctgacctac ggcgtgcagt gcttcagccg     840
ctaccccgac cacatgaagc agcacgactt cttcaagtcc gccatgcccg aaggctacgt     900
ccaggagcgc accatcttct tcaaggacga cggcaactac aagacccgcg ccgaggtgaa     960
gttcgagggc gacacccctg tgaaccgcat cgagctgaag ggcatcgact tcaaggagga    1020
cggcaacatc ctggggcaca agctggagta caactacaac agccacaacg tctatatcat    1080
ggccgacaag cagaagaacg gcatcaaggt gaacttcaag atccgccaca acatcgagga    1140
cggcagcgtg cagctcgccg accactacca gcagaacacc cccatcggcg acggccccgt    1200
gctgctgccc gacaaccact acctgagcac ccagtccaag ctgagcaaag ccccaacga    1260 gaagcgcgat cacatggtcc tgctggagtt cgtgaccgcc gccgggatca ctctcggcat    1320
ggacgagctg tacaagaagc ttggatagct agctagctag ctcgaggacg cttccgagta    1380
cggtacaggg tcgaccacgt gcggaccgag cggccgcagg aaccctagt gatggagttg    1440 gccactccct ctctgcgcgc tcgctcgctc actgaggccg ggcgaccaaa ggtcgcccga    1500
cgccggggct tgccgggc ggcctcagtg agcgagcgag cgcgcagctg cctgcagggg    1560
cgcctgatgc ggtattttct ccttacgcat ctgtgcggta tttcacaccg catacgtcaa    1620
```

```
agcaaccata gtacgcgccc tgtagcggcg cattaagcgc ggcgggtgtg gtggttacgc   1680
gcagcgtgac cgctacactt gccagcgccc tagcgcccgc tcctttcgct ttcttccctt   1740
cctttctcgc cacgttcgcc ggctttcccc gtcaagctct aaatcggggg ctcccttag    1800
ggttccgatt tagtgcttta cggcacctcg accccaaaaa acttgatttg ggtgatggtt    1860
cacgtagtgg gccatcgccc tgatagacgg ttttttcgccc tttgacgttg gagtccacgt   1920
tctttaatag tggactcttg ttccaaactg gaacaacact caaccctatc tcggctatt    1980
cttttgattt ataagggatt ttgccgattt cggcctattg gttaaaaaat gagctgattt    2040
aacaaaaatt taacgcgaat tttaacaaaa tattaacgtt tacaatttta tggtgcactc    2100
tcagtacaat ctgctctgat gccgcatagt taagccagcc ccgacacccg ccaacacccg    2160
ctgacgcgcc ctgacgggct tgtctgctcc cggcatccgc ttacagacaa gctgtgaccg    2220
tctccgggag ctgcatgtgt cagaggtttt caccgtcatc accgaaacgc gcgagacgaa    2280
agggcctcgt gatacgccta ttttataggg ttaatgtcat gataataatg gtttcttaga    2340
cgtcaggtgg cacttttcgg ggaaatgtgc gcggaacccc tatttgttta ttttttctaaa   2400
tacattcaaa tatgtatccg ctcatgagac aataaccctg ataaatgctt caataatatt    2460
gaaaaaggaa gagtatgagt attcaacatt tccgtgtcgc ccttattccc ttttttgcgg    2520
cattttgcct tcctgttttt gctcacccag aaacgctggt gaaagtaaaa gatgctgaag    2580
atcagttggg tgcacgagtg ggttacatcg aactggatct caacagcggt aagatccttg    2640
agagttttcg ccccgaagaa cgttttccaa tgatgagcac ttttaaagtt ctgctatgtg    2700
gcgcggtatt atcccgtatt gacgccgggc aagagcaact cggtcgccgc atacactatt    2760
ctcagaatga cttggttgag tactcaccag tcacagaaaa gcatcttacg gatggcatga    2820
cagtaagaga attatgcagt gctgccataa ccatgagtga taacactgcg gccaacttac    2880
ttctgacaac gatcggagga ccgaaggagc taaccgcttt tttgcacaac atgggggatc    2940
atgtaactcg ccttgatcgt tgggaaccgg agctgaatga agccatacca aacgacgagc    3000
gtgacaccac gatgcctgta gcaatggcaa caacgttgcg caaactatta actggcgaac    3060
tacttactct agcttcccgg caacaattaa tagactggat ggaggcggat aaagttgcag    3120
gaccacttct gcgctcggcc cttccggctg gctggtttat tgctgataaa tctggagccg    3180
gtgagcgtgg gtctcgcggt atcattgcag cactggggcc agatggtaag ccctcccgta    3240
tcgtagttat ctacacgacg gggagtcagg caactatgga tgaacgaaat agacagatcg    3300
ctgagatagg tgcctcactg attaagcatt ggtaactgtc agaccaagtt tactcatata    3360
tactttagat tgatttaaaa cttcattttt aatttaaaag gatctaggtg aagatccttt    3420
ttgataatct catgaccaaa atcccttaac gtgagttttc gttccactga gcgtcagacc    3480
ccgtagaaaa gatcaaagga tcttcttgag atcctttttt tctgcgcgta atctgctgct    3540
tgcaaacaaa aaaaccaccg ctaccagcgg tggtttgttt gccggatcaa gagctaccaa    3600
ctcttttttcc gaaggtaact ggcttcagca gagcgcagat accaaatact gtccttctag    3660
tgtagccgta gttaggccac cacttcaaga actctgtagc accgcctaca tacctcgctc    3720
tgctaatcct gttaccagtg gctgctgcca gtggcgataa gtcgtgtctt accgggttgg    3780
actcaagacg atagttaccg gataaggcgc agcggtcggg ctgaacgggg ggttcgtgca    3840
cacagcccag cttggagcga acgacctaca ccgaactgag atacctacag cgtgagctat    3900
gagaaagcgc cacgcttccc gaagggagaa aggcggacag gtatccggta agcggcaggg    3960
tcggaacagg agagcgcacg agggagcttc caggggggaaa cgcctggtat ctttatagtc    4020
```

| | |
|---|---|
| ctgtcgggtt tcgccacctc tgacttgagc gtcgattttt gtgatgctcg tcaggggggc | 4080 |
| ggagcctatg gaaaaacgcc agcaacgcgg cctttttacg gttcctggcc ttttgctggc | 4140 |
| cttttgctca catgt | 4155 |

<210> SEQ ID NO 77
<211> LENGTH: 4157
<212> TYPE: DNA
<213> ORGANISM: Artificial Sequence
<220> FEATURE:
<223> OTHER INFORMATION: Synthetic

<400> SEQUENCE: 77

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgacg gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gagacgcttc cgagtacggt acaggggatc | 540 |
| cagggtggag gaggttctgg aggcggtgga agtggtggcg gaggtagcgg tggaggaggt | 600 |
| tctatggtgt ctaaggaatt catggtgagc aagggcgagg agctgttcac cggggtggtg | 660 |
| cccatcctgg tcgagctgga cggcgacgta acggccaca agttcagcgt gtccggcgag | 720 |
| ggcgagggcg atgccaccta cggcaagctg accctgaagt tcatctgcac caccggcaag | 780 |
| ctgcccgtgc cctggcccac cctcgtgacc accctgacct acggcgtgca gtgcttcagc | 840 |
| cgctaccccg accacatgaa gcagcacgac ttcttcaagt ccgccatgcc cgaaggctac | 900 |
| gtccaggagc gcaccatctt cttcaaggac gacggcaact acaagacccg cgccgaggtg | 960 |
| aagttcgagg gcgacaccct ggtgaaccgc atcgagctga agggcatcga cttcaaggag | 1020 |
| gacggcaaca tcctggggca caagctggag tacaactaca acagccacaa cgtctatatc | 1080 |
| atggccgaca agcagaagaa cggcatcaag gtgaacttca gatccgcca caacatcgag | 1140 |
| gacggcagcg tgcagctcgc cgaccactac cagcagaaca cccccatcgg cgacggcccc | 1200 |
| gtgctgctgc ccgacaacca ctacctgagc acccagtcca agctgagcaa agaccccaac | 1260 |
| gagaagcgcg atcacatggt cctgctggag ttcgtgaccg ccgccgggat cactctcggc | 1320 |
| atggacgagc tgtacaagaa gcttggatag ctagctagct agctcgagga cgcttccgag | 1380 |
| tacggtacag ggtcgaccac gtgcggaccg agcggccgca ggaacccta gtgatggagt | 1440 |
| tggccactcc ctctctgcgc gctcgctcgc tcactgaggc cgggcgacca aaggtcgccc | 1500 |
| gacgcccggg ctttgcccgg gcggcctcag tgagcgagcg agcgcgcagc tgcctgcagg | 1560 |
| ggcgcctgat gcggtatttt ctccttacgc atctgtgcgg tatttcacac cgcatacgtc | 1620 |
| aaagcaacca tagtacgcgc cctgtagcgg cgcattaagc gcggcgggtg tggtggttac | 1680 |
| gcgcagcgtg accgctacac ttgccagcgc cctagcgccc gctcctttcg ctttcttccc | 1740 |
| ttcctttctc gccacgttcg ccggcttccc cgtcaagct ctaaatcggg ggctcccttt | 1800 |
| agggttccga tttagtgctt tacggcacct cgaccccaaa aaacttgatt tgggtgatgg | 1860 |

```
ttcacgtagt gggccatcgc cctgatagac ggttttttcgc cctttgacgt tggagtccac    1920
gttctttaat agtggactct tgttccaaac tggaacaaca ctcaaccota tctcgggcta    1980
ttcttttgat ttataaggga ttttgccgat ttcggcctat tggttaaaaa atgagctgat    2040
ttaacaaaaa tttaacgcga attttaacaa aatattaacg tttacaattt tatggtgcac    2100
tctcagtaca atctgctctg atgccgcata gttaagccag ccccgacacc cgccaacacc    2160
cgctgacgcg ccctgacggg cttgtctgct cccggcatcc gcttacagac aagctgtgac    2220
cgtctccggg agctgcatgt gtcagaggtt ttccaccgtca tcaccgaaac gcgcgagacg    2280
aaagggcctc gtgatacgcc tatttttata ggttaatgtc atgataataa tggtttctta    2340
gacgtcaggt ggcacttttc ggggaaatgt gcgcggaacc cctatttgtt tattttttcta   2400
aatacattca aatatgtatc cgctcatgag acaataaccc tgataaatgc ttcaataata    2460
ttgaaaaagg aagagtatga gtattcaaca tttccgtgtc gcccttattc ccttttttgc    2520
ggcattttgc cttcctgttt ttgctcaccc agaaacgctg gtgaaagtaa aagatgctga    2580
agatcagttg ggtgcacgag tgggttacat cgaactggat ctcaacagcg gtaagatcct    2640
tgagagtttt cgccccgaag aacgttttcc aatgatgagc acttttaaag ttctgctatg    2700
tggcgcggta ttatcccgta ttgacgccgg gcaagagcaa ctcggtcgcc gcatacacta    2760
ttctcagaat gacttggttg agtactcacc agtcacagaa aagcatctta cggatggcat    2820
gacagtaaga gaattatgca gtgctgccat aaccatgagt gataacactg cggccaactt    2880
acttctgaca acgatcggag gaccgaagga gctaaccgct tttttgcaca acatggggga    2940
tcatgtaact cgccttgatc gttgggaacc ggagctgaat gaagccatac caaacgacga    3000
gcgtgacacc acgatgcctg tagcaatggc aacaacgttg cgcaaactat taactggcga    3060
actacttact ctagcttccc ggcaacaatt aatagactgg atggaggcgg ataaagttgc    3120
aggaccactt ctgcgctcgg cccttccggc tggctggttt attgctgata aatctggagc    3180
cggtgagcgt gggtctcgcg gtatcattgc agcactgggg ccagatggta agccctcccg    3240
tatcgtagtt atctacacga cggggagtca ggcaactatg gatgaacgaa atagacagat    3300
cgctgagata ggtgcctcac tgattaagca ttggtaactg tcagaccaag tttactcata    3360
tatactttag attgatttaa aacttcattt ttaattttaaa aggatctagg tgaagatcct    3420
ttttgataat ctcatgacca aaatccctta acgtgagttt tcgttccact gagcgtcaga    3480
ccccgtagaa aagatcaaag gatcttcttg agatcctttt tttctgcgcg taatctgctg    3540
cttgcaaaca aaaaaaccac cgctaccagc ggtggtttgt ttgccggatc aagagctacc    3600
aactcttttt ccgaaggtaa ctggcttcag cagagcgcag ataccaaata ctgtccttct    3660
agtgtagccg tagttaggcc accacttcaa gaactctgta gcaccgccta catacctcgc    3720
tctgctaatc ctgttaccag tggctgctgc cagtggcgat aagtcgtgtc ttaccgggtt    3780
ggactcaaga cgatagttac cggataaggc gcagcggtcg gctgaacgg ggggttcgtg    3840
cacacagccc agcttggagc gaacgaccta caccgaactg agatacctac agcgtgagct    3900
atgagaaagc gccacgcttc ccgaagggag aaaggcggac aggtatccgg taagcggcag    3960
ggtcggaaca ggagagcgca cgagggagct tccaggggga aacgcctggt atctttatag    4020
tcctgtcggg tttcgccacc tctgacttga gcgtcgattt ttgtgatgct cgtcaggggg    4080
gcggagccta tggaaaaacg ccagcaacgc ggccttttta cggttcctgg ccttttgctg    4140
gccttttgct cacatgt                                                   4157
```

```
<210> SEQ ID NO 78
<211> LENGTH: 4156
<212> TYPE: DNA
<213> ORGANISM: Artificial Sequence
<220> FEATURE:
<223> OTHER INFORMATION: Synthetic

<400> SEQUENCE: 78
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aggacgaaa caccgacgct tccgagtacg     420
gtacgtttta gagctagaaa tagcaagtta aaataaggct agtccgttat caacttgaaa     480
aagtggcacc gagtcggtgc ttttttcta gagacgcttc cgagtacggt acaggaggat     540
ccggtggagg aggttctgga ggcggtggaa gtggtggcgg aggtagcggt ggaggaggtt     600
ctatggtgtc taaggaattc atggtgagca agggcgagga gctgttcacc ggggtggtgc     660
ccatcctggt cgagctggac ggcgacgtaa acggccacaa gttcagcgtg tccggcgagg     720
gcgagggcga tgccacctac ggcaagctga ccctgaagtt catctgcacc accggcaagc     780
tgcccgtgcc ctggcccacc ctcgtgacca ccctgaccta cggcgtgcag tgcttcagcc     840
gctaccccga ccacatgaag cagcacgact tcttcaagtc cgccatgccc gaaggctacg     900
tccaggagcg caccatcttc ttcaaggacg acggcaacta caagacccgc gccgaggtga     960
agttcgaggg cgacaccctg gtgaaccgca tcgagctgaa gggcatcgac ttcaaggagg    1020
acggcaacat cctggggcac aagctggagt acaactacaa cagccacaac gtctatatca    1080
tggccgacaa gcagaagaac ggcatcaagg tgaacttcaa gatccgccac aacatcgagg    1140
acggcagcgt gcagctcgcc gaccactacc agcagaacac ccccatcggc gacggccccg    1200
tgctgctgcc cgacaaccac tacctgagca cccagtccaa gctgagcaaa gaccccaacg    1260
agaagcgcga tcacatggtc ctgctggagt tcgtgaccgc cgccgggatc actctcggca    1320
tggacgagct gtacaagaag cttggatagc tagctagcta gctcgaggac gcttccgagt    1380
acggtacagg gtcgaccacg tgcggaccga gcggccgcag gaaccccctag tgatggagtt    1440
ggccactccc tctctgcgcg ctcgctcgct cactgaggcc gggcgaccaa aggtcgcccg    1500
acgcccgggc tttgcccggg cggcctcagt gagcgagcga gcgcgcagct gcctgcaggg    1560
gcgcctgatg cggtattttc tccttacgca tctgtgcggt atttcacacc gcatacgtca    1620
aagcaaccat agtacgcgcc ctgtagcggc gcattaagcg cggcgggtgt ggtggttacg    1680
cgcagcgtga ccgctacact tgccagcgcc ctagcgcccg ctcctttcgc tttcttccct    1740
tcctttctcg ccacgttcgc cggctttccc cgtcaagctc taaatcgggg gctcccttta    1800
gggttccgat ttagtgcttt acggcacctc gaccccaaaa aacttgattt gggtgatggt    1860
tcacgtagtg gccatcgcc ctgatagacg gttttcgcc ctttgacgtt ggagtccacg    1920
ttctttaata gtggactctt gttccaaact ggaacaacac tcaaccctat ctcgggctat    1980
tcttttgatt tataagggat tttgccgatt tcggcctatt ggttaaaaaa tgagctgatt    2040
taacaaaaat ttaacgcgaa ttttaacaaa atattaacgt ttacaatttt atggtgcact    2100
```

| | |
|---|---|
| ctcagtacaa tctgctctga tgccgcatag ttaagccagc cccgacaccc gccaacaccc | 2160 |
| gctgacgcgc cctgacgggc ttgtctgctc ccggcatccg cttacagaca agctgtgacc | 2220 |
| gtctccggga gctgcatgtg tcagaggttt tcaccgtcat caccgaaacg cgcgagacga | 2280 |
| aagggcctcg tgatacgcct attttatag gttaatgtca tgataataat ggtttcttag | 2340 |
| acgtcaggtg gcacttttcg gggaaatgtg cgcggaaccc ctatttgttt attttctaa | 2400 |
| atacattcaa atatgtatcc gctcatgaga caataaccct gataaatgct tcaataatat | 2460 |
| tgaaaaagga gagtatgag tattcaacat ttccgtgtcg cccttattcc cttttttgcg | 2520 |
| gcattttgcc ttcctgtttt tgctcaccca gaaacgctgg tgaaagtaaa agatgctgaa | 2580 |
| gatcagttgg gtgcacgagt gggttacatc gaactggatc tcaacagcgg taagatcctt | 2640 |
| gagagttttc gccccgaaga acgttttcca atgatgagca cttttaaagt tctgctatgt | 2700 |
| ggcgcggtat tatcccgtat tgacgccggg caagagcaac tcggtcgccg catacactat | 2760 |
| tctcagaatg acttggttga gtactcacca gtcacagaaa agcatcttac ggatggcatg | 2820 |
| acagtaagag aattatgcag tgctgccata accatgagtg ataacactgc ggccaactta | 2880 |
| cttctgacaa cgatcggagg accgaaggag ctaaccgctt ttttgcacaa catgggggat | 2940 |
| catgtaactc gccttgatcg ttgggaaccg gagctgaatg aagccatacc aaacgacgag | 3000 |
| cgtgacacca cgatgcctgt agcaatggca acaacgttgc gcaaactatt aactggcgaa | 3060 |
| ctacttactc tagcttcccg gcaacaatta atagactgga tggaggcgga taaagttgca | 3120 |
| ggaccacttc tgcgctcggc ccttccggct ggctggttta ttgctgataa atctggagcc | 3180 |
| ggtgagcgtg ggtctcgcgg tatcattgca gcactgggc cagatggtaa gccctcccgt | 3240 |
| atcgtagtta tctacacgac ggggagtcag gcaactatgg atgaacgaaa tagacagatc | 3300 |
| gctgagatag gtgcctcact gattaagcat tggtaactgt cagaccaagt ttactcatat | 3360 |
| atactttaga ttgatttaaa acttcatttt taatttaaaa ggatctaggt gaagatcctt | 3420 |
| tttgataatc tcatgaccaa aatcccttaa cgtgagtttt cgttccactg agcgtcagac | 3480 |
| cccgtagaaa agatcaaagg atcttcttga gatccttttt ttctgcgcgt aatctgctgc | 3540 |
| ttgcaaacaa aaaaaccacc gctaccagcg gtggtttgtt tgccggatca agagctacca | 3600 |
| actcttttc cgaaggtaac tggcttcagc agagcgcaga taccaaatac tgtccttcta | 3660 |
| gtgtagccgt agttaggcca ccacttcaag aactctgtag caccgcctac atacctcgct | 3720 |
| ctgctaatcc tgttaccagt ggctgctgcc agtggcgata agtcgtgtct taccgggttg | 3780 |
| gactcaagac gatagttacc ggataaggcg cagcggtcgg gctgaacggg gggttcgtgc | 3840 |
| acacagccca gcttggagcg aacgacctac accgaactga gatacctaca gcgtgagcta | 3900 |
| tgagaaagcg ccacgcttcc cgaagggaga aaggcggaca ggtatccggt aagcggcagg | 3960 |
| gtcggaacag gagagcgcac gagggagctt ccaggggaa acgcctggta tctttatagt | 4020 |
| cctgtcgggt ttcgccacct ctgacttgag cgtcgatttt tgtgatgctc gtcaggggg | 4080 |
| cggagcctat ggaaaaacgc cagcaacgcg gccttttac ggttcctggc cttttgctgg | 4140 |
| ccttttgctc acatgt | 4156 |

<210> SEQ ID NO 79
<211> LENGTH: 3463
<212> TYPE: DNA
<213> ORGANISM: Artificial Sequence
<220> FEATURE:
<223> OTHER INFORMATION: Synthetic

<400> SEQUENCE: 79

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttttcta gacctgtacc gtactcggaa gcgtcggatc     540 catacccttca cgatgtaccg gattacgcac tcgccttgaa gctggcaggg ctcgacttgt     600
agctagctag ctagaagatc aagaccagct agttttaaag caagagcata gtcaggaacg     660
tcatagggat aaagctcgag cctgtaccgt actcggaagc gtccacgtgc ggaccgagcg     720
gccgcaggaa cccctagtga tggagttggc cactccctct ctgcgcgctc gctcgctcac     780
tgaggccggg cgaccaaagg tcgcccgacg cccgggcttt gccgggcgg cctcagtgag     840 cgagcgagcg cgcagctgcc tgcaggggcg cctgatgcgg tattttctcc ttacgcatct     900
gtgcggtatt tcacaccgca tacgtcaaag caaccatagt acgcgccctg tagcggcgca     960
ttaagcgcgg cgggtgtggt ggttacgcgc agcgtgaccg ctacacttgc cagcgcccta    1020
gcgcccgctc ctttcgcttt cttcccttcc tttctcgcca cgttcgccgg ctttccccgt    1080
caagctctaa atcgggggct ccctttaggg ttccgattta gtgctttacg gcacctcgac    1140
cccaaaaaac ttgatttggg tgatggttca cgtagtgggc catcgccctg atagacggtt    1200
tttcgccctt tgacgttgga gtccacgttc tttaatagtg gactcttgtt ccaaactgga    1260
acaacactca accctatctc gggctattct tttgatttat aagggatttt gccgatttcg    1320
gcctattggt taaaaatga gctgatttaa caaaaattta acgcgaattt taacaaaata    1380
ttaacgttta caatttttatg gtgcactctc agtacaatct gctctgatgc cgcatagtta    1440
agccagcccc gacacccgcc aacacccgct gacgcgccct gacgggcttg tctgctcccg    1500
gcatccgctt acagacaagc tgtgaccgtc tccgggagct gcatgtgtca gaggttttca    1560
ccgtcatcac cgaaacgcgc gagacgaaag ggcctcgtga tacgcctatt tttataggtt    1620
aatgtcatga taataatggt ttcttagacg tcaggtggca cttttcgggg aaatgtgcgc    1680 ggaacccccta tttgtttatt tttctaaata cattcaaata tgtatccgct catgagacaa    1740
taaccctgat aaatgcttca ataatattga aaaggaaga gtatgagtat tcaacatttc    1800
cgtgtcgccc ttattccctt ttttgcggca ttttgccttc ctgtttttgc tcacccagaa    1860
acgctggtga agtaaaaga tgctgaagat cagttgggtg cacgagtggg ttacatcgaa    1920
ctggatctca acagcggtaa gatccttgag agttttcgcc ccgaagaacg ttttccaatg    1980
atgagcactt ttaaagttct gctatgtggc gcggtattat cccgtattga cgccgggcaa    2040
gagcaactcg gtcgccgcat acactattct cagaatgact tggttgagta ctcaccagtc    2100
acagaaaagc atcttacgga tggcatgaca gtaagagaat tatgcagtgc tgccataacc    2160
atgagtgata acactgcggc caacttactt ctgacaacga tcggaggacc gaaggagcta    2220
accgcttttt tgcacaacat gggggatcat gtaactcgcc ttgatcgttg ggaaccggag    2280
ctgaatgaag ccataccaaa cgacgagcgt gacaccacga tgcctgtagc aatggcaaca    2340
```

| | | |
|---|---|---|
| acgttgcgca aactattaac tggcgaacta cttactctag cttcccggca acaattaata | 2400 |
| gactggatgg aggcggataa agttgcagga ccacttctgc gctcggccct tccggctggc | 2460 |
| tggtttattg ctgataaatc tggagccggt gagcgtgggt ctcgcggtat cattgcagca | 2520 |
| ctggggccag atggtaagcc ctcccgtatc gtagttatct acacgacggg gagtcaggca | 2580 |
| actatggatg aacgaaatag acagatcgct gagataggtg cctcactgat taagcattgg | 2640 |
| taactgtcag accaagttta ctcatatata ctttagattg atttaaaact tcatttttaa | 2700 |
| tttaaaagga tctaggtgaa gatcctttttt gataatctca tgaccaaaat cccttaacgt | 2760 |
| gagttttcgt tccactgagc gtcagacccc gtagaaaaga tcaaaggatc ttcttgagat | 2820 |
| cctttttttc tgcgcgtaat ctgctgcttg caaacaaaaa aaccaccgct accagcggtg | 2880 |
| gtttgtttgc cggatcaaga gctaccaact cttttttccga aggtaactgg cttcagcaga | 2940 |
| gcgcagatac caaatactgt ccttctagtg tagccgtagt taggccacca cttcaagaac | 3000 |
| tctgtagcac cgcctacata cctcgctctg ctaatcctgt taccagtggc tgctgccagt | 3060 |
| ggcgataagt cgtgtcttac cgggttggac tcaagacgat agttaccgga taaggcgcag | 3120 |
| cggtcgggct gaacggggg ttcgtgcaca cagcccagct tggagcgaac gacctacacc | 3180 |
| gaactgagat acctacagcg tgagctatga gaaagcgcca cgcttcccga agggagaaag | 3240 |
| gcggacaggt atccggtaag cggcagggtc ggaacaggag agcgcacgag ggagcttcca | 3300 |
| gggggaaacg cctggtatct ttatagtcct gtcgggtttc gccacctctg acttgagcgt | 3360 |
| cgattttttgt gatgctcgtc aggggggcgg agcctatgga aaaacgccag caacgcggcc | 3420 |
| tttttacggt tcctggcctt ttgctggcct tttgctcaca tgt | 3463 |

<210> SEQ ID NO 80
<211> LENGTH: 3461
<212> TYPE: DNA
<213> ORGANISM: Artificial Sequence
<220> FEATURE:
<223> OTHER INFORMATION: Synthetic

<400> SEQUENCE: 80

| | | |
|---|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gacctgtacc gtactcggaa gcgtcggatc | 540 |
| ctacccttac gatgtaccgg attacgcact cgccttgaag ctggcagggc tcgacttgta | 600 |
| gctagctagc tagaagatca agaccagcta gttttaaagc aagagcatag tcaggaacgt | 660 |
| catagggata agctcgagcc tgtaccgtac tcggaagcgt ccacgtgcgg accgagcggc | 720 |
| cgcaggaacc cctagtgatg gagttggcca ctccctctct gcgcgctcgc tcgctcactg | 780 |
| aggccgggcg accaaaggtc gcccgacgcc cgggctttgc ccgggcggcc tcagtgagcg | 840 |
| agcgagcgcg cagctgcctg caggggcgcc tgatgcggta ttttctcctt acgcatctgt | 900 |
| gcggtatttc acaccgcata cgtcaaagca accatagtac gcgccctgta gcggcgcatt | 960 |

```
aagcgcggcg ggtgtggtgg ttacgcgcag cgtgaccgct acacttgcca gcgccctagc    1020
gcccgctcct ttcgctttct tcccttcctt tctcgccacg ttcgccggct ttccccgtca    1080
agctctaaat cggggctcc ctttagggtt ccgatttagt gctttacggc acctcgaccc    1140
caaaaaactt gatttgggtg atggttcacg tagtgggcca tcgccctgat agacggtttt    1200 tcgcccttg acgttggagt ccacgttctt taatagtgga ctcttgttcc aaactggaac    1260
aacactcaac cctatctcgg gctattcttt tgatttataa gggattttgc cgatttcggc    1320
ctattggtta aaaatgagc tgatttaaca aaaatttaac gcgaatttta acaaaatatt    1380
aacgtttaca attttatggt gcactctcag tacaatctgc tctgatgccg catagttaag    1440
ccagccccga cacccgccaa cacccgctga cgcgccctga cgggcttgtc tgctcccggc    1500
atccgcttac agacaagctg tgaccgtctc cgggagctgc atgtgtcaga ggttttcacc    1560
gtcatcaccg aaacgcgcga gacgaaaggg cctcgtgata cgcctatttt tataggttaa    1620
tgtcatgata ataatggttt cttagacgtc aggtggcact tttcggggaa atgtgcgcgg    1680 aaccccctatt tgtttatttt tctaaataca ttcaaatatg tatccgctca tgagacaata    1740
accctgataa atgcttcaat aatattgaaa aggaagagt atgagtattc aacatttccg    1800
tgtcgccctt attcccttt ttgcggcatt ttgccttcct gttttgctc acccagaaac    1860 gctggtgaaa gtaaaagatg ctgaagatca gttgggtgca cgagtgggtt acatcgaact    1920
ggatctcaac agcggtaaga tccttgagag ttttcgcccc gaagaacgtt ttccaatgat    1980
gagcactttt aaagttctgc tatgtggcgc ggtattatcc cgtattgacg ccgggcaaga    2040
gcaactcggt cgccgcatac actattctca gaatgacttg gttgagtact caccagtcac    2100
agaaaagcat cttacggatg gcatgacagt aagagaatta tgcagtgctg ccataaccat    2160
gagtgataac actgcggcca acttacttct gacaacgatc ggaggaccga aggagctaac    2220
cgcttttttg cacaacatgg gggatcatgt aactcgcctt gatcgttggg aaccggagct    2280
gaatgaagcc ataccaaacg acgagcgtga caccacgatg cctgtagcaa tggcaacaac    2340
gttgcgcaaa ctattaactg gcgaactact tactctagct tcccggcaac aattaataga    2400
ctggatggag gcggataaag ttgcaggacc acttctgcgc tcggcccttc cggctggctg    2460
gtttattgct gataaatctg gagccggtga gcgtgggtct cgcggtatca ttgcagcact    2520
ggggccagat ggtaagccct cccgtatcgt agttatctac acgacgggga gtcaggcaac    2580
tatggatgaa cgaaatagac agatcgctga gataggtgcc tcactgatta agcattggta    2640
actgtcagac caagtttact catatatact ttagattgat ttaaaacttc atttttaatt    2700
taaaaggatc taggtgaaga tcctttttga atctcatg accaaaatcc cttaacgtga    2760
gttttcgttc cactgagcgt cagacccgt agaaaagatc aaaggatctt cttgagatcc    2820 ttttttctg cgcgtaatct gctgcttgca acaaaaaaa ccaccgctac cagcggtggt    2880
ttgtttgccg gatcaagagc taccaactct ttttccgaag gtaactggct tcagcagagc    2940
gcagatacca aatactgtcc ttctagtgta gccgtagtta ggccaccact tcaagaactc    3000
tgtagcaccg cctacatacc tcgctctgct aatcctgtta ccagtggctg ctgccagtgg    3060
cgataagtcg tgtcttaccg ggttggactc aagacgatag ttaccggata aggcgcagcg    3120
gtcgggctga acggggggtt cgtgcacaca gcccagcttg gagcgaacga cctacaccga    3180
actgagatac ctacagcgtg agctatgaga aagcgccacg cttcccgaag ggagaaaggc    3240
ggacaggtat ccggtaagcg gcagggtcgg aacaggagag cgcacgaggg agcttccagg    3300
```

| gggaaacgcc tggtatcttt atagtcctgt cgggtttcgc cacctctgac ttgagcgtcg | 3360 |
| attttttgtga tgctcgtcag gggggcggag cctatggaaa aacgccagca acgcggcctt | 3420 |
| tttacggttc ctggccttttt gctggccttt tgctcacatg t | 3461 |

<210> SEQ ID NO 81
<211> LENGTH: 3462
<212> TYPE: DNA
<213> ORGANISM: Artificial Sequence
<220> FEATURE:
<223> OTHER INFORMATION: Synthetic

<400> SEQUENCE: 81

| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgac gtagaaagta ataatttctt gggtagtttg | 300 |
| cagttttaaa attatgttttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gacctgtacc gtactcggaa gcgtcggatc | 540 |
| caataccctt acgatgtacc ggattacgca ctcgccttga agctggcagg gctcgacttg | 600 |
| tagctagcta gctagaagat caagaccagc tagttttaaa gcaagagcat agtcaggaac | 660 |
| gtcatagga tagctcgagc ctgtaccgta ctcggaagcg tccacgtgcg gaccgagcgg | 720 |
| ccgcaggaac ccctagtgat ggagttggcc actccctctc tgcgcgctcg ctcgctcact | 780 |
| gaggccgggc gaccaaaggt cgcccgacgc ccgggctttg cccgggcggc ctcagtgagc | 840 |
| gagcgagcgc gcagctgcct gcaggggcgc ctgatgcggt attttctcct tacgcatctg | 900 |
| tgcggtattt cacaccgcat acgtcaaagc aaccatagta cgcgccctgt agcggcgcat | 960 |
| taagcgcggc gggtgtggtg gttacgcgca gcgtgaccgc tacacttgcc agcgccctag | 1020 |
| cgcccgctcc tttcgctttc ttcccttcct ttctcgccac gttcgccggc tttccccgtc | 1080 |
| aagctctaaa tcggggggctc cctttagggt tccgatttag tgctttacgg cacctcgacc | 1140 |
| ccaaaaaact tgatttgggt gatggttcac gtagtgggcc atcgccctga tagacggttt | 1200 |
| ttcgcccttt gacgttggag tccacgttct ttaatagtgg actcttgttc caaactggaa | 1260 |
| caacactcaa ccctatctcg ggctattctt ttgatttata agggattttg ccgatttcgg | 1320 |
| cctattggtt aaaaaatgag ctgatttaac aaaaatttaa cgcgaatttt aacaaaatat | 1380 |
| taacgtttac aattttatgg tgcactctca gtacaatctg ctctgatgcc gcatagttaa | 1440 |
| gccagccccg acacccgcca cacccgctg acgcgccctg acgggcttgt ctgctcccgg | 1500 |
| catccgctta cagacaagct gtgaccgtct ccggagctg catgtgtcag aggttttcac | 1560 |
| cgtcatcacc gaaacgcgcg agacgaaagg gcctcgtgat acgcctattt ttataggtta | 1620 |
| atgtcatgat aataatggtt tcttagacgt caggtggcac ttttcgggga atgtgcgcg | 1680 |
| gaacccctat ttgtttattt ttctaaatac attcaaatat gtatccgctc atgagacaat | 1740 |
| aaccctgata aatgcttcaa taatattgaa aaaggaagag tatgagtatt caacatttcc | 1800 |
| gtgtcgccct tattcccttt tttgcggcat tttgccttcc tgttttttgct cacccagaaa | 1860 |
| cgctggtgaa agtaaaagat gctgaagatc agttgggtgc acgagtgggt tacatcgaac | 1920 |

```
tggatctcaa cagcggtaag atccttgaga gttttcgccc cgaagaacgt tttccaatga    1980
tgagcacttt taaagttctg ctatgtggcg cggtattatc ccgtattgac gccgggcaag    2040
agcaactcgg tcgccgcata cactattctc agaatgactt ggttgagtac tcaccagtca    2100
cagaaaagca tcttacggat ggcatgacag taagagaatt atgcagtgct gccataacca    2160
tgagtgataa cactgcggcc aacttacttc tgacaacgat cggaggaccg aaggagctaa    2220 ccgcttttt gcacaacatg ggggatcatg taactcgcct tgatcgttgg gaaccggagc     2280
tgaatgaagc cataccaaac gacgagcgtg acaccacgat gcctgtagca atggcaacaa    2340
cgttgcgcaa actattaact ggcgaactac ttactctagc ttcccggcaa caattaatag    2400
actggatgga ggcggataaa gttgcaggac cacttctgcg ctcggccctt ccggctggct    2460
ggtttattgc tgataaatct ggagccggtg agcgtgggtc tcgcggtatc attgcagcac    2520
tggggccaga tggtaagccc tcccgtatcg tagttatcta cacgacgggg agtcaggcaa    2580
ctatggatga acgaaataga cagatcgctg agataggtgc ctcactgatt aagcattggt    2640
aactgtcaga ccaagtttac tcatatatac tttagattga tttaaaactt cattttaat    2700 ttaaaaggat ctaggtgaag atcctttttg ataatctcat gaccaaaatc ccttaacgtg    2760
agttttcgtt ccactgagcg tcagaccccg tagaaaagat caaaggatct cttgagatc    2820 cttttttct gcgcgtaatc tgctgcttgc aaacaaaaaa accaccgcta ccagcggtgg    2880
tttgtttgcc ggatcaagag ctaccaactc ttttttccgaa ggtaactggc ttcagcagag    2940
cgcagatacc aaatactgtc cttctagtgt agccgtagtt aggccaccac ttcaagaact    3000
ctgtagcacc gcctacatac ctcgctctgc taatcctgtt accagtggct gctgccagtg    3060
gcgataagtc gtgtcttacc gggttggact caagacgata gttaccggat aaggcgcagc    3120
ggtcgggctg aacggggggt tcgtgcacac agcccagctt ggagcgaacg acctacaccg    3180
aactgagata cctacagcgt gagctatgag aaagcgccac gcttcccgaa gggagaaagg    3240
cggacaggta tccggtaagc ggcagggtcg gaacaggaga gcgcacgagg gagcttccag    3300
ggggaaacgc ctggtatctt tatagtcctg tcgggtttcg ccacctctga cttgagcgtc    3360
gatttttgtg atgctcgtca ggggggcgga gcctatggaa aaacgccagc aacgcggcct    3420
ttttacggtt cctggccttt tgctggcctt ttgctcacat gt                      3462
```

<210> SEQ ID NO 82
<211> LENGTH: 3457
<212> TYPE: DNA
<213> ORGANISM: Artificial Sequence
<220> FEATURE:
<223> OTHER INFORMATION: Synthetic

<400> SEQUENCE: 82

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtgaggg cctatttccc atgattcctt   180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
```

```
aagtggcacc gagtcggtgc tttttttcta gacctgtacc gtactcggaa gcgtcggatc    540
catacccttg cgatgtaccg gattacgcac cagctgcaaa acgcgtgaag ctcgactagc    600
tagctagcta gatctagttt aacacgctta gctgcaggag catagtcagg aacgtcatag    660
ggataaagct cgagcctgta ccgtactcgg aagcgtccac gtgcggaccg agcggccgca    720
ggaacccctg gtgatggagt tggccactcc ctctctgcgc gctcgctcgc tcactgaggc    780
cgggcgacca aggtcgcccg gacgcccggg ctttgcccgg gcggcctcag tgagcgagcg    840
agcgcgcagc tgcctgcagg ggcgcctgat gcggtatttt ctccttacgc atctgtgcgg    900
tatttcacac cgcatacgtc aaagcaacca tagtacgcgc cctgtagcgg cgcattaagc    960
gcggcgggtg tggtggttac gcgcagcgtg accgctacac ttgccagcgc cctagcgccc   1020
gctcctttcg ctttcttccc ttcctttctc gccacgttcg ccggctttcc ccgtcaagct   1080
ctaaatcggg gctccctttt agggttccga tttagtgctt tacggcacct cgaccccaaa   1140
aaacttgatt tgggtgatgg ttcacgtagt gggccatcgc cctgatagac ggttttttcgc  1200
cctttgacgt tggagtccac gttctttaat agtggactct tgttccaaac tggaacaaca   1260
ctcaacccta tctcgggcta ttcttttgat ttataaggga ttttgccgat ttcggcctat   1320
tggttaaaaa atgagctgat ttaacaaaaa tttaacgcga attttaacaa aatattaacg   1380
tttacaattt tatggtgcac tctcagtaca atctgctctg atgccgcata gttaagccag   1440
ccccgacacc cgccaacacc cgctgacgcg ccctgacggg cttgtctgct cccggcatcc   1500
gcttacagac aagctgtgac cgtctccggg agctgcatgt gtcagaggtt ttcaccgtca   1560
tcaccgaaac gcgcgagacg aaagggcctc gtgatacgcc tatttttata ggttaatgtc   1620
atgataataa tggtttctta gacgtcaggt ggcacttttc ggggaaatgt gcgcggaacc   1680
cctatttgtt tatttttcta aatacattca aatatgtatc cgctcatgag acaataaccc   1740
tgataaatgc ttcaataata ttgaaaaagg aagagtatga gtattcaaca tttccgtgtc   1800
gcccttattc cctttttttgc ggcatttttgc cttcctgttt ttgctcaccc agaaacgctg   1860
gtgaaagtaa aagatgctga agatcagttg ggtgcacgag tgggttacat cgaactggat   1920
ctcaacagcg gtaagatcct tgagagtttt cgccccgaag aacgttttcc aatgatgagc   1980
acttttaaag ttctgctatg tggcgcggta ttatcccgta ttgacgccgg gcaagagcaa   2040
ctcggtcgcc gcatacacta ttctcagaat gacttggttg agtactcacc agtcacagaa   2100
aagcatctta cggatggcat gacagtaaga gaattatgca gtgctgccat aaccatgagt   2160
gataacactg cggccaactt acttctgaca acgatcggag gaccgaagga gctaaccgct   2220
tttttgcaca acatggggga tcatgtaact cgccttgatc gttgggaacc ggagctgaat   2280
gaagccatac caaacgacga gcgtgacacc acgatgcctg tagcaatggc aacaacgttg   2340
cgcaaactat taactggcga actacttact ctagcttccc ggcaacaatt aatagactgg   2400
atggaggcgg ataaagttgc aggaccactt ctgcgctcgg cccttccggc tggctggttt   2460
attgctgata aatctggagc cggtgagcgt gggtctcgcg gtatcattgc agcactgggg   2520
ccagatggta agccctcccg tatcgtagtt atctacacga cggggagtca ggcaactatg   2580
gatgaacgaa atagacagat cgctgagata ggtgcctcac tgattaagca ttggtaactg   2640
tcagaccaag tttactcata tatactttag attgatttaa aacttcattt ttaatttaaa   2700
aggatctagg tgaagatcct ttttgataat ctcatgacca aaatccctta acgtgagttt   2760
tcgttccact gagcgtcaga ccccgtagaa aagatcaaag gatcttcttg agatcctttt   2820
tttctgcgcg taatctgctg cttgcaaaca aaaaaaccac cgctaccagc ggtggtttgt   2880
```

```
ttgccggatc aagagctacc aactcttttt ccgaaggtaa ctggcttcag cagagcgcag    2940
ataccaaata ctgtccttct agtgtagccg tagttaggcc accacttcaa gaactctgta    3000
gcaccgccta catacctcgc tctgctaatc ctgttaccag tggctgctgc cagtggcgat    3060
aagtcgtgtc ttaccgggtt ggactcaaga cgatagttac cggataaggc gcagcggtcg    3120
ggctgaacgg ggggttcgtg cacacagccc agcttggagc gaacgaccta caccgaactg    3180
agatacctac agcgtgagct atgagaaagc gccacgcttc ccgaagggag aaaggcggac    3240
aggtatccgg taagcggcag ggtcggaaca ggagagcgca cgagggagct ccaggggga    3300 aacgcctggt atctttatag tcctgtcggg tttcgccacc tctgacttga gcgtcgattt    3360
ttgtgatgct cgtcaggggg gcggagccta tggaaaaacg ccagcaacgc ggccttttta    3420
cggttcctgg ccttttgctg gccttttgct cacatgt    3457
```

<210> SEQ ID NO 83
<211> LENGTH: 3455
<212> TYPE: DNA
<213> ORGANISM: Artificial Sequence
<220> FEATURE:
<223> OTHER INFORMATION: Synthetic

<400> SEQUENCE: 83

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttcta gacctgtacc gtactcggaa gcgtcggatc     540 ctaccttac gatgtaccgg attacgcacc agctgcaaaa cgcgtgaagc tcgactagct     600
agctagctag atctagttta acacgcttag ctgcaggagc atagtcagga acgtcatagg     660
gataagctcg agcctgtacc gtactcggaa gcgtccacgt gcggaccgag cggccgcagg     720 aaccctagt gatggagttg gccactccct ctctgcgcgc tcgctcgctc actgaggccg     780
ggcgaccaaa ggtcgcccga cgcccgggct ttgcccgggc ggcctcagtg agcgagcgag     840
cgcgcagctg cctgcagggg cgcctgatgc ggtattttct ccttacgcat ctgtgcggta     900
tttcacaccg catacgtcaa agcaaccata gtacgcgccc tgtagcggcg cattaagcgc     960
ggcgggtgtg gtggttacgc gcagcgtgac cgctacactt gccagcgccc tagcgcccgc    1020
tcctttcgct ttcttccctt cctttctcgc cacgttcgcc ggctttcccc gtcaagctct    1080
aaatcggggg ctccctttag ggttccgatt tagtgcttta cggcacctcg accccaaaaa    1140
acttgatttg ggtgatggtt cacgtagtgg gccatcgccc tgatagacgg ttttcgccc     1200 tttgacgttg gagtccacgt tctttaatag tggactcttg ttccaaactg gaacaacact    1260
caaccctatc tcgggctatt cttttgattt ataagggatt ttgccgattt cggcctattg    1320
gttaaaaaat gagctgattt aacaaaaatt taacgcgaat tttaacaaaa tattaacgtt    1380
tacaatttta tggtgcactc tcagtacaat ctgctctgat gccgcatagt taagccagcc    1440
```

```
ccgacacccg ccaacacccg ctgacgcgcc ctgacgggct tgtctgctcc cggcatccgc    1500
ttacagacaa gctgtgaccg tctccgggag ctgcatgtgt cagaggtttt caccgtcatc    1560
accgaaacgc gcgagacgaa agggcctcgt gatacgccta ttttataggg ttaatgtcat    1620
gataataatg gtttcttaga cgtcaggtgg cacttttcgg ggaaatgtgc gcggaacccc    1680
tatttgttta tttttctaaa tacattcaaa tatgtatccg ctcatgagac aataaccctg    1740
ataaatgctt caataatatt gaaaaggaa gagtatgagt attcaacatt tccgtgtcgc    1800
ccttattccc ttttttgcgg cattttgcct tcctgttttt gctcacccag aaacgctggt    1860
gaaagtaaaa gatgctgaag atcagttggg tgcacgagtg ggttacatcg aactggatct    1920
caacagcggt aagatccttg agagttttcg ccccgaagaa cgttttccaa tgatgagcac    1980
ttttaaagtt ctgctatgtg gcgcggtatt atcccgtatt gacgccgggc aagagcaact    2040
cggtcgccgc atacactatt ctcagaatga cttggttgag tactcaccag tcacagaaaa    2100
gcatcttacg gatggcatga cagtaagaga attatgcagt gctgccataa ccatgagtga    2160
taacactgcg gccaacttac ttctgacaac gatcggagga ccgaaggagc taaccgcttt    2220
tttgcacaac atgggggatc atgtaactcg ccttgatcgt tgggaaccgg agctgaatga    2280
agccatacca aacgacgagc gtgacaccac gatgcctgta gcaatggcaa caacgttgcg    2340
caaactatta actggcgaac tacttactct agcttcccgg caacaattaa tagactggat    2400
ggaggcggat aaagttgcag gaccacttct gcgctcggcc cttccggctg gctggtttat    2460
tgctgataaa tctggagccg gtgagcgtgg gtctcgcggt atcattgcag cactggggcc    2520
agatggtaag ccctcccgta tcgtagttat ctacacgacg gggagtcagg caactatgga    2580
tgaacgaaat agacagatcg ctgagatagg tgcctcactg attaagcatt ggtaactgtc    2640
agaccaagtt tactcatata ctttagat tgatttaaaa cttcatttt aatttaaaag    2700 gatctaggtg aagatccttt ttgataatct catgaccaaa atcccttaac gtgagttttc    2760
gttccactga gcgtcagacc ccgtagaaaa gatcaaagga tcttcttgag atcctttttt    2820
tctgcgcgta atctgctgct tgcaaacaaa aaaaccaccg ctaccagcgg tggtttgttt    2880
gccggatcaa gagctaccaa ctcttttttcc gaaggtaact ggcttcagca gagcgcagat    2940
accaaatact gtccttctag tgtagccgta gttaggccac cacttcaaga actctgtagc    3000
accgcctaca tacctcgctc tgctaatcct gttaccagtg gctgctgcca gtggcgataa    3060
gtcgtgtctt accgggttgg actcaagacg atagttaccg gataaggcgc agcggtcggg    3120
ctgaacgggg ggttcgtgca cacagcccag cttggagcga acgacctaca ccgaactgag    3180
atacctacag cgtgagctat gagaaagcgc cacgcttccc gaagggagaa aggcggacag    3240
gtatccggta agcggcaggg tcggaacagg agagcgcacg agggagcttc caggggaaa    3300 cgcctggtat ctttatagtc ctgtcgggtt tcgccacctc tgacttgagc gtcgattttt    3360
gtgatgctcg tcaggggggc ggagcctatg gaaaaacgcc agcaacgcgg ccttttacg    3420 gttcctggcc ttttgctggc cttttgctca catgt                              3455
```

<210> SEQ ID NO 84
<211> LENGTH: 3456
<212> TYPE: DNA
<213> ORGANISM: Artificial Sequence
<220> FEATURE:
<223> OTHER INFORMATION: Synthetic

<400> SEQUENCE: 84

```
cctgcaggca gctgcgcgct cgctcgctca ctgaggccgc ccgggcaaag cccgggcgtc      60
```

```
gggcgacctt tggtcgcccg gcctcagtga gcgagcgagc gcgcagagag ggagtggcca    120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttcta gacctgtacc gtactcggaa gcgtcggatc      540 caatacccctt acgatgtacc ggattacgca ccagctgcaa aacgcgtgaa gctcgactag    600
ctagctagct agatctagtt taacacgctt agctgcagga gcatagtcag gaacgtcata    660
gggatagctc gagcctgtac cgtactcgga agcgtccacg tgcggaccga gcggccgcag    720
gaacccctag tgatggagtt ggccactccc tctctgcgcg ctcgctcgct cactgaggcc    780
gggcgaccaa aggtcgcccg acgcccgggc tttgcccggg cggcctcagt gagcgagcga    840
gcgcgcagct gcctgcaggg gcgcctgatg cggtattttc tccttacgca tctgtgcggt    900
atttcacacc gcatacgtca aagcaaccat agtacgcgcc ctgtagcggc gcattaagcg    960
cggcgggtgt ggtggttacg cgcagcgtga ccgctacact tgccagcgcc ctagcgcccg   1020 ctccttcgc ttcttccct tcctttctcg ccacgttcgc cggctttccc cgtcaagctc     1080
taaatcgggg gctcccttta gggttccgat ttagtgcttt acggcacctc gaccccaaaa    1140
aacttgattt gggtgatggt tcacgtagtg ggccatcgcc ctgatagacg ttttttcgcc    1200
ctttgacgtt ggagtccacg ttctttaata gtggactctt gttccaaact ggaacaacac    1260
tcaaccctat ctcgggctat tcttttgatt tataagggat tttgccgatt tcggcctatt    1320
ggttaaaaaa tgagctgatt taacaaaaat ttaacgcgaa ttttaacaaa atattaacgt    1380
ttacaatttt atggtgcact tcagtacaa tctgctctga tgccgcatag ttaagccagc     1440
cccgacaccc gccaacaccc gctgacgcgc cctgacgggc ttgtctgctc ccggcatccg    1500
cttacagaca agctgtgacc gtctccggga gctgcatgtg tcagaggttt tcaccgtcat    1560
caccgaaacg cgcgagacga aagggcctcg tgatacgcct atttttatag gttaatgtca    1620
tgataataat ggtttcttag acgtcaggtg cacttttcg gggaaatgtg cgcggaaccc     1680
ctatttgttt attttctaa atacattcaa atatgtatcc gctcatgaga caataaccct    1740
gataaatgct tcaataatat tgaaaaagga agagtatgag tattcaacat ttccgtgtcg    1800
cccttattcc cttttttgcg gcattttgcc ttcctgtttt tgctcaccca gaaacgctgg    1860
tgaaagtaaa agatgctgaa gatcagttgg gtgcacgagt gggttacatc gaactggatc    1920
tcaacagcgg taagatcctt gagagttttc gccccgaaga acgttttcca atgatgagca    1980
cttttaaagt tctgctatgt ggcgcggtat tatcccgtat tgacgccggg caagagcaac    2040
tcggtcgccg catacactat tctcagaatg acttggttga gtactcacca gtcacagaaa    2100
agcatcttac ggatggcatg acagtaagag aattatgcag tgctgccata accatgagtg    2160
ataacactgc ggccaactta cttctgacaa cgatcggagg accgaaggag ctaaccgctt    2220
ttttgcacaa catgggggat catgtaactc gccttgatcg ttgggaaccg gagctgaatg    2280
aagccatacc aaacgacgag cgtgacacca cgatgcctgt agcaatggca acaacgttgc    2340
gcaaactatt aactggcgaa ctacttactc tagcttcccg gcaacaatta atagactgga    2400
```

| | |
|---|---|
| tggaggcgga taaagttgca ggaccacttc tgcgctcggc ccttccggct ggctggttta | 2460 |
| ttgctgataa atctggagcc ggtgagcgtg ggtctcgcgg tatcattgca gcactggggc | 2520 |
| cagatggtaa gccctcccgt atcgtagtta tctacacgac ggggagtcag gcaactatgg | 2580 |
| atgaacgaaa tagacagatc gctgagatag gtgcctcact gattaagcat tggtaactgt | 2640 |
| cagaccaagt ttactcatat atactttaga ttgatttaaa acttcatttt taatttaaaa | 2700 |
| ggatctaggt gaagatcctt tttgataatc tcatgaccaa atcccttaa cgtgagtttt | 2760 |
| cgttccactg agcgtcagac cccgtagaaa agatcaaagg atcttcttga gatccttttt | 2820 |
| ttctgcgcgt aatctgctgc ttgcaaacaa aaaaaccacc gctaccagcg gtggtttgtt | 2880 |
| tgccggatca agagctacca actcttttc cgaaggtaac tggcttcagc agagcgcaga | 2940 |
| taccaaatac tgtccttcta gtgtagccgt agttaggcca ccacttcaag aactctgtag | 3000 |
| caccgcctac atacctcgct ctgctaatcc tgttaccagt ggctgctgcc agtggcgata | 3060 |
| agtcgtgtct taccgggttg gactcaagac gatagttacc ggataaggcg cagcggtcgg | 3120 |
| gctgaacggg gggttcgtgc acacagccca gcttggagcg aacgacctac accgaactga | 3180 |
| gatacctaca gcgtgagcta tgagaaagcg ccacgcttcc gaagggaga aaggcggaca | 3240 |
| ggtatccggt aagcggcagg gtcggaacag gagagcgcac gagggagctt ccaggggaa | 3300 |
| acgcctggta tctttatagt cctgtcgggt ttcgccacct ctgacttgag cgtcgatttt | 3360 |
| tgtgatgctc gtcagggggg cggagcctat ggaaaaacgc cagcaacgcg gccttttac | 3420 |
| ggttcctggc cttttgctgg ccttttgctc acatgt | 3456 |

<210> SEQ ID NO 85
<211> LENGTH: 4167
<212> TYPE: DNA
<213> ORGANISM: Artificial Sequence
<220> FEATURE:
<223> OTHER INFORMATION: Synthetic

<400> SEQUENCE: 85

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gagacgcttc cgagtacggt acaggggatc | 540 |
| ctacccttac gatgtaccgg attacgcagg aagcggagct actaacttca gcctgctgaa | 600 |
| gcaggctgga gacgtggagg agaaccctgg acctggtacc atggtgagca agggcgagga | 660 |
| ggataacatg gccatcatca aggagttcat gcgcttcaag gtgcacatgg agggctccgt | 720 |
| gaacggccac gagttcgaga tcgagggcga gggcgagggc cgcccctacg agggcaccca | 780 |
| gaccgccaag ctgaaggtga ccaagggtgg ccccctgccc ttcgcctggg acatcctgtc | 840 |
| ccctcagttc atgtacggct ccaaggccta cgtgaagcac cccgccgaca tccccgacta | 900 |
| cttgaagctg tccttcccg agggcttcaa gtgggagcgc gtgatgaact cgaggacgg | 960 |
| cggcgtggtg accgtgaccc aggactcctc cctgcaggac ggcgagttca tctacaaggt | 1020 |

```
gaagctgcgc ggcaccaact tccccctccga cggcccccgta atgcagaaga agaccatggg    1080
ctgggaggcc tcctccgagc ggatgtaccc cgaggacggc gccctgaagg gcagagatcaa    1140 gcagaggctg aagctgaagg acggcggcca ctacgacgct gaggtcaaga ccacctacaa    1200
ggccaagaag cccgtgcagc tgcccggcgc ctacaacgtc aacatcaagt tggacatcac    1260
ctcccacaac gaggactaca ccatcgtgga acagtacgaa cgcgccgagg ccgccactc     1320 caccggcggc atggacgagc tgtacaagaa gcttggatag ctagctagct agctcgagga    1380
cgcttccgag tacggtacag ggtcgaccac gtgcggaccg agcggccgca ggaaccccta    1440
gtgatggagt tggccactcc ctctctgcgc gctcgctcgc tcactgaggc cgggcgacca    1500
aaggtcgccc gacgcccggg ctttgcccgg gcggcctcag tgagcgagcg agcgcgcagc    1560
tgcctgcagg ggcgcctgat gcggtatttt ctccttacgc atctgtgcgg tatttcacac    1620
cgcatacgtc aaagcaacca tagtacgcgc cctgtagcgg cgcattaagc gcggcgggtg    1680
tggtggttac gcgcagcgtg accgctacac ttgccagcgc cctagcgccc gctcctttcg    1740
cttttcttcc cttcctttctc gccacgttcg ccggctttcc ccgtcaagct ctaaatcggg    1800 ggctccctt agggttccga tttagtgctt tacggcacct cgaccccaaa aaacttgatt    1860
tgggtgatgg ttcacgtagt gggccatcgc cctgatagac ggttttttcgc cctttgacgt    1920 tggagtccac gttctttaat agtggactct tgttccaaac tggaacaaca ctcaaccccta   1980 tctcgggcta ttcttttgat ttataaggga ttttgccgat ttcggcctat tggttaaaaaa   2040 atgagctgat ttaacaaaaa tttaacgcga attttaacaa aatattaacg tttacaattt    2100
tatggtgcac tctcagtaca atctgctctg atgccgcata gttaagccag ccccgacacc    2160
cgccaacacc cgctgacgcg ccctgacggg cttgtctgct cccggcatcc gcttacagac    2220
aagctgtgac cgtctccggg agctgcatgt gtcagaggtt ttcaccgtca tcaccgaaac    2280
gcgcgagacg aaagggcctc gtgatacgcc tatttttata ggttaatgtc atgataataa    2340
tggtttctta gacgtcaggt ggcactttc ggggaaatgt gcgcggaacc cctatttgtt    2400
tatttttcta aatacattca aatatgtatc cgctcatgag acaataaccc tgataaatgc    2460
ttcaataata ttgaaaaagg aagagtatga gtattcaaca tttccgtgtc gcccttattc    2520
ccttttttgc ggcattttgc cttcctgttt ttgctcaccc agaaacgctg gtgaaagtaa    2580
aagatgctga agatcagttg ggtgcacgag tgggttacat cgaactggat ctcaacagcg    2640
gtaagatcct tgagagtttt cgccccgaag aacgttttcc aatgatgagc acttttaaag    2700
ttctgctatg tggcgcggta ttatcccgta ttgacgccgg gcaagagcaa ctcggtcgcc    2760
gcatacacta ttctcagaat gacttggttg agtactcacc agtcacagaa aagcatctta    2820
cggatggcat gacagtaaga gaattatgca gtgctgccat aaccatgagt gataacactg    2880
cggccaactt acttctgaca acgatcggag gaccgaagga gctaaccgct tttttgcaca    2940
acatggggga tcatgtaact cgccttgatc gttgggaacc ggagctgaat gaagccatac    3000
caaacgacga gcgtgacacc acgatgcctg tagcaatggc aacaacgttg cgcaaactat    3060
taactggcga actacttact ctagcttccc ggcaacaatt aatagactgg atggaggcgg    3120
ataaagttgc aggaccactt ctgcgctcgg cccttccggc tggctggttt attgctgata    3180
aatctggagc cggtgagcgt gggtctcgcg gtatcattgc agcactgggg ccagatggta    3240
agccctcccg tatcgtagtt atctacacga cggggagtca ggcaactatg gatgaacgaa    3300
atagacagat cgctgagata ggtgcctcac tgattaagca ttggtaactg tcagaccaag    3360
```

```
tttactcata tatactttag attgatttaa aacttcattt ttaatttaaa aggatctagg    3420
tgaagatcct ttttgataat ctcatgacca aaatcccctta acgtgagttt tcgttccact   3480
gagcgtcaga ccccgtagaa aagatcaaag gatcttcttg agatcctttt tttctgcgcg   3540
taatctgctg cttgcaaaca aaaaaaccac cgctaccagc ggtggtttgt ttgccggatc   3600
aagagctacc aactctttt ccgaaggtaa ctggcttcag cagagcgcag ataccaaata   3660
ctgtccttct agtgtagccg tagttaggcc accacttcaa gaactctgta gcaccgccta   3720
catacctcgc tctgctaatc ctgttaccag tggctgctgc cagtggcgat aagtcgtgtc   3780
ttaccgggtt ggactcaaga cgatagttac cggataaggc gcagcggtcg ggctgaacgg   3840
ggggttcgtg cacacagccc agcttggagc gaacgaccta caccgaactg agatacctac   3900
agcgtgagct atgagaaagc gccacgcttc ccgaagggag aaaggcggac aggtatccgg   3960
taagcggcag ggtcggaaca ggagagcgca cgagggagct tccaggggga aacgcctggt   4020
atctttatag tcctgtcggg tttcgccacc tctgacttga gcgtcgattt ttgtgatgct   4080
cgtcaggggg gcggagccta tggaaaaacg ccagcaacgc ggccttttta cggttcctgg   4140
ccttttgctg gccttttgct cacatgt                                       4167
```

<210> SEQ ID NO 86
<211> LENGTH: 4169
<212> TYPE: DNA
<213> ORGANISM: Artificial Sequence
<220> FEATURE:
<223> OTHER INFORMATION: Synthetic

<400> SEQUENCE: 86

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggggatc    540
cagtacccct tacgatgtacc ggattacgca ggaagcggag ctactaactt cagcctgctg    600
aagcaggctg agacgtggaa ggagaacccct ggacctggta ccatggtgag caagggcgag    660
gaggataaca tggccatcat caaggagttc atgcgcttca aggtgcacat ggagggctcc    720
gtgaacggcc acgagttcga gatcgagggc gagggcgagg ccgcccccta cgagggcacc    780
cagaccgcca gctgaaggt gaccaagggt ggccccctgc ccttcgcctg ggacatcctg    840
tcccctcagt tcatgtacgg ctccaaggcc tacgtgaagc accccgccga catccccgac    900
tacttgaagc tgtccttccc cgagggcttc aagtgggagc gcgtgatgaa cttcgaggac    960
ggcggcgtgg tgaccgtgac ccaggactcc tccctgcagg acggcgagtt catctacaag   1020
gtgaagctgc gcggcaccaa cttcccctcc gacggccccg taatgcagaa gaagaccatg   1080
ggctgggagg cctcctccga gcggatgtac cccgaggacg gcgccctgaa gggcgagatc   1140
aagcagaggc tgaagctgaa ggacggcggc cactacgacg ctgaggtcaa gaccacctac   1200
aaggccaaga gcccgtgca gctgcccggc gcctacaacg tcaacatcaa gttggacatc   1260
```

```
acctcccaca acgaggacta caccatcgtg aacagtacg aacgcgccga gggccgccac    1320
tccaccggcg gcatggacga gctgtacaag aagcttggat agctagctag ctagctcgag    1380
gacgcttccg agtacggtac agggtcgacc acgtgcggac cgagcggccg caggaacccc    1440
tagtgatgga gttggccact ccctctctgc gcgctcgctc gctcactgag gccgggcgac    1500
caaaggtcgc ccgacgcccg ggctttgccc gggcggcctc agtgagcgag cgagcgcgca    1560
gctgcctgca ggggcgcctg atgcggtatt ttctccttac gcatctgtgc ggtatttcac    1620
accgcatacg tcaaagcaac catagtacgc gccctgtagc ggcgcattaa gcgcggcggg    1680
tgtggtggtt acgcgcagcg tgaccgctac acttgccagc gccctagcgc ccgctccttt    1740
cgctttcttc ccttcctttc tcgccacgtt cgccggcttt ccccgtcaag ctctaaatcg    1800
ggggctccct ttagggttcc gatttagtgc tttacggcac ctcgacccca aaaaacttga    1860
tttgggtgat ggttcacgta gtgggccatc gccctgatag acggttttc gccctttgac     1920 gttggagtcc acgttcttta atagtggact cttgttccaa actggaacaa cactcaaccc    1980
tatctcgggc tattcttttg atttataagg gattttgccg atttcggcct attggttaaa    2040
aaatgagctg atttaacaaa aatttaacgc gaattttaac aaaatattaa cgtttacaat    2100
tttatggtgc actctcagta caatctgctc tgatgccgca tagttaagcc agccccgaca    2160
cccgccaaca cccgctgacg cgccctgacg ggcttgtctg ctcccggcat ccgcttacag    2220
acaagctgtg accgtctccg ggagctgcat gtgtcagagg ttttcaccgt catcaccgaa    2280
acgcgcgaga cgaaagggcc tcgtgatacg cctatttta taggttaatg tcatgataat    2340
aatggtttct tagacgtcag gtggcacttt tcggggaaat gtgcgcggaa cccctatttg    2400
tttatttttc taaatacatt caaatatgta tccgctcatg agacaataac cctgataaat    2460
gcttcaataa tattgaaaaa ggaagagtat gagtattcaa catttccgtg tcgcccttat    2520 tcccttttt gcggcatttt gccttcctgt ttttgctcac ccagaaacgc tggtgaaagt     2580
aaaagatgct gaagatcagt tgggtgcacg agtgggttac atcgaactgg atctcaacag    2640
cggtaagatc cttgagagtt ttcgccccga agaacgtttt ccaatgatga gcacttttaa    2700
agttctgcta tgtggcgcgg tattatcccg tattgacgcc gggcaagagc aactcggtcg    2760
ccgcatacac tattctcaga atgacttggt tgagtactca ccagtcacag aaaagcatct    2820 tacgatggc atgacagtaa gagaattatg cagtgctgcc ataaccatga gtgataacac      2880
tgcggccaac ttacttctga caacgatcgg aggaccgaag gagctaaccg cttttttgca    2940
caacatgggg gatcatgtaa ctcgccttga tcgttgggaa ccggagctga atgaagccat    3000
accaaacgac gagcgtgaca ccacgatgcc tgtagcaatg gcaacaacgt tgcgcaaact    3060
attaactggc gaactactta ctctagcttc ccggcaacaa ttaatagact ggatggaggc    3120
ggataaagtt gcaggaccac ttctgcgctc ggcccttccg gctggctggt ttattgctga    3180
taaatctgga gccggtgagc gtgggtctcg cggtatcatt gcagcactgg ggccagatgg    3240
taagccctcc cgtatcgtag ttatctacac gacggggagt caggcaacta tggatgaacg    3300
aaatagacag atcgctgaga taggtgcctc actgattaag cattggtaac tgtcagacca    3360
agtttactca tatatacttt agattgattt aaaacttcat ttttaattta aaaggatcta    3420
ggtgaagatc cttttgata atctcatgac caaaatccct aacgtgagt tttcgttcca      3480 ctgagcgtca gaccccgtag aaaagatcaa aggatcttct tgagatcctt ttttctgcg     3540 cgtaatctgc tgcttgcaaa caaaaaaacc accgctacca gcggtggttt gtttgccgga    3600
```

| | |
|---|---|
| tcaagagcta ccaactctttt ttccgaaggt aactggcttc agcagagcgc agataccaaa | 3660 |
| tactgtccttt ctagtgtagc cgtagttagg ccaccacttc aagaactctg tagcaccgcc | 3720 |
| tacataccte gctctgctaa tcctgttacc agtggctgct gccagtggcg ataagtcgtg | 3780 |
| tcttaccggg ttggactcaa gacgatagtt accggataag gcgcagcggt cgggctgaac | 3840 |
| gggggggttcg tgcacacagc ccagcttgga gcgaacgacc tacaccgaac tgagatacct | 3900 |
| acagcgtgag ctatgagaaa gcgccacgct tcccgaaggg agaaaggcgg acaggtatcc | 3960 |
| ggtaagcggc agggtcggaa caggagagcg cacgagggag cttccagggg gaaacgcctg | 4020 |
| gtatctttat agtcctgtcg ggtttcgcca cctctgactt gagcgtcgat ttttgtgatg | 4080 |
| ctcgtcaggg gggcggagcc tatggaaaaa cgccagcaac gcggccttttt tacggttcct | 4140 |
| ggccttttgc tggccttttg ctcacatgt | 4169 |

<210> SEQ ID NO 87
<211> LENGTH: 4168
<212> TYPE: DNA
<213> ORGANISM: Artificial Sequence
<220> FEATURE:
<223> OTHER INFORMATION: Synthetic

<400> SEQUENCE: 87

| | |
|---|---|
| cctgcaggca gctgcgcgct cgctcgctca ctgaggccgc ccgggcaaag cccgggcgtc | 60 |
| gggcgaccttt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagatat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggaggat | 540 |
| cctacccctta cgatgtaccg gattacgcag gaagcggagc tactaacttc agcctgctga | 600 |
| agcaggctgg agacgtggag gagaaccctg gacctggtac catggtgagc aagggcgagg | 660 |
| aggataacat ggccatcatc aaggagttca tgcgcttcaa ggtgcacatg gagggctccg | 720 |
| tgaacggcca cgagttcgag atcgagggcg agggcgaggg ccgcccctac gagggcaccc | 780 |
| agaccgccaa gctgaaggtg accaagggtg gccccctgcc cttcgcctgg gacatcctgt | 840 |
| cccctcagtt catgtacggc tccaaggcct acgtgaagca ccccgccgac atccccgact | 900 |
| acttgaagct gtccttcccc gagggcttca gtgggagcg cgtgatgaac ttcgaggacg | 960 |
| gcggcgtggt gaccgtgacc caggactcct ccctgcagga cggcgagttc atctacaagg | 1020 |
| tgaagctgcg cggcaccaac ttcccctccg acggccccgt aatgcagaag aagaccatgg | 1080 |
| gctgggaggc ctcctccgag cggatgtacc ccgaggacgg cgccctgaag ggcgagatca | 1140 |
| agcagaggct gaagctgaag gacggcggcc actacgacgc tgaggtcaag accacctaca | 1200 |
| aggccaagaa gcccgtgcag ctgccccgcg cctacaacgt caacatcaag ttggacatca | 1260 |
| cctcccacaa cgaggactac accatcgtgg aacagtacga acgcgccgag ggccgccact | 1320 |
| ccaccgcgg catggacgag ctgtacaaga gcttggata gctagctagc tagctcgagg | 1380 |
| acgcttccga gtacggtaca gggtcgacca cgtgcggacc gagcggccgc aggaacccct | 1440 |
| agtgatggag ttggccactc cctctctgcg cgctcgctcg ctcactgagg ccgggcgacc | 1500 |

```
aaaggtcgcc cgacgcccgg gctttgcccg ggcggcctca gtgagcgagc gagcgcgcag   1560
ctgcctgcag gggcgcctga tgcggtattt tctccttacg catctgtgcg gtatttcaca   1620
ccgcatacgt caaagcaacc atagtacgcg ccctgtagcg gcgcattaag cgcggcgggt   1680
gtggtggtta cgcgcagcgt gaccgctaca cttgccagcg ccctagcgcc cgctcctttc   1740
gctttcttcc cttcctttct cgccacgttc gccggctttc cccgtcaagc tctaaatcgg   1800
gggctcccctt taggggttccg atttagtgct ttacggcacc tcgacccccaa aaaacttgat   1860
```

| | |
|---|---:|
| gggggttcgt gcacacagcc cagcttggag cgaacgacct acaccgaact gagatactta | 3900 |
| cagcgtgagc tatgagaaag cgccacgctt cccgaaggga gaaaggcgga caggtatccg | 3960 |
| gtaagcggca gggtcggaac aggagagcgc acgagggagc ttccaggggg aaacgcctgg | 4020 |
| tatctttata gtcctgtcgg gtttcgccac ctctgacttg agcgtcgatt tttgtgatgc | 4080 |
| tcgtcagggg ggcggagcct atggaaaaac gccagcaacg cggcctttt acggttcctg | 4140 |
| gccttttgct ggccttttgc tcacatgt | 4168 |

```
<210> SEQ ID NO 88
<211> LENGTH: 4396
<212> TYPE: DNA
<213> ORGANISM: Artificial Sequence
<220> FEATURE:
<223> OTHER INFORMATION: Synthetic

<400> SEQUENCE: 88
```

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gagacgcttc cgagtacggt acaggggatc | 540 |
| ctaccttac gatgtaccgg attacgcagg aagcggagct actaacttca gcctgctgaa | 600 |
| gcaggctgga gacgtggagg agaaccctgg acctggtacc atggtgagca agggcgagga | 660 |
| ggataacatg gccatcatca aggagttcat gcgcttcaag gtgcacatgg agggctccgt | 720 |
| gaacggccac gagttcgaga tcgagggcga gggcgagggc cgcccctacg agggcaccca | 780 |
| gaccgccaag ctgaaggtga ccaagggtgg ccccctgccc ttcgcctggg acatcctgtc | 840 |
| ccctcagttc atgtacggct ccaaggccta cgtgaagcac cccgccgaca tccccgacta | 900 |
| cttgaagctg tccttcccg agggcttcaa gtgggagcgc gtgatgaact tcgaggacgg | 960 |
| cggcgtggtg accgtgaccc aggactcctc cctgcaggac ggcgagttca tctacaaggt | 1020 |
| gaagctgcgc ggcaccaact tcccctccga cggccccgta atgcagaaga agaccatggg | 1080 |
| ctgggaggcc tcctccgagc ggatgtaccc cgaggacggc gccctgaagg gcgagatcaa | 1140 |
| gcagaggctg aagctgaagg acggcggcca ctacgacgct gaggtcaaga ccacctacaa | 1200 |
| ggccaagaag cccgtgcagc tgcccggcgc ctacaacgtc aacatcaagt tggacatcac | 1260 |
| ctcccacaac gaggactaca ccatcgtgga acagtacgaa cgcgccgagg gccgccactc | 1320 |
| caccggcggc atggacgagc tgtacaagta gctagctagc taggaattcc tagagctcgc | 1380 |
| tgatcagcct cgactgtgcc ttctagttgc cagccatctg ttgtttgccc ctccccgtg | 1440 |
| ccttccttga ccctggaagg tgccactccc actgtccttt cctaataaaa tgaggaaatt | 1500 |
| gcatcgcatt gtctgagtag gtgtcattct attctggggg gtgggtgggg caggacagc | 1560 |
| aagggggagg attgggaaga gaatagcagg catgctgggg actcgaggac gcttccgagt | 1620 |
| acggtacagg gtcgaccacg tgcggaccga cggccgcag gaaccctag tgatggagtt | 1680 |
| ggccactccc tctctgcgcg ctcgctcgct cactgaggcc gggcgaccaa aggtcgcccg | 1740 |

```
acgcccgggc tttgcccggg cggcctcagt gagcgagcga gcgcgcagct gcctgcaggg    1800
gcgcctgatg cggtattttc tccttacgca tctgtgcggt atttcacacc gcatacgtca    1860
aagcaaccat agtacgcgcc ctgtagcggc gcattaagcg cggcgggtgt ggtggttacg    1920
cgcagcgtga ccgctacact tgccagcgcc ctagcgccg  ctcctttcgc tttcttccct    1980
tcctttctcg ccacgttcgc cggctttccc cgtcaagctc taaatcgggg gctcccttta    2040
gggttccgat ttagtgcttt acggcacctc gaccccaaaa aacttgattt gggtgatggt    2100
tcacgtagtg ggccatcgcc ctgatagacg gttttttcgcc ctttgacgtt ggagtccacg   2160
ttctttaata gtggactctt gttccaaact ggaacaacac tcaaccctat ctcgggctat    2220
tcttttgatt tataagggat tttgccgatt tcggcctatt ggttaaaaaa tgagctgatt    2280
taacaaaaat ttaacgcgaa ttttaacaaa atattaacgt ttacaatttt atggtgcact    2340
ctcagtacaa tctgctctga tgccgcatag ttaagccagc cccgacaccc gccaacaccc    2400
gctgacgcgc cctgacgggc ttgtctgctc ccggcatccg cttacagaca agctgtgacc    2460
gtctccggga gctgcatgtg tcagaggttt tcaccgtcat caccgaaacg cgcgagacga    2520
aagggcctcg tgatacgcct atttttatag gttaatgtca tgataataat ggtttcttag    2580
acgtcaggtg gcacttttcg gggaaatgtg cgcggaaccc ctatttgttt attttttctaa   2640 atacattcaa atatgtatcc gctcatgaga caataaccct gataaatgct tcaataatat    2700
tgaaaaagga agagtatgag tattcaacat ttccgtgtcg cccttattcc cttttttgcg    2760 gcatttgcc  ttcctgtttt tgctcaccca gaaacgctgg tgaaagtaaa agatgctgaa    2820
gatcagttgg gtgcacgagt gggttacatc gaactggatc tcaacagcgg taagatcctt    2880
gagagttttc gccccgaaga cgttttccca atgatgagca cttttaaagt tctgctatgt    2940
ggcgcggtat tatcccgtat tgacgccggg caagagcaac tcggtcgccg catacactat    3000
tctcagaatg acttggttga gtactcacca gtcacagaaa agcatcttac ggatggcatg    3060
acagtaagag aattatgcag tgctgccata accatgagtg ataacactgc ggccaactta    3120
cttctgacaa cgatcggagg accgaaggag ctaaccgctt ttttgcacaa catgggggat    3180
catgtaactc gccttgatcg ttgggaaccg gagctgaatg aagccatacc aaacgacgag    3240
cgtgacacca cgatgcctgt agcaatggca acaacgttgc gcaaactatt aactggcgaa    3300
ctacttactc tagcttcccg gcaacaatta atagactgga tggaggcgga taaagttgca    3360
ggaccacttc tgcgctcggc ccttccggct ggctggttta ttgctgataa atctggagcc    3420
ggtgagcgtg ggtctcgcgg tatcattgca gcactgggc  cagatggtaa gccctcccgt    3480
atcgtagtta tctacacgac ggggagtcag gcaactatgg atgaacgaaa tagacagatc    3540
gctgagatag gtgcctcact gattaagcat tggtaactgt cagaccaagt ttactcatat    3600
atactttaga ttgatttaaa acttcatttt taatttaaaa ggatctaggt gaagatcctt    3660
tttgataatc tcatgaccaa aatcccttaa cgtgagtttt cgttccactg agcgtcagac    3720
cccgtagaaa agatcaaagg atcttcttga gatcctttt  ttctgcgcgt aatctgctgc    3780
ttgcaaacaa aaaaaccacc gctaccagcg gtggtttgtt tgccggatca agagctacca    3840
actctttttc cgaaggtaac tggcttcagc agagcgcaga taccaaatac tgtccttcta    3900
gtgtagccgt agttaggcca ccacttcaag aactctgtag caccgcctac atacctcgct    3960
ctgctaatcc tgttaccagt ggctgctgcc agtggcgata agtcgtgtct taccgggttg    4020
gactcaagac gatagttacc ggataaggcg cagcggtcgg gctgaacggg gggttcgtgc    4080
```

| | |
|---|---|
| acacagccca gcttggagcg aacgacctac accgaactga gatacctaca gcgtgagcta | 4140 |
| tgagaaagcg ccacgcttcc cgaagggaga aggcggaca ggtatccggt aagcggcagg | 4200 |
| gtcggaacag gagagcgcac gagggagctt ccaggggaa acgcctggta tctttatagt | 4260 |
| cctgtcgggt ttcgccacct ctgacttgag cgtcgatttt tgtgatgctc gtcagggggg | 4320 |
| cggagcctat ggaaaaacgc cagcaacgcg gcctttttac ggttcctggc cttttgctgg | 4380 |
| cctttgctc acatgt | 4396 |

<210> SEQ ID NO 89
<211> LENGTH: 4398
<212> TYPE: DNA
<213> ORGANISM: Artificial Sequence
<220> FEATURE:
<223> OTHER INFORMATION: Synthetic

<400> SEQUENCE: 89

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc tttttttcta gagacgcttc cgagtacggt acaggggatc | 540 |
| cagtacccctt acgatgtacc ggattacgca ggaagcggag ctactaactt cagcctgctg | 600 |
| aagcaggctg agacgtgga ggagaaccct ggacctggta ccatggtgag caagggcgag | 660 |
| gaggataaca tggccatcat caaggagttc atgcgcttca aggtgcacat ggagggctcc | 720 |
| gtgaacggcc acgagttcga gatcgagggc gagggcgagg ccgcccccta cgagggcacc | 780 |
| cagaccgcca gctgaaggt gaccaagggt ggccccctgc ccttcgcctg ggacatcctg | 840 |
| tcccctcagt tcatgtacgg ctccaaggcc tacgtgaagc accccgccga catccccgac | 900 |
| tacttgaagc tgtccttccc cgagggcttc aagtgggagc gcgtgatgaa cttcgaggac | 960 |
| ggcggcgtgg tgaccgtgac ccaggactcc tccctgcagg acggcgagtt catctacaag | 1020 |
| gtgaagctgc gcggcaccaa cttcccctcc gacggccccg taatgcagaa gaagaccatg | 1080 |
| ggctgggagg cctcctccga gcggatgtac cccgaggacg gcgccctgaa gggcgagatc | 1140 |
| aagcagaggc tgaagctgaa ggacggcggc cactacgacg ctgaggtcaa gaccacctac | 1200 |
| aaggccaaga gcccgtgca gctgcccggc gcctacaacg tcaacatcaa gttggacatc | 1260 |
| acctcccaca acgaggacta caccatcgtg aacagtacg aacgcgccga gggccgccac | 1320 |
| tccaccggcg gcatggacga gctgtacaag tagctagcta gctaggaatt cctagagctc | 1380 |
| gctgatcagc ctcgactgtg ccttctagtt gccagccatc tgttgtttgc cctcccccg | 1440 |
| tgccttcctt gaccctggaa ggtgccactc ccactgtcct ttcctaataa aatgaggaaa | 1500 |
| ttgcatcgca ttgtctgagt aggtgtcatt ctattctggg ggtgggtg gggcaggaca | 1560 |
| gcaagggga ggattggaa gagaatagca ggcatgctgg gactcgagg acgcttccga | 1620 |
| gtacggtaca gggtcgacca cgtgcggacc gagcggccga aggaacccct agtgatggag | 1680 |
| ttggccactc cctctctgcg cgctcgctcg ctcactgagg ccgggcgacc aaaggtcgcc | 1740 |

```
cgacgcccgg gctttgcccg ggcggcctca gtgagcgagc gagcgcgcag ctgcctgcag    1800
gggcgcctga tgcggtattt tctccttacg catctgtgcg gtatttcaca ccgcatacgt    1860
caaagcaacc atagtacgcg ccctgtagcg gcgcattaag cgcggcgggt gtggtggtta    1920
cgcgcagcgt gaccgctaca cttgccagcg ccctagcgcc cgctcctttc gctttcttcc    1980
cttcctttct cgccacgttc gccggctttc cccgtcaagc tctaaatcgg gggctccctt    2040
tagggttccg atttagtgct ttacggcacc tcgaccccaa aaacttgat ttgggtgatg     2100 gttcacgtag tgggccatcg ccctgataga cggttttttcg cccttttgacg ttggagtcca  2160 cgttctttaa tagtggactc ttgttccaaa ctggaacaac actcaaccct atctcgggct    2220
attcttttga tttataaggg attttgccga tttcggccta ttggttaaaa aatgagctga   2280
tttaacaaaa atttaacgcg aattttaaca aaatattaac gtttacaatt ttatggtgca    2340
ctctcagtac aatctgctct gatgccgcat agttaagcca gccccgacac ccgccaacac   2400
ccgctgacgc gccctgacgg gcttgtctgc tcccggcatc cgcttacaga caagctgtga    2460
ccgtctccgg gagctgcatg tgtcagaggt tttcaccgtc atccgaaa cgcgcgagac     2520 gaaagggcct cgtgatacgc ctatttttat aggttaatgt catgataata atggtttctt    2580
agacgtcagg tggcactttt cggggaaatg tgcgcggaac ccctatttgt ttatttttct    2640
aaatacattc aaatatgtat ccgctcatga caataacc ctgataaatg cttcaataat      2700
attgaaaaag gaagagtatg agtattcaac atttccgtgt cgcccttatt ccctttttttg   2760 cggcattttg ccttcctgtt tttgctcacc cagaaacgct ggtgaaagta aaagatgctg    2820
aagatcagtt gggtgcacga gtgggttaca tcgaactgga tctcaacagc ggtaagatcc    2880
ttgagagttt tcgccccgaa gaacgttttc caatgatgag cacttttaaa gttctgctat    2940
gtggcgcggt attatcccgt attgacgccg ggcaagagca actcggtcgc cgcatacact    3000
attctcagaa tgacttggtt gagtactcac cagtcacaga aaagcatctt acggatggca    3060
tgacagtaag agaattatgc agtgctgcca taaccatgag tgataacact gcggccaact    3120
tacttctgac aacgatcgga ggaccgaagg agctaaccgc ttttttgcac aacatggggg    3180
atcatgtaac tcgccttgat cgttgggaac cggagctgaa tgaagccata ccaaacgacg    3240
agcgtgacac cacgatgcct gtagcaatgg caacaacgtt gcgcaaacta ttaactggcg    3300
aactacttac tctagcttcc cggcaacaat taatagactg gatggaggcg gataaagttg    3360
caggaccact tctgcgctcg gcccttccgg ctggctggtt tattgctgat aaatctggag    3420
ccggtgagcg tgggtctcgc ggtatcattg cagcactggg gccagatggt aagccctccc    3480
gtatcgtagt tatctacacg acggggagtc aggcaactat ggatgaacga atagacaga    3540 tcgctgagat aggtgcctca ctgattaagc attggtaact gtcagaccaa gtttactcat    3600
atatacttta gattgattta aaacttcatt tttaatttaa aaggatctag gtgaagatcc    3660
tttttgataa tctcatgacc aaaatccctt aacgtgagtt ttcgttccac tgagcgtcag   3720
accccgtaga aaagatcaaa ggatcttctt gagatccttt ttttctgcgc gtaatctgct   3780
gcttgcaaac aaaaaaacca ccgctaccag cggtggtttg tttgccggat caagagctac    3840
caactctttt tccgaaggta actggcttca gcagagcgca gataccaaat actgtccttc    3900
tagtgtagcc gtagttaggc caccacttca agaactctgt agcaccgcct acatacctcg    3960
ctctgctaat cctgttacca gtggctgctg ccagtggcga taagtcgtgt cttaccgggt    4020
tggactcaag acgatagtta ccggataagg cgcagcggtc gggctgaacg gggggttcgt    4080
```

```
gcacacagcc cagcttggag cgaacgacct acaccgaact gagataccta cagcgtgagc    4140
tatgagaaag cgccacgctt cccgaaggga gaaaggcgga caggtatccg gtaagcggca    4200
gggtcggaac aggagagcgc acgagggagc ttccagggggg aaacgcctgg tatctttata   4260
gtcctgtcgg gtttcgccac ctctgacttg agcgtcgatt tttgtgatgc tcgtcagggg    4320
ggcggagcct atggaaaaac gccagcaacg cggccttttt acggttcctg gccttttgct    4380
ggccttttgc tcacatgt                                                  4398

<210> SEQ ID NO 90
<211> LENGTH: 4397
<212> TYPE: DNA
<213> ORGANISM: Artificial Sequence
<220> FEATURE:
<223> OTHER INFORMATION: Synthetic

<400> SEQUENCE: 90
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aggacgaaa caccgacgct tccgagtacg     420
gtacgtttta gagctagaaa tagcaagtta aaataaggct agtccgttat caacttgaaa    480
aagtggcacc gagtcggtgc tttttttcta gagacgcttc cgagtacggt acaggaggat    540
cctaccctta cgatgtaccg gattacgcag gaagcggagc tactaacttc agcctgctga    600
agcaggctgg agacgtggag gagaaccctg gacctggtac catggtgagc aagggcgagg    660
aggataacat ggccatcatc aaggagttca tgcgcttcaa ggtgcacatg gagggctccg    720
tgaacggcca cgagttcgag atcgagggcg agggcgaggg ccgcccctac gagggcaccc    780
agaccgccaa gctgaaggtg accaagggtg gccccctgcc cttcgcctgg gacatcctgt    840
cccctcagtt catgtacggc tccaaggcct acgtgaagca ccccgccgac atccccgact    900
acttgaagct gtccttcccc gagggcttca gtgggagcg cgtgatgaac ttcgaggacg    960
gcggcgtggt gaccgtgacc caggactcct ccctgcagga cggcgagttc atctacaagg    1020
tgaagctgcg cggcaccaac ttcccctccg acggccccgt aatgcagaag aagaccatgg    1080
gctgggaggc ctcctccgag cggatgtacc ccgaggacgg cgccctgaag ggcgagatca    1140
agcagaggct gaagctgaag gacggcggcc actacgacgc tgaggtcaag accacctaca    1200
aggccaagaa gcccgtgcag ctgcccggcg cctacaacgt caacatcaag ttggacatca    1260
cctcccacaa cgaggactac accatcgtgg aacagtacga acgcgccgag ggccgccact    1320
ccaccggcgg catggacgag ctgtacaagt agctagctag ctaggaattc ctagagctcg    1380
ctgatcagcc tcgactgtgc cttctagttg ccagccatct gttgtttgcc cctcccccgt    1440
gccttccttg accctggaag gtgccactcc cactgtcctt tcctaataaa atgaggaaat    1500
tgcatcgcat tgtctgagta ggtgtcattc tattctgggg ggtggggtgg ggcaggacag    1560
caagggggag gattgggaag agaatagcag catgctgggg gactcgagga cgcttccgag    1620
tacggtacag ggtcgaccac gtgcggaccg agcggccgca ggaacccctta gtgatggagt    1680 tggccactcc ctctctgcgc gctcgctcgc tcactgaggc cgggcgacca aaggtcgccc    1740
```

```
gacgcccggg ctttgcccgg gcggcctcag tgagcgagcg agcgcgcagc tgcctgcagg   1800
ggcgcctgat gcggtatttt ctccttacgc atctgtgcgg tatttcacac cgcatacgtc   1860
aaagcaacca tagtacgcgc cctgtagcgg cgcattaagc gcggcgggtg tggtggttac   1920
gcgcagcgtg accgctacac ttgccagcgc cctagcgccc gctcctttcg ctttcttccc   1980
ttcctttctc gccacgttcg ccggctttcc ccgtcaagct ctaaatcggg gctccctttt   2040
agggttccga tttagtgctt tacggcacct cgaccccaaa aaacttgatt tgggtgatgg   2100
ttcacgtagt gggccatcgc cctgatagac ggttttttcg cctttgacgt tggagtccac   2160
gttctttaat agtggactct tgttccaaac tggaacaaca ctcaaccccta tctcgggcta   2220 ttcttttgat ttataaggga ttttgccgat ttcggcctat tggttaaaaa atgagctgat   2280
ttaacaaaaa tttaacgcga attttaacaa aatattaacg tttacaattt tatggtgcac   2340
tctcagtaca atctgctctg atgccgcata gttaagccag ccccgacacc cgccaacacc   2400
cgctgacgcg ccctgacggg cttgtctgct cccggcatcc gcttacagac aagctgtgac   2460
cgtctccggg agctgcatgt gtcagaggtt ttcaccgtca tcaccgaaac gcgcgagacg   2520
aaagggcctc gtgatacgcc tatttttata ggttaatgtc atgataataa tggtttctta   2580
gacgtcaggt ggcacttttc ggggaaatgt gcgcggaacc cctatttgtt tattttttcta   2640 aatacattca aatatgtatc cgctcatgag acaataaccc tgataaatgc ttcaataata   2700
ttgaaaaagg aagagtatga gtattcaaca tttccgtgtc gcccttattc ccttttttgc   2760
ggcattttgc cttcctgttt ttgctcaccc agaaacgctg gtgaaagtaa aagatgctga   2820
agatcagttg ggtgcacgag tgggttacat cgaactggat ctcaacagcg gtaagatcct   2880
tgagagtttt cgccccgaag aacgttttcc aatgatgagc acttttaaag ttctgctatg   2940
tggcgcggta ttatcccgta ttgacgccgg gcaagagcaa ctcggtcgcc gcatacacta   3000
ttctcagaat gacttggttg agtactcacc agtcacagaa aagcatctta cggatggcat   3060
gacagtaaga gaattatgca gtgctgccat aaccatgagt gataacactg cggccaactt   3120
acttctgaca acgatcggag gaccgaagga gctaaccgct tttttgcaca acatggggga   3180
tcatgtaact cgccttgatc gttgggaacc ggagctgaat gaagccatac caaacgacga   3240
gcgtgacacc acgatgcctg tagcaatggc aacaacgttg cgcaaactat taactggcga   3300
actacttact ctagcttccc ggcaacaatt aatagactgg atggaggcgg ataaagttgc   3360
aggaccactt ctgcgctcgg cccttccggc tggctggttt attgctgata atctggagc    3420 cggtgagcgt gggtctcgcg gtatcattgc agcactgggg ccagatggta agccctcccg   3480
tatcgtagtt atctacacga cggggagtca ggcaactatg gatgaacgaa atagacagat   3540
cgctgagata ggtgcctcac tgattaagca ttggtaactg tcagaccaag tttactcata   3600
tatactttag attgatttaa aacttcattt ttaatttaaa aggatctagg tgaagatcct   3660
ttttgataat ctcatgacca aaatccctta acgtgagttt tcgttccact gagcgtcaga   3720
ccccgtagaa aagatcaaag gatcttcttg agatcctttt tttctgcgcg taatctgctg   3780
cttgcaaaca aaaaaaccac cgctaccagc ggtggtttgt ttgccggatc aagagctacc   3840
aactcttttt ccgaaggtaa ctggcttcag cagagcgcag ataccaaata ctgtccttct   3900
agtgtagccg tagttaggcc accacttcaa gaactctgta gcaccgccta catacctcgc   3960
tctgctaatc ctgttaccag tggctgctgc cagtggcgat aagtcgtgtc ttaccgggtt   4020
ggactcaaga cgatagttac cggataaggc gcagcggtcg gctgaacgg ggggttcgtg    4080
```

```
cacacagccc agcttggagc gaacgaccta caccgaactg agatacctac agcgtgagct    4140
atgagaaagc gccacgcttc ccgaagggag aaaggcggac aggtatccgg taagcggcag    4200
ggtcggaaca ggagagcgca cgagggagct tccaggggga aacgcctggt atctttatag    4260
tcctgtcggg tttcgccacc tctgacttga gcgtcgattt ttgtgatgct cgtcagggga    4320
gcggagccta tggaaaaacg ccagcaacgc ggcctttta cggttcctgg cctttgctg     4380 gcctttgct cacatgt                                                    4397

<210> SEQ ID NO 91
<211> LENGTH: 4232
<212> TYPE: DNA
<213> ORGANISM: Artificial Sequence
<220> FEATURE:
<223> OTHER INFORMATION: Synthetic

<400> SEQUENCE: 91
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aggacgaaa caccgacgct tccgagtacg    420
gtacgtttta gagctagaaa tagcaagtta aaataaggct agtccgttat caacttgaaa    480
aagtggcacc gagtcggtgc ttttttcta gagacgcttc cgagtacggt cagggatc      540 ctaccttac gatgtaccgg attacgcata gctagctagc tagggatcga attcgcttat    600
cgataatcaa cctctggatt acaaaatttg tgaaagattg actggtattc ttaactatgt    660
tgctcctttt acgctatgtg gatacgctgc tttaatgcct ttgtatcatg ctattgcttc    720
ccgtatggct ttcatttct cctccttgta taaatcctgg ttgctgtctc tttatgagga    780
gttgtggccc gttgtcaggc aacgtggcgt ggtgtgcact gtgtttgctg acgcaacccc    840
cactggttgg ggcattgcca ccacctgtca gctccttcc gggactttcg ctttcccct     900 ccctattgcc acgcggaac tcatcgccgc ctgccttgcc cgctgctgga cagggctcg     960 gctgttgggc actgacaatt ccgtggtgtt gtcggggaaa tcatcgtcct tccttggct    1020 gctcgcctat gttgccacct ggattctgcg cgggacgtcc ttctgctacg tcccttcggc   1080
cctcaatcca gcggaccttc cttcccgcgg cctgctgccg gctctgcggc tcttccgcg    1140 tcttcgcctt cgccctcaga cgagtcggat ctccctttgg gccgcctccc cgcatcgata   1200
ccgctcgata gatctcgact gtgccttcta gttgccagcc atctgttgtt tgcccctccc   1260
ccgtgccttc cttgaccctg gaaggtgcca ctcccactgt cctttcctaa taaaatgagg   1320
aaattgcatc gcattgtctg agtaggtgtc attctattct ggggggtggg gtggggcagg   1380
acagcaaggg ggaggattgg gaagacaata gcaggcatgc tggggatgcg gtgggctcta   1440
tggctcgagg acgcttccga gtacggtaca ggcacgtgcg gaccgagcgg ccgcaggaac   1500
ccctagtgat ggagttggcc actccctctc tgcgcgctcg ctcgctcact gaggccgggc   1560
gaccaaaggt cgcccgacgc ccgggctttg cccgggcggg ctcagtgagc gagcgagcgc   1620
gcagctgcct gcaggggcgc ctgatgcggt attttctcct tacgcatctg tgcggtattt   1680
cacaccgcat acgtcaaagc aaccatagta cgcgccctgt agcggcgcat taagcgcggc   1740
```

```
gggtgtggtg gttacgcgca gcgtgaccgc tacacttgcc agcgccctag cgcccgctcc    1800
tttcgctttc ttcccttcct ttctcgccac gttcgccggc tttccccgtc aagctctaaa    1860 tcggggctc  cctttagggt tccgatttag tgctttacgg cacctcgacc ccaaaaaact    1920
tgatttgggt gatggttcac gtagtgggcc atcgccctga tagacggttt ttcgcccttt    1980
gacgttggag tccacgttct ttaatagtgg actcttgttc caaactggaa caacactcaa    2040
ccctatctcg ggctattctt ttgatttata agggattttg ccgatttcgg cctattggtt    2100
aaaaaatgag ctgatttaac aaaaatttaa cgcgaatttt aacaaaatat taacgtttac    2160
aattttatgg tgcactctca gtacaatctg ctctgatgcc gcatagttaa gccagccccg    2220
acacccgcca acacccgctg acgcgccctg acgggcttgt ctgctcccgg catccgctta    2280
cagacaagct gtgaccgtct ccgggagctg catgtgtcag aggttttcac cgtcatcacc    2340
gaaacgcgcg agacgaaagg gcctcgtgat acgcctattt ttataggtta atgtcatgat    2400
aataatggtt tcttagacgt caggtggcac ttttcgggga atgtgcgcg  aaccccctat    2460 ttgtttattt ttctaaatac attcaaatat gtatccgctc atgagacaat aaccctgata    2520
aatgcttcaa taatattgaa aaaggaagag tatgagtatt caacatttcc gtgtcgccct    2580 tattccctt  tttgcggcat tttgccttcc tgttttgct  cacccagaaa cgctggtgaa    2640
agtaaaagat gctgaagatc agttgggtgc acgagtgggt tacatcgaac tggatctcaa    2700
cagcggtaag atccttgaga gttttcgccc cgaagaacgt tttccaatga tgagcacttt    2760
taaagttctg ctatgtggcg cggtattatc ccgtattgac gccgggcaag agcaactcgg    2820
tcgccgcata cactattctc agaatgactt ggttgagtac tcaccagtca cagaaaagca    2880
tcttacggat ggcatgacag taagagaatt atgcagtgct gccataacca tgagtgataa    2940
cactgcggcc aacttacttc tgacaacgat cggaggaccg aaggagctaa ccgcttttt     3000 gcacaacatg ggggatcatg taactcgcct tgatcgttgg gaaccggagc tgaatgaagc    3060
cataccaaac gacgagcgtg acaccacgat gcctgtagca atggcaacaa cgttgcgcaa    3120
actattaact ggcgaactac ttactctagc ttcccggcaa caattaatag actggatgga    3180
ggcggataaa gttgcaggac cacttctgcg ctcggccctt ccggctggct ggtttattgc    3240
tgataaatct ggagccggtg agcgtgggtc tcgcggtatc attgcagcac tggggccaga    3300
tggtaagccc tcccgtatcg tagttatcta cacgacgggg agtcaggcaa ctatggatga    3360
acgaaataga cagatcgctg agataggtgc ctcactgatt aagcattggt aactgtcaga    3420
ccaagtttac tcatatatac tttagattga tttaaaactt catttttaat ttaaaaggat    3480
ctaggtgaag atcctttttg ataatctcat gaccaaaatc ccttaacgtg agttttcgtt    3540
ccactgagcg tcagaccccg tagaaaagat caaaggatct tcttgagatc ctttttttct    3600
gcgcgtaatc tgctgcttgc aaacaaaaaa accaccgcta ccagcggtgg tttgtttgcc    3660
ggatcaagag ctaccaactc tttttccgaa ggtaactggc ttcagcagag cgcagatacc    3720
aaatactgtc cttctagtgt agccgtagtt aggccaccac ttcaagaact ctgtagcacc    3780
gcctacatac ctcgctctgc taatcctgtt accagtggct gctgccagtg gcgataagtc    3840
gtgtcttacc gggttggact caagacgata gttaccggat aaggcgcagc ggtcgggctg    3900
aacggggggt tcgtgcacac agcccagctt ggagcgaacg acctacaccg aactgagata    3960
cctacagcgt gagctatgag aaagcgccac gcttcccgaa gggagaaagg cggacaggta    4020
tccggtaagc ggcagggtcg gaacaggaga gcgcacgagg gagcttccag ggggaaacgc    4080
```

-continued

```
ctggtatctt tatagtcctg tcgggtttcg ccacctctga cttgagcgtc gattttgtg       4140 atgctcgtca ggggggcgga gcctatggaa aaacgccagc aacgcggcct ttttacggtt       4200
cctggccttt tgctggcctt ttgctcacat gt                                    4232
```

<210> SEQ ID NO 92
<211> LENGTH: 4234
<212> TYPE: DNA
<213> ORGANISM: Artificial Sequence
<220> FEATURE:
<223> OTHER INFORMATION: Synthetic

<400> SEQUENCE: 92

```
cctgcaggca gctgcgcgct cgctcgctca ctgaggccgc ccgggcaaag cccgggcgtc         60
gggcgacctt tggtcgcccg gcctcagtga gcgagcgagc gcgcagagag ggagtggcca        120
actccatcac taggggttcc tgcggccgca cgcgtgaggg cctatttccc atgattcctt        180
catatttgca tatacgatac aaggctgtta gagagataat tggaattaat ttgactgtaa       240
acacaaagat attagtacaa atacgtgacg tagaaagta ataatttctt gggtagtttg        300
cagttttaaa attatgtttt aaaatggact atcatatgct taccgtaact tgaaagtatt       360
tcgatttctt ggctttatat atcttgtgga aaggacgaaa caccgacgct tccgagtacg       420
gtacgtttta gagctagaaa tagcaagtta aaataaggct agtccgttat caacttgaaa       480
aagtggcacc gagtcggtgc ttttttcta gagacgcttc cgagtacggt acaggggatc        540
cagtacccct acgatgtacc ggattacgca tagctagcta gctagggatc gaattcgctt       600
atcgataatc aacctctgga ttacaaaatt tgtgaaagat tgactggtat tcttaactat       660
gttgctcctt ttacgctatg tggatacgct gctttaatgc ctttgtatca tgctattgct       720
tcccgtatgg ctttcatttt ctcctccttg tataaatcct ggttgctgtc tctttatgag       780
gagttgtggc ccgttgtcag gcaacgtggc gtggtgtgca ctgtgtttgc tgacgcaacc       840
cccactggtt ggggcattgc caccacctgt cagctccttt ccgggacttt cgctttcccc       900
ctccctattg ccacggcgga actcatcgcc gcctgccttg cccgctgctg gacaggggct       960
cggctgttgg gcactgacaa ttccgtggtg ttgtcgggga aatcatcgtc ctttccttgg      1020
ctgctcgcct atgttgccac ctggattctg cgcgggacgt ccttctgcta cgtcccttcg      1080
gccctcaatc cagcggacct tccttcccgc ggcctgctgc cggctctgcg gcctcttccg      1140
cgtcttcgcc ttcgccctca gacgagtcgg atctcccttt gggccgcctc cccgcatcga      1200
taccgctcga tagatctcga ctgtgccttc tagttgccag ccatctgttg tttgcccctc      1260
ccccgtgcct tccttgaccc tggaaggtgc cactcccact gtcctttcct aataaaatga      1320
ggaaattgca tcgcattgtc tgagtaggtg tcattctatt ctgggggtg gggtggggca      1380 ggacagcaag ggggaggatt gggaagacaa tagcaggcat gctggggatg cggtgggctc      1440
tatggctcga ggacgcttcc gagtacggta caggcacgtg cggaccgagc ggccgcagga      1500 accccctagtg atggagttgg ccactccctc tctgcgcgct cgctcgctca ctgaggccgg      1560
gcgaccaaag gtcgcccgac gcccgggctt tgcccgggcg gcctcagtga gcgagcgagc      1620
gcgcagctgc ctgcagggc gcctgatgcg gtattttctc cttacgcatc tgtgcggtat      1680
ttcacaccgc atacgtcaaa gcaaccatag tacgcgccct gtagcggcgc attaagcgcg     1740
gcgggtgtgg tggttacgcg cagcgtgacc gctacacttg ccagcgccct agcgcccgct     1800 ccttttcgctt tcttcccttc ctttctcgcc acgttcgccg gctttccccg tcaagctcta     1860 aatcggggc tccctttagg gttccgattt agtgctttac ggcacctcga ccccaaaaaa     1920
```

```
cttgatttgg gtgatggttc acgtagtggg ccatcgccct gatagacggt ttttcgccct    1980
ttgacgttgg agtccacgtt ctttaatagt ggactcttgt tccaaactgg aacaacactc    2040
aaccctatct cgggctattc ttttgattta taagggattt tgccgatttc ggcctattgg    2100
ttaaaaaatg agctgattta acaaaaattt aacgcgaatt ttaacaaaat attaacgttt    2160
acaattttat ggtgcactct cagtacaatc tgctctgatg ccgcatagtt aagccagccc    2220
cgacacccgc caacacccgc tgacgcgccc tgacgggctt gtctgctccc ggcatccgct    2280
tacagacaag ctgtgaccgt ctccgggagc tgcatgtgtc agaggttttc accgtcatca    2340
ccgaaacgcg cgagacgaaa gggcctcgtg atacgcctat ttttataggt taatgtcatg    2400
ataataatgg tttcttagac gtcaggtggc acttttcggg gaaatgtgcg cggaacccct    2460
atttgtttat ttttctaaat acattcaaat atgtatccgc tcatgagaca ataaccctga    2520
taaatgcttc aataatattg aaaaaggaag agtatgagta ttcaacattt ccgtgtcgcc    2580
cttattccct tttttgcggc attttgcctt cctgtttttg ctcacccaga aacgctggtg    2640
aaagtaaaag atgctgaaga tcagttgggt gcacgagtgg gttacatcga actggatctc    2700
aacagcggta agatccttga gtttttcgc cccgaagaac gttttccaat gatgagcact    2760
tttaaagttc tgctatgtgg cgcggtatta tcccgtattg acgccgggca agagcaactc    2820
ggtcgccgca tacactattc tcagaatgac ttggttgagt actcaccagt cacagaaaag    2880
catcttacgg atggcatgac agtaagagaa ttatgcagtg ctgccataac catgagtgat    2940
aacactgcgg ccaacttact tctgacaacg atcggaggac cgaaggagct aaccgctttt    3000
ttgcacaaca tgggggatca tgtaactcgc cttgatcgtt gggaaccgga gctgaatgaa    3060
gccataccaa acgacgagcg tgacaccacg atgcctgtag caatggcaac aacgttgcgc    3120
aaactattaa ctggcgaact acttactcta gcttcccggc aacaattaat agactggatg    3180
gaggcggata aagttgcagg accacttctg cgctcggccc ttccggctgg ctggtttatt    3240
gctgataaat ctggagccgg tgagcgtggg tctcgcggta tcattgcagc actggggcca    3300
gatggtaagc cctcccgtat cgtagttatc tacacgacgg ggagtcaggc aactatggat    3360
gaacgaaata gacagatcgc tgagataggt gcctcactga ttaagcattg gtaactgtca    3420
gaccaagttt actcatatat actttagatt gatttaaaac ttcattttta atttaaaagg    3480
atctaggtga agatcctttt tgataatctc atgaccaaaa tcccttaacg tgagttttcg    3540
ttccactgag cgtcagaccc cgtagaaaag atcaaaggat cttcttgaga tcctttttt    3600 ctgcgcgtaa tctgctgctt gcaaacaaaa aaaccaccgc taccagcggt ggtttgtttg    3660
ccggatcaag agctaccaac tcttttccg aaggtaactg gcttcagcag agcgcagata    3720
ccaaatactg tccttctagt gtagccgtag ttaggccacc acttcaagaa ctctgtagca    3780
ccgcctacat acctcgctct gctaatcctg ttaccagtgg ctgctgccag tggcgataag    3840
tcgtgtctta ccgggttgga ctcaagacga tagttaccgg ataaggcgca gcggtcgggc    3900
tgaacggggg gttcgtgcac acagcccagc ttggagcgaa cgacctacac cgaactgaga    3960
tacctacagc gtgagctatg agaaagcgcc acgcttcccg aagggagaaa ggcggacagg    4020
tatccggtaa gcggcagggt cggaacagga gagcgcacga gggagcttcc agggggaaac    4080
gcctggtatc tttatagtcc tgtcgggttt cgccacctct gacttgagcg tcgatttttg    4140
tgatgctcgt caggggggcg gagcctatgg aaaaacgcca gcaacgcggc ctttttacgg    4200
ttcctggcct tttgctggcc ttttgctcac atgt                                4234
```

<210> SEQ ID NO 93
<211> LENGTH: 4233
<212> TYPE: DNA
<213> ORGANISM: Artificial Sequence
<220> FEATURE:
<223> OTHER INFORMATION: Synthetic

<400> SEQUENCE: 93

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | taggggttcc | tgcggccgca | cgcgtgaggg | cctatttccc | atgattcctt | 180 |
| catatttgca | tatacgatac | aaggctgtta | gagagataat | tggaattaat | ttgactgtaa | 240 |
| acacaaagat | attagtacaa | atacgtgacg | tagaaagta | ataatttctt | gggtagtttg | 300 |
| cagttttaaa | attatgtttt | aaaatggact | atcatatgct | taccgtaact | tgaaagtatt | 360 |
| tcgatttctt | ggctttatat | atcttgtgga | aaggacgaaa | caccgacgct | tccgagtacg | 420 |
| gtacgtttta | gagctagaaa | tagcaagtta | aaataaggct | agtccgttat | caacttgaaa | 480 |
| aagtggcacc | gagtcggtgc | ttttttttcta | gagacgcttc | cgagtacggt | acaggaggat | 540 |
| cctacccctta | cgatgtaccg | gattacgcat | agctagctag | ctagggatcg | aattcgctta | 600 |
| tcgataatca | acctctggat | tacaaaattt | gtgaaagatt | gactggtatt | cttaactatg | 660 |
| ttgctccttt | tacgctatgt | ggatacgctg | ctttaatgcc | tttgtatcat | gctattgctt | 720 |
| cccgtatggc | tttcattttc | tcctccttgt | ataaatcctg | gttgctgtct | ctttatgagg | 780 |
| agttgtggcc | cgttgtcagg | caacgtggcg | tggtgtgcac | tgtgtttgct | gacgcaaccc | 840 |
| ccactggttg | ggcattgcc | accacctgtc | agctcctttc | cgggactttc | gctttccccc | 900 |
| tccctattgc | cacggcggaa | ctcatcgccg | cctgccttgc | ccgctgctgg | acaggggctc | 960 |
| ggctgttggg | cactgacaat | tccgtggtgt | tgtcgggaa | atcatcgtcc | tttccttggc | 1020 |
| tgctcgccta | tgttgccacc | tggattctgc | gcgggacgtc | cttctgctac | gtcccttcgg | 1080 |
| ccctcaatcc | agcggacctt | ccttcccgcg | gcctgctgcc | ggctctgcgg | cctcttccgc | 1140 |
| gtcttcgcct | tcgccctcag | acgagtcgga | tctcccttg | gccgcctcc | ccgcatcgat | 1200 |
| accgctcgat | agatctcgac | tgtgccttct | agttgccagc | catctgttgt | ttgcccctcc | 1260 |
| cccgtgcctt | ccttgaccct | ggaaggtgcc | actcccactg | tcctttccta | ataaaatgag | 1320 |
| gaaattgcat | cgcattgtct | gagtaggtgt | cattctattc | tggggggtgg | ggtggggcag | 1380 |
| gacagcaagg | gggaggattg | ggaagacaat | agcaggcatg | ctggggatgc | ggtgggctct | 1440 |
| atggctcgag | gacgcttccg | agtacggtac | aggcacgtgc | ggaccgagcg | gccgcaggaa | 1500 |
| cccctagtga | tggagttggc | cactccctct | ctgcgcgctc | gctcgctcac | tgaggccggg | 1560 |
| cgaccaaagg | tcgcccgacg | cccgggcttt | gcccgggcgg | cctcagtgag | cgagcgagcg | 1620 |
| cgcagctgcc | tgcaggggcg | cctgatgcgg | tattttctcc | ttacgcatct | gtgcggtatt | 1680 |
| tcacaccgca | tacgtcaaag | caaccatagt | acgcgccctg | tagcggcgca | ttaagcgcgg | 1740 |
| cgggtgtggt | ggttacgcgc | agcgtgaccg | ctacacttgc | cagcgcccta | gcgcccgctc | 1800 |
| ctttcgcttt | cttcccttcc | tttctcgcca | cgttcgccgg | ctttccccgt | caagctctaa | 1860 |
| atcgggggct | ccctttaggg | ttccgattta | gtgctttacg | gcacctcgac | cccaaaaaac | 1920 |
| ttgatttggg | tgatggttca | cgtagtgggc | catcgccctg | atagacggtt | tttcgccctt | 1980 |
| tgacgttgga | gtccacgttc | tttaatagtg | gactcttgtt | ccaaactgga | acaacactca | 2040 |
| accctatctc | gggctattct | tttgatttat | aagggatttt | gccgatttcg | gcctattggt | 2100 |

```
taaaaaatga gctgatttaa caaaaattta acgcgaattt taacaaaata ttaacgttta   2160
caattttatg gtgcactctc agtacaatct gctctgatgc cgcatagtta agccagcccc   2220
gacacccgcc aacacccgct gacgcgcccct gacgggcttg tctgctcccg gcatccgctt   2280
acagacaagc tgtgaccgtc tccgggagct gcatgtgtca gaggttttca ccgtcatcac   2340
cgaaacgcgc gagacgaaag ggcctcgtga tacgcctatt tttataggtt aatgtcatga   2400
taataatggt ttcttagacg tcaggtggca cttttcgggg aaatgtgcgc ggaaccccta   2460
tttgtttatt tttctaaata cattcaaata tgtatccgct catgagacaa taaccctgat   2520
aaatgcttca ataatattga aaaggaaga gtatgagtat tcaacatttc cgtgtcgccc   2580
ttattccctt ttttgcggca ttttgccttc ctgtttttgc tcacccagaa acgctggtga   2640
aagtaaaaga tgctgaagat cagttgggtg cacgagtggg ttacatcgaa ctggatctca   2700
acagcggtaa gatccttgag agttttcgcc ccgaagaacg ttttccaatg atgagcactt   2760
ttaaagttct gctatgtggc gcggtattat cccgtattga cgccgggcaa gagcaactcg   2820
gtcgccgcat acactattct cagaatgact tggttgagta ctcaccagtc acagaaaagc   2880
atcttacgga tggcatgaca gtaagagaat tatgcagtgc tgccataacc atgagtgata   2940
acactgcggc caacttactt ctgacaacga tcggaggacc gaaggagcta accgcttttt   3000
tgcacaacat gggggatcat gtaactcgcc ttgatcgttg ggaaccggag ctgaatgaag   3060
ccataccaaa cgacgagcgt gacaccacga tgcctgtagc aatggcaaca acgttgcgca   3120
aactattaac tggcgaacta cttactctag cttcccggca acaattaata gactggatgg   3180
aggcggataa agttgcagga ccacttctgc gctcggccct tccggctggc tggtttattg   3240
ctgataaatc tggagccggt gagcgtgggt ctcgcggtat cattgcagca ctggggccag   3300
atggtaagcc ctcccgtatc gtagttatct acacgacggg gagtcaggca actatggatg   3360
aacgaaatag acagatcgct gagataggtg cctcactgat taagcattgg taactgtcag   3420
accaagttta ctcatatata ctttagattg atttaaaact tcatttttaa tttaaaagga   3480
tctaggtgaa gatcctttt gataatctca tgaccaaaat cccttaacgt gagttttcgt   3540
tccactgagc gtcagacccc gtagaaaaga tcaaaggatc ttcttgagat cctttttttc   3600
tgcgcgtaat ctgctgcttg caaacaaaaa aaccaccgct accagcggtg gtttgtttgc   3660
cggatcaaga gctaccaact ctttttccga aggtaactgg cttcagcaga gcgcagatac   3720
caaatactgt ccttctagtg tagccgtagt taggccacca cttcaagaac tctgtagcac   3780
cgcctacata cctcgctctg ctaatcctgt taccagtggc tgctgccagt ggcgataagt   3840
cgtgtcttac cgggttggac tcaagacgat agttaccgga taaggcgcag cggtcgggct   3900 gaacggggg ttcgtgcaca cagcccagct tggagcgaac gacctacacc gaactgagat   3960
acctacagcg tgagctatga gaaagcgcca cgcttcccga agggagaaag gcggacaggt   4020
atccggtaag cggcagggtc ggaacaggag agcgcacgag ggagcttcca gggggaaacg   4080
cctggtatct ttatagtcct gtcgggtttc gccacctctg acttgagcgt cgatttttgt   4140
gatgctcgtc aggggggcgg agcctatgga aaaacgccag caacgcggcc ttttacggt    4200 tcctggcctt ttgctggcct tttgctcaca tgt                                4233
```

<210> SEQ ID NO 94
<211> LENGTH: 3403
<212> TYPE: DNA
<213> ORGANISM: Artificial Sequence
<220> FEATURE:

<223> OTHER INFORMATION: Synthetic

<400> SEQUENCE: 94

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa atacgtgac gtagaaagta ataatttctt gggtagtttg      300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttttcta gacctgtacc gtactcggaa gcgtcggatc     540
cataccctta cgatgtaccg gattacgcat agctagctag ctagagcata gtcaggaacg     600
tcatagggat aaagctcgag cctgtaccgt actcggaagc gtccacgtgc ggaccgagcg     660
gccgcaggaa ccctagtga tggagttggc cactccctct ctgcgcgctc gctcgctcac      720
tgaggccggg cgaccaaagg tcgcccgacg cccgggcttt gccgggcgg cctcagtgag      780
cgagcgagcg cgcagctgcc tgcaggggcg cctgatgcgg tattttctcc ttacgcatct     840
gtgcggtatt tcacaccgca tacgtcaaag caaccatagt acgcgccctg tagcggcgca     900
ttaagcgcgg cgggtgtggt ggttacgcgc agcgtgaccg ctacacttgc cagcgcccta     960
gcgcccgctc ctttcgcttt cttcccttcc tttctcgcca cgttcgccgg ctttccccgt    1020
caagctctaa atcgggggct cccctttaggg ttccgattta gtgctttacg gcacctcgac    1080
cccaaaaaac ttgatttggg tgatggttca cgtagtgggc catcgccctg atagacggtt    1140
tttcgccctt tgacgttgga gtccacgttc tttaatagtg gactcttgtt ccaaactgga    1200
acaacactca accctatctc gggctattct tttgatttat aagggatttt gccgatttcg    1260
gcctattggt taaaaaatga gctgatttaa caaaaattta acgcgaattt taacaaaata    1320
ttaacgttta caattttatg gtgcactctc agtacaatct gctctgatgc cgcatagtta    1380
agccagcccc gacacccgcc aacacccgct gacgcgccct gacgggcttg tctgctcccg    1440
gcatccgctt acagacaagc tgtgaccgtc tccgggagct gcatgtgtca gaggttttca    1500
ccgtcatcac cgaaacgcgc gagacgaaag gcctcgtga tacgcctatt tttataggtt    1560
aatgtcatga taataatggt ttcttagacg tcaggtggca cttttcgggg aaatgtgcgc    1620
ggaaccccta tttgtttatt tttctaaata cattcaaata tgtatccgct catgagacaa    1680
taaccctgat aaatgcttca ataatattga aaaggaaga gtatgagtat tcaacatttc    1740
cgtgtcgccc ttattccctt ttttgcggca ttttgccttc ctgtttttgc tcacccagaa    1800
acgctggtga agtaaaaga tgctgaagat cagttgggtg cacgagtggg ttacatcgaa    1860
ctggatctca acagcggtaa gatccttgag agttttcgcc ccgaagaacg ttttccaatg    1920
atgagcactt ttaaagttct gctatgtggc gcggtattat cccgtattga cgccgggcaa    1980
gagcaactcg gtcgccgcat acactattct cagaatgact tggttgagta ctcaccagtc    2040
acagaaaagc atcttacgga tggcatgaca gtaagagaat tatgcagtgc tgccataacc    2100
atgagtgata acactgcggc caacttactt ctgacaacga tcggaggacc gaaggagcta    2160
accgcttttt tgcacaacat ggggatcat gtaactcgcc ttgatcgttg gaaccggag     2220
ctgaatgaag ccataccaaa cgacgagcgt gacaccacga tgcctgtagc aatggcaaca    2280
```

```
acgttgcgca aactattaac tggcgaacta cttactctag cttcccggca acaattaata    2340
gactggatgg aggcggataa agttgcagga ccacttctgc gctcggccct tccggctggc    2400
tggtttattg ctgataaatc tggagccggt gagcgtgggt ctcgcggtat cattgcagca    2460
ctggggccag atggtaagcc ctcccgtatc gtagttatct acacgacggg gagtcaggca    2520
actatggatg aacgaaatag acagatcgct gagataggtg cctcactgat taagcattgg    2580
taactgtcag accaagttta ctcatatata ctttagattg atttaaaact tcattttaa     2640 tttaaaagga tctaggtgaa gatccttttt gataatctca tgaccaaaat cccttaacgt    2700
gagttttcgt tccactgagc gtcagacccc gtagaaaaga tcaaaggatc ttcttgagat    2760
cctttttttc tgcgcgtaat ctgctgcttg caaacaaaaa aaccaccgct accagcggtg    2820
gtttgtttgc cggatcaaga gctaccaact cttttccga aggtaactgg cttcagcaga    2880
gcgcagatac caaatactgt ccttctagtg tagccgtagt taggccacca cttcaagaac    2940
tctgtagcac cgcctacata cctcgctctg ctaatcctgt taccagtggc tgctgccagt    3000
ggcgataagt cgtgtcttac cgggttggac tcaagacgat agttaccgga taaggcgcag    3060
cggtcgggct gaacggggggg ttcgtgcaca cagcccagct tggagcgaac gacctacacc    3120
gaactgagat acctacagcg tgagctatga gaaagcgcca cgcttcccga agggagaaag    3180
gcggacaggt atccggtaag cggcagggtc ggaacaggag agcgcacgag ggagcttcca    3240
gggggaaacg cctggtatct ttatagtcct gtcgggtttc gccacctctg acttgagcgt    3300
cgatttttgt gatgctcgtc agggggggcgg agcctatgga aaaacgccag caacgcggcc    3360 ttttttacggt tcctggcctt ttgctggcct tttgctcaca tgt                     3403
```

<210> SEQ ID NO 95
<211> LENGTH: 3401
<212> TYPE: DNA
<213> ORGANISM: Artificial Sequence
<220> FEATURE:
<223> OTHER INFORMATION: Synthetic

<400> SEQUENCE: 95

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aggacgaaa caccgacgct tccgagtacg     420
gtacgtttta gagctagaaa tagcaagtta aaataaggct agtccgttat caacttgaaa     480
aagtggcacc gagtcggtgc ttttttttcta gacctgtacc gtactcggaa gcgtcggatc    540
ctacccttac gatgtaccgg attacgcata gctagctagc tagagcatag tcaggaacgt    600
catagggata agctcgagcc tgtaccgtac tcggaagcgt ccacgtgcgg accgagcggc     660
cgcaggaacc cctagtgatg gagttggcca ctccctctct gcgcgctcgc tcgctcactg    720
aggccgggcg accaaaggtc gcccgacgcc cgggctttgc ccgggcggcc tcagtgagcg    780
agcgagcgcg cagctgcctg caggggcgcc tgatgcggta ttttctcctt acgcatctgt    840
gcggtatttc acaccgcata cgtcaaagca accatagtac gcgccctgta gcggcgcatt    900
```

-continued

```
aagcgcggcg ggtgtggtgg ttacgcgcag cgtgaccgct acacttgcca gcgccctagc    960
gcccgctcct ttcgctttct tcccttcctt tctcgccacg ttcgccggct ttccccgtca   1020
agctctaaat cggggctcc ctttagggtt ccgatttagt gctttacggc acctcgaccc   1080
caaaaaactt gatttgggtg atggttcacg tagtgggcca tcgccctgat agacggtttt   1140
tcgcccttg acgttggagt ccacgttctt taatagtgga ctcttgttcc aaactggaac   1200
aacactcaac cctatctcgg gctattcttt tgatttataa gggattttgc cgatttcggc   1260
ctattggtta aaaatgagc tgatttaaca aaaatttaac gcgaatttta acaaaatatt   1320
aacgtttaca atttatggt gcactctcag tacaatctgc tctgatgccg catagttaag   1380
ccagccccga cacccgccaa cacccgctga cgcgccctga cgggcttgtc tgctcccggc   1440
atccgcttac agacaagctg tgaccgtctc cgggagctgc atgtgtcaga ggttttcacc   1500
gtcatcaccg aaacgcgcga gacgaaaggg cctcgtgata cgcctatttt tataggttaa   1560
tgtcatgata taatggtttc ttagacgtc aggtggcact tttcggggaa atgtgcgcgg   1620
aaccccatt tgtttatttt tctaaataca ttcaaatatg tatccgctca tgagacaata   1680
accctgataa atgcttcaat aatattgaaa aggaagagt atgagtattc aacatttccg   1740
tgtcgccctt attccctttt ttgcggcatt ttgccttcct gttttgctc acccagaaac   1800
gctggtgaaa gtaaaagatg ctgaagatca gttgggtgca cgagtgggtt acatcgaact   1860
ggatctcaac agcggtaaga tccttgagag ttttcgcccc gaagaacgtt ttccaatgat   1920
gagcactttt aaagttctgc tatgtggcgc ggtattatcc cgtattgacg ccgggcaaga   1980
gcaactcggt cgccgcatac actattctca gaatgacttg gttgagtact caccagtcac   2040
agaaaagcat cttacggatg gcatgacagt aagagaatta tgcagtgctg ccataaccat   2100
gagtgataac actgcggcca acttacttct gacaacgatc ggaggaccga aggagctaac   2160
cgcttttttg cacaacatgg ggatcatgt aactcgcctt gatcgttggg aaccggagct   2220
gaatgaagcc ataccaaacg acgagcgtga ccacgatg cctgtagcaa tggcaacaac   2280
gttgcgcaaa ctattaactg gcgaactact tactctagct tcccggcaac aattaataga   2340
ctggatggag gcggataaag ttgcaggacc acttctgcgc tcggcccttc cggctggctg   2400
gtttattgct gataaatctg gagccggtga gcgtgggtct cgcggtatca ttgcagcact   2460
ggggccagat ggtaagccct cccgtatcgt agttatctac acgacgggga gtcaggcaac   2520
tatggatgaa cgaaatagac agatcgctga gataggtgcc tcactgatta gcattggta   2580
actgtcagac caagtttact catatatact ttagattgat ttaaaacttc attttttaatt   2640
taaaaggatc taggtgaaga tccttttga taatctcatg accaaaatcc cttaacgtga   2700
gttttcgttc cactgagcgt cagaccccgt agaaaagatc aaaggatctt cttgagatcc   2760
ttttttttctg cgcgtaatct gctgcttgca acaaaaaaa ccaccgctac cagcggtggt   2820
ttgtttgccg gatcaagagc taccaactct ttttccgaag gtaactggct tcagcagagc   2880
gcagatacca atactgtcc ttctagtgta gccgtagtta ggccaccact tcaagaactc   2940
tgtagcaccg cctacatacc tcgctctgct aatcctgtta ccagtggctg ctgccagtgg   3000
cgataagtcg tgtcttaccg ggttggactc aagacgatag ttaccggata aggcgcagcg   3060
gtcgggctga acgggggt cgtgcacaca gcccagcttg gagcgaacga cctacaccga   3120
actgagatac ctacagcgtg agctatgaga aagcgccacg cttcccgaag ggagaaaggc   3180
ggacaggtat ccggtaagcg gcagggtcgg aacaggagag cgcacgaggg agcttccagg   3240
gggaaacgcc tggtatcttt atagtcctgt cgggtttcgc cacctctgac ttgagcgtcg   3300
```

```
atttttgtga tgctcgtcag gggggcggag cctatggaaa aacgccagca acgcggcctt   3360
tttacggttc ctggccttttt gctggccttt tgctcacatg t                     3401
```

<210> SEQ ID NO 96
<211> LENGTH: 3402
<212> TYPE: DNA
<213> ORGANISM: Artificial Sequence
<220> FEATURE:
<223> OTHER INFORMATION: Synthetic

<400> SEQUENCE: 96

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300 cagtttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttcta gacctgtacc gtactcggaa gcgtcggatc    540 caatacccctt acgatgtacc ggattacgca tagctagcta gctagagcat agtcaggaac    600
gtcataggga tagctcgagc ctgtaccgta ctcggaagcg tccacgtgcg gaccgagcgg    660
ccgcaggaac ccctagtgat ggagttggcc actccctctc tgcgcgctcg ctcgctcact    720
gaggccgggc gaccaaaggt cgcccgacgc ccgggctttg cccgggcggc ctcagtgagc    780
gagcgagcgc gcagctgcct gcaggggcgc ctgatgcggt attttctcct tacgcatctg    840
tgcggtattt cacaccgcat acgtcaaagc aaccatagta cgcgccctgt agcggcgcat    900
taagcgcggc gggtgtggtg gttacgcgca gcgtgaccgc tacacttgcc agcgccctag    960
cgcccgctcc tttcgctttc ttcccttcct ttctcgccac gttcgccggc tttccccgtc   1020
aagctctaaa tcggggctc cctttagggt tccgatttag tgctttacgg cacctcgacc   1080
ccaaaaaact tgatttgggt gatggttcac gtagtgggcc atcgccctga tagacggttt   1140
ttcgcccttt gacgttggag tccacgttct ttaatagtgg actcttgttc caaactggaa   1200
caacactcaa ccctatctcg ggctattctt ttgatttata agggattttg ccgatttcgg   1260
cctattggtt aaaaaatgag ctgatttaac aaaaatttaa cgcgaatttt aacaaaatat   1320
taacgtttac aattttatgg tgcactctca gtacaatctg ctctgatgcc gcatagttaa   1380
gccagccccg acaccgcca acaccgctg acgcgcctg acgggcttgt ctgctcccgg   1440
catccgctta cagacaagct gtgaccgtct ccgggagctg catgtgtcag aggttttcac   1500
cgtcatcacc gaaacgcgcg agacgaaagg gcctcgtgat acgcctattt ttataggtta   1560
atgtcatgat aataatggtt tcttagacgt caggtggcac ttttcgggga atgtgcgcg   1620 gaacccctat ttgtttattt ttctaaatac attcaaatat gtatccgctc atgagacaat   1680
aaccctgata aatgcttcaa taatattgaa aaaggaagag tatgagtatt caacatttcc   1740
gtgtcgccct tattcccttt tttgcggcat tttgccttcc tgtttttgct cacccagaaa   1800
cgctggtgaa agtaaaagat gctgaagatc agttgggtgc acgagtgggt tacatcgaac   1860
tggatctcaa cagcggtaag atccttgaga gttttcgccc cgaagaacgt tttccaatga   1920
```

| | |
|---|---|
| tgagcacttt taaagttctg ctatgtggcg cggtattatc ccgtattgac gccgggcaag | 1980 |
| agcaactcgg tcgccgcata cactattctc agaatgactt ggttgagtac tcaccagtca | 2040 |
| cagaaaagca tcttacggat ggcatgacag taagagaatt atgcagtgct gccataacca | 2100 |
| tgagtgataa cactgcggcc aacttacttc tgacaacgat cggaggaccg aaggagctaa | 2160 |
| ccgcttttt gcacaacatg ggggatcatg taactcgcct tgatcgttgg gaaccggagc | 2220 |
| tgaatgaagc cataccaaac gacgagcgtg acaccacgat gcctgtagca atggcaacaa | 2280 |
| cgttgcgcaa actattaact ggcgaactac ttactctagc ttcccggcaa caattaatag | 2340 |
| actggatgga ggcggataaa gttgcaggac cacttctgcg ctcggccctt ccggctggct | 2400 |
| ggtttattgc tgataaatct ggagccggtg agcgtgggtc tcgcggtatc attgcagcac | 2460 |
| tggggccaga tggtaagccc tcccgtatcg tagttatcta cacgacgggg agtcaggcaa | 2520 |
| ctatggatga acgaaataga cagatcgctg agataggtgc ctcactgatt aagcattggt | 2580 |
| aactgtcaga ccaagtttac tcatatatac tttagattga tttaaaactt cattttaat | 2640 |
| ttaaaaggat ctaggtgaag atcctttttg ataatctcat gaccaaaatc ccttaacgtg | 2700 |
| agttttcgtt ccactgagcg tcagacccg tagaaaagat caaaggatct tcttgagatc | 2760 |
| cttttttct gcgcgtaatc tgctgcttgc aaacaaaaaa accaccgcta ccagcggtgg | 2820 |
| tttgtttgcc ggatcaagag ctaccaactc tttttccgaa ggtaactggc ttcagcagag | 2880 |
| cgcagatacc aaatactgtc cttctagtgt agccgtagtt aggccaccac ttcaagaact | 2940 |
| ctgtagcacc gcctacatac ctcgctctgc taatcctgtt accagtggct gctgccagtg | 3000 |
| gcgataagtc gtgtcttacc gggttggact caagacgata gttaccggat aaggcgcagc | 3060 |
| ggtcgggctg aacggggggt tcgtgcacac agcccagctt ggagcgaacg acctacaccg | 3120 |
| aactgagata cctacagcgt gagctatgag aaagcgccac gcttcccgaa gggagaaagg | 3180 |
| cggacaggta tccggtaagc ggcagggtcg aacaggaga gcgcacgagg gagcttccag | 3240 |
| ggggaaacgc ctggtatctt tatagtcctg tcgggtttcg ccacctctga cttgagcgtc | 3300 |
| gatttttgtg atgctcgtca ggggggcgga gcctatggaa aaacgccagc aacgcggcct | 3360 |
| ttttacggtt cctggccttt tgctggcctt ttgctcacat gt | 3402 |

<210> SEQ ID NO 97
<211> LENGTH: 3409
<212> TYPE: DNA
<213> ORGANISM: Artificial Sequence
<220> FEATURE:
<223> OTHER INFORMATION: Synthetic

<400> SEQUENCE: 97

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gacctgtacc gtactcggaa gcgtcggatc | 540 |
| cagaacaaaa actcatctca gaagaggatc tgtagctagc tagctagaag tcttcctcc | 600 |

```
gaaataagct tctgctcaag ctcgagcctg taccgtactc ggaagcgtcc acgtgcggac    660
cgagcggccg caggaacccc tagtgatgga gttggccact ccctctctgc gcgctcgctc    720
gctcactgag gccgggcgac caaaggtcgc ccgacgcccg ggctttgccc gggcggcctc    780
agtgagcgag cgagcgcgca gctgcctgca ggggcgcctc atgcggtatt ttctccttac    840
gcatctgtgc ggtatttcac accgcatacg tcaaagcaac catagtacgc gccctgtagc    900
ggcgcattaa gcgcggcggg tgtggtggtt acgcgcagcg tgaccgctac acttgccagc    960
gccctagcgc ccgctccttt cgctttcttc ccttcctttc tcgccacgtt cgccggcttt   1020
ccccgtcaag ctctaaatcg ggggctccct ttagggttcc gatttagtgc tttacggcac   1080
ctcgacccca aaaaacttga tttgggtgat ggttcacgta gtgggccatc gccctgatag   1140
acggtttttc gccctttgac gttggagtcc acgttcttta atagtggact cttgttccaa   1200
actggaacaa cactcaaccc tatctcgggc tattcttttg atttataagg gattttgccg   1260
atttcggcct attggttaaa aaatgagctg atttaacaaa aatttaacgc gaattttaac   1320
aaaatattaa cgtttacaat tttatggtgc actctcagta caatctgctc tgatgccgca   1380
tagttaagcc agccccgaca cccgccaaca cccgctgacg cgccctgacg gcttgtctg    1440 ctcccggcat ccgcttacag acaagctgtg accgtctccg ggagctgcat gtgtcagagg   1500
ttttcaccgt catcaccgaa acgcgcgaga cgaaagggcc tcgtgatacg cctattttta   1560
taggttaatg tcatgataat aatggtttct tagacgtcag gtggcacttt tcggggaaat   1620
gtgcgcggaa cccctatttg tttattttc taaatacatt caaatatgta tccgctcatg   1680
agacaataac cctgataaat gcttcaataa tattgaaaaa ggaagagtat gagtattcaa   1740
catttccgtg tcgcccttat tcccttttttt gcggcatttt gccttcctgt ttttgctcac   1800
ccagaaacgc tggtgaaagt aaaagatgct gaagatcagt tgggtgcacg agtgggttac   1860
atcgaactgg atctcaacag cggtaagatc cttgagagtt ttcgccccga gaacgttttt   1920
ccaatgatga gcacttttaa agttctgcta tgtggcgcgg tattatcccg tattgacgcc   1980
gggcaagagc aactcggtcg ccgcatacac tattctcaga atgacttggt tgagtactca   2040
ccagtcacag aaaagcatct tacggatggc atgacagtaa gagaattatg cagtgctgcc   2100
ataaccatga gtgataacac tgcggccaac ttacttctga caacgatcgg aggaccgaag   2160
gagctaaccg cttttttgca acatgggg gatcatgtaa ctcgccttga tcgttgggaa   2220
ccggagctga atgaagccat accaaacgac gagcgtgaca ccacgatgcc tgtagcaatg   2280
gcaacaacgt tgcgcaaact attaactggc gaactactta ctctagcttc ccggcaacaa   2340
ttaatagact ggatggaggc ggataaagtt gcaggaccac ttctgcgctc ggcccttccg   2400
gctggctggt ttattgctga taaatctgga gccggtgagc gtgggtctcg cggtatcatt   2460
gcagcactgg ggccagatgg taagccctcc cgtatcgtag ttatctacac gacggggagt   2520
caggcaacta tggatgaacg aaatagacag atcgctgaga taggtgcctc actgattaag   2580
cattggtaac tgtcagacca agtttactca tatatacttt agattgattt aaaacttcat   2640
ttttaattta aaaggatcta ggtgaagatc ctttttgata atctcatgac caaaatccct   2700
taacgtgagt tttcgttcca ctgagcgtca gaccccgtag aaaagatcaa aggatcttct   2760
tgagatcctt ttttctgcg cgtaatctgc tgcttgcaaa caaaaaaacc accgctacca   2820
gcggtggttt gtttgccgga tcaagagcta ccaactcttt ttccgaaggt aactggcttc   2880
agcagagcgc agataccaaa tactgtcctt ctagtgtagc cgtagttagg ccaccacttc   2940
```

-continued

| | |
|---|---|
| aagaactctg tagcaccgcc tacataccct gctctgctaa tcctgttacc agtggctgct | 3000 |
| gccagtggcg ataagtcgtg tcttaccggg ttggactcaa gacgatagtt accggataag | 3060 |
| gcgcagcggt cgggctgaac ggggggttcg tgcacacagc ccagcttgga gcgaacgacc | 3120 |
| tacaccgaac tgagatacct acagcgtgag ctatgagaaa gcgccacgct tcccgaaggg | 3180 |
| agaaaggcgg acaggtatcc ggtaagcggc agggtcggaa caggagagcg cacgagggag | 3240 |
| cttccagggg gaaacgcctg gtatctttat agtcctgtcg ggtttcgcca cctctgactt | 3300 |
| gagcgtcgat ttttgtgatg ctcgtcaggg gggcggagcc tatggaaaaa cgccagcaac | 3360 |
| gcggcctttt tacggttcct ggccttttgc tggccttttg ctcacatgt | 3409 |

```
<210> SEQ ID NO 98
<211> LENGTH: 3407
<212> TYPE: DNA
<213> ORGANISM: Artificial Sequence
<220> FEATURE:
<223> OTHER INFORMATION: Synthetic

<400> SEQUENCE: 98
```

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gacctgtacc gtactcggaa cgtcggatc | 540 |
| cgaacaaaaa ctcatctcag aaggatct gtagctagct agctagaagg tcttcctccg | 600 |
| aaataagctt ctgctcagct cgagcctgta ccgtactcgg aagcgtccac gtgcggaccg | 660 |
| agcggccgca ggaacccta gtgatggagt tggccactcc ctctctgcgc gctcgctcgc | 720 |
| tcactgaggc cgggcgacca aaggtcgccc gacgcccggg cttgccgg gcggcctcag | 780 |
| tgagcgagcg agcgcgcagc tgcctgcagg ggcgcctgat gcggtatttt ctccttacgc | 840 |
| atctgtgcgg tatttcacac cgcatacgtc aaagcaacca tagtacgcgc cctgtagcgg | 900 |
| cgcattaagc gcggcgggtg tggtggttac gcgcagcgtg accgctacac ttgccagcgc | 960 |
| cctagcgccc gctcctttcg ctttcttccc ttcctttctc gccacgttcg ccggctttcc | 1020 |
| ccgtcaagct ctaaatcggg ggctcccttt agggttccga tttagtgctt tacggcacct | 1080 |
| cgaccccaaa aaacttgatt tgggtgatgg ttcacgtagt gggccatcgc cctgatagac | 1140 |
| ggtttttcgc cctttgacgt tggagtccac gttctttaat agtggactct tgttccaaac | 1200 |
| tggaacaaca ctcaacccta tctcgggcta ttcttttgat ttataaggga ttttgccgat | 1260 |
| ttcggcctat tggttaaaaa atgagctgat ttaacaaaaa tttaacgcga attttaacaa | 1320 |
| aatattaacg tttacaattt tatggtgcac tctcagtaca atctgctctg atgccgcata | 1380 |
| gttaagccag ccccgacacc cgccaacacc cgctgacgcg ccctgacggg cttgtctgct | 1440 |
| cccggcatcc gcttacagac aagctgtgac cgtctccggg agctgcatgt gtcagaggtt | 1500 |
| ttcaccgtca tcaccgaaac gcgcgagacg aaagggcctc gtgatacgcc tatttttata | 1560 |
| ggttaatgtc atgataataa tggtttctta gacgtcaggt ggcactttc ggggaaatgt | 1620 |

```
gcgcggaacc cctatttgtt tattttttcta aatacattca aatatgtatc cgctcatgag   1680
acaataaccc tgataaatgc ttcaataata ttgaaaaagg aagagtatga gtattcaaca   1740
tttccgtgtc gcccttattc cctttttttgc ggcattttgc cttcctgttt ttgctcaccc   1800
agaaacgctg gtgaaagtaa aagatgctga agatcagttg ggtgcacgag tgggttacat   1860
cgaactggat ctcaacagcg gtaagatcct tgagagtttt cgccccgaag aacgttttcc   1920
aatgatgagc acttttaaag ttctgctatg tggcgcggta ttatcccgta ttgacgccgg   1980
gcaagagcaa ctcggtcgcc gcatacacta ttctcagaat gacttggttg agtactcacc   2040
agtcacagaa aagcatctta cggatggcat gacagtaaga gaattatgca gtgctgccat   2100
aaccatgagt gataacactg cggccaactt acttctgaca acgatcggag gaccgaagga   2160
gctaaccgct tttttgcaca acatggggga tcatgtaact cgccttgatc gttgggaacc   2220
ggagctgaat gaagccatac caaacgacga gcgtgacacc acgatgcctg tagcaatggc   2280
aacaacgttg cgcaaactat taactggcga actacttact ctagcttccc ggcaacaatt   2340
aatagactgg atggaggcgg ataaagttgc aggaccactt ctgcgctcgg cccttccggc   2400
tggctggttt attgctgata atctggagcc ggtgagcgt gggtctcgcg gtatcattgc   2460
agcactgggg ccagatggta agccctcccg tatcgtagtt atctacacga cggggagtca   2520
ggcaactatg gatgaacgaa atagacagat cgctgagata ggtgcctcac tgattaagca   2580
ttggtaactg tcagaccaag tttactcata tatactttag attgatttaa aacttcattt   2640
ttaatttaaa aggatctagg tgaagatcct ttttgataat ctcatgacca aaatccctta   2700
acgtgagttt tcgttccact gagcgtcaga ccccgtagaa aagatcaaag gatcttcttg   2760
agatcctttt tttctgcgcg taatctgctg cttgcaaaca aaaaaaccac cgctaccagc   2820
ggtggtttgt ttgccggatc aagagctacc aactcttttt ccgaaggtaa ctggcttcag   2880
cagagcgcag ataccaaata ctgtccttct agtgtagccg tagttaggcc accacttcaa   2940
gaactctgta gcaccgccta catacctcgc tctgctaatc ctgttaccag tggctgctgc   3000
cagtggcgat aagtcgtgtc ttaccgggtt ggactcaaga cgatagttac cggataaggc   3060
gcagcggtcg ggctgaacgg ggggttcgtg cacacagccc agcttggagc gaacgaccta   3120
caccgaactg agatacctac agcgtgagct atgagaaagc gccacgcttc ccgaagggag   3180
aaaggcggac aggtatccgg taagcggcag ggtcggaaca ggagagcgca cgaggagct   3240 tccaggggga aacgcctggt atctttatag tcctgtcggg tttcgccacc tctgacttga   3300
gcgtcgattt ttgtgatgct cgtcaggggg gcggagccta tggaaaaacg ccagcaacgc   3360 ggcctttta cggttcctgg ccttttgctg gccttttgct cacatgt         3407
```

<210> SEQ ID NO 99  
<211> LENGTH: 3408  
<212> TYPE: DNA  
<213> ORGANISM: Artificial Sequence  
<220> FEATURE:  
<223> OTHER INFORMATION: Synthetic

<400> SEQUENCE: 99

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tcggccgca cgcgtgaggg cctatttccc atgattcctt    180
catatttgca tatacgatac aaggctgtta gagagataat tggaattaat ttgactgtaa    240
```

```
acacaaagat attagtacaa aatacgtgac gtagaaagta ataatttctt gggtagtttg      300
cagttttaaa attatgtttt aaaatggact atcatatgct taccgtaact tgaaagtatt      360
tcgatttctt ggctttatat atcttgtgga aaggacgaaa caccgacgct tccgagtacg      420
gtacgtttta gagctagaaa tagcaagtta aaataaggct agtccgttat caacttgaaa      480
aagtggcacc gagtcggtgc ttttttttcta gacctgtacc gtactcggaa gcgtcggatc      540
caagaacaaa aactcatctc agaagaggat ctgtagctag ctagctagaa ggtcttcctc      600
cgaaataagc ttctgctcgc tcgagcctgt accgtactcg gaagcgtcca cgtgcggacc      660
gagcggccgc aggaacccct agtgatggag ttggccactc cctctctgcg cgctcgctcg      720
ctcactgagg ccgggcgacc aaaggtcgcc cgacgcccgg gctttgcccg gcggcctca      780
gtgagcgagc gagcgcgcag ctgcctgcag gggcgcctga tgcggtattt tctccttacg      840
catctgtgcg gtatttcaca ccgcatacgt caaagcaacc atagtacgcg ccctgtagcg      900
gcgcattaag cgcggcgggt gtggtggtta cgcgcagcgt gaccgctaca cttgccagcg      960
ccctagcgcc cgctcctttc gctttcttcc cttcctttct cgccacgttc gccggctttc     1020
cccgtcaagc tctaaatcgg gggctcccctt tagggttccg atttagtgct ttacggcacc     1080
tcgaccccaa aaaacttgat ttgggtgatg gttcacgtag tgggccatcg ccctgataga     1140
cggttttttcg ccctttgacg ttggagtcca cgttctttaa tagtggactc ttgttccaaa     1200
ctggaacaac actcaaccct atctcgggct attcttttga tttataaggg attttgccga     1260
tttcggccta ttggttaaaa aatgagctga tttaacaaaa atttaacgcg aattttaaca     1320
aaatattaac gtttacaatt ttatggtgca ctctcagtac aatctgctct gatgccgcat     1380
agttaagcca gccccgacac ccgccaacac ccgctgacgc gccctgacgg gcttgtctgc     1440
tcccggcatc cgcttacaga caagctgtga ccgtctccgg gagctgcatg tgtcagaggt     1500
tttcaccgtc atcaccgaaa cgcgcgagac gaaagggcct cgtgatacgc ctatttttat     1560
aggttaatgt catgataata atggtttctt agacgtcagg tggcactttt cggggaaatg     1620
tgcgcggaac ccctatttgt ttatttttct aaatacattc aaatatgtat ccgctcatga     1680
gacaataacc ctgataaatg cttcaataat attgaaaaag gaagagtatg agtattcaac     1740
atttccgtgt cgcccttatt cccttttttg cggcattttg ccttcctgtt tttgctcacc     1800
cagaaacgct ggtgaaagta aaagatgctg aagatcagtt gggtgcacga gtgggttaca     1860
tcgaactgga tctcaacagc ggtaagatcc ttgagagttt tcgccccgaa gaacgttttc     1920
caatgatgag cacttttaaa gttctgctat gtggcgcggt attatcccgt attgacgccg     1980
ggcaagagca actcggtcgc cgcatacact attctcagaa tgacttggtt gagtactcac     2040
cagtcacaga aaagcatctt acggatggca tgacagtaag agaattatgc agtgctgcca     2100
taaccatgag tgataacact gcggccaact tacttctgac aacgatcgga ggaccgaagg     2160
agctaaccgc ttttttgcac aacatggggg atcatgtaac tcgccttgat cgttgggaac     2220
cggagctgaa tgaagccata ccaaacgacg agcgtgacac cacgatgcct gtagcaatgg     2280
caacaacgtt gcgcaaacta ttaactggcg aactacttac tctagcttcc cggcaacaat     2340
taatagactg gatggaggcg gataaagttg caggaccact tctgcgctcg gcccttccgg     2400
ctggctggtt tattgctgat aaatctggag ccggtgagcg tgggtctcgc ggtatcattg     2460
cagcactggg gccagatggt aagccctccc gtatcgtagt tatctacacg acggggagtc     2520
aggcaactat ggatgaacga aatagacaga tcgctgagat aggtgcctca ctgattaagc     2580
attggtaact gtcagaccaa gtttactcat atatacttta gattgattta aaacttcatt     2640
```

```
tttaatttaa aaggatctag gtgaagatcc tttttgataa tctcatgacc aaaatcccct   2700
aacgtgagtt ttcgttccac tgagcgtcag accccgtaga aaagatcaaa ggatcttct   2760 gagatccttt ttttctgcgc gtaatctgct gcttgcaaac aaaaaaacca ccgctaccag   2820
cggtggtttg tttgccggat caagagctac caactctttt tccgaaggta actggcttca   2880
gcagagcgca gataccaaat actgtccttc tagtgtagcc gtagttaggc caccacttca   2940
agaactctgt agcaccgcct acatacccg ctctgctaat cctgttacca gtggctgctg   3000
ccagtggcga taagtcgtgt cttaccgggt tggactcaag acgatagtta ccggataagg   3060
cgcagcggtc gggctgaacg gggggttcgt gcacacagcc cagcttggag cgaacgacct   3120
acaccgaact gagataccta cagcgtgagc tatgagaaag cgccacgctt cccgaaggga   3180
gaaaggcgga caggtatccg gtaagcggca gggtcggaac aggagagcgc acgagggagc   3240
ttccaggggg aaacgcctgg tatctttata gtcctgtcgg gtttcgccac ctctgacttg   3300
agcgtcgatt tttgtgatgc tcgtcagggg gcggagcct atggaaaaac gccagcaacg   3360
cggccttttt acggttcctg gccttttgct ggccttttgc tcacatgt   3408
```

<210> SEQ ID NO 100
<211> LENGTH: 3388
<212> TYPE: DNA
<213> ORGANISM: Artificial Sequence
<220> FEATURE:
<223> OTHER INFORMATION: Synthetic

<400> SEQUENCE: 100

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggggatc    540
cgtttagcta gctagctagg ccaccatgga acaaaaactc atctcagaag aggatctggc    600
tcgaggacgc ttccgagtac ggtacaggca cgtgcggacc gagcggccgc aggaacccct    660
agtgatggag ttggccactc cctctctgcg cgctcgctcg ctcactgagg ccgggcgacc    720
aaaggtcgcc cgacgcccgg gctttgcccg ggcggcctca gtgagcgagc gagcgcgcag    780
ctgcctgcag gggcgcctga tgcggtattt tctccttacg catctgtgcg gtatttcaca    840
ccgcatacgt caaagcaacc atagtacgcg ccctgtagcg gcgcattaag cgcggcgggt    900
gtggtggtta cgcgcagcgt gaccgctaca cttgccagcg ccctagcgcc cgctcctttc    960
gctttcttcc cttcctttct cgccacgttc gccggctttc cccgtcaagc tctaaatcgg   1020
gggctccctt tagggttccg atttagtgct ttacggcacc tcgaccccaa aaaacttgat   1080
ttgggtgatg gttcacgtag tgggccatcg ccctgataga cggttttttcg ccctttgacg   1140 ttggagtcca cgttctttaa tagtggactc ttgttccaaa ctggaacaac actcaaccct   1200
atctcgggct attcttttga tttataaggg attttgccga tttcggccta ttggttaaaa   1260
```

```
aatgagctga tttaacaaaa atttaacgcg aattttaaca aaatattaac gtttacaatt    1320
ttatggtgca ctctcagtac aatctgctct gatgccgcat agttaagcca gccccgacac    1380
ccgccaacac ccgctgacgc gccctgacgg gcttgtctgc tcccggcatc cgcttacaga    1440
caagctgtga ccgtctccgg gagctgcatg tgtcagaggt tttcaccgtc atcaccgaaa    1500
cgcgcgagac gaaagggcct cgtgatacgc ctatttttat aggttaatgt catgataata    1560
atggtttctt agacgtcagg tggcactttt cggggaaatg tgcgcggaac ccctatttgt    1620
ttatttttct aaatacattc aaatatgtat ccgctcatga caataaacc ctgataaatg     1680
cttcaataat attgaaaaag gaagagtatg agtattcaac atttccgtgt cgcccttatt    1740
cccttttttg cggcattttg ccttcctgtt tttgctcacc cagaaacgct ggtgaaagta    1800
aaagatgctg aagatcagtt gggtgcacga gtgggttaca tcgaactgga tctcaacagc    1860
ggtaagatcc ttgagagttt tcgccccgaa gaacgttttc caatgatgag cacttttaaa    1920
gttctgctat gtggcgcggt attatcccgt attgacgccg ggcaagagca actcggtcgc    1980
cgcatacact attctcagaa tgacttggtt gagtactcac cagtcacaga aaagcatctt    2040
acggatggca tgacagtaag agaattatgc agtgctgcca taaccatgag tgataacact    2100
gcggccaact tacttctgac aacgatcgga ggaccgaagg agctaaccgc ttttttgcac    2160
aacatggggg atcatgtaac tcgccttgat cgttgggaac cggagctgaa tgaagccata    2220
ccaaacgacg agcgtgacac cacgatgcct gtagcaatgg caacaacgtt gcgcaaacta    2280
ttaactggcg aactacttac tctagcttcc cggcaacaat taatagactg gatggaggcg    2340
gataaagttg caggaccact tctgcgctcg gcccttccgg ctggctggtt tattgctgat    2400
aaatctggag ccggtgagcg tgggtctcgc ggtatcattg cagcactggg gccagatggt    2460
aagccctccc gtatcgtagt tatctacacg acggggagtc aggcaactat ggatgaacga    2520
aatagacaga tcgctgagat aggtgcctca ctgattaagc attggtaact gtcagaccaa    2580
gtttactcat atatacttta gattgattta aaacttcatt tttaatttaa aaggatctag    2640
gtgaagatcc tttttgataa tctcatgacc aaaatccctt aacgtgagtt ttcgttccac    2700
tgagcgtcag accccgtaga aaagatcaaa ggatcttctt gagatccttt ttttctgcgc    2760
gtaatctgct gcttgcaaac aaaaaaacca ccgctaccag cggtggtttg tttgccggat    2820
caagagctac caactctttt tccgaaggta actggcttca gcagagcgca gataccaaat    2880
actgtccttc tagtgtagcc gtagttaggc caccacttca agaactctgt agcaccgcct    2940
acatacctcg ctctgctaat cctgttacca gtggctgctg ccagtggcga taagtcgtgt    3000
cttaccgggt tggactcaag acgatagtta ccggataagg cgcagcggtc gggctgaacg    3060
gggggttcgt gcacacagcc cagcttggag cgaacgacct acaccgaact gagatacctsa    3120
cagcgtgagc tatgagaaag cgccacgctt cccgaaggga gaaaggcgga caggtatccg    3180
gtaagcggca gggtcggaac aggagagcgc acgagggagc ttccaggggg aaacgcctgg    3240
tatctttata gtcctgtcgg gtttcgccac ctctgacttg agcgtcgatt tttgtgatgc    3300
tcgtcagggg gcggagcct atggaaaaac gccagcaacg cggccttttt acggttcctg     3360
gccttttgct ggccttttgc tcacatgt                                        3388
```

<210> SEQ ID NO 101
<211> LENGTH: 3389
<212> TYPE: DNA
<213> ORGANISM: Artificial Sequence
<220> FEATURE:
<223> OTHER INFORMATION: Synthetic

<400> SEQUENCE: 101

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa atacgtgac gtagaaagta ataatttctt gggtagtttg     300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttcta gagacgcttc cgagtacggt acaggggatc     540
cgtttagcta gctagctagg ccaccatgga acaaaaactc atctcagaag aggatctggg    600
ctcgaggacg cttccgagta cggtacaggc acgtgcggac cgagcggccg caggaacccc    660
tagtgatgga gttggccact ccctctctgc gcgctcgctc gctcactgag gccgggcgac    720
caaaggtcgc ccgacgcccg ggcttttgccc gggcggcctc agtgagcgag cgagcgcgca   780
gctgcctgca ggggcgcctg atgcggtatt ttctccttac gcatctgtgc ggtatttcac    840
accgcatacg tcaaagcaac catagtacgc gccctagc ggcgcattaa gcgcggcggg     900
tgtggtggtt acgcgcagcg tgaccgctac acttgccagc gccctagcgc ccgctccttt    960
cgctttcttc ccttcctttc tcgccacgtt cgccggcttt cccgtcaag ctctaaatcg    1020
ggggctccct ttagggttcc gatttagtgc tttacggcac ctcgacccca aaaaacttga   1080
tttgggtgat ggttcacgta gtgggccatc gccctgatag acggttttc gcccttttgac   1140
gttggagtcc acgttcttta atagtggact cttgttccaa actggaacaa cactcaaccc   1200
tatctcgggc tattcttttg atttataagg gatttttgccg attcggcct attggttaaa   1260
aaatgagctg atttaacaaa aatttaacgc gaattttaac aaaatattaa cgtttacaat   1320
tttatggtgc actctcagta caatctgctc tgatgccgca tagttaagcc agccccgaca   1380
cccgccaaca cccgctgacg cgccctgacg ggcttgtctg ctcccggcat ccgcttacag   1440
acaagctgtg accgtctccg ggagctgcat gtgtcagagg ttttcaccgt catcaccgaa   1500
acgcgcgaga cgaaagggcc tcgtgatacg cctatttta taggttaatg tcatgataat   1560
aatggtttct tagacgtcag gtggcacttt tcggggaaat gtgcgcggaa ccctatttg   1620
tttattttc taaatacatt caaatatgta tccgctcatg agacaataac cctgataaat   1680
gcttcaataa tattgaaaaa ggaagagtat gagtattcaa catttccgtg tcgcccttat   1740
tccctttttt gcggcatttt gccttcctgt ttttgctcac ccagaaacgc tggtgaaagt   1800
aaaagatgct gaagatcagt tgggtgcacg agtgggttac atcgaactgg atctcaacag   1860
cggtaagatc cttgagagtt ttcgccccga agaacgtttt ccaatgatga gcacttttaa   1920
agttctgcta tgtggcgcgg tattatcccg tattgacgcc gggcaagagc aactcggtcg   1980
ccgcatacac tattctcaga atgacttggt tgagtactca ccagtcacag aaaagcatct   2040
tacgatggc atgacagtaa gagaattatg cagtgctgcc ataaccatga gtgataacac   2100
tgcggccaac ttacttctga caacgatcgg aggaccgaag gagctaaccg ctttttttgca  2160
caacatgggg gatcatgtaa ctcgccttga tcgttgggaa ccggagctga atgaagccat   2220
accaaacgac gagcgtgaca ccacgatgcc tgtagcaatg gcaacaacgt tgcgcaaact   2280
```

```
attaactggc gaactactta ctctagcttc ccggcaacaa ttaatagact ggatggaggc    2340
ggataaagtt gcaggaccac ttctgcgctc ggcccttccg gctggctggt ttattgctga    2400
taaatctgga gccggtgagc gtgggtctcg cggtatcatt gcagcactgg ggccagatgg    2460
taagccctcc cgtatcgtag ttatctacac gacggggagt caggcaacta tggatgaacg    2520
aaatagacag atcgctgaga taggtgcctc actgattaag cattggtaac tgtcagacca    2580
agtttactca tatatacttt agattgattt aaaacttcat ttttaattta aaaggatcta    2640
ggtgaagatc cttttgata atctcatgac caaaatccct aacgtgagt tttcgttcca    2700 ctgagcgtca gacccgtag aaagatcaa aggatcttct tgagatcctt ttttctgcg    2760 cgtaatctgc tgcttgcaaa caaaaaaacc accgctacca gcggtggttt gtttgccgga    2820
tcaagagcta ccaactcttt ttccgaaggt aactggcttc agcagagcgc agataccaaa    2880
tactgtcctt ctagtgtagc cgtagttagg ccaccacttc aagaactctg tagcaccgcc    2940 tacataccte gctctgctaa tcctgttacc agtggctgct gccagtggcg ataagtcgtg    3000
tcttaccggg ttggactcaa gacgatagtt accggataag gcgcagcggt cgggctgaac    3060
ggggggttcg tgcacacagc ccagcttgga gcgaacgacc tacaccgaac tgagatacct    3120
acagcgtgag ctatgagaaa gcgccacgct cccgaaggg agaaaggcgg acaggtatcc    3180
ggtaagcggc agggtcggaa caggagagcg cacgagggag cttccagggg gaaacgcctg    3240
gtatctttat agtcctgtcg ggtttcgcca cctctgactt gagcgtcgat ttttgtgatg    3300
ctcgtcaggg gggcggagcc tatggaaaaa cgccagcaac gcggcctttt tacggttcct    3360
ggccttttgc tggccttttg ctcacatgt                                      3389
```

<210> SEQ ID NO 102
<211> LENGTH: 3387
<212> TYPE: DNA
<213> ORGANISM: Artificial Sequence
<220> FEATURE:
<223> OTHER INFORMATION: Synthetic

<400> SEQUENCE: 102

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggggatc    540
cgtttagcta gctagctagg ccaccatgga acaaaaactc atctcagaag aggatctgct    600
cgaggacgct tccgagtacg gtacaggcac gtgcggaccg agcggccgca ggaaccccta    660
gtgatggagt tggccactcc ctctctgcgc gctcgctcgc tcactgaggc cgggcgacca    720
aaggtcgccc gacgcccggg ctttgccggg gcggcctcag tgagcgagcg agcgcgcagc    780
tgcctgcagg ggcgcctgat gcggtatttt ctccttacgc atctgtgcgg tatttcacac    840
cgcatacgtc aaagcaacca tagtacgcgc cctgtagcgg cgcattaagc gcggcgggtg    900
tggtggttac gcgcagcgtg accgctacac ttgccagcgc cctagcgccc gctcctttcg    960
```

```
ctttcttccc ttcctttctc gccacgttcg ccggcttcc ccgtcaagct ctaaatcggg    1020
ggctcccttt agggttccga tttagtgctt tacggcacct cgaccccaaa aaacttgatt    1080
tgggtgatgg ttcacgtagt gggccatcgc cctgatagac ggttttcgc cctttgacgt    1140 tggagtccac gttctttaat agtggactct gttccaaac tggaacaaca ctcaaccta    1200 tctcgggcta ttcttttgat ttataaggga ttttgccgat tcggcctat tggttaaaaa    1260 atgagctgat ttaacaaaaa tttaacgcga attttaacaa aatattaacg tttacaattt    1320
tatggtgcac tctcagtaca atctgctctg atgccgcata gttaagccag ccccgacacc    1380
cgccaacacc cgctgacgcg ccctgacggg cttgtctgct cccggcatcc gcttacagac    1440
aagctgtgac cgtctccggg agctgcatgt gtcagaggtt ttcaccgtca tcaccgaaac    1500
gcgcgagaca aagggcctc gtgatacgcc tatttttata ggttaatgtc atgataataa    1560
tggtttctta gacgtcaggt ggcacttttc ggggaaatgt gcgcggaacc cctatttgtt    1620
tatttttcta atacattca aatatgtatc cgctcatgag acaataaccc tgataaatgc    1680
ttcaataata ttgaaaaagg aagagtatga gtattcaaca tttccgtgtc gcccttattc    1740
ccttttttgc ggcattttgc cttcctgttt ttgctcaccc agaaacgctg gtgaaagtaa    1800
aagatgctga agatcagttg ggtgcacgag tgggttacat cgaactggat ctcaacagcg    1860
gtaagatcct tgagtttt cgccccgaag aacgtttcc aatgatgagc acttttaaag    1920
ttctgctatg tggcgcggta ttcccgta ttgacgccgg gcaagagcaa ctcggtcgcc    1980
gcatacacta ttctcagaat gacttggttg agtactcacc agtcacagaa aagcatctta    2040
cggatggcat gacagtaaga gaattatgca gtgctgccat aaccatgagt gataacactg    2100
cggccaactt acttctgaca acgatcgag gaccgaagga gctaaccgct tttttgcaca    2160
acatggggga tcatgtaact cgccttgatc gttgggaacc ggagctgaat gaagccatac    2220
caaacgacga gcgtgacacc acgatgcctg tagcaatggc aacaacgttg cgcaaactat    2280
taactggcga actacttact ctagcttccc ggcaacaatt aatagactgg atggaggcgg    2340
ataaagttgc aggaccactt ctgcgctcgg cccttccggc tggctggttt attgctgata    2400
aatctggagc cggtgagcgt gggtctcgcg gtatcattgc agcactgggg ccagatggta    2460
agccctcccg tatcgtagtt atctacacga cggggagtca ggcaactatg gatgaacgaa    2520
atagacagat cgctgagata ggtgcctcac tgattaagca ttggtaactg tcagaccaag    2580
tttactcata tatactttag attgatttaa aacttcattt ttaatttaaa aggatctagg    2640
tgaagatcct ttttgataat ctcatgacca aaatccctta acgtgagttt tcgttccact    2700
gagcgtcaga ccccgtagaa aagatcaaag gatcttcttg atccttttt tttctgcgcg    2760 taatctgctg cttgcaaaca aaaaaaccac cgctaccagc ggtggtttgt ttgccggatc    2820
aagagctacc aactcttttt ccgaaggtaa ctggcttcag cagagcgcag ataccaaata    2880
ctgtccttct agtgtagccg tagttaggcc accacttcaa gaactctgta gcaccgccta    2940
catacctcgc tctgctaatc ctgttaccag tggctgctgc cagtggcgat aagtcgtgtc    3000
ttaccgggtt ggactcaaga cgatagttac cggataaggc gcagcggtcg gctgaacgg    3060 ggggttcgtg cacacagccc agcttggagc gaacgaccta caccgaactg agatacctac    3120
agcgtgagct atgagaaagc gccacgcttc ccgaagggag aaaggcggac aggtatccgg    3180
taagcggcag ggtcggaaca ggagagcgca cgagggagct tccaggggga aacgcctggt    3240
atctttatag tcctgtcggg tttcgccacc tctgacttga gcgtcgattt ttgtgatgct    3300
```

| | |
|---|---:|
| cgtcaggggg gcggagccta tgaaaaacg ccagcaacgc ggccttttta cggttcctgg | 3360 |
| ccttttgctg gccttttgct cacatgt | 3387 |

<210> SEQ ID NO 103
<211> LENGTH: 3433
<212> TYPE: DNA
<213> ORGANISM: Artificial Sequence
<220> FEATURE:
<223> OTHER INFORMATION: Synthetic

<400> SEQUENCE: 103

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gacctgtacc gtactcggaa gcgtcggatc | 540 |
| caggtaagcc tatccctaac cctctcctcg gtctcgattc tacgtagcta gctagctaga | 600 |
| gtggagtcca gtcccagaag tggattggga atgggtttgc caagctcgag cctgtaccgt | 660 |
| actcggaagc gtccacgtgc ggaccgagcg gccgcaggaa cccctagtga tggagttggc | 720 |
| cactccctct ctgcgcgctc gctcgctcac tgaggccggg cgaccaaagg tcgcccgacg | 780 |
| cccgggctt gccgggcgg cctcagtgag cgagcgagcg cgcagctgcc tgcaggggcg | 840 |
| cctgatgcgg tattttctcc ttacgcatct gtgcggtatt tcacaccgca tacgtcaaag | 900 |
| caaccatagt acgcgccctg tagcggcgca ttaagcgcgg cgggtgtggt ggttacgcgc | 960 |
| agcgtgaccg ctacacttgc cagcgcccta gcgcccgctc ctttcgcttt cttcccttcc | 1020 |
| tttctcgcca cgttcgccgg ctttccccgt caagctctaa atcggggggct cccttaggg | 1080 |
| ttccgattta gtgctttacg gcacctcgac cccaaaaaac ttgatttggg tgatggttca | 1140 |
| cgtagtgggc catcgccctg atagacggtt tttcgccctt tgacgttgga gtccacgttc | 1200 |
| tttaatagtg gactcttgtt ccaaactgga acaacactca accctatctc gggctattct | 1260 |
| tttgatttat aagggatttt gccgatttcg gcctattggt taaaaaatga gctgatttaa | 1320 |
| caaaaattta acgcgaattt taacaaaata ttaacgttta caatttatg gtgcactctc | 1380 |
| agtacaatct gctctgatgc cgcatagtta agccagcccc gacacccgcc aacacccgct | 1440 |
| gacgcgccct gacgggcttg tctgctcccg gcatccgctt acagacaagc tgtgaccgtc | 1500 |
| tccgggagct gcatgtgtca gaggttttca ccgtcatcac cgaaacgcgc gagacgaaag | 1560 |
| ggcctcgtga tacgcctatt tttataggtt aatgtcatga taataatggt ttcttagacg | 1620 |
| tcaggtggca cttttcgggg aaatgtgcgc ggaacccta tttgtttatt tttctaaata | 1680 |
| cattcaaata tgtatccgct catgagacaa taaccctgat aaatgcttca ataatattga | 1740 |
| aaaaggaaga gtatgagtat tcaacatttc cgtgtcgccc ttattccctt ttttgcggca | 1800 |
| ttttgccttc ctgtttttgc tcacccagaa acgctggtga agtaaaaga tgctgaagat | 1860 |
| cagttgggtg cacgagtggg ttacatcgaa ctggatctca acagcggtaa gatccttgag | 1920 |
| agttttcgcc ccgaagaacg ttttccaatg atgagcactt taaagttct gctatgtggc | 1980 |

```
gcggtattat cccgtattga cgccgggcaa gagcaactcg gtcgccgcat acactattct    2040
cagaatgact tggttgagta ctcaccagtc acagaaaagc atcttacgga tggcatgaca    2100
gtaagagaat tatgcagtgc tgccataacc atgagtgata acactgcggc caacttactt    2160
ctgacaacga tcggaggacc gaaggagcta accgcttttt tgcacaacat gggggatcat    2220
gtaactcgcc ttgatcgttg ggaaccggag ctgaatgaag ccataccaaa cgacgagcgt    2280
gacaccacga tgcctgtagc aatggcaaca acgttgcgca aactattaac tggcgaacta    2340
cttactctag cttcccggca acaattaata gactggatgg aggcggataa agttgcagga    2400
ccacttctgc gctcggccct tccggctggc tggtttattg ctgataaatc tggagccggt    2460
gagcgtgggt ctcgcggtat cattgcagca ctggggccag atggtaagcc ctcccgtatc    2520
gtagttatct acacgacggg gagtcaggca actatggatg aacgaaatag acagatcgct    2580
gagataggtg cctcactgat taagcattgg taactgtcag accaagttta ctcatatata    2640
ctttagattg atttaaaact tcattttta tttaaaagga tctaggtgaa gatcctttt     2700 gataatctca tgaccaaaat cccttaacgt gagttttcgt tccactgagc gtcagacccc    2760
gtagaaaaga tcaaaggatc ttcttgagat cctttttttc tgcgcgtaat ctgctgcttg    2820
caaacaaaaa aaccaccgct accagcggtg gtttgtttgc cggatcaaga gctaccaact    2880
ctttttccga aggtaactgg cttcagcaga gcgcagatac caaatactgt ccttctagtg    2940
tagccgtagt taggccacca cttcaagaac tctgtagcac cgcctacata cctcgctctg    3000
ctaatcctgt taccagtggc tgctgccagt ggcgataagt cgtgtcttac cgggttggac    3060
tcaagacgat agttaccgga taaggcgcag cggtcgggct gaacggggg ttcgtgcaca    3120 cagcccagct tggagcgaac gacctacacc gaactgagat acctacagcg tgagctatga    3180
gaaagcgcca cgcttcccga agggagaaag gcggacaggt atccggtaag cggcagggtc    3240
ggaacaggag agcgcacgag ggagcttcca gggggaaacg cctggtatct ttatagtcct    3300
gtcgggtttc gccacctctg acttgagcgt cgatttttgt gatgctcgtc agggggggcgg    3360 agcctatgga aaaacgccag caacgcggcc ttttacggt tcctggcctt ttgctggcct    3420
tttgctcaca tgt                                                       3433

<210> SEQ ID NO 104
<211> LENGTH: 3431
<212> TYPE: DNA
<213> ORGANISM: Artificial Sequence
<220> FEATURE:
<223> OTHER INFORMATION: Synthetic

<400> SEQUENCE: 104
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttttcta gacctgtacc gtactcggaa gcgtcggatc     540
```

```
cggtaagcct atccctaacc ctctcctcgg tctcgattct acgtagctag ctagctagag    600
tggagtccag tcccagaagt ggattgggaa tgggtttgcc agctcgagcc tgtaccgtac    660
tcggaagcgt ccacgtgcgg accgagcggc cgcaggaacc cctagtgatg gagttggcca    720
ctccctctct gcgcgctcgc tcgctcactg aggcccgggcg accaaaggtc gcccgacgcc    780
cgggctttgc ccgggcggcc tcagtgagcg agcgagcgcg cagctgcctg caggggcgcc    840
tgatgcggta ttttctcctt acgcatctgt gcggtatttc acaccgcata cgtcaaagca    900
accatagtac gcgccctgta gcggcgcatt aagcgcggcg ggtgtggtgg ttacgcgcag    960
cgtgaccgct acacttgcca gcgccctagc gcccgctcct ttcgctttct tcccttcctt   1020
tctcgccacg ttcgccggct ttccccgtca agctctaaat cggggggctcc ctttagggtt   1080
ccgatttagt gctttacggc acctcgaccc caaaaaactt gatttgggtg atggttcacg   1140
tagtgggcca tcgccctgat agacggtttt tcgccctttg acgttggagt ccacgttctt   1200
taatagtgga ctcttgttcc aaactggaac aacactcaac cctatctcgg gctattcttt   1260
tgatttataa gggattttgc cgatttcggc ctattggtta aaaaatgagc tgatttaaca   1320
aaaatttaac gcgaatttta acaaaatatt aacgtttaca attttatggt gcactctcag   1380
tacaatctgc tctgatgccg catagttaag ccagccccga cacccgccaa cacccgctga   1440
cgcgccctga cgggcttgtc tgctcccggc atccgcttac agacaagctg tgaccgtctc   1500
cgggagctgc atgtgtcaga ggttttcacc gtcatcaccg aaacgcgcga cgcgaaaggg   1560
cctcgtgata cgcctatttt tataggttaa tgtcatgata ataatggttt cttagacgtc   1620
aggtggcact tttcggggaa atgtgcgcgg aaccccctatt tgtttatttt tctaaataca   1680
ttcaaatatg tatccgctca tgagacaata accctgataa atgcttcaat aatattgaaa   1740
aaggaagagt atgagtattc aacatttccg tgtcgccctt attccctttt ttgcggcatt   1800
ttgccttcct gttttgctc acccagaaac gctggtgaaa gtaaaagatg ctgaagatca   1860
gttgggtgca cgagtgggtt acatcgaact ggatctcaac agcggtaaga tccttgagag   1920
ttttcgcccc gaagaacgtt ttccaatgat gagcactttt aaagttctgc tatgtggcgc   1980
ggtattatcc cgtattgacg ccgggcaaga gcaactcggt cgccgcatac actattctca   2040
gaatgacttg gttgagtact caccagtcac agaaaagcat cttacggatg gcatgacagt   2100
aagagaatta tgcagtgctg ccataaccat gagtgataac actgcggcca acttacttct   2160
gacaacgatc ggaggaccga aggagctaac cgcttttttg cacaacatgg gggatcatgt   2220
aactcgcctt gatcgttggg aaccggagct gaatgaagcc ataccaaacg acgagcgtga   2280
caccacgatg cctgtagcaa tggcaacaac gttgcgcaaa ctattaactg gcgaactact   2340
tactctagct tccccggcaac aattaataga ctggatggag gcggataaag ttgcaggacc   2400
acttctgcgc tcggcccttc cggctggctg gtttattgct gataaatctg gagccggtga   2460
gcgtgggtct cgcggtatca ttgcagcact ggggccagat ggtaagccct cccgtatcgt   2520
agttatctac acgacgggga gtcaggcaac tatggatgaa cgaaatagac agatcgctga   2580
gataggtgcc tcactgatta agcattggta actgtcagac caagtttact catatatact   2640
ttagattgat ttaaaacttc atttttaatt taaaaggatc taggtgaaga tcctttttga   2700
taatctcatg accaaaatcc cttaacgtga gttttcgttc cactgagcgt cagaccccgt   2760
agaaaagatc aaaggatctt cttgagatcc ttttttctg cgcgtaatct gctgcttgca   2820
aacaaaaaaa ccaccgctac cagcggtggt ttgtttgccg gatcaagagc taccaactct   2880
ttttccgaag gtaactggct tcagcagagc gcagatacca aatactgtcc ttctagtgta   2940
```

```
gccgtagtta ggccaccact tcaagaactc tgtagcaccg cctacatacc tcgctctgct    3000
aatcctgtta ccagtggctg ctgccagtgg cgataagtcg tgtcttaccg ggttggactc    3060
aagacgatag ttaccggata aggcgcagcg gtcgggctga acgggggggtt cgtgcacaca    3120 gcccagcttg gagcgaacga cctacaccga actgagatac ctacagcgtg agctatgaga    3180
aagcgccacg cttcccgaag ggagaaaggc ggacaggtat ccggtaagcg gcagggtcgg    3240
aacaggagag cgcacgaggg agcttccagg gggaaacgcc tggtatcttt atagtcctgt    3300
cgggtttcgc cacctctgac ttgagcgtcg attttttgtga tgctcgtcag ggggggcggag   3360 cctatggaaa aacgccagca acgcggcctt tttacggttc ctggccttttt gctggccttt    3420 tgctcacatg t                                                          3431
```

<210> SEQ ID NO 105
<211> LENGTH: 3432
<212> TYPE: DNA
<213> ORGANISM: Artificial Sequence
<220> FEATURE:
<223> OTHER INFORMATION: Synthetic

<400> SEQUENCE: 105

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300 cagtttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttttcta gacctgtacc gtactcggaa gcgtcggatc     540
caaggtaagc ctatccctaa ccctctcctc ggtctcgatt ctacgtagct agctagctag     600
agtggagtcc agtcccagaa gtggattggg aatgggtttg ccgctcgagc ctgtaccgta     660
ctcggaagcg tccacgtgcg gaccgagcgg ccgcaggaac ccctagtgat ggagttggcc     720
actccctctc tgcgcgctcg ctcgctcact gaggccgggc gaccaaaggt cgcccgacgc     780
ccgggctttg cccgggcggc ctcagtgagc gagcgagcgc gcagctgcct gcaggggcgc     840
ctgatgcggt attttctcct tacgcatctg tgcggtattt cacaccgcat acgtcaaagc     900
aaccatagta cgcgccctgt agcggcgcat taagcgcggc gggtgtggtg gttacgcgca     960
gcgtgaccgc tacacttgcc agcgccctag cgcccgctcc tttcgctttc ttcccttcct    1020
ttctcgccac gttcgccggc tttccccgtc aagctctaaa tcgggggctc cctttagggt    1080
tccgatttag tgctttacgg cacctcgacc ccaaaaaact tgatttgggt gatggttcac    1140
gtagtgggcc atcgccctga tagacggttt ttcgcccttt gacgttggag tccacgttct    1200
ttaatagtgg actcttgttc caaactggaa caacactcaa ccctatctcg gctattcttt    1260
ttgatttata gggatttttg ccgatttcgg cctattggtt aaaaaatgag ctgatttaac    1320
aaaaatttaa cgcgaatttt aacaaaatat taacgtttac aatttttatgg tgcactctca    1380 gtacaatctg ctctgatgcc gcatagttaa gccagccccg acacccgcca acacccgctg    1440
acgcgccctg acgggcttgt ctgctcccgg catccgctta cagacaagct gtgaccgtct    1500
```

| | |
|---|---|
| ccgggagctg catgtgtcag aggttttcac cgtcatcacc gaaacgcgcg agacgaaagg | 1560 |
| gcctcgtgat acgcctattt ttataggtta atgtcatgat aataatggtt tcttagacgt | 1620 |
| caggtggcac ttttcgggga aatgtgcgcg gaacccctat ttgtttattt ttctaaatac | 1680 |
| attcaaatat gtatccgctc atgagacaat aaccctgata aatgcttcaa taatattgaa | 1740 |
| aaaggaagag tatgagtatt caacatttcc gtgtcgccct tattcccttt tttgcggcat | 1800 |
| tttgccttcc tgttttttgct cacccagaaa cgctggtgaa agtaaaagat gctgaagatc | 1860 |
| agttgggtgc acgagtgggt tacatcgaac tggatctcaa cagcggtaag atccttgaga | 1920 |
| gttttcgccc cgaagaacgt tttccaatga tgagcacttt taaagttctg ctatgtggcg | 1980 |
| cggtattatc ccgtattgac gccgggcaag agcaactcgg tcgccgcata cactattctc | 2040 |
| agaatgactt ggttgagtac tcaccagtca cagaaaagca tcttacggat ggcatgacag | 2100 |
| taagagaatt atgcagtgct gccataacca tgagtgataa cactgcggcc aacttacttc | 2160 |
| tgacaacgat cggaggaccg aaggagctaa ccgcttttttt gcacaacatg ggggatcatg | 2220 |
| taactcgcct tgatcgttgg gaaccggagc tgaatgaagc cataccaaac gacgagcgtg | 2280 |
| acaccacgat gcctgtagca atggcaacaa cgttgcgcaa actattaact ggcgaactac | 2340 |
| ttactctagc ttcccggcaa caattaatag actggatgga ggcggataaa gttgcaggac | 2400 |
| cacttctgcg ctcggccctt ccggctggct ggtttattgc tgataaatct ggagccggtg | 2460 |
| agcgtgggtc tcgcggtatc attgcagcac tggggccaga tggtaagccc tcccgtatcg | 2520 |
| tagttatcta cacgacgggg agtcaggcaa ctatggatga acgaaataga cagatcgctg | 2580 |
| agataggtgc ctcactgatt aagcattggt aactgtcaga ccaagtttac tcatatatac | 2640 |
| tttagattga tttaaaactt cattttaat ttaaaaggat ctaggtgaag atcctttttg | 2700 |
| ataatctcat gaccaaaatc ccttaacgtg agttttcgtt ccactgagcg tcagacccccg | 2760 |
| tagaaaagat caaaggatct tcttgagatc ctttttttct gcgcgtaatc tgctgcttgc | 2820 |
| aaacaaaaaa accaccgcta ccagcggtgg tttgtttgcc ggatcaagag ctaccaactc | 2880 |
| tttttccgaa ggtaactggc ttcagcagag cgcagatacc aaatactgtc cttctagtgt | 2940 |
| agccgtagtt aggccaccac ttcaagaact ctgtagcacc gcctacatac ctcgctctgc | 3000 |
| taatcctgtt accagtggct gctgccagtg gcgataagtc gtgtcttacc gggttggact | 3060 |
| caagacgata gttaccggat aaggcgcagc ggtcgggctg aacggggggt tcgtgcacac | 3120 |
| agcccagctt ggagcgaacg acctacaccg aactgagata cctacagcgt gagctatgag | 3180 |
| aaagcgccac gcttcccgaa gggagaaagg cggacaggta tccggtaagc ggcagggtcg | 3240 |
| gaacaggaga gcgcacgagg gagcttccag ggggaaacgc ctggtatctt tatagtcctg | 3300 |
| tcgggtttcg ccacctctga cttgagcgtc gatttttgtg atgctcgtca gggggggcgga | 3360 |
| gcctatggaa aaacgccagc aacgcggcct ttttacggtt cctggccttt tgctggcctt | 3420 |
| ttgctcacat gt | 3432 |

<210> SEQ ID NO 106
<211> LENGTH: 6190
<212> TYPE: DNA
<213> ORGANISM: Artificial Sequence
<220> FEATURE:
<223> OTHER INFORMATION: Synthetic

<400> SEQUENCE: 106

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |

```
actccatcac tagggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccggaaga gcgagctctt    420
ctgttttaga gctagaaata gcaagttaaa ataaggctag tccgttatca acttgaaaaa    480
gtggcaccga gtcggtgctt ttttctaga ggctccggtg cccgtcagtg ggcagagcgc    540
acatcgccca cagtccccga gaagttgggg ggaggggtcg gcaattgaac cggtgcctag    600
agaaggtggc gcgggtaaa ctgggaaagt gatgtcgtgt actggctccg ccttttcccc    660
gagggtgggg gagaaccgta tataagtgca gtagtcgccg tgaacgttct ttttcgcaac    720
gggtttgccg ccagaacaca ggtaagtgcc gtgtgtggtt cccgcgggcc tggcctcttt    780
acgggttatg gcccttgcgt gccttgaatt acttccactg gctgcagtac gtgattcttg    840
atcccgagct tcgggttgga agtgggtggg agagttcgag gccttgcgct taaggagccc    900
cttcgcctcg tgcttgagtt gaggcctggc ctgggcgctg gggccgccgc gtgcgaatct    960
ggtggcacct tcgcgcctgt ctcgctgctt tcgataagtc tctagccatt taaaattttt    1020
gatgacctgc tgcgacgctt tttttctggc aagatagtct tgtaaatgcg ggccaagatc    1080
tgcacactgg tatttcggtt tttggggccg cgggcggcga cggggcccgt gcgtcccagc    1140
gcacatgttc ggcgaggcgg ggcctgcgag cgcggccacc gagaatcgga cgggggtagt    1200
ctcaagctgg ccggcctgct ctggtgcctg gcctcgcgcc gccgtgtatc gccccgccct    1260
gggcggcaag gctggcccgg tcggcaccag ttgcgtgagc ggaaagatgg ccgcttcccg    1320
gccctgctgc agggagctca aaatggagga cgcggcgctc gggagagcgg gcgggtgagt    1380
cacccacaca aaggaaaagg ccttttccgt cctcagccgt cgcttcatgt gactccacgg    1440
agtaccgggc gccgtccagg cacctcgatt agttctcgag cttttggagt acgtcgtctt    1500
taggttgggg ggaggggttt tatgcgatgg agtttcccca cactgagtgg gtggagactg    1560
aagttaggcc agcttggcac ttgatgtaat tctccttgga atttgccctt tttgagtttg    1620
gatcttggtt cattctcaag cctcagacag tggttcaaag ttttttttctt ccatttcagg    1680 tgtcgtgagg taccgccacc atgcccaaga agaagaggaa ggtgtccaat ctcctgactg    1740
ttcaccagaa cctccctgcg ctgccagtag atgccactag cgatgaggtc aggaaaaatc    1800
tcatggatat gtttagggat agacaggcgt tttctgaaca cacctggaaa atgctgctta    1860
gcgtgtgccg atcctgggca gcctggtgta agctgaacaa tcgcaaatgg ttccccgccg    1920
agccggagga cgtgcgcgat tacctgctgt atctccaggc aagagggctg ctgtcaaga    1980 ctatccagca gcacttgggc caactgaata tgctgcatcg acgcagcggg ctcccccggc    2040
ctagcgattc aaacgcagtc tcccttgtta tgaggagaat tagaaaggaa aacgtagatg    2100
cgggtgagag ggctaagcag gctctcgctt ttgagcggac tgatttcgac caggtcagat    2160
ccctgatgga aacagcgat cggtgccagg acatcaggaa cctcgcattt ctgggaattg    2220
catataacac acttctgcgc atagctgaga tcgcccggat cagagtgaaa gacatcagtc    2280
gaacggacgg cggccggatg cttattcata ttggacgcac aaagacattg gtcagcaccg    2340
ctggcgttga aaaggccttg tccctgggcg taacgaagct ggtggaaaga tggatctcag    2400
tgtccggcgt ggctgacgac cctaataatt acttgttctg tcgagtgaga aaaaacggag    2460
```

```
tcgccgcgcc ctctgccacc agccaattga gtacacgggc ccttgaaggg atctttgagg     2520
caacccaccg actcatatac ggagccaagg atgacagtgg ccagaggtat ctcgcctggt     2580
caggtcattc tgctagggtg ggggccgcac gagacatggc gcgggcagga gtctccatac     2640
cagagattat gcaagctgga ggttggacaa atgtgaacat cgttatgaac tatatccgca     2700
atcttgactc tgaaaccggg gccatggtga gactgctcga agatggtgac taggaattcg     2760
atatcaagct tatcgataat caacctctgg attacaaaat tgtgaaaga ttactggta      2820 ttcttaacta tgttgctcct tttacgctat gtggatacgc tgctttaatg cctttgtatc     2880
atgctattgc ttcccgtatg ctttcatttt tctcctcctt gtataaatcc tggttgctgt     2940
ctctttatga ggagttgtgg cccgttgtca ggcaacgtgg cgtggtgtgc actgtgtttg     3000
ctgacgcaac ccccactggt tgggcattg ccaccacctg tcagctcctt tccgggactt      3060
tcgctttccc cctccctatt gccacggcgg aactcatcgc cgcctgcctt gcccgctgct     3120
ggacaggggc tcggctgttg ggcactgaca attccgtggt gttgtcgggg aaatcatcgt     3180
cctttccttg gctgctcgcc tgtgttgcca cctggattct gcgcgggacg tccttctgct     3240
acgtcccttc ggccctcaat ccagcggacc ttccttcccg cggcctgctg ccggctctgc     3300
ggcctcttcc gcgtcttcgc cttcgccctc agacgagtcg gatctccctt gggccgcct      3360 ccccgcatcg ataccgagcg ctaataaaag atctttattt tcattagatc tgtgtgttgg     3420
ttttttgtgt cacgtgcgga ccgagcgcc gcaggaaccc ctagtgatgg agttggccac      3480
tccctctctg cgcgctcgct cgctcactga ggccgggcga ccaaaggtcg cccgacgccc     3540
gggctttgcc cgggcggcct cagtgagcga gcgagcgcgc agctgcctgc aggggcgcct     3600
gatgcggtat tttctcctta cgcatctgtg cggtatttca caccgcatac gtcaaagcaa     3660
ccatagtacg cgccctgtag cggcgcatta agcgcggcgg gtgtggtggt tacgcgcagc     3720
gtgaccgcta cacttgccag cgccctagcg cccgctcctt tcgctttctt cccttccttt     3780
ctcgccacgt tcgccggctt tccccgtcaa gctctaaatc gggggctccc tttagggttc     3840
cgatttagtg ctttacggca cctcgacccc aaaaaacttg atttgggtga tggttcacgt     3900
agtgggccat cgccctgata gacggttttt cgccctttga cgttggagtc cacgttcttt     3960
aatagtggac tcttgttcca aactggaaca acactcaacc ctatctcggg ctattctttt     4020
gatttataag ggattttgcc gatttcggcc tattggttaa aaaatgagct gatttaacaa     4080
aaatttaacg cgaattttaa caaaatatta acgtttacaa ttttatggtg cactctcagt     4140
acaatctgct ctgatgccgc atagttaagc cagccccgac acccgccaac acccgctgac     4200
gcgccctgac gggcttgtct gctcccggca tccgcttaca gacaagctgt gaccgtctcc     4260
gggagctgca tgtgtcagag gttttcaccg tcatcaccga aacgcgcgag acgaaagggc     4320
ctcgtgatac gcctattttt ataggttaat gtcatgataa taatggtttc ttagacgtca     4380
ggtggcactt ttcggggaaa tgtgcgcgga acccctattt gtttattttt ctaaatacat     4440
tcaaatatgt atccgctcat gagacaataa ccctgataaa tgcttcaata atattgaaaa     4500
aggaagagta tgagtattca acatttccgt gtcgccctta ttccctttt tgcggcattt      4560 tgccttcctg ttttgctca cccagaaacg ctggtgaaag taaaagatgc tgaagatcag      4620
ttgggtgcac gagtgggtta catcgaactg gatctcaaca gcggtaagat ccttgagagt     4680
tttcgccccg aagaacgttt tccaatgatg agcactttta aagttctgct atgtggcgcg     4740
gtattatccc gtattgacgc cgggcaagag caactcggtc gccgcataca ctattctcag     4800
aatgacttgg ttgagtactc accagtcaca gaaaagcatc ttacggatgg catgacagta     4860
```

```
agagaattat gcagtgctgc cataaccatg agtgataaca ctgcggccaa cttacttctg    4920
acaacgatcg gaggaccgaa ggagctaacc gcttttttgc acaacatggg ggatcatgta    4980
actcgccttg atcgttggga accggagctg aatgaagcca taccaaacga cgagcgtgac    5040
accacgatgc ctgtagcaat ggcaacaacg ttgcgcaaac tattaactgg cgaactactt    5100
actctagctt cccggcaaca attaatagac tggatggagg cggataaagt tgcaggacca    5160
cttctgcgct cggcccttcc ggctggctgg tttattgctg ataaatctgg agccggtgag    5220
cgtgggtctc gcggtatcat tgcagcactg gggccagatg gtaagccctc ccgtatcgta    5280
gttatctaca cgacggggag tcaggcaact atggatgaac gaaatagaca gatcgctgag    5340
ataggtgcct cactgattaa gcattggtaa ctgtcagacc aagtttactc atatatactt    5400
tagattgatt taaaacttca tttttaattt aaaaggatct aggtgaagat ccttttttgat    5460 aatctcatga ccaaaatccc ttaacgtgag ttttcgttcc actgagcgtc agaccccgta    5520
gaaaagatca aaggatcttc ttgagatcct ttttttctgc gcgtaatctg ctgcttgcaa    5580
acaaaaaaac caccgctacc agcggtggtt tgtttgccgg atcaagagct accaactctt    5640
tttccgaagg taactggctt cagcagagcg cagataccaa atactgtcct tctagtgtag    5700
ccgtagttag gccaccactt caagaactct gtagcaccgc ctacatacct cgctctgcta    5760
atcctgttac cagtggctgc tgccagtggc gataagtcgt gtcttaccgg gttggactca    5820
agacgatagt taccggataa ggcgcagcgg tcgggctgaa cggggggttc gtgcacacag    5880
cccagcttgg agcgaacgac ctacaccgaa ctgagatacc tacagcgtga gctatgagaa    5940
agcgccacgc ttcccgaagg gagaaaggcg gacaggtatc cggtaagcgg cagggtcgga    6000
acaggagagc gcacgaggga gcttccaggg ggaaacgcct ggtatcttta tagtcctgtc    6060
gggtttcgcc acctctgact tgagcgtcga ttttttgtgat gctcgtcagg gggcggagc    6120 ctatggaaaa acgccagcaa cgcggccttt ttacggttcc tggccttttg ctggcctttt    6180
gctcacatgt                                                           6190

<210> SEQ ID NO 107
<211> LENGTH: 5488
<212> TYPE: DNA
<213> ORGANISM: Artificial Sequence
<220> FEATURE:
<223> OTHER INFORMATION: Synthetic

<400> SEQUENCE: 107
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa     240
acacaaagat attagtacaa atacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccggaaga gcagctctt     420 ctgtttttaga gctagaaata gcaagttaaa ataaggctag tccgttatca acttgaaaaa     480
gtggcaccga tcggtgcctt ttttctaga ctgcagaggg ccctgcgtat gagtgcaagt     540
gggttttagg accaggatga ggcggggtgg gggtgcctac ctgacgaccg accccgaccc     600
actggacaag cacccaaccc ccattcccca aattgcgcat ccccctatcag agaggggag     660
```

-continued

```
gggaaacagg atgcggcgag gcgcgtgcgc actgccagct tcagcaccgc ggacagtgcc   720 ttcgccccg cctggcggcg cgcgccaccg ccgcctcagc actgaaggcg cgctgacgtc    780
actcgccggt cccccgcaaa ctccccttcc cggccacctt ggtcgcgtcc gcgccgccgc   840
cggcccagcc ggaccgcacc acgcgaggcg cgagataggg gggcacgggc gcgaccatct   900
gcgctgcggc gccggcgact cagcgctgcc tcagtctgcg gtgggcagcg gaggagtcgt   960
gtcgtgcctg agagcgcagt cgagaaggta ccgccaccat gcccaagaag aagaggaagg   1020
tgtccaatct cctgactgtt caccagaacc tccctgcgct gccagtagat gccactagcg   1080
atgaggtcag gaaaaatctc atggatatgt ttagggatag acaggcgttt tctgaacaca   1140
cctggaaaat gctgcttagc gtgtgccgat cctgggcagc ctggtgtaag ctgaacaatc   1200
gcaaatggtt ccccgccgag ccggaggacg tgcgcgatta cctgctgtat ctccaggcaa   1260
gagggctggc tgtcaagact atccagcagc acttgggcca actgaatatg ctgcatcgac   1320
gcagcgggct cccccggcct agcgattcaa acgcagtctc ccttgttatg aggagaatta   1380
gaaaggaaaa cgtagatgcg ggtgagaggg ctaagcaggc tctcgctttt gagcggactg   1440
atttcgacca ggtcagatcc ctgatggaga acagcgatcg gtgccaggac atcaggaacc   1500
tcgcatttct gggaattgca tataacacac ttctgcgcat agctgagatc gcccggatca   1560
gagtgaaaga catcagtcga acggacggcg gccggatgct tattcatatt ggacgcacaa   1620
agacattggt cagcaccgct ggcgttgaaa aggccttgtc cctgggcgta cgaagctgg    1680 tggaaagatg gatctcagtg tccggcgtgg ctgacgaccc taataattac ttgttctgtc   1740
gagtgagaaa aaacggagtc gccgcgcccct ctgccaccag ccaattgagt acacgggccc   1800
ttgaagggat ctttgaggca acccaccgac tcatatacgg agccaaggat gacagtggcc   1860
agaggtatct cgcctggtca ggtcattctg ctagggtggg ggccgcacga gacatggcgc   1920
gggcaggagt ctccatacca gagattatgc aagctggagg ttggacaaat gtgaacatcg   1980
ttatgaacta tatccgcaat cttgactctg aaaccgggc catggtgaga ctgctcgaag   2040
atggtgacta ggaattcgat atcaagctta tcgataatca acctctggat tacaaaattt   2100
gtgaaagatt gactggtatt cttaactatg ttgctccttt tacgctatgt ggatacgctg   2160
ctttaatgcc tttgtatcat gctattgctt cccgtatggc tttcattttc tcctccttgt   2220
ataaatcctg gttgctgtct ctttatgagg agttgtggcc cgttgtcagg caacgtggcg   2280
tggtgtgcac tgtgtttgct gacgcaaccc ccactggttg gggcattgcc accacctgtc   2340
agctcctttc cgggactttc gctttccccc tccctattgc cacggcggaa ctcatcgccg   2400
cctgccttgc ccgctgctgg acaggggctc ggctgttggg cactgacaat tccgtggtgt   2460
tgtcggggaa atcatcgtcc tttccttggc tgctcgcctg tgttgccacc tggattctgc   2520
gcgggacgtc cttctgctac gtcccttcgg ccctcaatcc agcggacctt ccttcccgcg   2580
gcctgctgcc ggctctgcgg cctcttccgc gtcttcgcct tcgccctcag acgagtcgga   2640
tctccctttg ggccgcctcc ccgcatcgat accgagcgct aataaaagat ctttatttc    2700 attagatctg tgtgttggtt ttttgtgtca cgtgcggacc gagcggccgc aggaacccct   2760
agtgatggag ttggccactc cctctctgcg cgctcgctcg ctcactgagg ccgggcgacc   2820
aaaggtcgcc cgacgcccgg gctttgcccg ggcggcctca gtgagcgagc gagcgcgcag   2880
ctgcctgcag gggcgcctga tgcggtattt tctccttacg catctgtgcg gtatttcaca   2940
ccgcatacgt caaagcaacc atagtacgcg ccctgtagcg gcgcattaag cgcggcgggt   3000
gtggtggtta cgcgcagcgt gaccgctaca cttgccagcg ccctagcgcc cgctcctttc   3060
```

```
gctttcttcc cttcctttct cgccacgttc gccggctttc cccgtcaagc tctaaatcgg    3120
gggctcccTT tagggttccg atttagtgct ttacggcacc tcgaccccaa aaacttgat    3180 ttgggtgatg gttcacgtag tgggccatcg ccctgataga cggttttTCg cccTTTgacg    3240
ttggagtcca cgttctttaa tagtggactc ttgttccaaa ctggaacaac actcaaccct    3300
atctcgggct attcttttga tttataaggg attttgccga tttcggccta ttggttaaaa    3360
aatgagctga tttaacaaaa atttaacgcg aattttaaca aaatattaac gtttacaatt    3420
ttatggtgca ctctcagtac aatctgctct gatgccgcat agttaagcca gccccgacac    3480
ccgccaacac ccgctgacgc gccctgacgg gcttgtctgc tcccggcatc cgcttacaga    3540
caagctgtga ccgtctccgg gagctgcatg tgtcagaggt tttcaccgtc atcaccgaaa    3600
cgcgcgagac gaaagggcct cgtgatacgc ctatttttat aggttaatgt catgataata    3660
atggtttctt agacgtcagg tggcactttt cggggaaatg tgcgcggaac ccctatttgt    3720
ttatttttct aaatacattc aaatatgtat ccgctcatga caataaccc tgataaatg    3780 cttcaataat attgaaaaag gaagagtatg agtattcaac atttccgtgt cgcccttatt    3840
ccctttttTg cggcattttg ccttcctgtt tttgctcacc cagaaacgct ggtgaaagta    3900
aaagatgctg aagatcagtt gggtgcacga gtgggttaca tcgaactgga tctcaacagc    3960
ggtaagatcc ttgagagttt tcgccccgaa gaacgttttc caatgatgag cacttttaaa    4020
gttctgctat gtggcgcggt attatcccgt attgacgccg ggcaagagca actcggtcgc    4080
cgcatacact attctcagaa tgacttggtt gagtactcac cagtcacaga aaagcatctt    4140
acggatggca tgacagtaag agaattatgc agtgctgcca taaccatgag tgataacact    4200
gcggccaact tacttctgac aacgatcgga ggaccgaagg agctaaccgc ttttttgcac    4260
aacatggggg atcatgtaac tcgccttgat cgttgggaac cggagctgaa tgaagccata    4320
ccaaacgacg agcgtgacac cacgatgcct gtagcaatgg caacaacgtt gcgcaaacta    4380
ttaactggcg aactacttac tctagcttcc cggcaacaat aatagactgg atggaggcg    4440 gataaagttg caggaccact tctgcgctcg gcccttccgg ctggctggtt tattgctgat    4500
aaatctggag ccggtgagcg tgggtctcgc ggtatcattg cagcactggg gccagatggt    4560
aagccctccc gtatcgtagt tatctacacg acggggagtc aggcaactat ggatgaacga    4620
aatagacaga tcgctgagat aggtgcctca ctgattaagc attggtaact gtcagaccaa    4680
gtttactcat atatacttta gattgattta aaacttcatt tttaatttaa aaggatctag    4740
gtgaagatcc ttttttgataa tctcatgacc aaaatccctt aacgtgagtt tcgttccac    4800 tgagcgtcag accccgtaga aaagatcaaa ggatcttctt gagatccttt ttttctgcgc    4860
gtaatctgct gcttgcaaac aaaaaaacca ccgctaccag cggtggtttg tttgccggat    4920
caagagctac caactctttt tccgaaggta actggcttca gcagagcgca gataccaaat    4980
actgtccttc tagtgtagcc gtagttaggc caccacttca agaactctgt agcaccgcct    5040
acatacctcg ctctgctaat cctgttacca gtggctgctg ccagtggcga taagtcgtgt    5100
cttaccgggt tggactcaag acgatagtta ccggataagg cgcagcggtc gggctgaacg    5160
gggggttcgt gcacacagcc cagcttggag cgaacgacct acaccgaact gagatacct a    5220 cagcgtgagc tatgagaaag cgccacgctt cccgaaggga gaaggcgga caggtatccg    5280 gtaagcggca gggtcggaac aggagagcgc acgagggagc ttccaggggg aaacgcctgg    5340
tatctttata gtcctgtcgg gtttcgccac ctctgacttg agcgtcgatt tttgtgatgc    5400
```

```
tcgtcagggg ggcggagcct atggaaaaac gccagcaacg cggccttttt acggttcctg    5460 gcctttgct ggccttttgc tcacatgt                                         5488

<210> SEQ ID NO 108
<211> LENGTH: 7807
<212> TYPE: DNA
<213> ORGANISM: Artificial Sequence
<220> FEATURE:
<223> OTHER INFORMATION: Synthetic

<400> SEQUENCE: 108
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt      180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aggacgaaa caccgacgct tccgagtacg     420
gtacgtttta gagctagaaa tagcaagtta aaataaggct agtccgttat caacttgaaa    480
aagtggcacc gagtcggtgc ttttttcta gagacgcttc cgagtacggt acaggggatc     540
ctacccttac gatgtaccgg attacgcagg aagcggagct actaacttca gcctgctgaa    600
gcaggctgga gacgtggagg agaaccctgg acctggtacc cccaagaaga agaggaaggt    660
gtccaatctc ctgactgttc accagaacct ccctgcgctg ccagtagatg ccactagcga    720
tgaggtcagg aaaaatctca tggatatgtt tagggataga caggcgtttt ctgaacacac    780
ctggaaaatg ctgcttagcg tgtgccgatc ctgggcagcc tggtgtaagc tgaacaatcg    840
caaatggttc cccgccgagc cggaggacgt gcgcgattac ctgctgtatc tccaggcaag    900
agggctggct gtcaagacta ccagcagca cttgggccaa ctgaatatgc tgcatcgacg    960
cagcgggctc ccccggccta gcgattcaaa cgcagtctcc cttgttatga ggagaattag   1020
aaaggaaaac gtagatgcgg gtgagagggc taagcaggct ctcgcttttg agcggactga   1080
tttcgaccag gtcagatccc tgatggagaa cagcgatcgg tgccaggaca tcaggaacct   1140
cgcatttctg ggaattgcat ataacacact tctgcgcata gctgagatcg cccggatcag   1200
agtgaaagac atcagtcgaa cggacggcgg ccggatgctt attcatattg gacgcacaaa   1260
gacattggtc agcaccgctg gcgttgaaaa ggccttgtcc ctgggcgtaa cgaagctggt   1320
ggaaagatgg atctcagtgt ccggcgtggc tgacgaccct aataattact tgttctgtcg   1380
agtgagaaaa aacggagtcg ccgcgccctc tgccaccagc caattgagta cacgggccct   1440
tgaagggatc tttgaggcaa cccaccgact catatacgga gccaaggatg acagtggcca   1500
gaggtatctc gcctggtcag gtcattctgc tagggtgggg gccgcacgag acatggcgcg   1560
ggcaggagtc tccataccag agattatgca agctggaggt tggacaaatg tgaacatcgt   1620
tatgaactat atccgcaatc ttgactctga accgggggcc atggtgagac tgctcgaaga   1680
tggtgacaag cttggatagc tagctagcta gctcgaggac gcttccgagt acggtacagg   1740
gtcgacggcc ctgcgtatgg ggcagagcgc acatcgccca cagtccccga aagttgggg    1800 ggagggtcg gcaattgaac gggtgcctag agaaggtggc gcggggtaaa ctgggaaagt   1860
gatgtcgtgt actggctccg ccttttttccc gagggtgggg gagaaccgta tataagtgca   1920
gtagtcgccg tgaacgttct ttttcgcaac gggtttgccg ccagaacaca gctgaagctt   1980
```

```
cgaggggctc gcatctctcc ttcacgcgcc cgccgccta cctgaggccg ccatccacgc   2040
cggttgagtc gcgttctgcc gcctcccgcc tgtggtgcct cctgaactgc gtccgccgtc   2100
taggtaagtt taaagctcag gtcgagaccg ggcctttgtc cggcgctccc ttggagccta   2160
cctagactca gccggctctc cacgcttttgc ctgaccctgc ttgctcaact ctacgtcttt   2220
gtttcgtttt ctgttctgcg ccgttacaga tccaagctgt gaccggcgcc tacaccggtg   2280
ccaccatggg ccccaagaaa aacggaagg tggccgctgc agggatacat ggggttcctg     2340
cagccgataa aaatacagt atcggtctgg acataggcac taattctgtc ggttgggccg     2400
tgataacaga tgaatataaa gtaccttcca aaaaattcaa ggttctggga aacacagata    2460
gacacagtat aaaaaagaac ctgattggcg ctttgctctt tgacagcggt gagaccgcag    2520
aggcaactcg cttgaagcgg accgcccggc gaaggtacac acgacgcaag aaccgaattt    2580
gttacctcca ggaaatattc agtaacgaaa tggccaaagt tgacgattct ttttccatc    2640 gccttgaaga atccttcctg gtagaagaag ataagaagca tgagagacac ccaatatttg   2700
ggaatatagt tgacgaagtc gcatatcacg agaagtaccc tactatatat caccttcgga   2760
aaaaactggt cgattcaact gacaaagccg acttgagact catatacctg gcccttgctc   2820
acatgatcaa gttccggggc cactttctga ttgaaggcga cctcaatccc gacaatagcg   2880
acgtagacaa gctgtttatc caactcgttc aaacctataa ccagctcttc gaagagaacc   2940
caataaatgc tagtggggtc gatgccaaag ctattttgag tgctaggctg tcaaagagta   3000
gaaggttgga gaacctgatc gcacaactgc ccggtgagaa gaagaacggc cttttttggga  3060 acttgattgc tctctccctt ggccttaccc ctaactttaa atccaacttc gatcttgctg   3120
aggatgctaa gctccaactg tccaaggaca cctacgacga cgacttggat aaccttctgg   3180
cccagatagg tgatcagtac gcagatcttt tcttggcagc caagaatctg tctgacgcaa   3240
tcttgcttag tgcatcctg agggtgaata ctgaaataac taaggctcca ctttccgcct    3300
ctatgatcaa gcgctacgac gaacaccatc aagacctgac ccttttgaag gccttggtta   3360
gacaacaact gcctgaaaaa tacaaggaaa tattcttcga ccagtctaag aacggttatg   3420
ccggatatat cgacgggggg gcatcacagg aggaattcta taaatttata aagcctatct   3480
tggagaaaat ggacggaacc gaagaactcc tcgtaaagct taaccgcgaa gaccttttgc   3540
gaaagcagcg gactttcgat aacggctcta ttcctcacca aatccacctc ggggagcttc   3600
acgcaatatt gcgaaggcag gaggacttct atccattctt gaaggataat cgggaaaaaa   3660
ttgaaaaaat tcttacattt cggattcctt actacgtggg tcctctggcc cgcgggaata   3720
gtcggtttgc atggatgact cggaagtctg aggaaactat cacaccatgg aatttttgaag  3780 aagtggtaga caaaggggct tccgctcagt ctttcataga gaggatgact aattttgata   3840
aaaacctgcc taacgaaaag gtactcccca agcattcact tctttatgaa tatttcactg   3900
tctacaacga gctgactaag gttaaatatg taaccgaagg tatgcggaag ccagcattcc   3960
tgagtggtga gcagaagaag gcaatcgtag acctttttgtt caaaaccaac cgaaaggtga  4020
cagtaaaaca actcaaggaa gactatttta agaaaataga gtgtttgtct tatgagaccg   4080
aaatcctcac cgtggagtac gggctcctgc ctatcggaaa aattgtcgaa aagcgcatag   4140
agtgcactgt ttactctgta gataacaatg gaaacatata cacacagccc gtagcacagt   4200
ggcacgatcg aggcgagcag gaggtctttg aatattgcct ggaagacggc agtcttataa   4260
gggcaacaaa ggatcacaaa tttatgaccg tagatggaca aatgcttccc atcgacgaga   4320
```

```
tctttgagcg cgagcttgac ttgatgagag tggataacct gcctaattag gaattcgata    4380
tcaagcttat cgataatcaa cctctggatt acaaaatttg tgaaagattg actggtattc    4440
ttaactatgt tgctccttt  acgctatgtg gatacgctgc tttaatgcct ttgtatcatg    4500
ctattgcttc ccgtatggct ttcattttct cctccttgta taaatcctgg ttgctgtctc    4560
tttatgagga gttgtggccc gttgtcaggc aacgtggcgt ggtgtgcact gtgtttgctg    4620
acgcaacccc cactggttgg ggcattgcca ccacctgtca gctcctttcc gggactttcg    4680
ctttccccct cccattgcc  acggcggaac tcatcgccgc ctgccttgcc cgctgctgga    4740 cagggctcg  gctgttgggc actgacaatt ccgtggtgtt gtcggggaaa tcatcgtcct    4800
ttccttggct gctcgcctgt gttgccacct ggattctgcg cgggacgtcc ttctgctacg    4860
tcccttcggc cctcaatcca gcggaccttc cttcccgcgg cctgctgccg gctctgcggc    4920
ctcttccgcg tcttcgcctt cgccctcaga cgagtcggat ctccctttgg gccgcctccc    4980
cgcatcgata ccgagcgcta ataaaagatc tttattttca ttagatctgt gtgttggttt    5040
tttgtgtcac gtgcggaccg agcggccgca ggaaccccta gtgatggagt tggccactcc    5100
ctctctgcgc gctcgctcgc tcactgaggc cgggcgacca aggtcgccc  gacgcccggg    5160 ctttgccgg  gcggcctcag tgagcgagcg agcgcgcagc tgcctgcagg ggcgcctgat    5220
gcggtatttt ctccttacgc atctgtgcgg tatttcacac cgcatacgtc aaagcaacca    5280
tagtacgcgc cctgtagcgg cgcattaagc gcggcgggtg tggtggttac gcgcagcgtg    5340
accgctacac ttgccagcgc cctagcgccc gctcctttcg ctttcttccc ttcctttctc    5400
gccacgttcg ccggctttcc ccgtcaagct ctaaatcggg ggctcccttt agggttccga    5460
tttagtgctt tacggcacct cgaccccaaa aaacttgatt tgggtgatgg ttcacgtagt    5520
gggccatcgc cctgatagac ggtttttcgc cctttgacgt tggagtccac gttctttaat    5580
agtggactct tgttccaaac tggaacaaca ctcaaccccta tctcgggcta ttcttttgat    5640
ttataaggga ttttgccgat ttcggcctat tggttaaaaa atgagctgat ttaacaaaaa    5700
tttaacgcga attttaacaa aatattaacg tttacaattt tatggtgcac tctcagtaca    5760
atctgctctg atgccgcata gttaagccag ccccgacacc cgccaacacc cgctgacgcg    5820
ccctgacggg cttgtctgct cccggcatcc gcttacagac aagctgtgac cgtctccggg    5880
agctgcatgt gtcagaggtt ttcaccgtca tcaccgaaac gcgcgagacg aaagggcctc    5940
gtgatacgcc tatttttata ggttaatgtc atgataataa tggtttctta gacgtcaggt    6000
ggcacttttc ggggaaatgt gcgcggaacc cctatttgtt tatttttcta aatacattca    6060
aatatgtatc cgctcatgag acaataaccc tgataaatgc ttcaataata ttgaaaaagg    6120
aagagtatga gtattcaaca tttccgtgtc gcccttattc cctttttgc  ggcatttgc     6180 cttcctgttt ttgctcaccc agaaacgctg gtgaaagtaa aagatgctga agatcagttg    6240
ggtgcacgag tgggttacat cgaactggat ctcaacagcg gtaagatcct tgagagtttt    6300
cgccccgaag aacgttttcc aatgatgagc acttttaaag ttctgctatg tggcgcggta    6360
ttatcccgta ttgacgccgg gcaagagcaa ctcggtcgcc gcatacacta ttctcagaat    6420
gacttggttg agtactcacc agtcacagaa aagcatctta cggatggcat gacagtaaga    6480
gaattatgca gtgctgccat aaccatgagt gataacactg cggccaactt acttctgaca    6540
acgatcggag gaccgaagga gctaaccgct tttttgcaca acatggggga tcatgtaact    6600
cgccttgatc gttgggaacc ggagctgaat gaagccatac caaacgacga gcgtgacacc    6660
acgatgcctg tagcaatggc aacaacgttg cgcaaactat taactggcga actacttact    6720
```

```
ctagcttccc ggcaacaatt aatagactgg atggaggcgg ataaagttgc aggaccactt    6780
ctgcgctcgg cccttccggc tggctggttt attgctgata atctggagc cggtgagcgt    6840 gggtctcgcg gtatcattgc agcactgggg ccagatggta agccctcccg tatcgtagtt    6900
atctacacga cggggagtca ggcaactatg gatgaacgaa atagacagat cgctgagata    6960
ggtgcctcac tgattaagca ttggtaactg tcagaccaag tttactcata tatactttag    7020
attgatttaa aacttcattt ttaatttaaa aggatctagg tgaagatcct tttttgataat   7080 ctcatgacca aaatccctta acgtgagttt tcgttccact gagcgtcaga ccccgtagaa    7140
aagatcaaag gatcttcttg agatcctttt tttctgcgcg taatctgctg cttgcaaaca    7200 aaaaaccac cgctaccagc ggtggtttgt ttgccggatc aagagctacc aactcttttt     7260
ccgaaggtaa ctggcttcag cagagcgcag ataccaaata ctgtccttct agtgtagccg    7320
tagttaggcc accacttcaa gaactctgta gcaccgccta catacctcgc tctgctaatc    7380
ctgttaccag tggctgctgc cagtggcgat aagtcgtgtc ttaccgggtt ggactcaaga    7440
cgatagttac cggataaggc gcagcggtcg ggctgaacgg ggggttcgtg cacacagccc    7500
agcttggagc gaacgaccta caccgaactg agatacctac agcgtgagct atgagaaagc    7560
gccacgcttc ccgaagggag aaaggcggac aggtatccgg taagcggcag gtcggaaca    7620 ggagagcgca cgagggagct ccaggggga aacgcctggt atctttatag tcctgtcggg    7680
tttcgccacc tctgacttga gcgtcgattt ttgtgatgct cgtcaggggg cggagccta    7740 tgaaaaacg ccagcaacgc ggccttttta cggttcctgg ccttttgctg gccttttgct    7800
cacatgt                                                              7807
```

<210> SEQ ID NO 109
<211> LENGTH: 7809
<212> TYPE: DNA
<213> ORGANISM: Artificial Sequence
<220> FEATURE:
<223> OTHER INFORMATION: Synthetic

<400> SEQUENCE: 109

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttctca gagacgcttc cgagtacggt acaggggatc    540
cagtaccctt acgatgtacc ggattacgca ggaagcggag ctactaactt cagcctgctg    600
aagcaggctg gagacgtgga ggagaaccct ggacctggta ccccaagaa gaagaggaag    660 gtgtccaatc tcctgactgt tcaccagaac ctccctgcgc tgccagtaga tgccactagc    720
gatgaggtca ggaaaaatct catggatatg tttagggata gacaggcgtt ttctgaacac    780
acctggaaaa tgctgcttag cgtgtgccga tcctgggcag cctggtgtaa gctgaacaat    840
cgcaaatggt tccccgccga gccggaggac gtgcgcgatt acctgctgta tctccaggca    900
```

```
agagggctgg ctgtcaagac tatccagcag cacttgggcc aactgaatat gctgcatcga    960
cgcagcgggc tcccccggcc tagcgattca aacgcagtct cccttgttat gaggagaatt   1020
agaaaggaaa acgtagatgc gggtgagagg gctaagcagg ctctcgcttt tgagcggact   1080
gatttcgacc aggtcagatc cctgatggag aacagcgatc ggtgccagga catcaggaac   1140
ctcgcatttc tgggaattgc atataacaca cttctgcgca tagctgagat cgcccggatc   1200
agagtgaaag acatcagtcg aacggacggc ggccggatgc ttattcatat tggacgcaca   1260
aagacattgg tcagcaccgc tggcgttgaa aaggccttgt ccctgggcgt aacgaagctg   1320
gtggaaagat ggatctcagt gtccggcgtg gctgacgacc ctaataatta cttgttctgt   1380
cgagtgagaa aaaacggagt cgccgcgccc tctgccacca gccaattgag tacacgggcc   1440
cttgaaggga tctttgaggc aacccaccga ctcatatacg gagccaagga tgacagtggc   1500
cagaggtatc tcgcctggtc aggtcattct gctagggtgg gggccgcacg agacatggcg   1560
cgggcaggag tctccatacc agagattatg caagctggag gttggacaaa tgtgaacatc   1620
gttatgaact atatccgcaa tcttgactct gaaaccgggg ccatggtgag actgctcgaa   1680
gatggtgaca agcttggata gctagctagc tagctcgagg acgcttccga gtacggtaca   1740
gggtcgacgg ccctgcgtat ggggcagagc gcacatcgcc cacagtcccc gagaagttgg   1800
ggggagggt cggcaattga acgggtgcct agagaaggtg gcgcggggta aactgggaaa   1860
gtgatgtcgt gtactggctc cgccttttc ccgagggtgg gggagaaccg tatataagtg   1920
cagtagtcgc cgtgaacgtt cttttttcgca acgggtttgc cgccagaaca cagctgaagc   1980
ttcgagggc tcgcatctct ccttcacgcg cccgccgccc tacctgaggc cgccatccac   2040
gccggttgag tcgcgttctg ccgcctcccg cctgtggtgc ctcctgaact gcgtccgccg   2100
tctaggtaag tttaaagctc aggtcgagac cgggccttg tccggcgctc ccttggagcc   2160
tacctagact cagccggctc tccacgcttt gcctgaccct gcttgctcaa ctctacgtct   2220
ttgtttcgtt ttctgttctg cgccgttaca gatccaagct gtgaccggcg cctacaccgg   2280
tgccaccatg ggccccaaga aaaacggaa ggtggccgct gcagggatac atggggttcc   2340
tgcagccgat aaaaaataca gtatcggtct ggacataggc actaattctg tcggttgggc   2400
cgtgataaca gatgaatata agtaccttc caaaaaattc aaggttctgg aaacacaga    2460
tagacacagt ataaaaaaga acctgattgg cgctttgctc tttgacagcg gtgagaccgc   2520
agaggcaact cgcttgaagc ggaccgcccg gcgaaggtac acacgacgca agaaccgaat   2580
ttgttacctc caggaaatat tcagtaacga aatggccaaa gttgacgatt ctttttttcca   2640
tcgccttgaa gaatccttcc tggtagaaga agataagaag catgagagac acccaatatt   2700
tgggaatata gttgacgaag tcgcatatca cgagaagtac cctactatat atcaccttcg   2760
gaaaaaactg gtcgattcaa ctgacaaagc cgacttgaga ctcatatacc tggcccttgc   2820
tcacatgatc aagttccggg gccactttct gattgaaggc gacctcaatc ccgacaatag   2880
cgacgtagac aagctgttta tccaactcgt tcaaacctat aaccagctct cgaagagaa    2940
cccaataaat gctagtgggg tcgatgccaa agctattttg agtgctaggc tgtcaaagag   3000
tagaaggttg gagaacctga tcgcacaact gcccggtgag aagaagaacg gccttttggg   3060
gaacttgatt gctctctccc ttggccttac ccctaacttt aaatccaact cgatcttgc    3120
tgaggatgct aagctccaac tgtccaagga cacctacgac gacgacttgg ataaccttct   3180
ggcccagata ggtgatcagt acgcagatct ttcttggca gccaagaatc tgtctgacgc   3240
aatcttgctt agtgacatcc tgagggtgaa tactgaaata actaaggctc cactttccgc   3300
```

```
ctctatgatc aagcgctacg acgaacacca tcaagacctg acccttttga aggccttggt    3360
tagacaacaa ctgcctgaaa aatacaagga aatattcttc gaccagtcta agaacggtta    3420
tgccggatat atcgacgggg gggcatcaca ggaggaattc tataaattta taaagcctat    3480
cttggagaaa atggacggaa ccgaagaact cctcgtaaag cttaaccgcg aagaccttt     3540
gcgaaagcag cggactttcg ataacggctc tattcctcac caaatccacc tcggggagct    3600
tcacgcaata ttgcgaaggc aggaggactt ctatccattc ttgaaggata atcgggaaaa    3660
aattgaaaaa attcttacat ttcggattcc ttactacgtg ggtcctctgg cccgcgggaa    3720
tagtcggttt gcatggatga ctcggaagtc tgaggaaact atcacaccat ggaattttga    3780
agaagtggta gacaaagggg cttccgctca gtctttcata gagaggatga ctaattttga    3840
taaaaacctg cctaacgaaa aggtactccc caagcattca cttctttatg aatatttcac    3900
tgtctacaac gagctgacta aggttaaata tgtaaccgaa ggtatgcgga agccagcatt    3960
cctgagtggt gagcagaaga aggcaatcgt agaccttttg ttcaaaacca accgaaaggt    4020
gacagtaaaa caactcaagg aagactattt taagaaaata gagtgtttgt cttatgagac    4080
cgaaatcctc accgtggagt acgggctcct gcctatcggg aaaattgtcg aaaagcgcat    4140
agagtgcact gtttactctg tagataacaa tggaaacata tacacacagc ccgtagcaca    4200
gtggcacgat cgaggcgagc aggaggtctt tgaatattgc ctggaagacg gcagtcttat    4260
aagggcaaca aaggatcaca aatttatgac cgtagatgga caaatgcttc ccatcgacga    4320
gatctttgag cgcgagcttg acttgatgag agtggataac ctgcctaatt aggaattcga    4380
tatcaagctt atcgataatc aacctctgga ttacaaaatt tgtgaaagat tgactggtat    4440
tcttaactat gttgctcctt ttacgctatg tggatacgct gctttaatgc ctttgtatca    4500
tgctattgct tcccgtatgg ctttcatttt ctcctccttg tataaatcct ggttgctgtc    4560
tctttatgag gagttgtggc ccgttgtcag gcaacgtggc gtggtgtgca ctgtgtttgc    4620
tgacgcaacc cccactggtt ggggcattgc caccacctgt cagctccttt ccgggacttt    4680
cgctttcccc ctccctattg ccacggcgga actcatcgcc gcctgccttg cccgctgctg    4740
gacaggggct cggctgttgg gcactgacaa ttccgtggtg ttgtcgggga aatcatcgtc    4800
ctttccttgg ctgctcgcct gtgttgccac ctggattctg cgcggacgt ccttctgcta    4860
cgtcccttcg gccctcaatc cagcggacct tccttcccgc ggcctgctgc cggctctgcg    4920
gcctcttccg cgtcttcgcc ttcgccctca gacgagtcgg atctcccttt gggccgcctc    4980
cccgcatcga taccgagcgc taataaaaga tctttatttt cattagatct gtgtgttggt    5040
tttttgtgtc acgtgcggac cgagcggccg caggaaccc tagtgatgga gttggccact    5100
ccctctctgc gcgctcgctc gctcactgag gccgggcgac caaggtcgc ccgacgcccg    5160
ggctttgccc gggcggcctc agtgagcgag cgagcgcgca gctgcctgca ggggcgcctg    5220
atgcggtatt ttctccttac gcatctgtgc ggtatttcac accgcatacg tcaaagcaac    5280
catagtacgc gccctgtagc ggcgcattaa gcgcggcggg tgtggtggtt acgcgcagcg    5340
tgaccgctac acttgccagc gccctagcgc ccgctccttt cgctttcttc ccttcctttc    5400
tcgccacgtt cgccggcttt ccccgtcaag ctctaaatcg gggctccct ttagggttcc    5460
gatttagtgc tttacggcac ctcgacccca aaaaacttga tttgggtgat ggttcacgta    5520
gtgggccatc gccctgatag acggtttttc gccctttgac gttggagtcc acgttcttta    5580
atagtggact cttgttccaa actggaacaa cactcaaccc tatctcgggc tattcttttg    5640
```

```
atttataagg gattttgccg atttcggcct attggttaaa aaatgagctg atttaacaaa     5700
aatttaacgc gaattttaac aaaatattaa cgtttacaat tttatggtgc actctcagta     5760
caatctgctc tgatgccgca tagttaagcc agccccgaca cccgccaaca cccgctgacg     5820
cgccctgacg ggcttgtctg ctcccggcat ccgcttacag acaagctgtg accgtctccg     5880
ggagctgcat gtgtcagagg ttttcaccgt catcaccgaa acgcgcgaga cgaaagggcc     5940
tcgtgatacg cctattttta taggttaatg tcatgataat aatggtttct tagacgtcag     6000
gtggcacttt tcggggaaat gtgcgcggaa cccctatttg tttatttttc taaatacatt     6060
caaatatgta tccgctcatg agacaataac cctgataaat gcttcaataa tattgaaaaa     6120
ggaagagtat gagtattcaa catttccgtg tcgcccttat tcccttttt gcggcatttt       6180
gccttcctgt ttttgctcac ccagaaacgc tggtgaaagt aaaagatgct gaagatcagt     6240
tgggtgcacg agtgggttac atcgaactgg atctcaacag cggtaagatc cttgagagtt     6300
ttcgccccga agaacgtttt ccaatgatga gcacttttaa agttctgcta tgtggcgcgg     6360
tattatcccg tattgacgcc gggcaagagc aactcggtcg ccgcatacac tattctcaga     6420
atgacttggt tgagtactca ccagtcacag aaaagcatct tacggatggc atgacagtaa     6480
gagaattatg cagtgctgcc ataaccatga gtgataacac tgcggccaac ttacttctga     6540
caacgatcgg aggaccgaag gagctaaccg cttttttgca caacatgggg gatcatgtaa     6600
ctcgccttga tcgttgggaa ccggagctga atgaagccat accaaacgac gagcgtgaca     6660
ccacgatgcc tgtagcaatg gcaacaacgt tgcgcaaact attaactggc gaactactta     6720
ctctagcttc ccggcaacaa ttaatagact ggatggaggc ggataaagtt gcaggaccac     6780
ttctgcgctc ggcccttccg gctggctggt ttattgctga taaatctgga gccggtgagc     6840
gtgggtctcg cggtatcatt gcagcactgg ggccagatgg taagccctcc cgtatcgtag     6900
ttatctacac gacggggagt caggcaacta tggatgaacg aaatagacag atcgctgaga     6960
taggtgcctc actgattaag cattggtaac tgtcagacca agtttactca tatatacttt     7020
agattgattt aaaacttcat ttttaattta aaaggatcta ggtgaagatc ctttttgata     7080
atctcatgac caaaatccct taacgtgagt tttcgttcca ctgagcgtca gaccccgtag     7140
aaaagatcaa aggatcttct tgagatcctt ttttctgcg cgtaatctgc tgcttgcaaa       7200
caaaaaaacc accgctacca gcggtggttt gtttgccgga tcaagagcta ccaactcttt     7260
ttccgaaggt aactggcttc agcagagcgc agataccaaa tactgtcctt ctagtgtagc     7320
cgtagttagg ccaccacttc aagaactctg tagcaccgcc tacatacctc gctctgctaa     7380
tcctgttacc agtggctgct gccagtggcg ataagtcgtg tcttaccggg ttggactcaa     7440
gacgatagtt accggataag cgcagcggt cgggctgaac ggggggttcg tgcacacagc       7500
ccagcttgga gcgaacgacc tacaccgaac tgagatacct acagcgtgag ctatgagaaa     7560
gcgccacgct tcccgaaggg agaaaggcgg acaggtatcc ggtaagcggc agggtcggaa     7620
caggagagcg cacgagggag cttccagggg gaaacgcctg gtatctttat agtcctgtcg     7680
ggtttcgcca cctctgactt gagcgtcgat ttttgtgatg ctcgtcaggg ggcggagcc       7740
tatgaaaaaa cgccagcaac gcggcctttt tacggttcct ggccttttgc tggccttttg     7800
ctcacatgt                                                              7809
```

<210> SEQ ID NO 110  
<211> LENGTH: 7808  
<212> TYPE: DNA  
<213> ORGANISM: Artificial Sequence

```
<220> FEATURE:
<223> OTHER INFORMATION: Synthetic

<400> SEQUENCE: 110
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggaggat    540
cctaccctta cgatgtaccg gattacgcag gaagcggagc tactaacttc agcctgctga    600
agcaggctgg agacgtggag gagaaccctg gacctggtac ccccaagaag aagaggaagg    660
tgtccaatct cctgactgtt caccagaacc tccctgcgct gccagtagat gccactagcg    720
atgaggtcag gaaaaatctc atggatatgt ttagggatag acaggcgttt tctgaacaca    780
cctggaaaat gctgcttagc gtgtgccgat cctgggcagc ctggtgtaag ctgaacaatc    840
gcaaatggtt ccccgccgag ccggaggacg tgcgcgatta cctgctgtat ctccaggcaa    900
gagggctggc tgtcaagact atccagcagc acttgggcca actgaatatg ctgcatcgac    960
gcagcgggct ccccggcct agcgattcaa acgcagtctc ccttgttatg aggagaatta   1020
gaaaggaaaa cgtagatgcg ggtgagaggg ctaagcaggc tctcgctttt gagcggactg   1080
atttcgacca ggtcagatcc ctgatggaga acagcgatcg gtgccaggac atcaggaacc   1140
tcgcatttct gggaattgca tataacacac ttctgcgcat agctgagatc gcccggatca   1200
gagtgaaaga catcagtcga acggacggcg gccggatgct tattcatatt ggacgcacaa   1260
agacattggt cagcaccgct ggcgttgaaa aggccttgtc cctgggcgta acgaagctgg   1320
tggaaagatg gatctcagtg tccggcgtgg ctgacgaccc taataattac ttgttctgtc   1380
gagtgagaaa aaacggagtc gccgcgcccct ctgccaccag ccaattgagt acacgggccc   1440
ttgaagggat ctttgaggca acccaccgac tcatatacgg agccaaggat gacagtggcc   1500
agaggtatct cgcctggtca ggtcattctg ctagggtggg ggccgcacga gacatggcgc   1560
gggcaggagt ctccatacca gagattatgc aagctggagg ttggacaaat gtgaacatcg   1620
ttatgaacta tatccgcaat cttgactctg aaaccggggc catggtgaga ctgctcgaag   1680
atggtgacaa gcttggatag ctagctagct agctcgagga cgcttccgag tacggtacag   1740
ggtcgacggc cctgcgtatg gggcagagcg cacatcgccc acagtccccg agaagttggg   1800 gggagggtc ggcaattgaa cgggtgccta gagaaggtgg cgcggggtaa actgggaaag   1860
tgatgtcgtg tactggctcc gccttttttcc cgagggtggg ggagaaccgt atataagtgc   1920
agtagtcgcc gtgaacgttc ttttcgcaa cgggtttgcc gccagaacac agctgaagct   1980 tcgagggggct cgcatctctc cttcacgcgc ccgccgccct acctgaggcc gccatccacg   2040
ccggttgagt cgcgttctgc cgcctcccgc ctgtggtgcc tcctgaactg cgtccgccgt   2100
ctaggtaagt ttaaagctca ggtcgagacc gggccttttgt ccggcgctcc cttggagcct   2160
acctagactc agccggctct ccacgctttg cctgaccctg cttgctcaac tctacgtctt   2220
```

```
tgtttcgttt tctgttctgc gccgttacag atccaagctg tgaccggcgc ctacaccggt      2280
gccaccatgg gccccaagaa aaaacggaag gtggccgctg cagggataca tggggttcct      2340
gcagccgata aaaatacag tatcggtctg gacataggca ctaattctgt cggttgggcc       2400
gtgataacag atgaatataa agtaccttcc aaaaaattca aggttctggg aaacacagat      2460
agacacagta taaaaagaa cctgattggc gctttgctct ttgacagcgg tgagaccgca       2520
gaggcaactc gcttgaagcg gaccgcccgg cgaaggtaca cacgacgcaa gaaccgaatt      2580
tgttacctcc aggaaatatt cagtaacgaa atggccaaag ttgacgattc ttttttccat     2640
cgccttgaag aatccttcct ggtagaagaa gataagaagc atgagagaca cccaatattt      2700
gggaatatag ttgacgaagt cgcatatcac gagaagtacc ctactatata tcaccttcgg     2760
aaaaaactgg tcgattcaac tgacaaagcc gacttgagac tcatataccct ggcccttgct    2820 cacatgatca agttccgggg ccactttctg attgaaggcg acctcaatcc cgacaatagc     2880
gacgtagaca agctgtttat ccaactcgtt caaacctata accagctctt cgaagagaac    2940
ccaataaatg ctagtggggt cgatgccaaa gctattttga gtgctaggct gtcaaagagt     3000
agaaggttgg agaacctgat cgcacaactg cccggtgaga agaagaacgg ccttttgggg    3060
aacttgattg ctctctccct tggccttacc cctaacttta atccaacctt cgatcttgct   3120
gaggatgcta agctccaact gtccaaggac acctacgacg acgacttgga taaccttctg    3180
gcccagatag tgatcagta cgcagatctt ttccttggcag ccaagaatct gtctgacgca   3240
atcttgctta gtgacatcct gagggtgaat actgaaataa ctaaggctcc actttccgcc    3300
tctatgatca agcgctacga cgaacaccat caagacctga ccccttttgaa ggccttggtt  3360 agacaacaac tgcctgaaaa atacaaggaa atattcttcg accagtctaa gaacggttat   3420
gccggatata tcgacggggg ggcatcacag gaggaattct ataaatttat aaagcctatc    3480
ttggagaaaa tggacggaac cgaagaactc ctcgtaaagc ttaaccgcga agacttttg    3540 cgaaagcagc ggactttcga taacggctct attcctcacc aaatccacct cggggagctt    3600
cacgcaatat tgcgaaggca ggaggacttc tatccattct tgaaggataa tcgggaaaaa   3660
attgaaaaaa ttcttacatt tcggattcct tactacgtgg gtcctctggc ccgcgggaat     3720
agtcggtttg catggatgac tcggaagtct gaggaaacta tcacaccatg gaattttgaa   3780
gaagtggtag acaaaggggc ttccgctcag tcttttcatag agaggatgac taattttgat  3840
aaaaacctgc ctaacgaaaa ggtactcccc aagcattcac ttctttatga atatttcact   3900
gtctacaacg agctgactaa ggttaaatat gtaaccgaag gtatgcggaa gccagcattc    3960
ctgagtggtg agcagaagaa ggcaatcgta gacctttttgt tcaaaaccaa ccgaaaggtg    4020 acagtaaaaac aactcaagga agactatttt aagaaaatag agtgtttgtc ttatgagacc    4080
gaaatcctca ccgtggagta cgggctcctg cctatcggga aaattgtcga aaagcgcata    4140
gagtgcactg tttactctgt agataacaat ggaaacatat acacacagcc cgtagcacag    4200
tggcacgatc gaggcgagca ggaggtcttt gaatattgcc tggaagacgg cagtcttata    4260
agggcaacaa aggatcacaa atttatgacc gtagatggac aaatgcttcc catcgacgag   4320
atctttgagc gcgagcttga cttgatgaga gtggataacc tgcctaatta ggaattcgat    4380
atcaagctta tcgataatca acctctggat tacaaaattt gtgaaagatt gactggtatt    4440
cttaactatg ttgctccttt tacgctatgt ggatacgctg ctttaatgcc tttgtatcat    4500
gctattgctt cccgtatggc tttcattttc tcctccttgt ataaatcctg gttgctgtct    4560
ctttatgagg agttgtggcc cgttgtcagg caacgtggcg tggtgtgcac tgtgtttgct    4620
```

```
gacgcaaccc ccactggttg gggcattgcc accacctgtc agctcctttc cgggactttc    4680
gctttccccc tccctattgc cacggcggaa ctcatcgccg cctgccttgc ccgctgctgg    4740
acagggctc ggctgttggg cactgacaat tccgtggtgt tgtcgggaa atcatcgtcc      4800
tttccttggc tgctcgcctg tgttgccacc tggattctgc gcgggacgtc cttctgctac    4860
gtcccttcgg ccctcaatcc agcggacctt ccttcccgcg gcctgctgcc ggctctgcgg    4920
cctcttccgc gtcttcgcct tcgccctcag acgagtcgga tctcccttg ggccgcctcc     4980
ccgcatcgat accgagcgct aataaaagat ctttattttc attagatctg tgtgttggtt    5040
ttttgtgtca cgtgcggacc gagcggccgc aggaacccct agtgatggag ttggccactc    5100
cctctctgcg cgctcgctcg ctcactgagg ccggcgacc aaaggtcgcc cgacgcccgg     5160
gctttgcccg gcggcctca gtgagcgagc gagcgcgcag ctgcctgcag gggcgcctga     5220
tgcggtattt tctccttacg catctgtgcg gtatttcaca ccgcatacgt caaagcaacc    5280
atagtacgcg ccctgtagcg gcgcattaag cgcggcgggt gtggtggtta cgcgcagcgt    5340
gaccgctaca cttgccagcg ccctagcgcc cgctcctttc gctttcttcc cttcctttct    5400
cgccacgttc gccggctttc cccgtcaagc tctaaatcgg gggctccctt tagggttccg    5460
atttagtgct ttacggcacc tcgaccccaa aaaacttgat ttgggtgatg gttcacgtag    5520
tgggccatcg ccctgataga cggtttttcg ccctttgacg ttggagtcca cgttctttaa    5580
tagtggactc ttgttccaaa ctggacaac actcaaccct atctcgggct attcttttga     5640
tttataaggg attttgccga tttcggccta ttggttaaaa atgagctga tttaacaaaa     5700
atttaacgcg aattttaaca aaatattaac gtttacaatt ttatggtgca ctctcagtac    5760
aatctgctct gatgccgcat agttaagcca gccccgacac ccgccaacac ccgctgacgc    5820
gccctgacgg gcttgtctgc tcccggcatc cgcttacaga caagctgtga ccgtctccgg    5880
gagctgcatg tgtcagaggt tttcaccgtc atcaccgaaa cgcgcgagac gaaagggcct    5940
cgtgatacgc ctatttttat aggttaatgt catgataata atggtttctt agacgtcagg    6000
tggcactttt cggggaaatg tgcgcggaac ccctatttgt ttatttttct aaatacattc    6060
aaatatgtat ccgctcatga acaataaccc tgataaatg cttcaataat attgaaaaag    6120
gaagagtatg agtattcaac atttccgtgt cgcccttatt cccttttttg cggcattttg    6180
ccttcctgtt tttgctcacc cagaaacgct ggtgaaagta aaagatgctg aagatcagtt    6240
gggtgcacga gtgggttaca tcgaactgga tctcaacagc ggtaagatcc ttgagagttt    6300
tcgccccgaa gaacgttttc caatgatgag cacttttaaa gttctgctat gtggcgcggt    6360
attatcccgt attgacgccg ggcaagagca actcggtcgc cgcatacact attctcagaa    6420
tgacttggtt gagtactcac cagtcacaga aaagcatctt acggatggca tgacagtaag    6480
agaattatgc agtgctgcca taaccatgag tgataacact gcggccaact tacttctgac    6540
aacgatcgga ggaccgaagg agctaaccgc ttttttgcac aacatggggg atcatgtaac    6600
tcgccttgat cgttgggaac cggagctgaa tgaagccata ccaaacgacg agcgtgacac    6660
cacgatgcct gtagcaatgg caacaacgtt gcgcaaacta ttaactggcg aactacttac    6720
tctagcttcc cggcaacaat taatagactg gatgaggcg ataaagttg caggaccact      6780
tctgcgctcg gcccttccgg ctggctggtt tattgctgat aaatctggag ccggtgagcg    6840
tgggtctcgc ggtatcattg cagcactggg gccagatggt aagccctccc gtatcgtagt    6900
tatctacacg acggggagtc aggcaactat ggatgaacga atagacaga tcgctgagat     6960
```

| | |
|---|---|
| aggtgcctca ctgattaagc attggtaact gtcagaccaa gtttactcat atatacttta | 7020 |
| gattgattta aaacttcatt tttaatttaa aaggatctag gtgaagatcc tttttgataa | 7080 |
| tctcatgacc aaaatccctt aacgtgagtt ttcgttccac tgagcgtcag accccgtaga | 7140 |
| aaagatcaaa ggatcttctt gagatccttt ttttctgcgc gtaatctgct gcttgcaaac | 7200 |
| aaaaaaacca ccgctaccag cggtggtttg tttgccggat caagagctac caactctttt | 7260 |
| tccgaaggta actggcttca gcagagcgca gataccaaat actgtccttc tagtgtagcc | 7320 |
| gtagttaggc caccacttca agaactctgt agcaccgcct acatacctcg ctctgctaat | 7380 |
| cctgttacca gtggctgctg ccagtggcga taagtcgtgt cttaccgggt tggactcaag | 7440 |
| acgatagtta ccggataagg cgcagcggtc gggctgaacg gggggttcgt gcacacagcc | 7500 |
| cagcttggag cgaacgacct acaccgaact gagatacctacagcgtgagc tatgagaaag | 7560 |
| cgccacgctt cccgaaggga aaaggcgga caggtatccg gtaagcggca gggtcggaac | 7620 |
| aggagagcgc acgagggagc ttccaggggg aaacgcctgg tatctttata gtcctgtcgg | 7680 |
| gtttcgccac ctctgacttg agcgtcgatt tttgtgatgc tcgtcagggg ggcggagcct | 7740 |
| atggaaaaac gccagcaacg cggccttttt acggttcctg gccttttgct ggccttttgc | 7800 |
| tcacatgt | 7808 |

<210> SEQ ID NO 111
<211> LENGTH: 7392
<212> TYPE: DNA
<213> ORGANISM: Artificial Sequence
<220> FEATURE:
<223> OTHER INFORMATION: Synthetic

<400> SEQUENCE: 111

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggggatc | 540 |
| ctacccttac gatgtaccgg attacgcagg aagcggagct actaacttca gcctgctgaa | 600 |
| gcaggctgga gacgtggagg agaaccctgg acctggtacc cccaagaaga agaggaaggt | 660 |
| gtccaatctc ctgactgttc accagaacct ccctgcgctg ccagtagatg ccactagcga | 720 |
| tgaggtcagg aaaaatctca tggatatgtt tagggataga caggcgtttt ctgaacacac | 780 |
| ctggaaaatg ctgcttagcg tgtgccgatc ctgggcagcc tggtgtaagc tgaacaatcg | 840 |
| caaatggttc ccgccgagc cggaggacgt gcgcgattac ctgctgtatc tccaggcaag | 900 |
| agggctggct gtcaagacta ccagcagca cttgggccaa ctgaatatgc tgcatcgacg | 960 |
| cagcgggctc ccccggccta gcgattcaaa cgcagtctcc cttgttatga ggagaattag | 1020 |
| aaaggaaaac gtagatgcgg gtgagagggc taagcaggct ctcgcttttg agcggactga | 1080 |
| tttcgaccag gtcagatccc tgatggagaa cagcgatcgg tgccaggaca tcaggaacct | 1140 |
| cgcatttctg ggaattgcat ataacacact tctgcgcata gctgagatcg cccggatcag | 1200 |

```
agtgaaagac atcagtcgaa cggacggcgg ccggatgctt attcatattg gacgcacaaa    1260
gacattggtc agcaccgctg gcgttgaaaa ggccttgtcc ctgggcgtaa cgaagctggt    1320
ggaaagatgg atctcagtgt ccggcgtggc tgacgaccct aataattact tgttctgtcg    1380
agtgagaaaa aacggagtcg ccgcgccctc tgccaccagc caattgagta cacgggccct    1440
tgaagggatc tttgaggcaa cccaccgact catatacgga gccaaggatg acagtggcca    1500
gaggtatctc gcctggtcag gtcattctgc tagggtgggg gccgcacgag acatggcgcg    1560
ggcaggagtc tccataccag agattatgca agctggaggt tggacaaatg tgaacatcgt    1620
tatgaactat atccgcaatc ttgactctga accgggggcc atggtgagac tgctcgaaga    1680
tggtgacaag cttggatagc tagctagcta gctcgagaac ttgtttattg cagcttataa    1740
tggttacaaa taaagcaata gcatcacaaa tttcacaaat aaagcatttt tttcactgca    1800
ttctagttgt ggtttgtcca aactcatcaa tgtatcttac tcgaggacgc ttccgagtac    1860
ggtacagggt cgacggccct gcgtatgggg cagagcgcac atcgcccaca gtccccgaga    1920 agttggggggg aggggtcggc aattgaacgg gtgcctagag aaggtggcgc ggggtaaact    1980
gggaaagtga tgtcgtgtac tggctccgcc ttttcccga gggtgggga gaaccgtata    2040 taagtgcagt agtcgccgtg aacgttcttt ttcgcaacgg gtttgccgcc agaacacagc    2100
tgaagcttcg aggggctcgc atctctcctt cacgcgcccg ccgccctacc tgaggccgcc    2160
atccacgccg gttgagtcgc gttctgccgc ctcccgcctg tggtgcctcc tgaactgcgt    2220
ccgccgtcta ggtaagttta agctcaggt cgagaccggg cctttgtccg gcgctccctt    2280
ggagcctacc tagactcagc cggctctcca cgctttgcct gaccctgctt gctcaactct    2340
acgtctttgt ttcgttttct gttctgcgcc gttacagatc caagctgtga ccggcgccta    2400
caccggtgcc accatgggcc ccaagaaaaa acggaaggtg gccgctgcag ggatacatgg    2460
ggttcctgca gccgataaaa aatacagtat cggtctggac ataggcacta attctgtcgg    2520
ttgggccgtg ataacagatg aatataaagt accttccaaa aaattcaagg ttctgggaaa    2580
cacagataga cacagtataa aaaagaacct gattggcgct ttgctctttg acagcggtga    2640
gaccgcagag gcaactcgct tgaagcggac cgccccggcga aggtacacac gacgcaagaa    2700
ccgaatttgt tacctccagg aaatattcag taacgaaatg gccaaagttg acgattcttt    2760
tttccatcgc cttgaagaat ccttcctggt agaagaagat aagaagcatg agagacaccc    2820
aatatttggg aatatagttg acgaagtcgc atatcacgag aagtacccta ctatatatca    2880
ccttcggaaa aaactggtcg attcaactga caaagccgac ttgagactca tatacctggc    2940
ccttgctcac atgatcaagt tccggggcca ctttctgatt gaaggcgacc tcaatcccga    3000
caatagcgac gtagacaagc tgtttatcca actcgttcaa acctataacc agctcttcga    3060
agagaaccca ataaatgcta gtggggtcga tgccaaagct attttgagtg ctaggctgtc    3120
aaagagtaga aggttggaga acctgatcgc acaactgccc ggtgagaaga gaacggcct    3180 tttttgggaac ttgattgctc tctcccttgg ccttacccct aactttaaat ccaacttcga    3240
tcttgctgag gatgctaagc tccaactgtc caaggacacc tacgacgacg acttggataa    3300
ccttctggcc cagataggtg atcagtacgc agatctttc ttggcagcca agaatctgtc    3360
tgacgcaatc ttgcttagtg acatcctgag ggtgaatact gaaataacta aggctccact    3420
ttccgcctct atgatcaagc gctacgacga acaccatcaa gacctgaccc ttttgaaggc    3480
cttggttaga caacaactgc ctgaaaaata caaggaaata ttcttcgacc agtctaagaa    3540
```

```
cggttatgcc ggatatatcg acggggggc atcacaggag gaattctata aatttataaa    3600
gcctatcttg gagaaaatgg acggaaccga agaactcctc gtaaagctta accgcgaaga   3660
ccttttgcga aagcagcgga ctttcgataa cggctctatt cctcaccaaa tccacctcgg   3720
ggagcttcac gcaatattgc gaaggcagga ggacttctat ccattcttga aggataatcg   3780
ggaaaaaatt gaaaaaattc ttacatttcg gattccttac tacgtgggtc ctctggcccg   3840
cgggaatagt cggtttgcat ggatgactcg gaagtctgag gaaactatca caccatggaa   3900
ttttgaagaa gtggtagaca aagggcttc cgctcagtct ttcatagaga ggatgactaa    3960
ttttgataaa aacctgccta acgaaaaggt actccccaag cattcacttc tttatgaata   4020
tttcactgtc tacaacgagc tgactaaggt taaatatgta accgaaggta tgcggaagcc   4080
agcattcctg agtggtgagc agaagaaggc aatcgtagac cttttgttca aaaccaaccg   4140
aaaggtgaca gtaaaacaac tcaaggaaga ctattttaag aaaatagagt gtttgtctta   4200
tgagaccgaa atcctcaccg tggagtacgg gctcctgcct atcgggaaaa ttgtcgaaaa   4260
gcgcatagag tgcactgttt actctgtaga taacaatgga acatataca cacagcccgt    4320
agcacagtgg cacgatcgag gcgagcagga ggtctttgaa tattgcctgg aagacggcag   4380
tcttataagg gcaacaaagg atcacaaatt tatgaccgta gatggacaaa tgcttcccat   4440
cgacgagatc tttgagcgcg agcttgactt gatgagagtg gataacctgc ctaattagga   4500
attcgatatc aacttgttta ttgcagctta taatggttac aaataaagca atagcatcac   4560
aaatttcaca ataaagcat tttttttcact gcattctagt tgtggtttgt ccaaactcat    4620
caatgtatct tacacgtgcg gaccgagcgg ccgcaggaac ccctagtgat ggagttggcc   4680
actccctctc tgcgcgctcg ctcgctcact gaggccgggc gaccaaaggt cgcccgacgc   4740
ccgggctttg cccgggcggc ctcagtgagc gagcgagcgc gcagctgcct gcaggggcgc   4800
ctgatgcggt attttctcct tacgcatctg tgcggtattt cacaccgcat acgtcaaagc   4860
aaccatagta cgcgccctgt agcggcgcat taagcgcggc gggtgtggtg ttacgcgca    4920
gcgtgaccgc tacacttgcc agcgccctag cgcccgctcc tttcgctttc ttcccttcct   4980
ttctcgccac gttcgccggc tttccccgtc aagctctaaa tcgggggctc cctttagggt   5040
tccgatttag tgctttacgg cacctcgacc ccaaaaaact tgatttgggt gatggttcac   5100
gtagtgggcc atcgccctga tagacggttt ttcgcccttt gacgttggag tccacgttct   5160
ttaatagtgg actcttgttc caaactggaa caacactcaa ccctatctcg ggctattctt   5220
ttgatttata agggattttg ccgatttcgg cctattggtt aaaaaatgag ctgatttaac   5280
aaaaatttaa cgcgaatttt aacaaaatat taacgtttac aattttatgg tgcactctca   5340
gtacaatctg ctctgatgcc gcatagttaa gccagcccg acaccgcca acacccgctg      5400
acgcgccctg acgggcttgt ctgctcccgg catccgctta cagacaagct gtgaccgtct   5460
ccgggagctg catgtgtcag aggttttcac cgtcatcacc gaaacgcgcg agacgaaagg   5520
gcctcgtgat acgcctattt ttataggtta atgtcatgat aataatggtt cttagacgt    5580
caggtggcac ttttcgggga atgtgcgcg gaacccctat ttgtttattt ttctaaatac    5640
attcaaatat gtatccgctc atgagacaat aaccctgata aatgcttcaa taatattgaa   5700
aaaggaagag tatgagtatt caacatttcc gtgtcgccct tattcccttt tttgcggcat   5760
tttgccttcc tgtttttgct cacccagaaa cgctggtgaa agtaaaagat gctgaagatc   5820
agttgggtgc acgagtgggt tacatcgaac tggatctcaa cagcggtaag atccttgaga   5880
gttttcgccc cgaagaacgt tttccaatga tgagcacttt taaagttctg ctatgtggcg   5940
```

```
cggtattatc ccgtattgac gccgggcaag agcaactcgg tcgccgcata cactattctc    6000
agaatgactt ggttgagtac tcaccagtca cagaaaagca tcttacggat ggcatgacag    6060
taagagaatt atgcagtgct gccataacca tgagtgataa cactgcggcc aacttacttc    6120
tgacaacgat cggaggaccg aaggagctaa ccgcttttt gcacaacatg ggggatcatg     6180
taactcgcct tgatcgttgg aaccggagc tgaatgaagc cataccaaac gacgagcgtg     6240
acaccacgat gcctgtagca atggcaacaa cgttgcgcaa actattaact ggcgaactac    6300
ttactctagc ttcccggcaa caattaatag actggatgga ggcggataaa gttgcaggac    6360
cacttctgcg ctcggccctt ccggctggct ggtttattgc tgataaatct ggagccggtg    6420
agcgtgggtc tcgcggtatc attgcagcac tggggccaga tggtaagccc tcccgtatcg    6480
tagttatcta cacgacgggg agtcaggcaa ctatggatga acgaaataga cagatcgctg    6540
agataggtgc ctcactgatt aagcattggt aactgtcaga ccaagtttac tcatatatac    6600
tttagattga tttaaaactt cattttaat ttaaaaggat ctaggtgaag atcctttttg     6660
ataatctcat gaccaaaatc ccttaacgtg agttttcgtt ccactgagcg tcagaccccg    6720
tagaaaagat caaaggatct tcttgagatc ctttttttct gcgcgtaatc tgctgcttgc    6780
aaacaaaaaa accaccgcta ccagcggtgg tttgtttgcc ggatcaagag ctaccaactc    6840 ttttttccgaa ggtaactggc ttcagcagag cgcagatacc aaatactgtc cttctagtgt   6900
agccgtagtt aggccaccac ttcaagaact ctgtagcacc gcctacatac ctcgctctgc    6960
taatcctgtt accagtggct gctgccagtg gcgataagtc gtgtcttacc gggttggact    7020
caagacgata gttaccggat aaggcgcagc ggtcgggctg aacggggggt tcgtgcacac    7080
agcccagctt ggagcgaacg acctacaccg aactgagata cctacagcgt gagctatgag    7140
aaagcgccac gcttcccgaa gggagaaagg cggacaggta tccggtaagc ggcagggtcg    7200
gaacaggaga gcgcacgagg gagcttccag ggggaaacgc ctggtatctt tatagtcctg    7260
tcgggtttcg ccacctctga cttgagcgtc gatttttgtg atgctcgtca ggggggcgga    7320
gcctatggaa aaacgccagc aacgcggcct ttttacggtt cctggccttt tgctggcctt    7380
ttgctcacat gt                                                        7392
```

<210> SEQ ID NO 112
<211> LENGTH: 7394
<212> TYPE: DNA
<213> ORGANISM: Artificial Sequence
<220> FEATURE:
<223> OTHER INFORMATION: Synthetic

<400> SEQUENCE: 112

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tcggccgca cgcgtgaggg cctatttccc atgattcctt        180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttcta gagacgcttc cgagtacggt acaggggatc      540
```

-continued

```
cagtaccctt acgatgtacc ggattacgca ggaagcggag ctactaactt cagcctgctg    600
aagcaggctg agacgtgga ggagaaccct ggacctggta cccccaagaa gaagaggaag    660
gtgtccaatc tcctgactgt tcaccagaac ctccctgcgc tgccagtaga tgccactagc    720
gatgaggtca ggaaaaatct catggatatg tttagggata gacaggcgtt ttctgaacac    780
acctggaaaa tgctgcttag cgtgtgccga tcctgggcag cctggtgtaa gctgaacaat    840
cgcaaatggt tccccgccga gccggaggac gtgcgcgatt acctgctgta tctccaggca    900
agagggctgg ctgtcaagac tatccagcag cacttgggcc aactgaatat gctgcatcga    960
cgcagcgggc tcccccggcc tagcgattca acgcagtct cccttgttat gaggagaatt   1020
agaaaggaaa acgtagatgc gggtgagagg gctaagcagg ctctcgcttt tgagcggact   1080
gatttcgacc aggtcagatc cctgatggag aacagcgatc ggtgccagga catcaggaac   1140
ctcgcatttc tgggaattgc atataacaca cttctgcgca tagctgagat cgcccggatc   1200
agagtgaaag acatcagtcg aacggacggc ggccggatgc ttattcatat tggacgcaca   1260
aagacattgg tcagcaccgc tggcgttgaa aaggccttgt ccctgggcgt aacgaagctg   1320
gtggaaagat ggatctcagt gtccggcgtg gctgacgacc ctaataatta cttgttctgt   1380
cgagtgagaa aaacggagt cgccgcgccc tctgccacca gccaattgag tacacgggcc   1440
cttgaaggga tctttgaggc aacccaccga ctcatatacg gagccaagga tgacagtggc   1500
cagaggtatc tcgcctggtc aggtcattct gctagggtgg gggccgcacg agacatggcg   1560
cgggcaggag tctccatacc agagattatg caagctggag gttggacaaa tgtgaacatc   1620
gttatgaact atatccgcaa tcttgactct gaaaccgggg ccatggtgag actgctcgaa   1680
gatggtgaca agcttggata gctagctagc tagctcgaga acttgtttat tgcagcttat   1740
aatggttaca aataaagcaa tagcatcaca aatttcacaa ataaagcatt ttttcactg    1800 cattctagtt gtggtttgtc caaactcatc aatgtatctt actcgaggac gcttccgagt   1860
acggtacagg gtcgacggcc ctgcgtatgg ggcagagcgc acatcgccca cagtccccga   1920
gaagttgggg ggaggggtcg gcaattgaac gggtgcctag agaaggtggc gcggggtaaa   1980
ctgggaaagt gatgtcgtgt actggctccg cctttttccc gagggtgggg gagaaccgta   2040
tataagtgca gtagtcgccg tgaacgttct ttttcgcaac gggtttgccg ccagaacaca   2100
gctgaagctt cgaggggctc gcatctctcc ttcacgcgcc cgccgcccta cctgaggccg   2160
ccatccacgc cggttgagtc gcgttctgcc gcctcccgcc tgtggtgcct cctgaactgc   2220
gtccgccgtc taggtaagtt taaagctcag gtcgagaccg gcctttgtc cggcgctccc    2280 ttggagccta cctagactca gccggctctc cacgctttgc ctgaccctgc ttgctcaact   2340
ctacgtcttt gtttcgtttt ctgttctgcg ccgttacaga tccaagctgt gaccggcgcc   2400
tacaccggtg ccaccatggg ccccaagaaa aaacggaagg tggccgctgc agggatacat   2460
ggggttcctg cagccgataa aaatacagt atcggtctgg acataggcac taattctgtc   2520
ggttgggccg tgataacaga tgaatataaa gtaccttcca aaaaattcaa ggttctggga   2580
aacacagata gacacagtat aaaaagaac ctgattggcg cttttgctctt tgacagcggt   2640 gagaccgcag aggcaactcg cttgaagcgg accgccggc gaaggtacac acgacgcaag   2700
aaccgaattt gttacctcca ggaaatattc agtaacgaaa tggccaaagt tgacgattct   2760
tttttccatc gccttgaaga atccttcctg gtagaagaag ataagaagca tgagagacac   2820
ccaatatttg gaatatagt tgacgaagtc gcatatcacg agaagtaccc tactatatat   2880 cacttcgga aaaaactggt cgattcaact gacaaagccg acttgagact catataccctg   2940
```

-continued

```
gcccttgctc acatgatcaa gttccggggc cactttctga ttgaaggcga cctcaatccc   3000
gacaatagcg acgtagacaa gctgtttatc caactcgttc aaacctataa ccagctcttc   3060
gaagagaacc caataaatgc tagtggggtc gatgccaaag ctattttgag tgctaggctg   3120
tcaaagagta gaaggttgga gaacctgatc gcacaactgc ccggtgagaa gaagaacggc   3180
cttttgggga acttgattgc tctctcccct tggccttaccc ctaactttaa atccaacttc   3240
gatcttgctg aggatgctaa gctccaactg tccaaggaca cctacgacga cgacttggat   3300
aaccttctgg cccagatagg tgatcagtac gcagatcttt tcttggcagc caagaatctg   3360
tctgacgcaa tcttgcttag tgacatcctg agggtgaata ctgaaataac taaggctcca   3420
ctttccgcct ctatgatcaa gcgctacgac gaacaccatc aagacctgac ccttttgaag   3480
gccttggtta gacaacaact gcctgaaaaa tacaaggaaa tattcttcga ccagtctaag   3540
aacggttatg ccggatatat cgacgggggg gcatcacagg aggaattcta taaatttata   3600
aagcctatct tggagaaaat ggacggaacc gaagaactcc tcgtaaagct taaccgcgaa   3660
gacctttttgc gaaagcagcg gactttcgat aacggctcta ttcctcacca aatccacctc   3720
ggggagcttc acgcaatatt gcgaaggcag gaggacttct atccattctt gaaggataat   3780
cgggaaaaaa ttgaaaaaat tcttacattt cggattcctt actacgtggg tcctctggcc   3840
cgcgggaata gtcggtttgc atggatgact cggaagtctg aggaaactat cacaccatgg   3900
aattttgaag aagtggtaga caaaggggct tccgctcagt ctttcataga gaggatgact   3960
aattttgata aaaacctgcc taacgaaaag gtactcccca agcattcact tctttatgaa   4020
tatttcactg tctacaacga gctgactaag gttaaatatg taaccgaagg tatgcggaag   4080
ccagcattcc tgagtggtga gcagaagaag gcaatcgtag acctttttgtt caaaaccaac   4140
cgaaaggtga cagtaaaaca actcaaggaa gactatttta agaaaataga gtgtttgtct   4200
tatgagaccg aaatcctcac cgtggagtac gggctcctgc ctatcgggaa aattgtcgaa   4260
aagcgcatag agtgcactgt ttactctgta gataacaatg gaaacatata cacacagccc   4320
gtagcacagt ggcacgatcg aggcgagcag gaggtctttg aatattgcct ggaagacggc   4380
agtcttataa gggcaacaaa ggatcacaaa tttatgaccg tagatggaca aatgcttccc   4440
atcgacgaga tctttgagcg cgagcttgac ttgatgagag tggataacct gcctaattag   4500
gaattcgata tcaacttgtt tattgcagct tataatggtt acaataaaag caatagcatc   4560
acaaatttca caaataaagc atttttttca ctgcattcta gttgtggttt gtccaaactc   4620
atcaatgtat cttacacgtg cggaccgagc ggccgcagga ccccctagtg atggagttgg   4680
ccactccctc tctgcgcgct cgctcgctca ctgaggccgg gcgaccaaag gtcgcccgac   4740
gcccgggctt tgcccgggcg gcctcagtga gcgagcgagc gcgcagctgc ctgcaggggc   4800
gcctgatgcg gtattttctc cttacgcatc tgtgcggtat ttcacaccgc atacgtcaaa   4860
gcaaccatag tacgcgccct gtagcggcgc attaagcgcg gcgggtgtgg tggttacgcg   4920
cagcgtgacc gctacacttg ccagcgccct agcgcccgct cctttcgctt tcttcccttc   4980
ctttctcgcc acgttcgccg gctttccccg tcaagctcta aatcggggc tcccctttagg   5040
gttccgattt agtgctttac ggcacctcga ccccaaaaaa cttgatttgg gtgatggttc   5100
acgtagtggg ccatcgccct gatagacggt ttttcgccct tgacgttgg agtccacgtt   5160
ctttaatagt ggactcttgt tccaaactgg aacaacactc aaccctatct cgggctattc   5220
ttttgattta agggatttt gccgatttc ggcctattgg ttaaaaatg agctgattta   5280
```

```
acaaaaattt aacgcgaatt ttaacaaaat attaacgttt acaattttat ggtgcactct   5340
cagtacaatc tgctctgatg ccgcatagtt aagccagccc cgacacccgc caacacccgc   5400
tgacgcgccc tgacgggctt gtctgctccc ggcatccgct tacagacaag ctgtgaccgt   5460
ctccgggagc tgcatgtgtc agaggttttc accgtcatca ccgaaacgcg cgagacgaaa   5520
gggcctcgtg atacgcctat ttttataggt taatgtcatg ataataatgg tttcttagac   5580
gtcaggtggc acttttcggg gaaatgtgcg cggaacccct atttgtttat ttttctaaat   5640
acattcaaat atgtatccgc tcatgagaca ataaccctga taaatgcttc aataatattg   5700
aaaaaggaag agtatgagta ttcaacattt ccgtgtcgcc cttattccct ttttgcggc    5760 attttgcctt cctgtttttg ctcacccaga aacgctggtg aaagtaaaag atgctgaaga   5820
tcagttgggt gcacgagtgg gttacatcga actggatctc aacagcggta agatccttga   5880
gagttttcgc cccgaagaac gttttccaat gatgagcact tttaaagttc tgctatgtgg   5940
cgcggtatta tcccgtattg acgccgggca agagcaactc ggtcgccgca tacactattc   6000
tcagaatgac ttggttgagt actcaccagt cacagaaaag catcttacgg atggcatgac   6060
agtaagagaa ttatgcagtg ctgccataac catgagtgat aacactgcgg ccaacttact   6120
tctgacaacg atcggaggac cgaaggagct aaccgctttt ttgcacaaca tgggggatca   6180
tgtaactcgc cttgatcgtt gggaaccgga gctgaatgaa gccataccaa acgacgagcg   6240
tgacaccacg atgcctgtag caatggcaac aacgttgcgc aaactattaa ctggcgaact   6300
acttactcta gcttcccggc aacaattaat agactggatg gaggcggata agttgcagg    6360 accacttctg cgctcggccc ttccggctgg ctggtttatt gctgataaat ctggagccgg   6420
tgagcgtggg tctcgcggta tcattgcagc actggggcca gatggtaagc cctcccgtat   6480
cgtagttatc tacacgacgg ggagtcaggc aactatggat gaacgaaata cagatcgc    6540 tgagataggt gcctcactga ttaagcattg gtaactgtca gaccaagttt actcatatat   6600
actttagatt gatttaaaac ttcatttttta atttaaaagg atctaggtga agatcctttt   6660
tgataatctc atgaccaaaa tcccttaacg tgagttttcg ttccactgag cgtcagaccc   6720
cgtagaaaag atcaaaggat cttcttgaga tcctttttt ctgcgcgtaa tctgctgctt    6780
gcaaacaaaa aaaccaccgc taccagcggt ggtttgtttg ccggatcaag agctaccaac   6840
tctttttccg aaggtaactg gcttcagcag agcgcagata ccaaatactg tccttctagt   6900
gtagccgtag ttaggccacc acttcaagaa ctctgtagca ccgcctacat acctcgctct   6960
gctaatcctg ttaccagtgg ctgctgccag tggcgataag tcgtgtctta ccgggttgga   7020
ctcaagacga tagttaccgg ataaggcgca gcggtcgggc tgaacggggg gttcgtgcac   7080
acagcccagc ttggagcgaa cgacctacac cgaactgaga tacctacagc gtgagctatg   7140
agaaagcgcc acgcttcccg aagggagaaa ggcggacagg tatccggtaa gcggcagggt   7200
cggaacagga gagcgcacga gggagcttcc agggggaaac gcctggtatc tttatagtcc   7260
tgtcgggttt cgccacctct gacttgagcg tcgatttttg tgatgctcgt caggggggcg   7320
gagcctatgg aaaaacgcca gcaacgcggc ctttttacgg ttcctggcct tttgctggcc   7380
ttttgctcac atgt                                                    7394

<210> SEQ ID NO 113
<211> LENGTH: 7393
<212> TYPE: DNA
<213> ORGANISM: Artificial Sequence
<220> FEATURE:
<223> OTHER INFORMATION: Synthetic
```

<400> SEQUENCE: 113

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccgca cgcgtgaggg cctatttccc atgattcctt   180
catatttgca tatacgatac aaggctgtta gagagataat tggaattaat ttgactgtaa   240
acacaaagat attagtacaa atacgtgac gtagaaagta ataatttctt gggtagtttg    300
cagttttaaa attatgtttt aaaatggact atcatatgct taccgtaact tgaaagtatt   360
tcgatttctt ggctttatat atcttgtgga aaggacgaaa caccgacgct tccgagtacg   420
gtacgtttta gagctagaaa tagcaagtta aaataaggct agtccgttat caacttgaaa   480
aagtggcacc gagtcggtgc ttttttttcta gagacgcttc cgagtacggt acaggaggat   540
cctaccctta cgatgtaccg gattacgcag gaagcggagc tactaacttc agcctgctga   600
agcaggctgg agacgtggag gagaaccctg gacctggtac ccccaagaag aagaggaagg   660
tgtccaatct cctgactgtt caccagaacc tccctgcgct gccagtagat gccactagcg   720
atgaggtcag gaaaaatctc atggatatgt ttagggatag acaggcgttt tctgaacaca   780
cctggaaaat gctgcttagc gtgtgccgat cctgggcagc ctggtgtaag ctgaacaatc   840
gcaaatggtt ccccgccgag ccggaggacg tgcgcgatta cctgctgtat ctccaggcaa   900
gagggctggc tgtcaagact atccagcagc acttgggcca actgaatatg ctgcatcgac   960
gcagcgggct ccccggcct agcgattcaa acgcagtctc ccttgttatg aggagaatta  1020
gaaaggaaaa cgtagatgcg ggtgagaggg ctaagcaggc tctcgctttt gagcggactg  1080
atttcgacca ggtcagatcc ctgatggaga acagcgatcg gtgccaggac atcaggaacc  1140
tcgcatttct gggaattgca tataacacac ttctgcgcat agctgagatc gcccggatca  1200
gagtgaaaga catcagtcga acggacggcg gccggatgct tattcatatt ggacgcacaa  1260
agacattggt cagcaccgct ggcgttgaaa aggccttgtc cctgggcgta acgaagctgg  1320
tggaaagatg gatctcagtg tccggcgtgg ctgacgaccc taataattac ttgttctgtc  1380
gagtgagaaa aaacggagtc gccgcgccct ctgccaccag ccaattgagt acacgggccc  1440
ttgaagggat cttttgaggca acccaccgac tcatatacgg agccaaggat gacagtggcc  1500
agaggtatct cgcctggtca ggtcattctg ctagggtggg ggccgcacga gacatggcgc  1560
gggcaggagt ctccatacca gagattatgc aagctggagg ttggacaaat gtgaacatcg  1620
ttatgaacta tatccgcaat cttgactctg aaaccggggc catggtgaga ctgctcgaag  1680
atggtgacaa gcttggatag ctagctagct agctcgagaa cttgtttatt gcagcttata  1740
atggttacaa ataaagcaat agcatcacaa atttcacaaa taaagcattt ttttcactgc  1800
attctagttg tggtttgtcc aaactcatca atgtatctta ctcgaggacg cttccgagta  1860
cggtacaggg tcgacggccc tgcgtatggg gcagagcgca catcgcccac agtccccgag  1920
aagttggggg gaggggtcgg caattgaacg ggtgcctaga aaggtggcg cggggtaaac   1980
tgggaaagtg atgtcgtgta ctggctccgc ctttttcccg agggtggggg agaaccgtat  2040
ataagtgcag tagtcgccgt gaacgttctt tttcgcaacg ggtttgccgc cagaacacag  2100
ctgaagcttc gaggggctcg catctctcct tcacgcgccc gccgccctac ctgaggccgc  2160
catccacgcc ggttgagtcg cgttctgccg cctcccgcct gtggtgcctc ctgaactgcg  2220
tccgccgtct aggtaagttt aaagctcagg tcgagaccgg gcctttgtcc ggcgctccct  2280
```

```
tggagcctac ctagactcag ccggctctcc acgctttgcc tgaccctgct tgctcaactc    2340
tacgtctttg tttcgttttc tgttctgcgc cgttacagat ccaagctgtg accggcgcct    2400
acaccggtgc caccatgggc cccaagaaaa acggaaggt ggccgctgca gggatacatg     2460
gggttcctgc agccgataaa aaatacagta tcggtctgga cataggcact aattctgtcg    2520
gttgggccgt gataacagat gaatataaag taccttccaa aaaattcaag gttctgggaa    2580
acacagatag acacagtata aaaaagaacc tgattggcgc tttgctcttt gacagcggtg    2640
agaccgcaga ggcaactcgc ttgaagcgga ccgcccggcg aaggtacaca cgacgcaaga    2700
accgaatttg ttacctccag gaaatattca gtaacgaaat ggccaaagtt gacgattctt    2760
ttttccatcg ccttgaagaa tccttcctgg tagaagaaga taagaagcat gagagacacc    2820
caatatttgg gaatatagtt gacgaagtcg catatcacga gaagtaccct actatatatc    2880
accttcggaa aaaactggtc gattcaactg acaaagccga cttgagactc atatacctgg    2940
cccttgctca catgatcaag ttccggggcc actttctgat tgaaggcgac ctcaatcccg    3000
acaatagcga cgtagacaag ctgttttatcc aactcgttca aacctataac cagctcttcg    3060
aagagaaccc aataaatgct agtgggggtcg atgccaaagc tattttgagt gctaggctgt    3120
caaagagtag aaggttggag aacctgatcg cacaactgcc cggtgagaag aagaacggcc    3180
tttttgggaa cttgattgct ctctcccttg gccttacccc taactttaaa tccaacttcg    3240
atcttgctga ggatgctaag ctccaactgt ccaaggacac ctacgacgac gacttggata    3300
accttctggc ccagataggt gatcagtacg cagatctttt cttggcagcc aagaatctgt    3360
ctgacgcaat cttgcttagt gacatcctga gggtgaatac tgaaataact aaggctccac    3420
tttccgcctc tatgatcaag cgctacgacg aacaccatca agacctgacc cttttgaagg    3480
ccttggttag acaacaactg cctgaaaaat acaaggaaat attcttcgac cagtctaaga    3540
acggttatgc cggatatatc gacggggggg catcacagga ggaattctat aaatttataa    3600
agcctatctt ggagaaaatg gacggaaccg aagaactcct cgtaaagctt aaccgcgaag    3660
accttttgcg aaagcagcgg actttcgata acggctctat tcctcaccaa atccacctcg    3720
gggagcttca cgcaatattg cgaaggcagg aggacttcta tccattcttg aaggataatc    3780
gggaaaaaat tgaaaaaatt cttacatttc ggattcctta ctacgtgggt cctctggccc    3840
gcgggaatag tcggtttgca tggatgactc ggaagtctga ggaaactatc acaccatgga    3900
attttgaaga agtggtagac aaaggggctt ccgctcagtc tttcatagag aggatgacta    3960
attttgataa aaacctgcct aacgaaaagg tactccccaa gcattcactt ctttatgaat    4020
atttcactgt ctacaacgag ctgactaagg ttaaatatgt aaccgaaggt atgcggaagc    4080
cagcattcct gagtggtgag cagaagaagg caatcgtaga cctttttgttc aaaaccaacc    4140 gaaaggtgac agtaaaacaa ctcaaggaag actattttaa gaaaatagag tgtttgtctt    4200
atgagaccga atcctcacc gtggagtacg ggctcctgcc tatcgggaaa attgtcgaaa     4260
agcgcataga gtgcactgtt tactctgtag ataacaatgg aaacatatac acacagcccg    4320
tagcacagtg gcacgatcga ggcgagcagg aggtctttga atattgcctg gaagacggca    4380
gtcttataag ggcaacaaag gatcacaaat ttatgaccgt agatgacaa atgcttccca    4440 tcgacgagat ctttgagcgc gagcttgact tgatgagagt ggataacctg cctaattagg    4500
aattcgatat caacttgttt attgcagctt ataatggtta caaataaagc aatagcatca    4560
caaatttcac aaataaagca ttttttcac tgcattctag ttgtggtttg tccaaactca     4620
tcaatgtatc ttacacgtgc ggaccgagcg gccgcaggaa cccctagtga tggagttggc    4680
```

-continued

```
cactccctct ctgcgcgctc gctcgctcac tgaggccggg cgaccaaagg tcgcccgacg   4740
cccgggcttt gcccgggcgg cctcagtgag cgagcgagcg cgcagctgcc tgcaggggcg   4800
cctgatgcgg tattttctcc ttacgcatct gtgcggtatt tcacaccgca tacgtcaaag   4860
caaccatagt acgcgccctg tagcggcgca ttaagcgcgg cgggtgtggt ggttacgcgc   4920
agcgtgaccg ctacacttgc cagcgcccta gcgcccgctc ctttcgcttt cttcccttcc   4980
tttctcgcca cgttcgccgg ctttccccgt caagctctaa atcggggggct ccctttaggg   5040 ttccgattta gtgctttacg gcacctcgac cccaaaaaac ttgatttggg tgatggttca   5100
cgtagtgggc catcgccctg atagacggtt tttcgccctt tgacgttgga gtccacgttc   5160
tttaatagtg gactcttgtt ccaaactgga acaacactca accctatctc gggctattct   5220
tttgatttat aagggatttt gccgatttcg gcctattggt taaaaaatga gctgatttaa   5280
caaaaattta acgcgaattt taacaaaata ttaacgttta caattttatg gtgcactctc   5340
agtacaatct gctctgatgc cgcatagtta agccagcccc gacacccgcc aacacccgct   5400
gacgcgccct gacgggcttg tctgctcccg gcatccgctt acagacaagc tgtgaccgtc   5460
tccgggagct gcatgtgtca gaggttttca ccgtcatcac cgaaacgcgc gagacgaaag   5520
ggcctcgtga tacgcctatt tttataggtt aatgtcatga taataatggt ttcttagacg   5580
tcaggtggca cttttcgggg aaatgtgcgc ggaacccta tttgtttatt tttctaaata   5640
cattcaaata tgtatccgct catgagacaa taaccctgat aaatgcttca ataatattga   5700
aaaaggaaga gtatgagtat tcaacatttc cgtgtcgccc ttattccctt ttttgcggca   5760
ttttgccttc ctgtttttgc tcacccagaa acgctggtga agtaaaaga tgctgaagat   5820 cagttgggtg cacagtggg ttacatcgaa ctggatctca acagcggtaa gatccttgag   5880
agttttcgcc ccgaagaacg ttttccaatg atgagcactt ttaaagttct gctatgtggc   5940
gcggtattat cccgtattga cgccgggcaa gagcaactcg gtcgccgcat acactattct   6000
cagaatgact tggttgagta ctcaccagtc acagaaaagc atcttacgga tggcatgaca   6060
gtaagagaat tatgcagtgc tgccataacc atgagtgata acactgcggc caacttactt   6120
ctgacaacga tcggaggacc gaaggagcta accgcttttt tgcacaacat gggggatcat   6180
gtaactcgcc ttgatcgttg ggaaccggag ctgaatgaag ccataccaaa cgacgagcgt   6240
gacaccacga tgcctgtagc aatggcaaca acgttgcgca aactattaac tggcgaacta   6300
cttactctag cttcccggca acaattaata gactggatgg aggcggataa agttgcagga   6360
ccacttctgc gctcggccct tccggctggc tggtttattg ctgataaatc tggagccggt   6420
gagcgtgggt ctcgcggtat cattgcagca ctggggccag atggtaagcc ctcccgtatc   6480
gtagttatct acacgacggg gagtcaggca actatggatg aacgaaatag acagatcgct   6540
gagataggtg cctcactgat taagcattgg taactgtcag accaagttta ctcatatata   6600
ctttagattg atttaaaact tcatttttaa tttaaaagga tctaggtgaa gatcctttt   6660 gataatctca tgaccaaaat cccttaacgt gagttttcgt tccactgagc gtcagacccc   6720
gtagaaaaga tcaaaggatc ttcttgagat cctttttttc tgcgcgtaat ctgctgcttg   6780
caaacaaaaa aaccaccgct accagcggtg gtttgtttgc cggatcaaga gctaccaact   6840
ctttttccga aggtaactgg cttcagcaga gcgcagatac caaatactgt ccttctagtg   6900
tagccgtagt taggccacca cttcaagaac tctgtagcac cgcctacata cctgctctg   6960 ctaatcctgt taccagtggc tgctgccagt ggcgataagt cgtgtcttac cgggttggac   7020
```

-continued

```
tcaagacgat agttaccgga taaggcgcag cggtcgggct gaacgggggg ttcgtgcaca    7080
cagcccagct tggagcgaac gacctacacc gaactgagat acctacagcg tgagctatga    7140
gaaagcgcca cgcttcccga agggagaaag gcggacaggt atccggtaag cggcagggtc    7200
ggaacaggag agcgcacgag ggagcttcca gggggaaacg cctggtatct ttatagtcct    7260
gtcgggtttc gccacctctg acttgagcgt cgattttgt gatgctcgtc aggggggcgg     7320
agcctatgga aaacgccag caacgcggcc ttttacggt tcctggcctt ttgctggcct      7380
tttgctcaca tgt                                                       7393
```

<210> SEQ ID NO 114
<211> LENGTH: 7539
<212> TYPE: DNA
<213> ORGANISM: Artificial Sequence
<220> FEATURE:
<223> OTHER INFORMATION: Synthetic

<400> SEQUENCE: 114

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtgaggg cctatttccc atgattcctt    180
catatttgca tatacgatac aaggctgtta gagagataat tggaattaat ttgactgtaa    240
acacaaagat attagtacaa atacgtgac gtagaaagta ataatttctt gggtagtttg     300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttcta gagacgcttc cgagtacggt acaggggatc      540
ctacccttac gatgtaccgg attacgcata gctagctagc tagggatcga attcgcttat    600
cgataatcaa cctctggatt acaaaatttg tgaaagattg actggtattc ttaactatgt    660
tgctcctttt acgctatgtg gatacgctgc tttaatgcct ttgtatcatg ctattgcttc    720
ccgtatggct ttcattttct cctccttgta taaatcctgg ttgctgtctc tttatgagga    780
gttgtggccc gttgtcaggc aacgtggcgt ggtgtgcact gtgtttgctg acgcaacccc    840
cactggttgg ggcattgcca ccacctgtca gctccttcc gggactttcg ctttcccct       900 ccctattgcc acggcggaac tcatcgccgc ctgccttgcc cgctgctgga caggggctcg    960
gctgttgggc actgacaatt ccgtggtgtt gtcggggaaa tcatcgtcct ttccttggct   1020
gctcgcctat gttgccacct ggattctgcg cgggacgtcc ttctgctacg tcccttcggc   1080
cctcaatcca gcggaccttc cttcccgcgg cctgctgccg gctctgcggc ctcttccgcg   1140
tcttcgcctt cgccctcaga cgagtcggat ctcccttgg gccgcctccc cgcatcgata   1200
ccgctcgata gatctcgact gtgccttcta gttgccagcc atctgttgtt tgcccctccc   1260
ccgtgccttc cttgaccctg gaaggtgcca ctcccactgt cctttcctaa taaaatgagg   1320
aaattgcatc gcattgtctg agtaggtgtc attctattct ggggggtggg gtggggcagg   1380
acagcaaggg ggaggattgg gaagacaata gcaggcatgc tggggatgcg gtgggctcta   1440
tggctcgagg acgcttccga gtacggtaca gggtcgacgg ccctgcgtat ggggcagagc   1500
gcacatcgcc cacagtcccc gagaagttgg ggggagggt cggcaattga acgggtgcct   1560
agagaaggtg gcgcggggta aactgggaaa gtgatgtcgt gtactggctc cgccttttc    1620 ccgagggtgg gggagaaccg tatataagtg cagtagtcgc cgtgaacgtt cttttttcgca  1680
```

```
acgggtttgc cgccagaaca cagctgaagc ttcgagggc tcgcatctct ccttcacgcg    1740
cccgccgccc tacctgaggc cgccatccac gccggttgag tcgcgttctg ccgcctcccg    1800
cctgtggtgc ctcctgaact gcgtccgccg tctaggtaag tttaaagctc aggtcgagac    1860
cgggcctttg tccggcgctc ccttggagcc tacctagact cagccggctc tccacgcttt    1920
gcctgaccct gcttgctcaa ctctacgtct ttgtttcgtt ttctgttctg cgccgttaca    1980
gatccaagct gtgaccggcg cctacaccgg tgccaccatg ggcccaaga aaaacggaa    2040 ggtggccgct gcagggatac atggggttcc tgcagccgat aaaaaataca gtatcggtct    2100
ggacataggc actaattctg tcggttgggc cgtgataaca gatgaatata agtaccttc    2160 caaaaaattc aaggttctgg gaaacacaga tagacacagt ataaaaaaga acctgattgg    2220
cgctttgctc tttgacagcg gtgagaccgc agaggcaact cgcttgaagc ggaccgcccg    2280
gcgaaggtac acacgacgca agaaccgaat tgttacctc caggaaatat tcagtaacga    2340
aatggccaaa gttgacgatt cttttttcca tcgccttgaa gaatccttcc tggtagaaga    2400
agataagaag catgagagac acccaatatt tgggaatata gttgacgaag tcgcatatca    2460
cgagaagtac cctactatat atcaccttcg gaaaaaactg gtcgattcaa ctgacaaagc    2520
cgacttgaga ctcatatacc tggcccttgc tcacatgatc aagttccggg ccactttct    2580 gattgaaggc gacctcaatc ccgacaatag cgacgtagac aagctgttta tccaactcgt    2640
tcaaacctat aaccagctct tcgaagagaa cccaataaat gctagtgggg tcgatgccaa    2700
agctattttg agtgctaggc tgtcaaagag tagaaggttg gagaacctga tcgcacaact    2760
gcccggtgag aagaagaacg gccttttggg gaacttgatt gctctctccc ttggccttac    2820
ccctaacttt aaatccaact tcgatcttgc tgaggatgct aagctccaac tgtccaagga    2880
cacctacgac gacgacttgg ataaccttct ggcccagata ggtgatcagt acgcagatct    2940
tttcttggca gccaagaatc tgtctgacgc aatcttgctt agtgacatcc tgagggtgaa    3000
tactgaaata actaaggctc cactttccgc ctctatgatc aagcgctacg acgaacacca    3060
tcaagacctg acccttttga aggccttggt tagacaacaa ctgcctgaaa aatacaagga    3120
aatattcttc gaccagtcta agaacggtta tgccggatat atcgacgggg gggcatcaca    3180
ggaggaattc tataaattta aaagcctat cttggagaaa atggacgaa ccgaagaact    3240 cctcgtaaag cttaaccgcg aagaccttt gcgaaagcag cggactttcg ataacggctc    3300
tattcctcac caaatccacc tcggggagct tcacgcaata ttgcgaaggc aggaggactt    3360
ctatccattc ttgaaggata atcgggaaaa aattgaaaaa attcttacat ttcggattcc    3420
ttactacgtg ggtcctctgg cccgcgggaa tagtcggttt gcatggatga ctcggaagtc    3480
tgaggaaact atcacaccat ggaattttga agaagtggta gacaaagggg cttccgctca    3540
gtctttcata gagaggatga ctaattttga taaaaacctg cctaacgaaa aggtactccc    3600
caagcattca cttctttatg aatatttcac tgtctacaac gagctgacta aggttaaata    3660
tgtaaccgaa ggtatgcgga agccagcatt cctgagtggt gagcagaaga aggcaatcgt    3720
agaccttttg ttcaaaacca accgaaaggt gacagtaaaa caactcaagg aagactattt    3780
taagaaaata gagtgtttgt cttatgagac cgaaatcctc accgtggagt acgggctcct    3840
gcctatcggg aaaattgtcg aaaagcgcat agagtgcact gtttactctg tagataacaa    3900
tggaaacata tacacacagc ccgtagcaca gtggcacgat cgaggcgagc aggaggtctt    3960
tgaatattgc ctggaagacg gcagtcttat aagggcaaca aaggatcaca aatttatgac    4020
```

```
cgtagatgga caaatgcttc ccatcgacga gatctttgag cgcgagcttg acttgatgag    4080
agtggataac ctgcctaatt aggaattcga tatcaagctt atcgataatc aacctctgga    4140
ttacaaaatt tgtgaaagat tgactggtat tcttaactat gttgctcctt ttacgctatg    4200
tggatacgct gctttaatgc ctttgtatca tgctattgct tcccgtatgg ctttcatttt    4260
ctcctccttg tataaatcct ggttgctgtc tctttatgag gagttgtggc ccgttgtcag    4320
gcaacgtggc gtggtgtgca ctgtgtttgc tgacgcaacc cccactggtt ggggcattgc    4380
caccacctgt cagctccttt ccgggacttt cgctttcccc ctccctattg ccacggcgga    4440
actcatcgcc gctgccttg cccgctgctg acaggggct cggctgttgg gcactgacaa    4500
ttccgtggtg ttgtcgggga atcatcgtc ctttccttgg ctgctcgcct gtgttgccac    4560
ctggattctg cgcgggacgt ccttctgcta cgtcccttcg gccctcaatc cagcggacct    4620
tccttcccgc ggcctgctgc cggctctgcg gcctcttccg cgtcttcgcc ttcgccctca    4680
gacgagtcgg atctcccttt gggccgcctc ccgcatcga taccgagcgc taataaaaga    4740
tctttatttt cattagatct gtgtgttggt tttttgtgtc acgtgcggac cgagcggccg    4800
caggaacccc tagtgatgga gttggccact ccctctctgc gcgctcgctc gctcactgag    4860
gccgggcgac caaaggtcgc ccgacgcccg ggctttgccc gggcggcctc agtgagcgag    4920
cgagcgcgca gctgcctgca ggggcgcctg atgcggtatt ttctccttac gcatctgtgc    4980
ggtatttcac accgcatacg tcaaagcaac catagtacgc gccctgtagc ggcgcattaa    5040
gcgcggcggg tgtggtggtt acgcgcagcg tgaccgctac acttgccagc gccctagcgc    5100
ccgctccttt cgctttcttc ccttcctttc tcgccacgtt cgccggcttt cccgtcaag    5160 ctctaaatcg gggctccct ttagggttcc gatttagtgc tttacggcac ctcgaccccca    5220 aaaaacttga tttgggtgat ggttcacgta gtgggccatc gccctgatag acggtttttc    5280
gccctttgac gttggagtcc acgttcttta atagtggact cttgttccaa actggaacaa    5340
cactcaaccc tatctcgggc tattcttttg atttataagg gattttgccg atttcggcct    5400
attggttaaa aaatgagctg atttaacaaa aatttaacgc gaattttaac aaaatattaa    5460
cgtttacaat tttatggtgc actctcagta caatctgctc tgatgccgca tagttaagcc    5520
agccccgaca cccgccaaca cccgctgacg cgccctgacg gcttgtctg ctcccggcat    5580 ccgcttacag acaagctgtg accgtctccg ggagctgcat gtgtcagagg ttttcaccgt    5640
catcaccgaa acgcgcgaga cgaaagggcc tcgtgatacg cctatttta taggttaatg    5700 tcatgataat aatggtttct tagacgtcag gtggcacttt tcggggaaat gtgcgcggaa    5760
cccctatttg tttatttttc taaatacatt caaatatgta tccgctcatg agacaataac    5820
cctgataaat gcttcaataa tattgaaaaa ggaagagtat gagtattcaa catttccgtg    5880
tcgcccttat tccctttttt gcggcatttt gccttcctgt ttttgctcac ccagaaacgc    5940
tggtgaaagt aaaagatgct gaagatcagt tgggtgcacg agtgggttac atcgaactgg    6000
atctcaacag cggtaagatc cttgagagtt ttcgccccga agaacgtttt ccaatgatga    6060 gcactttaa agttctgcta tgtggcgcgg tattatcccg tattgacgcc gggcaagagc    6120
aactcggtcg ccgcatacac tattctcaga atgacttggt tgagtactca ccagtcacag    6180
aaaagcatct tacggatggc atgacagtaa gagaattatg cagtgctgcc ataaccatga    6240
gtgataacac tgcggccaac ttacttctga caacgatcgg aggaccgaag gagctaaccg    6300
cttttttgca acatgggg gatcatgtaa ctcgccttga tcgttgggaa ccggagctga    6360
atgaagccat accaaacgac gagcgtgaca ccacgatgcc tgtagcaatg gcaacaacgt    6420
```

```
tgcgcaaaact attaactggc gaactactta ctctagcttc ccggcaacaa ttaatagact    6480
ggatggaggc ggataaagtt gcaggaccac ttctgcgctc ggcccttccg gctggctggt    6540
ttattgctga taaatctgga gccggtgagc gtgggtctcg cggtatcatt gcagcactgg    6600
ggccagatgg taagccctcc cgtatcgtag ttatctacac gacggggagt caggcaacta    6660
tggatgaacg aaatagacag atcgctgaga taggtgcctc actgattaag cattggtaac    6720
tgtcagacca agtttactca tatatacttt agattgattt aaaacttcat ttttaattta    6780
aaaggatcta ggtgaagatc ctttttgata atctcatgac caaaatccct aacgtgagt    6840
tttcgttcca ctgagcgtca gaccccgtag aaaagatcaa aggatcttct tgagatcctt    6900
tttttctgcg cgtaatctgc tgcttgcaaa caaaaaaacc accgctacca gcggtggttt    6960
gtttgccgga tcaagagcta ccaactcttt ttccgaaggt aactggcttc agcagagcgc    7020
agataccaaa tactgtcctt ctagtgtagc cgtagttagg ccaccacttc aagaactctg    7080
tagcaccgcc tacatacctc gctctgctaa tcctgttacc agtggctgct gccagtggcg    7140
ataagtcgtg tcttaccggg ttggactcaa gacgatagtt accggataag cgcagcggt    7200
cgggctgaac ggggggttcg tgcacacagc ccagcttgga gcgaacgacc tacaccgaac    7260
tgagatacct acagcgtgag ctatgagaaa gcgccacgct cccgaaggg agaaaggcgg    7320
acaggtatcc ggtaagcggc agggtcggaa caggagagcg cacgagggag cttccagggg    7380
gaaacgcctg gtatctttat agtcctgtcg ggtttcgcca cctctgactt gagcgtcgat    7440
ttttgtgatg ctcgtcaggg gggcggagcc tatggaaaaa cgccagcaac gcggcctttt    7500
tacggttcct ggccttttgc tggccttttg ctcacatgt                          7539

<210> SEQ ID NO 115
<211> LENGTH: 7541
<212> TYPE: DNA
<213> ORGANISM: Artificial Sequence
<220> FEATURE:
<223> OTHER INFORMATION: Synthetic

<400> SEQUENCE: 115
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttttcta gagacgcttc cgagtacggt acaggggatc     540
cagtacccct acgatgtacc ggattacgca tagctagcta gctagggatc gaattcgctt     600
atcgataatc aacctctgga ttacaaaatt tgtgaaagat tgactggtat tcttaactat     660
gttgctcctt ttacgctatg tggatacgct gctttaatgc ctttgtatca tgctattgct     720
tcccgtatgg ctttcatttt ctcctccttg tataaatcct ggttgctgtc tctttatgag     780
gagttgtggc ccgttgtcag gcaacgtggc gtggtgtgca ctgtgtttgc tgacgcaacc     840
cccactggtt ggggcattgc caccacctgt cagctccttt ccgggacttt cgctttcccc     900
```

```
ctccctattg ccacggcgga actcatcgcc gcctgccttg cccgctgctg acaggggct    960
cggctgttgg gcactgacaa ttccgtggtg ttgtcgggga aatcatcgtc ctttccttgg   1020
ctgctcgcct atgttgccac ctggattctg cgcgggacgt ccttctgcta cgtcccttcg   1080
gccctcaatc cagcggacct tccttcccgc ggcctgctgc cggctctgcg gcctcttccg   1140
cgtcttcgcc ttcgccctca gacgagtcgg atctcccttt gggccgcctc cccgcatcga   1200
taccgctcga tagatctcga ctgtgccttc tagttgccag ccatctgttg tttgcccctc   1260
ccccgtgcct tccttgaccc tggaaggtgc cactcccact gtcctttcct aataaaatga   1320
ggaaattgca tcgcattgtc tgagtaggtg tcattctatt ctgggggtg gggtggggca    1380
ggacagcaag ggggaggatt gggaagacaa tagcaggcat gctggggatg cggtgggctc   1440
tatggctcga ggacgcttcc gagtacggta cagggtcgac ggccctgcgt atggggcaga   1500
gcgcacatcg cccacagtcc ccgagaagtt ggggggaggg gtcggcaatt gaacgggtgc   1560
ctagagaagg tggcgcgggg taaactggga aagtgatgtc gtgtactggc tccgcctttt   1620
tcccgagggt gggggagaac cgtatataag tgcagtagtc gccgtgaacg ttcttttttcg  1680
caacgggttt gccgccagaa cacagctgaa gcttcgaggg gctcgcatct ctccttcacg   1740
cgcccgccgc cctacctgag gccgccatcc acgccggttg agtcgcgttc tgccgcctcc   1800
cgcctgtggt gcctcctgaa ctgcgtccgc cgtctaggta agtttaaagc tcaggtcgag   1860
accgggcctt tgtccggcgc tcccttggag cctacctaga ctcagccggc tctccacgct   1920
ttgcctgacc ctgcttgctc aactctacgt ctttgtttcg ttttctgttc tgcgccgtta   1980
cagatccaag ctgtgaccgg cgcctacacc ggtgccacca tgggcccaa gaaaaaacgg    2040
aaggtggccg ctgcagggat acatggggtt cctgcagccg ataaaaaata cagtatcggt   2100
ctggacatag gcactaattc tgtcggttgg gccgtgataa cagatgaata taagtacct    2160
tccaaaaaat tcaaggttct gggaaacaca gatagacaca gtataaaaaa gaacctgatt   2220
ggcgctttgc tctttgacag cggtgagacc gcagaggcaa ctcgcttgaa gcggaccgcc   2280
cggcgaaggt acacacgacg caagaaccga atttgttacc tccaggaaat attcagtaac   2340
gaaatggcca aagttgacga ttcttttttc catcgccttg aagaatcctt cctggtagaa   2400
gaagataaga agcatgagag cacccaata tttgggaata tagttgacga agtcgcatat    2460
cacgagaagt accctactat atatcacctt cggaaaaaac tggtcgattc aactgacaaa   2520
gccgacttga gactcatata cctggcccct gctcacatga tcaagttccg gggccacttt   2580
ctgattgaag cgaccctcaa tcccgacaat agcgacgtag acaagctgtt tatccaactc   2640
gttcaaacct ataaccagct cttcgaagag aacccaataa atgctagtgg ggtcgatgcc   2700
aaagctattt tgagtgctag gctgtcaaag agtagaaggt tggagaacct gatcgcacaa   2760
ctgcccggtg agaagaagaa cggccttttt gggaacttga ttgctctctc ccttggcctt   2820
acccctaact ttaaatccaa cttcgatctt gctgaggatg ctaagctcca actgtccaag   2880
gacacctacg acgacgactt ggataacctt ctggcccaga taggtgatca gtacgcagat   2940
cttttcttgg cagccaagaa tctgtctgac gcaatcttgc ttagtgacat cctgagggtg   3000
aatactgaaa taactaaggc tccactttcc gcctctatga tcaagcgcta cgacgaacac   3060
catcaagacc tgacccttt gaaggccttg gttagacaac aactgcctga aaaatacaag    3120
gaaatattct tcgaccagtc taagaacggt tatgccggat atatcgacgg gggggcatca   3180
caggaggaat tctataaatt tataaagcct atccttggaga aaatggacgg aaccgaagaa   3240
ctcctcgtaa agcttaaccg cgaagacctt ttgcgaaagc agcggacttt cgataacggc   3300
```

```
tctattcctc accaaatcca cctcggggag cttcacgcaa tattgcgaag gcaggaggac    3360
ttctatccat tcttgaagga taatcgggaa aaaattgaaa aaattcttac atttcggatt    3420
ccttactacg tgggtcctct ggcccgcggg aatagtcggt ttgcatggat gactcggaag    3480
tctgaggaaa ctatcacacc atggaatttt gaagaagtgg tagacaaagg ggcttccgct    3540
cagtctttca tagagaggat gactaatttt gataaaaacc tgcctaacga aaaggtactc    3600
cccaagcatt cacttcttta tgaatatttc actgtctaca acgagctgac taaggttaaa    3660
tatgtaaccg aaggtatgcg gaagccagca ttcctgagtg gtgagcagaa aaaggcaatc    3720
gtagaccttt tgttcaaaac caaccgaaag gtgacagtaa aacaactcaa ggaagactat    3780
tttaagaaaa tagagtgttt gtcttatgag accgaaatcc tcaccgtgga gtacgggctc    3840
ctgcctatcg ggaaaattgt cgaaaagcgc atagagtgca ctgtttactc tgtagataac    3900
aatggaaaca tatacacaca gcccgtagca cagtggcacg atcgaggcga gcaggaggtc    3960
tttgaatatt gcctggaaga cggcagtctt ataaggcaa caaaggatca caaatttatg    4020
accgtagatg gacaaatgct tcccatcgac gagatctttg agcgcgagct tgacttgatg    4080
agagtggata acctgcctaa ttaggaattc gatatcaagc ttatcgataa tcaacctctg    4140
gattacaaaa tttgtgaaag attgactggt attcttaact atgttgctcc ttttacgcta    4200
tgtggatacg ctgctttaat gcctttgtat catgctattg cttcccgtat ggctttcatt    4260
ttctcctcct tgtataaatc ctggttgctg tctctttatg aggagttgtg gcccgttgtc    4320
aggcaacgtg gcgtggtgtg cactgtgttt gctgacgcaa cccccactgg ttggggcatt    4380
gccaccacct gtcagctcct ttccgggact ttcgctttcc cctccctat tgccacggcg    4440 gaactcatcg ccgcctgcct tgccgcctgc tggacagggg ctcggctgtt gggcactgac    4500
aattccgtgg tgttgtcggg gaaatcatcg tcctttcctt ggctgctcgc ctgtgttgcc    4560
acctggattc tgcgcgggac gtccttctgc tacgtccctt cggccctcaa tccagcggac    4620
cttccttccc gcggcctgct gccggctctg cggcctcttc cgcgtcttcg ccttcgccct    4680
cagacgagtc ggatctccct ttgggccgcc tccccgcatc gataccgagc gctaataaaa    4740
gatctttatt ttcattagat ctgtgtgttg gttttttgtg tcacgtgcgg accgagcggc    4800
cgcaggaacc cctagtgatg gagttggcca ctccctctct gcgcgctcgc tcgctcactg    4860
aggccgggcg accaaaggtc gcccgacgcc cgggctttgc ccgggcggcc tcagtgagcg    4920
agcgagcgcg cagctgcctg caggggcgcc tgatgcggta ttttctcctt acgcatctgt    4980
gcggtatttc acaccgcata cgtcaaagca accatagtac gcgccctgta gcggcgcatt    5040
aagcgcggcg ggtgtggtgg ttacgcgcag cgtgaccgct acacttgcca gcgccctagc    5100
gcccgctcct ttcgctttct tcccttcctt tctcgccacg ttcgccggct ttccccgtca    5160
agctctaaat cggggctcc ctttagggtt ccgatttagt gctttacggc acctcgaccc    5220
caaaaaactt gatttgggtg atggttcacg tagtgggcca tcgccctgat agacggtttt    5280
tcgccctttg acgttggagt ccacgttctt taatagtgga ctcttgttcc aaactggaac    5340
aacactcaac cctatctcgg gctattcttt tgatttataa gggattttgc cgatttcggc    5400
ctattggtta aaaaatgagc tgatttaaca aaaatttaac gcgaatttta acaaaatatt    5460
aacgtttaca attttatggt gcactctcag tacaatctgc tctgatgccg catagttaag    5520
ccagccccga caccccgccaa cacccgctga gcgccctga cgggcttgtc tgctcccggc    5580
atccgcttac agacaagctg tgaccgtctc cgggagctgc atgtgtcaga ggttttcacc    5640
```

| | |
|---|---|
| gtcatcaccg aaacgcgcga gacgaaaggg cctcgtgata cgcctatttt tataggttaa | 5700 |
| tgtcatgata ataatggttt cttagacgtc aggtggcact tttcggggaa atgtgcgcgg | 5760 |
| aaccccctatt tgtttatttt tctaaataca ttcaaatatg tatccgctca tgagacaata | 5820 |
| accctgataa atgcttcaat aatattgaaa aaggaagagt atgagtattc aacatttccg | 5880 |
| tgtcgccctt attccctttt ttgcggcatt ttgccttcct gttttttgctc acccagaaac | 5940 |
| gctggtgaaa gtaaaagatg ctgaagatca gttgggtgca cgagtgggtt acatcgaact | 6000 |
| ggatctcaac agcggtaaga tccttgagag ttttcgcccc gaagaacgtt ttccaatgat | 6060 |
| gagcactttt aaagttctgc tatgtggcgc ggtattatcc cgtattgacg ccgggcaaga | 6120 |
| gcaactcggt cgccgcatac actattctca gaatgacttg gttgagtact caccagtcac | 6180 |
| agaaaagcat cttacggatg gcatgacagt aagagaatta tgcagtgctg ccataaccat | 6240 |
| gagtgataac actgcggcca acttacttct gacaacgatc ggaggaccga aggagctaac | 6300 |
| cgcttttttg cacaacatgg ggatcatgt aactcgcctt gatcgttggg aaccggagct | 6360 |
| gaatgaagcc ataccaaacg acgagcgtga caccacgatg cctgtagcaa tggcaacaac | 6420 |
| gttgcgcaaa ctattaactg gcgaactact tactctagct tcccggcaac aattaataga | 6480 |
| ctggatggag gcggataaag ttgcaggacc acttctgcgc tcggcccttc cggctggctg | 6540 |
| gtttattgct gataaatctg gagccggtga gcgtgggtct cgcggtatca ttgcagcact | 6600 |
| ggggccagat ggtaagccct cccgtatcgt agttatctac acgacgggga gtcaggcaac | 6660 |
| tatggatgaa cgaaatagac agatcgctga gataggtgcc tcactgatta agcattggta | 6720 |
| actgtcagac caagtttact catatatact ttagattgat ttaaaacttc attttttaatt | 6780 |
| taaaaggatc taggtgaaga tcctttttga atctcatg accaaaatcc cttaacgtga | 6840 |
| gttttcgttc cactgagcgt cagaccccgt agaaaagatc aaaggatctt cttgagatcc | 6900 |
| ttttttttctg cgcgtaatct gctgcttgca acaaaaaaa ccaccgctac cagcggtggt | 6960 |
| ttgtttgccg gatcaagagc taccaactct ttttccgaag gtaactggct tcagcagagc | 7020 |
| gcagatacca aatactgtcc ttctagtgta gccgtagtta ggccaccact tcaagaactc | 7080 |
| tgtagcaccg cctacatacc tcgctctgct aatcctgtta ccagtggctg ctgccagtgg | 7140 |
| cgataagtcg tgtcttaccg ggttggactc aagacgatag ttaccggata aggcgcagcg | 7200 |
| gtcgggctga acgggggggtt cgtgcacaca gcccagcttg gagcgaacga cctacaccga | 7260 |
| actgagatac ctacagcgtg agctatgaga aagcgccacg cttcccgaag ggagaaaggc | 7320 |
| ggacaggtat ccggtaagcg gcagggtcgg aacaggagag cgcacgaggg agcttccagg | 7380 |
| gggaaacgcc tggtatcttt atagtcctgt cgggtttcgc cacctctgac ttgagcgtcg | 7440 |
| attttttgtga tgctcgtcag gggggcggag cctatggaaa aacgccagca acgcggcctt | 7500 |
| tttacggttc ctggcctttt gctggccttt tgctcacatg t | 7541 |

<210> SEQ ID NO 116
<211> LENGTH: 7540
<212> TYPE: DNA
<213> ORGANISM: Artificial Sequence
<220> FEATURE:
<223> OTHER INFORMATION: Synthetic

<400> SEQUENCE: 116

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |

```
catatttgca tatacgatac aaggctgtta gagagataat tggaattaat ttgactgtaa    240
acacaaagat attagtacaa atacgtgac  gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gagacgcttc cgagtacggt acaggaggat    540 cctacccttta cgatgtaccg gattacgcat agctagctag ctagggatcg aattcgctta   600
tcgataatca acctctggat tacaaaattt gtgaaagatt gactggtatt cttaactatg    660
ttgctccttt tacgctatgt ggatacgctg ctttaatgcc tttgtatcat gctattgctt    720
cccgtatggc tttcattttc tcctccttgt ataaatcctg gttgctgtct ctttatgagg    780
agttgtggcc cgttgtcagg caacgtggcg tggtgtgcac tgtgtttgct gacgcaaccc    840
ccactggttg gggcattgcc accacctgtc agctcctttc cgggactttc gctttccccc    900
tccctattgc cacggcggaa ctcatcgccg cctgccttgc ccgctgctgg acaggggctc    960
ggctgttggg cactgacaat tccgtggtgt tgtcggggaa atcatcgtcc tttccttggc   1020
tgctcgccta tgttgccacc tggattctgc gcgggacgtc cttctgctac gtcccttcgg   1080
ccctcaatcc agcggacctt ccttcccgcg gcctgctgcc ggctctgcgg cctcttccgc   1140
gtcttcgcct tcgccctcag acgagtcgga tctcccttttg ggccgcctcc ccgcatcgat   1200
accgctcgat agatctcgac tgtgccttct agttgccagc catctgttgt ttgcccctcc   1260
cccgtgcctt ccttgacccct ggaaggtgcc actcccactg tcctttccta ataaaatgag   1320
gaaattgcat cgcattgtct gagtaggtgt cattctattc tgggggggtgg ggtggggcag   1380 gacagcaagg gggaggattg ggaagacaat agcaggcatg ctggggatgc ggtgggctct   1440
atggctcgag gacgcttccg agtacggtac agggtcgacg gccctgcgta tgggcagag    1500 cgcacatcgc ccacagtccc cgagaagttg gggggagggg tcggcaattg aacgggtgcc   1560
tagagaaggt ggcgcggggt aaactgggaa agtgatgtcg tgtactggct ccgccttttt   1620
cccgagggtg ggggagaacc gtatataagt gcagtagtcg ccgtgaacgt tcttttttcgc  1680 aacgggtttg ccgccagaac acagctgaag cttcgagggg ctcgcatctc tccttcacgc   1740
gcccgccgcc ctacctgagg ccgccatcca cgccggttga gtcgcgttct gccgcctccc   1800
gcctgtggtg cctcctgaac tgcgtccgcc gtctaggtaa gtttaaagct caggtcgaga   1860
ccgggccttt gtccggcgct cccttggagc ctacctagac tcagccggct ctccacgctt   1920
tgcctgaccc tgcttgctca actctacgtc tttgtttcgt tttctgttct gcgccgttac   1980
agatccaagc tgtgaccggc gcctacaccg gtgccaccat gggccccaag aaaaaacgga   2040
aggtggccgc tgcagggata catgggggttc ctgcagccga taaaaaatac agtatcggtc   2100
tggacatagg cactaattct gtcggttggg ccgtgataac agatgaatat aaagtacctt   2160
ccaaaaaatt caaggttctg ggaaacacag atagacacag tataaaaaag aacctgattg   2220
gcgctttgct cttttgacagc ggtgagaccg cagaggcaac tcgcttgaag cggaccgccc   2280
ggcgaaggta cacgacgcgc aagaaccgaa tttgttacct ccaggaaata ttcagtaacg   2340
aaatggccaa agttgacgat tcttttttttcc atcgccttga agaatccttc ctggtagaag   2400
aagataagaa gcatgagaga cacccaatat ttgggaatat agttgacgaa gtcgcatatc   2460
acgagaagta ccctactata tatcaccttc ggaaaaaact ggtcgattca actgacaaag   2520
```

-continued

```
ccgacttgag actcatatac ctggcccttg ctcacatgat caagttccgg ggccactttc    2580
tgattgaagg cgacctcaat cccgacaata gcgacgtaga caagctgttt atccaactcg    2640
ttcaaaccta taaccagctc ttcgaagaga acccaataaa tgctagtggg gtcgatgcca    2700
aagctatttt gagtgctagg ctgtcaaaga gtagaaggtt ggagaacctg atcgcacaac    2760
tgcccggtga aagaagaac ggccttttg gaacttgat tgctctctcc cttggcctta      2820
cccctaactt taaatccaac ttcgatcttg ctgaggatgc taagctccaa ctgtccaagg    2880
acacctacga cgacgacttg gataaccttc tggcccagat aggtgatcag tacgcagatc    2940
tttttcttggc agccaagaat ctgtctgacg caatcttgct tagtgacatc ctgagggtga   3000
atactgaaat aactaaggct ccactttccg cctctatgat caagcgctac gacgaacacc    3060
atcaagacct gacccttttg aaggccttgg ttagacaaca actgcctgaa aaatacaagg    3120
aaatattctt cgaccagtct aagaacggtt atgccggata tatcgacggg ggggcatcac    3180
aggaggaatt ctataaattt ataaagccta tcttggagaa aatggacgga accgaagaac    3240
tcctcgtaaa gcttaaccgc gaagaccttt tgcgaaagca gcggactttc gataacggct    3300
ctattcctca ccaaatccac ctcggggagc ttcacgcaat attgcgaagg caggaggact    3360
tctatccatt cttgaaggat aatcgggaaa aaattgaaaa aattcttaca tttcggattc    3420
cttactacgt gggtcctctg gcccgcggga atagtcggtt tgcatggatg actcggaagt    3480
ctgaggaaac tatcacacca tggaattttg aagaagtggt agacaaaggg gcttccgctc    3540
agtctttcat agagaggatg actaattttg ataaaaacct gcctaacgaa aaggtactcc    3600
ccaagcattc acttctttat gaatatttca ctgtctacaa cgagctgact aaggttaaat    3660
atgtaaccga aggtatgcgg aagccagcat tcctgagtgg tgagcagaag aaggcaatcg    3720
tagacctttt gttcaaaacc aaccgaaagg tgacagtaaa acaactcaag gaagactatt    3780
ttaagaaaat agagtgtttg tcttatgaga ccgaaatcct caccgtggag tacgggctcc    3840
tgcctatcgg gaaaattgtc gaaaagcgca tagagtgcac tgtttactct gtagataaca    3900
atggaaacat atacacacag cccgtagcac agtggcacga tcgaggcgag caggaggtct    3960
ttgaatattg cctggaagac ggcagtctta aagggcaac aaaggatcac aaatttatga    4020
ccgtagatgg acaaatgctt cccatcgacg agatctttga gcgcgagctt gacttgatga    4080
gagtggataa cctgcctaat taggaattcg atatcaagct tatcgataat caacctctgg    4140
attacaaaat ttgtgaaaga ttgactggta ttcttaacta tgttgctcct tttacgctat    4200
gtggatacgc tgctttaatg cctttgtatc atgctattgc ttcccgtatg ctttcatttt    4260
tctcctcctt gtataaatcc tggttgctgt ctctttatga ggagttgtgg cccgttgtca    4320
ggcaacgtgg cgtggtgtgc actgtgtttg ctgacgcaac ccccactggt tgggcattg     4380
ccaccacctg tcagctcctt tccgggactt tcgctttccc ctccctatt gccacggcgg     4440
aactcatcgc cgcctgcctt gcccgctgct ggacaggggc tcggctgttg ggcactgaca    4500
attccgtggt gttgtcgggg aaatcatcgt cctttccttg gctgctcgcc tgtgttgcca    4560
cctggattct gcgcgggacg tccttctgct acgtcccttc ggccctcaat ccagcggacc    4620
ttccttcccg cggcctgctg ccggctctgc ggcctcttcc gcgtcttcgc cttcgccctc    4680
agacgagtcg gatctcccct tgggccgcct ccccgcatcg ataccgagcg ctaataaaag    4740
atctttattt tcattagatc tgtgtgttgg ttttttgtgt cacgtgcgga ccgagcggcc    4800
gcaggaaccc ctagtgatgg agttggccac tccctctctg cgcgctcgct cgctcactga    4860
ggccgggcga ccaaaggtcg cccgacgccc gggctttgcc cgggcggcct cagtgagcga    4920
```

```
gcgagcgcgc agctgcctgc aggggcgcct gatgcggtat tttctcctta cgcatctgtg    4980
cggtatttca caccgcatac gtcaaagcaa ccatagtacg cgccctgtag cggcgcatta    5040
agcgcggcgg gtgtggtggt tacgcgcagc gtgaccgcta cacttgccag cgccctagcg    5100
cccgctcctt tcgctttctt cccttccttt ctcgccacgt tcgccggctt tccccgtcaa    5160
gctctaaatc gggggctccc tttagggttc cgatttagtg ctttacggca cctcgacccc    5220
aaaaaacttg atttgggtga tggttcacgt agtgggccat cgccctgata gacgttttt    5280
cgccctttga cgttggagtc cacgttcttt aatagtggac tcttgttcca aactggaaca    5340
acactcaacc ctatctcggg ctattctttt gatttataag ggattttgcc gatttcggcc    5400
tattggttaa aaatgagctg atttaacaa aaatttaacg cgaattttaa caaaatatta    5460
acgtttacaa ttttatggtg cactctcagt acaatctgct ctgatgccgc atagttaagc    5520
cagccccgac acccgccaac acccgctgac gcgccctgac gggcttgtct gctcccggca    5580
tccgcttaca gacaagctgt gaccgtctcc gggagctgca tgtgtcagag gttttcaccg    5640
tcatcaccga aacgcgcgag acgaaagggc ctcgtgatac gcctatttt ataggttaat    5700
gtcatgataa taatggtttc ttagacgtca ggtggcactt ttcggggaaa tgtgcgcgga    5760
acccctattt gtttattttt ctaaatacat tcaaatatgt atccgctcat gagacaataa    5820
ccctgataaa tgcttcaata atattgaaaa aggaagagta tgagtattca acatttccgt    5880
gtcgccctta ttccctttt tgcggcattt tgccttcctg ttttgctca cccagaaacg    5940
ctggtgaaag taaaagatgc tgaagatcag ttgggtgcac gagtgggtta catcgaactg    6000
gatctcaaca gcggtaagat ccttgagagt tttcgccccg aagaacgttt tccaatgatg    6060
agcacttta aagttctgct atgtggcgcg gtattatccc gtattgacgc cgggcaagag    6120
caactcggtc gccgcataca ctattctcag aatgacttgg ttgagtactc accagtcaca    6180
gaaaagcatc ttacggatgg catgacagta agagaattat gcagtgctgc cataaccatg    6240
agtgataaca ctgcggccaa cttacttctg acaacgatcg gaggaccgaa ggagctaacc    6300
gcttttttgc acaacatggg ggatcatgta actcgccttg atcgttggga accggagctg    6360
aatgaagcca taccaaacga cgagcgtgac accacgatgc ctgtagcaat ggcaacaacg    6420
ttgcgcaaac tattaactgg cgaactactt actctagctt cccggcaaca attaatagac    6480
tggatggagg cggataaagt tgcaggacca cttctgcgct cggcccttcc ggctggctgg    6540
tttattgctg ataaatctgg agccggtgag cgtgggtctc gcggtatcat tgcagcactg    6600
gggccagatg gtaagccctc ccgtatcgta gttatctaca cgacggggag tcaggcaact    6660
atggatgaac gaaatagaca gatcgctgag ataggtgcct cactgattaa gcattggtaa    6720
ctgtcagacc aagtttactc atatatactt tagattgatt taaaacttca tttttaattt    6780
aaaaggatct aggtgaagat cctttttgat aatctcatga ccaaaatccc ttaacgtgag    6840
ttttcgttcc actgagcgtc agaccccgta gaaaagatca aggatcttc ttgagatcct    6900
ttttttctgc gcgtaatctg ctgcttgcaa acaaaaaaac caccgctacc agcggtggtt    6960
tgtttgccgg atcaagagct accaactctt tttccgaagg taactggctt cagcagagcg    7020
cagataccaa atactgtcct tctagtgtag ccgtagttag gccaccactt caagaactct    7080
gtagcaccgc ctacatacct cgctctgcta atcctgttac cagtggctgc tgccagtggc    7140
gataagtcgt gtcttaccgg gttggactca agacgatagt taccggataa ggcgcagcgg    7200
tcgggctgaa cggggggttc gtgcacacag cccagcttgg agcgaacgac ctacaccgaa    7260
```

| | |
|---|---:|
| ctgagatacc tacagcgtga gctatgagaa agcgccacgc ttcccgaagg gagaaaggcg | 7320 |
| gacaggtatc cggtaagcgg cagggtcgga acaggagagc gcacgaggga gcttccaggg | 7380 |
| ggaaacgcct ggtatcttta tagtcctgtc gggtttcgcc acctctgact tgagcgtcga | 7440 |
| tttttgtgat gctcgtcagg ggggcggagc ctatggaaaa acgccagcaa cgcggccttt | 7500 |
| ttacggttcc tggccttttg ctggccttttt gctcacatgt | 7540 |

<210> SEQ ID NO 117
<211> LENGTH: 6707
<212> TYPE: DNA
<213> ORGANISM: Artificial Sequence
<220> FEATURE:
<223> OTHER INFORMATION: Synthetic
<400> SEQUENCE: 117

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggggatc | 540 |
| ctacccttac gatgtaccgg attacgcata gctagctagc tagagcatag tcaggaacgt | 600 |
| catagggata actcgaggac gcttccgagt acgtacagg gtcgacggcc ctgcgtatgg | 660 |
| ggcagagcgc acatcgccca cagtccccga aagttgggg ggaggggtcg gcaattgaac | 720 |
| gggtgcctag agaaggtggc gcggggtaaa ctgggaaagt gatgtcgtgt actggctccg | 780 |
| ccttttttccc gagggtgggg gagaaccgta tataagtgca gtagtcgccg tgaacgttct | 840 |
| ttttcgcaac gggtttgccg ccagaacaca gctgaagctt cgaggggctc gcatctctcc | 900 |
| ttcacgcgcc cgccgcccta cctgaggccg ccatccacgc cggttgagtc gcgttctgcc | 960 |
| gcctcccgcc tgtggtgcct cctgaactgc gtccgccgtc taggtaagtt taaagctcag | 1020 |
| gtcgagaccg ggcctttgtc cggcgctccc ttggagccta cctagactca gccggctctc | 1080 |
| cacgctttgc ctgaccctgc ttgctcaact ctacgtcttt gtttcgtttt ctgttctgcg | 1140 |
| ccgttacaga tccaagctgt gaccggcgcc tacaccggtg ccaccatggg ccccaagaaa | 1200 |
| aaacggaagg tggccgctgc agggatacat ggggttcctg cagccgataa aaatacagt | 1260 |
| atcggtctgg acataggcac taattctgtc ggttgggccg tgataacaga tgaatataaa | 1320 |
| gtaccttcca aaaaattcaa ggttctggga acacagata gacacagtat aaaaaagaac | 1380 |
| ctgattggcg ctttgctctt tgacagcggt gagaccgcag aggcaactcg cttgaagcgg | 1440 |
| accgcccggc gaaggtacac acgacgcaag aaccgaattt gttacctcca ggaaatattc | 1500 |
| agtaacgaaa tggccaaagt tgacgattct ttttccatc gccttgaaga atccttcctg | 1560 |
| gtagaagaag ataagaagca tgagagacac ccaatatttg gaatatagt tgacgaagtc | 1620 |
| gcatatcacg agaagtaccc tactatatat caccttcgga aaaaactggt cgattcaact | 1680 |
| gacaaagccg acttgagact catatacctg gcccttgctc acatgatcaa gttccggggc | 1740 |
| cactttctga ttgaaggcga cctcaatccc gacaatagcg acgtagacaa gctgtttatc | 1800 |

```
caactcgttc aaacctataa ccagctcttc gaagagaacc caataaatgc tagtggggtc  1860
gatgccaaag ctattttgag tgctaggctg tcaaagagta gaaggttgga gaacctgatc  1920
gcacaactgc ccggtgagaa gaagaacggc cttttgggga acttgattgc tctctccctt  1980
ggccttaccc ctaactttaa atccaacttc gatcttgctg aggatgctaa gctccaactg  2040
tccaaggaca cctacgacga cgacttggat aaccttctgg cccagatagg tgatcagtac  2100
gcagatcttt tcttggcagc caagaatctg tctgacgcaa tcttgcttag tgacatcctg  2160
agggtgaata ctgaaataac taaggctcca cttttccgcct ctatgatcaa gcgctacgac  2220
gaacaccatc aagacctgac ccttttgaag gccttggtta gacaacaact gcctgaaaaa  2280
tacaaggaaa tattcttcga ccagtctaag aacggttatg ccggatatat cgacgggggg  2340
gcatcacagg aggaattcta taaatttata aagcctatct tggagaaaat ggacggaacc  2400
gaagaactcc tcgtaaagct taaccgcgaa gacctttttgc gaaagcagcg gactttcgat  2460
aacggctcta ttcctcacca aatccactcc ggggagcttc acgcaatatt gcgaaggcag  2520
gaggacttct atccattctt gaaggataat cgggaaaaaa ttgaaaaaat tcttacattt  2580
cggattcctt actacgtggg tcctctggcc cgcgggaata gtcggtttgc atggatgact  2640
cggaagtctg aggaaactat cacaccatgg aattttgaag aagtggtaga caaaggggct  2700
tccgctcagt ctttcataga gaggatgact aattttgata aaaacctgcc taacgaaaag  2760
gtactcccca agcattcact tctttatgaa tatttcactg tctacaacga gctgactaag  2820
gttaaatatg taaccgaagg tatgcggaag ccagcattcc tgagtggtga gcagaagaag  2880
gcaatcgtag acctttgttt caaaaccaac cgaaaggtga cagtaaaaca actcaaggaa  2940
gactatttta agaaaataga gtgtttgtct tatgagaccg aaatcctcac cgtggagtac  3000
gggctcctgc ctatcgggaa aattgtcgaa aagcgcatag agtgcactgt ttactctgta  3060
gataacaatg gaaacatata cacacagccc gtagcacagt ggcacgatcg aggcgagcag  3120
gaggtctttg aatattgcct ggaagacggc agtcttataa gggcaacaaa ggatcacaaa  3180
tttatgaccg tagatggaca aatgcttccc atcgacgaga tctttgagcg cgagcttgac  3240
tgatgagag tggataacct gcctaattag gaattcgata tcaagcttat cgataatcaa  3300
cctctggatt acaaaatttg tgaaagattg actggtattc ttaactatgt tgctcctttt  3360
acgctatgtg gatacgctgc tttaatgcct ttgtatcatg ctattgcttc ccgtatggct  3420
ttcattttct cctccttgta taaatcctgg ttgctgtctc tttatgagga gttgtggccc  3480
gttgtcaggc aacgtggcgt ggtgtgcact gtgtttgctg acgcaacccc cactggttgg  3540
ggcattgcca ccacctgtca gctcctttcc gggactttcg ctttccccct ccctattgcc  3600
acggcggaac tcatcgccgc ctgccttgcc cgctgctgga caggggctcg gctgttgggc  3660
actgacaatt ccgtggtgtt gtcggggaaa tcatcgtcct tccttggct gctcgcctgt  3720
gttgccacct ggattctgcg cgggacgtcc ttctgctacg tcccttcggc cctcaatcca  3780
gcggaccttc cttcccgcgg cctgctgccg gctctgcggc ctcttccgcg tcttcgcctt  3840
cgccctcaga cgagtcggat ctccctttgg gccgcctccc cgcatcgata ccgagcgcta  3900
ataaagatc tttattttca ttagatctgt gtgttggttt tttgtgtcac gtgcggaccg  3960
agcggccgca ggaacccta gtgatggagt tggccactcc ctctctgcgc gctcgctcgc  4020
tcactgaggc cgggcgacca aaggtcgccc gacgcccggg cttttgccgg gcggcctcag  4080
tgagcgagcg agcgcgcagc tgcctgcagg ggcgcctgat gcggtatttt ctccttacgc  4140
```

```
atctgtgcgg tatttcacac cgcatacgtc aaagcaacca tagtacgcgc cctgtagcgg    4200
cgcattaagc gcggcgggtg tggtggttac gcgcagcgtg accgctacac ttgccagcgc    4260
cctagcgccc gctcctttcg ctttcttccc ttcctttctc gccacgttcg ccggctttcc    4320
ccgtcaagct ctaaatcggg ggctcccttt agggttccga tttagtgctt tacggcacct    4380
cgaccccaaa aaacttgatt tgggtgatgg ttcacgtagt gggccatcgc cctgatagac    4440
ggttttcgc cctttgacgt tggagtccac gttctttaat agtggactct tgttccaaac    4500
tggaacaaca ctcaacccta tctcgggcta ttcttttgat ttataaggga ttttgccgat    4560
ttcggcctat tggttaaaaa atgagctgat ttaacaaaaa tttaacgcga attttaacaa    4620
aatattaacg tttacaattt tatggtgcac tctcagtaca atctgctctg atgccgcata    4680
gttaagccag ccccgacacc cgccaacacc cgctgacgcg ccctgacggg cttgtctgct    4740
cccggcatcc gcttacagac aagctgtgac cgtctccggg agctgcatgt gtcagaggtt    4800
ttcaccgtca tcaccgaaac gcgcgagacg aaagggcctc gtgatacgcc tatttttata    4860
ggttaatgtc atgataataa tggtttctta gacgtcaggt ggcactttc ggggaaatgt    4920
gcgcggaacc cctatttgtt tatttttcta aatacattca aatatgtatc cgctcatgag    4980
acaataaccc tgataaatgc ttcaataata ttgaaaaagg aagagtatga gtattcaaca    5040
tttccgtgtc gcccttattc cctttttgc ggcattttgc cttcctgttt ttgctcaccc    5100
agaaacgctg gtgaaagtaa aagatgctga agatcagttg ggtgcacgag tgggttacat    5160
cgaactggat ctcaacagcg gtaagatcct tgagagtttt cgccccgaag aacgttttcc    5220
aatgatgagc acttttaaag ttctgctatg tggcgcggta ttatcccgta ttgacgccgg    5280
gcaagagcaa ctcggtcgcc gcatacacta ttctcagaat gacttggttg agtactcacc    5340
agtcacagaa aagcatctta cggatggcat gacagtaaga gaattatgca gtgctgccat    5400
aaccatgagt gataacactg cggccaactt acttctgaca acgatcggag gaccgaagga    5460
gctaaccgct tttttgcaca acatggggga tcatgtaact cgccttgatc gttgggaacc    5520
ggagctgaat gaagccatac caaacgacga gcgtgacacc acgatgcctg tagcaatggc    5580
aacaacgttg cgcaaactat taactggcga actacttact ctagcttccc ggcaacaatt    5640
aatagactgg atggaggcgg ataaagttgc aggaccactt ctgcgctcgg cccttccggc    5700
tggctggttt attgctgata atctggagc cggtgagcgt gggtctcgcg gtatcattgc    5760
agcactgggg ccagatggta agccctcccg tatcgtagtt atctacacga cggggagtca    5820
ggcaactatg gatgaacgaa atagacagat cgctgagata ggtgcctcac tgattaagca    5880
ttggtaactg tcagaccaag tttactcata tatactttag attgatttaa aacttcattt    5940
ttaatttaaa aggatctagg tgaagatcct tttgataat ctcatgacca aaatccctta    6000
acgtgagttt tcgttccact gagcgtcaga ccccgtagaa aagatcaaag gatcttcttg    6060
agatccttt tttctgcgcg taatctgctg cttgcaaaca aaaaaaccac cgctaccagc    6120
ggtggtttgt ttgccggatc aagagctacc aactctttt ccgaaggtaa ctggcttcag    6180
cagagcgcag ataccaaata ctgtccttct agtgtagccg tagttaggcc accacttcaa    6240
gaactctgta gcaccgccta catacctcgc tctgctaatc ctgttaccag tggctgctgc    6300
cagtggcgat aagtcgtgtc ttaccgggtt ggactcaaga cgatagttac cggataaggc    6360
gcagcggtcg ggctgaacgg ggggttcgtg cacacagccc agcttggagc gaacgaccta    6420
caccgaactg agatacctac agcgtgagct atgagaaagc gccacgcttc ccgaagggag    6480
aaaggcggac aggtatccgg taagcggcag ggtcggaaca ggagagcgca cgagggagct    6540
```

-continued

```
tccaggggga aacgcctggt atctttatag tcctgtcggg tttcgccacc tctgacttga      6600
gcgtcgattt ttgtgatgct cgtcaggggg gcggagccta tggaaaaacg ccagcaacgc      6660
ggccttttta cggttcctgg cctttttgctg gccttttgct cacatgt                  6707
```

<210> SEQ ID NO 118
<211> LENGTH: 6708
<212> TYPE: DNA
<213> ORGANISM: Artificial Sequence
<220> FEATURE:
<223> OTHER INFORMATION: Synthetic

<400> SEQUENCE: 118

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggggttcc tgcggccgca cgcgtgaggg cctatttccc atgattcctt      180
catatttgca tatcgatac aaggctgtta gagagataat tggaattaat ttgactgtaa       240
acacaaagat attagtacaa atacgtgac gtagaaagta ataatttctt gggtagtttg       300
cagttttaaa attatgtttt aaaatggact atcatatgct taccgtaact tgaaagtatt      360
tcgatttctt ggctttatat atcttgtgga aaggacgaaa caccgacgct tccgagtacg      420
gtacgtttta gagctagaaa tagcaagtta aaataaggct agtccgttat caacttgaaa      480
aagtggcacc gagtcggtgc ttttttcta gagacgcttc cgagtacggt acaggggatc       540 cagtacccctt acgatgtacc ggattacgca tagctagcta gctagagcat agtcaggaac     600
gtcataggga tactcgagga cgcttccgag tacggtacag ggtcgacggc cctgcgtatg      660
gggcagagcg cacatcgccc acagtccccg agaagttggg gggagggggtc ggcaattgaa      720 cgggtgccta gagaaggtgg cgcggggtaa actgggaaag tgatgtcgtg tactggctcc     780 gccttttttcc cgagggtggg ggagaaccgt atataagtgc agtagtcgcc gtgaacgttc    840
tttttcgcaa cgggtttgcc gccagaacac agctgaagct cgaggggct cgcatctctc      900 cttcacgcgc ccgccgccct acctgaggcc gccatccacg ccggttgagt cgcgttctgc     960
cgcctcccgc ctgtggtgcc tcctgaactg cgtccgccgt ctaggtaagt ttaaagctca     1020
ggtcgagacc gggcctttgt ccggcgctcc cttggagcct acctagactc agccggctct    1080 ccacgcttttg cctgacccctg cttgctcaac tctacgtctt tgtttcgttt tctgttctgc   1140
gccgttacag atccaagctg tgaccggcgc ctacaccggt gccaccatgg gccccaagaa    1200
aaaacggaag gtgccgctg cagggataca tgggggttcct gcagccgata aaaaatacag     1260
tatcggtctg gacataggca ctaattctgt cggttgggcc gtgataacag atgaatataa    1320
agtaccttcc aaaaaattca aggttctggg aaacacagat agacacagta taaaaagaa     1380 cctgattggc gctttgctct ttgacagcgg tgagaccgca gaggcaactc gcttgaagcg    1440
gaccgcccgg cgaaggtaca cacgacgcaa gaaccgaatt tgttacctcc aggaaatatt    1500
cagtaacgaa atggccaaag ttgacgattc tttttttccat cgccttgaag aatccttcct   1560
ggtagaagaa gataagaagc atgagagaca cccaatatttt gggaatatag ttgacgaagt   1620
cgcatatcac gagaagtacc ctactatata tcaccttcgg aaaaaactgg tcgattcaac   1680
tgacaaagcc gacttgagac tcatatacct ggcccttgct cacatgatca agttccgggg   1740
ccactttctg attgaaggcg acctcaatcc gacaatagc gacgtagaca agctgttttat   1800 ccaactcgtt caaacctata accagctctt cgaagagaac ccaataaatg ctagtggggt   1860
```

```
cgatgccaaa gctatttga gtgctaggct gtcaaagagt agaaggttgg agaacctgat    1920
cgcacaactg cccggtgaga agaagaacgg ccttttgggg aacttgattg ctctctccct    1980
tggccttacc cctaacttta atccaacttc gatcttgct gaggatgcta agctccaact    2040
gtccaaggac acctacgacg acgacttgga taaccttctg ccccagatag gtgatcagta    2100
cgcagatctt ttcttggcag ccaagaatct gtctgacgca atcttgctta gtgacatcct    2160
gagggtgaat actgaaataa ctaaggctcc actttccgcc tctatgatca agcgctacga    2220
cgaacaccat caagacctga cccttttgaa ggccttggtt agacaacaac tgcctgaaaa    2280
atacaaggaa atattcttcg accagtctaa gaacggttat gccggatata tcgacggggg    2340
ggcatcacag gaggaattct ataaatttat aaagcctatc ttggagaaaa tggacggaac    2400
cgaagaactc ctcgtaaagc ttaaccgcga agaccttttg cgaaagcagc ggactttcga    2460
taacggctct attcctcacc aaatccacct cggggagctt cacgcaatat tgcgaaggca    2520
ggaggacttc tatccattct tgaaggataa tcgggaaaaa attgaaaaaa ttcttacatt    2580
tcggattcct tactacgtgg gtcctctggc ccgcgggaat agtcggtttg catgatgac    2640
tcggaagtct gaggaaacta tcacaccatg gaattttgaa gaagtggtag acaaaggggc    2700
ttccgctcag tcttctatag agaggatgac taattttgat aaaaaacctgc ctaacgaaaa    2760
ggtactcccc aagcattcac ttctttatga atatttcact gtctacaacg agctgactaa    2820
ggttaaatat gtaaccgaag gtatgcgaaa gccagcattc ctgagtggtg agcagaagaa    2880
ggcaatcgta gacctttgt tcaaaaccaa ccgaaggtg acagtaaaac aactcaagga    2940
agactatttt aagaaaatag agtgtttgtc ttatgagacc gaaatcctca ccgtggagta    3000
cgggctcctg cctatcggga aaattgtcga aaagcgcata gagtgcactg tttactctgt    3060
agataacaat ggaaacatat acacacagcc cgtagcacag tggcacgatc gaggcgagca    3120
ggaggtcttt gaatattgcc tggaagacgg cagtcttata agggcaacaa aggatcacaa    3180
atttatgacc gtagatggac aaatgcttcc catcgacgag atctttgagc gcagccttga    3240
cttgatgaga gtggataacc tgcctaatta ggaattcgat atcaagctta tcgataatca    3300
acctctggat tacaaaattt tgtgaaagat tgactggtatt cttaactatg ttgctccttt    3360
tacgctatgt ggatacgctg ctttaatgcc tttgtatcat gctattgctt cccgtatggc    3420
tttcattttc tcctccttgt ataaatcctg gttgctgtct cttttatgag gagttgtggcc    3480
cgttgtcagg caacgtggcg tggtgtgcac tgtgtttgct gacgcaaccc ccactggttg    3540
gggcattgcc accacctgtc agctccttc cgggactttc gctttccccc tcctattgc    3600
cacggcggaa ctcatcgccg cctgccttgc ccgctgctgg acaggggctc ggctgttggg    3660
cactgacaat tccgtggtgt tgtcggggaa atcatcgtcc tttccttggc tgctcgcctg    3720
tgttgccacc tggattctgc gcgggacgtc cttctgctac gtcccttcgg ccctcaatcc    3780
agcggacctt ccttcccgcg gcctgctgcc ggctctgcgg cctcttccgc gtcttcgcct    3840
tcgccctcag acgagtcgga tctcccttg gccgcctcc ccgcatcgat accgagcgct    3900
aataaaagat cttattttc attagatctg tgtgttggtt ttttgtgtca cgtgcggacc    3960
gagcggccgc aggaacccct agtgatggag ttggccactc cctctctgcg cgctcgctcg    4020
ctcactgagg ccgggcgacc aaaggtcgcc cgacgcccgg gctttgcccg gcggcctca    4080
gtgagcgagc gagcgcgcag ctgcctgcag gggcgcctga tgcggtattt tctccttacg    4140
catctgtgcg gtatttcaca ccgcatacgt caaagcaacc atagtacgcg ccctgtagcg    4200
gcgcattaag cgcggcgggt gtggtggtta cgcgcagcgt gaccgctaca cttgccagcg    4260
```

-continued

```
ccctagcgcc cgctcctttc gctttcttcc cttcctttct cgccacgttc gccggctttc    4320
cccgtcaagc tctaaatcgg gggctcccTT taggGTtccg atttagtgct ttacggcacc    4380
tcgaccccaa aaacttgaTT ttgggtgatg gttcacgtag tgggccatcg ccctgataga    4440 cggttttTTcg cccTTtgacg ttggagtcca cgttcttTaa tagtggactc ttgttccaaa    4500
ctggaacaac actcaaccct atctcgggct attcttTtga tttataaggg attttgccga    4560
tttcggccta ttggttaaaa aatgagctga ttTaacaaaa atttaacgcg aatTTtaaca    4620
aaatattaac gtttacaatt ttatggtgca ctctcagtac aatctgctct gatgccgcat    4680
agttaagcca gccccgacac ccgccaacac ccgctgacgc gccctgacgg gcttgtctgc    4740
tcccggcatc cgcttacaga caagctgtga ccgtctccgg gagctgcatg tgtcagaggt    4800
tttcaccgtc atcaccgaaa cgcgcgagac gaaagggcct cgtgatacgc ctatTTTTat    4860
aggttaatgt catgataata atggtttctt agacgtcagg tggcactTTT cggggaaatg    4920
tgcgcggaac ccctatttgt ttatTTTtct aaatacattc aaatatgtat ccgctcatga    4980
gacaataacc ctgataaatg cttcaataat attgaaaaag gaagagtatg agtattcaac    5040
atttccgtgt cgcccttatt cccttTTTtg cggcattTtg ccttcctgtt tttgctcacc    5100
cagaaacgct ggtgaaagta aaagatgctg aagatcagtt gggtgcacga gtgggttaca    5160
tcgaactgga tctcaacagc ggtaagatcc ttgagagttt cgccccgaa gaacgttTTc    5220 caatgatgag cactTTtaaa gttctgctat gtggcgcggt attatcccgt attgacgccg    5280
ggcaagagca actcggtcgc cgcatacact attctcagaa tgacttggtt gagtactcac    5340
cagtcacaga aaagcatctt acggatggca tgacagtaag agaattatgc agtgctgcca    5400
taaccatgag tgataacact gcggccaact tacttctgac aacgatcgga ggaccgaagg    5460
agctaaccgc ttTTttgcac aacatggggg atcatgtaac tcgccttgat cgttgggaac    5520
cggagctgaa tgaagccata ccaaacgacg agcgtgacac cacgatgcct gtagcaatgg    5580
caacaacgtt gcgcaaacta ttaactggcg aactacttac tctagcttcc cggcaacaat    5640
taatagactg gatggaggcg gataaagttg caggaccact tctgcgctcg gcccttccgg    5700
ctggctggtt tattgctgat aaatctggag ccggtgagcg tgggtctcgc ggtatcattg    5760
cagcactggg gccagatggt aagccctccc gtatcgtagt tatctacacg acggggagtc    5820
aggcaactat ggatgaacga aatagacaga tcgctgagat aggtgcctca ctgattaagc    5880
attggtaact gtcagaccaa gtTTactcat atactttta gattgattTa aaacttcatt    5940
tttaatttaa aaggatctag gtgaagatcc ttTTtgataa tctcatgacc aaaatccctt    6000
aacgtgagTT ttcgTTccac tgagcgtcag accccgtaga aaagatcaaa ggatcttctt    6060
gagatccttT tttTctgcgc gtaatctgct gcttgcaaac aaaaaaacca ccgctaccag    6120
cggtggTTTg tttgccggat caagagctac caactctttt tccgaaggta actggcttca    6180
gcagagcgca gataccaaat actgtccttc tagtgtagcc gtagttaggc caccacttca    6240
agaactctgt agcaccgcct acatacctcg ctctgctaat cctgttacca gtggctgctg    6300
ccagtggcga taagtcgtgt cttaccgggt tggactcaag acgatagTTa ccggataagg    6360
cgcagcggtc gggctgaacg gggggTTcgt gcacacagcc cagcttggag cgaacgacct    6420
acaccgaact gagatacccta cagcgtgagc tatgagaaag cgccacgctt cccgaaggga    6480
gaaaggcgga caggtatccg gtaagcggca gggtcggaac aggagagcgc acagggagc    6540 ttccagggg aaacgcctgg tatctTTata gtcctgtcgg gtttcgccac ctctgacttg    6600
```

| | |
|---|---:|
| agcgtcgatt tttgtgatgc tcgtcagggg ggcggagcct atggaaaaac gccagcaacg | 6660 |
| cggccttttt acggttcctg gccttttgct ggccttttgc tcacatgt | 6708 |

<210> SEQ ID NO 119
<211> LENGTH: 6709
<212> TYPE: DNA
<213> ORGANISM: Artificial Sequence
<220> FEATURE:
<223> OTHER INFORMATION: Synthetic

<400> SEQUENCE: 119

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa atacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttttcta gagacgcttc cgagtacggt acaggaggat | 540 |
| cctacccttta cgatgtaccg gattacgcat agctagctag ctagagcata gtcaggaacg | 600 |
| tcatagggat aagctcgagg acgcttccga gtacggtaca gggtcgacgg ccctgcgtat | 660 |
| ggggcagagc gcacatcgcc cacagtcccc gagaagttgg ggggaggggt cggcaattga | 720 |
| acgggtgcct agagaaggtg gcgcggggta aactgggaaa gtgatgtcgt gtactggctc | 780 |
| cgccttttc ccgagggtgg gggagaaccg tatataagtg cagtagtcgc cgtgaacgtt | 840 |
| cttttcgca acgggtttgc cgccagaaca cagctgaagc ttcgaggggc tcgcatctct | 900 |
| ccttcacgcg cccgccgccc tacctgaggc cgccatccac gccggttgag tcgcgttctg | 960 |
| ccgcctcccg cctgtggtgc ctcctgaact gcgtccgccg tctaggtaag tttaaagctc | 1020 |
| aggtcgagac cgggcctttg tccggcgctc ccttggagcc tacctagact cagccggctc | 1080 |
| tccacgcttt gcctgacct gcttgctcaa ctctacgtct ttgtttcgtt ttctgttctg | 1140 |
| cgccgttaca gatccaagct gtgaccggcg cctacaccgg tgccaccatg ggccccaaga | 1200 |
| aaaaacggaa ggtggccgct gcagggatac atggggttcc tgcagccgat aaaaaataca | 1260 |
| gtatcggtct ggacataggc actaattctg tcggttgggc cgtgataaca gatgaatata | 1320 |
| aagtaccttc caaaaaattc aaggttctgg gaaacacaga tagacacagt ataaaaaaga | 1380 |
| acctgattgg cgctttgctc tttgacagcg gtgagaccgc agaggcaact cgcttgaagc | 1440 |
| ggaccgcccg gcgaaggtac acacgacgca agaaccgaat ttgttacctc caggaaatat | 1500 |
| tcagtaacga aatggccaaa gttgacgatt cttttttcca tcgccttgaa gaatccttcc | 1560 |
| tggtagaaga agataagaag catgagagac acccaatatt tgggaatata gttgacgaag | 1620 |
| tcgcatatca cgagaagtac cctactatat atcaccttcg gaaaaaactg gtcgattcaa | 1680 |
| ctgacaaagc cgactgaga ctcatatacc tggcccttgc tcacatgatc aagttccggg | 1740 |
| gccactttct gattgaaggc gacctcaatc ccgacaatag cgacgtagac aagctgtttta | 1800 |
| tccaactcgt tcaaacctat aaccagctct cgaagagaa cccaataaat gctagtgggg | 1860 |
| tcgatgccaa agctattttg agtgctaggc tgtcaaagag tagaaggttg gagaacctga | 1920 |
| tcgcacaact gcccggtgag aagaagaacg gcctttttgg gaacttgatt gctctctctc | 1980 |

```
ttggccttac ccctaacttt aaatccaact tcgatcttgc tgaggatgct aagctccaac   2040
tgtccaagga cacctacgac gacgacttgg ataaccttct ggcccagata ggtgatcagt   2100
acgcagatct tttcttggca gccaagaatc tgtctgacgc aatcttgctt agtgacatcc   2160
tgagggtgaa tactgaaata actaaggctc cactttccgc ctctatgatc aagcgctacg   2220
acgaacacca tcaagacctg accctttga aggccttggt tagacaacaa ctgcctgaaa   2280
aatacaagga aatattcttc gaccagtcta agaacggtta tgccggatat atcgacgggg   2340
gggcatcaca ggaggaattc tataaattta taaagcctat cttggagaaa atggacggaa   2400
ccgaagaact cctcgtaaag cttaaccgcg aagacctttt gcgaaagcag cggactttcg   2460
ataacggctc tattcctcac caaatccacc tcggggagct tcacgcaata ttgcgaaggc   2520
aggaggactt ctatccattc ttgaaggata tcgggaaaa aattgaaaaa attcttacat   2580
ttcggattcc ttactacgtg ggtcctctgg cccgcgggaa tagtcggttt gcatggatga   2640
ctcggaagtc tgaggaaact atcacaccat ggaattttga agaagtggta gacaaagggg   2700
cttccgctca gtctttcata gagaggatga ctaattttga taaaaacctg cctaacgaaa   2760
aggtactccc caagcattca cttctttatg aatatttcac tgtctacaac gagctgacta   2820
aggttaaata tgtaaccgaa ggtatgcgga agccagcatt cctgagtggt gagcagaaga   2880
aggcaatcgt agaccttttg ttcaaaacca accgaaaggt gacagtaaaa caactcaagg   2940
aagactattt taagaaaata gagtgtttgt cttatgagac cgaaatcctc accgtggagt   3000
acgggctcct gcctatcggg aaaattgtcg aaaagcgcat agagtgcact gtttactctg   3060
tagataacaa tggaaacata tacacacagc ccgtagcaca gtggcacgat cgaggcgagc   3120
aggaggtctt tgaatattgc ctggaagacg gcagtcttat aagggcaaca aaggatcaca   3180
aatttatgac cgtagatgga caaatgcttc ccatcgacga gatctttgag cgcgagcttg   3240
acttgatgag agtggataac ctgcctaatt aggaattcga tatcaagctt atcgataatc   3300
aacctctgga ttacaaaatt tgtgaaagat tgactggtat tcttaactat gttgctcctt   3360
ttacgctatg tggatacgct gctttaatgc ctttgtatca tgctattgct tcccgtatgg   3420
ctttcatttt ctcctccttg tataaatcct ggttgctgtc tctttatgag gagttgtggc   3480
ccgttgtcag gcaacgtggc gtggtgtgca ctgtgtttgc tgacgcaacc cccactggtt   3540
ggggcattgc caccacctgt cagctccttt ccgggacttt cgctttcccc ctccctattg   3600
ccacggcgga actcatcgcc gcctgccttg cccgctgctg gacagggact cggctgttgg   3660
gcactgacaa ttccgtggtg ttgtcgggga atcatcgtc cttttcttgg ctgctcgcct   3720
gtgttgccac ctggattctg cgcgggacgt ccttctgcta cgtcccttcg gccctcaatc   3780
cagcggacct tccttcccgc ggcctgctgc cggctctgcg gcctcttccg cgtcttcgcc   3840
ttcgccctca gacgagtcgg atctcccttt gggccgcctc cccgcatcga taccgagcgc   3900
taataaaaga tctttatttt cattagatct gtgtgttggt tttttgtgtc acgtgcggac   3960
cgagcggccg caggaaccc tagtgatgga gttggccact ccctctctgc gcgctcgctc   4020
gctcactgag gccgggcgac caaaggtcgc ccgacgcccg ggctttgccc gggcggcctc   4080
agtgagcgag cgagcgcgca gctgcctgca ggggcgcctg atgcggtatt ttctccttac   4140
gcatctgtgc ggtatttcac accgcatacg tcaaagcaac catagtacgc gccctgtagc   4200
ggcgcattaa gcgcggcggg tgtggtggtt acgcgcagcg tgaccgctac acttgccagc   4260
gccctagcgc ccgctccttt cgctttcttc ccttcctttc tcgccacgtt cgccggcttt   4320
```

```
ccccgtcaag ctctaaatcg ggggctccct ttagggttcc gatttagtgc tttacggcac    4380
ctcgacccca aaaaacttga tttgggtgat ggttcacgta gtgggccatc gccctgatag    4440 acggttttc gcccttgac gttggagtcc acgttcttta atagtggact cttgttccaa    4500
actggaacaa cactcaaccc tatctcgggc tattcttttg attataagg gatttgccg    4560 atttcggcct attggttaaa aaatgagctg atttaacaaa aatttaacgc gaattttaac    4620
aaaatattaa cgtttacaat tttatggtgc actctcagta caatctgctc tgatgccgca    4680
tagttaagcc agccccgaca cccgccaaca cccgctgacg cgccctgacg ggcttgtctg    4740
ctcccggcat ccgcttacag acaagctgtg accgtctccg ggagctgcat gtgtcagagg    4800
ttttcaccgt catcaccgaa acgcgcgaga cgaaagggcc tcgtgatacg cctatttta    4860 taggttaatg tcatgataat aatggtttct tagacgtcag gtggcacttt tcggggaaat    4920
gtgcgcggaa cccctatttg tttattttc taaatacatt caaatatgta tccgctcatg    4980
agacaataac cctgataaat gcttcaataa tattgaaaaa ggaagagtat gagtattcaa    5040
catttccgtg tcgcccttat tccctttttt gcggcatttt gccttcctgt ttttgctcac    5100
ccagaaacgc tggtgaaagt aaaagatgct gaagatcagt tgggtgcacg agtgggttac    5160
atcgaactgg atctcaacag cggtaagatc cttgagagtt ttcgccccga agaacgtttt    5220
ccaatgatga gcactttaa agttctgcta tgtggcgcgg tattatcccg tattgacgcc    5280
gggcaagagc aactcggtcg ccgcatacac tattctcaga atgacttggt tgagtactca    5340
ccagtcacag aaaagcatct tacggatggc atgacagtaa gagaattatg cagtgctgcc    5400
ataaccatga gtgataacac tgcggccaac ttacttctga caacgatcgg aggaccgaag    5460
gagctaaccg cttttttgca acatgggg gatcatgtaa ctcgccttga tcgttgggaa    5520
ccggagctga atgaagccat accaaacgac gagcgtgaca ccacgatgcc tgtagcaatg    5580
gcaacaacgt tgcgcaaact attaactggc gaactactta ctctagcttc ccggcaacaa    5640
ttaatagact ggatggaggc ggataaagtt gcaggaccac ttctgcgctc ggcccttccg    5700
gctggctggt ttattgctga taaatctgga gccggtgagc gtgggtctcg cggtatcatt    5760
gcagcactgg ggccagatgg taagccctcc cgtatcgtag ttatctacac gacggggagt    5820
caggcaacta tggatgaacg aaatagacag atcgctgaga taggtgcctc actgattaag    5880
cattggtaac tgtcagacca agtttactca tatatacttt agattgattt aaaacttcat    5940
ttttaattta aaaggatcta ggtgaagatc ctttttgata atctcatgac caaaatccct    6000
taacgtgagt tttcgttcca ctgagcgtca gaccccgtag aaaagatcaa aggatcttct    6060
tgagatcctt ttttctgcg cgtaatctgc tgcttgcaaa caaaaaaacc accgctacca    6120
gcggtggttt gtttgccgga tcaagagcta ccaactcttt ttccgaaggt aactggcttc    6180
agcagagcgc agataccaaa tactgtcctt ctagtgtagc cgtagttagg ccaccacttc    6240
aagaactctg tagcaccgcc tacatacctc gctctgctaa tcctgttacc agtggctgct    6300
gccagtggcg ataagtcgtg tcttaccggg ttggactcaa gacgatagtt accggataag    6360
gcgcagcggt cgggctgaac ggggggttcg tgcacacagc ccagcttgga gcgaacgacc    6420
tacaccgaac tgagatacct acagcgtgag ctatgagaaa gcgccacgct tcccgaaggg    6480
agaaaggcgg acaggtatcc ggtaagcggc agggtcggaa caggagagcg cacgagggag    6540
cttccagggg gaaacgcctg gtatctttat agtcctgtcg gtttcgcca cctctgactt    6600 gagcgtcgat ttttgtgatg ctcgtcaggg gggcggagcc tatggaaaaa cgccagcaac    6660
gcggcctttt tacggttcct ggccttttgc tggccttttg ctcacatgt                6709
```

```
<210> SEQ ID NO 120
<211> LENGTH: 7447
<212> TYPE: DNA
<213> ORGANISM: Artificial Sequence
<220> FEATURE:
<223> OTHER INFORMATION: Synthetic

<400> SEQUENCE: 120
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact gaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttcta gagacgcttc cgagtacggt acaggggatc     540
cggtggagga ggttctggag gcggtggaag tggtggcgga ggtagcggtg gaggaggttc     600
tatggtgtct aaggaattca tggtgagcaa gggcgaggag gataacatgg ccatcatcaa     660
ggagttcatg cgcttcaagg tgcacatgga gggctccgtg aacggccacg agttcgagat     720
cgagggcgag ggcgagggcc gcccctacga gggcacccag accgccaagc tgaaggtgac     780
caagggtggc cccctgccct cgcctggga catcctgtcc cctcagttca tgtacggctc     840
caaggcctac gtgaagcacc ccgccgacat ccccgactac ttgaagctgt ccttccccga     900
gggcttcaag tgggagcgcg tgatgaactt cgaggacggc ggcgtggtga ccgtgaccca     960
ggactcctcc ctgcaggacg gcgagttcat ctacaaggtg aagctgcgcg gcaccaactt    1020
cccctccgac ggccccgtaa tgcagaagaa gaccatgggc tgggaggcct cctccgagcg    1080
gatgtacccc gaggacggcg ccctgaaggg cgagatcaag cagaggctga agctgaagga    1140
cggcggccac tacgacgctg aggtcaagac cacctacaag gccaagaagc ccgtgcagct    1200
gcccggcgcc tacaacgtca acatcaagtt ggacatcacc tcccacaacg aggactacac    1260
catcgtggaa cagtacgaac gcgccgaggg ccgccactcc accggcggca tggacgagct    1320
gtacaagaag cttggatagc tagctagcta gctcgaggac gcttccgagt acggtacagg    1380
gtcgacggcc ctgcgtatgg ggcagagcgc acatcgccca cagtccccga aagttgggg     1440
ggaggggtcg gcaattgaac gggtgcctag agaaggtggc gcggggtaaa ctgggaaagt    1500
gatgtcgtgt actggctccg cctttttccc gagggtgggg gagaaccgta tataagtgca    1560
gtagtcgccg tgaacgttct ttttcgcaac gggtttgccg ccagaacaca gctgaagctt    1620
cgaggggctc gcatctctcc ttcacgcgcc cgccgcccta cctgaggccg ccatccacgc    1680
cggttgagtc gcgttctgcc gcctcccgcc tgtggtgcct cctgaactgc gtccgccgtc    1740
taggtaagtt taaagctcag gtcgagaccg ggcctttgtc cggcgctccc ttggagccta    1800
cctagactca gccggctctc cacgcttttgc ctgaccctgc ttgctcaact ctacgtcttt    1860
gtttcgtttt ctgttctgcg ccgttacaga tccaagctgt gaccggcgcc tacaccggtg    1920
ccaccatggg cccccagaaa aaacggaagg tggccgctgc agggatacat ggggttcctg    1980
cagccgataa aaaatacagt atcggtctgg acataggcac taattctgtc ggttgggccg    2040
```

```
tgataacaga tgaatataaa gtaccttcca aaaaattcaa ggttctggga aacacagata   2100
gacacagtat aaaaaagaac ctgattggcg ctttgctctt tgacagcggt gagaccgcag   2160
aggcaactcg cttgaagcgg accgcccggc gaaggtacac acgacgcaag aaccgaattt   2220
gttacctcca ggaaatattc agtaacgaaa tggccaaagt tgacgattct tttttccatc   2280
gccttgaaga atccttcctg gtagaagaag ataagaagca tgagagacac ccaatatttg   2340
ggaatatagt tgacgaagtc gcatatcacg agaagtaccc tactatatat caccttcgga   2400
aaaaactggt cgattcaact gacaaagccg acttgagact catatacctg gcccttgctc   2460
acatgatcaa gttccggggc cactttctga ttgaaggcga cctcaatccc gacaatagcg   2520
acgtagacaa gctgtttatc caactcgttc aaacctataa ccagctcttc gaagagaacc   2580
caataaatgc tagtgggtc gatgccaaag ctattttgag tgctaggctg tcaaagagta   2640
gaaggttgga gaacctgatc gcacaactgc ccggtgagaa gaagaacggc cttttgggga   2700
acttgattgc tctctccctt ggccttaccc ctaactttaa atccaacttc gatcttgctg   2760
aggatgctaa gctccaactg tccaaggaca cctacgacga cgacttggat aaccttctgg   2820
cccagatagg tgatcagtac gcagatcttt tcttggcagc caagaatctg tctgacgcaa   2880
tcttgcttag tgacatcctg agggtgaata ctgaaataac taaggctcca ctttccgcct   2940
ctatgatcaa gcgctacgac gaacaccatc aagacctgac cctttgaag gccttggtta   3000 gacaacaact gcctgaaaaa tacaaggaaa tattcttcga ccagtctaag aacggttatg   3060
ccggatatat cgacggggg gcatcacagg aggaattcta taaatttata aagcctatct   3120
tggagaaaat ggacggaacc gaagaactcc tcgtaaagct taaccgcgaa gacctttgc   3180 gaaagcagcg gactttcgat aacggctcta ttcctcacca aatccacctc ggggagcttc   3240
acgcaatatt gcgaaggcag gaggacttct atccattctt gaaggataat cgggaaaaaa   3300
ttgaaaaaat tcttacattt cggattcctt actacgtggg tcctctggcc cgcgggaata   3360
gtcggtttgc atggatgact cggaagtctg aggaaactat cacaccatgg aattttgaag   3420
aagtggtaga caaaggggct tccgctcagt cttttcataga gaggatgact aattttgata   3480
aaaacctgcc taacgaaaag gtactcccca agcattcact tctttatgaa tatttcactg   3540
tctacaacga gctgactaag gttaaatatg taaccgaagg tatgcggaag ccagcattcc   3600
tgagtggtga gcagaagaag gcaatcgtag acctttttgtt caaaaccaac cgaaaggtga   3660
cagtaaaaca actcaaggaa gactatttta agaaaataga gtgtttgtct tatgagaccg   3720
aaatcctcac cgtggagtac gggctcctgc ctatcgggaa aattgtcgaa aagcgcatag   3780
agtgcactgt ttactctgta gataacaatg gaaacatata cacacagccc gtagcacagt   3840
ggcacgatcg aggcgagcag gaggtctttg aatattgcct ggaagacggc agtcttataa   3900
gggcaacaaa ggatcacaaa tttatgaccg tagatggaca aatgcttccc atcgacgaga   3960
tctttgagcg cgagcttgac ttgatgagag tggataacct gcctaattag gaattcgata   4020
tcaagcttat cgataatcaa cctctggatt acaaaatttg tgaaagattg actggtattc   4080
ttaactatgt tgctcctttt acgctatgtg gatacgctgc tttaatgcct ttgtatcatg   4140
ctattgcttc ccgtatggct ttcattttct cctccttgta taaatcctgg ttgctgtctc   4200
tttatgagga gttgtggccc gttgtcaggc aacgtggcgt ggtgtgcact gtgtttgctg   4260
acgcaacccc cactggttgg ggcattgcca ccacctgtca gctcctttcc gggactttcg   4320
ctttccccct ccctattgcc acggcggaac tcatcgccgc ctgccttgcc cgctgctgga   4380 cagggctcg gctgttgggc actgacaatt ccgtggtgtt gtcggggaaa tcatcgtcct   4440
```

```
ttccttggct gctcgcctgt gttgccacct ggattctgcg cgggacgtcc ttctgctacg    4500
tcccttcggc cctcaatcca gcggaccttc cttcccgcgg cctgctgccg gctctgcggc    4560
ctcttccgcg tcttcgcctt cgccctcaga cgagtcggat ctccctttgg gccgcctccc    4620
cgcatcgata ccgagcgcta ataaaagatc tttattttca ttagatctgt gtgttggttt    4680
tttgtgtcac gtgcggaccg agcggccgca ggaaccccta gtgatggagt tggccactcc    4740
ctctctgcgc gctcgctcgc tcactgaggc cgggcgacca aggtcgccc gacgcccggg     4800 ctttgcccgg gcggcctcag tgagcgagcg agcgcgcagc tgcctgcagg ggcgcctgat    4860
gcggtatttt ctccttacgc atctgtgcgg tatttcacac cgcatacgtc aaagcaacca    4920
tagtacgcgc cctgtagcgg cgcattaagc gcggcgggtg tggtggttac gcgcagcgtg    4980
accgctacac ttgccagcgc cctagcgccc gctcctttcg ctttcttccc ttcctttctc    5040
gccacgttcg ccggctttcc ccgtcaagct ctaaatcggg ggctcccttt agggttccga    5100
tttagtgctt tacggcacct cgaccccaaa aaacttgatt tgggtgatgg ttcacgtagt    5160
gggccatcgc cctgatagac ggttttttcgc cctttgacgt tggagtccac gttctttaat    5220
agtggactct tgttccaaac tggaacaaca ctcaacccta tctcgggcta ttcttttgat    5280
ttataaggga ttttgccgat ttcggcctat tggttaaaaa atgagctgat ttaacaaaaa    5340
tttaacgcga attttaacaa aatattaacg tttacaattt tatggtgcac tctcagtaca    5400
atctgctctg atgccgcata gttaagccag ccccgacacc cgccaacacc cgctgacgcg    5460
ccctgacggg cttgtctgct cccggcatcc gcttacagac aagctgtgac cgtctccggg    5520
agctgcatgt gtcagaggtt ttcaccgtca tcaccgaaac gcgcgagacg aaagggcctc    5580
gtgatacgcc tattttttata ggttaatgtc atgataataa tggtttctta gacgtcaggt    5640 ggcactttt ggggaaatgt gcgcggaacc cctatttgtt tatttttcta aatacattca    5700
aatatgtatc cgctcatgag acaataaccc tgataaatgc ttcaataata ttgaaaagg    5760 aagagtatga gtattcaaca tttccgtgtc gcccttattc cctttttgc ggcattttgc     5820 cttcctgttt ttgctcaccc agaaacgctg gtgaaagtaa aagatgctga agatcagttg    5880
ggtgcacgag tgggttacat cgaactggat ctcaacagcg gtaagatcct tgagagtttt    5940
cgccccgaag aacgttttcc aatgatgagc acttttaaag ttctgctatg tggcgcggta    6000
ttatcccgta ttgacgccgg gcaagagcaa ctcggtcgcc gcatacacta ttctcagaat    6060
gacttggttg agtactcacc agtcacagaa aagcatctta cggatggcat gacagtaaga    6120
gaattatgca gtgctgccat aaccatgagt gataacactg cggccaactt acttctgaca    6180
acgatcggag gaccgaagga gctaaccgct tttttgcaca acatggggga tcatgtaact    6240
cgccttgatc gttgggaacc ggagctgaat gaagccatac caaacgacga gcgtgacacc    6300
acgatgcctg tagcaatggc aacaacgttg cgcaaactat taactggcga actacttact    6360
ctagcttccc ggcaacaatt aatagactgg atggaggcgg ataaagttgc aggaccactt    6420
ctgcgctcgg cccttccggc tggctggttt attgctgata aatctggagc cggtgagcgt    6480
gggtctcgcg gtatcattgc agcactgggg ccagatggta agccctcccg tatcgtagtt    6540
atctacacga cggggagtca ggcaactatg gatgaacgaa atagacagat cgctgagata    6600
ggtgcctcac tgattaagca ttggtaactg tcagaccaag tttactcata tatactttag    6660
attgatttaa aacttcattt ttaatttaaa aggatctagg tgaagatcct ttttgataat    6720
ctcatgacca aaatccctta acgtgagttt tcgttccact gagcgtcaga ccccgtagaa    6780
```

| | |
|---|---|
| aagatcaaag gatcttcttg agatcctttt tttctgcgcg taatctgctg cttgcaaaca | 6840 |
| aaaaaaccac cgctaccagc ggtggtttgt ttgccggatc aagagctacc aactcttttt | 6900 |
| ccgaaggtaa ctggcttcag cagagcgcag ataccaaata ctgtccttct agtgtagccg | 6960 |
| tagttaggcc accacttcaa gaactctgta gcaccgccta catacctcgc tctgctaatc | 7020 |
| ctgttaccag tggctgctgc cagtggcgat aagtcgtgtc ttaccgggtt ggactcaaga | 7080 |
| cgatagttac cggataaggc gcagcggtcg ggctgaacgg ggggttcgtg cacacagccc | 7140 |
| agcttggagc gaacgaccta caccgaactg agatacctac agcgtgagct atgagaaagc | 7200 |
| gccacgcttc ccgaagggag aaaggcggac aggtatccgg taagcggcag gtcggaaca | 7260 |
| ggagagcgca cgagggagct tccaggggga aacgcctggt atctttatag tcctgtcggg | 7320 |
| tttcgccacc tctgacttga gcgtcgattt ttgtgatgct cgtcaggggg gcggagccta | 7380 |
| tggaaaaacg ccagcaacgc ggcctttta cggttcctgg ccttttgctg gccttttgct | 7440 |
| cacatgt | 7447 |

<210> SEQ ID NO 121
<211> LENGTH: 7449
<212> TYPE: DNA
<213> ORGANISM: Artificial Sequence
<220> FEATURE:
<223> OTHER INFORMATION: Synthetic

<400> SEQUENCE: 121

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc ttttttcta gagacgcttc cgagtacggt acaggggatc | 540 |
| cagggtggag gaggttctgg aggcggtgga agtggtggcg gaggtagcgg tggaggaggt | 600 |
| tctatggtgt ctaaggaatt catggtgagc aagggcgagg aggataacat ggccatcatc | 660 |
| aaggagttca tgcgcttcaa ggtgcacatg gagggctccg tgaacggcca cgagttcgag | 720 |
| atcgagggcg agggcgaggg ccgcccctac gagggcaccc agaccgccaa gctgaaggtg | 780 |
| accaaggtg gcccctgcc cttcgcctgg gacatcctgt cccctcagtt catgtacggc | 840 |
| tccaaggcct acgtgaagca ccccgccgac atccccgact acttgaagct gtccttcccc | 900 |
| gagggcttca gtgggagcg cgtgatgaac ttcgaggacg gcggcgtggt gaccgtgacc | 960 |
| caggactcct ccctgcagga cggcgagttc atctacaagg tgaagctgcg cggcaccaac | 1020 |
| ttcccctccg acggccccgt aatgcagaag aagaccatgg gctgggaggc ctcctccgag | 1080 |
| cggatgtacc ccgaggacgg cgccctgaag ggcgagatca gcagaggct gaagctgaag | 1140 |
| gacggcggcc actacgacgc tgaggtcaag accacctaca aggccaagaa gcccgtgcag | 1200 |
| ctgcccggcg cctacaacgt caacatcaag ttggacatca cctcccacaa cgaggactac | 1260 |
| accatcgtgg aacagtacga acgcgccgag ggccgccact ccaccggcgg catggacgag | 1320 |
| ctgtacaaga gcttggata gctagctagc tagctcgagg acgcttccga gtacggtaca | 1380 |

```
gggtcgacgg ccctgcgtat ggggcagagc gcacatcgcc cacagtcccc gagaagttgg    1440
ggggaggggt cggcaattga acgggtgcct agagaaggtg gcgcggggta aactgggaaa    1500
gtgatgtcgt gtactggctc cgccttttc ccgagggtgg gggagaaccg tatataagtg    1560
cagtagtcgc cgtgaacgtt cttttcgca acgggtttgc cgccagaaca cagctgaagc    1620
ttcgaggggc tcgcatctct ccttcacgcg cccgccgccc tacctgaggc cgccatccac    1680
gccggttgag tcgcgttctg ccgcctcccg cctgtggtgc ctcctgaact gcgtccgccg    1740
tctaggtaag tttaaagctc aggtcgagac cgggcctttg tccggcgctc ccttggagcc    1800
tacctagact cagccggctc tccacgcttt gcctgaccct gcttgctcaa ctctacgtct    1860
ttgtttcgtt ttctgttctg cgccgttaca gatccaagct gtgaccggcg cctacaccgg    1920
tgccaccatg ggcccaaga aaaacggaa ggtggccgct gcagggatac atggggttcc    1980
tgcagccgat aaaaaataca gtatcggtct ggacataggc actaattctg tcggttgggc    2040
cgtgataaca gatgaatata agtaccttc caaaaaattc aaggttctgg aaacacaga    2100 tagacacagt ataaaaaaga acctgattgg cgctttgctc tttgacagcg gtgagaccgc    2160
agaggcaact cgcttgaagc ggaccgcccg gcgaaggtac acacgacgca agaaccgaat    2220
ttgttacctc caggaaatat tcagtaacga aatggccaaa gttgacgatt ctttttcca    2280 tcgccttgaa gaatccttcc tggtagaaga agataagaag catgagagac acccaatatt    2340
tgggaatata gttgacgaag tcgcatatca cgagaagtac cctactatat atcaccttcg    2400
gaaaaaactg gtcgattcaa ctgacaaagc cgacttgaga ctcatatacc tggcccttgc    2460
tcacatgatc aagttccggg gccactttct gattgaaggc gacctcaatc ccgacaatag    2520
cgacgtagac aagctgtttta tccaactcgt tcaaacctat aaccagctct tcgaagagaa    2580
cccaataaat gctagtgggg tcgatgccaa agctattttg agtgctaggc tgtcaaagag    2640
tagaaggttg gagaacctga tcgcacaact gcccggtgag aagaagaacg cctttttgg    2700 gaacttgatt gctctctccc ttggccttac ccctaacttt aaatccaact tcgatcttgc    2760
tgaggatgct aagctccaac tgtccaagga cacctacgac gacgacttgg ataacccttct    2820 ggcccagata ggtgatcagt acgcagatct tttcttggca gccaagaatc tgtctgacgc    2880
aatcttgctt agtgacatcc tgagggtgaa tactgaaata actaaggctc cactttccgc    2940
ctctatgatc aagcgctacg acgaacacca tcaagacctg acccttttga aggccttggt    3000
tagacaacaa ctgcctgaaa aatacaagga aatattcttc gaccagtcta agaacggtta    3060
tgccggatat atcgacgggg gggcatcaca ggaggaattc tataaattta taagcctat    3120 cttggagaaa atggacggaa ccgaagaact cctcgtaaag cttaaccgcg aagacctttt    3180
gcgaaagcag cggactttcg ataacggctc tattcctcac caaatccacc tgggggagct    3240
tcacgcaata ttgcgaaggc aggaggactt ctatccattc ttgaaggata atcgggaaaa    3300
aattgaaaaa attcttacat ttcggattcc ttactacgtg ggtcctctgg cccgcgggaa    3360
tagtcggttt gcatggatga ctcggaagtc tgaggaaact atcacaccat ggaatttga    3420 agaagtggta gacaaagggg cttccgctca gtctttcata gagaggatga ctaatttga    3480 taaaaacctg cctaacgaaa aggtactccc caagcattca cttctttatg aatatttcac    3540
tgtctacaac gagctgacta aggttaaata tgtaaccgaa ggtatgcgga agccagcatt    3600
cctgagtggt gagcagaaga aggcaatcgt agacctttg ttcaaaacca accgaaaggt    3660
gacagtaaaa caactcaagg aagactattt taagaaaata gagtgtttgt cttatgagac    3720
```

```
cgaaatcctc accgtggagt acgggctcct gcctatcggg aaaattgtcg aaaagcgcat    3780
agagtgcact gtttactctg tagataacaa tggaaacata tacacacagc ccgtagcaca    3840
gtggcacgat cgaggcgagc aggaggtctt tgaatattgc ctggaagacg gcagtcttat    3900
aagggcaaca aaggatcaca aatttatgac cgtagatgga caaatgcttc ccatcgacga    3960
gatctttgag cgcgagcttg acttgatgag agtggataac ctgcctaatt aggaattcga    4020
tatcaagctt atcgataatc aacctctgga ttacaaaatt tgtgaaagat tgactggtat    4080
tcttaactat gttgctcctt ttacgctatg tggatacgct gctttaatgc ctttgtatca    4140
tgctattgct tcccgtatgg ctttcatttt ctcctccttg tataaatcct ggttgctgtc    4200
tctttatgag gagttgtggc ccgttgtcag gcaacgtggc gtggtgtgca ctgtgtttgc    4260
tgacgcaacc cccactggtt ggggcattgc caccacctgt cagctccttt ccgggacttt    4320
cgctttcccc ctccctattg ccacggcgga actcatcgcc gcctgccttg cccgctgctg    4380
gacaggggct cggctgttgg gcactgacaa ttccgtggtg ttgtcgggga aatcatcgtc    4440
ctttccttgg ctgctcgcct gtgttgccac ctggattctg cgcgggacgt ccttctgcta    4500
cgtcccttcg gccctcaatc cagcggacct tccttcccgc ggcctgctgc cggctctgcg    4560
gcctcttccg cgtcttcgcc ttcgccctca gacgagtcgg atctcccttt gggccgcctc    4620
cccgcatcga taccgagcgc taataaaaga tctttatttt cattagatct gtgtgttggt    4680
tttttgtgtc acgtgcggac cgagcggccg caggaacccc tagtgatgga gttggccact    4740
ccctctctgc gcgctcgctc gctcactgag gccgggcgac caaaggtcgc ccgacgcccg    4800
ggctttgccc gggcggcctc agtgagcgag cgagcgcgca gctgcctgca ggggcgcctg    4860
atgcggtatt ttctccttac gcatctgtgc ggtatttcac accgcatacg tcaaagcaac    4920
catagtacgc gccctgtagc ggcgcattaa gcgcggcggg tgtggtggtt acgcgcagcg    4980
tgaccgctac acttgccagc gccctagcgc ccgctccttt cgctttcttc ccttcctttc    5040
tcgccacgtt cgccggcttt ccccgtcaag ctctaaatcg gggctccct ttagggttcc    5100
gatttagtgc tttacggcac ctcgacccca aaaaacttga tttgggtgat ggttcacgta    5160
gtgggccatc gccctgatag acggtttttc gccctttgac gttggagtcc acgttcttta    5220
atagtggact cttgttccaa actggaacaa cactcaaccc tatctcgggc tattcttttg    5280
atttataagg gattttgccg atttcggcct attggttaaa aaatgagctg atttaacaaa    5340
aatttaacgc gaattttaac aaaatattaa cgtttacaat tttatggtgc actctcagta    5400
caatctgctc tgatgccgca tagttaagcc agccccgaca cccgccaaca cccgctgacg    5460
cgccctgacg ggcttgtctg ctcccggcat ccgcttacag acaagctgtg accgtctccg    5520
ggagctgcat gtgtcagagg ttttcaccgt catcaccgaa acgcgcgaga cgaaagggcc    5580
tcgtgatacg cctattttta taggttaatg tcatgataat aatggtttct tagacgtcag    5640
gtggcacttt tcggggaaat gtgcgcggaa cccctatttg tttatttttc taaatacatt    5700
caaatatgta tccgctcatg agacaataac cctgataaat gcttcaataa tattgaaaaa    5760
ggaagagtat gagtattcaa catttccgtg tcgcccttat tccctttttt gcggcatttt    5820
gccttcctgt ttttgctcac ccagaaacgc tggtgaaagt aaaagatgct gaagatcagt    5880
tgggtgcacg agtgggttac atcgaactgg atctcaacag cggtaagatc cttgagagtt    5940
ttcgccccga agaacgtttt ccaatgatga gcacttttaa agttctgcta tgtggcgcgg    6000
tattatcccg tattgacgcc gggcaagagc aactcggtcg ccgcatacac tattctcaga    6060
atgacttggt tgagtactca ccagtcacag aaaagcatct tacggatggc atgacagtaa    6120
```

```
gagaattatg cagtgctgcc ataaccatga gtgataacac tgcggccaac ttacttctga    6180
caacgatcgg aggaccgaag gagctaaccg cttttttgca caacatgggg gatcatgtaa    6240
ctcgccttga tcgttgggaa ccggagctga atgaagccat accaaacgac gagcgtgaca    6300
ccacgatgcc tgtagcaatg gcaacaacgt tgcgcaaact attaactggc gaactactta    6360
ctctagcttc ccggcaacaa ttaatagact ggatggaggc ggataaagtt gcaggaccac    6420
ttctgcgctc ggcccttccg gctggctggt ttattgctga taaatctgga gccggtgagc    6480
gtgggtctcg cggtatcatt gcagcactgg ggccagatgg taagccctcc cgtatcgtag    6540
ttatctacac gacggggagt caggcaacta tggatgaacg aaatagacag atcgctgaga    6600
taggtgcctc actgattaag cattggtaac tgtcagacca agtttactca tatatacttt    6660
agattgattt aaaacttcat ttttaattta aaaggatcta ggtgaagatc cttttttgata    6720
atctcatgac caaaatccct taacgtgagt tttcgttcca ctgagcgtca gaccccgtag    6780
aaaagatcaa aggatcttct tgagatcctt ttttctgcg cgtaatctgc tgcttgcaaa    6840
caaaaaaacc accgctacca gcggtggttt gtttgccgga tcaagagcta ccaactcttt    6900
ttccgaaggt aactggcttc agcagagcgc agataccaaa tactgtcctt ctagtgtagc    6960
cgtagttagg ccaccacttc aagaactctg tagcaccgcc tacatacctc gctctgctaa    7020
tcctgttacc agtggctgct gccagtggcg ataagtcgtg tcttaccggg ttggactcaa    7080
gacgatagtt accggataag gcgcagcggt cgggctgaac ggggggttcg tgcacacagc    7140
ccagcttgga gcgaacgacc tacaccgaac tgagatacct acagcgtgag ctatgagaaa    7200
gcgccacgct tcccgaaggg agaaaggcgg acaggtatcc ggtaagcggc agggtcggaa    7260
caggagagcg cacgagggag cttccagggg gaaacgcctg gtatctttat agtcctgtcg    7320
ggtttcgcca cctctgactt gagcgtcgat ttttgtgatg ctcgtcaggg gggcggagcc    7380
tatggaaaaa cgccagcaac gcggcctttt tacggttcct ggccttttgc tggccttttg    7440
ctcacatgt                                                           7449
```

<210> SEQ ID NO 122
<211> LENGTH: 7448
<212> TYPE: DNA
<213> ORGANISM: Artificial Sequence
<220> FEATURE:
<223> OTHER INFORMATION: Synthetic

<400> SEQUENCE: 122

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc tgcggccgca cgcgtgaggg cctatttccc atgattcctt     180
catatttgca tatacgatac aaggctgtta gagagataat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccgacgct tccgagtacg     420
gtacgtttta gagctagaaa tagcaagtta aaataaggct agtccgttat caacttgaaa     480
aagtggcacc gagtcggtgc ttttttcta gagacgcttc cgagtacggt acaggaggat     540
ccggtggagg aggttctgga ggcggtggaa gtggtggcgg aggtagcggt ggaggaggtt     600
ctatggtgtc taaggaattc atggtgagca agggcgagga ggataacatg gccatcatca     660
```

```
aggagttcat gcgcttcaag gtgcacatgg agggctccgt gaacggccac gagttcgaga    720
tcgagggcga gggcgagggc cgcccctacg agggcaccca gaccgccaag ctgaaggtga    780
ccaagggtgg ccccctgccc ttcgcctggg acatcctgtc ccctcagttc atgtacggct    840
ccaaggccta cgtgaagcac cccgccgaca tccccgacta cttgaagctg tccttccccg    900
agggcttcaa gtgggagcgc gtgatgaact tcgaggacgg cggcgtggtg accgtgaccc    960
aggactcctc cctgcaggac ggcgagttca tctacaaggt gaagctgcgc ggcaccaact   1020
tccccctcga cggccccgta atgcagaaga agaccatggg ctgggaggcc tcctccgagc   1080
ggatgtaccc cgaggacggc gccctgaagg gcgagatcaa gcagaggctg aagctgaagg   1140
acggcggcca ctacgacgct gaggtcaaga ccacctacaa ggccaagaag cccgtgcagc   1200
tgcccgcgc ctacaacgtc aacatcaagt tggacatcac ctcccacaac gaggactaca   1260
ccatcgtgga acagtacgaa cgcgccgagg ccgccactc caccggcggc atggacgagc   1320
tgtacaagaa gcttggatag ctagctagct agctcgagga cgcttccgag tacggtacag   1380
ggtcgacggc cctgcgtatg gggcagagcg cacatcgccc acagtccccg agaagttggg   1440
gggagggggtc ggcaattgaa cgggtgccta gagaaggtgg cgcggggtaa actgggaaag   1500
tgatgtcgtg tactggctcc gccttttttcc cgagggtggg ggagaaccgt atataagtgc   1560
agtagtcgcc gtgaacgttc tttttcgcaa cgggtttgcc gccagaacac agctgaagct   1620
tcgaggggct cgcatctctc cttcacgcgc ccgccgccct acctgaggcc gccatccacg   1680
ccggttgagt cgcgttctgc cgcctcccgc ctgtggtgcc tcctgaactg cgtccgccgt   1740
ctaggtaagt ttaaagctca ggtcgagacc gggcctttgt ccggcgctcc cttggagcct   1800
acctagactc agccggctct ccacgctttg cctgaccctg cttgctcaac tctacgtctt   1860
tgtttcgttt tctgttctgc gccgttacag atccaagctg tgaccggcgc ctacaccggt   1920
gccaccatgg gccccaagaa aaacggaag gtggccgctg cagggataca tggggttcct   1980
gcagccgata aaaatacag tatcggtctg gacataggca ctaattctgt cggttgggcc   2040
gtgataacag atgaatataa agtaccttcc aaaaaattca aggttctggg aaacacagat   2100
agacacagta taaaaaagaa cctgattggc gctttgctct ttgacagcgg tgagaccgca   2160
gaggcaactc gcttgaagcg gaccgcccgg cgaaggtaca cacgacgcaa gaaccgaatt   2220
tgttacctcc aggaaatatt cagtaacgaa atggccaaag ttgacgattc tttttttccat   2280
cgccttgaag aatccttcct ggtagaagaa gataagaagc atgagagaca cccaatattt   2340
gggaatatag ttgacgaagt cgcatatcac gagaagtacc ctactatata tcaccttcgg   2400
aaaaaactgg tcgattcaac tgacaaagcc gacttgagac tcatatacct ggcccttgct   2460
cacatgatca agttccgggg ccactttctg attgaaggcg acctcaatcc cgacaatagc   2520
gacgtagaca agctgtttat ccaactcgtt caaacctata ccagctcttc gaagagaac   2580
ccaataaatg ctagtggggt cgatgccaaa gctattttga gtgctaggct gtcaaagagt   2640
agaaggttgg agaacctgat cgcacaactg cccggtgaga agaagaacgg cctttttggg   2700
aacttgattg ctctctcccct tggccttacc cctaacttta aatccaactt cgatcttgct   2760
gaggatgcta agctccaact gtccaaggac acctacgacg acgacttgga taaccttctg   2820
gcccagatag gtgatcagta cgcagatctt ttcttggcag ccaagaatct gtctgacgca   2880
atcttgctta gtgacatcct gagggtgaat actgaaataa ctaaggctcc actttccgcc   2940
tctatgatca agcgctacga cgaacaccat caagacctga cccttttgaa ggccttggtt   3000
agacaacaac tgcctgaaaa atacaaggaa atattcttcg accagtctaa gaacggttat   3060
```

```
gccggatata tcgacggggg ggcatcacag gaggaattct ataaatttat aaagcctatc   3120
ttggagaaaa tggacggaac cgaagaactc ctcgtaaagc ttaaccgcga agacctttg   3180 cgaaagcagc ggactttcga taacggctct attcctcacc aaatccacct cggggagctt   3240
cacgcaatat tgcgaaggca ggaggacttc tatccattct tgaaggataa tcgggaaaaa   3300
attgaaaaaa ttcttacatt tcggattcct tactacgtgg gtcctctggc ccgcgggaat   3360
agtcggtttg catggatgac tcggaagtct gaggaaacta tcacaccatg gaattttgaa   3420
gaagtggtag acaaaggggc ttccgctcag tctttcatag agaggatgac taattttgat   3480
aaaaacctgc ctaacgaaaa ggtactcccc aagcattcac ttctttatga atatttcact   3540
gtctacaacg agctgactaa ggttaaatat gtaaccgaag gtatgcggaa gccagcattc   3600
ctgagtggtg agcagaagaa ggcaatcgta gacctttgt tcaaaaccaa ccgaaaggtg   3660
acagtaaaac aactcaagga agactatttt aagaaaatag agtgtttgtc ttatgagacc   3720
gaaatcctca ccgtggagta cgggctcctg cctatcggga aaattgtcga aaagcgcata   3780
gagtgcactg tttactctgt agataacaat ggaaacatat acacacagcc cgtagcacag   3840
tggcacgatc gaggcgagca ggaggtcttt gaatattgcc tggaagacgg cagtcttata   3900
agggcaacaa aggatcacaa atttatgacc gtagatggac aaatgcttcc catcgacgag   3960
atctttgagc gcgagcttga cttgatgaga gtggataacc tgcctaatta ggaattcgat   4020
atcaagctta tcgataatca acctctggat tacaaaattt gtgaaagatt gactggtatt   4080
cttaactatg ttgctccttt tacgctatgt ggatacgctg ctttaatgcc tttgtatcat   4140
gctattgctt cccgtatggc tttcattttc tcctccttgt ataaatcctg gttgctgtct   4200
ctttatgagg agttgtggcc cgttgtcagg caacgtggcg tggtgtgcac tgtgtttgct   4260
gacgcaaccc ccactggttg gggcattgcc accacctgtc agctcctttc cgggactttc   4320
gctttccccc tccctattgc cacggcggaa ctcatcgccg cctgccttgc ccgctgctgg   4380
acaggggctc ggctgttggg cactgacaat tccgtggtgt tgtcggggaa atcatcgtcc   4440
tttccttggc tgctcgcctg tgttgccacc tggattctgc gcgggacgtc cttctgctac   4500
gtcccttcgg ccctcaatcc agcggacctt ccttcccgcg gcctgctgcc ggctctgcgg   4560
cctcttccgc gtcttcgcct tcgccctcag acgagtcgga tctccctttg gccgcctcc   4620 ccgcatcgat accgagcgct aataaaagat ctttatttc attagatctg tgtgttggtt   4680
ttttgtgtca cgtgcggacc gagcggccgc aggaacccct agtgatggag ttggccactc   4740
cctctctgcg cgctcgctcg ctcactgagg ccgggcgacc aaaggtcgcc cgacgcccgg   4800
gctttgcccg gcggcctca gtgagcgagc gagcgcgcag ctgcctgcag gggcgcctga   4860
tgcggtattt tctccttacg catctgtgcg gtatttcaca ccgcatacgt caaagcaacc   4920
atagtacgcg ccctgtagcg gcgcattaag cgcggcgggt gtggtggtta cgcgcagcgt   4980
gaccgctaca cttgccagcg ccctagcgcc cgctccttt gctttcttcc cttcctttct   5040
cgccacgttc gccggctttc cccgtcaagc tctaaatcgg gggctccctt tagggttccg   5100
atttagtgct ttacggcacc tcgaccccaa aaaacttgat ttgggtgatg gttcacgtag   5160
tgggccatcg ccctgataga cggttttttcg ccctttgacg ttggagtcca cgttctttaa   5220
tagtggactc ttgttccaaa ctggaacaac actcaaccct atctcgggct attcttttga   5280
tttataaggg attttgccga tttcggccta ttggttaaaa aatgagctga tttaacaaaa   5340
atttaacgcg aattttaaca aaatattaac gtttacaatt ttatggtgca ctctcagtac   5400
```

| | |
|---|---|
| aatctgctct gatgccgcat agttaagcca gccccgacac ccgccaacac ccgctgacgc | 5460 |
| gccctgacgg gcttgtctgc tcccggcatc cgcttacaga caagctgtga ccgtctccgg | 5520 |
| gagctgcatg tgtcagaggt tttcaccgtc atcaccgaaa cgcgcgagac gaaagggcct | 5580 |
| cgtgatacgc ctatttttat aggttaatgt catgataata atggtttctt agacgtcagg | 5640 |
| tggcactttt cggggaaatg tgcgcggaac ccctatttgt ttatttttct aaatacattc | 5700 |
| aaatatgtat ccgctcatga gacaataacc ctgataaatg cttcaataat attgaaaaag | 5760 |
| gaagagtatg agtattcaac atttccgtgt cgcccttatt cccttttttg cggcattttg | 5820 |
| ccttcctgtt tttgctcacc cagaaacgct ggtgaaagta aaagatgctg aagatcagtt | 5880 |
| gggtgcacga gtgggttaca tcgaactgga tctcaacagc ggtaagatcc ttgagagttt | 5940 |
| tcgccccgaa gaacgttttc caatgatgag cacttttaaa gttctgctat gtggcgcggt | 6000 |
| attatcccgt attgacgccg ggcaagagca actcggtcgc cgcatacact attctcagaa | 6060 |
| tgacttggtt gagtactcac cagtcacaga aaagcatctt acggatggca tgacagtaag | 6120 |
| agaattatgc agtgctgcca taaccatgag tgataacact gcggccaact tacttctgac | 6180 |
| aacgatcgga ggaccgaagg agctaaccgc ttttttgcac aacatggggg atcatgtaac | 6240 |
| tcgccttgat cgttgggaac cggagctgaa tgaagccata ccaaacgacg agcgtgacac | 6300 |
| cacgatgcct gtagcaatgg caacaacgtt gcgcaaacta ttaactggcg aactacttac | 6360 |
| tctagcttcc cggcaacaat taatagactg gatggaggcg gataaagttg caggaccact | 6420 |
| tctgcgctcg gcccttccgg ctggctggtt tattgctgat aaatctggag ccggtgagcg | 6480 |
| tgggtctcgc ggtatcattg cagcactggg gccagatggt aagccctccc gtatcgtagt | 6540 |
| tatctacacg acggggagtc aggcaactat ggatgaacga aatagacaga tcgctgagat | 6600 |
| aggtgcctca ctgattaagc attggtaact gtcagaccaa gtttactcat atatacttta | 6660 |
| gattgattta aaacttcatt tttaatttaa aaggatctag gtgaagatcc ttttgataa | 6720 |
| tctcatgacc aaaatccctt aacgtgagtt ttcgttccac tgagcgtcag accccgtaga | 6780 |
| aaagatcaaa ggatcttctt gagatccttt ttttctgcgc gtaatctgct gcttgcaaac | 6840 |
| aaaaaaacca ccgctaccag cggtggtttg tttgccggat caagagctac caactctttt | 6900 |
| tccgaaggta actggcttca gcagagcgca gataccaaat actgtccttc tagtgtagcc | 6960 |
| gtagttaggc caccacttca agaactctgt agcaccgcct acatacctcg ctctgctaat | 7020 |
| cctgttacca gtggctgctg ccagtggcga taagtcgtgt cttaccgggt tggactcaag | 7080 |
| acgatagtta ccggataagg cgcagcggtc gggctgaacg gggggttcgt gcacacagcc | 7140 |
| cagcttggag cgaacgacct acaccgaact gagataccta cagcgtgagc tatgagaaag | 7200 |
| cgccacgctt cccgaaggga gaaaggcgga caggtatccg gtaagcggca gggtcggaac | 7260 |
| aggagagcgc acgagggagc ttccaggggg aaacgcctgg tatctttata gtcctgtcgg | 7320 |
| gtttcgccac ctctgacttg agcgtcgatt tttgtgatgc tcgtcagggg gcggagccta | 7380 |
| atggaaaaac gccagcaacg cggccttttt acggttcctg gccttttgct ggccttttgc | 7440 |
| tcacatgt | 7448 |

<210> SEQ ID NO 123
<211> LENGTH: 7456
<212> TYPE: DNA
<213> ORGANISM: Artificial Sequence
<220> FEATURE:
<223> OTHER INFORMATION: Synthetic

<400> SEQUENCE: 123

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac taggggttcc tgcggccgca cgcgtgaggg cctatttccc atgattcctt   180
catatttgca tatacgatac aaggctgtta gagagataat tggaattaat ttgactgtaa   240
acacaaagat attagtacaa aatacgtgac gtagaaagta ataatttctt gggtagtttg   300
cagttttaaa attatgtttt aaaatggact atcatatgct taccgtaact tgaaagtatt   360
tcgatttctt ggctttatat atcttgtgga aaggacgaaa caccgacgct tccgagtacg   420
gtacgtttta gagctagaaa tagcaagtta aaataaggct agtccgttat caacttgaaa   480
aagtggcacc gagtcggtgc ttttttttcta gagacgcttc cgagtacggt acaggggatc   540
cggtggagga ggtctggag gcggtggaag tggtggcgga ggtagcggtg gaggaggttc   600
tatggtgtct aaggaattca tggtgagcaa gggcgaggag ctgttcaccg gggtggtgcc   660
catcctggtc gagctggacg gcgacgtaaa cggccacaag ttcagcgtgt ccggcgaggg   720
cgagggcgat gccacctacg gcaagctgac cctgaagttc atctgcacca ccggcaagct   780
gcccgtgccc tggcccaccc tcgtgaccac cctgacctac ggcgtgcagt gcttcagccg   840
ctaccccgac cacatgaagc agcacgactt cttcaagtcc gccatgcccg aaggctacgt   900
ccaggagcgc accatcttct tcaaggacga cggcaactac aagacccgcg ccgaggtgaa   960
gttcgagggc gacaccctgg tgaaccgcat cgagctgaag ggcatcgact tcaaggagga  1020
cggcaacatc ctggggcaca gctggagta caactacaac agccacaacg tctatatcat  1080
ggccgacaag cagaagaacg gcatcaaggt gaacttcaag atccgccaca acatcgagga  1140
cggcagcgtg cagctcgccg accactacca gcagaacacc cccatcggcg acggccccgt  1200
gctgctgccc gacaaccact acctgagcac ccagtccaag ctgagcaaag accccaacga  1260
gaagcgcgat cacatggtcc tgctggagtt cgtgaccgcc gccgggatca ctctcggcat  1320
ggacgagctg tacaagaagc ttggatagct agctagctag ctcgaggacg cttccgagta  1380
cggtacaggg tcgacggccc tgcgtatggg gcagagcgca catcgcccac agtccccgag  1440
aagttggggg gaggggtcgg caattgaacg ggtgcctaga aaggtggcg cggggtaaac  1500 tgggaaagtg atgtcgtgta ctggctccgc ctttttcccg agggtggggg agaaccgtat  1560
ataagtgcag tagtcgccgt gaacgttctt tttcgcaacg ggtttgccgc cagaacacag  1620
ctgaagcttc gaggggctcg catctctcct tcacgcgccc gccgccctac ctgaggccgc  1680
catccacgcc ggttgagtcg cgttctgccg cctcccgcct gtggtgcctc ctgaactgcg  1740
tccgccgtct aggtaagttt aaagctcagg tcgagaccgg gcctttgtcc ggcgctccct  1800
tggagcctac ctagactcag ccggctctcc acgctttgcc tgaccctgct tgctcaactc  1860
tacgtctttg tttcgttttc tgttctgcgc cgttacagat ccaagctgtg accggcgcct  1920
acaccggtgc caccatgggc cccaagaaaa acggaaggt ggccgctgca gggatacatg  1980
gggttcctgc agccgataaa aaatacagta tcggtctgga cataggcact aattctgtcg  2040
gttgggccgt gataacagat gaatataaag taccttccaa aaaattcaag gttctgggaa  2100
acacagatag acacagtata aaaaagaacc tgattggcgc tttgctcttt gacagcggtg  2160
agaccgcaga ggcaactcgc ttgaagcgga ccgcccggcg aaggtacaca cgacgcaaga  2220
accgaatttg ttacctccag gaaatattca gtaacgaaat ggccaaagtt gacgattctt  2280
ttttccatcg ccttgaagaa tccttcctgg tagaagaaga taagaagcat gagagacacc  2340
```

-continued

```
caatatttgg gaatatagtt gacgaagtcg catatcacga gaagtaccct actatatatc    2400
accttcggaa aaaactggtc gattcaactg acaaagccga cttgagactc atatacctgg    2460
cccttgctca catgatcaag ttccggggcc actttctgat tgaaggcgac ctcaatcccg    2520
acaatagcga cgtagacaag ctgtttatcc aactcgttca aacctataac cagctcttcg    2580
aagagaaccc aataaatgct agtggggtcg atgccaaagc tattttgagt gctaggctgt    2640
caaagagtag aaggttggag aacctgatcg cacaactgcc cggtgagaag aagaacggcc    2700
tttttgggaa cttgattgct ctctcccttg ccttacccc taactttaaa tccaacttcg     2760
atcttgctga ggatgctaag ctccaactgt ccaaggacac ctacgacgac gacttggata    2820
accttctggc ccagataggt gatcagtacg cagatctttt cttggcagcc aagaatctgt    2880
ctgacgcaat cttgcttagt gacatcctga gggtgaatac tgaaataact aaggctccac    2940
tttccgcctc tatgatcaag cgctacgacg aacaccatca agacctgacc cttttgaagg    3000
ccttggttag acaacaactg cctgaaaaat acaggaaat attcttcgac cagtctaaga    3060
acggttatgc cggatatatc gacggggggg catcacagga ggaattctat aaatttataa    3120
agcctatctt ggagaaaatg gacggaaccg aagaactcct cgtaaagctt aaccgcgaag    3180
accttttgcg aaagcagcgg actttcgata acggctctat tcctcaccaa atccacctcg    3240
gggagcttca cgcaatattg cgaaggcagg aggacttcta tccattcttg aaggataatc    3300
gggaaaaaat tgaaaaaatt cttacatttc ggattcctta ctacgtgggt cctctggccc    3360
gcgggaatag tcggtttgca tggatgactc ggaagtctga ggaaactatc acaccatgga    3420
attttgaaga agtggtagac aaaggggctt ccgctcagtc tttcatagag aggatgacta    3480
attttgataa aaacctgcct aacgaaaagg tactccccaa gcattcactt ctttatgaat    3540
atttcactgt ctacaacgag ctgactaagg ttaaatatgt aaccgaaggt atgcggaagc    3600
cagcattcct gagtggtgag cagaagaagg caatcgtaga ccttttgttc aaaaccaacc    3660
gaaaggtgac agtaaaacaa ctcaaggaag actattttaa gaaaatagag tgttgtctt    3720 atgagaccga aatcctcacc gtggagtacg ggctcctgcc tatcgggaaa attgtcgaaa    3780
agcgcataga gtgcactgtt tactctgtag ataacaatgg aaacatatac acacagcccg    3840
tagcacagtg gcacgatcga ggcgagcagg aggtctttga atattgcctg gaagacggca    3900
gtcttataag ggcaacaaag gatcacaaat ttatgaccgt agatggacaa atgcttccca    3960
tcgacgagat ctttgagcgc gagcttgact tgatgagagt ggataacctg cctaattagg    4020
aattcgatat caagcttatc gataatcaac ctctggatta caaaatttgt gaaagattga    4080
ctggtattct taactatgtt gctccttta cgctatgtgg atacgctgct ttaatgcctt    4140
tgtatcatgc tattgcttcc cgtatggctt tcattttctc ctccttgtat aaatcctggt    4200
tgctgtctct ttatgaggag ttgtggcccg ttgtcaggca acgtggcgtg gtgtgcactg    4260
tgtttgctga cgcaacccc actggttggg gcattgccac cacctgtcag ctcctttccg    4320
ggactttcgc tttcccctc cctattgcca cggcggaact catcgccgcc tgccttgccc    4380
gctgctggac aggggctcgg ctgttgggca ctgacaattc cgtggtgttg tcggggaaat    4440
catcgtcctt tccttggctg ctcgcctgtg ttgccacctg gattctgcgc gggacgtcct    4500
tctgctacgt cccttcggcc ctcaatccag cggaccttcc ttcccgcggc ctgctgccgg    4560
ctctgcggcc tcttccgcgt cttcgccttc gccctcagac gagtcggatc tccctttggg    4620
ccgcctcccc gcatcgatac cgagcgctaa taaaagatct ttattttcat tagatctgtg    4680
tgttggtttt ttgtgtcacg tgcggaccga gcggccgcag gaacccctag tgatggagtt    4740
```

```
ggccactccc tctctgcgcg ctcgctcgct cactgaggcc gggcgaccaa aggtcgcccg    4800
acgcccgggc tttgcccggg cggcctcagt gagcgagcga gcgcgcagct gcctgcaggg    4860
gcgcctgatg cggtattttc tccttacgca tctgtgcggt atttcacacc gcatacgtca    4920
aagcaaccat agtacgcgcc ctgtagcggc gcattaagcg cggcgggtgt ggtggttacg    4980
cgcagcgtga ccgctacact tgccagcgcc ctagcgcccg ctcctttcgc tttcttccct    5040
tcctttctcg ccacgttcgc cggctttccc cgtcaagctc taaatcgggg ctccctttta    5100
gggttccgat ttagtgcttt acggcacctc gaccccaaaa aacttgattt gggtgatggt    5160
tcacgtagtg ggccatcgcc ctgatagacg ttttttcgcc ctttgacgtt ggagtccacg    5220
ttctttaata gtggactctt gttccaaact ggaacaacac tcaaccctat ctcgggctat    5280
tcttttgatt tataagggat tttgccgatt tcggcctatt ggttaaaaaa tgagctgatt    5340
taacaaaaat ttaacgcgaa ttttaacaaa atattaacgt ttacaatttt atggtgcact    5400
ctcagtacaa tctgctctga tgccgcatag ttaagccagc cccgacaccc gccaacaccc    5460
gctgacgcgc cctgacgggc ttgtctgctc ccggcatccg cttacagaca agctgtgacc    5520
gtctccggga gctgcatgtg tcagaggttt tcaccgtcat caccgaaacg cgcgagacga    5580
aagggcctcg tgatacgcct atttttatag gttaatgtca tgataataat ggtttcttag    5640
acgtcaggtg gcacttttcg gggaaatgtg cgcggaaccc ctatttgttt attttttctaa    5700
atacattcaa atatgtatcc gctcatgaga caataaccct gataaatgct tcaataatat    5760
tgaaaaagga agagtatgag tattcaacat ttccgtgtcg cccttattcc cttttttgcg    5820
gcatttttgcc ttcctgtttt tgctcaccca gaaacgctgg tgaaagtaaa agatgctgaa    5880
gatcagttgg gtgcacgagt gggttacatc gaactggatc tcaacagcgg taagatcctt    5940
gagagttttc gccccgaaga acgttttcca atgatgagca cttttaaagt tctgctatgt    6000
ggcgcggtat tatcccgtat tgacgccggg caagagcaac tcggtcgccg catacactat    6060
tctcagaatg acttggttga gtactcacca gtcacagaaa agcatcttac ggatggcatg    6120
acagtaagag aattatgcag tgctgccata accatgagtg ataacactgc ggccaactta    6180
cttctgacaa cgatcggagg accgaaggag ctaaccgctt ttttgcacaa catgggggat    6240
catgtaactc gccttgatcg ttgggaaccg gagctgaatg aagccatacc aaacgacgag    6300
cgtgacacca cgatgcctgt agcaatggca acaacgttgc gcaaactatt aactggcgaa    6360
ctacttactc tagcttcccg gcaacaatta atagactgga tggaggcgga taaagttgca    6420
ggaccacttc tgcgctcggc ccttccggct ggctggttta ttgctgataa atctggagcc    6480
ggtgagcgtg ggtctcgcgg tatcattgca gcactggggc cagatggtaa gccctcccgt    6540
atcgtagtta tctacacgac ggggagtcag gcaactatgg atgaacgaaa tagacagatc    6600
gctgagatag gtgcctcact gattaagcat tggtaactgt cagaccaagt ttactcatat    6660
atactttaga ttgatttaaa acttcatttt taatttaaaa ggatctaggt gaagatcctt    6720
tttgataatc tcatgaccaa aatcccttaa cgtgagtttt cgttccactg agcgtcagac    6780
cccgtagaaa agatcaaagg atcttcttga gatccttttt ttctgcgcgt aatctgctgc    6840
ttgcaaacaa aaaaaccacc gctaccagcg gtggtttgtt tgccggatca agagctacca    6900
actctttttc cgaaggtaac tggcttcagc agagcgcaga taccaaatac tgtccttcta    6960
gtgtagccgt agttaggcca ccacttcaag aactctgtag caccgcctac atacctcgct    7020
ctgctaatcc tgttaccagt ggctgctgcc agtggcgata agtcgtgtct taccgggttg    7080
```

```
gactcaagac gatagttacc ggataaggcg cagcggtcgg gctgaacggg gggttcgtgc   7140
acacagccca gcttggagcg aacgacctac accgaactga gatacctaca gcgtgagcta   7200
tgagaaagcg ccacgcttcc cgaagggaga aaggcggaca ggtatccggt aagcggcagg   7260
gtcggaacag gagagcgcac gagggagctt ccaggggaa acgcctggta tctttatagt    7320
cctgtcgggt ttcgccacct ctgacttgag cgtcgatttt tgtgatgctc gtcagggggg   7380
cggagcctat ggaaaaacgc cagcaacgcg gcctttttac ggttcctggc cttttgctgg   7440
ccttttgctc acatgt                                                   7456

<210> SEQ ID NO 124
<211> LENGTH: 7458
<212> TYPE: DNA
<213> ORGANISM: Artificial Sequence
<220> FEATURE:
<223> OTHER INFORMATION: Synthetic

<400> SEQUENCE: 124
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca   120
actccatcac taggggttcc tgcggccgca cgcgtgaggg cctatttccc atgattcctt   180
catatttgca tatacgatac aaggctgtta gagagataat tggaattaat ttgactgtaa   240
acacaaagat attagtacaa aatacgtgac gtagaaagta ataatttctt gggtagtttg   300
cagttttaaa attatgtttt aaaatggact atcatatgct taccgtaact tgaaagtatt   360
tcgatttctt ggctttatat atcttgtgga aaggacgaaa caccgacgct tccgagtacg   420
gtacgtttta gagctagaaa tagcaagtta aaataaggct agtccgttat caacttgaaa   480
aagtggcacc gagtcggtgc ttttttcta gagacgcttc cgagtacggt acaggggatc     540
cagggtggag gaggttctgg aggcggtgga agtggtggcg gaggtagcgg tggaggaggt   600
tctatggtgt ctaaggaatt catggtgagc aagggcgagg agctgttcac cggggtggtg   660
cccatcctgg tcgagctgga cggcgacgta aacggccaca agttcagcgt gtccggcgag   720
ggcgagggca tgccacccta cggcaagctg accctgaagt tcatctgcac caccggcaag   780
ctgcccgtgc cctggcccac cctcgtgacc accctgacct acggcgtgca gtgcttcagc   840
cgctaccccg accacatgaa gcagcacgac ttcttcaagt ccgccatgcc cgaaggctac   900
gtccaggagc gcaccatctt cttcaaggac gacggcaact acaagacccg cgccgaggtg   960
aagttcgagg gcgacaccct ggtgaaccgc atcgagctga agggcatcga cttcaaggag  1020
gacggcaaca tcctggggca agctggagta caactacaa cagccacaa cgtctatatc    1080 atggccgaca gcagaagaa cggcatcaag gtgaacttca agatccgcca caacatcgag   1140
gacggcagcg tgcagctcgc cgaccactac cagcagaaca cccccatcgg cgacggcccc  1200
gtgctgctgc ccgacaacca ctacctgagc acccagtcca gctgagcaa agaccccaac    1260 gagaagcgcg atcacatggt cctgctggag ttcgtgaccg ccgccgggat cactctcggc   1320
atggacgagc tgtacaagaa gcttggatag ctagctagct agctcgagga cgcttccgag   1380
tacggtacag ggtcgacggc cctgcgtatg gggcagagcg cacatcgccc acagtccccg   1440
agaagttggg gggaggggtc ggcaattgaa cgggtgccta gagaaggtgg cgcggggtaa   1500
actgggaaag tgatgtcgtg tactggctcc gcctttttcc cgagggtggg ggagaaccgt   1560
atataagtgc agtagtcgcc gtgaacgttc ttttcgcaa cgggtttgcc gccagaacac   1620
agctgaagct cgagggggct cgcatctctc cttcacgcgc ccgccgccct acctgaggcc  1680
```

```
gccatccacg ccggttgagt cgcgttctgc cgcctcccgc ctgtggtgcc tcctgaactg    1740
cgtccgccgt ctaggtaagt ttaaagctca ggtcgagacc gggcctttgt ccggcgctcc    1800
cttggagcct acctagactc agccggctct ccacgctttg cctgaccctg cttgctcaac    1860
tctacgtctt tgtttcgttt tctgttctgc gccgttacag atccaagctg tgaccggcgc    1920
ctacaccggt gccaccatgg gccccaagaa aaacggaag gtggccgctg cagggataca     1980
tggggttcct gcagccgata aaaatacag tatcggtctg dacataggca ctaattctgt     2040
cggttgggcc gtgataacag atgaatataa agtaccttcc aaaaaattca aggttctggg    2100
aaacacagat agacacagta taaaaagaa cctgattggc gctttgctct ttgacagcgg     2160
tgagaccgca gaggcaactc gcttgaagcg gaccgcccgg cgaaggtaca cacgacgcaa    2220
gaaccgaatt tgttacctcc aggaaatatt cagtaacgaa atggccaaag ttgacgattc    2280
ttttttccat cgccttgaag aatccttcct ggtagaagaa gataagaagc atgagagaca    2340 cccaatatt gggaatatag ttgacgaagt cgcatatcac gagaagtacc ctactatata     2400
tcaccttcgg aaaaaactgg tcgattcaac tgacaaagcc gacttgagac tcatatacct    2460
ggcccttgct cacatgatca agttccgggg ccacttctg attgaaggcg acctcaatcc     2520
cgacaatagc gacgtagaca agctgtttat ccaactcgtt caaacctata accagctctt    2580
cgaagagaac ccaataaatg ctagtgggt cgatgccaaa gctattttga gtgctaggct     2640
gtcaaagagt agaaggttgg agaacctgat cgcacaactg cccggtgaga agaagaacgg    2700
cctttttggg aacttgattg ctctctccct tggccttacc cctaacttta aatccaactt    2760
cgatcttgct gaggatgcta agctccaact gtccaaggac acctacgacg acgacttgga    2820
taaccttctg gcccagatag gtgatcagta cgcagatctt ttcttggcag ccaagaatct    2880
gtctgacgca atcttgctta gtgacatcct gagggtgaat actgaaataa ctaaggctcc    2940
actttccgcc tctatgatca agcgctacga cgaacaccat caagacctga ccctttгaa     3000 ggccttggtt agacaacaac tgcctgaaaa atacaaggaa atattcttcg accagtctaa    3060
gaacggttat gccggatata tcgacggggg ggcatcacag gaggaattct ataaatttat    3120
aaagcctatc ttggagaaaa tggacggaac cgaagaactc ctcgtaaagc ttaaccgcga    3180
agaccttttg cgaaagcagc ggacttcga taacggctct attcctcacc aaatccacct    3240
cggggagctt cacgcaatat tgcgaaggca ggaggactc tatccattct tgaaggataa     3300
tcgggaaaaa attgaaaaaa ttcttacatt tcggattcct tactacgtgg gtcctctggc    3360
ccgcgggaat agtcggtttg catggatgac tcggaagtct gaggaaacta tcacaccatg    3420 gaatttgaa gaagtggtag acaaaggggc ttccgctcag tctttcatag agaggatgac     3480
taattttgat aaaaacctgc ctaacgaaaa ggtactcccc aagcattcac ttctttatga    3540
atatttcact gtctacaacg agctgactaa ggttaaatat gtaaccgaag gtatgcggaa    3600
gccagcattc ctgagtggtg agcagaagaa ggcaatcgta gacctttttgt tcaaaaccaa    3660 ccgaaaggtg acagtaaaac aactcaagga agactatttt aagaaaatag agtgtttgtc    3720
ttatgagacc gaaatcctca ccgtggagta cgggctcctg cctatcggga aaattgtcga    3780
aaagcgcata gagtgcactg tttactctgt agataacaat ggaaacatat acacacagcc    3840
cgtagcacag tggcacgatc gaggcgagca ggaggtcttt gaatattgcc tggaagacgg    3900
cagtcttata agggcaacaa aggatcacaa atttatgacc gtagatggac aaatgcttcc    3960
catcgacgag atctttgagc gcgagcttga cttgatgaga gtggataacc tgcctaatta    4020
```

```
ggaattcgat atcaagctta tcgataatca acctctggat tacaaaattt gtgaaagatt    4080
gactggtatt cttaactatg ttgctccttt tacgctatgt ggatacgctg ctttaatgcc    4140
tttgtatcat gctattgctt cccgtatggc tttcattttc tcctccttgt ataaatcctg    4200
gttgctgtct ctttatgagg agttgtggcc cgttgtcagg caacgtggcg tggtgtgcac    4260
tgtgtttgct gacgcaaccc ccactggttg gggcattgcc accacctgtc agctcctttc    4320
cgggactttc gctttccccc tccctattgc cacggcggaa ctcatcgccg cctgccttgc    4380
ccgctgctgg acagggcctc ggctgttggg cactgacaat tccgtggtgt tgtcggggaa    4440
atcatcgtcc tttccttggc tgctcgcctg tgttgccacc tggattctgc gcggacgtc     4500
cttctgctac gtcccttcgg ccctcaatcc agcggacctt ccttcccgcg gcctgctgcc    4560
ggctctgcgg cctcttccgc gtcttcgcct tcgccctcag acgagtcgga tctccctttg    4620
ggccgcctcc ccgcatcgat accgagcgct aataaaagat ctttattttc attagatctg    4680
tgtgttggtt ttttgtgtca cgtgcggacc gagcggccgc aggaaccccct agtgatggag   4740
ttggccactc cctctctgcg cgctcgctcg ctcactgagg ccgggcgacc aaaggtcgcc    4800
cgacgcccgg gctttgcccg gcggcctca gtgagcgagc gagcgcgcag ctgcctgcag     4860
gggcgcctga tgcggtattt tctccttacg catctgtgcg gtatttcaca ccgcatacgt    4920
caaagcaacc atagtacgcg ccctgtagcg gcgcattaag gcggcgggt gtggtggtta     4980
cgcgcagcgt gaccgctaca cttgccagcg ccctagcgcc cgctcctttc gctttcttcc    5040
cttcctttct cgccacgttc gccggctttc cccgtcaagc tctaaatcgg gggctccctt    5100
tagggttccg atttagtgct ttacggcacc tcgaccccaa aaaacttgat ttgggtgatg    5160
gttcacgtag tgggccatcg ccctgataga cggtttttcg ccctttgacg ttggagtcca    5220
cgttctttaa tagtggactc ttgttccaaa ctggaacaac actcaaccct atctcgggct    5280
attcttttga tttataaggg attttgccga tttcggccta ttggttaaaa aatgagctga    5340
tttaacaaaa atttaacgcg aattttaaca aaatattaac gtttacaatt ttatggtgca    5400
ctctcagtac aatctgctct gatgccgcat agttaagcca gccccgacac ccgccaacac    5460
ccgctgacgc gccctgacgg gcttgtctgc tcccggcatc cgcttacaga caagctgtga    5520
ccgtctccgg gagctgcatg tgtcagaggt tttcaccgtc atcaccgaaa cgcgcgagac    5580
gaaagggcct cgtgatacgc ctatttttat aggttaatgt catgataata atggtttctt    5640
agacgtcagg tggcactttt cggggaaatg tgcgcggaac ccctatttgt ttatttttct    5700
aaatacattc aaatatgtat ccgctcatga caataaacc ctgataaatg cttcaataat     5760
attgaaaaag gaagagtatg agtattcaac atttccgtgt cgcccttatt ccctttttg     5820
cggcattttg ccttcctgtt tttgctcacc cagaaacgct ggtgaaagta aaagatgctg    5880
aagatcagtt gggtgcacga gtgggttaca tcgaactgga tctcaacagc ggtaagatcc    5940
ttgagagttt tcgccccgaa gaacgttttc caatgatgag cacttttaaa gttctgctat    6000
gtggcgcggt attatcccgt attgacgccg ggcaagagca actcggtcgc cgcatacact    6060
attctcagaa tgacttggtt gagtactcac cagtcacaga aaagcatctt acggatggca    6120
tgacagtaag agaattatgc agtgctgcca taaccatgag tgataacact gcggccaact    6180
tacttctgac aacgatcgga ggaccgaagg agctaaccgc ttttttgcac aacatggggg    6240
atcatgtaac tcgccttgat cgttgggaac cggagctgaa tgaagccata ccaaacgacg    6300
agcgtgacac cacgatgcct gtagcaatgg caacaacgtt gcgcaaacta ttaactggcg    6360
aactacttac tctagcttcc cggcaacaat taatagactg gatggaggcg gataaagttg    6420
```

```
caggaccact tctgcgctcg gcccttccgg ctggctggtt tattgctgat aaatctggag    6480
ccggtgagcg tgggtctcgc ggtatcattg cagcactggg gccagatggt aagccctccc    6540
gtatcgtagt tatctacacg acggggagtc aggcaactat ggatgaacga aatagacaga    6600
tcgctgagat aggtgcctca ctgattaagc attggtaact gtcagaccaa gtttactcat    6660
atatacttta gattgattta aaacttcatt tttaatttaa aaggatctag gtgaagatcc    6720
tttttgataa tctcatgacc aaaatccctt aacgtgagtt ttcgttccac tgagcgtcag    6780
accccgtaga aaagatcaaa ggatcttctt gagatccttt ttttctgcgc gtaatctgct    6840
gcttgcaaac aaaaaaacca ccgctaccag cggtggtttg tttgccggat caagagctac    6900
caactctttt tccgaaggta actggcttca gcagagcgca gataccaaat actgtccttc    6960
tagtgtagcc gtagttaggc caccacttca agaactctgt agcaccgcct acatacctcg    7020
ctctgctaat cctgttacca gtggctgctg ccagtggcga taagtcgtgt cttaccgggt    7080
tggactcaag acgatagtta ccggataagg cgcagcggtc gggctgaacg ggggggttcgt    7140 gcacacagcc cagcttggag cgaacgacct acaccgaact gagatacccta cagcgtgagc    7200 tatgagaaag cgccacgctt cccgaaggga gaaaggcgga caggtatccg gtaagcggca    7260
gggtcggaac aggagagcgc acgagggagc ttccaggggg aaacgcctgg tatctttata    7320
gtcctgtcgg gtttcgccac ctctgacttg agcgtcgatt tttgtgatgc tcgtcagggg    7380
ggcggagcct atggaaaaac gccagcaacg cggccttttt acggttcctg gccttttgct    7440
ggccttttgc tcacatgt                                                  7458

<210> SEQ ID NO 125
<211> LENGTH: 7457
<212> TYPE: DNA
<213> ORGANISM: Artificial Sequence
<220> FEATURE:
<223> OTHER INFORMATION: Synthetic

<400> SEQUENCE: 125
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat ggaattaat ttgactgtaa      240 acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aggacgaaa caccgacgct tccgagtacg      420
gtacgtttta gagctagaaa tagcaagtta aaataaggct agtccgttat caacttgaaa     480
aagtggcacc gagtcggtgc tttttttcta gagacgcttc cgagtacggt acaggaggat     540
ccggtggagg aggttctgga ggcggtggaa gtggtggcgg aggtagcggt ggaggaggtt     600
ctatggtgtc taaggaattc atggtgagca agggcgagga gctgttcacc ggggtggtgc     660
ccatcctggt cgagctggac ggcgacgtaa acggccacaa gttcagcgtg tccggcgagg     720
gcgagggcga tgccacctac ggcaagctga ccctgaagtt catctgcacc accggcaagc     780
tgcccgtgcc ctggcccacc ctcgtgacca ccctgaccta cggcgtgcag tgcttcagcc     840
gctaccccga ccacatgaag cagcacgact tcttcaagtc cgccatgccc gaaggctacg     900
tccaggagcg caccatcttc ttcaaggacg acggcaacta caagacccgc gccgaggtga     960
```

-continued

```
agttcgaggg cgacaccctg gtgaaccgca tcgagctgaa gggcatcgac ttcaaggagg    1020
acggcaacat cctggggcac aagctggagt acaactacaa cagccacaac gtctatatca    1080
tggccgacaa gcagaagaac ggcatcaagg tgaacttcaa gatccgccac aacatcgagg    1140
acggcagcgt gcagctcgcc gaccactacc agcagaacac ccccatcggc gacggccccg    1200
tgctgctgcc cgacaaccac tacctgagca cccagtccaa gctgagcaaa gaccccaacg    1260
agaagcgcga tcacatggtc ctgctggagt tcgtgaccgc cgccgggatc actctcggca    1320
tggacgagct gtacaagaag cttggatagc tagctagcta gctcgaggac gcttccgagt    1380
acggtacagg gtcgacggcc ctgcgtatgg ggcagagcgc acatcgccca cagtccccga    1440
gaagttgggg ggaggggtcg gcaattgaac gggtgcctag agaaggtggc gcggggtaaa    1500 ctggaaagt gatgtcgtgt actggctccg ccttttcccc gagggtgggg gagaaccgta    1560
tataagtgca gtagtcgccg tgaacgttct ttttcgcaac gggtttgccg ccagaacaca    1620
gctgaagctt cgaggggctc gcatctctcc ttcacgcgcc cgccgcccta cctgaggccg    1680
ccatccacgc cggttgagtc gcgttctgcc gcctcccgcc tgtggtgcct cctgaactgc    1740
gtccgccgtc taggtaagtt taaagctcag gtcgagaccg ggcctttgtc cggcgctccc    1800
ttggagccta cctagactca gccggctctc cacgctttgc ctgaccctgc ttgctcaact    1860
ctacgtcttt gtttcgtttt ctgttctgcg ccgttacaga tccaagctgt gaccggcgcc    1920
tacaccggtg ccaccatggg ccccaagaaa aaacggaagg tggccgctgc agggatacat    1980
ggggttcctg cagccgataa aaaatacagt atcggtctgg acataggcac taattctgtc    2040
ggttgggccg tgataacaga tgaatataaa gtaccttcca aaaaattcaa ggttctggga    2100
aacacagata gacacagtat aaaaagaac ctgattggcg ctttgctctt tgacagcggt    2160
gagaccgcag aggcaactcg cttgaagcgg accgcccggc gaaggtacac acgacgcaag    2220
aaccgaattt gttacctcca ggaaatattc agtaacgaaa tggccaaagt tgacgattct    2280
tttttccatc gccttgaaga atccttcctg gtagaagaag ataagaagca tgagagacac    2340
ccaatatttg ggaatatagt tgacgaagtc gcatatcacg agaagtaccc tactatatat    2400
caccttcgga aaaaactggt cgattcaact gacaaagccg acttgagact catatacctg    2460
gcccttgctc acatgatcaa gttccggggc cactttctga ttgaaggcga cctcaatccc    2520
gacaatagcg acgtagacaa gctgtttatc caactcgttc aaacctataa ccagctcttc    2580
gaagagaacc caataaatgc tagtggggtc gatgccaaag ctattttgag tgctaggctg    2640
tcaaagagta aaggttgga gaacctgatc gcacaactgc ccggtgagaa gaagaacggc    2700 cttttttggga acttgattgc tctctcccctt ggccttaccc ctaactttaa atccaacttc    2760
gatcttgctg aggatgctaa gctccaactg tccaaggaca cctacgacga cgacttggat    2820
aaccttctgg cccagatagg tgatcagtac gcagatcttt tcttggcagc caagaatctg    2880
tctgacgcaa tcttgcttag tgacatcctg agggtgaata ctgaaataac taaggctcca    2940 cttttccgcct ctatgatcaa gcgctacgac gaacaccatc aagacctgac ccttttgaag    3000
gccttggtta gacaacaact gcctgaaaaa tacaaggaaa tattcttcga ccagtctaag    3060
aacggttatg ccggatatat cgacgggggg gcatcacagg aggaattcta taaatttata    3120
aagcctatct tggagaaaat ggacggaacc gaagaactcc tcgtaaagct taaccgcgaa    3180 gacctttgc gaaagcagcg gactttcgat aacggctcta ttcctcacca aatccacctc    3240
ggggagcttc acgcaatatt gcgaaggcag gaggacttct atccattctt gaaggataat    3300
cgggaaaaaa ttgaaaaaat tcttacattt cggattcctt actacgtggg tcctctggcc    3360
```

-continued

```
cgcgggaata gtcggtttgc atggatgact cggaagtctg aggaaactat cacaccatgg    3420
aattttgaag aagtggtaga caaaggggct tccgctcagt ctttcataga gaggatgact    3480
aattttgata aaaacctgcc taacgaaaag gtactcccca agcattcact tctttatgaa    3540
tatttcactg tctacaacga gctgactaag gttaaatatg taaccgaagg tatgcggaag    3600
ccagcattcc tgagtggtga gcagaagaag gcaatcgtag accttttgtt caaaaccaac    3660
cgaaaggtga cagtaaaaca actcaaggaa gactattta agaaaataga gtgtttgtct    3720
tatgagaccg aaatcctcac cgtggagtac gggctcctgc ctatcgggaa aattgtcgaa    3780
aagcgcatag agtgcactgt ttactctgta gataacaatg aaacatata cacacagccc    3840
gtagcacagt ggcacgatcg aggcgagcag gaggtctttg aatattgcct ggaagacggc    3900
agtcttataa gggcaacaaa ggatcacaaa tttatgaccg tagatggaca aatgcttccc    3960
atcgacgaga tctttgagcg cgagcttgac ttgatgagag tggataacct gcctaattag    4020
gaattcgata tcaagcttat cgataatcaa cctctggatt acaaaatttg tgaaagattg    4080
actggtattc ttaactatgt tgctcctttt acgctatgtg gatacgctgc tttaatgcct    4140
ttgtatcatg ctattgcttc ccgtatggct ttcattttct cctccttgta taaatcctgg    4200
ttgctgtctc tttatgagga gttgtggccc gttgtcaggc aacgtggcgt ggtgtgcact    4260
gtgtttgctg acgcaacccc cactggttgg ggcattgcca ccacctgtca gctcctttcc    4320
gggactttcg ctttccccct ccctattgcc acggcggaac tcatcgccgc ctgccttgcc    4380
cgctgctgga caggggctcg gctgttgggc actgacaatt ccgtggtgtt gtcgggaaa    4440
tcatcgtcct tccttggct gctcgcctgt gttgccacct ggattctgcg cgggacgtcc    4500
ttctgctacg tcccttcggc cctcaatcca cggaccttc cttcccgcgg cctgctgccg    4560
gctctgcggc ctcttccgcg tcttcgcctt cgccctcaga cgagtcggat ctccctttgg    4620
gccgcctccc cgcatcgata ccgagcgcta ataaagatc tttattttca ttagatctgt    4680
gtgttggttt tttgtgtcac gtgcggaccg agcggccgca ggaaccccta gtgatggagt    4740
tggccactcc ctctctgcgc gctcgctcgc tcactgaggc cgggcgacca aaggtcgccc    4800
gacgcccggg ctttgcccgg gcggcctcag tgagcgagcg agcgcgcagc tgcctgcagg    4860
ggcgcctgat gcggtatttt ctccttacgc atctgtgcgg tatttcacac cgcatacgtc    4920
aaagcaacca tagtacgcgc cctgtagcgg cgcattaagc gcggcgggtg tggtggttac    4980
gcgcagcgtg accgctacac ttgccagcgc cctagcgccc gctcctttcg ctttcttccc    5040
ttcctttctc gccacgttcg ccggctttcc ccgtcaagct ctaaatcggg ggctcccttt    5100
agggttccga tttagtgctt acggcacct cgaccccaaa aaacttgatt tgggtgatgg    5160
ttcacgtagt gggccatcgc cctgatagac ggттттттcgc ccттттgacgт tggagtccac    5220
gttctttaat agtggactct tgttccaaac tggaacaaca ctcaacccta tctcgggcta    5280
ttcttttgat ttataaggga ttttgccgat ttcggcctat tggttaaaaa atgagctgat    5340
ttaacaaaaa tttaacgcga ттттттaacaa aatattaacg tttacaattt tatggtgcac    5400
tctcagtaca atctgctctg atgccgcata gttaagccag ccccgacacc cgccaacacc    5460
cgctgacgcg ccctgacggg cttgtctgct cccggcatcc gcttacagac aagctgtgac    5520
cgtctccggg agctgcatgt gtcagaggtt tcaccgtca tcaccgaaac gcgcgagacg    5580
aaagggcctc gtgatacgcc tatttttata ggttaatgtc atgataataa tggtttctta    5640
gacgtcaggt ggcacttttc ggggaaatgt gcgcggaacc cctatttgtt tatttttcta    5700
```

-continued

| | |
|---|---|
| aatacattca aatatgtatc cgctcatgag acaataaccc tgataaatgc ttcaataata | 5760 |
| ttgaaaaagg aagagtatga gtattcaaca tttccgtgtc gcccttattc ccttttttgc | 5820 |
| ggcattttgc cttcctgttt ttgctcaccc agaaacgctg gtgaaagtaa aagatgctga | 5880 |
| agatcagttg ggtgcacgag tgggttacat cgaactggat ctcaacagcg gtaagatcct | 5940 |
| tgagagtttt cgccccgaag aacgttttcc aatgatgagc acttttaaag ttctgctatg | 6000 |
| tggcgcggta ttatcccgta ttgacgccgg gcaagagcaa ctcggtcgcc gcatacacta | 6060 |
| ttctcagaat gacttggttg agtactcacc agtcacagaa aagcatctta cggatggcat | 6120 |
| gacagtaaga gaattatgca gtgctgccat aaccatgagt gataacactg cggccaactt | 6180 |
| acttctgaca acgatcggag gaccgaagga gctaaccgct tttttgcaca acatggggga | 6240 |
| tcatgtaact cgccttgatc gttgggaacc ggagctgaat gaagccatac caaacgacga | 6300 |
| gcgtgacacc acgatgcctg tagcaatggc aacaacgttg cgcaaactat taactggcga | 6360 |
| actacttact ctagcttccc ggcaacaatt aatagactgg atggaggcgg ataaagttgc | 6420 |
| aggaccactt ctgcgctcgg cccttccggc tggctggttt attgctgata aatctggagc | 6480 |
| cggtgagcgt gggtctcgcg gtatcattgc agcactgggg ccagatggta agccctcccg | 6540 |
| tatcgtagtt atctacacga cggggagtca ggcaactatg gatgaacgaa atagacagat | 6600 |
| cgctgagata ggtgcctcac tgattaagca ttggtaactg tcagaccaag tttactcata | 6660 |
| tatactttag attgatttaa aacttcattt ttaatttaaa aggatctagg tgaagatcct | 6720 |
| ttttgataat ctcatgacca aaatccctta acgtgagttt tcgttccact gagcgtcaga | 6780 |
| ccccgtagaa aagatcaaag gatcttcttg agatcctttt tttctgcgcg taatctgctg | 6840 |
| cttgcaaaca aaaaaaccac cgctaccagc ggtggtttgt ttgccggatc aagagctacc | 6900 |
| aactcttttt ccgaaggtaa ctggcttcag cagagcgcag ataccaaata ctgtccttct | 6960 |
| agtgtagccg tagttaggcc accacttcaa gaactctgta gcaccgccta catacctcgc | 7020 |
| tctgctaatc ctgttaccag tggctgctgc cagtggcgat aagtcgtgtc ttaccgggtt | 7080 |
| ggactcaaga cgatagttac cggataaggc gcagcggtcg ggctgaacgg ggggttcgtg | 7140 |
| cacacagccc agcttggagc gaacgaccta caccgaactg agatacctac agcgtgagct | 7200 |
| atgagaaagc gccacgcttc ccgaagggag aaaggcggac aggtatccgg taagcggcag | 7260 |
| ggtcggaaca ggagagcgca cgagggagct tccaggggga aacgcctggt atctttatag | 7320 |
| tcctgtcggg tttcgccacc tctgacttga gcgtcgattt ttgtgatgct cgtcaggggg | 7380 |
| gcggagccta tggaaaaacg ccagcaacgc ggcctttttta cggttcctgg ccttttgctg | 7440 |
| gccttttgct cacatgt | 7457 |

<210> SEQ ID NO 126
<211> LENGTH: 7059
<212> TYPE: DNA
<213> ORGANISM: Artificial Sequence
<220> FEATURE:
<223> OTHER INFORMATION: Synthetic

<400> SEQUENCE: 126

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |

```
cagttttaaa attatgtttt aaaatggact atcatatgct taccgtaact tgaaagtatt    360
tcgatttctt ggctttatat atcttgtgga aaggacgaaa caccggaaga gcgagctctt    420
ctgttttaga gctagaaata gcaagttaaa ataaggctag tccgttatca acttgaaaaa    480
gtggcaccga gtcggtgctt ttttctaga ctgcagaggg ccctgcgtat ggggcagagc     540
gcacatcgcc cacagtcccc gagaagttgg gggaggggt cggcaattga acgggtgcct     600
agagaaggtg gcgcgggta aactgggaaa gtgatgtcgt gtactggctc cgccttttc      660
ccgagggtgg gggagaaccg tatataagtg cagtagtcgc cgtgaacgtt cttttcgca    720
acgggtttgc cgccagaaca cagctgaagc ttcgagggc tcgcatctct ccttcacgcg     780
cccgccgccc tacctgaggc cgccatccac gccggttgag tcgcgttctg ccgcctcccg    840
cctgtggtgc ctcctgaact gcgtccgccg tctaggtaag tttaaagctc aggtcgagac    900
cgggcctttg tccggcgctc ccttggagcc tacctagact cagccggctc tccacgcttt    960
gcctgaccct gcttgctcaa ctctacgtct ttgtttcgtt ttctgttctg cgccgttaca   1020
gatccaagct gtgaccggcg cctacaccgg tgccaccatg atcaagatag caacacgcaa   1080
gtatcttggc aaacagaacg tgtacgatat cggggtcgag cgcgatcata acttcgccct   1140
caagaatgga tttatagcaa gttgtttcga ttccgtcgaa atctccggcg tagaggatcg   1200
atttaacgct agtttgggaa cctatcacga cctcctcaag atcataaagg caaggacttc  1260
cttggacaac gaggaaaacg aagatatttt ggaggacatt gtccttaccc ttactctgtt   1320
cgaagatcgg gaaatgatag aggagcgcct taaaacatac gctcacctgt ttgatgataa   1380
ggttatgaag cagcttaagc gaagaaggta cacagggtgg ggtcgccttt caaggaaact   1440
tatcaacgga attcgagata acaaagcgg taagaccata ttggattttt tgaaatcaga   1500
tggcttcgca aaccgggcct ttgcagccct gatcgctgat gattccctga cttttaaaga   1560
ggatatacaa aaagcccagg tttccggaca aggcgactcc ttgcatgagc atatcgccaa   1620
tctggccggc agtcccgcta ttaaaaaggg aatacttcag acagtgaagg tggtcgatga   1680
gctcgtgaag gtaatgggcc ggcacaagcc tgaaaatatt gttatcgaaa tggccagaga   1740
aaatcaaact actcagaagg ggcaaaagaa ttcaagagag cgaatgaaac gaattgaaga   1800
gggtatcaaa gagttgggct cccaaatttt gaaggagcac cctgtcgaaa cacccaact    1860
tcaaaatgaa aagctgtatc tctattacct ccaaaacgga cgggatatgt atgttgacca   1920
ggagcttgac ataaatcgcc tttcagacta tgatgttgat catatagtgc ctcaaagctt   1980
cttgaaagac gacagcatag ataataaggt acttacacga agtgataaaa acagaggtaa   2040
gagtgacaac gttcccagcg aagaagttgt taaaagatg aagaactact ggaggcaatt    2100
gctgaacgct aaacttatca cacagagaaa gtttgataat ttgacaaagg ctgaacgggg   2160
tggactgagc gaactggata aggcaggatt catcaagcgg cagctcgttg aaacacgaca   2220
aattacaaag catgtagctc agatacttga ctcacgaatg aataccaaat acgatgagaa   2280
cgataaactt ataagagaag tcaaagtgat aaccctgaaa tcaaagcttg tttctgactt   2340
taggaaggat ttccagttct acaaagtacg ggaaatcaac aattatcatc atgctcacga   2400
cgcctatttg aacgcagtag tcggtacagc cctgattaaa aaatatccaa agcttgaaag   2460
cgagtttgtt tatggcgatt acaaggtcta tgacgtgaga aaaatgattg ctaagtccga   2520
acaagaaatt gggaaggcca ctgccaaata tttcttttat tccaacatca tgaacttctt   2580
taaaaccgag attactctgg ctaatggcga gatccgcaaa agacctctca ttgaaacaaa   2640
```

```
tggcgaaacc ggagaaattg tctgggataa ggggcgggac ttcgcaacag tccgaaaagt    2700
gttgtcaatg ccccaagtta acatagtgaa aaaaaccgaa gtgcaaactg gcggcttttc    2760
caaagaatcc atcttgccaa agaggaacag tgacaagctg atcgccagga aaaagattg    2820
ggaccccaaa aaatacgggg gtttcgattc acccaccgta gcttatagcg ttcttgttgt    2880
agccaaagtc gagaaggaa atccaaaaa gcttaagtcc gtgaaagagc ttctcgggat    2940
cactattatg gaaggtcat cttttgaaaa gaatcctatc gattttttgg aggctaaggg    3000
ttataaagag gtgaaaaagg atcttataat taagctccct aagtatagtc tgtttgagtt    3060
ggaaaacggg cggaaacgaa tgttggcctc cgccggggag cttcaaaagg gcaatgaact    3120
ggccttgcca tccaagtacg taaattttct ttatctggcc tctcattacg aaaaactgaa    3180
aggctccccc gaggacaacg agcagaaaca attgttcgtc gagcaacaca gcactactt    3240
ggacgaaata attgaacaaa tctcagagtt ctctaagcgc gtaatacttg ccgacgcaaa    3300
tctggataaa gtcctctccg catacaataa acaccgcgac aagccaattc gggagcaagc    3360
tgagaacatc atacacctct ttacactgac taaccttgga gctcccgctg catttaagta    3420
tttcgacacc acaatcgatc gaaagagata cacaagcact aaagaagtac tcgatgccac    3480
tttgattcac caaagtatca caggtctta cgaaactaga atcgacctga gccaacttgg    3540
cggagacgct tccctgggta gtggtagccc aaaaaagaag cggaaggtag aggaccccaa    3600
gaagaaacgc aaagtagact aggaattcga tatcaagctt atcgataatc aacctctgga    3660
ttacaaaatt tgtgaaagat tgactggtat tcttaactat gttgctcctt ttacgctatg    3720
tggatacgct gctttaatgc ctttgtatca tgctattgct tcccgtatgg ctttcatttt    3780
ctcctccttg tataaatcct ggttgctgtc tctttatgag gagttgtggc ccgttgtcag    3840
gcaacgtggc gtggtgtgca ctgtgtttgc tgacgcaacc cccactggtt ggggcattgc    3900
caccacctgt cagctccttt ccgggacttt cgctttcccc ctccctattg ccacggcgga    3960
actcatcgcc gcctgccttg cccgctgctg gacaggggct cggctgttgg gcactgacaa    4020
ttccgtggtg ttgtcgggga atcatcgtc cttccttgg ctgctcgcct gtgttgccac    4080
ctggattctg cgcgggacgt ccttctgcta cgtcccttcg ccctcaatc cagcggacct    4140
tccttcccgc ggcctgctgc cggctctgcg gcctcttccg cgtcttcgcc ttcgccctca    4200
gacgagtcgg atctcccttt gggccgcctc cccgcatcga taccgagcgc taataaaaga    4260
tctttatttt cattagatct gtgtgttggt tttttgtgtc acgtgcggac cgagcggccg    4320
caggaaccc tagtgatgga gttggccact ccctctctgc gcgctcgctc gctcactgag    4380
gccgggcgac caaaggtcgc ccgacgcccg ggctttgccc gggcggcctc agtgagcgag    4440
cgagcgcgca gctgcctgca ggggcgcctg atgcggtatt ttctccttac gcatctgtgc    4500
ggtatttcac accgcatacg tcaaagcaac catagtacgc gccctgtagc ggcgcattaa    4560
gcgcggcggg tgtggtggtt acgcgcagcg tgaccgctac acttgccagc gccctagcgc    4620
ccgctccttt cgctttcttc ccttcctttc tcgccacgtt cgccggcttt ccccgtcaag    4680
ctctaaatcg ggggctccct ttagggttcc gatttagtgc tttacggcac ctcgacccca    4740
aaaaacttga tttgggtgat ggttcacgta gtgggccatc gccctgatag acggtttttc    4800
gccctttgac gttggagtcc acgttcttta atagtggact cttgttccaa actggaacaa    4860
cactcaaccc tatctcgggc tattcttttg atttataagg gattttgccg atttcggcct    4920
attggttaaa aaatgagctg atttaacaaa aatttaacgc gaattttaac aaaatattaa    4980
cgtttacaat tttatggtgc actctcagta caatctgctc tgatgccgca tagttaagcc    5040
```

```
agccccgaca cccgccaaca cccgctgacg cgccctgacg ggcttgtctg ctcccggcat    5100
ccgcttacag acaagctgtg accgtctccg ggagctgcat gtgtcagagg ttttcaccgt    5160
catcaccgaa acgcgcgaga cgaaagggcc tcgtgatacg cctattttta taggttaatg    5220
tcatgataat aatggtttct tagacgtcag gtggcacttt tcggggaaat gtgcgcggaa    5280
cccctatttg tttatttttc taaatacatt caaatatgta tccgctcatg agacaataac    5340
cctgataaat gcttcaataa tattgaaaaa ggaagagtat gagtattcaa catttccgtg    5400
tcgcccttat tcccttttt gcggcatttt gccttcctgt ttttgctcac ccagaaacgc    5460
tggtgaaagt aaaagatgct gaagatcagt tgggtgcacg agtgggttac atcgaactgg    5520
atctcaacag cggtaagatc cttgagagtt tcgccccga agaacgtttt ccaatgatga    5580
gcacttttaa agttctgcta tgtggcgcgg tattatcccg tattgacgcc gggcaagagc    5640
aactcggtcg ccgcatacac tattctcaga atgacttggt tgagtactca ccagtcacag    5700
aaaagcatct tacggatggc atgacagtaa gagaattatg cagtgctgcc ataaccatga    5760
gtgataacac tgcggccaac ttacttctga acgatcgg aggaccgaag gagctaaccg    5820
cttttttgca caacatgggg gatcatgtaa ctcgccttga tcgttgggaa ccggagctga    5880
atgaagccat accaaacgac gagcgtgaca ccacgatgcc tgtagcaatg gcaacaacgt    5940
tgcgcaaact attaactggc gaactactta ctctagcttc ccggcaacaa ttaatagact    6000
ggatggaggc ggataaagtt gcaggaccac ttctgcgctc ggcccttccg gctggctggt    6060
ttattgctga taaatctgga gccggtgagc gtgggtctcg cggtatcatt gcagcactgg    6120
ggccagatgg taagccctcc cgtatcgtag ttatctacac gacggggagt caggcaacta    6180
tggatgaacg aaatagacag atcgctgaga taggtgcctc actgattaag cattggtaac    6240
tgtcagacca agtttactca tatatacttt agattgattt aaaacttcat ttttaattta    6300
aaaggatcta ggtgaagatc ctttttgata atctcatgac caaaatccct taacgtgagt    6360
tttcgttcca ctgagcgtca gaccccgtag aaaagatcaa aggatcttct tgagatcctt    6420
tttttctgcg cgtaatctgc tgcttgcaaa caaaaaaacc accgctacca gcggtggttt    6480
gtttgccgga tcaagagcta ccaactcttt ttccgaaggt aactggcttc agcagagcgc    6540
agataccaaa tactgtcctt ctagtgtagc cgtagttagg ccaccacttc aagaactctg    6600
tagcaccgcc tacatacctc gctctgctaa tcctgttacc agtggctgct gccagtggcg    6660
ataagtcgtg tcttaccggg ttggactcaa gacgatagtt accggataag gcgcagcggt    6720
cgggctgaac ggggggttcg tgcacacagc ccagcttgga gcgaacgacc tacaccgaac    6780
tgagatacct acagcgtgag ctatgagaaa gcgccacgct tcccgaaggg agaaaggcgg    6840
acaggtatcc ggtaagcggc agggtcgaa caggagagcg cacagggag cttcaggg     6900
gaaacgcctg gtatctttat agtcctgtcg gtttcgcca cctctgactt gagcgtcgat    6960
ttttgtgatg ctcgtcaggg gggcggagcc tatggaaaaa cgccagcaac gcggcctttt    7020
tacggttcct ggccttttgc tggccttttg ctcacatgt                          7059
```

<210> SEQ ID NO 127
<211> LENGTH: 7059
<212> TYPE: DNA
<213> ORGANISM: Artificial Sequence
<220> FEATURE:
<223> OTHER INFORMATION: Synthetic

<400> SEQUENCE: 127

-continued

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccgca cgcgtgaggg cctatttccc atgattcctt   180
catatttgca tatacgatac aaggctgtta gagagataat tggaattaat ttgactgtaa   240
acacaaagat attagtacaa aatacgtgac gtagaaagta ataatttctt gggtagtttg   300
cagtttttaaa attatgtttt aaaatggact atcatatgct taccgtaact tgaaagtatt   360
tcgatttctt ggctttatat atcttgtgga aaggacgaaa caccggaaga gcgagctctt   420
ctgttttaga gctagaaata gcaagttaaa ataaggctag tccgttatca acttgaaaaa   480
gtggcaccga gtcggtgctt ttttttctaga ctgcagaggg ccctgcgtat ggggcagagc   540
gcacatcgcc cacagtcccc gagaagttgg ggggaggggt cggcaattga acgggtgcct   600
agagaaggtg gcgcggggta aactgggaaa gtgatgtcgt gtactggctc cgcctttttc   660
ccgagggtgg gggagaaccg tatataagtg cagtagtcgc cgtgaacgtt cttttttcgca   720
acgggtttgc cgccagaaca cagctgaagc ttcgaggggc tcgcatctct ccttcacgcg   780
cccgccgccc tacctgaggc cgccatccac gccggttgag tcgcgttctg ccgcctcccg   840
cctgtggtgc ctcctgaact gcgtccgccg tctaggtaag tttaaagctc aggtcgagac   900
cgggcctttg tccggcgctc ccttggagcc tacctagact cagccggctc tccacgcttt   960
gcctgaccct gcttgctcaa ctctacgtct ttgtttcgtt ttctgttctg cgccgttaca  1020
gatccaagct gtgaccggcg cctacaccgg tgccaccatg atcaagatag caacacgcaa  1080
gtatcttggc aaacagaacg tgtacgatat cggggtcgag cgcgatcata acttcgccct  1140
caagaatgga tttatagcaa gttgtttcga ttccgtcgaa atctccggcg tagaggatcg  1200
atttaacgct agtttgggaa cctatcacga cctcctcaag atcataaagg acaaggactt  1260
cttggacaac gaggaaaacg aagatatttt ggaggacatt gtccttaccc ttactctgtt  1320
cgaagatcgg gaaatgatag aggagcgcct taaaacatac gctcacctgt ttgatgataa  1380
ggttatgaag cagcttaagc gaagaaggta cacagggtgg ggtcgccttt caaggaaact  1440
tatcaacgga attcgagata aacaaagcgg taagaccata ttggattttt tgaaatcaga  1500
tggcttcgca aaccggaact ttatgcaact catccatgat gattccctga cttttaaaga  1560
ggatatacaa aaagcccagg tttccggaca aggcgactcc ttgcatgagc atatcgccaa  1620
tctggccggc agtcccgcta ttaaaagggg aatacttcag acagtgaagg tggtcgatga  1680
gctcgtgaag gtaatgggcc ggcacaagcc tgaaaatatt gttatcgaaa tggccagaga  1740
aaatcaaact actcagaagg ggcaaaagaa ttcaagagag cgaatgaaac gaattgaaga  1800
gggtatcaaa gagtttgggct cccaaatttt gaaggagcac cctgtcgaaa cacccaact  1860
tcaaaatgaa aagctgtatc tctattacct ccaaaacgga cgggatatgt atgttgacca  1920
ggagcttgac ataaatcgcc tttcagacta tgatgttgat catatagtgc ctcaaagctt  1980
cttgaaagac gacagcatag ataataaggt acttacacga agtgataaaa acagaggtaa  2040
gagtgacaac gttcccagcg aagaagttgt taaaaagatg aagaactact ggaggcaatt  2100
gctgaacgct aaacttatca cacagagaaa gtttgataat ttgacaaagg ctgaacgggg  2160
tggactgagc gaactggata aggcaggatt catcaagcgg cagctcgttg aaacacgaca  2220
aattacaaag catgtagctc agatacttga ctcacgaatg aataccaaat acgatgagaa  2280
cgataaactt ataagagaag tcaaagtgat aaccctgaaa tcaagcttg tttctgactt  2340
taggaaggat ttccagttct acaaagtacg ggaaatcaac aattatcatc atgctcacga  2400
```

```
cgcctatttg aacgcagtag tcggtacagc cctgattaaa aaatatccaa agcttgaaag    2460
cgagtttgtt tatggcgatt acaaggtcta tgacgtgaga aaaatgattg ctaagtccga    2520
acaagaaatt gggaaggcca ctgccaaata tttctttat tccaacatca tgaacttctt    2580
taaaaccgag attactctgg ctaatggcga gatccgcaaa agacctctca ttgaaacaaa    2640
tggcgaaacc ggagaaattg tctgggataa ggggcgggac ttcgcaacag tccgaaaagt    2700
gttgtcaatg ccccaagtta acatagtgaa aaaaccgaa gtgcaaactg gcggtttttc     2760
caaagaatcc atcttgccaa agaggaacag tgacaagctg atcgccagga aaaagattg     2820 ggaccccaaa aaatacgggg gtttcgattc acccaccgta gcttatagcg ttcttgttgt    2880
agccaaagtc gagaaggaa atccaaaaa gcttaagtcc gtgaaagagc ttctcgggat     2940
cactattatg gaaggtcat cttttgaaaa gaatcctatc gatttttgg aggctaaggg     3000 ttataaagag gtgaaaagg atcttataat taagctccct aagtatagtc tgtttgagtt    3060
ggaaacgggg cggaaacgaa tgttggcctc cgccggggag cttcaaaagg caatgaact    3120 ggccttgcca tccaagtacg taaattttct ttatctggcc tctcattacg aaaaactgaa    3180
aggctccccc gaggacaacg agcagaaaca attgttcgtc gagcaacaca agcactactt    3240
ggacgaaata attgaacaaa tctcagagtt ctctaagcgc gtaatacttg ccgacgcaaa    3300
tctggataaa gtcctctccg catacaataa acaccgcgac aagccaattc gggagcaagc    3360
tgagaacatc atacacctct ttacactgac taaccttgga gctcccgctg catttaagta    3420
tttcgacacc acaatcgatc gaaagagata cacaagcact aaagaagtac tcgatgccac    3480
tttgattcac caaagtatca caggtctta cgaaactaga atcgacctga ccaacttgg    3540 cggagacgct tccctgggta gtggtagccc aaaaaagaag cggaaggtag aggaccccaa    3600
gaagaaacgc aaagtagact aggaattcga tatcaagctt atcgataatc aacctctgga    3660
ttacaaaatt tgtgaaagat tgactggtat tcttaactat gttgctcctt ttacgctatg    3720
tggatacgct gctttaatgc ctttgtatca tgctattgct tcccgtatgg ctttcatttt    3780
ctcctccttg tataaatcct ggttgctgtc tctttatgag gagttgtggc ccgttgtcag    3840
gcaacgtggc gtggtgtgca ctgtgtttgc tgacgcaacc cccactggtt ggggcattgc    3900
caccacctgt cagctccttt ccgggacttt cgctttcccc ctccctattg ccacggcgga    3960
actcatcgcc gcctgccttg cccgctgctg gacaggggct cggctgttgg cactgacaa    4020 ttccgtggtg ttgtcgggga atcatcgtc ctttccttgg ctgctcgcct gtgttgccac    4080
ctggattctg cgcgggacgt ccttctgcta cgtcccttcg ccctcaatc cagcggacct    4140 tccttcccgc ggcctgctgc cggctctgcg gcctcttccg cgtcttcgcc ttcgccctca    4200
gacgagtcgg atctcccttt gggccgcctc cccgcatcga taccgagcgc taataaaaga    4260
tctttatttt cattagatct gtgtgttggt tttttgtgtc acgtgcggac cgagcggccg    4320 caggaaccccc tagtgatgga gttggccact ccctctctgc gcgctcgctc gctcactgag    4380
gccgggcgac caaaggtcgc ccgacgcccg ggctttgccc gggcggcctc agtgagcgag    4440
cgagcgcgca gctgcctgca ggggcgcctg atgcggtatt ttctccttac gcatctgtgc    4500
ggtatttcac accgcatacg tcaaagcaac catagtacgc gccctgtagc ggcgcattaa    4560
gcgcggcggg tgtggtggtt acgcgcagcg tgaccgctac acttgccagc gccctagcgc    4620
ccgctccttt cgctttcttc ccttcctttc tcgccacgtt cgccggcttt ccccgtcaag    4680
ctctaaatcg ggggctccct ttagggttcc gatttagtgc tttacggcac ctcgacccca    4740
```

```
aaaaacttga tttgggtgat ggttcacgta gtgggccatc gccctgatag acggttttc    4800
gccctttgac gttggagtcc acgttcttta atagtggact cttgttccaa actggaacaa    4860
cactcaaccc tatctcgggc tattcttttg atttataagg gattttgccg atttcggcct    4920
attggttaaa aaatgagctg atttaacaaa aatttaacgc gaattttaac aaaatattaa    4980
cgtttacaat tttatggtgc actctcagta caatctgctc tgatgccgca tagttaagcc    5040
agccccgaca cccgccaaca cccgctgacg cgccctgacg ggcttgtctg ctcccggcat    5100
ccgcttacag acaagctgtg accgtctccg ggagctgcat gtgtcagagg ttttcaccgt    5160
catcaccgaa acgcgcgaga cgaaagggcc tcgtgatacg cctatttta taggttaatg    5220
tcatgataat aatggtttct tagacgtcag gtggcacttt tcggggaaat gtgcgcggaa    5280
ccctattg tttatttc taaatacatt caaatatgta tccgctcatg agacaataac    5340
cctgataaat gcttcaataa tattgaaaaa ggaagagtat gagtattcaa catttccgtg    5400
tcgcccttat ccctttttt gcggcatttt gccttcctgt ttttgctcac ccagaaacgc    5460
tggtgaaagt aaaagatgct gaagatcagt tgggtgcacg agtgggttac atcgaactgg    5520
atctcaacag cggtaagatc cttgagagtt ttcgccccga agaacgtttt ccaatgatga    5580
gcacttttaa agttctgcta tgtggcgcgg tattatcccg tattgacgcc gggcaagagc    5640
aactcggtcg ccgcatacac tattctcaga atgacttggt tgagtactca ccagtcacag    5700
aaaagcatct tacggatggc atgacagtaa gagaattatg cagtgctgcc ataaccatga    5760
gtgataacac tgcggccaac ttacttctga caacgatcgg aggaccgaag gagctaaccg    5820
cttttttgca acatggggg gatcatgtaa ctcgccttga tcgttgggaa ccggagctga    5880
atgaagccat accaaacgac gagcgtgaca ccacgatgcc tgtagcaatg gcaacaacgt    5940
tgcgcaaact attaactggc gaactactta ctctagcttc ccggcaacaa ttaatagact    6000
ggatggaggc ggataaagtt gcaggaccac ttctgcgctc ggcccttccg gctggctggt    6060
ttattgctga taaatctgga gccggtgagc gtgggtctcg cggtatcatt gcagcactgg    6120
ggccagatgg taagccctcc cgtatcgtag ttatctacac gacggggagt caggcaacta    6180
tggatgaacg aaatagacag atcgctgaga taggtgcctc actgattaag cattggtaac    6240
tgtcagacca agtttactca tatatacttt agattgattt aaaacttcat ttttaattta    6300
aaaggatcta ggtgaagatc ctttttgata atctcatgac caaaatccct taacgtgagt    6360
tttcgttcca ctgagcgtca gaccccgtag aaaagatcaa aggatcttct tgagatcctt    6420
tttttctgcg cgtaatctgc tgcttgcaaa caaaaaaacc accgctacca gcggtggttt    6480
gtttgccgga tcaagagcta ccaactcttt ttccgaaggt aactggcttc agcagagcgc    6540
agataccaaa tactgtcctt ctagtgtagc cgtagttagg ccaccacttc aagaactctg    6600
tagcaccgcc tacatacctc gctctgctaa tcctgttacc agtggctgct gccagtggcg    6660
ataagtcgtg tcttaccggg ttggactcaa gacgatagtt accggataag gcgcagcggt    6720
cgggctgaac ggggggttcg tgcacacagc ccagcttgga gcgaacgacc tacaccgaac    6780
tgagatacct acagcgtgag ctatgagaaa gcgccacgct tcccgaaggg agaaaggcgg    6840
acaggtatcc ggtaagcggc agggtcggaa caggagagcg cacgagggag cttccagggg    6900
gaaacgcctg gtatctttat agtcctgtcg ggtttcgcca cctctgactt gagcgtcgat    6960
ttttgtgatg ctcgtcaggg gggcggagcc tatggaaaaa cgccagcaac gcggcctttt    7020
tacggttcct ggccttttgc tggccttttg ctcacatgt                           7059
```

```
<210> SEQ ID NO 128
<211> LENGTH: 23
<212> TYPE: DNA
<213> ORGANISM: Artificial Sequence
<220> FEATURE:
<223> OTHER INFORMATION: Synthetic

<400> SEQUENCE: 128
gatgtatgaa gatgatgacg agg                                              23

<210> SEQ ID NO 129
<211> LENGTH: 23
<212> TYPE: DNA
<213> ORGANISM: Artificial Sequence
<220> FEATURE:
<223> OTHER INFORMATION: Synthetic

<400> SEQUENCE: 129
agtgacatcc tcagccaaag tgg                                              23

<210> SEQ ID NO 130
<211> LENGTH: 23
<212> TYPE: DNA
<213> ORGANISM: Artificial Sequence
<220> FEATURE:
<223> OTHER INFORMATION: Synthetic

<400> SEQUENCE: 130
gtaaagtcag ctaactctct cgg                                              23

<210> SEQ ID NO 131
<211> LENGTH: 23
<212> TYPE: DNA
<213> ORGANISM: Artificial Sequence
<220> FEATURE:
<223> OTHER INFORMATION: Synthetic

<400> SEQUENCE: 131
gaaagagaaa gagccagcag agg                                              23

<210> SEQ ID NO 132
<211> LENGTH: 23
<212> TYPE: DNA
<213> ORGANISM: Artificial Sequence
<220> FEATURE:
<223> OTHER INFORMATION: Synthetic

<400> SEQUENCE: 132
agaaaagggt gtccgtgtgc tgg                                              23

<210> SEQ ID NO 133
<211> LENGTH: 23
<212> TYPE: DNA
<213> ORGANISM: Artificial Sequence
<220> FEATURE:
<223> OTHER INFORMATION: Synthetic

<400> SEQUENCE: 133
ggctcttcag tgcaccaggg ggg                                              23

<210> SEQ ID NO 134
<211> LENGTH: 23
<212> TYPE: DNA
<213> ORGANISM: Artificial Sequence
<220> FEATURE:
<223> OTHER INFORMATION: Synthetic
```

<400> SEQUENCE: 134
gaagaaggaa atccggaacg tgg                                         23

<210> SEQ ID NO 135
<211> LENGTH: 23
<212> TYPE: DNA
<213> ORGANISM: Artificial Sequence
<220> FEATURE:
<223> OTHER INFORMATION: Synthetic

<400> SEQUENCE: 135
taccacatca tccacagatg agg                                         23

<210> SEQ ID NO 136
<211> LENGTH: 23
<212> TYPE: DNA
<213> ORGANISM: Artificial Sequence
<220> FEATURE:
<223> OTHER INFORMATION: Synthetic

<400> SEQUENCE: 136
ggacaagggg aaagatatca ggg                                         23

<210> SEQ ID NO 137
<211> LENGTH: 23
<212> TYPE: DNA
<213> ORGANISM: Artificial Sequence
<220> FEATURE:
<223> OTHER INFORMATION: Synthetic

<400> SEQUENCE: 137
tatctaaggg agagctggca ggg                                         23

<210> SEQ ID NO 138
<211> LENGTH: 23
<212> TYPE: DNA
<213> ORGANISM: Artificial Sequence
<220> FEATURE:
<223> OTHER INFORMATION: Synthetic

<400> SEQUENCE: 138
gtttaagtca gtcagttaat ggg                                         23

<210> SEQ ID NO 139
<211> LENGTH: 23
<212> TYPE: DNA
<213> ORGANISM: Artificial Sequence
<220> FEATURE:
<223> OTHER INFORMATION: Synthetic

<400> SEQUENCE: 139
cctgtacctg ccgctgtcat tgg                                         23

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
gatgtatgaa gatgatgacg                                             20

<210> SEQ ID NO 141
<211> LENGTH: 21

```
<212> TYPE: DNA
<213> ORGANISM: Artificial Sequence
<220> FEATURE:
<223> OTHER INFORMATION: Synthetic

<400> SEQUENCE: 141
gagtgacatc ctcagccaaa g                                              21

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
gtaaagtcag ctaactctct                                                20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
gaaagagaaa gagccagcag                                                20

<210> SEQ ID NO 144
<211> LENGTH: 21
<212> TYPE: DNA
<213> ORGANISM: Artificial Sequence
<220> FEATURE:
<223> OTHER INFORMATION: Synthetic

<400> SEQUENCE: 144
gagaaaaggg tgtccgtgtg c                                              21

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
ggctcttcag tgcaccaggg                                                20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
gaagaaggaa atccggaacg                                                20

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147
```

```
gtaccacatc atccacagat g                                              21
```

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148

```
ggacaagggg aaagatatca                                                20
```

<210> SEQ ID NO 149
<211> LENGTH: 21
<212> TYPE: DNA
<213> ORGANISM: Artificial Sequence
<220> FEATURE:
<223> OTHER INFORMATION: Synthetic

<400> SEQUENCE: 149

```
gtatctaagg gagagctggc a                                              21
```

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150

```
gtttaagtca gtcagttaat                                                20
```

<210> SEQ ID NO 151
<211> LENGTH: 21
<212> TYPE: DNA
<213> ORGANISM: Artificial Sequence
<220> FEATURE:
<223> OTHER INFORMATION: Synthetic

<400> SEQUENCE: 151

```
gcctgtacct gccgctgtca t                                              21
```

<210> SEQ ID NO 152
<211> LENGTH: 3741
<212> TYPE: DNA
<213> ORGANISM: Artificial Sequence
<220> FEATURE:
<223> OTHER INFORMATION: Synthetic

<400> SEQUENCE: 152

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggcttcc tgcggccgca cgcgtgaggg cctatttccc atgattcctt    180
catatttgca tatacgatac aaggctgtta gagagataat tggaattaat ttgactgtaa    240
acacaaagat attagtacaa aatacgtgac gtagaaagta ataatttctt gggtagtttg    300
cagttttaaa attatgtttt aaaatggact atcatatgct taccgtaact tgaaagtatt    360
tcgatttctt ggctttatat atcttgtgga aaggacgaaa caccgacgct tccgagtacg    420
gtacgtttta gagctagaaa tagcaagtta aaataaggct agtccgttat caacttgaaa    480
aagtggcacc gagtcggtgc ttttttttcta gacctgtacc gtactcggaa gcgtcggatc    540
cctagctagc tagctaaagg tcctcctcgc tgatcagttt ctgctcagcc ttagctgcgg    600
```

-continued

```
cttctttagc tgctgcttct gcggtagaat caaggcccag aagtgggttg gggatgggtt    660
tcccggcttt tgcagctgct tcttttgcgg cggcttcggc tgcatagtcg gggacatcat    720
agggatatgc cttggcagct gcttccttgg cagcggcttc ggccagatcc tcttcgctaa    780
tcaactttg ctctgcttta gctgcagcct ccttggcggc agcttctgca gtagaatcca    840
atcccaacag tgggtttgga attggtttcc cagctttggc ggcggcctcc ttagcagctg    900
cctcggcggc gtaatctggc acatcatatg ggtagctccc tccaccaccc tctcgagacc    960
tgtaccgtac tcggaagcgt ccacgtgcgg accgagcggc cgcaggaacc cctagtgatg   1020
gagttggcca ctccctctct gcgcgctcgc tcgctcactg aggccgggcg accaaaggtc   1080
gcccgacgcc cgggctttgc ccggcggcc tcagtgagcg agcgagcgcg cagctgcctg   1140
caggggcgc tgatgcggta ttttctcctt acgcatctgt gcggtatttc acaccgcata   1200
cgtcaaagca accatagtac gcgccctgta gcggcgcatt aagcgcggcg ggtgtggtgg   1260
ttacgcgcag cgtgaccgct acacttgcca gcgccctagc gcccgctcct ttcgctttct   1320
tcccttcctt tctcgccacg ttcgccggct ttccccgtca agctctaaat cggggggctcc   1380
ctttaggt ccgatttagt gctttacggc acctcgaccc caaaaaactt gatttgggtg   1440
atggttcacg tagtgggcca tcgccctgat agacggtttt tcgccctttg acgttggagt   1500
ccacgttctt taatagtgga ctcttgttcc aaactggaac aacactcaac cctatctcgg   1560
gctattcttt tgatttataa gggattttgc cgatttcggc ctattggtta aaaaatgagc   1620
tgatttaaca aaaatttaac gcgaattta acaaaatatt aacgtttaca attttatggt   1680
gcactctcag tacaatctgc tctgatgccg catagttaag ccagccccga caccgccaa    1740
caccgctga cgcgccctga cgggcttgtc tgctcccggc atccgcttac agacaagctg   1800
tgaccgtctc cgggagctgc atgtgtcaga ggttttcacc gtcatcaccg aaacgcgcga   1860
gacgaaaggg cctcgtgata cgcctatttt tataggttaa tgtcatgata ataatggttt   1920
cttagacgtc aggtggcact tttcggggaa atgtgcgcgg aacccctatt tgtttatttt   1980
tctaaataca ttcaaatatg tatccgctca tgagacaata accctgataa atgcttcaat   2040
aatattgaaa aaggaagagt atgagtattc aacatttccg tgtcgccctt attccctttt   2100
ttgcggcatt ttgccttcct gtttttgctc acccagaaac gctggtgaaa gtaaaagatg   2160
ctgaagatca gttgggtgca cgagtgggtt acatcgaact ggatctcaac agcggtaaga   2220
tccttgagag ttttcgcccc gaagaacgtt ttccaatgat gagcactttt aaagttctgc   2280
tatgtggcgc ggtattatcc cgtattgacg ccgggcaaga gcaactcggt cgccgcatac   2340
actattctca gaatgacttg gttgagtact caccagtcac agaaaagcat cttacggatg   2400
gcatgacagt aagagaatta tgcagtgctg ccataaccat gagtgataac actgcggcca   2460
acttacttct gacaacgatc ggaggaccga aggagctaac cgcttttttg cacaacatgg   2520
gggatcatgt aactcgcctt gatcgttggg aaccggagct gaatgaagcc ataccaaacg   2580
acgagcgtga ccacgatg cctgtagcaa tggcaacaac gttgcgcaaa ctattaactg   2640
gcgaactact tactctagct tcccggcaac aattaataga ctggatggag gcggataaag   2700
ttgcaggacc acttctgcgc tcggcccttc cggctggctg gtttattgct gataaatctg   2760
gagccggtga gcgtgggtct cgcggtatca ttgcagcact ggggccagat ggtaagccct   2820
cccgtatcgt agttatctac acgacgggga gtcaggcaac tatggatgaa cgaaatagac   2880
agatcgctga gataggtgcc tcactgatta agcattggta actgtcagac caagtttact   2940
```

| | |
|---|---:|
| catatatact ttagattgat ttaaaacttc attttaatt taaaaggatc taggtgaaga | 3000 |
| tccttttga taatctcatg accaaaatcc cttaacgtga gttttcgttc cactgagcgt | 3060 |
| cagaccccgt agaaaagatc aaaggatctt cttgagatcc ttttttctg cgcgtaatct | 3120 |
| gctgcttgca acaaaaaaa ccaccgctac cagcggtggt ttgtttgccg gatcaagagc | 3180 |
| taccaactct ttttccgaag gtaactggct tcagcagagc gcagatacca aatactgtcc | 3240 |
| ttctagtgta gccgtagtta ggccaccact tcaagaactc tgtagcaccg cctacatacc | 3300 |
| tcgctctgct aatcctgtta ccagtggctg ctgccagtgg cgataagtcg tgtcttaccg | 3360 |
| ggttggactc aagacgatag ttaccggata aggcgcagcg gtcgggctga acggggggtt | 3420 |
| cgtgcacaca gcccagcttg gagcgaacga cctacaccga actgagatac ctacagcgtg | 3480 |
| agctatgaga aagcgccacg cttcccgaag ggagaaaggc ggacaggtat ccggtaagcg | 3540 |
| gcagggtcgg aacaggagag cgcacgaggg agcttccagg gggaaacgcc tggtatcttt | 3600 |
| atagtcctgt cgggtttcgc cacctctgac ttgagcgtcg attttgtga tgctcgtcag | 3660 |
| gggggcggag cctatggaaa aacgccagca acgcggcctt tttacggttc ctggccttt | 3720 |
| gctggccttt tgctcacatg t | 3741 |

<210> SEQ ID NO 153
<211> LENGTH: 3740
<212> TYPE: DNA
<213> ORGANISM: Artificial Sequence
<220> FEATURE:
<223> OTHER INFORMATION: Synthetic

<400> SEQUENCE: 153

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggccgca cgcgtgaggg cctatttccc atgattcctt | 180 |
| catatttgca tatacgatac aaggctgtta gagagataat tggaattaat ttgactgtaa | 240 |
| acacaaagat attagtacaa aatacgtgac gtagaaagta ataatttctt gggtagtttg | 300 |
| cagttttaaa attatgtttt aaaatggact atcatatgct taccgtaact tgaaagtatt | 360 |
| tcgatttctt ggctttatat atcttgtgga aaggacgaaa caccgacgct tccgagtacg | 420 |
| gtacgtttta gagctagaaa tagcaagtta aaataaggct agtccgttat caacttgaaa | 480 |
| aagtggcacc gagtcggtgc tttttttcta gacctgtacc gtactcggaa gcgtcggatc | 540 |
| cctagctagc tagctaaagg tcctcctcgc tgatcagttt ctgctcagcc ttagctgcgg | 600 |
| cttctttagc tgctgcttct gcggtagaat caaggcccag aagtgggttg ggatgggtt | 660 |
| tcccggcttt tgcagctgct tcttttgcgg cggcttcggc tgcatagtcg gggacatcat | 720 |
| agggatatgc cttggcagct gcttccttgg cagcggcttc ggccagatcc tcttcgctaa | 780 |
| tcaactttg ctctgcttta gctgcagcct ccttggcggc agcttctgca gtagaatcca | 840 |
| atcccaacag tgggtttgga attggtttcc cagctttggc ggcggcctcc ttagcagctg | 900 |
| cctcggcggc gtaatctggc acatcatatg ggtagctccc tccaccaccc tctcgagcct | 960 |
| gtaccgtact cggaagcgtc cacgtgcgga ccgagcggcc gcaggaaccc ctagtgatgg | 1020 |
| agttggccac tccctctctg cgcgctcgct cgctcactga ggccgggcga ccaaaggtcg | 1080 |
| cccgacgccc gggctttgcc cggcggcct cagtgagcga gcgagcgcgc agctgcctgc | 1140 |
| aggggcgcct gatgcggtat tttctcctta cgcatctgtg cggtatttca caccgcatac | 1200 |
| gtcaaagcaa ccatagtacg cgccctgtag cggcgcatta agcgcggcgg gtgtggtggt | 1260 |

```
tacgcgcagc gtgaccgcta cacttgccag cgccctagcg cccgctcctt tcgctttctt    1320 cccttcctt  ctcgccacgt tcgccggctt tccccgtcaa gctctaaatc gggggctccc    1380
tttagggttc cgatttagtg ctttacggca cctcgacccc aaaaaacttg atttgggtga    1440
tggttcacgt agtgggccat cgccctgata acggttttt cgccctttga cgttggagtc     1500
cacgttcttt aatagtggac tcttgttcca aactggaaca acactcaacc ctatctcggg    1560
ctattctttt gatttataag ggattttgcc gatttcggcc tattggttaa aaatgagct     1620 gatttaacaa aaatttaacg cgaattttaa caaaatatta acgtttacaa ttttatggtg    1680
cactctcagt acaatctgct ctgatgccgc atagttaagc cagccccgac acccgccaac    1740
acccgctgac gcgccctgac gggcttgtct gctcccggca tccgcttaca gacaagctgt    1800
gaccgtctcc gggagctgca tgtgtcagag gttttcaccg tcatcaccga aacgcgcgag    1860
acgaaagggc ctcgtgatac gcctattttt ataggttaat gtcatgataa taatggtttc    1920
ttagacgtca ggtggcactt ttcggggaaa tgtgcgcgga acccctattt gtttatttt     1980 ctaaatacat tcaaatatgt atccgctcat gagacaataa ccctgataaa tgcttcaata    2040
atattgaaaa aggaagagta tgagtattca acatttccgt gtcgcccttat tcccttttt   2100 tgcggcattt tgccttcctg ttttgctca cccagaaacg ctggtgaaag taaaagatgc     2160
tgaagatcag ttgggtgcac gagtgggtta catcgaactg gatctcaaca gcggtaagat   2220
ccttgagagt tttcgccccg aagaacgttt tccaatgatg agcacttttaa agttctgct   2280 atgtggcgcg gtattatccc gtattgacgc cgggcaagag caactcggtc gccgcataca   2340
ctattctcag aatgacttgg ttgagtactc accagtcaca gaaaagcatc ttacggatgg   2400
catgacagta agagaattat gcagtgctgc cataaccatg agtgataaca ctgcggccaa    2460
cttacttctg acaacgatcg gaggaccgaa ggagctaacc gcttttttgc acaacatggg    2520
ggatcatgta actcgccttg atcgttggga accggagctg aatgaagcca taccaaacga    2580
cgagcgtgac accacgatgc ctgtagcaat ggcaacaacg ttgcgcaaac tattaactgg    2640
cgaactactt actctagctt cccggcaaca attaatagac tggatggagg cggataaagt    2700
tgcaggacca cttctgcgct cggcccttcc ggctggctgg tttattgctg ataaatctgg    2760
agccggtgag cgtgggtctc gcggtatcat tgcagcactg gggccagatg gtaagccctc    2820
ccgtatcgta gttatctaca cgacggggag tcaggcaact atggatgaac gaaatagaca    2880
gatcgctgag ataggtgcct cactgattaa gcattggtaa ctgtcagacc aagtttactc    2940
atatatactt tagattgatt taaaacttca ttttaattt aaaaggatct aggtgaagat     3000 ccttttttgat aatctcatga ccaaaatccc ttaacgtgag ttttcgttcc actgagcgtc   3060 agacccgta gaaaagatca aaggatcttc ttgagatcct ttttttctgc gcgtaatctg    3120
ctgcttgcaa acaaaaaaac caccgctacc agcggtggtt tgtttgccgg atcaagagct    3180
accaactctt tttccgaagg taactggctt cagcagagcg cagataccaa atactgtcct    3240
tctagtgtag ccgtagttag gccaccactt caagaactct gtagcaccgc ctacatacct    3300
cgctctgcta atcctgttac cagtggctgc tgccagtggc gataagtcgt gtcttaccgg    3360
gttggactca agacgatagt taccggataa ggcgcagcgg tcgggctgaa cggggggttc    3420
gtgcacacag cccagcttgg agcgaacgac ctacaccgaa ctgagatacc tacagcgtga    3480
gctatgagaa agcgccacgc ttcccgaagg gagaaaggcg acaggtatc cggtaagcgg     3540 cagggtcgga acaggagagc gcacgaggga gcttccaggg ggaaacgcct ggtatcttta    3600
```

```
tagtcctgtc gggtttcgcc acctctgact tgagcgtcga tttttgtgat gctcgtcagg    3660
ggggcggagc ctatggaaaa acgccagcaa cgcggccttt ttacggttcc tggccttttg    3720
ctggcctttt gctcacatgt                                                3740

<210> SEQ ID NO 154
<211> LENGTH: 3742
<212> TYPE: DNA
<213> ORGANISM: Artificial Sequence
<220> FEATURE:
<223> OTHER INFORMATION: Synthetic

<400> SEQUENCE: 154
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtgaggg cctatttccc atgattcctt     180
catatttgca tatacgatac aaggctgtta gagagataat tggaattaat ttgactgtaa     240
acacaaagat attagtacaa atacgtgacg tagaaagta ataatttctt gggtagtttg      300
cagttttaaa attatgtttt aaaatggact atcatatgct taccgtaact tgaaagtatt     360
tcgatttctt ggctttatat atcttgtgga aaggacgaaa caccgacgct ccgagtacg      420 gtacgtttta gagctagaaa tagcaagtta aaataaggct agtccgttat caacttgaaa     480
aagtggcacc gagtcggtgc ttttttttcta gacctgtacc gtactcggaa gcgtcggatc    540
cctagctagc tagctaaagg tcctcctcgc tgatcagttt ctgctcagcc ttagctgcgg     600
cttctttagc tgctgcttct gcggtagaat caaggcccag aagtgggttg gggatgggtt    660
tcccggcttt tgcagctgct tctttttgcgg cggcttcggc tgcatagtcg gggacatcat     720
agggatatgc cttggcagct gcttccttgg cagcggcttc ggccagatcc tcttcgctaa     780
tcaacttttg ctctgcttta gctgcagcct ccttggcggc agcttctgca gtagaatcca    840
atcccaacag tgggtttga attggtttcc cagctttggc ggcggcctcc ttagcagctg     900
cctcggcggc gtaatctggc acatcatatg ggtagctccc tccaccaccc tctcgagatc     960
ctgtaccgta ctcggaagcg tccacgtgcg gaccgagcgg ccgcaggaac ccctagtgat    1020
ggagttggcc actccctctc tgcgcgctcg ctcgctcact gaggccgggc gaccaaaggt    1080
cgcccgacgc ccgggctttg cccggcggc tcagtgagc gagcgagcgc gcagctgcct     1140
gcaggggcgc ctgatgcggt attttctcct tacgcatctg tgcggtattt cacaccgcat    1200
acgtcaaagc aaccatagta cgcgcccgt agcggcgcat taagcgcggc gggtgtggtg     1260
gttacgcgca gcgtgaccgc tacacttgcc agcgccctag cgcccgctcc tttcgctttc    1320
ttcccttcct ttctcgccac gttcgccggc ttttcccgtc aagctctaaa tcggggggctc    1380 cctttagggt tccgatttag tgctttacgg cacctcgacc ccaaaaaact tgatttgggt     1440
gatggttcac gtagtgggcc atcgccctga tagacggttt ttcgcccttt gacgttggag     1500
tccacgttct ttaatagtgg actcttgttc caaactggaa caacactcaa ccctatctcg    1560
ggctattctt ttgatttata agggattttg ccgatttcgg cctattggtt aaaaaatgag     1620
ctgatttaac aaaaatttaa cgcgaatttt aacaaaatat taacgtttac aattttatgg    1680
tgcactctca gtacaatctg ctctgatgcc gcatagttaa gccagccccg acacccgcca     1740
acacccgctg acgcgccctg acgggcttgt ctgctcccgg catccgctta cagacaagct    1800
gtgaccgtct ccgggagctg catgtgtcag aggttttcac cgtcatcacc gaaacgcgcg    1860
agacgaaagg gcctcgtgat acgcctattt ttataggtta atgtcatgat aataatggtt    1920
```

```
tcttagacgt caggtggcac ttttcgggga aatgtgcgcg gaaccccctat tgtttatttt   1980 ttctaaatac attcaaatat gtatccgctc atgagacaat aaccctgata aatgcttcaa   2040
taatattgaa aaaggaagag tatgagtatt caacatttcc gtgtcgccct tattcccttt   2100
tttgcggcat tttgccttcc tgttttgct cacccagaaa cgctggtgaa agtaaaagat    2160
gctgaagatc agttgggtgc acgagtgggt tacatcgaac tggatctcaa cagcggtaag   2220
atccttgaga gttttcgccc cgaagaacgt tttccaatga tgagcacttt taaagttctg   2280
ctatgtggcg cggtattatc ccgtattgac gccgggcaag agcaactcgg tcgccgcata   2340
cactattctc agaatgactt ggttgagtac tcaccagtca cagaaaagca tcttacggat   2400
ggcatgacag taagagaatt atgcagtgct gccataacca tgagtgataa cactgcggcc   2460
aacttacttc tgacaacgat cggaggaccg aaggagctaa ccgcttttt gcacaacatg    2520 ggggatcatg taactcgcct tgatcgttgg gaaccggagc tgaatgaagc cataccaaac   2580
gacgagcgtg acaccacgat gcctgtagca atggcaacaa cgttgcgcaa actattaact   2640
ggcgaactac ttactctagc ttcccggcaa caattaatag actggatgga ggcggataaa   2700
gttgcaggac cacttctgcg ctcggccctt ccggctggct ggtttattgc tgataaatct   2760
ggagccggtg agcgtgggtc tcgcggtatc attgcagcac tggggccaga tggtaagccc   2820
tcccgtatcg tagttatcta cacgacgggg agtcaggcaa ctatggatga acgaaataga   2880
cagatcgctg agataggtgc ctcactgatt aagcattggt aactgtcaga ccaagtttac   2940
tcatatatac tttagattga tttaaaactt catttttaat ttaaaaggat ctaggtgaag   3000
atcctttttg ataatctcat gaccaaaatc ccttaacgtg agttttcgtt ccactgagcg   3060
tcagaccccg tagaaaagat caaaggatct tcttgagatc ctttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
ggggggcgga gcctatggaa aaacgccagc aacgcggcct ttttacggtt cctggccttt   3720
tgctggcctt ttgctcacat gt                                            3742
```

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
gacacttcag aatacgctac                                                20

<210> SEQ ID NO 156
<211> LENGTH: 20
<212> TYPE: DNA

```
<213> ORGANISM: Artificial Sequence
<220> FEATURE:
<223> OTHER INFORMATION: Synthetic

<400> SEQUENCE: 156
cattcttccc agtacggtac                                                     20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
gaagcttctg aggacgttac                                                     20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
tgaaaaaggg agagatatca                                                     20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
ggaaaaagga aaaatatca                                                      20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
agacaaggga aagaaatcg                                                      20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
tgataaggga aaaatatca                                                      20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
ggaaaaggga aaaaaatca                                                      20
```

<210> SEQ ID NO 163
<211> LENGTH: 75
<212> TYPE: DNA
<213> ORGANISM: Artificial Sequence
<220> FEATURE:
<223> OTHER INFORMATION: Synthetic

<400> SEQUENCE: 163
aacctgctcg aatcccctca gcttgccact ttggctgagg atgtcactgc ggcgcttgct    60
aagcagggct tgtga                                                    75

<210> SEQ ID NO 164
<211> LENGTH: 75
<212> TYPE: DNA
<213> ORGANISM: Artificial Sequence
<220> FEATURE:
<223> OTHER INFORMATION: Synthetic

<400> SEQUENCE: 164
tcacaagccc tgcttagcaa gcgccgcagt gacatcctca gccaaagtgg caagctgagg    60
ggattcgagc aggtt                                                    75

<210> SEQ ID NO 165
<211> LENGTH: 24
<212> TYPE: PRT
<213> ORGANISM: Artificial Sequence
<220> FEATURE:
<223> OTHER INFORMATION: Synthetic

<400> SEQUENCE: 165

Asn Leu Leu Glu Ser Pro Gln Leu Ala Thr Leu Ala Glu Asp Val Thr
1               5                   10                  15

Ala Ala Leu Ala Lys Gln Gly Leu
            20

<210> SEQ ID NO 166
<211> LENGTH: 93
<212> TYPE: DNA
<213> ORGANISM: Artificial Sequence
<220> FEATURE:
<223> OTHER INFORMATION: Synthetic

<400> SEQUENCE: 166
aacagcagca ctcagacagt atcagacaag agcacgcaga cagtgctgcc ctatacggcc    60
accaaacaga agctaaggg caagaactag ggg                                 93

<210> SEQ ID NO 167
<211> LENGTH: 93
<212> TYPE: DNA
<213> ORGANISM: Artificial Sequence
<220> FEATURE:
<223> OTHER INFORMATION: Synthetic

<400> SEQUENCE: 167
gggctagttc ttgcccttag ctttctgttt ggtggccgta tagggcagca ctgtctgcgt    60
gctcttgtct gatactgtct gagtgctgct gtt                                93

<210> SEQ ID NO 168
<211> LENGTH: 29
<212> TYPE: PRT
<213> ORGANISM: Artificial Sequence
<220> FEATURE:

<223> OTHER INFORMATION: Synthetic

<400> SEQUENCE: 168

Asn Ser Ser Thr Gln Thr Val Ser Asp Lys Ser Thr Gln Thr Val Leu
1               5                   10                  15

Pro Tyr Thr Ala Thr Lys Gln Lys Ala Lys Gly Lys Asn
            20                  25

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
gatgtatgaa gatgatgacg                                           20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
agtgacatcc tcagccaaag                                           20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tcagccaaag tggcaagctg                                           20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
actgcggcgc ttgctaagca                                           20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
gtaaagtcag ctaactctct                                           20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
agaaaagggt gtccgtgtgc                    20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
ggctcttcag tgcaccaggg                    20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gaaagagaaa gagccagcag                    20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
gaagaaggaa atccggaacg                    20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
taccacatca tccacagatg                    20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
ccaggagtta gcggatcgtg                    20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
gctggcggcg gtcaaccaga                    20

<210> SEQ ID NO 181
<211> LENGTH: 20
<212> TYPE: DNA

```
<213> ORGANISM: Artificial Sequence
<220> FEATURE:
<223> OTHER INFORMATION: Synthetic

<400> SEQUENCE: 181
ggacaagggg aaagatatca                                                  20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
tatctaaggg agagctggca                                                  20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
gtttaagtca gtcagttaat                                                  20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
cctgtacctg ccgctgtcat                                                  20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ggaagaggat ttcggagagg                                                  20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
ggccaccaaa cagaaagcta                                                  20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
tttctgtttg gtggccgtat                                                  20
```

```
<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
aagctaaggg caagaactag                                                 20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
agtccaaaaa gcatggcagg                                                 20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
tctgcatgga tctgcgtgtc                                                 20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
cggtgaggag gccgaagagg                                                 20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
tccttcatct ttccgctcgt                                                 20

<210> SEQ ID NO 193
<211> LENGTH: 20
<212> TYPE: DNA
<213> ORGANISM: Artificial Sequence
<220> FEATURE:
<223> OTHER INFORMATION: Synthetic

<400> SEQUENCE: 193
ggatgacgat atcgctgcgc                                                 20

<210> SEQ ID NO 194
<211> LENGTH: 20
<212> TYPE: DNA
<213> ORGANISM: Artificial Sequence
<220> FEATURE:
```

<223> OTHER INFORMATION: Synthetic

<400> SEQUENCE: 194
ctgctgctgc acggggtcg                                            20

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
ggtctcggtg acccgccggt                                           20

<210> SEQ ID NO 196
<211> LENGTH: 23
<212> TYPE: DNA
<213> ORGANISM: Artificial Sequence
<220> FEATURE:
<223> OTHER INFORMATION: Synthetic

<400> SEQUENCE: 196
tgacctggtg tccgagtacc agc                                       23

<210> SEQ ID NO 197
<211> LENGTH: 23
<212> TYPE: DNA
<213> ORGANISM: Artificial Sequence
<220> FEATURE:
<223> OTHER INFORMATION: Synthetic

<400> SEQUENCE: 197
ggacagatgc tgcttgtctt ggc                                       23

<210> SEQ ID NO 198
<211> LENGTH: 19
<212> TYPE: DNA
<213> ORGANISM: Artificial Sequence
<220> FEATURE:
<223> OTHER INFORMATION: Synthetic

<400> SEQUENCE: 198
cgacgactca gcaacgtct                                            19

<210> SEQ ID NO 199
<211> LENGTH: 22
<212> TYPE: DNA
<213> ORGANISM: Artificial Sequence
<220> FEATURE:
<223> OTHER INFORMATION: Synthetic

<400> SEQUENCE: 199
gccaagagct catgcctaaa tg                                        22

<210> SEQ ID NO 200
<211> LENGTH: 19
<212> TYPE: DNA
<213> ORGANISM: Artificial Sequence
<220> FEATURE:
<223> OTHER INFORMATION: Synthetic

<400> SEQUENCE: 200
gttcttgggt ggcgcagtc                                            19

```
<210> SEQ ID NO 201
<211> LENGTH: 21
<212> TYPE: DNA
<213> ORGANISM: Artificial Sequence
<220> FEATURE:
<223> OTHER INFORMATION: Synthetic

<400> SEQUENCE: 201
cattagaggc gtgatgggga c                                      21

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
gccaaagatg tctctcgcat                                        20

<210> SEQ ID NO 203
<211> LENGTH: 25
<212> TYPE: DNA
<213> ORGANISM: Artificial Sequence
<220> FEATURE:
<223> OTHER INFORMATION: Synthetic

<400> SEQUENCE: 203
ttggtccaaa agaactcaac ataat                                  25

<210> SEQ ID NO 204
<211> LENGTH: 19
<212> TYPE: DNA
<213> ORGANISM: Artificial Sequence
<220> FEATURE:
<223> OTHER INFORMATION: Synthetic

<400> SEQUENCE: 204
aactccgtgg cagaacacg                                         19

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
cagactccaa ggtgggggaa                                        20

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
gatagcgtga ccaaaccgga                                        20

<210> SEQ ID NO 207
<211> LENGTH: 22
<212> TYPE: DNA
<213> ORGANISM: Artificial Sequence
<220> FEATURE:
<223> OTHER INFORMATION: Synthetic
```

<400> SEQUENCE: 207
acatcaccaa cacaggctgt aa                                              22

<210> SEQ ID NO 208
<211> LENGTH: 27
<212> TYPE: DNA
<213> ORGANISM: Artificial Sequence
<220> FEATURE:
<223> OTHER INFORMATION: Synthetic

<400> SEQUENCE: 208
gctcgagctt atccctatga cgttcct                                         27

<210> SEQ ID NO 209
<211> LENGTH: 24
<212> TYPE: DNA
<213> ORGANISM: Artificial Sequence
<220> FEATURE:
<223> OTHER INFORMATION: Synthetic

<400> SEQUENCE: 209
cggatcctac ccttacgatg tacc                                            24

<210> SEQ ID NO 210
<211> LENGTH: 38
<212> TYPE: DNA
<213> ORGANISM: Artificial Sequence
<220> FEATURE:
<223> OTHER INFORMATION: Synthetic

<400> SEQUENCE: 210
ggactatcat atgcttaccg taacttgaaa gtatttcg                             38

<210> SEQ ID NO 211
<211> LENGTH: 21
<212> TYPE: DNA
<213> ORGANISM: Artificial Sequence
<220> FEATURE:
<223> OTHER INFORMATION: Synthetic

<400> SEQUENCE: 211 ggaacccta gtgatggagt t                                                21

<210> SEQ ID NO 212
<211> LENGTH: 16
<212> TYPE: DNA
<213> ORGANISM: Artificial Sequence
<220> FEATURE:
<223> OTHER INFORMATION: Synthetic

<400> SEQUENCE: 212
cggcctcagt gagcga                                                     16

<210> SEQ ID NO 213
<211> LENGTH: 27
<212> TYPE: DNA
<213> ORGANISM: Artificial Sequence
<220> FEATURE:
<223> OTHER INFORMATION: Synthetic

<400> SEQUENCE: 213
ctcgagctta tccctatgac gttcctg                                         27

<210> SEQ ID NO 214
<211> LENGTH: 27

```
<212> TYPE: DNA
<213> ORGANISM: Artificial Sequence
<220> FEATURE:
<223> OTHER INFORMATION: Synthetic

<400> SEQUENCE: 214
ctatgctcta gctagctagc tatgcgt                                27

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
ggaagtttgc ctgcttagcg                                        20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
taaagaggat ccatcgccgc                                        20

<210> SEQ ID NO 217
<211> LENGTH: 21
<212> TYPE: DNA
<213> ORGANISM: Artificial Sequence
<220> FEATURE:
<223> OTHER INFORMATION: Synthetic

<400> SEQUENCE: 217
tcctgtctta tgcaggtggt c                                      21

<210> SEQ ID NO 218
<211> LENGTH: 22
<212> TYPE: DNA
<213> ORGANISM: Artificial Sequence
<220> FEATURE:
<223> OTHER INFORMATION: Synthetic

<400> SEQUENCE: 218
aaccttttag catctggccc at                                     22

<210> SEQ ID NO 219
<211> LENGTH: 22
<212> TYPE: DNA
<213> ORGANISM: Artificial Sequence
<220> FEATURE:
<223> OTHER INFORMATION: Synthetic

<400> SEQUENCE: 219
tgaaagatag tggcctcgtg aa                                     22

<210> SEQ ID NO 220
<211> LENGTH: 22
<212> TYPE: DNA
<213> ORGANISM: Artificial Sequence
<220> FEATURE:
<223> OTHER INFORMATION: Synthetic

<400> SEQUENCE: 220
```
cccaggtcct gattaactga ca                                              22

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
cctgctctga agacgtccag                                                 20

<210> SEQ ID NO 222
<211> LENGTH: 22
<212> TYPE: DNA
<213> ORGANISM: Artificial Sequence
<220> FEATURE:
<223> OTHER INFORMATION: Synthetic

<400> SEQUENCE: 222
ggtgagtcat ggtcaccact at                                              22

<210> SEQ ID NO 223
<211> LENGTH: 25
<212> TYPE: DNA
<213> ORGANISM: Artificial Sequence
<220> FEATURE:
<223> OTHER INFORMATION: Synthetic

<400> SEQUENCE: 223
catttgacat ccattctgat aaagc                                           25

<210> SEQ ID NO 224
<211> LENGTH: 22
<212> TYPE: DNA
<213> ORGANISM: Artificial Sequence
<220> FEATURE:
<223> OTHER INFORMATION: Synthetic

<400> SEQUENCE: 224
ccgaagagga gataaaggct gt                                              22

<210> SEQ ID NO 225
<211> LENGTH: 23
<212> TYPE: DNA
<213> ORGANISM: Artificial Sequence
<220> FEATURE:
<223> OTHER INFORMATION: Synthetic

<400> SEQUENCE: 225
gggagctttg gctccattac ata                                             23

<210> SEQ ID NO 226
<211> LENGTH: 23
<212> TYPE: DNA
<213> ORGANISM: Artificial Sequence
<220> FEATURE:
<223> OTHER INFORMATION: Synthetic

<400> SEQUENCE: 226
cggtaagaag agaccacaag gaa                                             23

<210> SEQ ID NO 227
<211> LENGTH: 23
<212> TYPE: DNA
<213> ORGANISM: Artificial Sequence

```
<220> FEATURE:
<223> OTHER INFORMATION: Synthetic

<400> SEQUENCE: 227
ggccatgagt ggaagatggt att                                          23

<210> SEQ ID NO 228
<211> LENGTH: 25
<212> TYPE: DNA
<213> ORGANISM: Artificial Sequence
<220> FEATURE:
<223> OTHER INFORMATION: Synthetic

<400> SEQUENCE: 228
tctcacagat taaagttagg gtgtc                                        25

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
gtgaaatgaa tccagatgga acct                                         24

<210> SEQ ID NO 230
<211> LENGTH: 21
<212> TYPE: DNA
<213> ORGANISM: Artificial Sequence
<220> FEATURE:
<223> OTHER INFORMATION: Synthetic

<400> SEQUENCE: 230
tccagtcaat tcccctttccg c                                           21

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
tggcaccagc atcatcaagt                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
ctatctcatg ccggctctcc                                              20

<210> SEQ ID NO 233
<211> LENGTH: 22
<212> TYPE: DNA
<213> ORGANISM: Artificial Sequence
<220> FEATURE:
<223> OTHER INFORMATION: Synthetic

<400> SEQUENCE: 233
gggcattggc aagagctgat aa                                           22
```

```
<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
attagggctg gctgtagtgg                                               20

<210> SEQ ID NO 235
<211> LENGTH: 24
<212> TYPE: DNA
<213> ORGANISM: Artificial Sequence
<220> FEATURE:
<223> OTHER INFORMATION: Synthetic

<400> SEQUENCE: 235 tgtcttttc catgactaca actc                                           24

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
tttgctacgc tttcttccca                                               20
```